(12) United States Patent
Qi et al.

(10) Patent No.: US 11,753,407 B2
(45) Date of Patent: Sep. 12, 2023

(54) COMPOUNDS FOR TREATING SPINAL MUSCULAR ATROPHY

(71) Applicants: PTC Therapeutics, Inc., South Plainfield, NJ (US); F. Hoffmann-La Roche AG, Basel (CH)

(72) Inventors: Hongyan Qi, Plainsboro, NJ (US); Soongyu Choi, Belle Mead, NJ (US); Amal Dakka, Whitehouse Station, NJ (US); Gary Mitchell Karp, Princeton Junction, NJ (US); Jana Narasimhan, Scotch Plains, NJ (US); Nikolai Naryshkin, East Brunswick, NJ (US); Anthony A. Yurpoff, Hillsborough, NJ (US); Marla L. Weetall, Morristown, NJ (US); Ellen Welch, Califon, NJ (US); Matthew G. Woll, Dunellen, NJ (US); Tianle Yang, Mountainside, NJ (US); Nanjing Zhang, Princeton, NJ (US); Xiaoyan Zhang, Belle Mead, NJ (US); Xin Zhao, Belle Mead, NJ (US); Luke Green, Basel (CH); Emmanuel Pinard, Linsdort (FR); Hasane Ratni, Habsheim (FR)

(73) Assignees: PTC Therapeutics, Inc., South Plainfield, NJ (US); F. Hoffmann-La Roche AG, Basel (CH)

( * ) Notice: Subject to any disclaimer, the term of this patent is extended or adjusted under 35 U.S.C. 154(b) by 0 days.

(21) Appl. No.: 17/062,853

(22) Filed: Oct. 5, 2020

(65) Prior Publication Data
US 2021/0276999 A1 Sep. 9, 2021

Related U.S. Application Data

(60) Continuation of application No. 16/541,401, filed on Aug. 15, 2019, now Pat. No. 10,851,101, which is a continuation of application No. 15/848,075, filed on Dec. 20, 2017, now abandoned, which is a division of application No. 15/248,052, filed on Aug. 26, 2016, now Pat. No. 9,879,007, which is a continuation of application No. 14/377,531, filed as application No. PCT/US2013/025292 on Feb. 8, 2013, now Pat. No. 9,586,955.

(60) Provisional application No. 61/597,523, filed on Feb. 10, 2012.

(51) Int. Cl.
C07D 487/04 (2006.01)
C07D 471/04 (2006.01)
A61K 31/519 (2006.01)
C07D 239/70 (2006.01)
C07D 519/00 (2006.01)

(52) U.S. Cl.
CPC .......... *C07D 471/04* (2013.01); *A61K 31/519* (2013.01); *C07D 239/70* (2013.01); *C07D 487/04* (2013.01); *C07D 519/00* (2013.01)

(58) Field of Classification Search
CPC ............................ C07D 487/04; A61K 31/519
USPC .......................................... 544/279; 514/249
See application file for complete search history.

(56) References Cited

U.S. PATENT DOCUMENTS

| | | |
|---|---|---|
| 3,558,618 A | 1/1971 | Trepanier |
| 4,122,274 A | 10/1978 | Juby |
| 4,342,870 A | 8/1982 | Kennis et al. |
| 5,089,633 A | 2/1992 | Powers et al. |
| 5,599,816 A | 2/1997 | Chu et al. |
| 6,630,488 B1 | 10/2003 | Lamothe et al. |
| 6,977,255 B2 | 12/2005 | Robertson et al. |
| 7,326,711 B2 | 2/2008 | Wang et al. |
| 7,399,767 B2 | 7/2008 | Zhang et al. |
| 7,569,337 B2 | 8/2009 | Auberson |
| 7,897,792 B2 | 3/2011 | Iikura et al. |
| 8,337,941 B2 | 12/2012 | Gubernator et al. |
| 8,633,019 B2 | 1/2014 | Paushkin et al. |
| 9,586,955 B2 | 3/2017 | Qi et al. |
| 9,617,268 B2 | 4/2017 | Woll et al. |
| 9,879,007 B2 | 1/2018 | Qi et al. |
| 9,969,754 B2 | 5/2018 | Ratni et al. |

(Continued)

FOREIGN PATENT DOCUMENTS

| | | |
|---|---|---|
| EP | 1227084 A1 | 6/1998 |
| JP | 1981-150091 | 3/1983 |

(Continued)

OTHER PUBLICATIONS

Wolff et. al., "Burger's Medicinal Chemistry and Drug Discovery," 5th Ed. Part 1, pp. 975-977 (1995). (Year: 1995).*

(Continued)

*Primary Examiner* — Jeffrey H Murray
(74) *Attorney, Agent, or Firm* — Jones Day

(57) ABSTRACT

Provided herein are compounds of Formula (I):

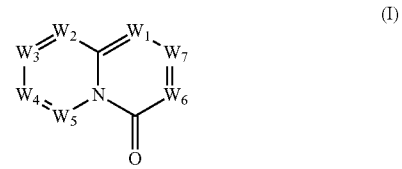

and forms thereof, wherein $w_1$, $w_2$, $w_3$, $w_4$, $w_5$, $w_6$ and $w_7$ are as defined herein, including compositions thereof and uses therewith for treating spinal muscular atrophy.

13 Claims, 23 Drawing Sheets
Specification includes a Sequence Listing.

(56) References Cited

U.S. PATENT DOCUMENTS

| | | |
|---|---|---|
| 10,208,067 B2 | 2/2019 | Gillespie et al. |
| 2003/0199526 A1 | 10/2003 | Choquette et al. |
| 2008/0255162 A1 | 10/2008 | Bruendl et al. |

FOREIGN PATENT DOCUMENTS

| | | |
|---|---|---|
| WO | WO1993023398 | 11/1993 |
| WO | WO 1996039407 | 12/1996 |
| WO | WO1998025930 | 6/1998 |
| WO | WO2002087589 | 11/2002 |
| WO | WO2004009558 | 1/2004 |
| WO | WO2004113335 | 12/2004 |
| WO | WO2005105801 | 11/2005 |
| WO | WO2007109211 | 12/2007 |
| WO | WO2009151546 | 12/2009 |
| WO | WO2009156861 | 12/2009 |
| WO | WO201019236 | 2/2010 |
| WO | WO2011050245 A1 | 4/2011 |
| WO | WO201162853 | 5/2011 |
| WO | WO2011062853 | 5/2011 |
| WO | WO201185990 | 7/2011 |
| WO | WO2011085990 | 7/2011 |
| WO | WO2013101974 | 7/2013 |
| WO | WO2013112788 | 8/2013 |
| WO | WO2013130689 | 9/2013 |
| WO | WO2013142236 | 9/2013 |

OTHER PUBLICATIONS

Banker, et. al., (1996), Modern Pharmaceuticals, p. 596. (Year: 1996).*
Chawla et al.; CRIPS 5(1); 2004; p. 9, col. 2, para.1. (Year: 2004).*
Newman et al.; Drug Discovery Today 8(19); 2003; p. 898, col. 2, Para.3. (Year: 2003).*
Le et al., 2005, "SMND7, the major product of the centromeric survival motor neuron (SMN2) gene, extends survival in mice with spinal muscular atrophy and associates with full-length SMN," *Human Molecular Genetics*, vol. 14(6) pp. 845-857 (2005).
Passini et al., 2001, "Antisense Oligonucleotides Delivered to the Mouse CNS Ameliorate Symptoms of Severe Spinal Muscular Atrophy," Sci Transl Med., vol. 3(72) (2001).
Hua et al., 2012, "Peripheral SMN restoration is essential for long-term rescue of a severe SMA mouse model," Nature, vol. 478(7367): pp. 123-126 (2012).
Coady et al., 2010, "Trans-splicing-mediated improvement in a severe mouse model of spinal muscular atrophy," J Neurosci., vol. 30(1), pp. 126-130 (2010).
Greene et al., 1991, Protective Groups in Organic Synthesis (1991), Wiley, New York.
Higuchi and W. Stella, 1987, "Pro-drugs as Novel Delivery Systems," vol. 14 of the A.C.S. Symposium Series, and in Bioreversible Carriers in Drug Design, ed. Edward B. Roche, American Pharmaceutical Association and Pergamon Press (1987).
Liu et al., 1996, "A novel nuclear structure containing the survival of motor neurons protein," EMBO J., vol. 15(14), pp. 3555-3565 (1996).
Jarecki et al., 2005, "Diverse small-molecule modulators of SMN expression found by high throughput compound screening: early leads towards a therapeutic for spinal muscular atrophy," *Human Molecular Genetics*, 14(14):2003-2018 (2005).
Knight et al., 2004, "Isoform-specific phosphoinositide 3-kinase inhibitors from an arylmorpholine scaffold," *Bioorganic & Medicinal Chemistry*, 12:4749-4759 (2004).
Kocar et al., 2002, "Transformations of 3-aminopyridazines. Synthesis of 4-oxo-4H-pyrimido[1,2-b]pyridazine and 1-(substituted pyridazin-3-yi)-1H-1,2,3-triazole derivatives,"Arkivoc 2002 (viii) 143-156 (2002).
Makhortova, et al. 2011, "A Screen for Regulators of Survival of Motor Neuron Protein Levels," *Nat Chern Biol*, 7(8):544-552 (2011).
PubChem compound CID 377422. Mar. 26, 2005. [Retrieved from the Internet Oct. 27, 2014: <http://pubchem.ncbi.nlm.nih.gov// compound/377422?from=summary>).
PCT International Search Report dated Aug. 30, 2013 in connection with PCT/US2013/025292.
PCT Written Opinion of the International Searching Authority dated Aug. 30, 2013 in connection with PCT/US2013/025292.
PCT International Search Report dated Oct. 24, 2013 with Publication No. WO 2013-119916 A3 in connection with PCT/US2013/ 025292.
PCT International Preliminary Report dated Aug. 21, 2014 in connection with PCT/US2013/025292.
Peng, Lijie, et al., 2011, "Identification of pyrido [1, 2-α] pyrimidine-4-ones as new molecules improving the transcriptional functions of estrogen-related receptor α", *Journal of medicinal chemistry*, 54.21 (2011): 7729-7733.
Knight et al., 2004, "Isoform-specific phosphoinositide 3-kinase inhibitors from an arylmorpholine scaffold," *Bioorganic & medicinal chemistry*, 12.17 (2004): 4749-4759.
Jarecki et al., 2005, "Diverse small-molecule modulators of SMN expression found by high-throughput compound screening: early leads towards a therapeutic for spinal muscular atrophy," Human molecular genetics 14.14 (2005): 2003-2018.
Kocar et al., 2002, "Transformations of 3-aminopyridazines. Synthesis of 4-oxo-4H-pyrimido [1, 2-b] pyridazine and 1-(substituted pyridazin-3-yl)-1H-1, 2, 3-triazole derivatives," Arkivoc (2002): 143-156.
NCBI Database accession No. CID377422, [online], 2005, retrieved on Jul. 4, 2016, URL, http://pubchem.nci.nlm.nih.gov/compound/ 377422.
Makhortova et al., 2011, "A screen for regulators of survival of motor neuron protein levels," Nature chemical biology, 7.8 (2011): 544-552.
Yuo et al., 2008, "5-(N-ethyl-N-isopropyl)-amiloride enhances SMN2 exon 7 inclusion and protein expression in spinal muscular atrophy cells," Annals of neurology 63.1 (2008): 26-34.
Shao, Ning, et al., 2012, "Synthesis and structure-activity relationship (SAR) study of 4-azabenzoxazole analogues as $H_3$ antagonists," *Bioorganic & medicinal chemistry letters* 22.5 (2012): 2075-2078.

* cited by examiner

```
tagcttcttacccgtactccaccgttggcagcacgatcgcacgtcccacgtgaaccattggtaaaccctgatgggatccataattcccccaccacctccc
atatgtccagattctcttgatgatgctgatgctttgggaagtatgttaatttcatggtacatgagtggctatcatactggctattatatggtaagtaatcac
tcagcatcttttcctgacaattttttgtagttatgtgactttgttttgtaaatttataaaatactacttgcttctctctttatattactaaaaaataaaaataa
aaaaatacaactgtctgaggcttaaattactcttgcattgtccctaagtataattttagttaattttaaaaagctttcatgctattgttagattattttgatt
atacacttttgaattgaaattatactttttctaaataatgttttaatctctgatttgaaattgattgtagggaatggaaaagatgggataattttcataaa
tgaaaaatgaaattctttttttttttttttttttgagacggagtcttgctctgttgcccaggctggagtgcaatggcgtgatcttggctcacagcaagct
ctgcctcctggattcacgccattctcctgcctcagcctcagaggtagctgggactacaggtgcctgccaccacgcctgtctaatttttgtattttttgtaa
agacagggtttcactgtgttagccaggatggtctcaatctcctgacccgtgatccacccgcctcggccttccaagagaaatgaaatttttaatgcac
aaagatctggggtaatgtgtaccacattgaaccttggggagtatggcttcaaacttgtcactttatacgttagtctcctacggacatgttctattgtatttt
agtcagaacatttaaaattattttattttattttattttttttttttttttgagacggagtctcgctctgtcacccaggctggagtacagtggcgcagtctcgg
ctcactgcaagctccgcctcccgggttcacgccattctcctgcctcagcctctccgagtagctgggactacaggcgcccgccaccacgcccggctaattt
ttttttatttttagtagagacggggtttcaccgtggtctcgatctcctgacctcgtgatccacccgcctcggcctcccaaagtgctgggattacaagcgtg
agccaccgcgcccggcctaaaattattttaaaagtaagctcttgtgccctgctaaaattatgatgtgatattgtaggcacttgtattttagtaaattaat
atagaagaaacaactgacttaaaggtgtatgtttttaaatgtatcatctgtgtgtgcccccattaatattcttatttaaaagttaaggccagacatggtgg
cttacaactgtaatcccaacagtttgtgaggccgaggcaggcagatcacttgaggtcaggagtttgagaccagcctggccaacatgatgaaaccttgt
ctctactaaaaataccaaaaaaaatttagccaggcatggtggcacatgcctgtaatccgagctacttgggaggctgtggcaggaaaattgctttaatct
gggaggcagaggttgcagtgagttgagattgtgccactgcactccacccttggtgacagagtgagattccatctcaaaaaaagaaaaaggcctggca
cggtggctcacacctataatcccagtactttgggaggtagaggcaggtggatcacttgaggttaggagttcaggaccagcctggccaacatggtgact
actccatttctactaaatacacaaaacttagcccagtggcgggcagttgtaatcccagctacttgagaggttgaggcaggagaatcacttgaacctgg
gaggcagaggttgcagtgagccgagatcacaccgctgcactctagcctggccaacagagtgagaatttgcggagggaaaaaaaagtcacgcttcag
ttgttgtagtataaccttggtatattgtatgtatcatgaattcctcattttaatgaccaaaaagtaataaatcaacagcttgtaatttgttttgagatcagtt
atctgactgtaacactgtaggcttttgtgttttttaaattatgaaatatttgaaaaaaatacataatgtatatataaagtattggtataatttatgttctaa
ataactttcttgagaaataattcacatggtgtgcagtttacctttgaaagtatacaagttggctgggcacaatggctcacgcctgtaatcccagcacttt
gggaggccaggcaggtggatcacgaggtcaggagatcgagaccatcctggctaacatggtgaaaccccgtctctactaaaagtacaaaaacaaat
tagccgggcatgttggcgggcaccttttgtcccagctgctcgggaggctgaggcaggagagtggcgtgaacccaggaggtggagcttgcagtgagcc
gagattgtgccagtgcactccagcctgggcgacagagcgagactctgtctcaaaaaataaaataaaaaagaaagtatacaagtcagtggttttggttt
tcagttatgcaaccatcactacaatttaagaacattttcatcaccccaaaaagaaaccctgttaccttcattttccccagccctaggcagtcagtacactt
tctgtctctatgaatttgtctattttagatattatatataaacggaattatacgatatgtggtcttttgtgtctggcttctttcacttagcatgctattttcaag
attcatccatgctgtagaatgcaccagtactgcattccttcttattgctgaatattctgttgtttggttatatcacattttatccattcatcagttcatggaca
tttaggttgtttttatttttgggctataatgaataatgttgctatgaacattcgtttgtgttcttttttgttttttggttttttgggttttttttgttttgttttgtttt
tgagacagtcttgctctgtcctaagctggagtgcagtggcatgatcttggcttactgcaagctctgcctcccgggttcacaccattctcctgcctcagc
ccgacaagtagctgggactacaggcgtgtgccaccatgcacggctaattttttgtattttagtagagatggggtttcaccgtgttagccaggatggtct
cgatctcctgacctcgtgatctgcctgcctaggcctcccaaagtgctgggattacaggcgtgagccactgcacctggccttaagtgttttaatacgtcat
tgccttaagctaacaattcttaacctttgttctactgaagccacgtggttgagataggctctgagtctagctttaacctctatctttttgtcttagaaatct
aagcagaatgcaaatgactaagaataatgttgttgaaataacataaaataggttataactttgatactcattagtaacaaatctttcaatacatcttac
ggtctgttaggtgtagattagtaatgaagtgggaagccactgcaagctagtatacatgtagggaaagatagaaagcattgaagcagaagagagac
agaggacatttgggctagatctgacaagaaaaacaaatgttttagtattaattttgactttaaatttttttttatttagtgaatactggtgtttaatggtc
tcattttaataagtatgacacaggtagtttaaggtcatatattttatttgatgaaaataaggtataggccgggcacggtggctcacacctgtaatcccag
cactttggaggccgaggcaggcggatcacctgaggtcgggagttagagactagcctcaacatggagaaaccccgtctctactaaaaaaaatacaa
aattaggcgggcgtggt
```

Figure 2a ggtgcatgcctgtaatcccagctactcaggaggctgaggcaggagaattgcttgaacctgggaggtggaggttgcggtgagccgagatcacctcattg
cactccagcctgggcaacaagagcaaaactccatctcaaaaaaaaaaaaataaggtataagcgggctcaggaacatcattggacatactgaaaga
agaaaaatcagctgggcgcagtggctcacgccggtaatcccaacactttgggaggccaaggcaggcgaatcacctgaagtcgggagttccagatca
gcctgaccaacatggagaaaccctgtctctactaaaaatacaaaactagccgggcatggtggcgcatgcctgtaatcccagctacttgggaggctgag
gcaggagaattgcttgaaccgagaaggcggaggttgcggtgagccaagattgcaccattgcactccagcctgggcaacaagagcgaaactccgtctc
aaaaaaaaaaggaagaaaaaatattttttaaattaattagtttatttattttttaagatggagttttgccctgtcacccaggctggggtgcaatggtgca
atctcggctcactgcaacctccgcctcctgggttcaagtgattctcctgcctcagcttcccgagtagctgtgattacagccatatgccaccacgcccagc
cagttttgtgttttgttttgttttttgttttttttttttgagagggtgtcttgctctgtccccaagctggagtgcagcggcgcgatcttggctcactgcaagct
ctgcctcccaggttcacaccattctcttgcctcagcctcccgagtagctgggactacaggtgcccgccaccacacccggctaatttttttgtgttttagta
gagatggggtttcactgtgttagccaggatggtctcgatctcctgacctttgatccacccgcctcagcctccccaagtgctgggattataggcgtgagc
cactgtgcccggcctagtcttgtattttagtagagtcgggatttctccatgttggtcaggctgttctccaaatccgacctcaggtgatccgcccgccttgg
cctccaaaagtgcaaggcaaggcattacaggcatgagccactgtgaccggcaatgttttaaatttttacatttaaatttatttttagagaccaggtc
tcactctattgctcaggctggagtgcaagggcacattcacagctcactgcagccttgacctccagggctcaagcagtcctctcacctcagtttcccgagt
agctgggactacagtgataatgccactgcacctggctaattttattttatttatttattttttttgagacagagtcttgctctgtcacccaggctggagt
gcagtggtgtaaatctcagctcactgcagcctccgcctcctgggttcaagtgattctcctgcctcaacctcccaagtagctgggattagaggtccccacc
accatgcctggctaattttttgtactttcagtagaaacggggttttgccatgttggccaggctgttctcgaactcctgagctcaggtgatccaactgtctcg
gcctcccaaagtgctgggattacaggcgtgagccactgtgcctagcctgagccaccacgccggcctaatttttaaattttttgtagagacagggtctcat
tatgttgcccagggtggtgtcaagctccaggtctcaagtgatccccctacctccgcctcccaaagttgtgggattgtaggcatgagccactgcaagaaa
accttaactgcagcctaataattgttttctttgggataacttttaaagtacattaaaagactatcaacttaatttctgatcatattttgttgaataaaataa
gtaaaatgtcttgtgaaacaaaatgcttttaacatccatataaagctatctatatagctatctatatctatatagctatttttttttaacttcctttatttt
ccttacagggttttagacaaaatcaaaaagaaggaaggtgctcacattccttaaatataaggagtaagtctgccagcattatgaaagtgaatcttactt
ttgtaaaactttatggtttgtggaaaacaaatgttttgaacatttaaaaagttcagatgttagaaagttgaaaggttaatgtaaaacaatcaatattaa
agaattttgatgccaaaactattagataaaaggttaatctacatccctactagaattctcatacttaactggttggttgtgtggaagaaacatactttcac
aataaagagctttaggatatgatgccattttatatcactagtaggcagaccagcagactttttttattgtgatatgggataacctaggcatactgcact
gtacactctgacatatgaagtgctctagtcaagtttaactggtgtccacagaggacatggtttaactggaattcgtcaagcctctggttctaatttctcat
ttgcaggaaatgctggcatagagcagcacggatccgaagacgccaaaaacataaagaaaggcccggcgccattctatcctctagaggatggaaccg
ctggagagcaactgcataaggctatgaagagatacgccctggttcctggaacaattgcttttacagatgcacatatcgaggtgaacatcacgtacgcg
gaatacttcgaaatgtccgttcggttggcagaagctatgaaacgatatgggctgaatacaaatcacagaatcgtcgtatgcagtgaaaactctcttca
attctttatgccggtgttgggcgcgttatttatcggagttgcagttgcgcccgcgaacgacatttataatgaacgtgaattgctcaacagtatgaacattt
cgcagcctaccgtagtgtttgtttccaaaaaggggttgcaaaaaattttgaacgtgcaaaaaaaattaccaataatccagaaaattattatcatggatt
ctaaaacggattaccagggatttcagtcgatgtacacgttcgtcacatctcatctacctcccggttttaatgaatacgattttgtaccagagtcctttgat
cgtgacaaaacaattgcactgataatgaattcctctggatctactgggttacctaagggtgtggcccttccgcatagaactgcctgcgtcagattctcgc
atgccagagatcctatttttggcaatcaaatcattccggatactgcgattttaagtgttgttccattccatcacggttttggaatgtttactacactcggat
atttgatatgtggatttcgagtcgtcttaatgtatagatttgaagaagagctgtttttacgatcccttcaggattacaaaattcaaagtgcgttgctagta
ccaacccctattttcattcttcgccaaaagcactctgattgacaaatacgatttatctaatttacacgaaattgcttctgggggcgcacctcttcgaaaga
agtcggggaagcggttgcaaaacgcttccatcttccagggatacgacaaggatatgggctcactgagactacatcagctattctgattacacccgagg
gggatgataaaccgggcgcggtcggtaaagttgttccatttttgaagcgaaggttgtggatctggataccgggaaaacgctgggcgttaatcagaga
ggcgaattatgtgtcagaggacctatgattatgtccggttatgtaaacaatccggaagcgaccaacgccttgattgacaaggatggatggctacattct
ggagacatagcttactgggacgaagacgaacacttcttcatagttgaccgcttgaagtctttaattaaatacaaaggatatcaggtggcc

Figure 2a (continued)

cccgctgaattggaatcgatattgttacaacaccccaacatcttcgacgcgggcgtggcaggtcttcccgacgatgacgccggtgaacttcccgccgcc
gttgttgttttggagcacggaaagacgatgacggaaaaagagatcgtggattacgtcgccagtcaagtaacaaccgcgaaaaagttgcgcggagga
gttgtgtttgtggacgaagtaccgaaaggtcttaccggaaaactcgacgcaagaaaaatcagagagatcctcataaaggccaagaagggcggaaag
tccaaattgcgcggccgctaaatcgaaagtacaggactagccttcctagcaaccgcgggctgggagtctgagacatcactcaagatatatgctcggta
acgtatgctctagccatctaactattccctatgtcttataggg

SEQ ID NO. 21

Figure 2a (continued)

SEQUENCE LISTING

<160> NUMBER OF SEQ ID NOS: 21

<210> SEQ ID NO 1
<211> LENGTH: 19
<212> TYPE: DNA
<213> ORGANISM: Artificial Sequence
<220> FEATURE:
<223> OTHER INFORMATION: SMN Forward Primer A

<400> SEQUENCE: 1
gaaggaaggt gctcacatt                                             19

<210> SEQ ID NO 2
<211> LENGTH: 22
<212> TYPE: DNA
<213> ORGANISM: Artificial Sequence
<220> FEATURE:
<223> OTHER INFORMATION: SMN Reverse Primer A

<400> SEQUENCE: 2
tctttatgtt tttggcgtct tc                                         22

<210> SEQ ID NO 3
<211> LENGTH: 26
<212> TYPE: DNA
<213> ORGANISM: Artificial Sequence
<220> FEATURE:
<223> OTHER INFORMATION: SMN Forward Probe A

<400> SEQUENCE: 3
aaggagaaat gctggcatag agcagc                                     26

<210> SEQ ID NO 4
<211> LENGTH: 21
<212> TYPE: DNA
<213> ORGANISM: Artificial Sequence
<220> FEATURE:
<223> OTHER INFORMATION: hGAPDH Forward Probe

<400> SEQUENCE: 4
cgcctggtca ccagggctgc t                                          21

<210> SEQ ID NO 5
<211> LENGTH: 21
<212> TYPE: DNA
<213> ORGANISM: Artificial Sequence
<220> FEATURE:
<223> OTHER INFORMATION: hGAPDH Forward Primer

<400> SEQUENCE: 5
caacggattt ggtcgtattg g                                          21

<210> SEQ ID NO 6
<211> LENGTH: 25
<212> TYPE: DNA
<213> ORGANISM: Artificial Sequence
<220> FEATURE:
<223> OTHER INFORMATION: hGAPDH Reverse Primer

<400> SEQUENCE: 6
tgatggcaac aatatccact ttacc                                      25

<210> SEQ ID NO 7
<211> LENGTH: 27
<212> TYPE: DNA
<213> ORGANISM: Artificial Sequence
<220> FEATURE:
<223> OTHER INFORMATION: SMN FL Forward Primer B

<400> SEQUENCE: 7
gctcacattc cttaaattaa ggagaaa                                    27

<210> SEQ ID NO 8
<211> LENGTH: 28

```
<212> TYPE: DNA
<213> ORGANISM: Artificial Sequence
<220> FEATURE:
<223> OTHER INFORMATION: SMN delta-7 Forward Primer B

<400> SEQUENCE: 8
tggctatcat actggctatt atatggaa                                           28

<210> SEQ ID NO 9
<211> LENGTH: 24
<212> TYPE: DNA
<213> ORGANISM: Artificial Sequence
<220> FEATURE:
<223> OTHER INFORMATION: SMN Reverse Primer B

<400> SEQUENCE: 9
tccagatctg tctgatcgtt tctt                                               24

<210> SEQ ID NO 10
<211> LENGTH: 30
<212> TYPE: DNA
<213> ORGANISM: Artificial Sequence
<220> FEATURE:
<223> OTHER INFORMATION: SMN Forward Probe B

<400> SEQUENCE: 10
ctggcataga gcagcactaa atgacaccac                                         30

<210> SEQ ID NO 11
<211> LENGTH: 21
<212> TYPE: DNA
<213> ORGANISM: Artificial Sequence
<220> FEATURE:
<223> OTHER INFORMATION: SMN Forward C

<400> SEQUENCE: 11
gatgctgatg ctttgggaag t                                                  21

<210> SEQ ID NO 12
<211> LENGTH: 22
<212> TYPE: DNA
<213> ORGANISM: Artificial Sequence
<220> FEATURE:
<223> OTHER INFORMATION: SMN Reverse C

<400> SEQUENCE: 12
cgcttcacat tccagatctg tc                                                 22

<210> SEQ ID NO 13
<211> LENGTH: 25
<212> TYPE: DNA
<213> ORGANISM: Artificial Sequence
<220> FEATURE:
<223> OTHER INFORMATION: SMN Forward D

<400> SEQUENCE: 13
atatgtccag attctcttga tgatg                                              25

<210> SEQ ID NO 14
<211> LENGTH: 11
<212> TYPE: DNA
<213> ORGANISM: Artificial Sequence
<220> FEATURE:
<223> OTHER INFORMATION: 5-prime end of exon 6 of the SMN2 gene

<400> SEQUENCE: 14
```

```
ataattcccc c                                                            11

<210> SEQ ID NO 15
<211> LENGTH: 6
<212> TYPE: DNA
<213> ORGANISM: Artificial Sequence
<220> FEATURE:
<223> OTHER INFORMATION: nucleic acid residue 23 of exon 8 of the SMN2
      gene

<400> SEQUENCE: 15 cagcac                                                                   6

<210> SEQ ID NO 16
<211> LENGTH: 28
<212> TYPE: DNA
<213> ORGANISM: Artificial Sequence
<220> FEATURE:
<223> OTHER INFORMATION: PCR forward primer

<400> SEQUENCE: 16
cgcggatcca taattccccc accacctc                                          28

<210> SEQ ID NO 17
<211> LENGTH: 28
<212> TYPE: DNA
<213> ORGANISM: Artificial Sequence
<220> FEATURE:
<223> OTHER INFORMATION: PCR reverse primer

<400> SEQUENCE: 17
cgcggatccg tgctgctcta tgccagca                                          28

<210> SEQ ID NO 18
<211> LENGTH: 6
<212> TYPE: DNA
<213> ORGANISM: Artificial Sequence
<220> FEATURE:
<223> OTHER INFORMATION: BamHI restriction endonuclease recognition
      sequence

<400> SEQUENCE: 18 ggatcc                                                                   6

<210> SEQ ID NO 19
<211> LENGTH: 70
<212> TYPE: DNA
<213> ORGANISM: Artificial Sequence
<220> FEATURE:
<223> OTHER INFORMATION: 5-prime DEG UTR

<400> SEQUENCE: 19
tagcttctta cccgtactcc accgttggca gcacgatcgc acgtcccacg tgaaccattg       60
gtaaaccctg                                                              70

<210> SEQ ID NO 20
<211> LENGTH: 120
<212> TYPE: DNA
<213> ORGANISM: Artificial Sequence
<220> FEATURE:
<223> OTHER INFORMATION: 3-prime DEG UTR

<400> SEQUENCE: 20
atcgaaagta caggactagc cttcctagca accgcgggct gggagtctga gacatcactc       60
aagatatatg ctcggtaacg tatgctctag ccatctaact attccctatg tcttataggg      120
```

<210> SEQ ID NO 21
<211> LENGTH: 8266
<212> TYPE: DNA
<213> ORGANISM: Artificial Sequence
<220> FEATURE:
<223> OTHER INFORMATION: DNA sequence of SMN2-A minigene

<400> SEQUENCE: 21

| | | | | | |
|---|---|---|---|---|---|
| tagcttctta | cccgtactcc | accgttggca | gcacgatcgc | acgtcccacg | tgaaccattg | 60 |
| gtaaaccctg | atgggatcca | taattccccc | accacctccc | atatgtccag | attctcttga | 120 |
| tgatgctgat | gctttgggaa | gtatgttaat | ttcatggtac | atgagtggct | atcatactgg | 180 |
| ctattatatg | gtaagtaatc | actcagcatc | ttttcctgac | aatttttttg | tagttatgtg | 240 |
| actttgtttt | gtaaatttat | aaaatactac | ttgcttctct | ctttatatta | ctaaaaaata | 300 |
| aaaataaaaa | aatacaactg | tctgaggctt | aaattactct | tgcattgtcc | ctaagtataa | 360 |
| ttttagttaa | ttttaaaaag | ctttcatgct | attgttagat | tattttgatt | atacactttt | 420 |
| gaattgaaat | tatacttttt | ctaaataatg | ttttaatctc | tgatttgaaa | ttgattgtag | 480 |
| ggaatggaaa | agatgggata | attttttcata | atgaaaaat | gaaattcttt | ttttttttt | 540 |
| tttttttttg | agacggagtc | ttgctctgtt | gcccaggctg | gagtgcaatg | gcgtgatctt | 600 |
| ggctcacagc | aagctctgcc | tcctggattc | acgccattct | cctgcctcag | cctcagaggt | 660 |
| agctgggact | acaggtgcct | gccaccacgc | ctgtctaatt | ttttgtattt | ttttgtaaag | 720 |
| acagggtttc | actgtgttag | ccaggatggt | ctcaatctcc | tgaccccgtg | atccacccgc | 780 |
| ctcggccttc | caagagaaat | gaatttttt | taatgcacaa | agatctgggg | taatgtgtac | 840 |
| cacattgaac | cttggggagt | atggcttcaa | acttgtcact | ttatacgtta | gtctcctacg | 900 |
| gacatgttct | attgtatttt | agtcagaaca | tttaaaatta | ttttattttta | ttttattttt | 960 |
| tttttttttt | tgagacggag | tctcgctctg | tcacccaggc | tggagtacag | tggcgcagtc | 1020 |
| tcggctcact | gcaagctccg | cctcccgggt | tcacgccatt | ctcctgcctc | agcctctccg | 1080 |
| agtagctggg | actacaggcg | cccgccacca | cgcccggcta | attttttttt | attttttagta | 1140 |
| gagacgggt | ttcaccgtgg | tctcgatctc | ctgacctcgt | gatccacccg | cctcggcctc | 1200 |
| ccaaagtgct | gggattacaa | gcgtgagcca | ccgcgcccgg | cctaaaatta | ttttttaaaag | 1260 |
| taagctcttg | tgccctgcta | aaattatgat | gtgatattgt | aggcacttgt | attttttagta | 1320 |
| aattaatata | gaagaaacaa | ctgacttaaa | ggtgtatgtt | tttaaatgta | tcatctgtgt | 1380 |
| gtgccccat | taatattctt | atttaaaagt | taaggccaga | catggtggct | tacaactgta | 1440 |
| atcccaacag | tttgtgaggc | cgaggcaggc | agatcacttg | aggtcaggag | tttgagacca | 1500 |
| gcctggccaa | catgatgaaa | ccttgtctct | actaaaaata | ccaaaaaaaa | tttagccagg | 1560 |
| catggtggca | catgcctgta | atccgagcta | cttgggaggc | tgtggcagga | aaattgcttt | 1620 |
| aatctgggag | gcagaggttg | cagtgagttg | agattgtgcc | actgcactcc | acccttggtg | 1680 |
| acagagtgag | attccatctc | aaaaaaagaa | aaaggcctgg | cacggtggct | cacacctata | 1740 |
| atcccagtac | tttgggaggt | agaggcaggt | ggatcacttg | aggttaggag | ttcaggacca | 1800 |
| gcctggccaa | catggtgact | actccatttc | tactaaaatac | acaaaactta | gcccagtggc | 1860 |
| gggcagttgt | aatcccagct | acttgagagg | ttgaggcagg | agaatcactt | gaacctggga | 1920 |
| ggcagaggtt | gcagtgagcc | gagatcacac | cgctgcactc | tagcctggcc | aacagagtga | 1980 |
| gaatttgcgg | agggaaaaaa | aagtcacgct | tcagttgttg | tagtataacc | ttggtatatt | 2040 |

```
gtatgtatca tgaattcctc attttaatga ccaaaaagta ataaatcaac agcttgtaat    2100
ttgttttgag atcagttatc tgactgtaac actgtaggct tttgtgtttt ttaaattatg    2160
aaatatttga aaaaaataca taatgtatat ataaagtatt ggtataattt atgttctaaa    2220
taactttctt gagaaataat tcacatggtg tgcagtttac ctttgaaagt atacaagttg    2280
gctgggcaca atggctcacg cctgtaatcc cagcactttg ggaggccagg gcaggtggat    2340
cacgaggtca ggagatcgag accatcctgg ctaacatggt gaaacccgt ctctactaaa     2400 agtacaaaaa caaattagcc gggcatgttg gcgggcacct tttgtcccag ctgctcggga    2460
ggctgaggca ggagagtggc gtgaacccag gaggtggagc ttgcagtgag ccgagattgt    2520
gccagtgcac tccagcctgg gcgacagagc gagactctgt ctcaaaaaat aaaataaaaa    2580
agaaagtata caagtcagtg gttttggttt tcagttatgc aaccatcact acaatttaag    2640
aacattttca tcaccccaaa aagaaaccct gttaccttca ttttcccag ccctaggcag     2700 tcagtacact ttctgtctct atgaatttgt ctattttaga tattatatat aaacggaatt    2760
atacgatatg tggtcttttg tgtctggctt ctttcactta gcatgctatt ttcaagattc    2820
atccatgctg tagaatgcac cagtactgca ttccttctta ttgctgaata ttctgttgtt    2880
tggttatatc acatttatc cattcatcag ttcatggaca tttaggttgt ttttattttt     2940
gggctataat gaataatgtt gctatgaaca ttcgtttgtg ttcttttgt tttttggtt      3000 ttttgggttt tttttgtttt gttttgttt ttgagacagt cttgctctgt ctcctaagct     3060
ggagtgcagt ggcatgatct tggcttactg caagctctgc ctcccgggtt cacaccattc    3120
tcctgcctca gccccgacaag tagctgggac tacaggcgtg tgccaccatg cacggctaat   3180 ttttttgtatt tttagtagag atggggtttc accgtgttag ccaggatggt ctcgatctcc   3240
tgacctcgtg atctgcctgc ctaggcctcc caaagtgctg ggattacagg cgtgagccac    3300
tgcacctggc cttaagtgtt tttaatacgt cattgcctta agctaacaat tcttaacctt    3360
tgttctactg aagccacgtg gttgagatag gctctgagtc tagcttttaa cctctatctt    3420
tttgtcttag aaatctaagc agaatgcaaa tgactaagaa taatgttgtt gaaataacat    3480
aaaataggtt ataactttga tactcattag taacaaatct ttcaatacat cttacggtct    3540
gttaggtgta gattagtaat gaagtgggaa gccactgcaa gctagtatac atgtagggaa    3600
agatagaaag cattgaagcc agaagagaga cagaggacat ttgggctaga tctgacaaga    3660
aaaacaaatg ttttagtatt aatttttgac tttaaatttt tttttattt agtgaatact     3720 ggtgtttaat ggtctcattt taataagtat gacacaggta gtttaaggtc atatattta     3780 tttgatgaaa ataaggtata ggccgggcac ggtggctcac acctgtaatc ccagcacttt    3840
gggaggccga ggcaggcgga tcacctgagg tcgggagtta gagactagcc tcaacatgga    3900 gaaacccgt ctctactaaa aaaatacaa aattaggcgg gcgtggtggt gcatgcctgt      3960
aatcccagct actcaggagg ctgaggcagg agaattgctt gaacctggga ggtgaggtt     4020 gcggtgagcc gagatcacct cattgcactc cagcctggga acaagagca aaactccatc     4080 tcaaaaaaaa aaaataagg tataagcggg ctcaggaaca tcattggaca tactgaaaga    4140
agaaaaatca gctgggcgca gtggctcacg ccggtaatcc caacactttg ggaggccaag    4200
gcaggcgaat cacctgaagt cgggagttcc agatcagcct gaccaacatg gagaaaccct    4260
gtctctacta aaaatacaaa actagccggg catggtggcg catgcctgta atcccagcta   4320
cttgggaggc tgaggcagga gaattgcttg aaccgagaag gcggaggttg cggtgagcca    4380
agattgcacc attgcactcc agcctgggca acaagagcga aactccgtct caaaaaaaa    4440
```

```
aggaagaaaa atattttttt aaattaatta gtttatttat tttttaagat ggagttttgc    4500
cctgtcaccc aggctggggt gcaatggtgc aatctcggct cactgcaacc tccgcctcct    4560
gggttcaagt gattctcctg cctcagcttc ccgagtagct gtgattacag ccatatgcca    4620
ccacgcccag ccagttttgt gttttgtttt gttttttgtt ttttttttttt gagagggtgt    4680 cttgctctgt cccccaagct ggagtgcagc ggcgcgatct tggctcactg caagctctgc    4740
ctcccaggtt cacaccattc tcttgcctca gcctcccgag tagctgggac tacaggtgcc    4800
cgccaccaca cccggctaat tttttgtgt tttagtaga gatggggttt cactgtgtta    4860
gccaggatgg tctcgatctc ctgacctttt gatccacccg cctcagcctc ccaagtgct    4920 gggattatag gcgtgagcca ctgtgcccgg cctagtcttg tatttttagt agagtcggga    4980
tttctccatg ttggtcaggc tgttctccaa atccgacctc aggtgatccg cccgccttgg    5040
cctccaaaag tgcaaggcaa ggcattacag gcatgagcca ctgtgaccgg caatgttttt    5100
aaatttttta catttaaatt ttatttttta gagaccaggt ctcactctat tgctcaggct    5160
ggagtgcaag ggcacattca cagctcactg cagccttgac ctccagggct caagcagtcc    5220
tctcacctca gttcccgag tagctgggac tacagtgata atgccactgc acctggctaa    5280
tttttatttt tatttattta ttttttttttg agacagagtc ttgctctgtc acccaggctg    5340
gagtgcagtg gtgtaaatct cagctcactg cagcctccgc ctcctgggtt caagtgattc    5400
tcctgcctca acctcccaag tagctgggat tagaggtccc caccaccatg cctggctaat    5460
tttttgtact ttcagtagaa acggggtttt gccatgttgg ccaggctgtt ctcgaactcc    5520
tgagctcagg tgatccaact gtctcggcct cccaaagtgc tgggattaca ggcgtgagcc    5580
actgtgccta gcctgagcca ccacgccggc ctaattttta aatttttttgt agagacaggg    5640 tctcattatg ttgcccaggg tggtgtcaag ctccaggtct caagtgatcc ccctacctcc    5700
gcctcccaaa gttgtgggat tgtaggcatg agccactgca agaaaacctt aactgcagcc    5760
taataattgt tttctttggg ataactttta aagtacatta aaagactatc aacttaattt    5820
ctgatcatat tttgttgaat aaaataagta aaatgtcttg tgaaacaaaa tgcttttttaa    5880 catccatata aagctatcta tatatagcta tctatatcta tatagctatt tttttttaact    5940 tcctttattt tccttacagg gttttagaca aaatcaaaaa gaaggaaggt gctcacattc    6000
cttaaatata aggagtaagt ctgccagcat tatgaaagtg aatcttactt ttgtaaaact    6060
ttatggtttg tggaaaacaa atgttttttga acatttaaaa agttcagatg ttagaaagtt    6120
gaaaggttaa tgtaaaacaa tcaatattaa agaattttga tgccaaaact attagataaa    6180
aggttaatct acatccctac tagaattctc atacttaact ggttggttgt gtggaagaaa    6240
catactttca caataaagag ctttaggata tgatgccatt ttatatcact agtaggcaga    6300
ccagcagact ttttttttatt gtgatatggg ataacctagg catactgcac tgtacactct    6360
gacatatgaa gtgctctagt caagtttaac tggtgtccac agaggacatg gtttaactgg    6420
aattcgtcaa gcctctggtt ctaatttctc atttgcagga aatgctggca tagagcagca    6480
cggatccgaa gacgccaaaa acataaagaa aggcccggcg ccattctatc ctctagagga    6540
tggaaccgct ggagagcaac tgcataaggc tatgaagaga tacgccctgg ttcctggaac    6600
aattgctttt acagatgcac atatcgaggt gaacatcacg tacgcggaat acttcgaaat    6660
gtccgttcgg ttggcagaag ctatgaaacg atatgggctg aatacaaatc acagaatcgt    6720
cgtatgcagt gaaaactctc ttcaattctt tatgccggtg ttgggcgcgt tatttatcgg    6780
```

```
agttgcagtt gcgcccgcga acgacattta taatgaacgt gaattgctca acagtatgaa    6840
catttcgcag cctaccgtag tgtttgtttc caaaaagggg ttgcaaaaaa ttttgaacgt    6900
gcaaaaaaaa ttaccaataa tccagaaaat tattatcatg gattctaaaa cggattacca    6960
gggatttcag tcgatgtaca cgttcgtcac atctcatcta cctcccggtt ttaatgaata    7020
cgattttgta ccagagtcct ttgatcgtga caaaacaatt gcactgataa tgaattcctc    7080
tggatctact gggttaccta agggtgtggc ccttccgcat agaactgcct gcgtcagatt    7140
ctcgcatgcc agagatccta tttttggcaa tcaaatcatt ccggatactg cgattttaag    7200
tgttgttcca ttccatcacg gttttggaat gtttactaca ctcggatatt tgatatgtgg    7260
atttcgagtc gtcttaatgt atagatttga agaagagctg ttttttacgat cccttcagga    7320
ttacaaaatt caaagtgcgt tgctagtacc aaccctattt tcattcttcg ccaaaagcac    7380
tctgattgac aaatacgatt tatctaattt acacgaaatt gcttctgggg gcgcacctct    7440
ttcgaaagaa gtcggggaag cggttgcaaa acgcttccat cttccaggga tacgacaagg    7500
atatgggctc actgagacta catcagctat tctgattaca cccagggggg atgataaacc    7560
gggcgcggtc ggtaaagttg ttccatttt tgaagcgaag gttgtggatc tggataccgg    7620
gaaaacgctg gcgttaatc agagaggcga attatgtgtc agaggaccta tgattatgtc    7680
cggttatgta acaatccgg aagcgaccaa cgccttgatt gacaaggatg gatggctaca    7740
ttctggagac atagcttact gggacgaaga cgaacacttc ttcatagttg accgcttgaa    7800
gtctttaatt aaatacaaag gatatcaggt ggccccgct gaattggaat cgatattgtt    7860
acaacacccc aacatcttcg acgcgggcgt ggcaggtctt cccgacgatg acgccggtga    7920
acttcccgcc gccgttgttg ttttggagca cggaaagacg atgacggaaa aagagatcgt    7980
ggattacgtc gccagtcaag taacaaccgc gaaaaagttg cgcggaggag ttgtgtttgt    8040
ggacgaagta ccgaaaggtc ttaccggaaa actcgacgca agaaaaatca gagagatcct    8100
cataaaggcc aagaagggcg gaaagtccaa attgcgcggc cgctaaatcg aaagtacagg    8160
actagccttc ctagcaaccg cgggctggga gtctgagaca tcactcaaga tatatgctcg    8220
gtaacgtatg ctctagccat ctaactattc cctatgtctt ataggg                  8266
```

COMPOUNDS FOR TREATING SPINAL MUSCULAR ATROPHY

CROSS-REFERENCE

This application is a continuation of U.S. patent application Ser. No. 16/541,401, filed Aug. 15, 2019, currently allowed, which is a continuation of U.S. patent application Ser. No. 15/848,075, filed Dec. 20, 2017, abandoned, which is a divisional of U.S. application Ser. No. 15/248,052, filed Aug. 26, 2016, issued as U.S. Pat. No. 9,879,007 on Jan. 30, 2018, which is a continuation of U.S. application Ser. No. 14/377,531, filed Aug. 8, 2014, issued as U.S. Pat. No. 9,586,955 on Mar. 7, 2017, which is a U.S. national stage application of International Patent Application No. PCT/US2013/025292, filed Feb. 8, 2013, which claims the benefit of priority to U.S. Provisional Application Ser. No. 61/597,523, filed Feb. 10, 2012, the entire contents of which are incorporated herein by reference in its entirety and for all purposes.

The technology described herein has not been made with U.S. Government support.

STATEMENT ON JOINT RESEARCH AGREEMENT

The subject matter disclosed was developed and the claimed invention was made by, or on behalf of, one or more parties to a joint research agreement that was in effect on or before the effective filing date of the claimed invention;

the claimed invention was made as a result of activities undertaken within the scope of the joint research agreement; and the application for patent for the claimed invention discloses or is amended to disclose the names of the parties to the joint research agreement. The parties to the joint research agreement are 1) F. Hoffmann-La Roche Ltd, 2) Hoffmann-La Roche Inc., 3) PTC Therapeutics, Inc. and 4) Spinal Muscular Atrophy Foundation.

INTRODUCTION

Provided herein are compounds, compositions thereof and uses therewith for treating Spinal Muscular Atrophy.

BACKGROUND

Spinal muscular atrophy (SMA), in its broadest sense, describes a collection of inherited and acquired central nervous system (CNS) diseases characterized by progressive motor neuron loss in the spinal cord and brainstem causing muscle weakness and muscle atrophy. The most common form of SMA is caused by mutations in the Survival Motor Neuron (SMN) gene and manifests over a wide range of severity affecting infants through adults (Crawford and Pardo, Neurobiol. Dis., 1996, 3:97).

Infantile SMA is the most severe form of this neurodegenerative disorder. Symptoms include muscle weakness, poor muscle tone, weak cry, limpness or a tendency to flop, difficulty sucking or swallowing, accumulation of secretions in the lungs or throat, feeding difficulties, and increased susceptibility to respiratory tract infections. The legs tend to be weaker than the arms and developmental milestones, such as lifting the head or sitting up, cannot be reached. In general, the earlier the symptoms appear, the shorter the lifespan. As the motor neuron cells deteriorate, symptoms appear shortly afterward. The severe forms of the disease are fatal and all forms have no known cure. The course of SMA is directly related to the rate of motor neuron cell deterioration and the resulting severity of weakness. Infants with a severe form of SMA frequently succumb to respiratory disease due to weakness in the muscles that support breathing. Children with milder forms of SMA live much longer, although they may need extensive medical support, especially those at the more severe end of the spectrum. The clinical spectrum of SMA disorders has been divided into the following five groups.

(a) Type 0 SMA (In Utero SMA) is the most severe form of the disease and begins before birth. Usually, the first symptom of Type 0 SMA is reduced movement of the fetus that can first be observed between 30 and 36 weeks of pregnancy. After birth, these newborns have little movement and have difficulties with swallowing and breathing.

(b) Type 1 SMA (Infantile SMA or Werdnig-Hoffmann disease) typically presents symptoms between 0 and 6 months. This form of SMA is also very severe. Patients never achieve the ability to sit, and death usually occurs within the first 2 years without ventilatory support.

(c) Type 2 SMA (Intermediate SMA) has an age of onset at 7-18 months. Patients achieve the ability to sit unsupported, but never stand or walk unaided. Prognosis in this group is largely dependent on the degree of respiratory involvement.

(d) Type 3 SMA (Juvenile SMA or Kugelberg-Welander disease) is generally diagnosed after 18 months. Type 3 SMA individuals are able to walk independently at some point during their disease course but often become wheelchair-bound during youth or adulthood.

(e) Type 4 SMA (Adult onset SMA). Weakness usually begins in late adolescence in the tongue, hands, or feet, then progresses to other areas of the body. The course of adult SMA is much slower and has little or no impact on life expectancy.

The SMN gene has been mapped by linkage analysis to a complex region in chromosome 5q. In humans, this region contains an approximately 500 thousand base pairs (kb) inverted duplication resulting in two nearly identical copies of the SMN gene. SMA is caused by an inactivating mutation or deletion of the telomeric copy of the gene (SMN1) in both chromosomes, resulting in the loss of SMN1 gene function. However, all patients retain the centromeric copy of the gene (SMN2), and the copy number of the SMN2 gene in SMA patients generally correlates inversely with the disease severity; i.e., patients with less severe SMA have more copies of SMN2. Nevertheless, SMN2 is unable to compensate completely for the loss of SMN1 function due to alternative splicing of exon 7 caused by a translationally silent C to T mutation in exon 7. As a result, the majority of transcripts produced from SMN2 lack exon 7 (SMN2 Δ7), and encode a truncated Smn protein that has an impaired function and is rapidly degraded.

The Smn protein is thought to play a role in RNA processing and metabolism, having a well characterized function of mediating the assembly of a specific class of RNA-protein complexes termed snRNPs. Smn may have other functions in motor neurons, however its role in preventing the selective degeneration of motor neurons is not well established.

In most cases, SMA is diagnosed based on clinical symptoms and by the absence of all copies of exon 7 in the SMN1 gene, as determined by genetic testing. However, in approximately 5% of cases, SMA is caused by mutations other than a deletion of the entire SMN1 gene or other than a deletion of the entire exon 7 in the SMN1 gene, some known and others not yet defined. In such cases, when the SMN1 gene test is not feasible or the SMN1 gene sequence does not show any abnormality, other tests such as an electromyography (EMG) or muscle biopsy may be indicated.

Medical care for SMA patients at present is limited to supportive therapy including respiratory, nutritional and rehabilitation care; there is no drug known to address the underlying cause of the disease. Current treatment for SMA consists of prevention and management of the secondary effects of chronic motor unit loss. The major management issue in Type 1 SMA is the prevention and early treatment of pulmonary problems, which are the primary cause of death in the majority of the cases. While some infants afflicted with SMA grow to be adults, those with Type 1 SMA have a life expectancy of less than two years.

Several mouse models of SMA have been developed. In particular, the SMNΔ7 model (Le et al., Hum. Mol. Genet., 2005, 14:845) carries both the SMN2 gene and several copies of the SMN2Δ7 cDNA and recapitulates many of the phenotypic features of Type 1 SMA. The SMNΔ7 model can be used for both SMN2 expression studies as well as the evaluation of motor function and survival. The C/C-allele mouse model (Jackson Laboratory strain No.: 008714) provides a less severe SMA disease model, with mice having reduced levels of both SMN2 full length (SMN2 FL) mRNA and Smn protein. The C/C-allele mouse phenotype has the SMN2 gene and a hybrid mSmn1-SMN2 gene that undergoes alternative splicing, but does not have overt muscle weakness. The C/C-allele mouse model is used for SMN2 expression studies.

As a result of improved understanding of the genetic basis and pathophysiology of SMA, several strategies for treatment have been explored, but none have yet demonstrated success in the clinic.

Gene replacement of SMN1, using viral delivery vectors, and cell replacement, using differentiated SMN1$^{+/+}$ stem cells, have demonstrated efficacy in animal models of SMA. More research is needed to determine the safety and immune response and to address the requirement for the initiation of treatment at the neonatal stage before these approaches can be applied to humans.

Correction of alternative splicing of SMN2 in cultured cells has also been achieved using synthetic nucleic acids as therapeutic agents: (i) antisense oligonucleotides that target sequence elements in SMN2 pre-mRNA and shift the outcome of the splicing reaction toward the generation of full length SMN2 mRNA (Passini et al., Sci. Transl. Med., 2011, 3:72ra18; and, Hua et al., Nature, 2011, 478:123) and (ii) trans-splicing RNA molecules that provide a fully functional RNA sequence that replace the mutant fragment during splicing and generate a full length SMN1 mRNA (Coady and Lorson, J Neurosci., 2010, 30:126).

Other approaches under exploration include searching for drugs that increase Smn levels, enhance residual Smn function, or compensate for loss of Smn. Aminoglycosides have been shown to enhance expression of stabilized Smn protein produced from SMN2 Δ7 mRNA by promoting the translational read-through of the aberrant stop codon, but have poor central nervous system penetration and are toxic after repeated dosing. Chemotherapeutic agents, such as aclarubicin, have been shown to increase Smn protein in cell culture; however, the toxicity profile of these drugs prohibits long-term use in SMA patients. Some drugs under clinical investigation for the treatment of SMA include transcription activators such as histone deacetylase ("HDAC") inhibitors (e.g., butyrates, valproic acid, and hydroxyurea), and mRNA stabilizers (mRNA decapping inhibitor RG3039 from Repligen), intended to increase the amount of total RNA transcribed from the SMN2 gene. However, the use of HDAC inhibitors or mRNA stabilizers does not address the underlying cause of SMA and may result in a global increase in transcription and gene expression with potential safety problems in humans.

In an alternative approach, neuroprotective agents such as olesoxime have been chosen for investigation. Such strategies are not aimed at increasing the production of functional Smn for the treatment of SMA, but instead are being explored to protect the Smn-deficient motor neurons from neurodegeneration.

A system designed to identify compounds that increase the inclusion of exon 7 of SMN into RNA transcribed from the SMN2 gene and certain benzooxazole and benzoisoxazole compounds identified thereby have been described in International Application PCT/US2009/003238 filed May 27, 2009 (published as International Publication Number WO2009/151546 and United States Publication Number US2011/0086833). A system designed to identify compounds that produce a stabilized Smn protein from SMN2 Δ7 mRNA and certain isoindolinone compounds identified thereby have been described in International Application PCT/US2009/004625 filed Aug. 13, 2009 (published as International Publication Number WO2010/019236 and United States Publication Number US2011/0172284). Each of the foregoing documents is herein incorporated in their entirety and for all purposes.

All other documents referred to herein are incorporated by reference into the present application as though fully set forth herein.

Despite the progress made in understanding the genetic basis and pathophysiology of SMA, there remains a need to identify compounds that alter the course of spinal muscular atrophy, one of the most devastating childhood neurological diseases.

SUMMARY

In one aspect, provided herein are compounds of Formula (I):

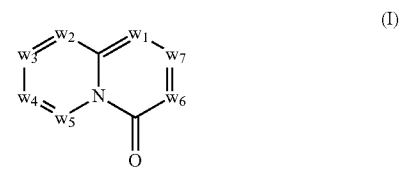

or a form thereof, wherein $w_1$, $w_2$, $w_3$, $w_4$, $w_5$, $w_6$ and $w_7$ are as defined herein. In one embodiment, provided herein is a pharmaceutical composition comprising a compound of Formula (I) or a form thereof, and a pharmaceutically acceptable carrier, excipient or diluent. In a specific embodiment, provided herein is a compound of Formula (I) or a form thereof, or a pharmaceutical composition thereof for treating spinal muscular atrophy (SMA).

SMA is caused by deletion or mutation of the SMN1 gene, resulting in selective degeneration of Smn-deficient motor neurons. Although human subjects retain several copies of the SMN2 gene, the small amount of functional Smn protein expressed from SMN2 does not fully compensate for the loss of Smn that would have been expressed from the SMN1 gene. The compounds, compositions thereof and uses therewith described herein are based, in part, on the Applicants discovery that a compound of Formula (I) increases the inclusion of exon 7 of SMN2 into mRNA that is transcribed from an SMN2 minigene. The minigene reproduces the alternative splicing reaction of exon 7 of SMN2 which results in exon 7 skipping in the majority of SMN2 transcripts. Thus, compounds of Formula (I) or a form thereof may be used to modulate inclusion of exon 7 of SMN2 into mRNA that is transcribed from the SMN2 gene. Applicants have also discovered that a compound of Formula (I) increases the inclusion of exon 7 of SMN1 into mRNA that is transcribed from an SMN1 minigene. Thus, compounds of Formula (I) or a form thereof may be used to modulate inclusion of exon 7 of SMN1 into mRNA that is transcribed from the SMN1 gene.

In a specific embodiment, provided herein are compounds of Formula (I) or a form thereof that may be used to modulate the inclusion of exon 7 of SMN2 into mRNA that is transcribed from the SMN2 gene. In another specific embodiment, provided herein are compounds of Formula (I) or a form thereof that may be used to modulate the inclusion of exon 7 of SMN1 into mRNA that is transcribed from the SMN1 gene. In yet another embodiment, provided herein are compounds of Formula (I) or a form thereof that may be used to modulate the inclusion of exon 7 of SMN1 and SMN2 into mRNA that is transcribed from the SMN1 and SMN2 genes, respectively.

In another aspect, provided herein is the use of a compound of Formula (I) or a form thereof for treating SMA. In a specific embodiment, provided herein is a method for treating SMA in a human subject in need thereof, comprising administering to the subject an effective amount of a compound of Formula (I) or a form thereof. The compound of Formula (I) or a form thereof is preferably administered to a human subject in a pharmaceutical composition. In another specific embodiment, provided herein is the use of a compound of Formula (I) for treating SMA, wherein the compound enhances the inclusion of exon 7 of SMN2 into mRNA that is transcribed from the SMN2 gene. Without being limited by theory, compounds of Formula (I) enhance inclusion of exon 7 of SMN2 into mRNA that is transcribed from the SMN2 gene and increase levels of Smn protein produced from the SMN2 gene, and thus can be used to treat SMA in a human subject in need thereof.

In another aspect, provided herein are primers and/or probes described below in the Biological Examples (e.g., SMN primers such as SEQ ID NO. 1, 7, 8, 11 or 13, and/or SEQ ID NO. 2, 9 or 12, and/or SMN probes such as a SEQ ID NO. 3 or 10) and the use of those primers and/or probes. In a specific embodiment, provided herein is an isolated nucleotide sequence comprising SEQ ID NO. 1, 2, 3, 7, 8, 9, 10, 11, 12 or 13. In another specific embodiment, provided herein is an isolated nucleotide sequence consisting essentially of SEQ ID NO. 1, 2, 3, 7, 8, 9, 10, 11, 12 or 13. In another specific embodiment, provided herein is an isolated nucleotide sequence consisting of SEQ ID NO. 1, 2, 3, 7, 8, 9, 10, 11, 12 or 13.

In certain embodiments, the amount of mRNA that is transcribed from the SMN1 gene and/or SMN2 gene and does not include exon 7 of SMN1 and/or SMN2 may be used as a biomarker for SMA, such as disclosed herein. In other embodiments, the amount of mRNA that is transcribed from the SMN1 and/or SMN2 gene and includes exon 7 of SMN1 and/or SMN2 may be used as a biomarker for treating a patient with a compound, such as disclosed herein. In a specific embodiment, the patient is an SMA patient. In another specific embodiment, the patient is not an SMA patient.

In certain embodiments, the amount of mRNA that is transcribed from the SMN1 and/or SMN2 gene and includes exon 7 of SMN1 and/or SMN2 as well as the amount of mRNA that is transcribed from the SMN1 and/or SMN2 gene and does not include exon 7 of SMN1 and/or SMN2 may be used as biomarkers for treating a patient with a compound, such as disclosed herein. In a specific embodiment, the patient is an SMA patient. In another specific embodiment, the patient is not an SMA patient.

In accordance with these embodiments, an SMN primer (s) and/or an SMN probe described below may be used in assays, such as PCR (e.g., qPCR), rolling circle amplification, and RT-PCR (e.g., endpoint RT-PCR and/or RT-qPCR) to assess and/or quantify the amount of mRNA that is transcribed from the SMN1 gene and/or SMN2 gene and does or does not include exon 7 of SMN1 and/or SMN2.

In a specific embodiment, a primer and/or probe described below in the Biological Examples (e.g., SMN primers such as SEQ ID NO. 1, 7, 8, 11 or 13 and/or SEQ ID NO. 2, 9 or 12, and/or SMN probes such as a SEQ ID NO. 3 or 10) is used in an assay, such as RT-PCR, RT-qPCR, endpoint RT-PCR, PCR, qPCR, rolling circle amplification, Northern blot or Southern blot (e.g., an assay such as described below in the Biological Examples), to determine whether a compound (e.g., a compound of Formula (I) or a form thereof) enhances the inclusion of exon 7 of SMN2 into mRNA that is transcribed from an SMN2 gene.

In a specific embodiment, a primer and/or probe described below in the Biological Examples (e.g., SMN primers such as SEQ ID NO. 1, 7, 8, 11 or 13 and/or SEQ ID NO. 2, 9 or 12, and/or SMN probes such as a SEQ ID NO. 3 or 10) is used in an assay, such as RT-PCR, RT-qPCR, endpoint RT-PCR, PCR, qPCR, rolling circle amplification, Northern blot or Southern blot (e.g., an assay such as described below in the Biological Examples), to determine whether a compound (e.g., a compound of Formula (I) or a form thereof) enhances the inclusion of exon 7 of SMN1 into mRNA that is transcribed from an SMN1 gene.

In a specific embodiment, a primer and/or probe described below in the Biological Examples (e.g., SMN primers such as SEQ ID NO. 1, 7, 8, 11 or 13 and/or SEQ ID NO. 2, 9 or 12, and/or SMN probes such as a SEQ ID NO. 3 or 10) is used in an assay, such as RT-PCR, RT-qPCR, endpoint RT-PCR, PCR, qPCR, rolling circle amplification, Northern blot or Southern blot (e.g., an assay such as described below in the Biological Examples), to determine whether a compound (e.g., a compound of Formula (I) or a form thereof) enhances the inclusion of exon 7 of SMN1 and/or SMN2 into mRNA that is transcribed from an SMN1 and/or SMN2 gene.

In another embodiment, a primer and/or probe described below in the Biological Examples (e.g., SMN primers such as SEQ ID NO. 7, 11 or 13 and/or SEQ ID NO. 9 or 12, and/or SMN probes such as a SEQ ID NO. 3 or 10) is used in an assay, such as RT-PCR, RT-qPCR, endpoint RT-PCR, PCR, qPCR, rolling circle amplification, Northern blot or Southern blot (e.g., an assay such as described below in the Biological Examples), to monitor the amount of mRNA that is transcribed from the SMN2 gene and includes exon 7 of SMN2 in a patient sample. In a specific embodiment, the patient is an SMA patient. In another specific embodiment, the patient is not an SMA patient.

In another embodiment, a primer and/or probe described below in the Biological Examples (e.g., SMN primers such as SEQ ID NO. 7, 11 or 13 and/or SEQ ID NO. 9 or 12, and/or SMN probes such as a SEQ ID NO. 3 or 10) is used in an assay, such as RT-PCR, RT-qPCR, endpoint RT-PCR, PCR, qPCR, rolling circle amplification, Northern blot or Southern blot (e.g., an assay such as described below in the Biological Examples), to monitor the amount of mRNA that is transcribed from the SMN1 gene and includes exon 7 of SMN1 in a patient sample. In a specific embodiment, the patient is an SMA patient. In another specific embodiment, the patient is not an SMA patient.

In another embodiment, a primer and/or probe described below in the Biological Examples (e.g., SMN primers such as SEQ ID NO. 7, 11 or 13 and/or SEQ ID NO. 9 or 12, and/or SMN probes such as a SEQ ID NO. 3 or 10) is used in an assay, such as RT-PCR, RT-qPCR, endpoint RT-PCR, PCR, qPCR, rolling circle amplification, Northern blot or Southern blot (e.g., an assay such as described below in the Biological Examples), to monitor the amount of mRNA that is transcribed from the SMN1 and/or SMN2 gene and includes exon 7 of SMN1 and/or SMN2 in a patient sample. In a specific embodiment, the patient is an SMA patient. In another specific embodiment, the patient is not an SMA patient.

In another embodiment, a primer and/or probe described below in the Biological Examples (e.g., SMN primers such as SEQ ID NO. 7, 8, 11 or 13 and/or SEQ ID NO. 9 or 12, and/or SMN probes such as a SEQ ID NO. 3 or 10) is used in an assay, such as RT-PCR, RT-qPCR, endpoint RT-PCR, PCR, qPCR, rolling circle amplification, Northern blot or Southern blot (e.g., an assay such as described below in the Biological Examples), to monitor a patient's response to a compound (e.g., a compound of Formula (I) or a form thereof). In a specific embodiment, the patient is an SMA patient. In another specific embodiment, the patient is not an SMA patient.

In another embodiment, provided herein is a method for determining whether a compound (e.g., a compound of Formula (I) disclosed herein) enhances the inclusion of exon 7 of SMN2 into mRNA that is transcribed from the SMN2 gene, comprising (a) contacting mRNA that is transcribed from an SMN2 minigene described herein or in International Application PCT/US2009/004625, filed Aug. 13, 2009 (published as International Publication Number WO2010/019236) or United States Publication Number US2011/0172284 in the presence of a compound (e.g., a compound of Formula (I) disclosed herein) with a primer(s) described herein (e.g., SEQ ID NO. 1 and/or 2) along with applicable components for, e.g., RT-PCR, RT-qPCR, PCR, endpoint RT-PCR, qPCR or rolling circle amplification; and (b) detecting the amount of mRNA that is transcribed from the minigene and includes exon 7 of the SMN2, wherein (1) an increase in the amount of mRNA that is transcribed from the minigene and includes exon 7 of SMN2 in the presence of the compound relative to the amount of mRNA that is transcribed from the minigene and includes exon 7 of SMN2 in the absence of the compound indicates that the compound enhances inclusion of exon 7 of SMN2 into mRNA that is transcribed from the SMN2 gene; and (2) no change or no substantial change in the amount of mRNA that is transcribed from the minigene and includes exon 7 of SMN2 in the presence of the compound relative to the amount of mRNA that is transcribed from the minigene and includes exon 7 of SMN2 in the absence of the compound indicates that the compound does not enhance the inclusion of exon 7 of SMN2 into mRNA that is transcribed from the SMN2 gene.

In another embodiment, provided herein is a method for determining whether a compound (e.g., a compound of Formula (I) disclosed herein) enhances the inclusion of exon 7 of SMN1 into mRNA that is transcribed from the SMN1 gene, comprising (a) contacting mRNA that is transcribed from an SMN1 minigene described in International Application PCT/US2009/004625, filed Aug. 13, 2009 (published as International Publication Number WO2010/019236) or United States Publication Number US2011/0172284 in the presence of a compound (e.g., a compound of Formula (I) disclosed herein) with a primer(s) described herein (e.g., SEQ ID NO. 1 and/or 2) along with applicable components for, e.g., RT-PCR, RT-qPCR, PCR, endpoint RT-PCR, qPCR or rolling circle amplification; and (b) detecting the amount of mRNA that is transcribed from the minigene and includes exon 7 of the SMN1, wherein (1) an increase in the amount of mRNA that is transcribed from the minigene and includes exon 7 of SMN1 in the presence of the compound relative to the amount of mRNA that is transcribed from the minigene and includes exon 7 of SMN1 in the absence of the compound indicates that the compound enhances inclusion of exon 7 of SMN1 into mRNA that is transcribed from the SMN1 gene; and (2) no change or no substantial change in the amount of mRNA that is transcribed from the minigene and includes exon 7 of SMN1 in the presence of the compound relative to the amount of mRNA that is transcribed from the minigene and includes exon 7 of SMN1 in the absence of the compound indicates that the compound does not enhance the inclusion of exon 7 of SMN1 into mRNA that is transcribed from the SMN1 gene.

In another embodiment, provided herein is a method for determining whether a compound (e.g., a compound of Formula (I) disclosed herein) enhances the inclusion of exon 7 of SMN2 into mRNA that is transcribed from the SMN2 gene, comprising (a) contacting mRNA that is transcribed from an SMN2 minigene described herein or in International Application PCT/US2009/004625, filed Aug. 13, 2009 (published as International Publication Number WO2010/019236) or United States Publication Number US2011/0172284 in the presence of a compound (e.g., a compound of Formula (I) disclosed herein) with a probe described herein (e.g., SEQ ID NO. 3 or 10) along with applicable components for, e.g., RT-PCR, RT-qPCR, endpoint RT-PCR, PCR, qPCR, rolling circle amplification and, as applicable, Northern blot or Southern blot; and (b) detecting the amount of mRNA that is transcribed from the minigene and includes exon 7 of the SMN2, wherein (1) an increase in the amount of mRNA that is transcribed from the minigene and includes exon 7 of SMN2 in the presence of the compound relative to the amount of mRNA that is transcribed from the minigene and includes exon 7 of SMN2 in the absence of the compound indicates that the compound enhances inclusion of exon 7 of SMN2 into mRNA that is transcribed from the SMN2 gene; and (2) no change or no substantial change in the amount of mRNA that is transcribed from the minigene and includes exon 7 of SMN2 in the presence of the compound relative to the amount of mRNA that is transcribed from the minigene and includes exon 7 of SMN2 in the absence of the compound indicates that the compound does not enhance the inclusion of exon 7 of SMN2 into mRNA that is transcribed from the SMN2 gene.

In another embodiment, provided herein is a method for determining whether a compound (e.g., a compound of Formula (I) disclosed herein) enhances the inclusion of exon 7 of SMN1 into mRNA that is transcribed from the SMN1 gene, comprising (a) contacting mRNA that is transcribed from an SMN1 minigene described in International Application PCT/US2009/004625, filed Aug. 13, 2009 (published as International Publication Number WO2010/019236) or United States Publication Number US2011/0172284 in the presence of a compound (e.g., a compound of Formula (I)

disclosed herein) with a probe described herein (e.g., SEQ ID NO. 3 or 10) along with applicable components for, e.g., RT-PCR, RT-qPCR, endpoint RT-PCR, PCR, qPCR, rolling circle amplification and, as applicable, Northern blot or Southern blot; and (b) detecting the amount of mRNA that is transcribed from the minigene and includes exon 7 of the SMN1, wherein (1) an increase in the amount of mRNA that is transcribed from the minigene and includes exon 7 of SMN1 in the presence of the compound relative to the amount of mRNA that is transcribed from the minigene and includes exon 7 of SMN1 in the absence of the compound indicates that the compound enhances inclusion of exon 7 of SMN1 into mRNA that is transcribed from the SMN1 gene; and (2) no change or no substantial change in the amount of mRNA that is transcribed from the minigene and includes exon 7 of SMN1 in the presence of the compound relative to the amount of mRNA that is transcribed from the minigene and includes exon 7 of SMN1 in the absence of the compound indicates that the compound does not enhance the inclusion of exon 7 of SMN2 into mRNA that is transcribed from the SMN2 gene.

In another embodiment, provided herein is a method for determining whether a compound (e.g., a compound of Formula (I) disclosed herein) enhances the inclusion of exon 7 of SMN2 into mRNA that is transcribed from the SMN2 gene, comprising (a) contacting mRNA that is transcribed from an SMN2 minigene described herein or in International Application PCT/US2009/004625, filed Aug. 13, 2009 (published as International Publication Number WO2010/019236) or United States Publication Number US2011/0172284 in the presence of a compound (e.g., a compound of Formula (I) disclosed herein) with a primer(s) (e.g., SEQ ID NO. 1 or 2) and/or a probe described herein (e.g., SEQ ID NO. 3 or 10) along with applicable components for, e.g, RT-PCR, RT-qPCR, endpoint RT-PCR, PCR, qPCR, rolling circle amplification and, as applicable, Northern blot or Southern blot; and (b) detecting the amount of mRNA that is transcribed from the minigene and includes exon 7 of the SMN2, wherein (1) an increase in the amount of mRNA that is transcribed from the minigene and includes exon 7 of SMN2 in the presence of the compound relative to the amount of mRNA that is transcribed from the minigene and includes exon 7 of SMN2 in the absence of the compound indicates that the compound enhances inclusion of exon 7 of SMN2 into mRNA that is transcribed from the SMN2 gene; and (2) no change or no substantial change in the amount of mRNA that is transcribed from the minigene and includes exon 7 of SMN2 in the presence of the compound relative to the amount of mRNA that is transcribed from the minigene and includes exon 7 of SMN2 in the absence of the compound indicates that the compound does not enhance the inclusion of exon 7 of SMN2 into mRNA that is transcribed from the SMN2 gene.

In another embodiment, provided herein is a method for determining whether a compound (e.g., a compound of Formula (I) disclosed herein) enhances the inclusion of exon 7 of SMN1 into mRNA that is transcribed from the SMN1 gene, comprising (a) contacting mRNA that is transcribed from an SMN1 minigene described in International Application PCT/US2009/004625, filed Aug. 13, 2009 (published as International Publication Number WO2010/019236) or United States Publication Number US2011/0172284 in the presence of a compound (e.g., a compound of Formula (I) disclosed herein) with a primer(s) (e.g., SEQ ID NO. 1 or 2) and/or a probe described herein (e.g., SEQ ID NO. 3 or 10) along with applicable components for, e.g., RT-PCR, RT-qPCR, endpoint RT-PCR, PCR, qPCR, rolling circle amplification and, as applicable, Northern blot or Southern blot; and (b) detecting the amount of mRNA that is transcribed from the minigene and includes exon 7 of the SMN1, wherein (1) an increase in the amount of mRNA that is transcribed from the minigene and includes exon 7 of SMN1 in the presence of the compound relative to the amount of mRNA that is transcribed from the minigene and includes exon 7 of SMN1 in the absence of the compound indicates that the compound enhances inclusion of exon 7 of SMN1 into mRNA that is transcribed from the SMN1 gene; and (2) no change or no substantial change in the amount of mRNA that is transcribed from the minigene and includes exon 7 of SMN1 in the presence of the compound relative to the amount of mRNA that is transcribed from the minigene and includes exon 7 of SMN1 in the absence of the compound indicates that the compound does not enhance the inclusion of exon 7 of SMN1 into mRNA that is transcribed from the SMN1 gene.

In another aspect, provided herein are kits comprising a primer and/or probe described below in the Biological Examples (e.g., SMN primers such as SEQ ID NO. 1, 7, 8, 11 or 13 and/or SEQ ID NO. 2, 9 or 12, and/or SMN probes such as a SEQ ID NO. 3 or 10) and the use thereof.

BRIEF DESCRIPTION OF THE FIGURES

FIGS. 2a and 2b, referenced in Biological Example 1, provide the DNA sequence of the minigene from the SMN2-A minigene construct SEQ ID NO. 21 (FIG. 2a). As shown in FIG. 2b, the following sub-sequences can be found:
1-70: 5'UTR (deg);
71-79: exon 6: start codon and BamHI site (atgggatcc);
80-190: exon 6;
191-5959: intron 6;
5960-6014: exon 7 with the adenine nucleotide "A" insert (position 6008);
6015-6458: intron 7;
6459-6481: part of exon 8;
6482-8146: BamHI site (sequence at the 5' end), luciferase coding sequence starting with codon 2 (without initiation codon), NotI site (sequence at the 3' end), TAA stop codon; and
8147-8266: 3'UTR (deg).

To generate the SMN1 version of the minigene, the sixth nucleotide of exon 7 (a thymine residue) of the SMN2-A minigene construct is changed to cytosine using site directed mutagenesis. Thus, similar to the SMN2-A minigene construct, the SMN1 minigene construct has a single adenine residue inserted after nucleic residue 48 of exon 7. The SMN1 minigene construct is referred to as SMN1-A. Similarly, the nucleotide inserted in the SMN1 minigene construct after nucleic residue 48 of exon 7 may also be selected alternatively from cytosine or thymine.

Figure 3A:
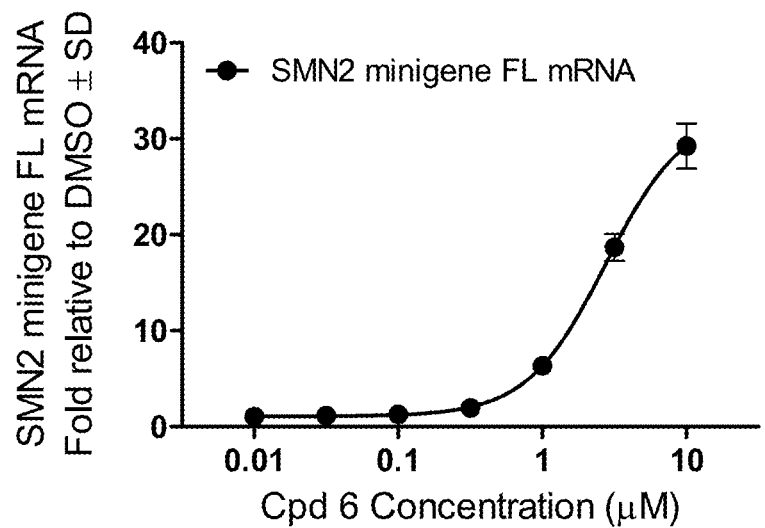
Figure 3B:
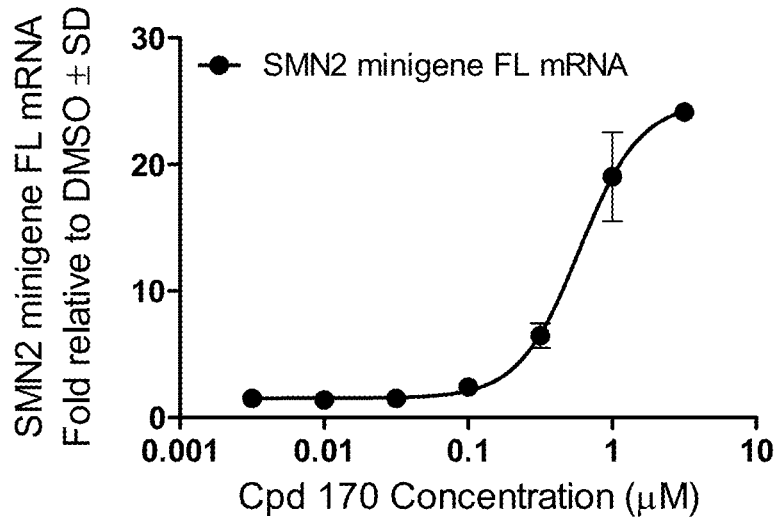

FIGS. 3a and 3b, referenced in Biological Example 2, show the correction of SMN2 minigene alternative splicing in cells treated with rising concentrations of Compound 6 (FIG. 3a) and Compound 170 (FIG. 3b) over a 24 hr period. The levels of full length SMN2 minigene mRNA were quantified using reverse transcription-quantitative PCR (RT-qPCR). The level of full length SMN2 minigene mRNA in compound-treated samples was normalized to that in vehicle-treated samples and plotted as a function of the compound concentration.

Figure 4A:
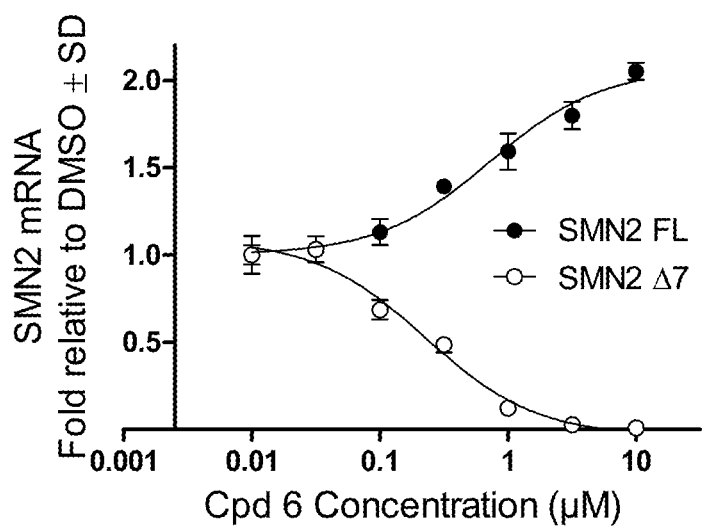
Figure 4B:
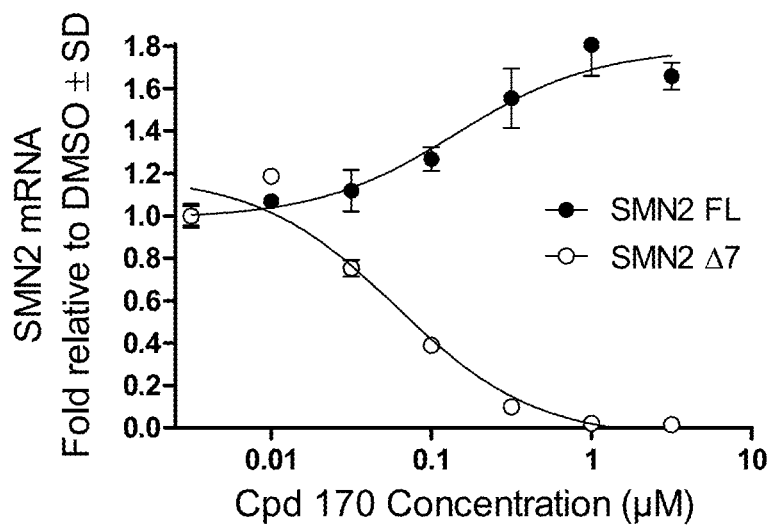

FIGS. 4a and 4b, referenced in Biological Example 3, show the correction of SMN2 alternative splicing in Type 1 SMA patient fibroblasts treated with rising concentrations of Compound 6 (FIG. 4a) and Compound 170 (FIG. 4b) over a 24 hr period. The levels of full length and Δ7 SMN2 mRNA were quantified using RT-qPCR. The levels of full length and Δ7 SMN2 mRNA in compound-treated samples were normalized to those in vehicle-treated samples and plotted as a function of the compound concentration.

Figure 5A:
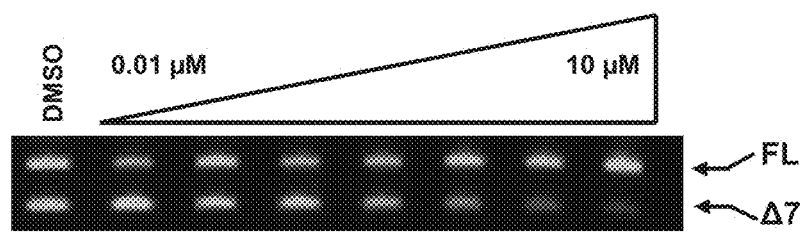
Figure 5B:
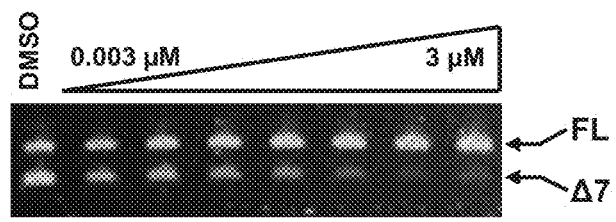

FIGS. 5a and 5b, referenced in Biological Example 4, show the correction of SMN2 alternative splicing in Type 1 SMA patient fibroblasts treated with rising concentrations of Compound 6 (FIG. 5a) and Compound 170 (FIG. 5b) over a 24 hr period. The full length and Δ7 SMN2 mRNA were amplified using reverse transcription-end point PCR (RT-PCR) and PCR products were separated using agarose gel electrophoresis. The top and bottom bands correspond to the full length and Δ7 SMN2 mRNA respectively. The intensity of each band is proportional to the amount of RNA present in the sample.

Figure 6A:
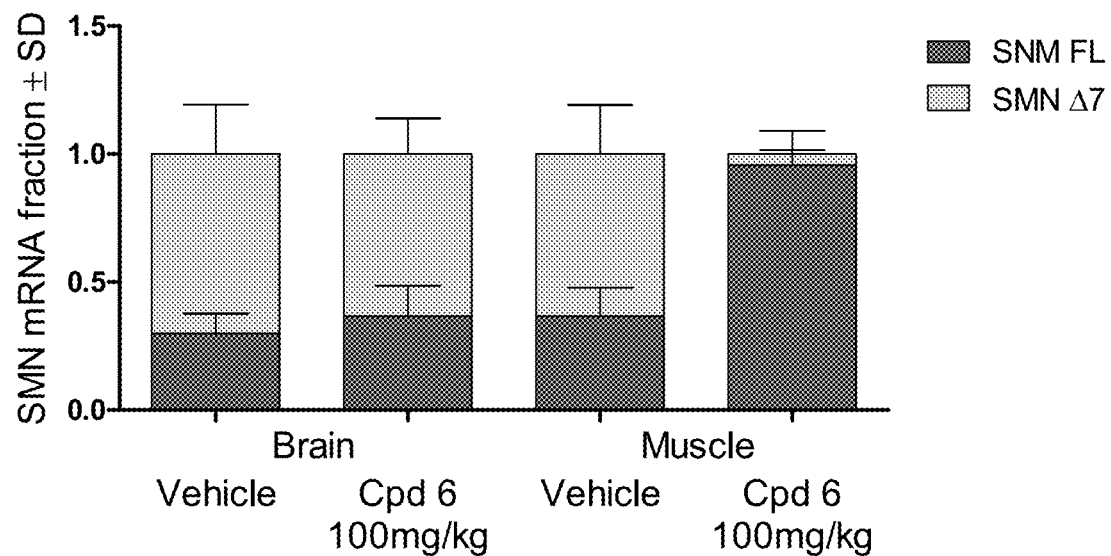
Figure 6B:
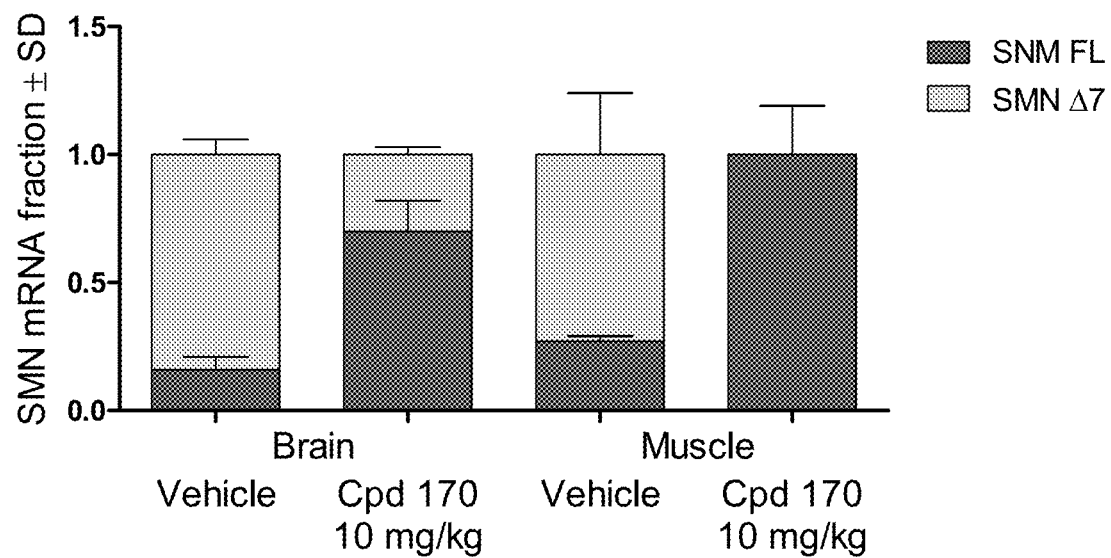

FIGS. 6a and 6b, referenced in Biological Example 5, show the correction of SMN2 alternative splicing (in both the SMN2 gene and the hybrid mouse Smn1-SMN2 gene) in brain and muscle tissues in a C/C-allele SMA mouse model resulting from treatment for 10 days twice per day (BID) with 10 mg/kg of Compound 6 (FIG. 6a) and Compound 170 (FIG. 6b). The levels of full length and Δ7 SMN2 mRNA were quantified using RT-qPCR, the combined full length and Δ7 SMN2 mRNA quantity was set to 1, and fractional quantities of full length and Δ7 SMN2 were calculated.

Figure 7A:
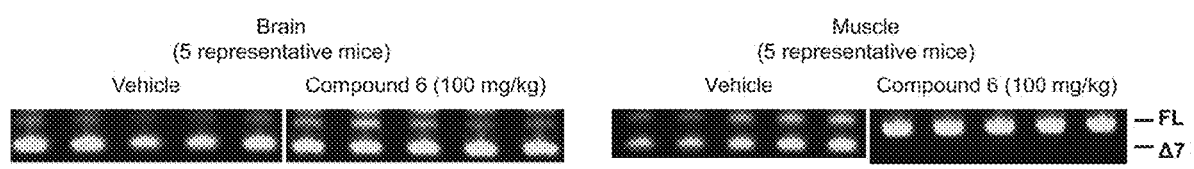
Figure 7B:
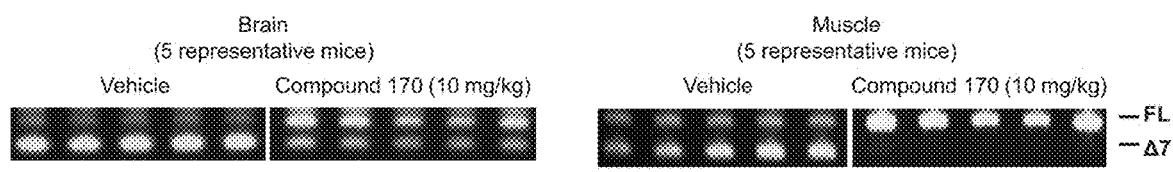

FIGS. 7a and 7b, referenced in Biological Example 6, show the correction of SMN2 alternative splicing (in both the SMN2 gene and the hybrid mouse Smn1-SMN2 gene) in brain and muscle tissues in a C/C-allele SMA mouse model resulting from treatment for 10 days BID with 10 mg/kg of Compound 6 (FIG. 7a) and Compound 170 (FIG. 7b). The full length and Δ7 SMN2 mRNA were amplified using RT-PCR. The PCR products were separated using agarose gel electrophoresis. The top and bottom bands correspond to the full length and Δ7 SMN2 mRNA, respectively. The intensity of each band is proportional to the amount of RNA present in the sample.

Figure 8A:
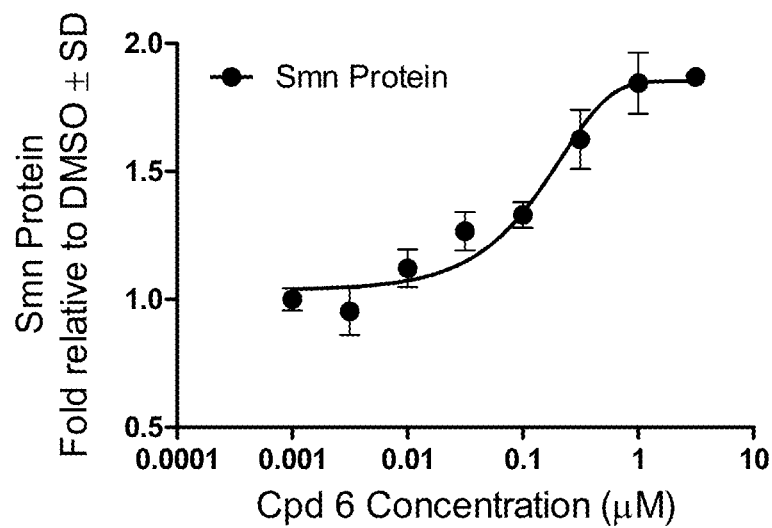
Figure 8B:
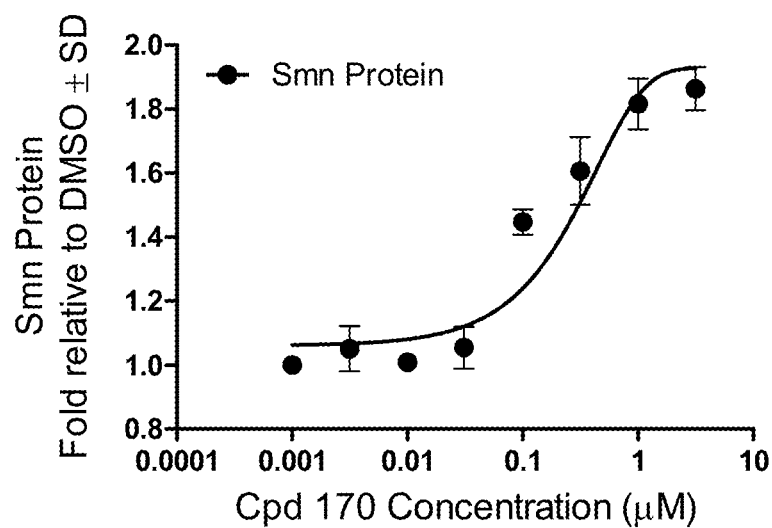

FIGS. 8a and 8b, referenced in Biological Example 7, show a dose dependent increase in Smn protein expression in SMA Type 1 human fibroblast cells treated over a 48 hour period with Compound 6 (FIG. 8a) and Compound 170 (FIG. 8b).

Figure 9A:
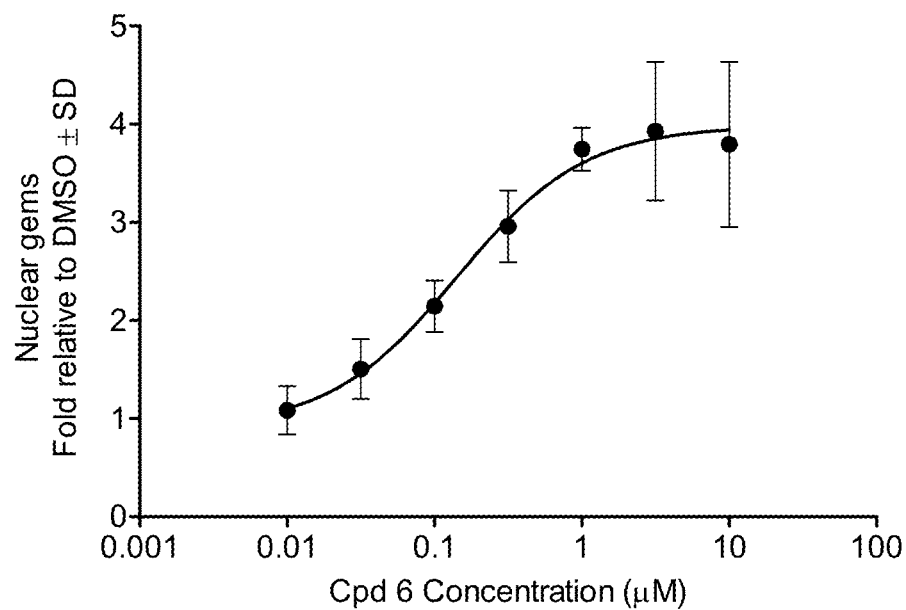
Figure 9B:
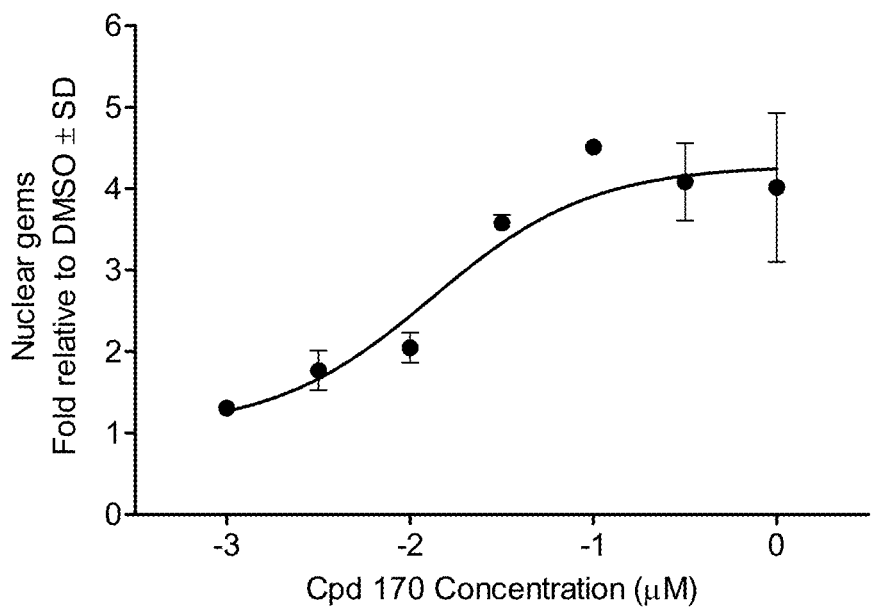

FIGS. 9a and 9b, referenced in Biological Example 8, show an increase in nuclear speckle counts (gems) in Type 1 SMA patient fibroblasts treated with Compound 6 (FIG. 9a) and Compound 170 (FIG. 9b) over a 48 hour period. Speckles were counted using fluorescence microscopy. The number of speckles in compound-treated samples was normalized to that in vehicle-treated samples and plotted as a function of the compound concentration.

Figure 10:
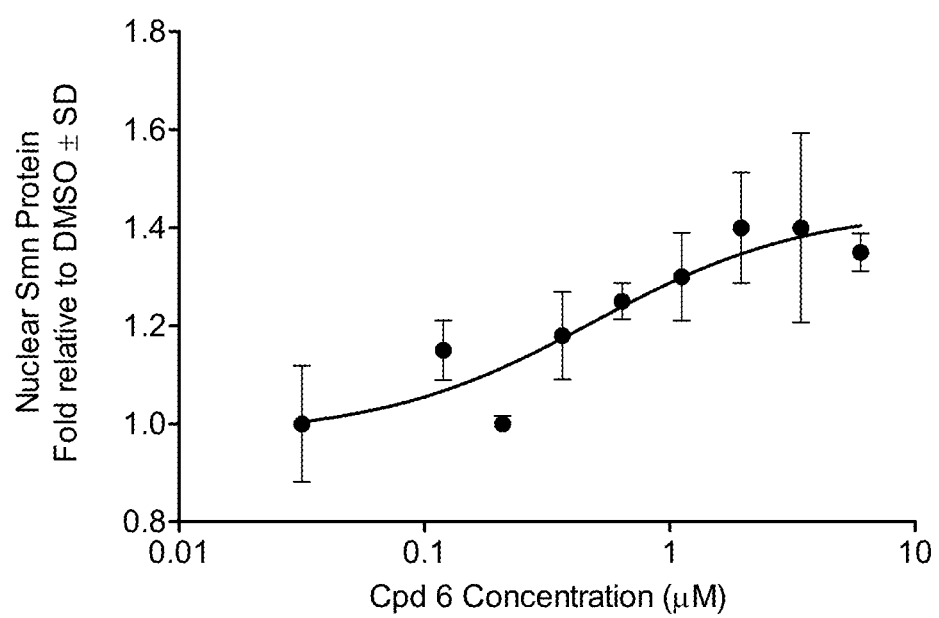

FIG. 10, referenced in Biological Example 9, shows an increase in Smn protein expression (black circles) in motor neurons generated from iPS cells generated from Type 1 SMA patient fibroblasts treated with Compound 6 (FIG. 10). The level of Smn protein was quantified using Smn immunostaining and confocal fluorescence microscopy. The level of Smn protein in compound-treated samples was normalized to that in vehicle-treated samples and plotted as a function of the compound concentration.

Figure 11A:
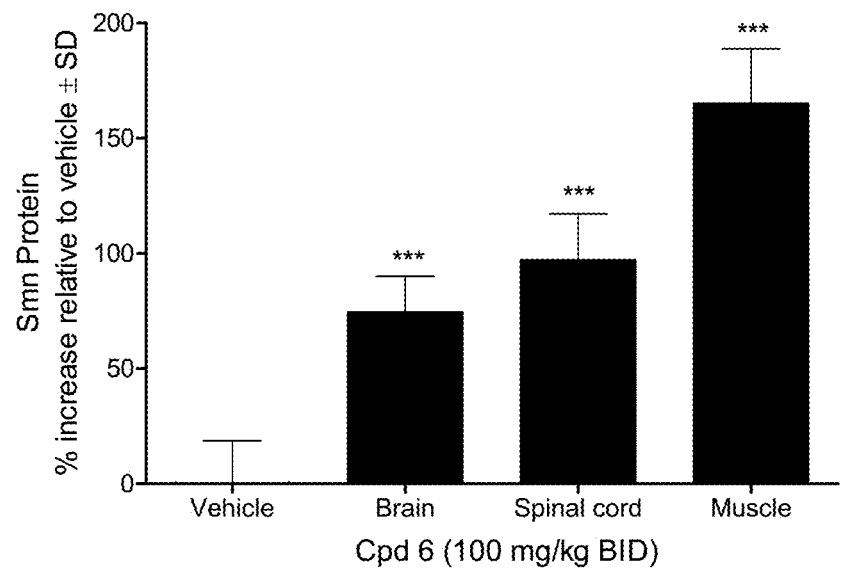
Figure 11B:
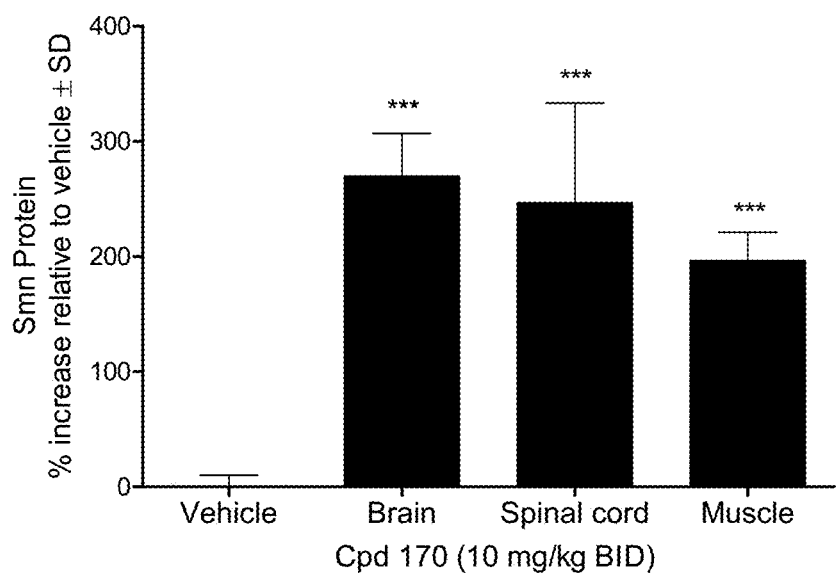

FIGS. 11a and 11b, referenced in Biological Example 11, show increased Smn protein expression in brain, spinal cord, and muscle tissues in a C/C-allele SMA mouse model resulting from treatment for 10 days BID with 100 mg/kg of Compound 6 (FIG. 11a, for n=10) and 10 mg/kg of Compound 170 (FIG. 11b, for n=5). The p value by ANOVA in each Figure is indicated with three stars (***) for p<0.001.

Figure 12A:
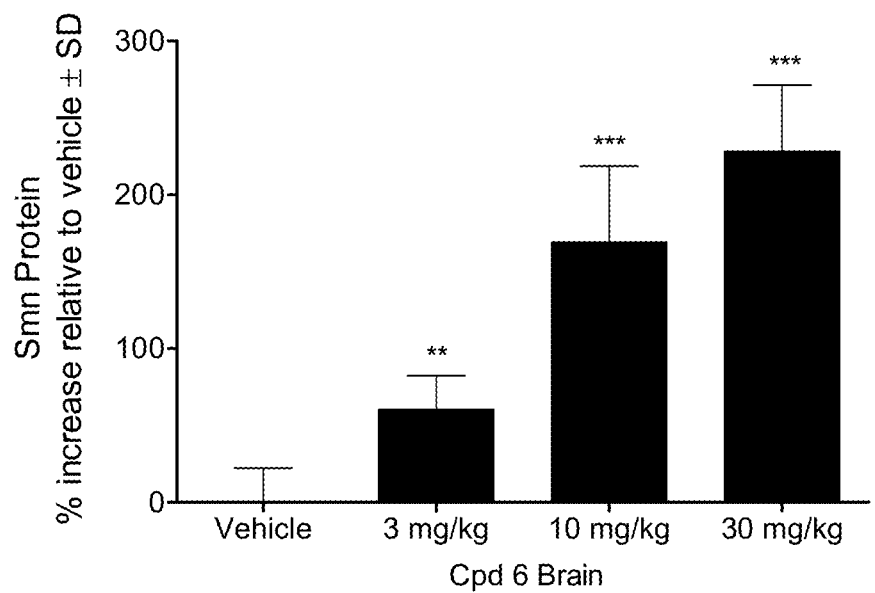
Figure 12B:
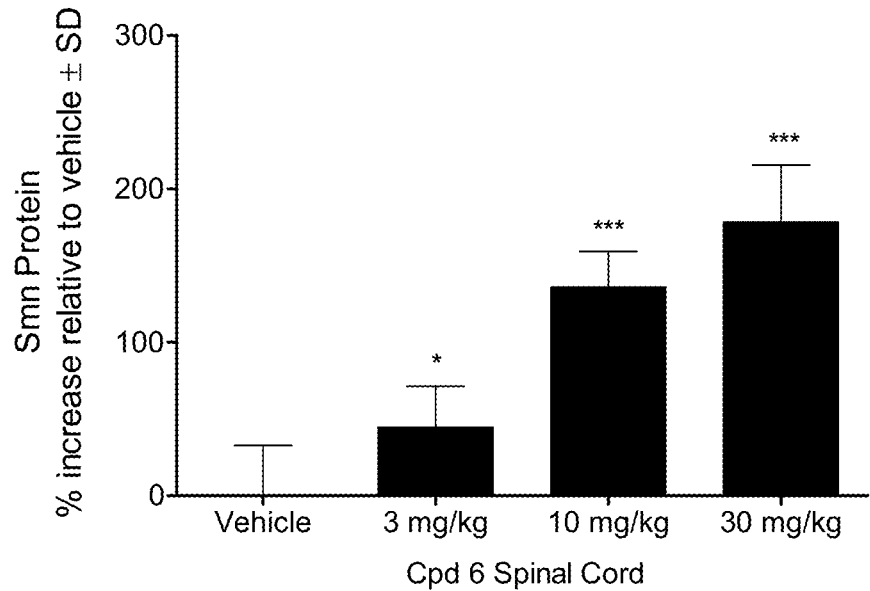
Figure 12C:
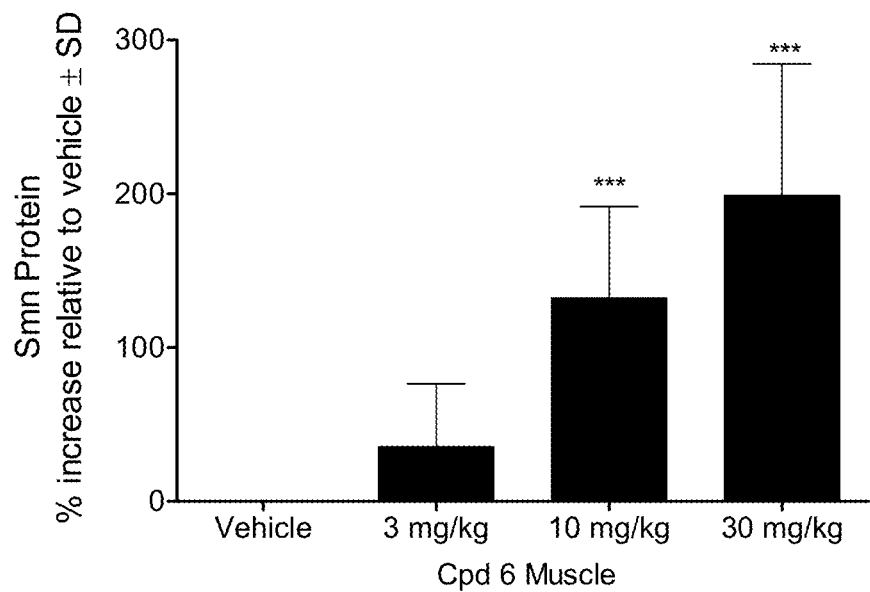
Figure 12D:
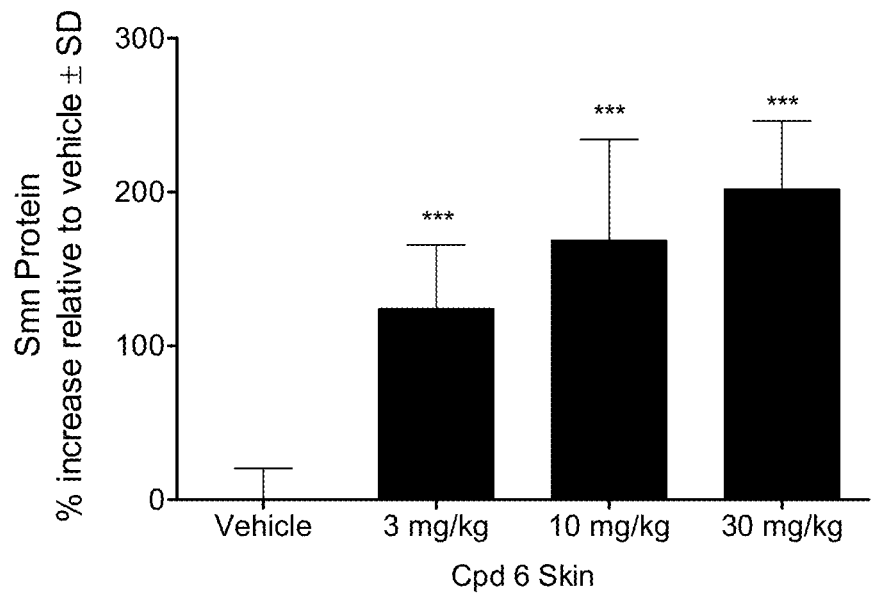
Figure 12E:
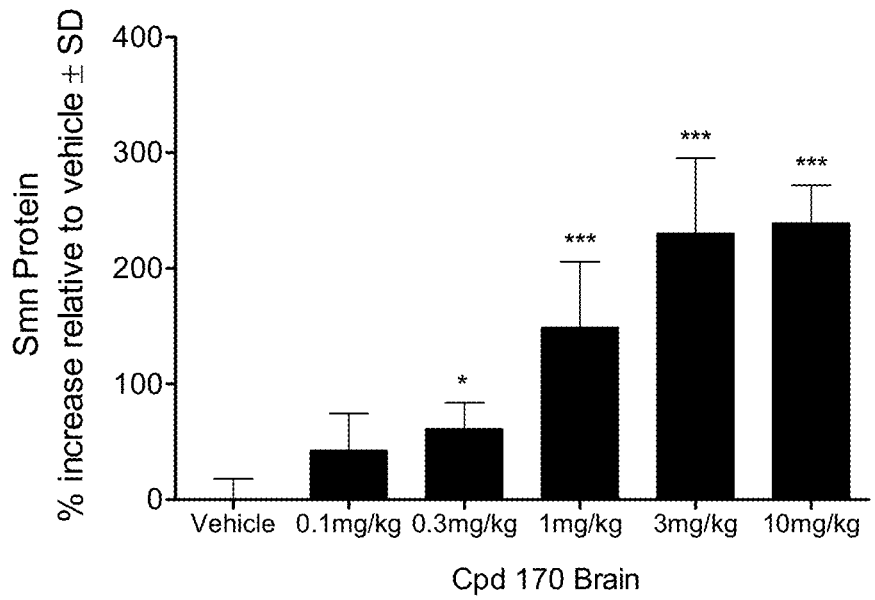
Figure 12F:
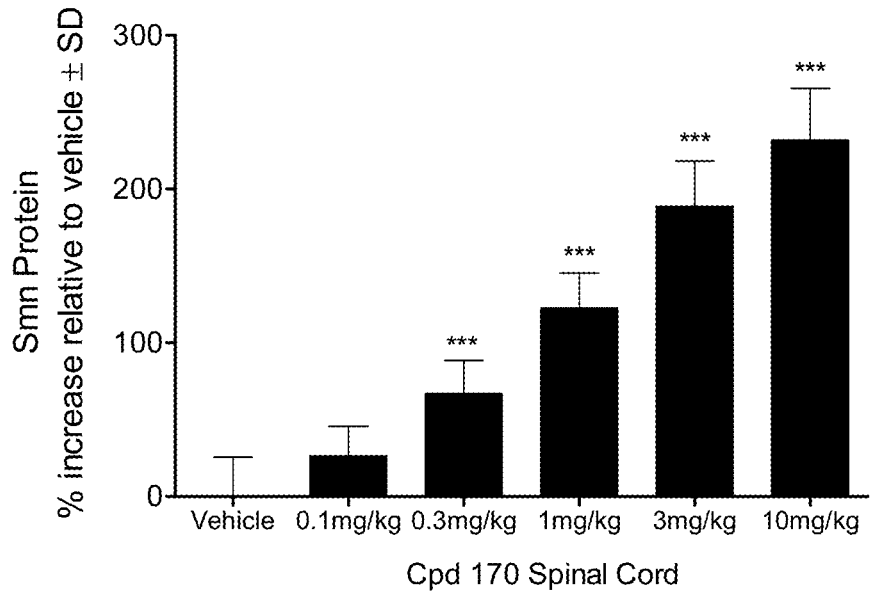
Figure 12G:
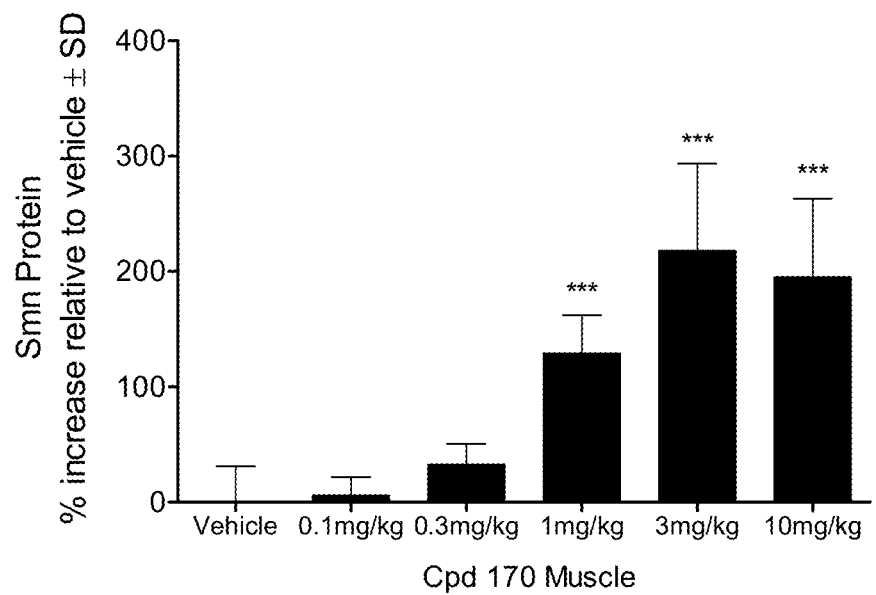

FIGS. 12a, 12b, 12c, 12d, 12e, 12f and 12g, referenced in Biological Example 12, show a dose dependent increase in Smn protein expression in tissues in a neonatal Δ7 SMA mouse model resulting from treatment for 7 days once per day (QD) with Compound 6 (brain, FIG. 12a; spinal cord, FIG. 12b; muscle, FIG. 12c; and skin, FIG. 12d, for n=6 to 9) and Compound 170 (brain, FIG. 12e; spinal cord, FIG. 12f; muscle, FIG. 12g, for n=7). The p value by ANOVA in each Figure is indicated with one star (*) for p<0.05, two stars () for p<0.01 and three stars (*) for p<0.001.

Figure 13A:
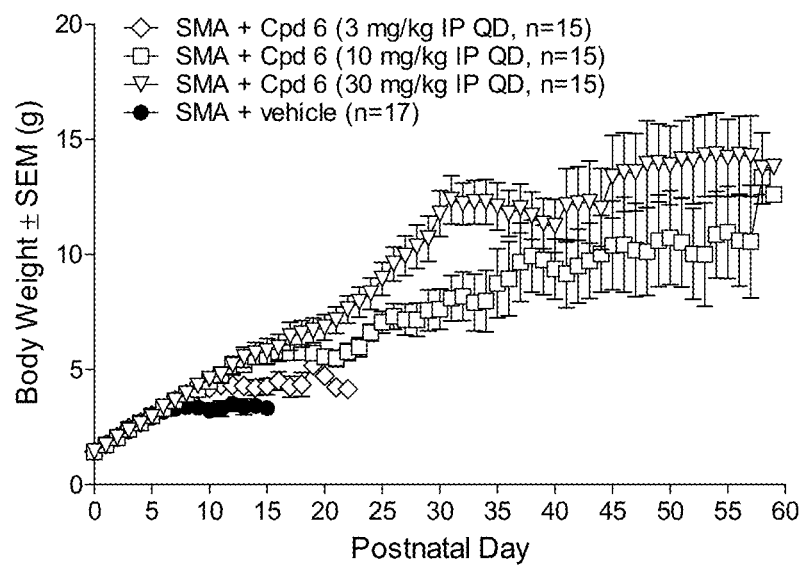
Figure 13B:
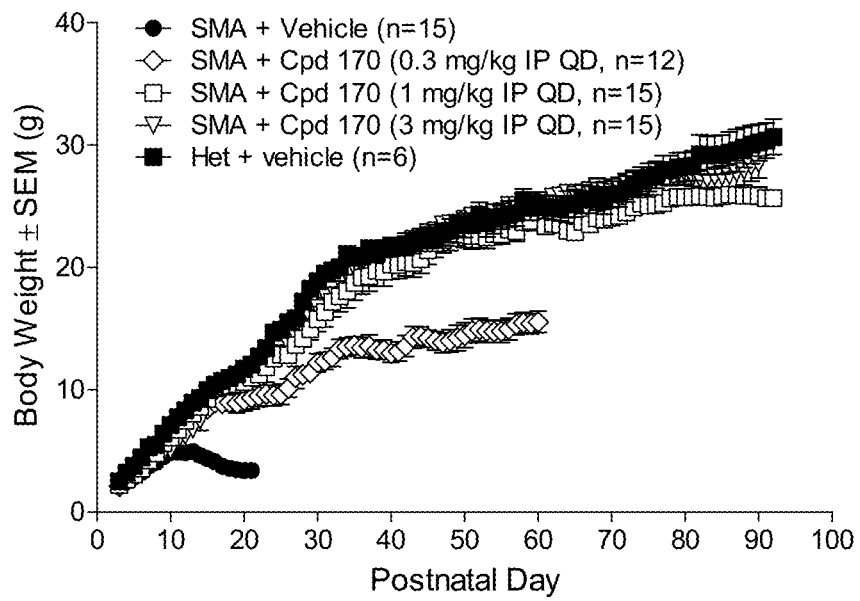

FIGS. 13a and 13b, referenced in Biological Example 13, show differences in body weight in a neonatal Δ7 SMA mouse model resulting from treatment up to Postnatal Day (PND) 59 with Compound 6 (FIG. 13a) and until PND 92 with Compound 170 (FIG. 13b).

Figure 14A:
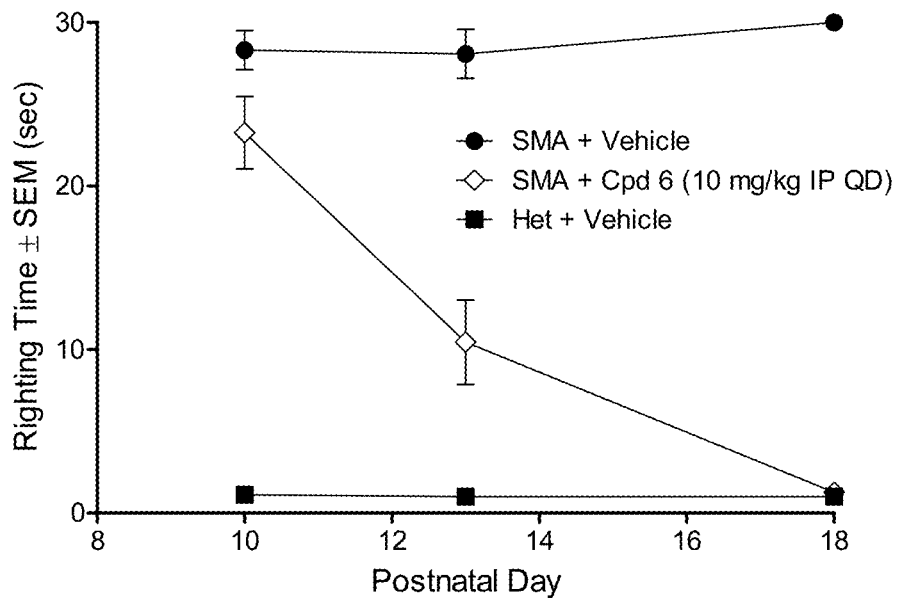
Figure 14B:
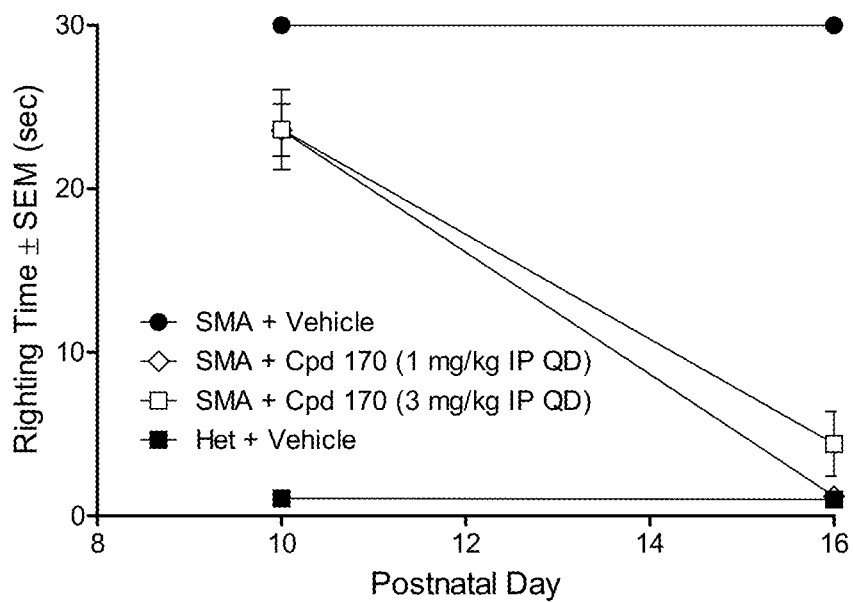

FIGS. 14a and 14b, referenced in Biological Example 14, show an improved righting reflex in a neonatal Δ7 SMA mouse model resulting from treatment with Compound 6 (FIG. 14a) and Compound 170 (FIG. 14b).

Figure 15A:
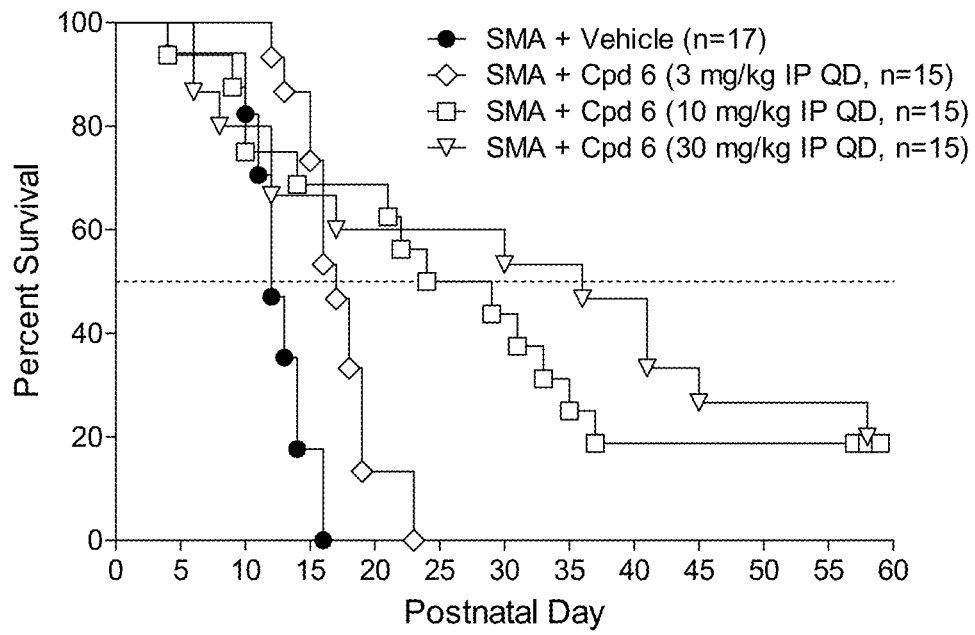
Figure 15B:
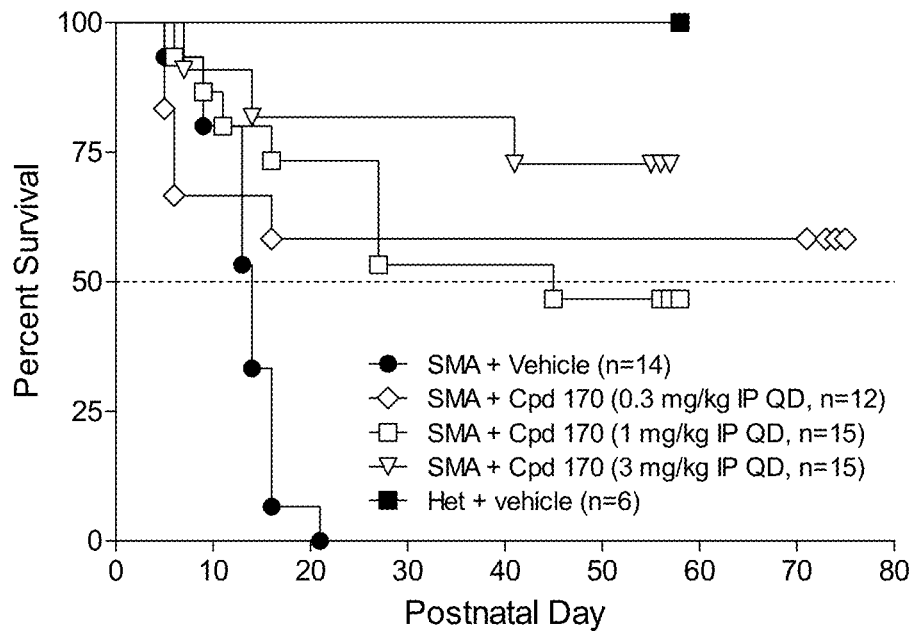

FIGS. 15a and 15b, referenced in Biological Example 15, show improved survival in a neonatal Δ7 SMA mouse model resulting from treatment with Compound 6 (FIG. 15a) and Compound 170 (FIG. 15b).

Figure 16A:
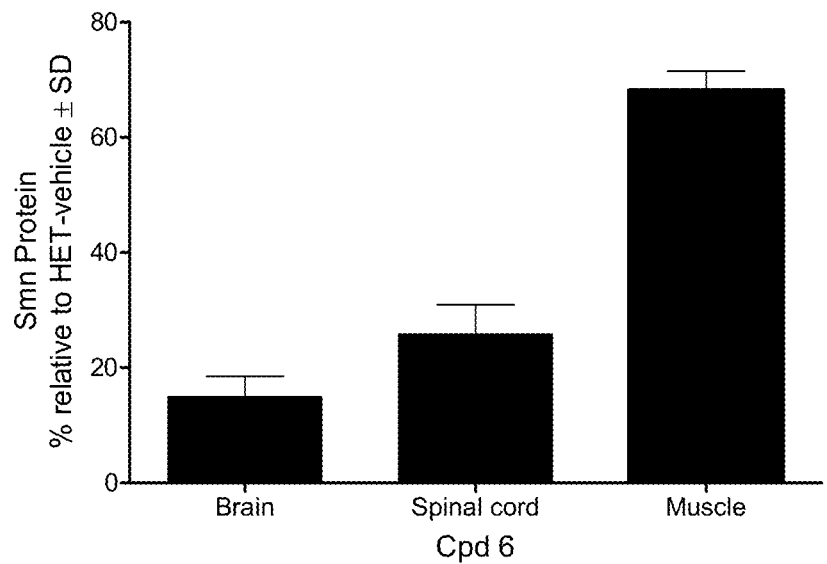
Figure 16B:
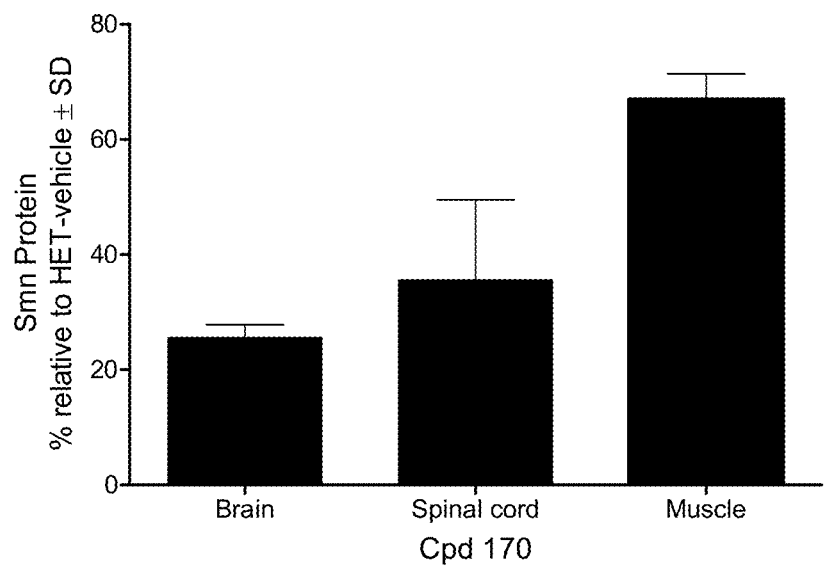

FIGS. 16a and 16b, referenced in Biological Example 15, show increased Smn protein expression in brain, spinal cord, and muscle tissues in a Δ7 SMA mouse model resulting from treatment with Compound 6 until PND 156 (FIG. 16a) and with Compound 170 until PND 185 (FIG. 16b) relative to vehicle treated and age-matched heterozygous mice, respectively.

Figure 17A:
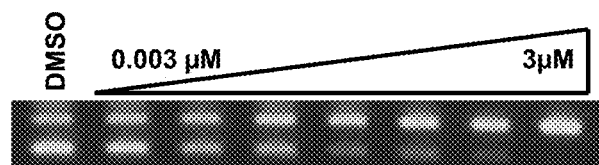
Figure 17B:
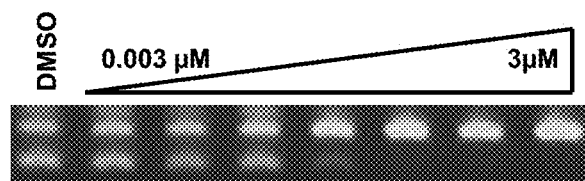

FIGS. 17a and 17b, referenced in Biological Example 16, show a dose dependent increase in SMN1 minigene FL mRNA and a dose dependent decrease in SMN1 minigene Δ7 mRNA in HEK293H human cells treated over a 7 hour period with Compound 6 (FIG. 17a) and Compound 170 (FIG. 17b). The full length and Δ7 SMN1 minigene mRNA were each amplified using RT-PCR and the resulting PCR products were separated using agarose gel electrophoresis. The top and bottom bands correspond to the full length and Δ7 SMN1 minigene mRNA, respectively. The intensity of each band is proportional to the amount of RNA present in the sample.

DETAILED DESCRIPTION

Provided herein are compounds of Formula (I):

$$\text{(I)}$$

or a form thereof, wherein:
$w_1$ and $w_5$ are independently C—$R_a$ or N;
$w_2$ is C—$R_b$ or N;
$w_3$, $w_4$ and $w_7$ are independently C—$R_1$, C—$R_2$, C—$R_a$ or N;
$w_6$ is C—$R_1$, C—$R_2$, C—$R_c$ or N;
wherein one of $w_3$, $w_4$, $w_6$ and $w_7$ is C—$R_1$ and one other of $w_3$, $w_4$, $w_6$ and $w_7$ is C—$R_2$, provided that,
when $w_3$ is C—$R_1$, then $w_6$ is C—$R_2$ and $w_4$ and $w_7$ are independently C—$R_a$ or N; or,
when $w_3$ is C—$R_2$, then $w_6$ is C—$R_1$ and $w_4$ and $w_7$ are independently C—$R_a$ or N; or,
when $w_4$ is C—$R_1$, then $w_7$ is C—$R_2$ and $w_3$ is C—$R_a$ or N and $w_6$ is C—$R_c$ or N; or,
when $w_4$ is C—$R_2$, then $w_7$ is C—$R_1$ and $w_3$ is C—$R_a$ or N and $w_6$ is C—$R_c$ or N; and,
wherein any one, two or three of $w_1$, $w_2$, $w_3$, $w_4$, $w_5$, $w_6$ and $w_7$ may optionally be N;
$R_1$ is $C_{1-8}$alkyl, amino, $C_{1-8}$alkyl-amino, $(C_{1-8}$alkyl$)_2$-amino, $C_{1-8}$alkoxy-$C_{1-8}$alkyl-amino, $(C_{1-8}$alkoxy-$C_{1-8}$alkyl$)_2$-amino, $(C_{1-8}$alkoxy-$C_{1-8}$alkyl$)(C_{1-8}$alkyl)amino, amino-$C_{1-8}$alkyl, $C_{1-8}$alkyl-amino-$C_{1-8}$alkyl, $(C_{1-8}$alkyl$)_2$-amino-$C_{1-8}$alkyl, $C_{1-8}$alkoxy-$C_{1-8}$alkyl-amino-$C_{1-8}$alkyl, $(C_{1-8}$alkoxy-$C_{1-8}$alkyl$)_2$-amino-$C_{1-8}$alkyl, $(C_{1-8}$alkoxy-$C_{1-8}$alkyl$)(C_{1-8}$alkyl)amino-$C_{1-8}$alkyl, amino-$C_{1-8}$alkyl-amino, (amino-$C_{1-8}$alkyl$)_2$-amino, (amino-$C_{1-8}$alkyl$)(C_{1-8}$alkyl)amino, $C_{1-8}$alkyl-amino-$C_{1-8}$alkyl-amino, $(C_{1-8}$alkyl-amino-$C_{1-8}$alkyl$)_2$-amino, $(C_{1-8}$alkyl-amino-$C_{1-8}$alkyl$)(C_{1-8}$alkyl)amino, $(C_{1-8}$alkyl$)_2$-amino-$C_{1-8}$alkyl-amino, $[(C_{1-8}$alkyl$)_2$-amino-$C_{1-8}$alkyl$](C_{1-8}$alkyl)amino, amino-$C_{1-8}$alkoxy, $C_{1-8}$alkyl-amino-$C_{1-8}$alkoxy, $(C_{1-8}$alkyl$)_2$-amino-$C_{1-8}$alkoxy, $C_{1-8}$alkoxy-$C_{1-8}$alkyl-amino-$C_{1-8}$alkoxy, $C_{1-8}$alkoxy-$C_{1-8}$alkyl-amino-$C_{1-8}$alkoxy, $(C_{1-8}$alkoxy-$C_{1-8}$alkyl$)(C_{1-8}$alkyl)amino-$C_{1-8}$alkoxy, amino-$C_{2-8}$alkenyl, $C_{1-8}$alkyl-amino-$C_{2-8}$alkenyl, $(C_{1-8}$alkyl$)_2$-amino-$C_{2-8}$alkenyl, amino-$C_{2-8}$alkynyl, $C_{1-8}$alkyl-amino-$C_{2-8}$alkynyl, $(C_{1-8}$alkyl$)_2$-amino-$C_{2-8}$alkynyl, halo-$C_{1-8}$alkyl-amino, (halo-$C_{1-8}$alkyl$)_2$-amino, (halo-$C_{1-8}$alkyl$)(C_{1-8}$alkyl)amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl$)_2$-amino, (hydroxy-$C_{1-8}$alkyl$)(C_{1-8}$alkyl)amino, hydroxy-$C_{1-8}$alkyl-amino-$C_{1-8}$alkyl, (hydroxy-$C_{1-8}$alkyl$)_2$-amino-$C_{1-8}$alkyl, (hydroxy-$C_{1-8}$alkyl$)(C_{1-8}$alkyl)amino-$C_{1-8}$alkyl, hydroxy-$C_{1-8}$alkyl-amino-$C_{1-8}$alkoxy, (hydroxy-$C_{1-8}$alkyl$)_2$-amino-$C_{1-8}$alkoxy, (hydroxy-$C_{1-8}$alkyl$)(C_{1-8}$alkyl)amino-$C_{1-8}$alkoxy, hydroxy-$C_{1-8}$alkyl-amino-$C_{1-8}$alkyl-amino, (hydroxy-$C_{1-8}$alkyl-amino-$C_{1-8}$alkyl$)_2$-amino, (hydroxy-$C_{1-8}$alkyl$)_2$-amino-$C_{1-8}$alkyl-amino, (hydroxy-$C_{1-8}$alkyl-amino-$C_{1-8}$alkyl)($C_{1-8}$alkyl)amino, (hydroxy-$C_{1-8}$alkyl$)(C_{1-8}$alkyl)amino-$C_{1-8}$alkyl-amino, [(hydroxy-$C_{1-8}$alkyl$)_2$-amino-$C_{1-8}$alkyl$](C_{1-8}$alkyl)amino, [(hydroxy-$C_{1-8}$alkyl)($C_{1-8}$alkyl)amino-$C_{1-8}$alkyl$](C_{1-8}$alkyl)amino, heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl$)_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl$)_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl$)_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl$)_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl$)_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl$)_2$-amino-$C_{1-8}$alkyl or (heteroaryl-$C_{1-8}$alkyl)($C_{1-8}$alkyl)amino-$C_{1-8}$alkyl;

wherein, each instance of heterocyclyl, $C_{3-14}$cycloalkyl, aryl and heteroaryl is optionally substituted with one, two or three $R_3$ substituents and optionally, with one additional $R_4$ substituent; or, wherein, each instance of heterocyclyl, $C_{3-14}$cycloalkyl, aryl and heteroaryl is optionally substituted with one, two, three or four $R_3$ substituents;

$R_2$ is aryl, aryl-amino, aryl-amino-carbonyl, heterocyclyl, heteroaryl or heteroaryl-amino;

wherein, each instance of aryl, heterocyclyl and heteroaryl is optionally substituted with one, two or three $R_6$ substituents and optionally, with one additional $R_7$ substituent;

$R_a$ is, in each instance, independently selected from hydrogen, halogen or $C_{1-8}$alkyl;

$R_b$ is hydrogen, halogen, $C_{1-8}$alkyl or $C_{1-8}$alkoxy;

$R_c$ is hydrogen, halogen or $C_{1-8}$alkyl;

$R_3$ is, in each instance, independently selected from cyano, halogen, hydroxy, oxo, $C_{1-8}$alkyl, halo-$C_{1-8}$alkyl, $C_{1-8}$alkyl-carbonyl, $C_{1-8}$alkoxy, halo-$C_{1-8}$alkoxy, $C_{1-8}$alkoxy-$C_{1-8}$alkyl, $C_{1-8}$alkoxy-carbonyl, amino, $C_{1-8}$alkyl-amino, $(C_{1-8}$alkyl$)_2$-amino, amino-$C_{1-8}$alkyl, $C_{1-8}$alkyl-amino-$C_{1-8}$alkyl, $(C_{1-8}$alkyl$)_2$-amino-$C_{1-8}$alkyl, amino-$C_{1-8}$alkyl-amino, $C_{1-8}$alkyl-amino-$C_{1-8}$alkyl-amino, $(C_{1-8}$alkyl-amino-$C_{1-8}$alkyl$)_2$-amino, $(C_{1-8}$alkyl$)_2$-amino-$C_{1-8}$alkyl-amino, $[(C_{1-8}$alkyl$)_2$-amino-$C_{1-8}$alkyl$]_2$-amino, $(C_{1-8}$alkyl-amino-$C_{1-8}$alkyl)($C_{1-8}$alkyl)amino, $[(C_{1-8}$alkyl$)_2$-amino-$C_{1-8}$alkyl]($C_{1-8}$alkyl)amino, $C_{1-8}$alkoxy-$C_{1-8}$alkyl-amino, $(C_{1-8}$alkoxy-$C_{1-8}$alkyl$)_2$-amino, $(C_{1-8}$alkoxy-$C_{1-8}$alkyl)($C_{1-8}$alkyl)amino, $C_{1-8}$alkyl-carbonyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl$)_2$-amino or (hydroxy-$C_{1-8}$alkyl)($C_{1-8}$alkyl)amino;

$R_4$ is $C_{3-14}$cycloalkyl, $C_{3-14}$cycloalkyl-$C_{1-8}$alkyl, $C_{3-14}$cycloalkyl-amino, aryl-$C_{1-8}$alkyl, aryl-$C_{1-8}$alkoxy-carbonyl, aryl-sulfonyloxy-$C_{1-8}$alkyl, heterocyclyl or heterocyclyl-$C_{1-8}$alkyl; wherein, each instance of $C_{3-14}$cycloalkyl, aryl and heterocyclyl is optionally substituted with one, two or three $R_5$ substituents;

$R_5$ is, in each instance, independently selected from halogen, hydroxy, cyano, nitro, $C_{1-8}$alkyl, halo-$C_{1-8}$alkyl, $C_{1-8}$alkoxy, halo-$C_{1-8}$alkoxy, amino, $C_{1-8}$alkyl-amino, $(C_{1-8}$alkyl$)_2$-amino or $C_{1-8}$alkyl-thio;

$R_6$ is, in each instance, independently selected from halogen, hydroxy, cyano, nitro, $C_{1-8}$alkyl, $C_{2-8}$alkenyl, halo-$C_{1-8}$alkyl, hydroxy-$C_{1-8}$alkyl, $C_{1-8}$alkoxy, halo-$C_{1-8}$alkoxy, $C_{1-8}$alkoxy-$C_{1-8}$alkyl, amino, $C_{1-8}$alkyl-amino, ($C_{1-8}$alkyl)$_2$-amino or $C_{1-8}$alkyl-thio; and, $R_7$ is $C_{3-14}$cycloalkyl, $C_{3-14}$cycloalkyl-oxy, aryl, heterocyclyl or heteroaryl.

EMBODIMENTS

In one embodiment of a compound of Formula (I), $w_1$ is C—$R_a$.

In another embodiment of a compound of Formula (I), $w_1$ is N.

In one embodiment of a compound of Formula (I), $w_2$ is C—$R_b$.

In another embodiment of a compound of Formula (I), $w_2$ is N.

In one embodiment of a compound of Formula (I), $w_3$ is C—$R_a$.

In another embodiment of a compound of Formula (I), $w_3$ is N.

In one embodiment of a compound of Formula (I), $w_4$ is C—$R_a$.

In another embodiment of a compound of Formula (I), $w_4$ is N.

In one embodiment of a compound of Formula (I), $w_5$ is C—$R_a$.

In another embodiment of a compound of Formula (I), $w_5$ is N.

In one embodiment of a compound of Formula (I), $w_6$ is C—Re.

In another embodiment of a compound of Formula (I), $w_6$ is N.

In one embodiment of a compound of Formula (I), $w_7$ is C—$R_a$.

In another embodiment of a compound of Formula (I), $w_7$ is N.

In one embodiment of a compound of Formula (I), $w_3$ is C—$R_1$ and $w_6$ is C—$R_2$.

In another embodiment of a compound of Formula (I), $w_3$ is C—$R_2$ and $w_6$ is C—$R_1$.

In one embodiment of a compound of Formula (I), $w_4$ is C—$R_1$ and $w_7$ is C—$R_2$.

In another embodiment of a compound of Formula (I), $w_4$ is C—$R_2$ and $w_7$ is C—$R_1$.

In one embodiment of a compound of Formula (I), $w_3$ is C—$R_1$, $w_6$ is C—$R_2$ and $w_1$, $w_4$, $w_5$ and $w_7$ are independently C—$R_a$ or N and $w_2$ is C—$R_b$ or N.

In another embodiment of a compound of Formula (I), $w_3$ is C—$R_2$, $w_6$ is C—$R_1$ and $w_1$, $w_4$, $w_5$ and $w_7$ are independently C—$R_a$ or N and $w_2$ is C—$R_b$ or N.

In one embodiment of a compound of Formula (I), $w_4$ is C—$R_1$, $w_7$ is C—$R_2$, $w_1$, $w_3$ and $w_5$ are independently C—$R_a$ or N, $w_2$ is C—$R_b$ or N and $w_6$ is C—$R_c$ or N.

In another embodiment of a compound of Formula (I), $w_4$ is C—$R_2$, $w_7$ is C—$R_1$, $w_1$, and $w_5$ are independently C—$R_a$ or N, $w_2$ is C—$R_b$ or N and $w_6$ is C—$R_c$ or N.

In one embodiment of a compound of Formula (I), $w_1$ and $w_2$ are N.

In one embodiment of a compound of Formula (I), $w_1$ and $w_3$ are N.

In one embodiment of a compound of Formula (I), $w_1$ and $w_4$ are N.

In one embodiment of a compound of Formula (I), $w_1$ and $w_5$ are N.

In one embodiment of a compound of Formula (I), $w_1$ and $w_6$ are N.

In one embodiment of a compound of Formula (I), $w_1$ and $w_7$ are N.

In one embodiment of a compound of Formula (I),
$R_1$ is $C_{1-8}$alkyl, amino, $C_{1-8}$alkyl-amino, ($C_{1-8}$alkyl)$_2$-amino, $C_{1-8}$alkoxy-$C_{1-8}$alkyl-amino, ($C_{1-8}$alkoxy-$C_{1-8}$alkyl)$_2$-amino, ($C_{1-8}$alkoxy-$C_{1-8}$alkyl)($C_{1-8}$alkyl)amino, amino-$C_{1-8}$alkyl, $C_{1-8}$alkyl-amino-$C_{1-8}$alkyl, ($C_{1-8}$alkyl)$_2$-amino-$C_{1-8}$alkyl, $C_{1-8}$alkoxy-$C_{1-8}$alkyl-amino-$C_{1-8}$alkyl, ($C_{1-8}$alkoxy-$C_{1-8}$alkyl)$_2$-amino-$C_{1-8}$alkyl, ($C_{1-8}$alkoxy-$C_{1-8}$alkyl)($C_{1-8}$alkyl)amino-$C_{1-8}$alkyl, amino-$C_{1-8}$alkyl-amino, (amino-$C_{1-8}$alkyl)$_2$-amino, (amino-$C_{1-8}$alkyl)($C_{1-8}$alkyl)amino, $C_{1-8}$alkyl-amino-$C_{1-8}$alkyl-amino, ($C_{1-8}$alkyl-amino-$C_{1-8}$alkyl)$_2$-amino, ($C_{1-8}$alkyl-amino-$C_{1-8}$alkyl)($C_{1-8}$alkyl)amino, ($C_{1-8}$alkyl)$_2$-amino-$C_{1-8}$alkyl-amino, [($C_{1-8}$alkyl)$_2$-amino-$C_{1-8}$alkyl]($C_{1-8}$alkyl)amino, amino-$C_{1-8}$alkoxy, $C_{1-8}$alkyl-amino-$C_{1-8}$alkoxy, ($C_{1-8}$alkyl)$_2$-amino-$C_{1-8}$alkoxy, $C_{1-8}$alkoxy-$C_{1-8}$alkyl-amino-$C_{1-8}$alkoxy, ($C_{1-8}$alkoxy-$C_{1-8}$alkyl)$_2$-amino-$C_{1-8}$alkoxy, ($C_{1-8}$alkoxy-$C_{1-8}$alkyl)($C_{1-8}$alkyl)amino-$C_{1-8}$alkoxy, amino-$C_{2-8}$alkenyl, $C_{1-8}$alkyl-amino-$C_{2-8}$alkenyl, ($C_{1-8}$alkyl)$_2$-amino-$C_{2-8}$alkenyl, amino-$C_{2-8}$alkynyl, $C_{1-8}$alkyl-amino-$C_{2-8}$alkynyl, ($C_{1-8}$alkyl)$_2$-amino-$C_{2-8}$alkynyl, halo-$C_{1-8}$alkyl-amino, (halo-$C_{1-8}$alkyl)$_2$-amino, (halo-$C_{1-8}$alkyl)($C_{1-8}$alkyl)amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino, (hydroxy-$C_{1-8}$alkyl)($C_{1-8}$alkyl)amino, hydroxy-$C_{1-8}$alkyl-amino-$C_{1-8}$alkyl, (hydroxy-$C_{1-8}$alkyl)$_2$-amino-$C_{1-8}$alkyl, (hydroxy-$C_{1-8}$alkyl)($C_{1-8}$alkyl)amino-$C_{1-8}$alkyl, hydroxy-$C_{1-8}$alkyl-amino-$C_{1-8}$alkoxy, (hydroxy-$C_{1-8}$alkyl)$_2$-amino-$C_{1-8}$alkoxy, (hydroxy-$C_{1-8}$alkyl)($C_{1-8}$alkyl)amino-$C_{1-8}$alkoxy, hydroxy-$C_{1-8}$alkyl-amino-$C_{1-8}$alkyl-amino, (hydroxy-$C_{1-8}$alkyl-amino-$C_{1-8}$alkyl)$_2$-amino, (hydroxy-$C_{1-8}$alkyl)$_2$-amino-$C_{1-8}$alkyl-amino, (hydroxy-$C_{1-8}$alkyl-amino-$C_{1-8}$alkyl)($C_{1-8}$alkyl)amino, (hydroxy-$C_{1-8}$alkyl)($C_{1-8}$alkyl)amino-$C_{1-8}$alkyl-amino, [(hydroxy-$C_{1-8}$alkyl)$_2$-amino-$C_{1-8}$alkyl]($C_{1-8}$alkyl)amino, [(hydroxy-$C_{1-8}$alkyl)($C_{1-8}$alkyl)amino-$C_{1-8}$alkyl]($C_{1-8}$alkyl)amino, heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-$C_{1-8}$alkyl or (heteroaryl-$C_{1-8}$alkyl)($C_{1-8}$alkyl)amino-$C_{1-8}$alkyl; wherein, each instance of heterocyclyl, $C_{3-14}$cycloalkyl, aryl and heteroaryl is optionally substituted with $R_3$ and $R_4$ substituents.

In another embodiment of a compound of Formula (I), $R_1$ is amino, ($C_{1-8}$alkyl)$_2$-amino, $C_{1-8}$alkoxy-$C_{1-8}$alkyl-amino, ($C_{1-8}$alkoxy-$C_{1-8}$alkyl)$_2$-amino, amino-$C_{1-8}$alkyl, $C_{1-8}$alkyl-amino-$C_{1-8}$alkyl, ($C_{1-8}$alkyl)$_2$-amino-$C_{1-8}$alkyl, $C_{1-8}$alkoxy-$C_{1-8}$alkyl-amino-$C_{1-8}$alkyl, ($C_{1-8}$alkoxy-$C_{1-8}$alkyl)$_2$-amino-$C_{1-8}$alkyl, ($C_{1-8}$alkoxy-$C_{1-8}$alkyl)($C_{1-8}$alkyl)amino-$C_{1-8}$alkyl, amino-$C_{1-8}$alkyl-amino, (amino-$C_{1-8}$alkyl)$_2$-amino, (amino-$C_{1-8}$alkyl)($C_{1-8}$alkyl)amino, $C_{1-8}$alkyl-amino-$C_{1-8}$alkyl-amino, ($C_{1-8}$alkyl-amino-$C_{1-8}$alkyl)$_2$-amino, ($C_{1-8}$alkyl-amino-$C_{1-8}$alkyl)($C_{1-8}$alkyl)amino, ($C_{1-8}$alkyl)$_2$-amino-$C_{1-8}$alkyl-amino, [($C_{1-8}$alkyl)$_2$-amino-$C_{1-8}$alkyl]($C_{1-8}$alkyl)amino, amino-$C_{1-8}$alkoxy, $C_{1-8}$alkyl-amino-$C_{1-8}$alkoxy, ($C_{1-8}$alkyl)$_2$-amino-$C_{1-8}$alkoxy, $C_{1-8}$alkoxy-$C_{1-8}$alkyl-amino-$C_{1-8}$alkoxy, ($C_{1-8}$alkoxy-$C_{1-8}$alkyl)$_2$-amino-$C_{1-8}$alkoxy, ($C_{1-8}$alkoxy-$C_{1-8}$alkyl)($C_{1-8}$alkyl)amino-$C_{1-8}$alkoxy, amino-$C_{2-8}$alkenyl, $C_{1-8}$alkyl-amino-$C_{2-8}$alkenyl, ($C_{1-8}$alkyl)$_2$-amino-$C_{2-8}$alkenyl, amino-$C_{2-8}$alkynyl, $C_{1-8}$alkyl-amino-$C_{2-8}$alkynyl, ($C_{1-8}$alkyl)$_2$-amino-$C_{2-8}$alkynyl, halo-$C_{1-8}$alkyl-amino, (halo-$C_{1-8}$alkyl)$_2$-amino, (halo-$C_{1-8}$alkyl)($C_{1-8}$alkyl)amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino, (hydroxy-$C_{1-8}$alkyl)($C_{1-8}$alkyl)amino, hydroxy-$C_{1-8}$alkyl-amino-$C_{1-8}$alkyl, (hydroxy-$C_{1-8}$alkyl)$_2$-amino-$C_{1-8}$alkyl, (hydroxy-$C_{1-8}$alkyl)($C_{1-8}$alkyl)amino-$C_{1-8}$alkyl, hydroxy-$C_{1-8}$alkyl-amino-$C_{1-8}$alkoxy, (hydroxy-$C_{1-8}$alkyl)$_2$-amino-$C_{1-8}$alkoxy, (hydroxy-$C_{1-8}$alkyl)($C_{1-8}$alkyl)amino-$C_{1-8}$alkoxy, hydroxy-$C_{1-8}$alkyl-amino-$C_{1-8}$alkyl-amino, (hydroxy-$C_{1-8}$alkyl)$_2$-amino-$C_{1-8}$alkyl-amino, (hydroxy-$C_{1-8}$alkyl-amino-$C_{1-8}$alkyl)($C_{1-8}$alkyl)amino, (hydroxy-$C_{1-8}$alkyl)($C_{1-8}$alkyl)amino-$C_{1-8}$alkyl-amino, [(hydroxy-$C_{1-8}$alkyl)$_2$-amino-$C_{1-8}$alkyl]($C_{1-8}$alkyl)amino, [(hydroxy-$C_{1-8}$alkyl)($C_{1-8}$alkyl)amino-$C_{1-8}$alkyl]($C_{1-8}$alkyl)amino, heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl; wherein, each instance of heterocyclyl, $C_{3-14}$cycloalkyl, aryl and heteroaryl is optionally substituted with $R_3$ and $R_4$ substituents.

In another embodiment of a compound of Formula (I), $R_1$ is $C_{1-8}$alkyl, amino, $C_{1-8}$alkyl-amino, ($C_{1-8}$alkyl)$_2$-amino, $C_{1-8}$alkoxy-$C_{1-8}$alkyl-amino, ($C_{1-8}$alkoxy-$C_{1-8}$alkyl)$_2$-amino, ($C_{1-8}$alkoxy-$C_{1-8}$alkyl)($C_{1-8}$alkyl)amino, amino-$C_{1-8}$alkyl, $C_{1-8}$alkyl-amino-$C_{1-8}$alkyl, ($C_{1-8}$alkyl)$_2$-amino-$C_{1-8}$alkyl, $C_{1-8}$alkoxy-$C_{1-8}$alkyl-amino-$C_{1-8}$alkyl, ($C_{1-8}$alkoxy-$C_{1-8}$alkyl)$_2$-amino-$C_{1-8}$alkyl, ($C_{1-8}$alkoxy-$C_{1-8}$alkyl)($C_{1-8}$alkyl)amino-$C_{1-8}$alkyl, amino-$C_{1-8}$alkyl-amino, (amino-$C_{1-8}$alkyl)$_2$-amino, (amino-$C_{1-8}$alkyl)($C_{1-8}$alkyl)amino, $C_{1-8}$alkyl-amino-$C_{1-8}$alkyl-amino, ($C_{1-8}$alkyl-amino-$C_{1-8}$alkyl)$_2$-amino, ($C_{1-8}$alkyl-amino-$C_{1-8}$alkyl)($C_{1-8}$alkyl)amino, ($C_{1-8}$alkyl)$_2$-amino-$C_{1-8}$alkyl-amino, [($C_{1-8}$alkyl)$_2$-amino-$C_{1-8}$alkyl]($C_{1-8}$alkyl)amino, amino-$C_{1-8}$alkoxy, $C_{1-8}$alkyl-amino-$C_{1-8}$alkoxy, ($C_{1-8}$alkyl)$_2$-amino-$C_{1-8}$alkoxy, $C_{1-8}$alkoxy-$C_{1-8}$alkyl-amino-$C_{1-8}$alkoxy, ($C_{1-8}$alkoxy-$C_{1-8}$alkyl)$_2$-amino-$C_{1-8}$alkoxy, ($C_{1-8}$alkoxy-$C_{1-8}$alkyl)($C_{1-8}$alkyl)amino-$C_{1-8}$alkoxy, amino-$C_{2-8}$alkenyl, $C_{1-8}$alkyl-amino-$C_{2-8}$alkenyl, ($C_{1-8}$alkyl)$_2$-amino-$C_{2-8}$alkenyl, amino-$C_{2-8}$alkynyl, $C_{1-8}$alkyl-amino-$C_{2-8}$alkynyl, ($C_{1-8}$alkyl)$_2$-amino-$C_{2-8}$alkynyl, halo-$C_{1-8}$alkyl-amino, (halo-$C_{1-8}$alkyl)$_2$-amino, (halo-$C_{1-8}$alkyl)($C_{1-8}$alkyl)amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino, (hydroxy-$C_{1-8}$alkyl)($C_{1-8}$alkyl)amino, hydroxy-$C_{1-8}$alkyl-amino-$C_{1-8}$alkyl, (hydroxy-$C_{1-8}$alkyl)$_2$-amino-$C_{1-8}$alkyl, (hydroxy-$C_{1-8}$alkyl)($C_{1-8}$alkyl)amino-$C_{1-8}$alkyl, hydroxy-$C_{1-8}$alkyl-amino-$C_{1-8}$alkoxy, (hydroxy-$C_{1-8}$alkyl)$_2$-amino-$C_{1-8}$alkoxy, (hydroxy-$C_{1-8}$alkyl)($C_{1-8}$alkyl)amino-$C_{1-8}$alkoxy, hydroxy-$C_{1-8}$alkyl-amino-$C_{1-8}$alkyl-amino, (hydroxy-$C_{1-8}$alkyl)$_2$-amino-$C_{1-8}$alkyl-amino, (hydroxy-$C_{1-8}$alkyl-amino-$C_{1-8}$alkyl)($C_{1-8}$alkyl)amino, (hydroxy-$C_{1-8}$alkyl)($C_{1-8}$alkyl)amino-$C_{1-8}$alkyl-amino, [(hydroxy-$C_{1-8}$alkyl)$_2$-amino-$C_{1-8}$alkyl]($C_{1-8}$alkyl)amino or [(hydroxy-$C_{1-8}$alkyl)($C_{1-8}$alkyl)amino-$C_{1-8}$alkyl]($C_{1-8}$alkyl)amino.

In another embodiment of a compound of Formula (I), $R_1$ is heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl; wherein, each instance of heterocyclyl, $C_{3-14}$cycloalkyl, aryl and heteroaryl is optionally substituted with $R_3$ and $R_4$ substituents.

In another embodiment of a compound of Formula (I), $R_1$ is heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl or heterocyclyl-carbonyl-oxy; wherein, each instance of heterocyclyl is optionally substituted with $R_3$ and $R_4$ substituents.

In another embodiment of a compound of Formula (I), $R_1$ is heterocyclyl optionally substituted with $R_3$ and $R_4$ substituents.

In another embodiment of a compound of Formula (I), $R_1$ is $C_{3-14}$cycloalkyl optionally substituted with $R_3$ and $R_4$ substituents.

In another embodiment of a compound of Formula (I), R$_1$ is aryl-C$_{1-8}$alkyl-amino, (aryl-C$_{1-8}$alkyl)$_2$-amino, (aryl-C$_{1-8}$alkyl)(C$_{1-8}$alkyl)amino, aryl-C$_{1-8}$alkyl-amino-C$_{1-8}$alkyl, (aryl-C$_{1-8}$alkyl)$_2$-amino-C$_{1-8}$alkyl or (aryl-C$_{1-8}$alkyl)(C$_{1-8}$alkyl)amino-C$_{1-8}$alkyl; wherein, each instance of aryl is optionally substituted with R$_3$ and R$_4$ substituents.

In another embodiment of a compound of Formula (I), R$_1$ is aryl-C$_{1-8}$alkyl-amino optionally substituted with R$_3$ and R$_4$ substituents.

In another embodiment of a compound of Formula (I), R$_1$ is heteroaryl, heteroaryl-C$_{1-8}$alkyl, heteroaryl-C$_{1-8}$alkoxy, heteroaryl-amino, heteroaryl-C$_{1-8}$alkyl-amino, (heteroaryl-C$_{1-8}$alkyl)$_2$-amino, (heteroaryl-C$_{1-8}$alkyl)(C$_{1-8}$alkyl)amino, heteroaryl-C$_{1-8}$alkyl-amino-C$_{1-8}$alkyl, (heteroaryl-C$_{1-8}$alkyl)$_2$-amino-C$_{1-8}$alkyl or (heteroaryl-C$_{1-8}$alkyl)(C$_{1-8}$alkyl)amino-C$_{1-8}$alkyl; wherein, each instance of heterocyclyl, C$_{3-14}$cycloalkyl, aryl and heteroaryl is optionally substituted with R$_3$ and R$_4$ substituents.

In another embodiment of a compound of Formula (I), R$_1$ is heteroaryl optionally substituted with R$_3$ and R$_4$ substituents.

In one embodiment of a compound of Formula (I), R$_1$ is heterocyclyl selected from azetidinyl, tetrahydrofuranyl, pyrrolidinyl, piperidinyl, piperazinyl, 1,4-diazepanyl, 1,2,5,6-tetrahydropyridinyl, 1,2,3,6-tetrahydropyridinyl, hexahydropyrrolo[3,4-b]pyrrol-(1H)-yl, (3aS,6aS)-hexahydropyrrolo[3,4-b]pyrrol-(1H)-yl, (3aR,6aR)-hexahydropyrrolo[3,4-b]pyrrol-(1H)-yl, hexahydropyrrolo[3,4-b]pyrrol-(2H)-yl, (3aS,6aS)-hexahydropyrrolo[3,4-b]pyrrol-(2H)-yl, hexahydropyrrolo[3,4-c]pyrrol-(1H)-yl, (3aR,6aS)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(2H)-one, hexahydropyrrolo[1,2-a]pyrazin-(1H)-yl, (7R,8aS)-hexahydropyrrolo[1,2-c]pyrazin-(1H)-yl, (8aS)-hexahydropyrrolo[1,2-a]pyrazin-(1H)-yl, (8aR)-hexahydropyrrolo[1,2-a]pyrazin-(1H)-yl, (8aS)-octahydropyrrolo[1,2-a]pyrazin-(1H)-yl, (8aR)-octahydropyrrolo[1,2-a]pyrazin-(1H)-yl, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 2,5-diazabicyclo[2.2.2]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 2,6-diazaspiro[3.3]heptyl, 2,7-diazaspiro[3.5]nonyl, 5,8-diazaspiro[3.5]nonyl, 2,7-diazaspiro[4.4]nonyl or 6,9-diazaspiro[4.5]decyl; wherein, each instance of heterocyclyl is optionally substituted with R$_3$ and R$_4$ substituents.

In another embodiment of a compound of Formula (I), R$_1$ is heterocyclyl selected from azetidin-1-yl, tetrahydrofuran-3-yl, pyrrolidin-1-yl, piperidin-1-yl, piperidin-4-yl, piperazin-1-yl, 1,4-diazepan-1-yl, 1,2,5,6-tetrahydropyridin-5-yl, 1,2,3,6-tetrahydropyridin-4-yl, hexahydropyrrolo[3,4-b]pyrrol-1(2H)-yl, (3aS,6aS)-hexahydropyrrolo[3,4-b]pyrrol-1(2H)-yl, (3aS,6aS)-hexahydropyrrolo[3,4-b]pyrrol-5(1H)-yl, (3aR,6aR)-hexahydropyrrolo[3,4-b]pyrrol-5(1H)-yl, hexahydropyrrolo[3,4-c]pyrrol-2(1H)-yl, (3aR,6aS)-hexahydropyrrolo[3,4-c]pyrrol-2(1H)-yl, octahydro-5H-pyrrolo[3,2-c]pyridin-5-yl, octahydro-6H-pyrrolo[3,4-b]pyridin-6-yl, (4aR,7aR)-octahydro-6H-pyrrolo[3,4-b]pyridin-6-yl, (4aS,7aS)-octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, (7R,8aS)-hexahydropyrrolo[1,2-a]pyrazin-2(1H)-yl, (8aS)-hexahydropyrrolo[1,2-a]pyrazin-2(1H)-yl, (8aR)-hexahydropyrrolo[1,2-a]pyrazin-2(1H)-yl, (8aS)-octahydropyrrolo[1,2-a]pyrazin-2(1H)-yl, (8aR)-octahydropyrrolo[1,2-a]pyrazin-2(1H)-yl, octahydro-2H-pyrido[1,2-a]pyrazin-2-yl, 3-azabicyclo[3.1.0]hex-3-yl, 8-azabicyclo[3.2.1]oct-3-yl, (1R,5S)-8-azabicyclo[3.2.1]oct-3-yl, 8-azabicyclo[3.2.1]oct-2-en-3-yl, (1R,5S)-8-azabicyclo[3.2.1]oct-2-en-3-yl, 9-azabicyclo[3.3.1]non-3-yl, (1R,5S)-9-azabicyclo[3.3.1]non-3-yl, 2,5-diazabicyclo[2.2.1]hept-2-yl, (1S,4S)-2,5-diazabicyclo[2.2.1]hept-2-yl, 2,5-diazabicyclo[2.2.2]oct-2-yl, 3,8-diazabicyclo[3.2.1]oct-3-yl, (1R,5S)-3,8-diazabicyclo[3.2.1]oct-3-yl, 1,4-diazabicyclo[3.2.2]non-4-yl, azaspiro[3.3]hept-2-yl, 2,6-diazaspiro[3.3]hept-2-yl, 2,7-diazaspiro[3.5]non-7-yl, 5,8-diazaspiro[3.5]non-8-yl, 2,7-diazaspiro[4.4]non-2-yl or 6,9-diazaspiro[4.5]dec-9-yl; wherein, each instance of heterocyclyl is optionally substituted with R$_3$ and R$_4$ substituents.

In another embodiment of a compound of Formula (I), R$_1$ is substituted heterocyclyl selected from 4-methyl-1,4-diazepan-1-yl, (3aS,6aS)-1-methylhexahydropyrrolo[3,4-b]pyrrol-5(1H)-yl, (3aS,6aS)-5-methylhexahydropyrrolo[3,4-b]pyrrol-1(2H)-yl, (3aR,6aR)-1-methylhexahydropyrrolo[3,4-b]pyrrol-5(1H)-yl, (3aR,6aS)-5-methylhexahydropyrrolo[3,4-c]pyrrol-2(1H)-yl, (3aR,6aS)-5-(2-hydroxyethyl)hexahydropyrrolo[3,4-c]pyrrol-2(1H)-yl, (3aR,6aS)-5-(propan-2-yl)hexahydropyrrolo[3,4-c]pyrrol-2(1H)-yl, (3aR,6aS)-5-ethylhexahydropyrrolo[3,4-c]pyrrol-2(1H)-yl, (4aR,7aR)-1-methyloctahydro-6H-pyrrolo[3,4-b]pyridin-6-yl, (4aR,7aR)-1-ethyloctahydro-6H-pyrrolo[3,4-b]pyridin-6-yl, (4aR,7aR)-1-(2-hydroxyethyl)octahydro-6H-pyrrolo[3,4-b]pyridin-6-yl, (4aS,7aS)-1-methyloctahydro-6H-pyrrolo[3,4-b]pyridin-6-yl, (4aS,7aS)-1-(2-hydroxyethyl)octahydro-6H-pyrrolo[3,4-b]pyridin-6-yl, (7R,8aS)-7-hydroxyhexahydropyrrolo[1,2-a]pyrazin-2(1H)-yl, (8aS)-8a-methyloctahydropyrrolo[1,2-a]pyrazin-2(1H)-yl, (8aR)-8a-methyloctahydropyrrolo[1,2-a]pyrazin-2(1H)-yl, (1R,5S,6s)-6-(dimethylamino)-3-azabicyclo[3.1.0]hex-3-yl, (1R,5S)-8-methyl-8-azabicyclo[3.2.1]oct-3-yl, 9-methyl-9-azabicyclo[3.3.1]non-3-yl, (3-exo)-9-methyl-9-azabicyclo[3.3.1]non-3-yl, (1R,5S)-9-methyl-9-azabicyclo[3.3.1]non-3-yl, (1S,4S)-5-methyl-2,5-diazabicyclo[2.2.1]hept-2-yl or (1S,4S)-5-ethyl-2,5-diazabicyclo[2.2.1]hept-2-yl.

In one embodiment of a compound of Formula (I), R$_1$ is heterocyclyl-C$_{1-8}$alkyl, wherein heterocyclyl is selected from morpholinyl, piperidinyl, piperazinyl, imidazolyl or pyrrolidinyl; and, wherein, each instance of heterocyclyl is optionally substituted with R$_3$ and R$_4$ substituents.

In another embodiment of a compound of Formula (I), R$_1$ is heterocyclyl-C$_{1-8}$alkyl selected from morpholin-4-yl-methyl, morpholin-4-yl-ethyl, morpholin-4-yl-propyl, piperidin-1-yl-methyl, piperazin-1-yl-methyl, piperazin-1-yl-ethyl, piperazin-1-yl-propyl, piperazin-1-yl-butyl, imidazol-1-yl-methyl, imidazol-1-yl-ethyl, imidazol-1-yl-propyl, imidazol-1-yl-butyl, pyrrolidin-1-yl-methyl, pyrrolidin-1-yl-ethyl, pyrrolidin-1-yl-propyl or pyrrolidin-1-yl-butyl;

wherein, each instance of heterocyclyl is optionally substituted with $R_3$ and $R_4$ substituents.

In one embodiment of a compound of Formula (I), $R_1$ is heterocyclyl-$C_{1-8}$alkoxy, wherein heterocyclyl is selected from pyrrolidinyl, piperidinyl or morpholinyl; and, wherein, each instance of heterocyclyl is optionally substituted with $R_3$ and $R_4$ substituents.

In another embodiment of a compound of Formula (I), $R_1$ is heterocyclyl-$C_{1-8}$alkoxy selected from pyrrolidin-2-yl-methoxy, pyrrolidin-2-yl-ethoxy, pyrrolidin-1-yl-methoxy, pyrrolidin-1-yl-ethoxy, piperidin-1-yl-methoxy, piperidin-1-yl-ethoxy, morpholin-4-yl-methoxy or morpholin-4-yl-ethoxy; wherein, each instance of heterocyclyl is optionally substituted with $R_3$ and $R_4$ substituents.

In one embodiment of a compound of Formula (I), $R_1$ is heterocyclyl-amino, wherein heterocyclyl is selected from azetidinyl, pyrrolidinyl, piperidinyl, 9-azabicyclo[3.3.1]nonyl or (1R,5S)-9-azabicyclo[3.3.1]nonyl; and, wherein, each instance of heterocyclyl is optionally substituted with $R_3$ and $R_4$ substituents.

In another embodiment of a compound of Formula (I), $R_1$ is heterocyclyl-amino selected from azetidin-3-yl-amino, pyrrolidin-3-yl-amino, piperidin-4-yl-amino, 9-azabicyclo[3.3.1]non-3-yl-amino, (1R,5S)-9-azabicyclo[3.3.1]non-3-yl-amino, 9-methyl-9-azabicyclo[3.3.1]non-3-yl-amino, (3-exo)-9-methyl-9-azabicyclo[3.3.1]non-3-yl-amino or (1R,5S)-9-methyl-9-azabicyclo[3.3.1]non-3-yl-amino; wherein, each instance of heterocyclyl is optionally substituted with $R_3$ and $R_4$ substituents.

In one embodiment of a compound of Formula (I), $R_1$ is (heterocyclyl)($C_{1-8}$alkyl)amino, wherein heterocyclyl is selected from pyrrolidinyl or piperidinyl; and, wherein, each instance of heterocyclyl is optionally substituted with $R_3$ and $R_4$ substituents.

In another embodiment of a compound of Formula (I), $R_1$ is (heterocyclyl)($C_{1-8}$alkyl)amino selected from (pyrrolidin-3-yl)(methyl)amino or (piperidin-4-yl)(methyl)amino; wherein, each instance of heterocyclyl is optionally substituted with $R_3$ and $R_4$ substituents.

In one embodiment of a compound of Formula (I), $R_1$ is heterocyclyl-amino-$C_{1-8}$alkyl, wherein heterocyclyl is selected from tetrahydrofuranyl; and, wherein, each instance of heterocyclyl is optionally substituted with $R_3$ and $R_4$ substituents.

In another embodiment of a compound of Formula (I), $R_1$ is heterocyclyl-amino-$C_{1-8}$alkyl, selected from 3-(tetrahydrofuran-3-yl-amino)propyl; wherein, each instance of heterocyclyl is optionally substituted with $R_3$ and $R_4$ substituents.

In one embodiment of a compound of Formula (I), $R_1$ is heterocyclyl-$C_{1-8}$alkyl-amino-$C_{1-8}$alkyl, wherein heterocyclyl is selected from tetrahydrofuranyl, thienyl or pyridinyl; and, wherein, each instance of heterocyclyl is optionally substituted with $R_3$ and $R_4$ substituents.

In another embodiment of a compound of Formula (I), $R_1$ is heterocyclyl-$C_{1-8}$alkyl-amino-$C_{1-8}$alkyl, selected from 3-[(tetrahydrofuran-2-ylmethyl)amino]propyl, 3-[(thienyl-3-ylmethyl)amino]propyl, 3-[(pyridin-2-ylmethyl)amino]propyl or 3-[(pyridin-4-ylmethyl)amino]propyl; wherein, each instance of heterocyclyl is optionally substituted with $R_3$ and $R_4$ substituents.

In one embodiment of a compound of Formula (I), $R_1$ is heterocyclyl-oxy, wherein heterocyclyl is selected from pyrrolidinyl or piperidinyl; and, wherein, each instance of heterocyclyl is optionally substituted with $R_3$ and $R_4$ substituents.

In another embodiment of a compound of Formula (I), $R_1$ is heterocyclyl-oxy selected from pyrrolidin-3-yl-oxy or piperidin-4-yl-oxy; wherein, each instance of heterocyclyl is optionally substituted with $R_3$ and $R_4$ substituents.

In one embodiment of a compound of Formula (I), $R_1$ is heterocyclyl-carbonyl, wherein heterocyclyl is selected from piperazinyl; and, wherein, each instance of heterocyclyl is optionally substituted with $R_3$ and $R_4$ substituents.

In another embodiment of a compound of Formula (I), $R_1$ is heterocyclyl-carbonyl selected from piperazin-1-yl-carbonyl; wherein, each instance of heterocyclyl is optionally substituted with $R_3$ and $R_4$ substituents.

In one embodiment of a compound of Formula (I), $R_1$ is heterocyclyl-carbonyl-oxy, wherein heterocyclyl is selected from piperazinyl; and, wherein, each instance of heterocyclyl is optionally substituted with $R_3$ and $R_4$ substituents.

In another embodiment of a compound of Formula (I), $R_1$ is heterocyclyl-carbonyl-oxy selected from piperazin-1-yl-carbonyl-oxy; wherein, each instance of heterocyclyl is optionally substituted with $R_3$ and $R_4$ substituents.

In one embodiment of a compound of Formula (I), $R_1$ is $C_{3-14}$cycloalkyl selected from cyclopropyl, cyclobutyl, cyclopentyl, cyclohexyl, cyclohexenyl or cycloheptyl; wherein, each instance of $C_{3-14}$cycloalkyl is optionally substituted with $R_3$ and $R_4$ substituents.

In another embodiment of a compound of Formula (I), $R_1$ is $C_{3-8}$cycloalkyl selected from cyclopropyl, cyclobutyl, cyclopentyl, cyclohexyl, cyclohexenyl or cycloheptyl; wherein, each instance of $C_{3-8}$cycloalkyl is optionally substituted with $R_3$ and $R_4$ substituents.

In one embodiment of a compound of Formula (I), $R_1$ is aryl-$C_{1-8}$alkyl-amino-$C_{1-8}$alkyl, wherein aryl is selected from phenyl; and, wherein, each instance of aryl is optionally substituted with $R_3$ and $R_4$ substituents.

In another embodiment of a compound of Formula (I), $R_1$ is aryl-$C_{1-8}$alkyl-amino-$C_{1-8}$alkyl selected from 3-(benzylamino)propyl; wherein, each instance of aryl is optionally substituted with $R_3$ and $R_4$ substituents.

In one embodiment of a compound of Formula (I), $R_1$ is heteroaryl, wherein heteroaryl is selected from pyridinyl; and, wherein, each instance of heteroaryl is optionally substituted with $R_3$ and $R_4$ substituents.

In another embodiment of a compound of Formula (I), $R_1$ is heteroaryl selected from pyridin-4-yl; wherein, each instance of heteroaryl is optionally substituted with $R_3$ and $R_4$ substituents.

In one embodiment of a compound of Formula (I), $R_1$ is heteroaryl-$C_{1-8}$alkyl, wherein heteroaryl is selected from 1H-imidazolyl; and, wherein, each instance of heteroaryl is optionally substituted with $R_3$ and $R_4$ substituents.

In another embodiment of a compound of Formula (I), $R_1$ is heteroaryl-$C_{1-8}$alkyl selected from 1H-imidazol-1-yl-methyl; wherein, each instance of heteroaryl is optionally substituted with $R_3$ and $R_4$ substituents.

In one embodiment of a compound of Formula (I), $R_1$ is (heteroaryl-$C_{1-8}$alkyl)($C_{1-8}$alkyl)amino, wherein heteroaryl is selected from pyridinyl; and, wherein, each instance of heteroaryl is optionally substituted with $R_3$ and $R_4$ substituents.

In another embodiment of a compound of Formula (I), $R_1$ is (heteroaryl-$C_{1-8}$alkyl)($C_{1-8}$alkyl)amino selected from (pyridin-3-ylmethyl)(methyl)amino; wherein, each instance of heteroaryl is optionally substituted with $R_3$ and $R_4$ substituents.

In one embodiment of a compound of Formula (I), $R_1$ is heteroaryl-$C_{1-8}$alkyl-amino-$C_{1-8}$alkyl, wherein heteroaryl is selected from thienyl or pyridinyl; and, wherein, each instance of heteroaryl is optionally substituted with $R_3$ and $R_4$ substituents.

In another embodiment of a compound of Formula (I), $R_1$ is heteroaryl-$C_{1-8}$alkyl-amino-$C_{1-8}$alkyl selected from thien-3-yl-methyl-amino-propyl, pyridin-2-yl-methyl-amino-propyl, pyridin-3-yl-methyl-amino-propyl or pyridin-4-yl-methyl-amino-propyl; wherein, each instance of heteroaryl is optionally substituted with $R_3$ and $R_4$ substituents.

In one embodiment of a compound of Formula (I), $R_3$ is selected from cyano, halogen, hydroxy, oxo, $C_{1-8}$alkyl, halo-$C_{1-8}$alkyl, $C_{1-8}$alkyl-carbonyl, $C_{1-8}$alkoxy, halo-$C_{1-8}$alkoxy, $C_{1-8}$alkoxy-$C_{1-8}$alkyl, $C_{1-8}$alkoxy-carbonyl, amino, $C_{1-8}$alkyl-amino, $(C_{1-8}$alkyl$)_2$-amino, amino-$C_{1-8}$alkyl, $C_{1-8}$alkyl-amino-$C_{1-8}$alkyl, $(C_{1-8}$alkyl$)_2$-amino-$C_{1-8}$alkyl, amino-$C_{1-8}$alkyl-amino, $C_{1-8}$alkyl-amino-$C_{1-8}$alkyl-amino, $(C_{1-8}$alkyl$)_2$-amino-$C_{1-8}$alkyl-amino, $C_{1-8}$alkoxy-$C_{1-8}$alkyl-amino, $C_{1-8}$alkyl-carbonyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl$)_2$-amino or (hydroxy-$C_{1-8}$alkyl)($C_{1-8}$alkyl)amino.

In another embodiment of a compound of Formula (I), $R_3$ is selected from cyano, halogen, hydroxy, oxo, $C_{1-8}$alkyl, halo-$C_{1-8}$alkyl, $C_{1-8}$alkoxy, $C_{1-8}$alkoxy-$C_{1-8}$alkyl, $C_{1-8}$alkoxy-carbonyl, amino, $C_{1-8}$alkyl-amino, $(C_{1-8}$alkyl$)_2$-amino, amino-$C_{1-8}$alkyl, $C_{1-8}$alkyl-amino-$C_{1-8}$alkyl, $(C_{1-8}$alkyl$)_2$-amino-$C_{1-8}$alkyl, $C_{1-8}$alkyl-amino-$C_{1-8}$alkyl-amino, $C_{1-8}$alkoxy-$C_{1-8}$alkyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl$)_2$-amino or (hydroxy-$C_{1-8}$alkyl)($C_{1-8}$alkyl)amino.

In one embodiment of a compound of Formula (I), $R_3$ is $C_{1-8}$alkyl selected from methyl, ethyl, propyl, isopropyl or tert-butyl.

In another embodiment of a compound of Formula (I), $R_3$ is $C_{1-8}$alkyl selected from ethyl, propyl, isopropyl or tert-butyl.

In one embodiment of a compound of Formula (I), $R_3$ is halo-$C_{1-8}$alkyl selected from trihalo-methyl, dihalo-methyl, halo-methyl, trihalo-ethyl, dihalo-ethyl, halo-ethyl, trihalo-propyl, dihalo-propyl or halo-propyl; wherein, halo is selected from fluoro, chloro, bromo or iodo.

In another embodiment of a compound of Formula (I), $R_3$ is halo-$C_{1-8}$alkyl selected from trihalo-methyl, dihalo-methyl, halo-methyl, trihalo-ethyl, dihalo-ethyl, trihalo-propyl or dihalo-propyl; wherein, halo is selected from fluoro, chloro, bromo or iodo.

In one embodiment of a compound of Formula (I), $R_3$ is hydroxy-$C_{1-8}$alkyl selected from hydroxy-methyl, hydroxy-ethyl, hydroxy-propyl, dihydroxy-propyl, hydroxy-butyl or dihydroxy-butyl.

In another embodiment of a compound of Formula (I), $R_3$ is hydroxy-$C_{1-8}$alkyl selected from hydroxy-methyl, dihydroxy-propyl, hydroxy-butyl or dihydroxy-butyl.

In one embodiment of a compound of Formula (I), $R_3$ is $C_{1-8}$alkoxy selected from methoxy, ethoxy, propoxy or isopropoxy.

In another embodiment of a compound of Formula (I), $R_3$ is halo-$C_{1-8}$alkoxy selected from trihalo-methoxy, dihalo-methoxy, halo-methoxy, trihalo-ethoxy, dihalo-ethoxy, halo-ethoxy, trihalo-propoxy, dihalo-propoxy or halo-propoxy; wherein, halo is selected from fluoro, chloro, bromo or iodo.

In one embodiment of a compound of Formula (I), $R_3$ is $C_{1-8}$alkoxy-carbonyl-amino selected from methoxy-carbonyl-amino, ethoxy-carbonyl-amino, propoxy-carbonyl-amino, isopropoxy-carbonyl-amino, tert-butoxy-carbonyl-amino.

In one embodiment of a compound of Formula (I), $R_4$ is $C_{3-14}$cycloalkyl selected from cyclopropyl, cyclobutyl, cyclopentyl, cyclohexyl or cycloheptyl; wherein, each instance of $C_{3-14}$cycloalkyl is optionally substituted with $R_5$ substituents.

In another embodiment of a compound of Formula (I), $R_4$ is $C_{3-8}$cycloalkyl selected from cyclopropyl, cyclobutyl, cyclopentyl, cyclohexyl or cycloheptyl; wherein, each instance of $C_{3-8}$cycloalkyl is optionally substituted with $R_5$ substituents.

In one embodiment of a compound of Formula (I), $R_4$ is $C_{3-14}$cycloalkyl-$C_{1-8}$alkyl, wherein $C_{3-14}$cycloalkyl is selected from cyclopropyl, cyclobutyl, cyclopentyl, cyclohexyl or cycloheptyl; and, wherein, each instance of $C_{3-14}$cycloalkyl is optionally substituted with $R_5$ substituents.

In another embodiment of a compound of Formula (I), $R_4$ is $C_{3-8}$cycloalkyl-$C_{1-8}$alkyl, wherein $C_{3-8}$cycloalkyl is selected from cyclopropyl, cyclobutyl, cyclopentyl, cyclohexyl or cycloheptyl; and, wherein, each instance of $C_{3-8}$cycloalkyl is optionally substituted with $R_5$ substituents.

In one embodiment of a compound of Formula (I), $R_4$ is $C_{3-14}$cycloalkyl-amino, wherein $C_{3-14}$cycloalkyl is selected from cyclopropyl, cyclobutyl, cyclopentyl, cyclohexyl or cycloheptyl; and, wherein, each instance of $C_{3-14}$cycloalkyl is optionally substituted with $R_5$ substituents.

In another embodiment of a compound of Formula (I), $R_4$ is $C_{3-8}$cycloalkyl-amino, wherein $C_{3-8}$cycloalkyl is selected from cyclopropyl, cyclobutyl, cyclopentyl, cyclohexyl or cycloheptyl; and, wherein, each instance of $C_{3-8}$cycloalkyl is optionally substituted with $R_5$ substituents.

In one embodiment of a compound of Formula (I), $R_4$ is aryl-$C_{1-8}$alkyl, aryl-$C_{1-8}$alkoxy-carbonyl or aryl-sulfonyloxy-$C_{1-8}$alkyl, wherein aryl is selected from phenyl; and, wherein, each instance of aryl is optionally substituted with $R_5$ substituents.

In another embodiment of a compound of Formula (I), $R_4$ is aryl-$C_{1-8}$alkyl or aryl-$C_{1-8}$alkoxy-carbonyl, wherein each instance of aryl is optionally substituted with $R_5$ substituents.

In one embodiment of a compound of Formula (I), $R_4$ is heterocyclyl selected from oxetanyl, pyrrolidinyl, piperidinyl, piperazinyl, 1,3-dioxanyl or morpholinyl, wherein each instance of heterocyclyl is optionally substituted with $R_5$ substituents.

In another embodiment of a compound of Formula (I), $R_4$ is heterocyclyl selected from oxetan-3-yl, pyrrolidin-1-yl, piperidin-1-yl, piperazin-1-yl, 1,3-dioxan-5-yl or morpholin-4-yl, wherein each instance of heterocyclyl is optionally substituted with $R_5$ substituents.

In one embodiment of a compound of Formula (I), $R_4$ is heterocyclyl-$C_{1-8}$alkyl, wherein each instance of heterocyclyl is selected from pyrrolidinyl or piperidinyl; and, wherein, each instance of heterocyclyl is optionally substituted with $R_5$ substituents.

In another embodiment of a compound of Formula (I), $R_4$ is heterocyclyl-$C_{1-8}$alkyl selected from pyrrolidin-1-yl-$C_{1-8}$alkyl or piperidin-1-yl-$C_{1-8}$alkyl, wherein each instance of heterocyclyl is optionally substituted with $R_5$ substituents.

In one embodiment of a compound of Formula (I), $R_5$ is selected from halogen, hydroxy, cyano, nitro, halo-$C_{1-8}$alkyl, $C_{1-8}$alkoxy, halo-$C_{1-8}$alkoxy, amino, $C_{1-8}$alkyl-amino, $(C_{1-8}$alkyl$)_2$-amino or $C_{1-8}$alkyl-thio; wherein, halogen and halo is selected from fluoro, chloro, bromo or iodo.

In one embodiment of a compound of Formula (I), $R_5$ is hydroxy.

In one embodiment of a compound of Formula (I), $R_5$ is $C_{1-8}$alkyl selected from methyl, ethyl, propyl, isopropyl, n-butyl or tert-butyl.

In another embodiment of a compound of Formula (I), $R_5$ is $C_{1-8}$alkyl selected from ethyl, propyl, isopropyl or tert-butyl.

In one embodiment of a compound of Formula (I), $R_5$ is halo-$C_{1-8}$alkyl selected from trihalo-methyl, dihalo-methyl, halo-methyl, trihalo-ethyl, dihalo-ethyl, halo-ethyl, trihalo-propyl, dihalo-propyl or halo-propyl; wherein, halo is selected from fluoro, chloro, bromo or iodo.

In one embodiment of a compound of Formula (I), $R_5$ is $C_{1-8}$alkoxy selected from methoxy, ethoxy, propoxy or isopropoxy.

In one embodiment of a compound of Formula (I), $R_5$ is halo-$C_{1-8}$alkoxy selected from trihalo-methoxy, dihalo-methoxy, halo-methoxy, trihalo-ethoxy, dihalo-ethoxy, halo-ethoxy, trihalo-propoxy, dihalo-propoxy or halo-propoxy; wherein, halo is selected from fluoro, chloro, bromo or iodo.

In one embodiment of a compound of Formula (I), $R_2$ is aryl selected from phenyl optionally substituted with $R_6$ and $R_7$ substituents.

In one embodiment of a compound of Formula (I), $R_2$ is aryl-amino, wherein aryl is selected from phenyl; and, wherein, each instance of aryl is optionally substituted with $R_6$ and $R_7$ substituents.

In another embodiment of a compound of Formula (I), $R_2$ is aryl-amino selected from phenyl-amino; wherein, each instance of aryl is optionally substituted with $R_6$ and $R_7$ substituents.

In one embodiment of a compound of Formula (I), $R_2$ is aryl-amino-carbonyl, wherein aryl is selected from phenyl; and, wherein, each instance of aryl is optionally substituted with $R_6$ and $R_7$ substituents.

In another embodiment of a compound of Formula (I), $R_2$ is aryl-amino-carbonyl selected from phenyl-amino-carbonyl; wherein, each instance of aryl is optionally substituted with $R_6$ and $R_7$ substituents.

In one embodiment of a compound of Formula (I),
$R_2$ is heterocyclyl selected from 1,2,3,6-tetrahydropyridinyl, 1,3-benzodioxolyl or 2,3-dihydro-1,4-benzodioxinyl; wherein, each instance of heterocyclyl is optionally substituted with $R_6$ and $R_7$ substituents.

In another embodiment of a compound of Formula (I),
$R_2$ is heterocyclyl selected from 1,2,3,6-tetrahydropyridin-4-yl, 1,3-benzodioxol-5-yl or 2,3-dihydro-1,4-benzodioxin-6-yl; wherein, each instance of heterocyclyl is optionally substituted with $R_6$ and $R_7$ substituents.

In one embodiment of a compound of Formula (I),
$R_2$ is heteroaryl selected from thienyl, 1H-pyrazolyl, 1H-imidazolyl, 1,3-thiazolyl, 1,2,4-oxadiazolyl, 1,3,4-oxadiazolyl, pyridinyl, pyrimidinyl, 1H-indolyl, 2H-indolyl, 1H-indazolyl, 2H-indazolyl, indolizinyl, benzofuranyl, benzothienyl, 1H-benzimidazolyl, 1,3-benzothiazolyl, 1,3-benzoxazolyl, 9H-purinyl, furo[3,2-b]pyridinyl, furo[3,2-c]pyridinyl, furo[2,3-c]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl, [1,3]oxazolo[4,5-b]pyridinyl or quinoxalinyl; wherein, each instance of heteroaryl is optionally substituted with $R_6$ and $R_7$ substituents.

In another embodiment of a compound of Formula (I), $R_2$ is heteroaryl selected from thien-2-yl, thien-3-yl, 1H-pyrazol-3-yl, 1H-pyrazol-4-yl, 1H-pyrazol-5-yl, 1H-imidazol-1-yl, 1H-imidazol-4-yl, 1,3-thiazol-2-yl, 1,2,4-oxadiazol-3-yl, 1,3,4-oxadiazol-2-yl, pyridin-2-yl, pyridin-3-yl, pyridin-4-yl, pyrimidin-4-yl, 1H-indol-3-yl, 1H-indol-4-yl, 1H-indol-5-yl, 1H-indol-6-yl, 1H-indazol-5-yl, 2H-indazol-5-yl, indolizin-2-yl, benzofuran-2-yl, benzofuran-5-yl, benzothien-2-yl, benzothien-3-yl, 1H-benzimidazol-2-yl, 1H-benzimidazol-6-yl, 1,3-benzoxazol-2-yl, 1,3-benzoxazol-5-yl, 1,3-benzoxazol-6-yl, 1,3-benzothiazol-2-yl, 1,3-benzothiazol-5-yl, 1,3-benzothiazol-6-yl, 9H-purin-8-yl, furo[3,2-b]pyridin-2-yl, furo[3,2-c]pyridin-2-yl, furo[2,3-c]pyridin-2-yl, thieno[3,2-c]pyridin-2-yl, thieno[2,3-d]pyrimidin-6-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrazolo[1,5-a]pyridin-2-yl, pyrazolo[1,5-a]pyrazin-2-yl, imidazo[1,2-a]pyridin-2-yl, imidazo[1,2-a]pyridin-6-yl, imidazo[1,2-a]pyrimidin-2-yl, imidazo[1,2-a]pyrimidin-6-yl, imidazo[1,2-c]pyrimidin-2-yl, imidazo[1,2-b]pyridazin-2-yl, imidazo[1,2-a]pyrazin-2-yl, imidazo[2,1-b][1,3]thiazol-6-yl, imidazo[2,1-b][1,3,4]thiadiazol-6-yl, [1,3]oxazolo[4,5-b]pyridin-2-yl or quinoxalin-2-yl; wherein, each instance of heteroaryl is optionally substituted with $R_6$ and $R_7$ substituents.

In another embodiment of a compound of Formula (I), $R_2$ is substituted heteroaryl selected from 4-methylthien-2-yl, 1-methyl-1H-pyrazol-3-yl, 4-methyl-1H-pyrazol-3-yl, 1-phenyl-1H-pyrazol-3-yl, 1-phenyl-1H-imidazol-4-yl, 2-methyl-1-(pyridin-2-yl)-1H-imidazol-4-yl, 4-methyl-1,3-thiazol-2-yl, 4-(trifluoromethyl)-1,3-thiazol-2-yl, 4-phenyl-1,3-thiazol-2-yl, 5-phenyl-1,2,4-oxadiazol-3-yl, 3-fluoropyridin-4-yl, 6-fluoropyridin-2-yl, 2-chloropyridin-4-yl, 4-chloropyridin-3-yl, 5-chloropyridin-2-yl, 6-methylpyridin-3-yl, 2-(trifluoromethyl)pyridin-3-yl, 4-(trifluoromethyl)pyridin-2-yl, 6-(trifluoromethyl)pyridin-2-yl, 2-methoxypyridin-4-yl, 4-methoxypyridin-3-yl, 6-methoxypyridin-2-yl, 2-ethoxypyridin-3-yl, 6-ethoxypyridin-2-yl, 6-(propan-2-yloxy)pyridin-2-yl, 6-(dimethylamino)pyridin-3-yl, 6-(methylsulfanyl)pyridin-2-yl, 6-(cyclobutyloxy)pyridin-2-yl, 6-(pyrrolidin-1-yl)pyridin-2-yl, 2-methylpyrimidin-4-yl, 2-(propan-2-yl)pyrimidin-4-yl, 2-cyclopropylpyrimidin-4-yl, 1-methyl-1H-indol-3-yl, 2-methyl-2H-indazol-5-yl, 2-methyl-1-benzofuran-5-yl, 1-methyl-1H-benzimidazol-2-yl, 4-methyl-1H-benzimidazol-2-yl 5-fluoro-1H-benzimidazol-2-yl, 4-fluoro-1,3-benzoxazol-2-yl, 5-fluoro-1,3-benzoxazol-2-yl, 4-chloro-1,3-benzoxazol-2-yl, 4-iodo-1,3-benzoxazol-2-yl, 2-methyl-1,3-benzoxazol-6-yl, 4-methyl-1,3-benzoxazol-2-yl, 4-(trifluoromethyl)-1,3-benzoxazol-2-yl, 7-(trifluoromethyl)-1,3-benzoxazol-2-yl, 2-methyl-1,3-benzothiazol-2-yl, 2-methyl-1,3-benzothiazol-5-yl, 2-methyl-1,3-benzothiazol-6-yl, 4-chloro-1,3-benzothiazol-2-yl, 7-chloro-1,3-benzothiazol-2-yl, 4-(trifluoromethyl)-1,3-benzothiazol-2-yl, 5-methylfuro[3,2-b]pyridin-2-yl, 4,6-dimethylfuro[3,2-c]pyridin-2-yl, 5,7-dimethylfuro[2,3-c]pyridin-2-yl, 4,6-dimethylthieno[3,2-c]pyridin-2-yl, 2,4-dimethylthieno[2,3-d]pyrimidin-6-yl, 1-methylpyrrolo[1,2-a]pyrazin-7-yl, 3-methylpyrrolo[1,2-a]pyrazin-7-yl, 1,3-dimethylpyrrolo[1,2-a]pyrazin-7-yl, 2-methylpyrrolo[1,2-b]pyridazin-2-yl, 4,6-dimethylpyrazolo[1,5-c]pyrazin-2-yl, 5-methylpyrazolo[1,5-c]pyridin-2-yl, 4,6-dimethylpyrazolo[1,5-c]pyrazin-2-yl, 2-chloroimidazo[2,1-b][1,3]thiazol-6-yl, 2-methylimidazo[2,1-b][1,3]thiazol-6-yl, 3-methylimidazo[2,1-b][1,3]thiazol-6-yl, 2-ethylimidazo[2,1-b][1,3]thiazol-6-yl, 2-methylimidazo[2,1-b][1,3,4]thiadiazol-6-yl, 6-cyanoimidazo[1,2-a]pyridin-2-yl (also referred to as 2-imidazo[1,2-a]pyridine-6-carbonitrile), 6-fluoroimidazo[1,2-a]pyridin-2-yl, 8-fluoroimidazo[1,2-a]pyridin-2-yl, 6,8-difluoroimidazo[1,2-c]pyridin-2-yl, 7-(trifluoromethyl)imidazo[1,2-a]pyridin-2-yl, 8-(trifluoromethyl)imidazo[1,2-a]pyridin-2-yl, 6-chloroimidazo[1,2-c]pyridin-2-yl, 7-chloroimidazo[1,2-c]pyridin-2-yl, 8-chloroimidazo[1,2-c]pyridin-2-yl, 8-bromoimidazo[1,2-c]pyridin-2-yl, 2-methylimidazo[1,2-c]pyridin-2-yl, 5-methylimidazo[1,2-c]pyridin-2-yl, 6-methylimidazo[1,2-c]pyridin-2-yl, 7-methylimidazo[1,2-c]pyridin-2-yl, 8-methylimidazo[1,2-c]pyridin-2-yl, 7-ethylimidazo[1,2-c]pyridin-2-yl, 8-ethylimidazo[1,2-c]pyridin-2-yl, 6,8-dimethylimidazo[1,2-c]pyridin-2-yl, 8-ethyl-6-methylimidazo[1,2-c]pyridin-2-yl, 7-methoxyimidazo[1,2-c]pyridin-2-yl, 8-methoxyimidazo[1,2-c]pyridin-2-yl, 6-fluoro-8-methylimidazo[1,2-c]pyridin-2-yl, 8-fluoro-6-methylimidazo[1,2-c]pyridin-2-yl, 8-chloro-6-methylimidazo[1,2-c]pyridin-2-yl, 6-methyl-8-nitroimidazo[1,2-c]pyridin-2-yl, 8-cyclopropylimidazo[1,2-c]pyridin-2-yl, 2-methylimidazo[1,2-c]pyridin-6-yl, 2-ethylimidazo[1,2-c]pyridin-6-yl, 2,3-dimethylimidazo[1,2-c]pyridin-6-yl, 2,8-dimethylimidazo[1,2-c]pyridin-6-yl, 2-(trifluoromethyl)imidazo[1,2-a]pyridin-6-yl, 8-chloro-2-methylimidazo[1,2-c]pyridin-6-yl, 8-fluoro-2-methylimidazo[1,2-c]pyridin-6-yl, 6-fluoroimidazo[1,2-c]pyrimidin-2-yl, 6-chloroimidazo[1,2-c]pyrimidin-2-yl, 6-methylimidazo[1,2-c]pyrimidin-2-yl, 7-methylimidazo[1,2-c]pyrimidin-2-yl, 2-methylimidazo[1,2-c]pyrimidin-6-yl, 6-methylimidazo[1,2-b]pyridazin-2-yl, 2-methyl-3-(1,2,3,6-tetrahydropyridin-4-yl)imidazo[1,2-b]pyridazin-6-yl, 6-methylimidazo[1,2-c]pyrazin-2-yl, 8-methylimidazo[1,2-c]pyrazin-2-yl, 6,8-dimethylimidazo[1,2-a]pyrazin-2-yl, 6-chloro-8-methylimidazo[1,2-c]pyrazin-2-yl, 6-methyl-8-(trifluoromethyl)imidazo[1,2-a]pyrazin-2-yl, 8-(methylsulfanyl)imidazo[1,2-a]pyrazin-2-yl, 2-methylimidazo[2,1-b][1,3]thiazol-6-yl, 3-methylimidazo[2,1-b][1,3]thiazol-6-yl or 2-methylimidazo[2,1-b][1,3,4]thiadiazol-6-yl.

In another embodiment of a compound of Formula (I), $R_2$ is heteroaryl selected from thienyl, 1H-pyrazolyl, 1H-imidazolyl, 1,3-thiazolyl, 1,2,4-oxadiazolyl, 1,3,4-oxadiazolyl, pyridinyl, pyrimidinyl, 1H-indolyl, 2H-indolyl, 1H-indazolyl, 2H-indazolyl, indolizinyl, benzofuranyl, benzothienyl, 1H-benzimidazolyl, 1,3-benzothiazolyl, 1,3-benzoxazolyl, 9H-purinyl; wherein, each instance of heteroaryl is optionally substituted with $R_6$ and $R_7$ substituents.

In another embodiment of a compound of Formula (I), $R_2$ is heteroaryl selected from furo[3,2-b]pyridinyl, furo[3,2-c]pyridinyl, furo[2,3-c]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl, [1,3]oxazolo[4,5-b]pyridinyl or quinoxalinyl; wherein, each instance of heteroaryl is optionally substituted with $R_6$ and $R_7$ substituents.

In one embodiment of a compound of Formula (I), $R_2$ is heteroaryl-amino, wherein heteroaryl is selected from pyridinyl or pyrimidinyl; and, wherein, each instance of heteroaryl is optionally substituted with $R_6$ and $R_7$ substituents.

In another embodiment of a compound of Formula (I), $R_2$ is heteroaryl-amino selected from pyridin-2-yl-amino, pyridin-3-yl-amino or pyrimidin-2-yl-amino; wherein, each instance of heteroaryl is optionally substituted with $R_6$ and $R_7$ substituents.

In one embodiment of a compound of Formula (I), $R_6$ is selected from halogen, hydroxy, cyano, nitro, $C_{1-8}$ alkyl, halo-$C_{1-8}$alkyl, hydroxy-$C_{1-8}$alkyl, $C_{1-8}$alkoxy, halo-$C_{1-8}$alkoxy, $C_{1-8}$alkoxy-$C_{1-8}$alkyl, $(C_{1-8}$alkyl$)_2$-amino or $C_{1-8}$alkyl-thio; wherein, halogen and halo is selected from fluoro, chloro, bromo or iodo.

In one embodiment of a compound of Formula (I), $R_6$ is $C_{1-8}$alkyl selected from methyl, ethyl, propyl, isopropyl or tert-butyl.

In another embodiment of a compound of Formula (I), $R_6$ is $C_{1-8}$alkyl selected from ethyl, propyl, isopropyl or tert-butyl.

In one embodiment of a compound of Formula (I), $R_6$ is $C_{2-8}$alkenyl selected from ethenyl, allyl or buta-1,3-dienyl.

In another embodiment of a compound of Formula (I), $R_6$ is $C_{2-8}$alkenyl selected from ethenyl or allyl.

In one embodiment of a compound of Formula (I), $R_6$ is halo-$C_{1-8}$alkyl selected from trihalo-methyl, dihalo-methyl, halo-methyl, trihalo-ethyl, dihalo-ethyl, halo-ethyl, trihalo-propyl, dihalo-propyl or halo-propyl; wherein, halo is selected from fluoro, chloro, bromo or iodo.

In one embodiment of a compound of Formula (I), $R_6$ is hydroxy-$C_{1-8}$alkyl selected from hydroxy-methyl, hydroxy-ethyl, hydroxy-propyl, dihydroxy-propyl, hydroxy-butyl or dihydroxy-butyl.

In another embodiment of a compound of Formula (I), $R_6$ is hydroxy-$C_{1-8}$alkyl selected from hydroxy-methyl, dihydroxy-propyl, hydroxy-butyl or dihydroxy-butyl.

In one embodiment of a compound of Formula (I), $R_6$ is $C_{1-8}$alkoxy selected from methoxy, ethoxy, propoxy or iso-propoxy.

In one embodiment of a compound of Formula (I), $R_6$ is halo-$C_{1-8}$alkoxy selected from trihalo-methoxy, dihalo-methoxy, halo-methoxy, trihalo-ethoxy, dihalo-ethoxy, halo-ethoxy, trihalo-propoxy, dihalo-propoxy or halo-propoxy; wherein, halo is selected from fluoro, chloro, bromo or iodo.

In one embodiment of a compound of Formula (I), $R_7$ is $C_{3-14}$cycloalkyl, $C_{3-14}$cycloalkyl-oxy, aryl, heterocyclyl or heteroaryl; wherein $C_{3-14}$cycloalkyl is selected from cyclopropyl or cyclobutoxy; wherein aryl is selected from phenyl; wherein heterocyclyl is selected from oxetanyl, pyrrolidinyl or 1,2,3,6-tetrahydropyridinyl; and, wherein heteroaryl is selected from thienyl or pyridinyl.

In another embodiment of a compound of Formula (I), $R_7$ is $C_{3-14}$cycloalkyl or $C_{3-14}$cycloalkyl-oxy, wherein each instance of $C_{3-14}$cycloalkyl is selected from cyclopropyl, cyclobutyl, cyclopentyl, cyclohexyl or cycloheptyl.

In another embodiment of a compound of Formula (I), $R_7$ is $C_{3-8}$cycloalkyl or $C_{3-8}$cycloalkyl-oxy, wherein each instance of $C_{3-8}$cycloalkyl is selected from cyclopropyl, cyclobutyl, cyclopentyl, cyclohexyl or cycloheptyl.

In one embodiment of a compound of Formula (I), $R_7$ is aryl selected from phenyl.

In one embodiment of a compound of Formula (I), $R_7$ is heterocyclyl selected from oxetanyl, pyrrolidinyl or 1,2,3,6-tetrahydropyridinyl.

In another embodiment of a compound of Formula (I), $R_7$ is heterocyclyl selected from oxetan-3-yl, pyrrolidin-1-yl or 1,2,3,6-tetrahydropyridin-4-yl.

In one embodiment of a compound of Formula (I), $R_7$ is heteroaryl selected from thienyl or pyridinyl.

In another embodiment of a compound of Formula (I), $R_7$ is heteroaryl selected from pyridinyl.

In one embodiment of a compound of Formula (I), $R_7$ is heteroaryl selected from thien-2-yl or pyridin-2-yl.

In another embodiment of a compound of Formula (I), $R_7$ is heteroaryl selected from pyridin-2-yl.

In one embodiment of a compound of Formula (I), $R_c$ is hydrogen or $C_{1-8}$alkyl.

In another embodiment of a compound of Formula (I),
$R_1$ is heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl; wherein, each instance of heterocyclyl, $C_{3-14}$cycloalkyl, aryl and heteroaryl is optionally substituted with $R_3$ and $R_4$ substituents; and,
wherein, heterocyclyl is selected from azetidinyl, tetrahydrofuranyl, pyrrolidinyl, piperidinyl, piperazinyl, 1,4-diazepanyl, 1,2,5,6-tetrahydropyridinyl, 1,2,3,6-tetrahydropyridinyl, hexahydropyrrolo[3,4-b]pyrrol-(1H)-yl, (3aS,6aS)-hexahydropyrrolo[3,4-b]pyrrol-(1H)-yl, (3aR,6aR)-hexahydropyrrolo[3,4-b]pyrrol-(1H)-yl, hexahydropyrrolo[3,4-b]pyrrol-(2H)-yl, (3aS,6aS)-hexahydropyrrolo[3,4-b]pyrrol-(2H)-yl, hexahydropyrrolo[3,4-c]pyrrol-(1H)-yl, (3aR,6aS)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(2H)-one, hexahydropyrrolo[1,2-a]pyrazin-(1H)-yl, (7R,8aS)-hexahydropyrrolo[1,2-a]pyrazin-(1H)-yl, (8aS)-hexahydropyrrolo[1,2-a]pyrazin-(1H)-yl, (8aR)-hexahydropyrrolo[1,2-a]pyrazin-(1H)-yl, (8aS)-octahydropyrrolo[1,2-a]pyrazin-(1H)-yl, (8aR)-octahydropyrrolo[1,2-a]pyrazin-(1H)-yl, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 2,5-diazabicyclo[2.2.2]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 2,6-diazaspiro[3.3]heptyl, 2,7-diazaspiro[3.5]nonyl, 5,8-diazaspiro[3.5]nonyl, 2,7-diazaspiro[4.4]nonyl or 6,9-diazaspiro[4.5]decyl.

In another embodiment of a compound of Formula (I),
$R_2$ is aryl, aryl-amino, aryl-amino-carbonyl, heterocyclyl, heteroaryl or heteroaryl-amino;
wherein, aryl is phenyl;
wherein, heterocyclyl is selected from 1,2,3,6-tetrahydropyridinyl, 1,3-benzodioxolyl or 2,3-dihydro-1,4-benzodioxinyl;
wherein, heteroaryl is selected from thienyl, 1H-pyrazolyl, 1H-imidazolyl, 1,3-thiazolyl, 1,2,4-oxadiazolyl, 1,3,4-oxadiazolyl, pyridinyl, pyrimidinyl, 1H-indolyl, 2H-indolyl, 1H-indazolyl, 2H-indazolyl, indolizinyl, benzofuranyl, benzothienyl, 1H-benzimidazolyl, 1,3-benzothiazolyl, 1,3-benzoxazolyl, 9H-purinyl, furo[3,2-b]pyridinyl, furo[3,2-c]pyridinyl, furo[2,3-c]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl, [1,3]oxazolo[4,5-b]pyridinyl or quinoxalinyl; and, wherein, each instance of aryl, heterocyclyl and heteroaryl is optionally substituted with $R_6$ and $R_7$ substituents.

In another embodiment of a compound of Formula (I),
$R_1$ is heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl;
wherein, heterocyclyl is selected from azetidinyl, tetrahydrofuranyl, pyrrolidinyl, piperidinyl, piperazinyl, 1,4-diazepanyl, 1,2,5,6-tetrahydropyridinyl, 1,2,3,6-tetrahydropyridinyl, hexahydropyrrolo[3,4-b]pyrrol-(1H)-yl, (3aS,6aS)-hexahydropyrrolo[3,4-b]pyrrol-(1H)-yl, (3aR,6aR)-hexahydropyrrolo[3,4-b]pyrrol-(1H)-yl, hexahydropyrrolo[3,4-b]pyrrol-(2H)-yl, (3aS,6aS)-hexahydropyrrolo[3,4-b]pyrrol-(2H)-yl, hexahydropyrrolo[3,4-c]pyrrol-(1H)-yl, (3aR,6aS)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(2H)-one, hexahydropyrrolo[1,2-a]pyrazin-(1H)-yl, (7R,8aS)-hexahydropyrrolo[1,2-c]pyrazin-(1H)-yl, (8aS)-hexahydropyrrolo[1,2-c]pyrazin-(1H)-yl, (8aR)-hexahydropyrrolo[1,2-c]pyrazin-(1H)-yl, (8aS)-octahydropyrrolo[1,2-c]pyrazin-(1H)-yl, (8aR)-octahydropyrrolo[1,2-c]pyrazin-(1H)-yl, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 2,5-diazabicyclo[2.2.2]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 2,6-diazaspiro[3.3]heptyl, 2,7-diazaspiro[3.5]nonyl, 5,8-diazaspiro[3.5]nonyl, 2,7-diazaspiro[4.4]nonyl or 6,9-diazaspiro[4.5]decyl; and, wherein, each instance of heterocyclyl, $C_{3-14}$cycloalkyl, aryl and heteroaryl is optionally substituted with $R_3$ and $R_4$ substituents; and $R_2$ is aryl, aryl-amino, aryl-amino-carbonyl, heterocyclyl, heteroaryl or heteroaryl-amino;

wherein, heterocyclyl is selected from 1,2,3,6-tetrahydropyridin-4-yl, 1,3-benzodioxol-5-yl or 2,3-dihydro-1,4-benzodioxin-6-yl;

wherein, heteroaryl is selected from thienyl, 1H-pyrazolyl, 1H-imidazolyl, 1,3-thiazolyl, 1,2,4-oxadiazolyl, 1,3,4-oxadiazolyl, pyridinyl, pyrimidinyl, 1H-indolyl, 2H-indolyl, 1H-indazolyl, 2H-indazolyl, indolizinyl, benzofuranyl, benzothienyl, 1H-benzimidazolyl, 1,3-benzothiazolyl, 1,3-benzoxazolyl, 9H-purinyl, furo[3,2-b]pyridinyl, furo[3,2-c]pyridinyl, furo[2,3-c]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl, [1,3]oxazolo[4,5-b]pyridinyl or quinoxalinyl; and, wherein, each instance of heterocyclyl and heteroaryl is optionally substituted with $R_6$ and $R_7$ substituents.

In another embodiment of a compound of Formula (I),
$R_1$ is $C_{1-8}$alkyl, amino, $C_{1-8}$alkyl-amino, $(C_{1-8}$alkyl$)_2$-amino, $C_{1-8}$alkoxy-$C_{1-8}$alkyl-amino, $(C_{1-8}$alkoxy-$C_{1-8}$alkyl$)_2$-amino, $(C_{1-8}$alkoxy-$C_{1-8}$alkyl$)(C_{1-8}$alkyl$)$amino, amino-$C_{1-8}$alkyl, $C_{1-8}$alkyl-amino-$C_{1-8}$alkyl, $(C_{1-8}$alkyl$)_2$-amino-$C_{1-8}$alkyl, $C_{1-8}$alkoxy-$C_{1-8}$alkyl-amino-$C_{1-8}$alkyl, $(C_{1-8}$alkoxy-$C_{1-8}$alkyl$)_2$-amino-$C_{1-8}$alkyl, $(C_{1-8}$alkoxy-$C_{1-8}$alkyl$)(C_{1-8}$alkyl$)$amino-$C_{1-8}$alkyl, amino-$C_{1-8}$alkyl-amino, (amino-$C_{1-8}$alkyl$)_2$-amino, (amino-$C_{1-8}$alkyl$)(C_{1-8}$alkyl$)$amino, $C_{1-8}$alkyl-amino-$C_{1-8}$alkyl-amino, $(C_{1-8}$alkyl-amino-$C_{1-8}$alkyl$)_2$-amino, $(C_{1-8}$alkyl-amino-$C_{1-8}$alkyl$)(C_{1-8}$alkyl$)$amino, $(C_{1-8}$alkyl$)_2$-amino-$C_{1-8}$alkyl-amino, $[(C_{1-8}$alkyl$)_2$-amino-$C_{1-8}$alkyl$](C_{1-8}$alkyl$)$amino, amino-$C_{1-8}$alkoxy, $C_{1-8}$alkyl-amino-$C_{1-8}$alkoxy, $(C_{1-8}$alkyl$)_2$-amino-$C_{1-8}$alkoxy, $C_{1-8}$alkoxy-$C_{1-8}$alkyl-amino-$C_{1-8}$alkoxy, $(C_{1-8}$alkoxy-$C_{1-8}$alkyl$)_2$-amino-$C_{1-8}$alkoxy, $(C_{1-8}$alkoxy-$C_{1-8}$alkyl$)(C_{1-8}$alkyl$)$amino-$C_{1-8}$alkoxy, amino-$C_{2-8}$alkenyl, $C_{1-8}$alkyl-amino-$C_{2-8}$alkenyl, $(C_{1-8}$alkyl$)_2$-amino-$C_{2-8}$alkenyl, amino-$C_{2-8}$alkynyl, $C_{1-8}$alkyl-amino-$C_{2-8}$alkynyl, $(C_{1-8}$alkyl$)_2$-amino-$C_{2-8}$alkynyl, halo-$C_{1-8}$alkyl-amino, (halo-$C_{1-8}$alkyl$)_2$-amino, (halo-$C_{1-8}$alkyl$)(C_{1-8}$alkyl$)$amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl$)_2$-amino, (hydroxy-$C_{1-8}$alkyl$)(C_{1-8}$alkyl$)$amino, hydroxy-$C_{1-8}$alkyl-amino-$C_{1-8}$alkyl, (hydroxy-$C_{1-8}$alkyl$)_2$-amino-$C_{1-8}$alkyl, (hydroxy-$C_{1-8}$alkyl$)(C_{1-8}$alkyl$)$amino-$C_{1-8}$alkyl, hydroxy-$C_{1-8}$alkyl-amino-$C_{1-8}$alkoxy, (hydroxy-$C_{1-8}$alkyl$)_2$-amino-$C_{1-8}$alkoxy, (hydroxy-$C_{1-8}$alkyl$)(C_{1-8}$alkyl$)$amino-$C_{1-8}$alkoxy, hydroxy-$C_{1-8}$alkyl-amino-$C_{1-8}$alkyl-amino, (hydroxy-$C_{1-8}$alkyl-amino-$C_{1-8}$alkyl$)_2$-amino, (hydroxy-$C_{1-8}$alkyl$)_2$-amino-$C_{1-8}$alkyl-amino, (hydroxy-$C_{1-8}$alkyl-amino-$C_{1-8}$alkyl$)(C_{1-8}$alkyl$)$amino, (hydroxy-$C_{1-8}$alkyl$)(C_{1-8}$alkyl$)$amino-$C_{1-8}$alkyl-amino, [(hydroxy-$C_{1-8}$alkyl$)_2$-amino-$C_{1-8}$alkyl$](C_{1-8}$alkyl$)$amino or [(hydroxy-$C_{1-8}$alkyl$)(C_{1-8}$alkyl$)$amino-$C_{1-8}$alkyl$](C_{1-8}$alkyl$)$amino; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of a compound of Formula (I),
$R_1$ is heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl$)_2$-amino, (heterocyclyl-$C_{1-8}$alkyl$)(C_{1-8}$alkyl$)$amino, heterocyclyl-$C_{1-8}$alkyl-amino-$C_{1-8}$alkyl, (heterocyclyl-$C_{1-8}$alkyl$)_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl$)_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl$)_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl$)_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl$)_2$-amino-$C_{1-8}$alkyl or (heteroaryl-$C_{1-8}$alkyl)($C_{1-8}$alkyl)amino-$C_{1-8}$alkyl; wherein, each instance of heterocyclyl, $C_{3-14}$cycloalkyl, aryl and heteroaryl is optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of a compound of Formula (I),
$R_1$ is heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl$)_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl$)_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl or heterocyclyl-carbonyl-oxy; wherein, each instance of heterocyclyl is optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of a compound of Formula (I),
$R_1$ is heterocyclyl optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of a compound of Formula (I), $R_1$ is $C_{3-14}$cycloalkyl optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of a compound of Formula (I), $R_1$ is aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl or (aryl-$C_{1-8}$alkyl)($C_{1-8}$alkyl)amino-$C_{1-8}$alkyl; wherein, each instance of aryl is optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of a compound of Formula (I), $R_1$ is aryl-$C_{1-8}$alkyl-amino optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of a compound of Formula (I), $R_1$ is heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl; wherein, each instance of heterocyclyl, $C_{3-14}$cycloalkyl, aryl and heteroaryl is optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of a compound of Formula (I), $R_1$ is heteroaryl optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

An embodiment of the compound of Formula (I) is a compound selected from Formula (II), Formula (III), Formula (IV), Formula (V), Formula (VI), Formula (VII), Formula (VIII), Formula (IX), Formula (X), Formula (XI), Formula (XII), Formula (XIII) or Formula (XIV):

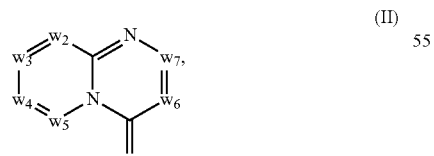

(II)

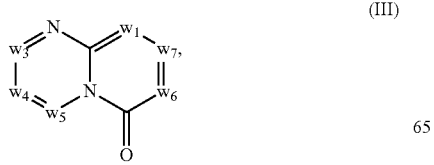

(III)

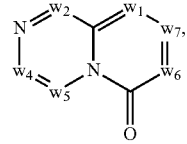

(IV)

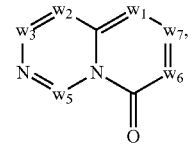

(V)

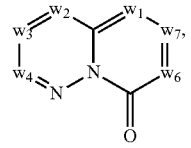

(VI)

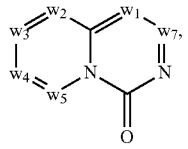

(VII)

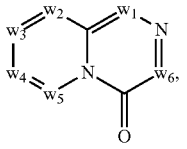

(VIII)

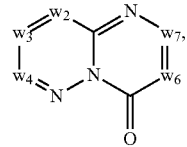

(IX)

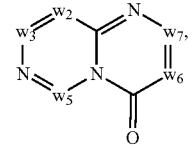

(X)

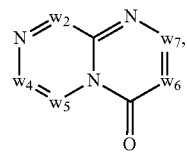

(XI)

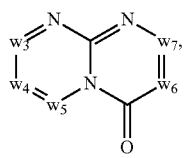

(XII)

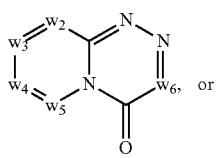

(XIII)

or

-continued (XIV)

or a form thereof.

In an embodiment of the compound of Formula (I), $w_3$ is $C-R_1$, $w_6$ is $C-R_2$, $w_1$, $w_4$, $w_5$ and $w_7$ are independently $C-R_a$ or N and $w_2$ is $C-R_b$ or N.

In another embodiment of the compound of Formula (I), $w_3$ is $C-R_2$, $w_6$ is $C-R_1$, $w_1$, $w_4$, $w_5$ and $w_7$ are independently $C-R_a$ or N and $w_2$ is $C-R_b$ or N.

In another embodiment of the compound of Formula (I), $w_4$ is $C-R_1$, $w_7$ is $C-R_2$, $w_1$, $w_3$ and $w_5$ are independently $C-R_a$ or N, $w_2$ is $C-R_b$ or N and $w_6$ is $C-R_c$ or N.

In another embodiment of the compound of Formula (I), $w_4$ is $C-R_2$, $w_7$ is $C-R_1$, $w_1$, $w_3$ and $w_5$ are independently $C-R_a$ or N, $w_2$ is $C-R_b$ or N and $w_6$ is $C-R_c$ or N.

In an embodiment of the compound of Formula (II), $w_3$ is $C-R_1$, $w_6$ is $C-R_2$, $w_4$, $w_5$ and $w_7$ are independently $C-R_a$ or N and $w_2$ is $C-R_b$ or N.

In another embodiment of the compound of Formula (II), $w_3$ is $C-R_2$, $w_6$ is $C-R_1$, $w_4$, $w_5$ and $w_7$ are independently $C-R_a$ or N and $w_2$ is $C-R_b$ or N.

In another embodiment of the compound of Formula (II), $w_4$ is $C-R_1$, $w_7$ is $C-R_2$, $w_3$ and $w_5$ are independently $C-R_a$ or N, $w_2$ is $C-R_b$ or N and $w_6$ is $C-R_c$ or N.

In another embodiment of the compound of Formula (II), $w_4$ is $C-R_2$, $w_7$ is $C-R_1$, $w_3$ and $w_5$ are independently $C-R_a$ or N, $w_2$ is $C-R_b$ or N and $w_6$ is $C-R_c$ or N.

In an embodiment of the compound of Formula (III), $w_3$ is $C-R_1$, $w_6$ is $C-R_2$ and $w_1$, $w_4$, $w_5$ and $w_7$ are independently $C-R_a$ or N.

In another embodiment of the compound of Formula (III), $w_3$ is $C-R_2$, $w_6$ is $C-R_1$ and $w_1$, $w_4$, $w_5$ and $w_7$ are independently $C-R_a$ or N.

In another embodiment of the compound of Formula (III), $w_4$ is $C-R_1$, $w_7$ is $C-R_2$, $w_1$, $w_3$ and $w_5$ are independently $C-R_a$ or N and $w_6$ is $C-R_c$ or N.

In another embodiment of the compound of Formula (III), $w_4$ is $C-R_2$, $w_7$ is $C-R_1$, $w_1$, $w_3$ and $w_5$ are independently $C-R_a$ or N and $w_6$ is $C-R_c$ or N.

In an embodiment of the compound of Formula (IV), $w_4$ is $C-R_1$, $w_7$ is $C-R_2$, $w_1$ and $w_5$ are independently $C-R_a$ or N, $w_2$ is $C-R_b$ or N and $w_6$ is $C-R_c$ or N.

In another embodiment of the compound of Formula (IV), $w_4$ is $C-R_2$, $w_7$ is $C-R_1$, $w_1$ and $w_5$ are independently $C-R_a$ or N, $w_2$ is $C-R_b$ or N and $w_6$ is $C-R_c$ or N.

In an embodiment of the compound of Formula (V), $w_3$ is $C-R_1$, $w_6$ is $C-R_2$, $w_1$, $w_5$ and $w_7$ are independently $C-R_a$ or N and $w_2$ is $C-R_b$ or N.

In another embodiment of the compound of Formula (V), $w_3$ is $C-R_2$, $w_6$ is $C-R_1$, $w_1$, $w_5$ and $w_7$ are independently $C-R_a$ or N and $w_2$ is $C-R_b$ or N.

In an embodiment of the compound of Formula (VI), $w_3$ is $C-R_1$, $w_6$ is $C-R_2$, $w_1$, and $w_7$ are independently $C-R_a$ or N and $w_2$ is $C-R_b$ or N.

In another embodiment of the compound of Formula (VI), $w_3$ is $C-R_2$, $w_6$ is $C-R_1$, $w_1$, $w_4$ and $w_7$ are independently $C-R_a$ or N and $w_2$ is $C-R_b$ or N.

In another embodiment of the compound of Formula (VI), $w_4$ is $C-R_1$, $w_7$ is $C-R_2$, $w_1$ and $w_3$ are independently $C-R_a$ or N, $w_2$ is $C-R_b$ or N and $w_6$ is $C-R_c$ or N.

In another embodiment of the compound of Formula (VI), $w_4$ is $C-R_2$, $w_7$ is $C-R_1$, $w_1$ and $w_3$ are independently $C-R_a$ or N, $w_2$ is $C-R_b$ or N and $w_6$ is $C-R_c$ or N.

In another embodiment of the compound of Formula (VII), $w_4$ is $C-R_1$, $w_7$ is $C-R_2$, $w_1$, $w_3$ and $w_5$ are $C-R_a$ or N and $w_2$ is $C-R_b$ or N.

In another embodiment of the compound of Formula (VII), $w_4$ is $C-R_2$, $w_7$ is $C-R_1$, $w_1$, $w_3$ and $w_5$ are $C-R_a$ or N and $w_2$ is $C-R_b$ or N.

In another embodiment of the compound of Formula (VIII), $w_3$ is $C-R_1$, $w_6$ is $C-R_2$, $w_1$, $w_4$ and $w_5$ are $C-R_a$ or N and $w_2$ is $C-R_b$ or N.

In another embodiment of the compound of Formula (VIII), $w_3$ is $C-R_2$, $w_6$ is $C-R_1$, $w_1$, $w_4$ and $w_5$ are $C-R_a$ or N and $w_2$ is $C-R_b$ or N.

In an embodiment of the compound of Formula (IX), $w_3$ is $C-R_1$, $w_6$ is $C-R_2$, $w_4$ and $w_7$ are independently $C-R_a$ or N and $w_2$ is $C-R_b$ or N.

In another embodiment of the compound of Formula (IX), $w_3$ is $C-R_2$, $w_6$ is $C-R_1$, and $w_7$ are independently $C-R_a$ or N and $w_2$ is $C-R_b$ or N.

In another embodiment of the compound of Formula (IX), $w_4$ is $C-R_1$, $w_7$ is $C-R_2$, is $C-R_b$ or N, $w_3$ is $C-R_a$ or N and $w_6$ is $C-R_c$ or N.

In another embodiment of the compound of Formula (IX), $w_4$ is $C-R_2$, $w_7$ is $C-R_1$, is $C-R_b$ or N, $w_3$ is $C-R_a$ or N and $w_6$ is $C-R_c$ or N.

In an embodiment of the compound of Formula (X), $w_3$ is $C-R_1$, $w_6$ is $C-R_2$, $w_2$ is $C-R_b$ or N and $w_5$ and $w_7$ are independently $C-R_a$ or N.

In another embodiment of the compound of Formula (X), $w_3$ is $C-R_2$, $w_6$ is $C-R_1$, is $C-R_b$ or N and $w_5$ and $w_7$ are independently $C-R_a$ or N.

In an embodiment of the compound of Formula (XI), $w_4$ is $C-R_1$, $w_7$ is $C-R_2$, $w_2$ is $C-R_b$ or N, $w_5$ is $C-R_a$ or N and $w_6$ is $C-R_c$ or N.

In another embodiment of the compound of Formula (XI), $w_4$ is $C-R_2$, $w_7$ is $C-R_1$, is $C-R_b$ or N, $w_5$ is $C-R_a$ or N and $w_6$ is $C-R_c$ or N.

In an embodiment of the compound of Formula (XII), $w_3$ is $C-R_1$, $w_6$ is $C-R_2$ and $w_4$, $w_5$ and $w_7$ are independently $C-R_a$ or N.

In another embodiment of the compound of Formula (XII), $w_3$ is $C-R_2$, $w_6$ is $C-R_1$ and $w_4$, $w_5$ and $w_7$ are independently $C-R_a$ or N.

In another embodiment of the compound of Formula (XII), $w_4$ is $C-R_1$, $w_7$ is $C-R_2$, $w_3$ and $w_5$ are independently $C-R_a$ or N and $w_6$ is $C-R_c$ or N.

In another embodiment of the compound of Formula (XII), $w_4$ is $C-R_2$, $w_7$ is $C-R_1$, $w_3$ and $w_5$ are independently $C-R_a$ or N and $w_6$ is $C-R_c$ or N.

In an embodiment of the compound of Formula (XIII), $w_3$ is $C-R_1$, $w_6$ is $C-R_2$, $w_2$ is $C-R_b$ or N and $w_4$ and $w_5$ are independently $C-R_a$ or N.

In another embodiment of the compound of Formula (XIII), $w_3$ is $C-R_2$, $w_6$ is $C-R_1$, $w_2$ is $C-R_b$ or N and $w_4$ and $w_5$ are independently $C-R_a$ or N.

In an embodiment of the compound of Formula (XIV), $w_4$ is $C-R_1$, $w_7$ is $C-R_2$, $w_2$ is $C-R_b$ or N and $w_3$ and $w_5$ are independently $C-R_a$ or N.

In another embodiment of the compound of Formula (XIV), $w_4$ is $C-R_2$, $w_7$ is $C-R_1$, $w_2$ is $C-R_b$ or N and $w_3$ and $w_5$ are independently $C-R_a$ or N.

Another embodiment of the compound of Formula (I) is a compound selected from Formula (II), Formula (III), Formula (IX), Formula (XI) or Formula (XII):

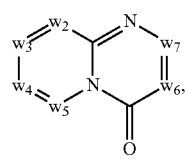
(II)

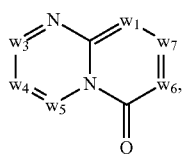
(III)

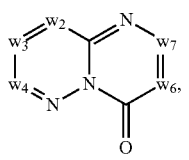
(IX)

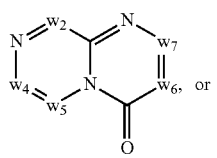
(XI)

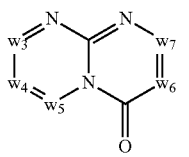
(XII)

or a form thereof.

Another embodiment of the compound of Formula (I) is a compound of Formula (II):

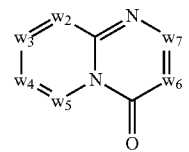
(II)

or a form thereof.

Another embodiment of the compound of Formula (I) is a compound of Formula (III):

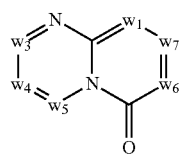
(III)

or a form thereof.

Another embodiment of the compound of Formula (I) is a compound of Formula (IV):

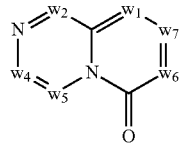
(IV)

or a form thereof.

Another embodiment of the compound of Formula (I) is a compound of Formula (V):

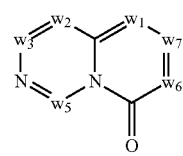
(V)

or a form thereof.

Another embodiment of the compound of Formula (I) is a compound of Formula (VI):

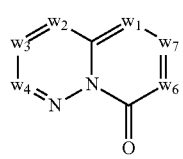
(VI)

or a form thereof.

Another embodiment of the compound of Formula (I) is a compound of Formula (VII):

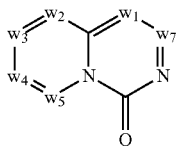
(VII)

or a form thereof.

Another embodiment of the compound of Formula (I) is a compound of Formula (VIII):

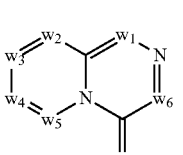
(VIII)

or a form thereof.

Another embodiment of the compound of Formula (I) is a compound of Formula (IX):

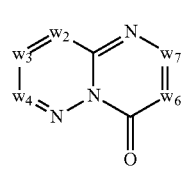

(IX)

or a form thereof.

Another embodiment of the compound of Formula (I) is a compound of Formula (X):

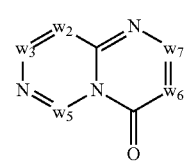

(X)

or a form thereof.

Another embodiment of the compound of Formula (I) is a compound of Formula (XI):

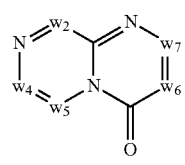

(XI)

or a form thereof.

Another embodiment of the compound of Formula (I) is a compound of Formula (XII):

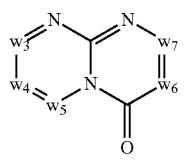

(XII)

or a form thereof.

Another embodiment of the compound of Formula (I) is a compound of Formula (XIII):

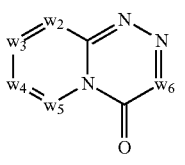

(XIII)

or a form thereof.

Another embodiment of the compound of Formula (I) is a compound of Formula (XIV):

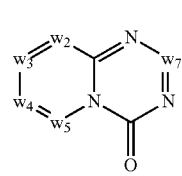

(XIV)

or a form thereof.

An embodiment of the compound of Formula (I), Formula (II), Formula (III), Formula (IV), Formula (V), Formula (VI), Formula (VII), Formula (VIII), Formula (IX), Formula (X), Formula (XI), Formula (XII), Formula (XIII) or Formula (XIV) is a compound selected from Formula (Ia), Formula (IIa), Formula (IIIa), Formula (IVa), Formula (Va), Formula (VIa), Formula (VIIa), Formula (VIIIa), Formula (IXa), Formula (Xa), Formula (XIa), Formula (XIIa), Formula (XIIIa) or Formula (XIVa), respectively:

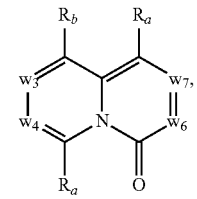

(Ia)

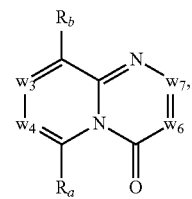

(IIa)

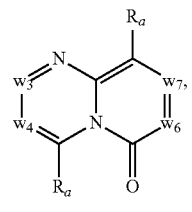

(IIIa)

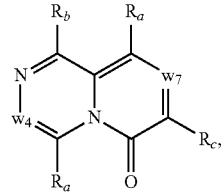

(IVa)

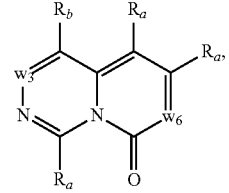

(Va)

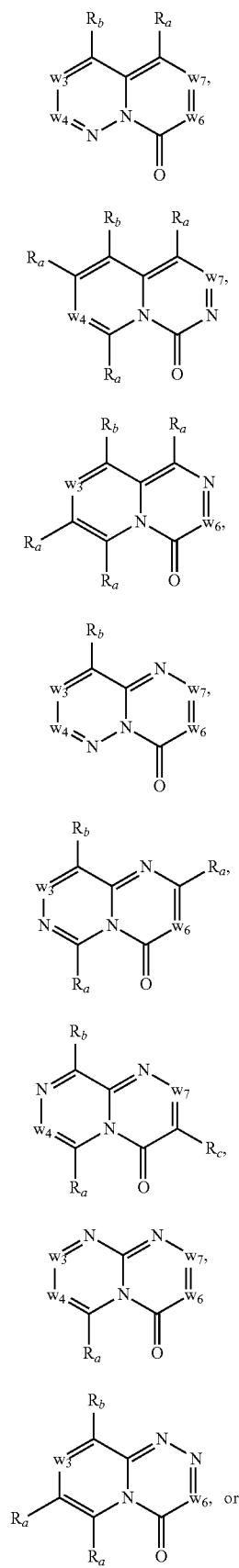

or a form thereof.

In an embodiment of the compound of Formula (Ia), one of $w_3$, $w_4$, $w_6$ and $w_7$ is C—$R_1$ and one other of $w_3$, $w_4$, $w_6$ and $w_7$ is C—$R_2$, provided that,
when $w_3$ is C—$R_1$, then $w_6$ is C—$R_2$ and $w_4$ and $w_7$ are independently C—$R_a$ or N; or,
when $w_3$ is C—$R_2$, then $w_6$ is C—$R_1$ and $w_4$ and $w_7$ are independently C—$R_a$ or N; or,
when $w_4$ is C—$R_1$, then $w_7$ is C—$R_2$ and $w_3$ is C—$R_a$ or N and $w_6$ is C—$R_c$ or N; or,
when $w_4$ is C—$R_2$, then $w_7$ is C—$R_1$ and $w_3$ is C—$R_a$ or N and $w_6$ is C—$R_c$ or N.

In an embodiment of the compound of Formula (IIa), one of $w_3$, $w_4$, $w_6$ and $w_7$ is C—$R_1$ and one other of $w_3$, $w_4$, $w_6$ and $w_7$ is C—$R_2$, provided that,
when $w_3$ is C—$R_1$, then $w_6$ is C—$R_2$ and $w_4$ and $w_7$ are independently C—$R_a$ or N; or,
when $w_3$ is C—$R_2$, then $w_6$ is C—$R_1$ and $w_4$ and $w_7$ are independently C—$R_a$ or N; or,
when $w_4$ is C—$R_1$, then $w_7$ is C—$R_2$ and $w_3$ is C—$R_a$ or N and $w_6$ is C—$R_c$ or N; or,
when $w_4$ is C—$R_2$, then $w_7$ is C—$R_1$ and $w_3$ is C—$R_a$ or N and $w_6$ is C—$R_c$ or N.

In an embodiment of the compound of Formula (IIIa), one of $w_3$, $w_4$, $w_6$ and $w_7$ is C—$R_1$ and one other of $w_3$, $w_4$, $w_6$ and $w_7$ is C—$R_2$, provided that,
when $w_3$ is C—$R_1$, then $w_6$ is C—$R_2$ and $w_4$ and $w_7$ are independently C—$R_a$ or N; or,
when $w_3$ is C—$R_2$, then $w_6$ is C—$R_1$ and $w_4$ and $w_7$ are independently C—$R_a$ or N; or,
when $w_4$ is C—$R_1$, then $w_7$ is C—$R_2$ and $w_3$ is C—$R_a$ or N and $w_6$ is C—$R_c$ or N; or,
when $w_4$ is C—$R_2$, then $w_7$ is C—$R_1$ and $w_3$ is C—$R_a$ or N and $w_6$ is C—$R_c$ or N.

In an embodiment of the compound of Formula (IVa), one of $w_4$ and $w_7$ is C—$R_1$ and the other is C—$R_2$, provided that, when $w_4$ is C—$R_1$, then $w_7$ is C—$R_2$; or, when $w_4$ is C—$R_2$, then $w_7$ is C—$R_1$.

In an embodiment of the compound of Formula (Va), one of $w_3$ and $w_6$ is C—$R_1$ and the other is C—$R_2$, provided that, when $w_3$ is C—$R_1$, then $w_6$ is C—$R_2$; or, when $w_3$ is C—$R_2$, then $w_6$ is C—$R_1$.

In an embodiment of the compound of Formula (VIa), one of $w_3$, $w_4$, $w_6$ and $w_7$ is C—$R_1$ and one other of $w_3$, $w_4$, $w_6$ and $w_7$ is C—$R_2$, provided that,
when $w_3$ is C—$R_1$, then $w_6$ is C—$R_2$ and $w_4$ and $w_7$ are independently C—$R_a$ or N; or,
when $w_3$ is C—$R_2$, then $w_6$ is C—$R_1$ and $w_4$ and $w_7$ are independently C—$R_a$ or N; or,
when $w_4$ is C—$R_1$, then $w_7$ is C—$R_2$ and $w_3$ is C—$R_a$ or N and $w_6$ is C—$R_c$ or N; or,
when $w_4$ is C—$R_2$, then $w_7$ is C—$R_1$ and $w_3$ is C—$R_a$ or N and $w_6$ is C—$R_c$ or N.

In an embodiment of the compound of Formula (VIIa), one of $w_4$ and $w_7$ is C—$R_1$ and the other is C—$R_2$, provided that, when $w_4$ is C—$R_1$, then $w_7$ is C—$R_2$; or, when $w_4$ is C—$R_2$, then $w_7$ is C—$R_1$.

In an embodiment of the compound of Formula (VIIIa), one of $w_3$ and $w_6$ is C—$R_1$ and the other is C—$R_2$, provided that, when $w_3$ is C—$R_1$, then $w_6$ is C—$R_2$; or, when $w_3$ is C—$R_2$, then $w_6$ is C—$R_1$.

In an embodiment of the compound of Formula (IXa), one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—$R_c$ or N.

In an embodiment of the compound of Formula (Xa), one of $w_3$ and $w_6$ is C—$R_1$ and the other is C—$R_2$, provided that, when $w_3$ is C—$R_1$, then $w_6$ is C—$R_2$; or, when $w_3$ is C—$R_2$, then $w_6$ is C—$R_1$.

In an embodiment of the compound of Formula (XIa), one of $w_4$ and $w_7$ is C—$R_1$ and the other is C—$R_2$, provided that, when $w_4$ is C—$R_1$, then $w_7$ is C—$R_2$; or, when $w_4$ is C—$R_2$, then $w_7$ is C—$R_1$.

In an embodiment of the compound of Formula (XIIa), one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—$R_c$ or N.

In an embodiment of the compound of Formula (XIIIa), one of $w_3$ and $w_6$ is C—$R_1$ and the other is C—$R_2$, provided that, when $w_3$ is C—$R_1$, then $w_6$ is C—$R_2$; or, when $w_3$ is C—$R_2$, then $w_6$ is C—$R_1$.

In an embodiment of the compound of Formula (XIVa), one of $w_4$ and $w_7$ is C—$R_1$ and the other is C—$R_2$, provided that, when $w_4$ is C—$R_1$, then $w_7$ is C—$R_2$; or, when $w_4$ is C—$R_2$, then $w_7$ is C—$R_1$.

An embodiment of the compound of Formula (I), Formula (II), Formula (III), Formula (IX), Formula (XI) or Formula (XII) is a compound selected from Formula (Ia), Formula (IIa), Formula (IIIa), Formula (IXa), Formula (XIa) or Formula (XIIa), respectively:

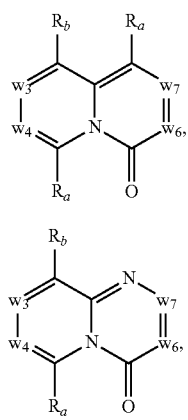

(Ia)

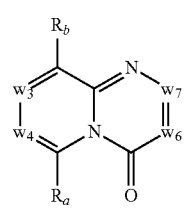

(IIa)

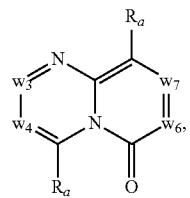

(IIIa)

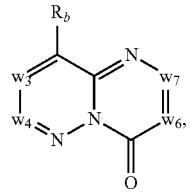

(IXa)

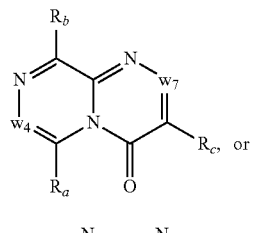

(XIa)

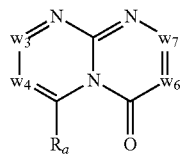

(XIIa)

or a form thereof.

Another embodiment of the compound of Formula (I) is a compound of Formula (Ia):

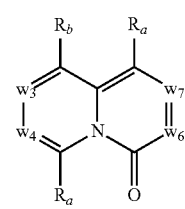

(Ia)

or a form thereof.

Another embodiment of the compound of Formula (II) is a compound of Formula (IIa):

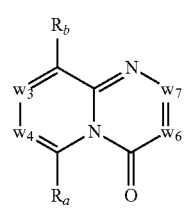

(IIa)

or a form thereof.

Another embodiment of the compound of Formula (III) is a compound of Formula (IIIa):

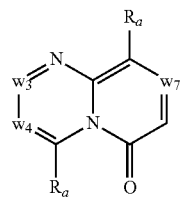

(IIIa)

or a form thereof.

Another embodiment of the compound of Formula (IV) is a compound of Formula (IVa):

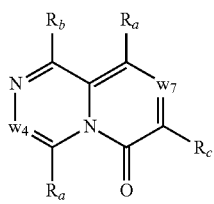

(IVa)

or a form thereof.

Another embodiment of the compound of Formula (V) is a compound of Formula (Va):

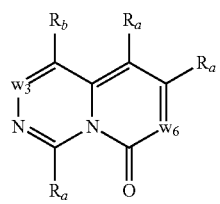

(Va)

or a form thereof.

Another embodiment of the compound of Formula (VI) is a compound of Formula (VIa):

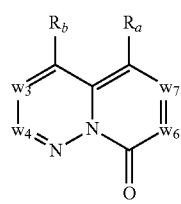

(VIa)

or a form thereof.

Another embodiment of the compound of Formula (VII) is a compound of Formula (VIIa):

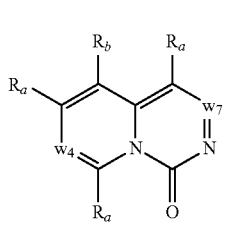

(VIIa)

or a form thereof.

Another embodiment of the compound of Formula (VIII) is a compound of Formula (VIIIa):

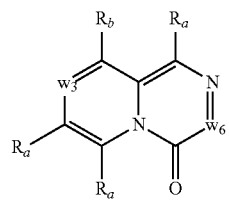

(VIIIa)

or a form thereof.

Another embodiment of the compound of Formula (IX) is a compound of Formula (IXa):

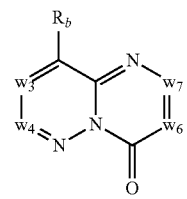

(IXa)

or a form thereof.

Another embodiment of the compound of Formula (X) is a compound of Formula (Xa):

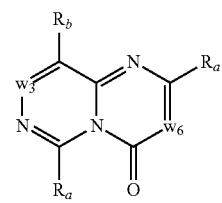

(Xa)

or a form thereof.

Another embodiment of the compound of Formula (XI) is a compound of Formula (XIa):

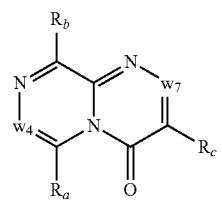

(XIa)

or a form thereof.

Another embodiment of the compound of Formula (XII) is a compound of Formula (XIIa):

(XIIa)

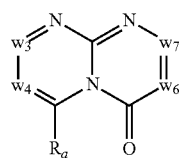

or a form thereof.

Another embodiment of the compound of Formula (XIII) is a compound of Formula (XIIIa):

(XIIIa)

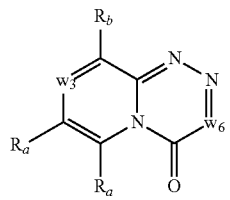

or a form thereof.

Another embodiment of the compound of Formula (XIV) is a compound of Formula (XIVa):

(XIVa)

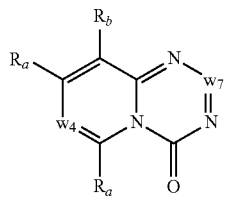

or a form thereof.

An embodiment of the compound of Formula (Ia) is a compound of Formula (Ia1), Formula (Ia2), Formula (Ia3) or Formula (Ia4):

(Ia1)

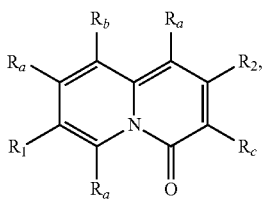

(Ia2)

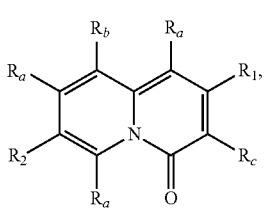

(Ia3)

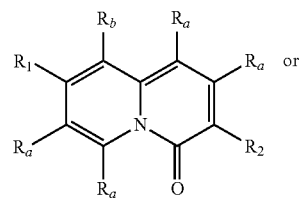

(Ia4)

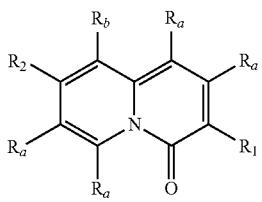

or a form thereof.

An embodiment of the compound of Formula (IIa) is a compound of Formula (IIa1), Formula (IIa2), Formula (IIa3) or Formula (IIa4):

(IIa1)

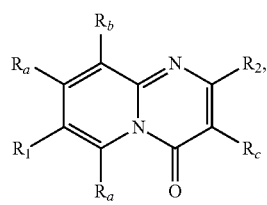

(IIa2)

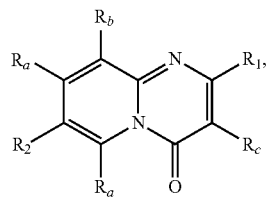

(IIa3)

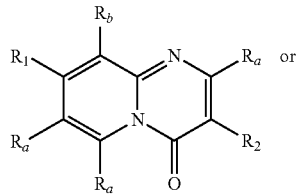

(IIa4)

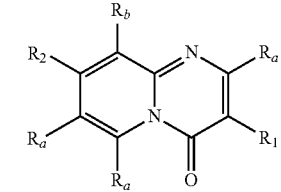

or a form thereof.

An embodiment of the compound of Formula (IIIa) is a compound of Formula (IIIa1), Formula (IIIa2), Formula (IIIa3) or Formula (IIIa4):

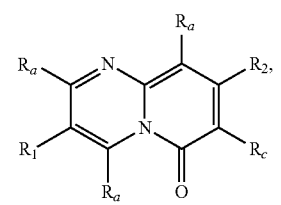
(IIIa1)

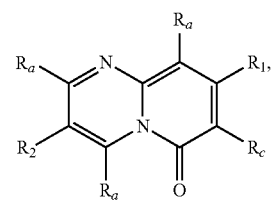
(IIIa2)

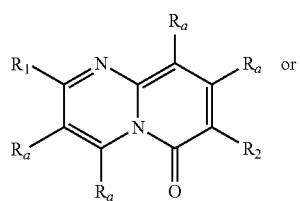
(IIIa3)

or

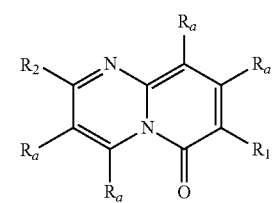
(IIIa4)

or a form thereof.

An embodiment of the compound of Formula (IVa) includes a compound of Formula (IVa1) or Formula (IVa2):

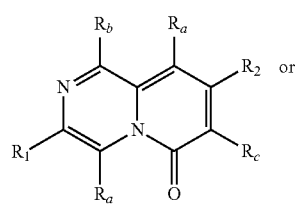
(IVa1)

or

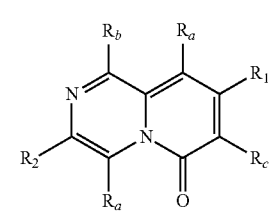
(IVa2)

or a form thereof.

An embodiment of the compound of Formula (Va) is a compound of Formula (Va1) or Formula (Va2):

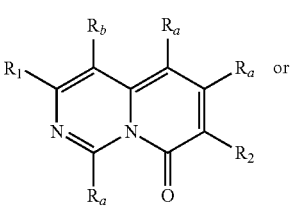
(Va1)

or

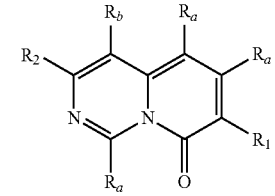
(Va2)

or a form thereof.

An embodiment of the compound of Formula (VIa) is a compound of Formula (VIa1), Formula (VIa2), Formula (VIa3) or Formula (VIa4):

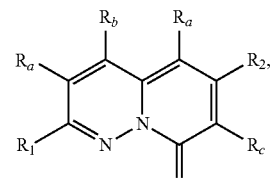
(VIa1)

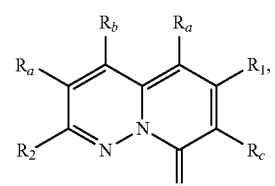
(VIa2)

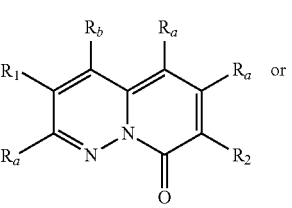
(VIa3)

or

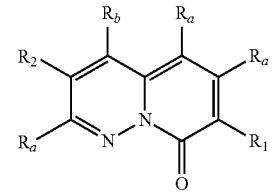
(VIa4)

or a form thereof.

An embodiment of the compound of Formula (VIIa) includes a compound of Formula (VIIa1) or Formula (VIIa2):

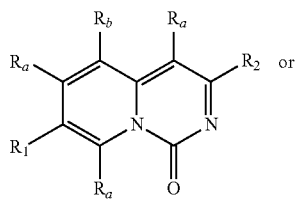
(VIIa1)

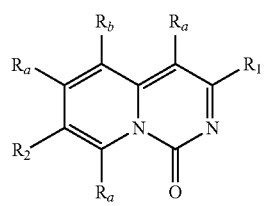
(VIIa2)

or a form thereof.

An embodiment of the compound of Formula (VIIIa) is a compound of Formula (VIIIa1) or Formula (VIIIa2):

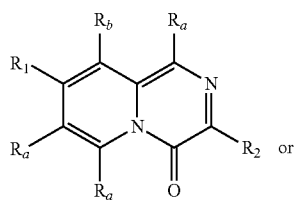
(VIIIa1)

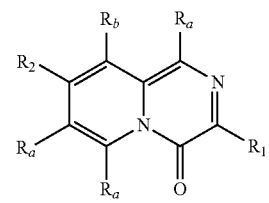
(VIIIa2)

or a form thereof.

An embodiment of the compound of Formula (IXa) is a compound of Formula (IXa1), Formula (IXa2), Formula (IXa3) or Formula (IXa4):

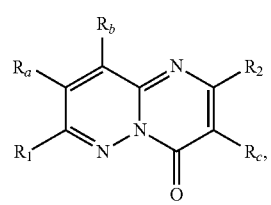
(IXa1)

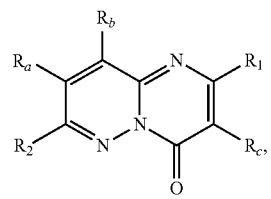
(IXa2)

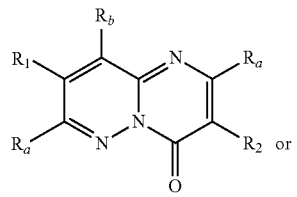
(IXa3)

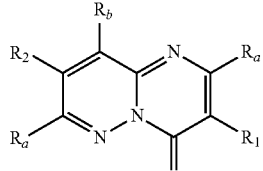
(IXa4)

or a form thereof.

An embodiment of the compound of Formula (Xa) is a compound of Formula (Xa1) or Formula (Xa2):

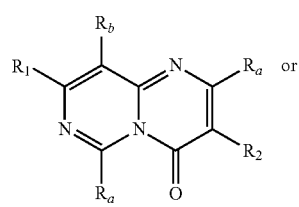
(Xa1)

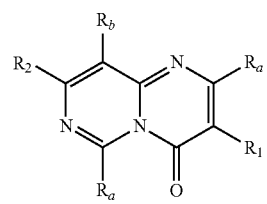
(Xa2)

or a form thereof.

An embodiment of the compound of Formula (XIa) is a compound of Formula (XIa1) or Formula (XIa2):

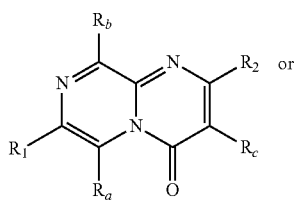
(XIa1)

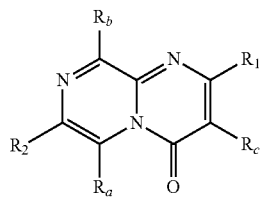
(XIa2)

or a form thereof.

An embodiment of the compound of Formula (XIIa) is a compound of Formula (XIIa1), Formula (XIIa2), Formula (XIIa3) or Formula (XIIa4):

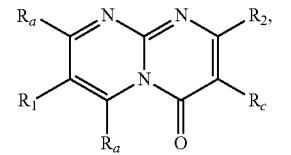
(XIIa1)

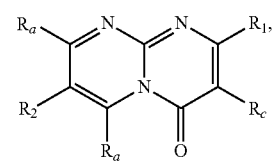
(XIIa2)

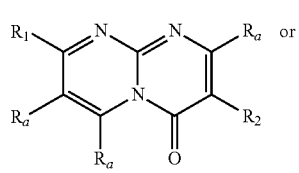
(XIIa3)

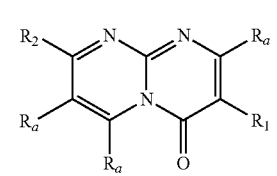
(XIIa4)

or a form thereof.

An embodiment of the compound of Formula (XIIIa) is a compound of Formula (XIIIa1) or Formula (XIIIa2).

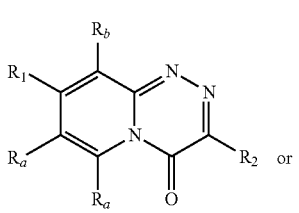
(XIIIa1)

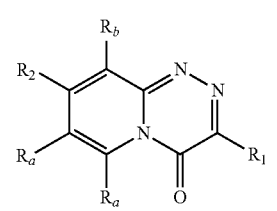
(XIIIa2)

or a form thereof.

An embodiment of the compound of Formula (XIVa) is a compound of Formula (XIVa1) or Formula (XIVa2):

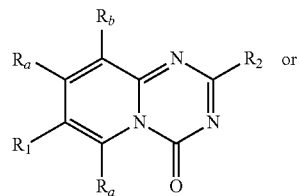
(XIVa1)

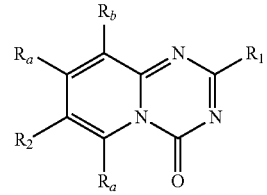
(XIVa2)

or a form thereof.

An embodiment of the compound of Formula (Ia) is a compound of Formula (Ia1):

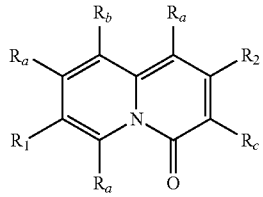
(Ia1)

or a form thereof.

An embodiment of the compound of Formula (Ia) is a compound of Formula (Ia2):

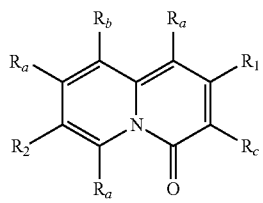
(Ia2)

or a form thereof.

An embodiment of the compound of Formula (Ia) is a compound of Formula (Ia3):

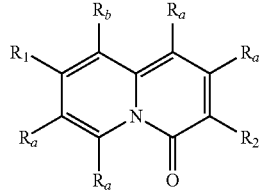
(Ia3)

or a form thereof.

An embodiment of the compound of Formula (Ia) is a compound of Formula (Ia4):

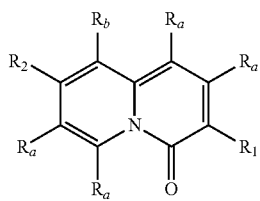

(Ia4)

or a form thereof.

An embodiment of the compound of Formula (IIa) is a compound of Formula (IIa1):

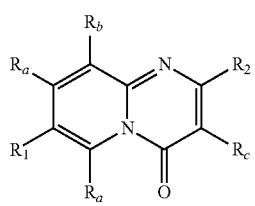

(IIa1)

or a form thereof.

An embodiment of the compound of Formula (IIa) is a compound of Formula (IIa2):

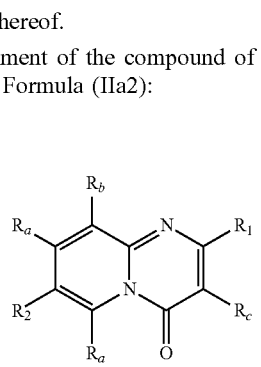

(IIa2)

or a form thereof.

An embodiment of the compound of Formula (IIa) is a compound of Formula (IIa3):

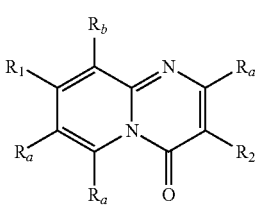

(IIa3)

or a form thereof.

An embodiment of the compound of Formula (IIa) is a compound of Formula (IIa4):

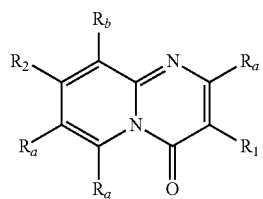

(IIa4)

or a form thereof.

An embodiment of the compound of Formula (IIIa) is a compound of Formula (IIIa1):

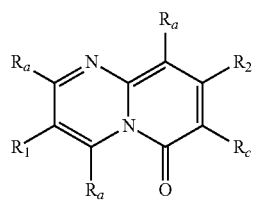

(IIIa1)

or a form thereof.

An embodiment of the compound of Formula (IIIa) is a compound of Formula (IIIa2):

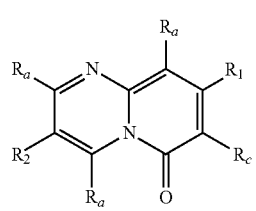

(IIIa2)

or a form thereof.

An embodiment of the compound of Formula (IIIa) is a compound of Formula (IIIa3):

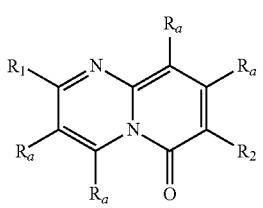

(IIIa3)

or a form thereof.

An embodiment of the compound of Formula (IIIa) is a compound of Formula (IIIa4):

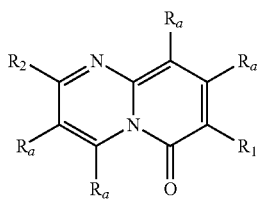

(IIIa4)

or a form thereof.

An embodiment of the compound of Formula (IVa) is a compound of Formula (IVa1):

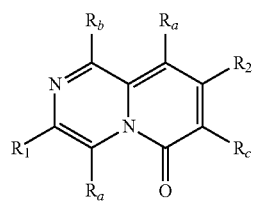

(IVa1)

or a form thereof.

An embodiment of the compound of Formula (IVa) is a compound of Formula (IVa2):

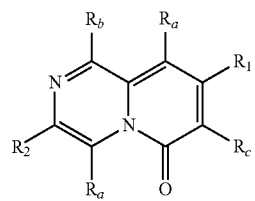

(IVa2)

or a form thereof.

An embodiment of the compound of Formula (Va) is a compound of Formula (Va1):

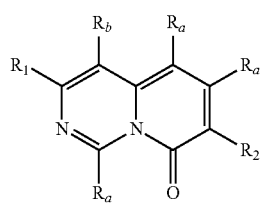

(Va1)

or a form thereof.

An embodiment of the compound of Formula (Va) is a compound of Formula (Va2):

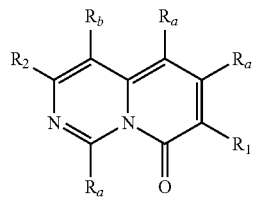

(Va2)

or a form thereof.

An embodiment of the compound of Formula (VIa) is a compound of Formula (VIa1):

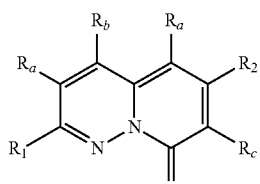

(VIa1)

or a form thereof.

An embodiment of the compound of Formula (VIa) is a compound of Formula (VIa2):

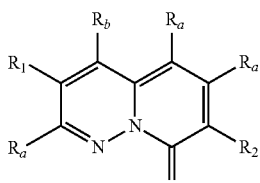

(VIa2)

or a form thereof.

An embodiment of the compound of Formula (VIa) is a compound of Formula Formula (VIa3):

(VIa3)

or a form thereof.

An embodiment of the compound of Formula (VIa) is a compound of Formula (VIa4):

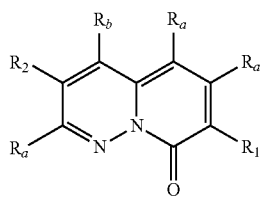

(VIa4)

or a form thereof.

An embodiment of the compound of Formula (VIIa) is a compound of Formula (VIIa1):

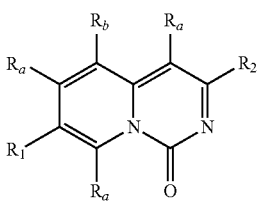

(VIIa1)

or a form thereof.

An embodiment of the compound of Formula (VIIa) is a compound of Formula (VIIa2):

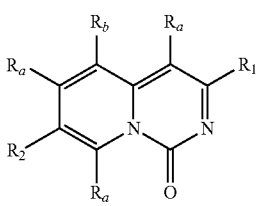

(VIIa2)

or a form thereof.

An embodiment of the compound of Formula (VIIIa) is a compound of Formula (VIIIa1):

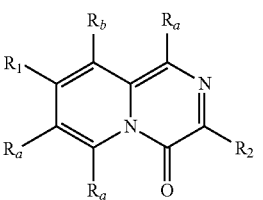

(VIIIa1)

or a form thereof.

An embodiment of the compound of Formula (VIIIa) is a compound of Formula (VIIIa2):

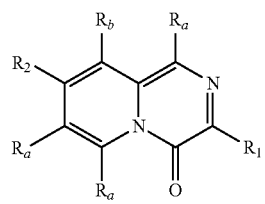

(VIIIa2)

or a form thereof.

An embodiment of the compound of Formula (IXa) is a compound of Formula (IXa1):

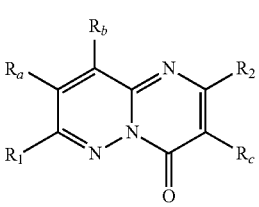

(IXa1)

or a form thereof.

An embodiment of the compound of Formula (IXa) is a compound of Formula (IXa2):

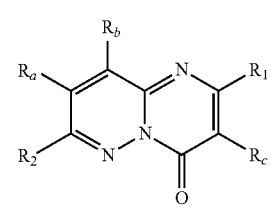

(IXa2)

or a form thereof.

An embodiment of the compound of Formula (IXa) is a compound of Formula (IXa3):

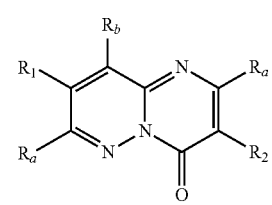

(IXa3)

or a form thereof.

An embodiment of the compound of Formula (IXa) is a compound of Formula (IXa4):

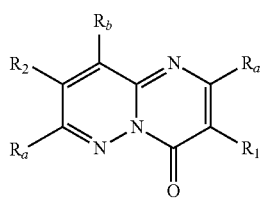

(IXa4)

or a form thereof.

An embodiment of the compound of Formula (Xa) is a compound of Formula (Xa1):

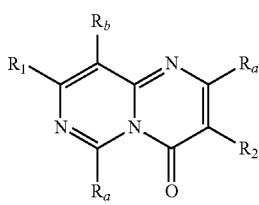

(Xa1)

or a form thereof.

An embodiment of the compound of Formula (Xa) is a compound of Formula (Xa2):

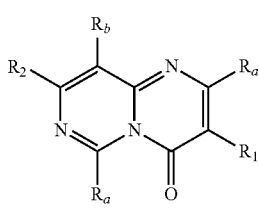

(Xa2)

or a form thereof.

An embodiment of the compound of Formula (XIa) is a compound of Formula (XIa1):

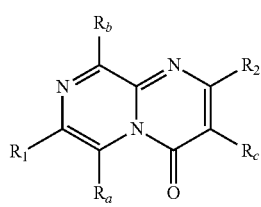

(XIa1)

or a form thereof.

An embodiment of the compound of Formula (XIa) is a compound of Formula (XIa2):

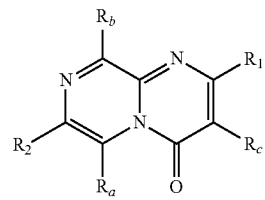

(XIa2)

or a form thereof.

An embodiment of the compound of Formula (XIIa) is a compound of Formula (XIIa1):

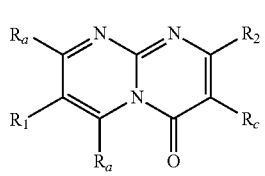

(XIIa1)

or a form thereof.

An embodiment of the compound of Formula (XIIa) is a compound of Formula (XIIa2):

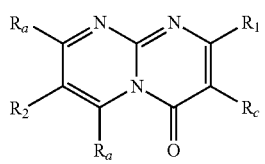

(XIIa2)

or a form thereof.

An embodiment of the compound of Formula (XIIa) is a compound of Formula (XIIa3):

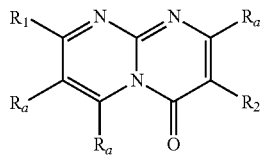

(XIIa3)

or a form thereof.

An embodiment of the compound of Formula (XIIa) is a compound of Formula (XIIa4):

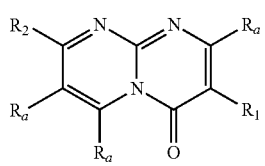

(XIIa4)

or a form thereof.

An embodiment of the compound of Formula (XIIIa) is a compound of Formula (XIIIa1):

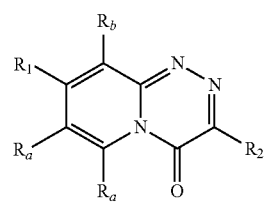
(XIIIa1)

or a form thereof.

An embodiment of the compound of Formula (XIIIa) is a compound of Formula (XIIIa2):

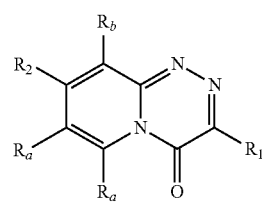
(XIIIa2)

or a form thereof.

An embodiment of the compound of Formula (XIVa) is a compound of Formula (XIVa1):

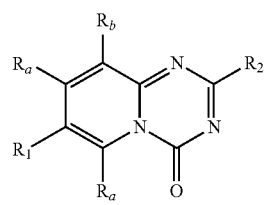
(XIVa1)

or a form thereof.

An embodiment of the compound of Formula (XIVa) is a compound of Formula (XIVa2):

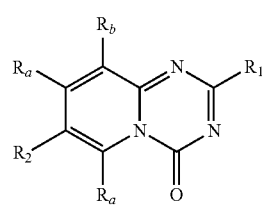
(XIVa2)

or a form thereof.

An embodiment of the compound of Formula (I) is a compound selected from the group consisting of:

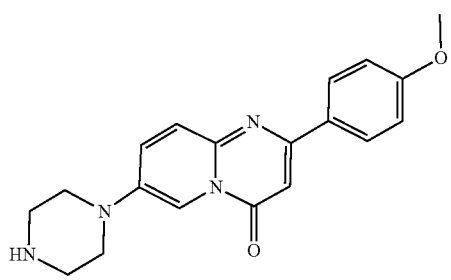
1

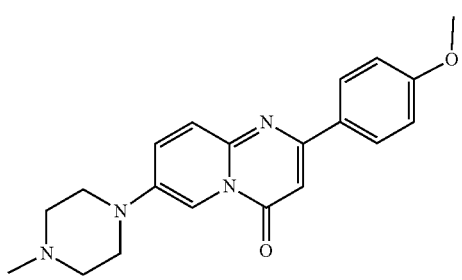
2

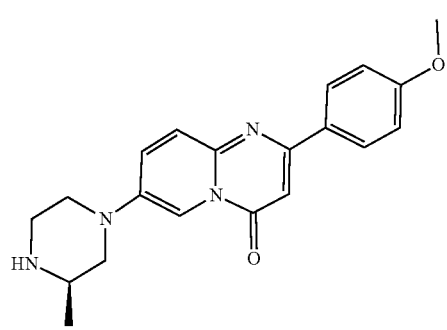
3

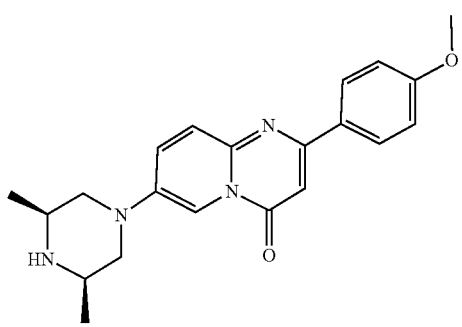
4

5

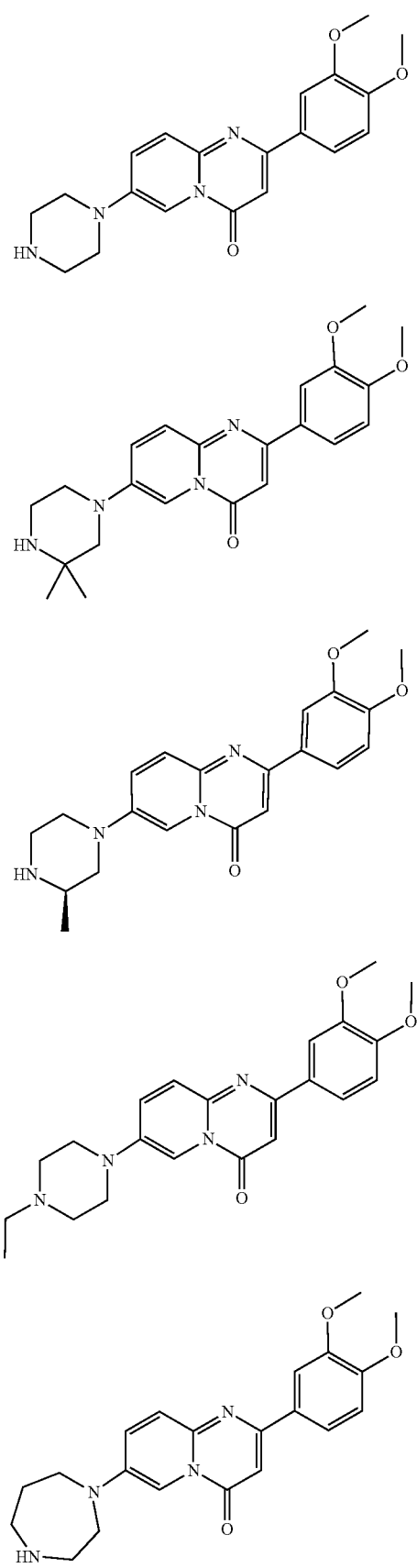
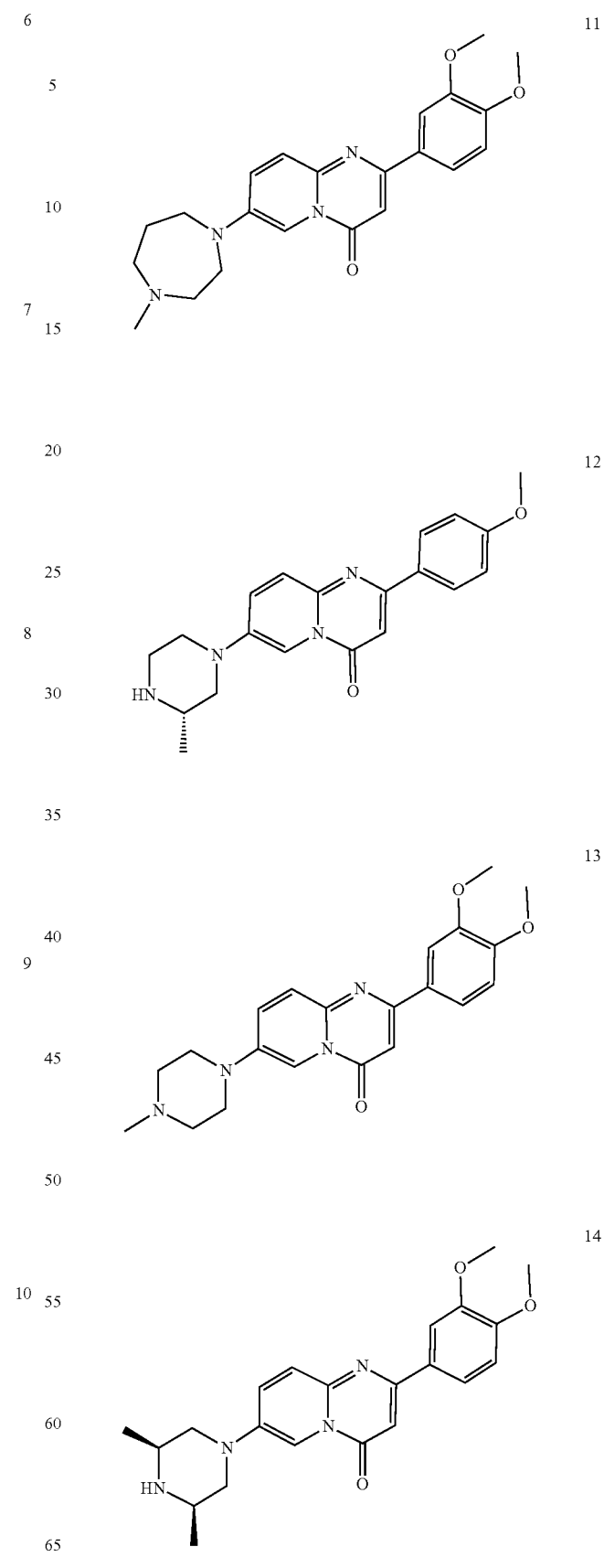

15
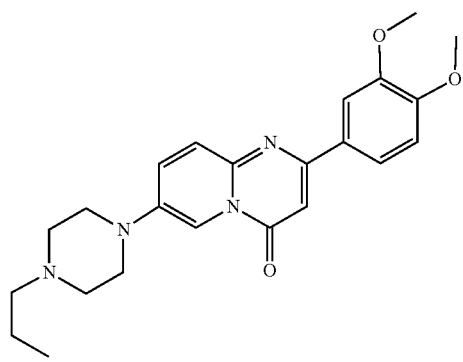
16
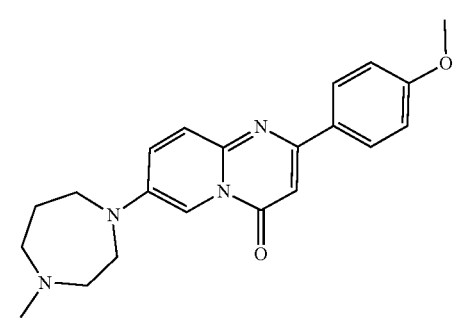
17
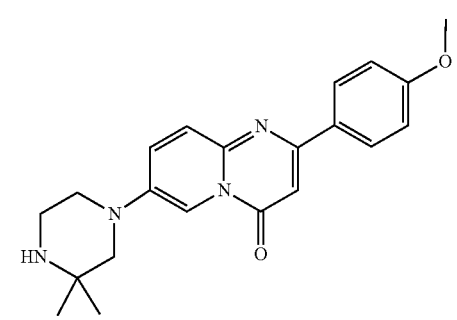
18
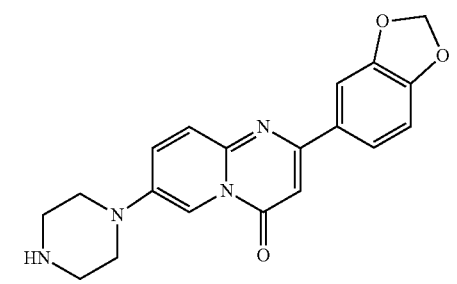
19
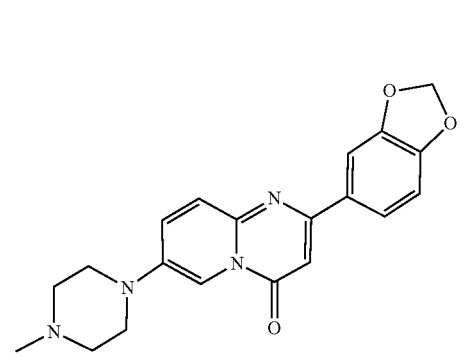
20
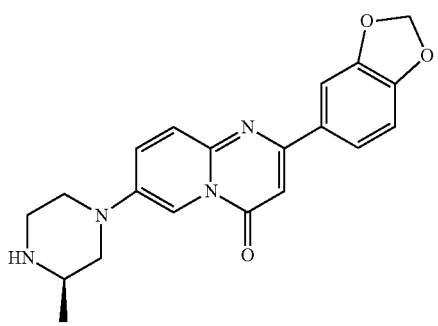
21
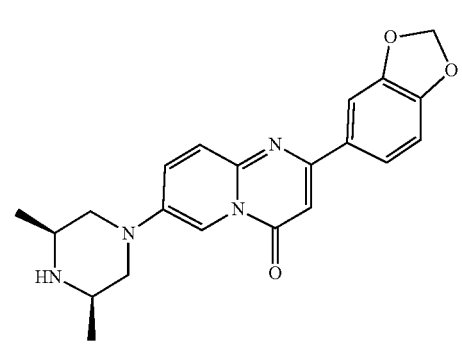
22
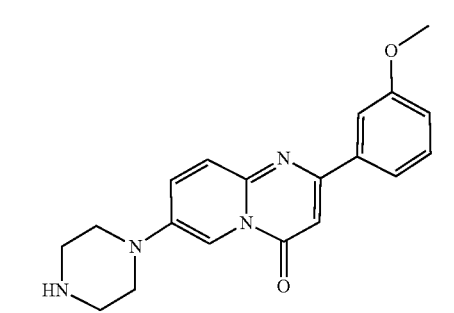
23
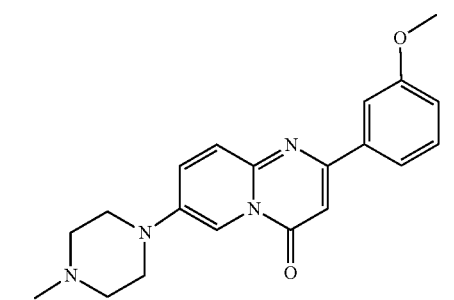
24
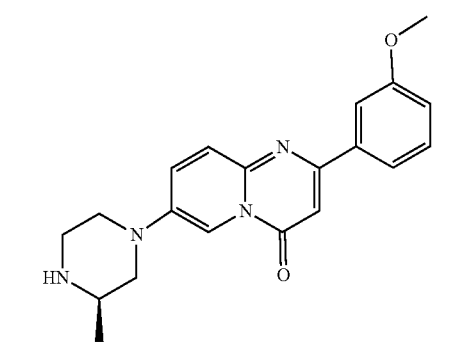

25
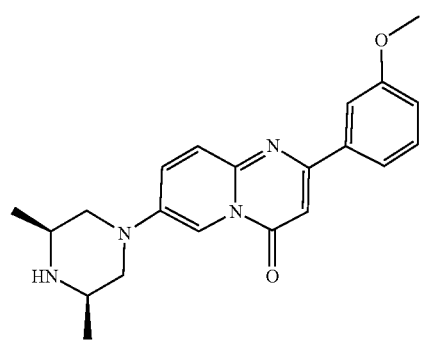
26
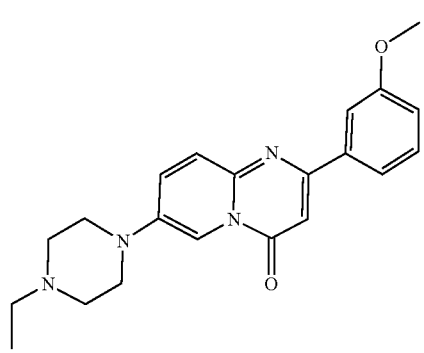
27
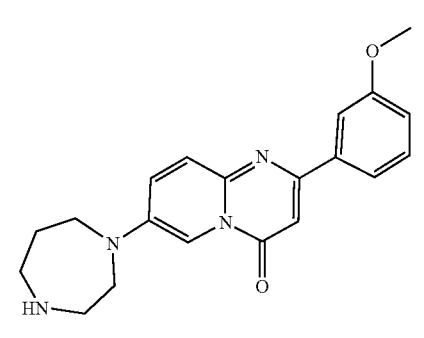
28
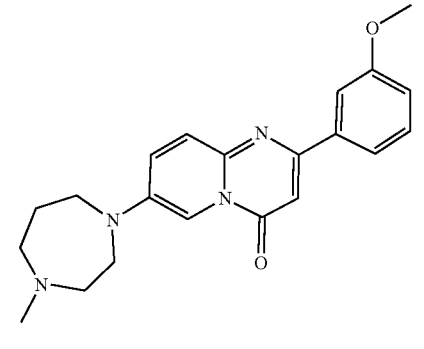
29
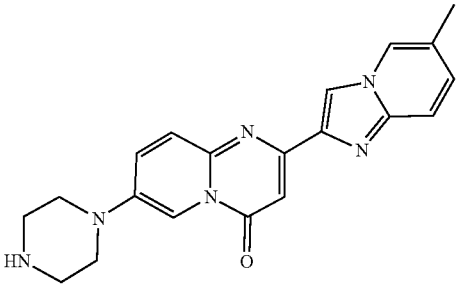
30
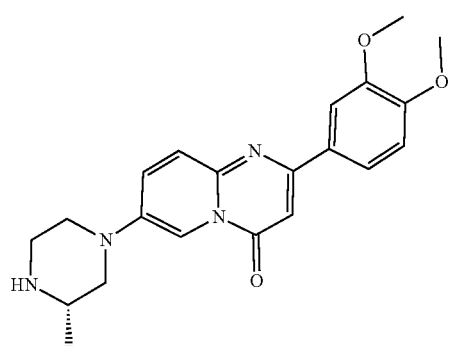
31
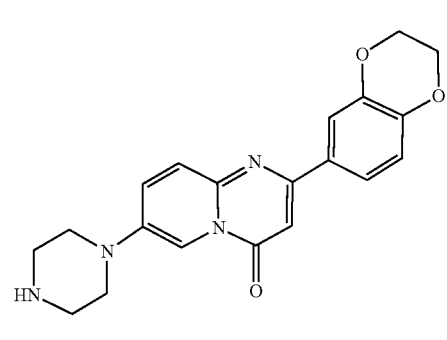
32
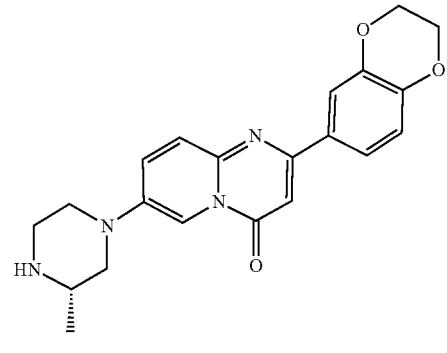
33
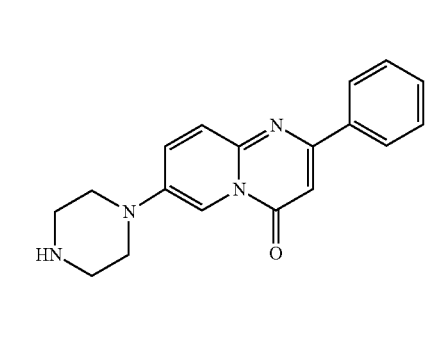
34
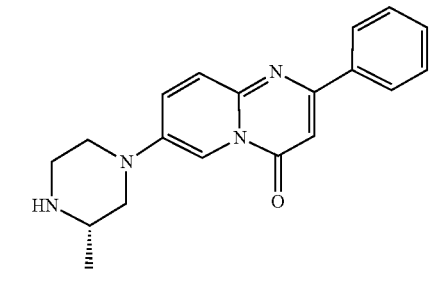

35
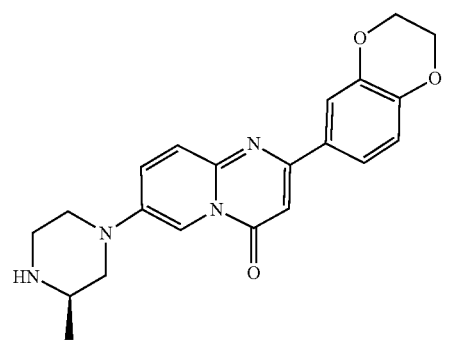
36
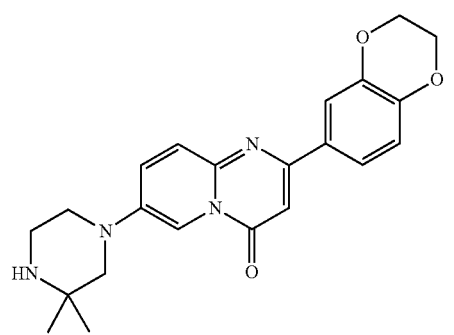
37
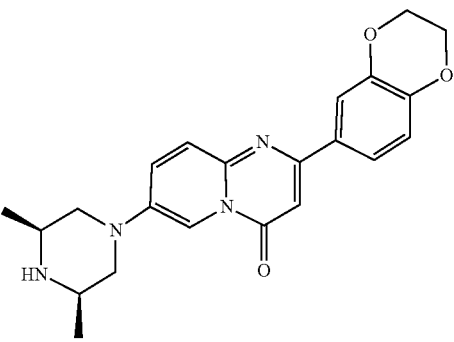
38
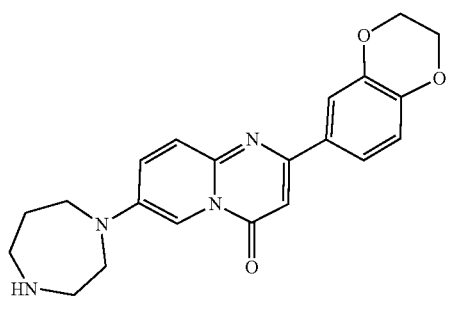
39
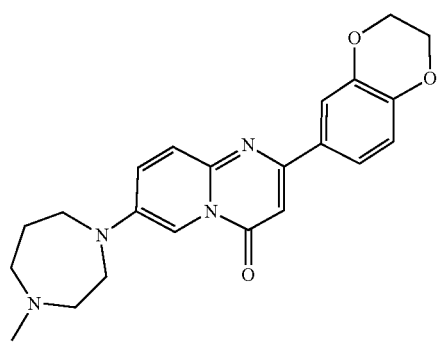
40
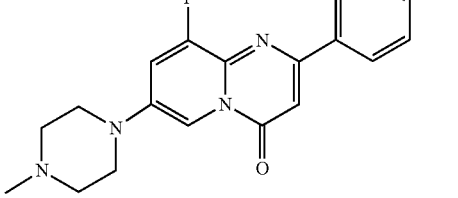
41
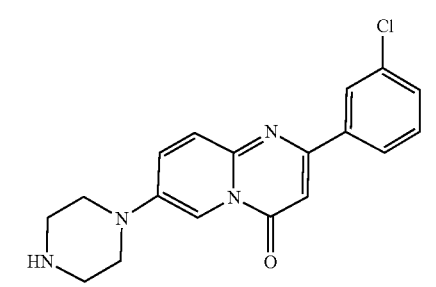
42
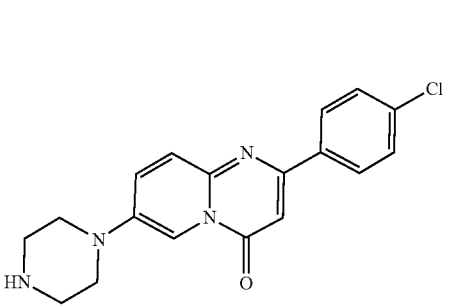
43
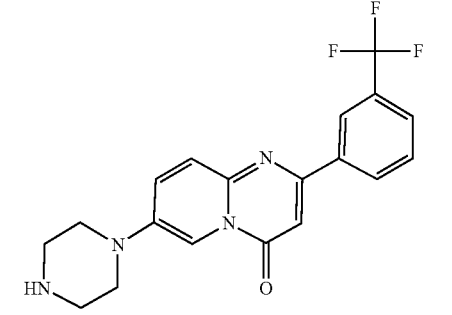

44
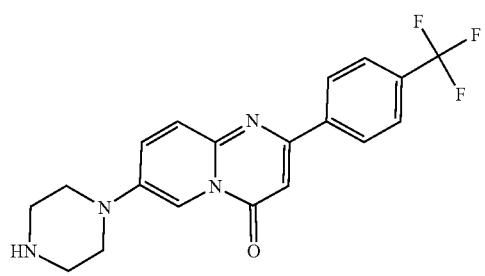
45
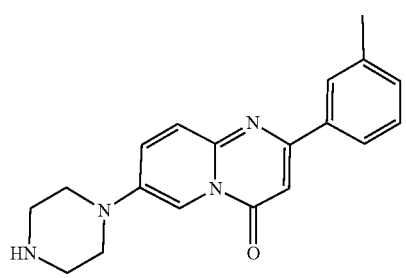
46
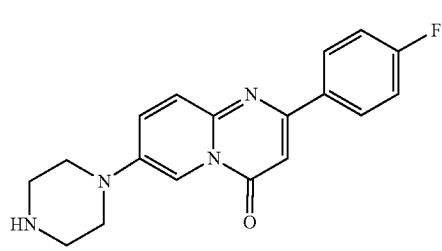
47
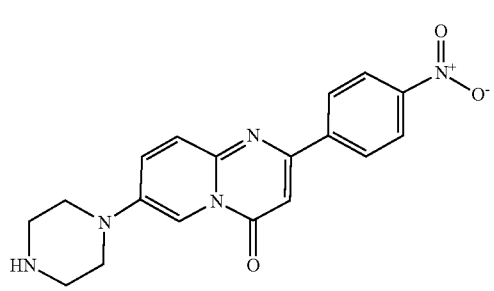
48
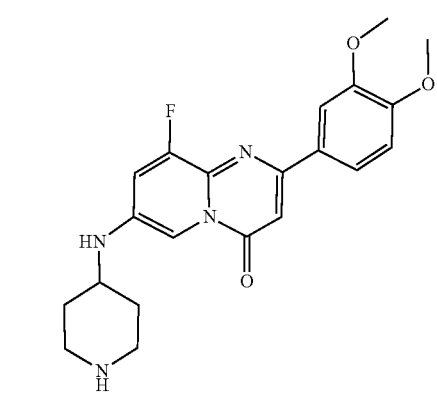
49
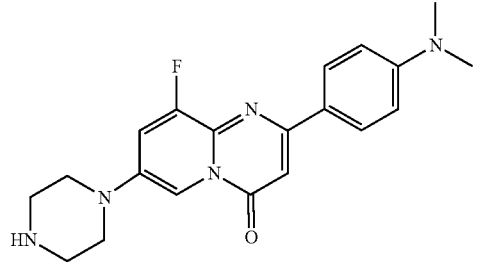
50
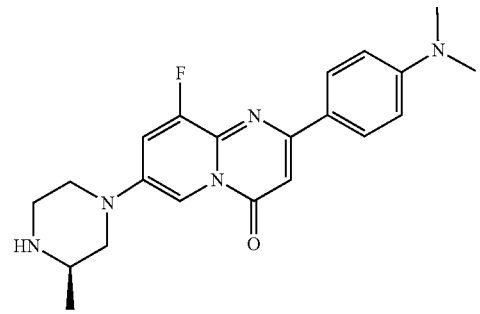
51
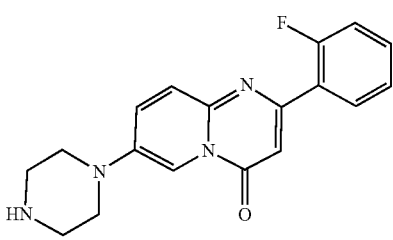
52
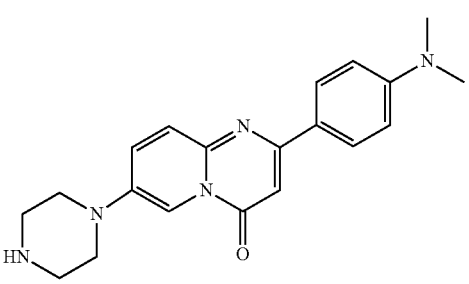
53

-continued
54
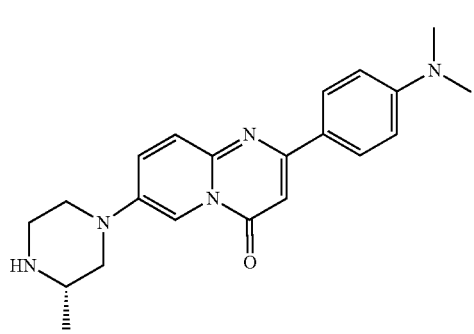
55
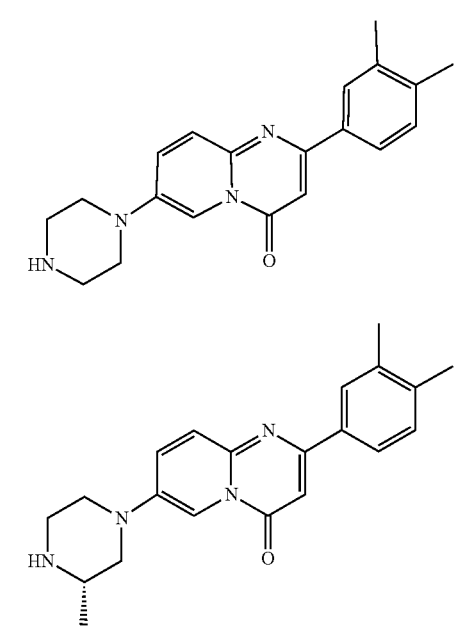
56
57
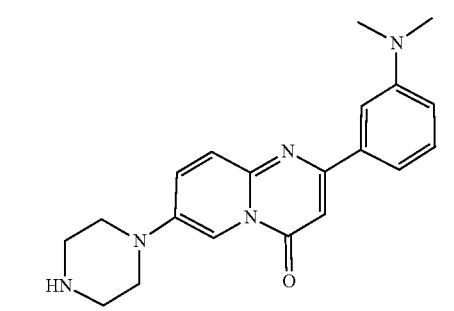
58
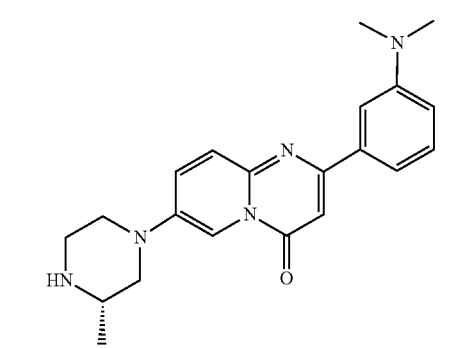
-continued
59
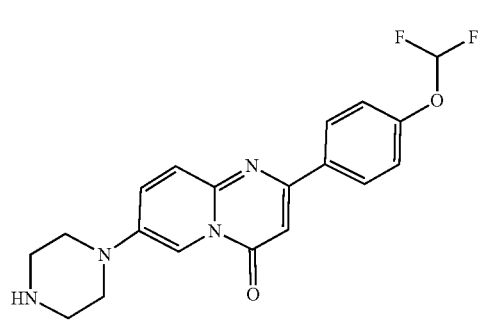
60
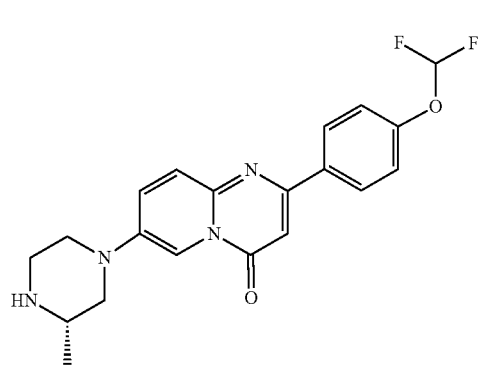
61
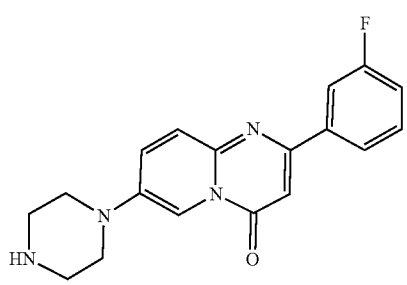
62
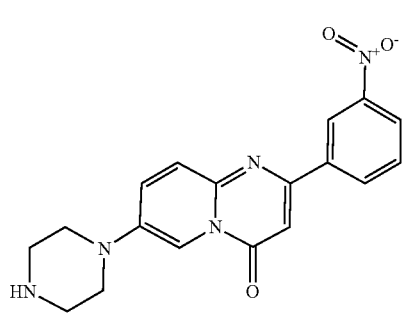
63
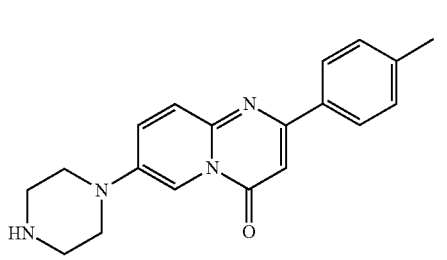

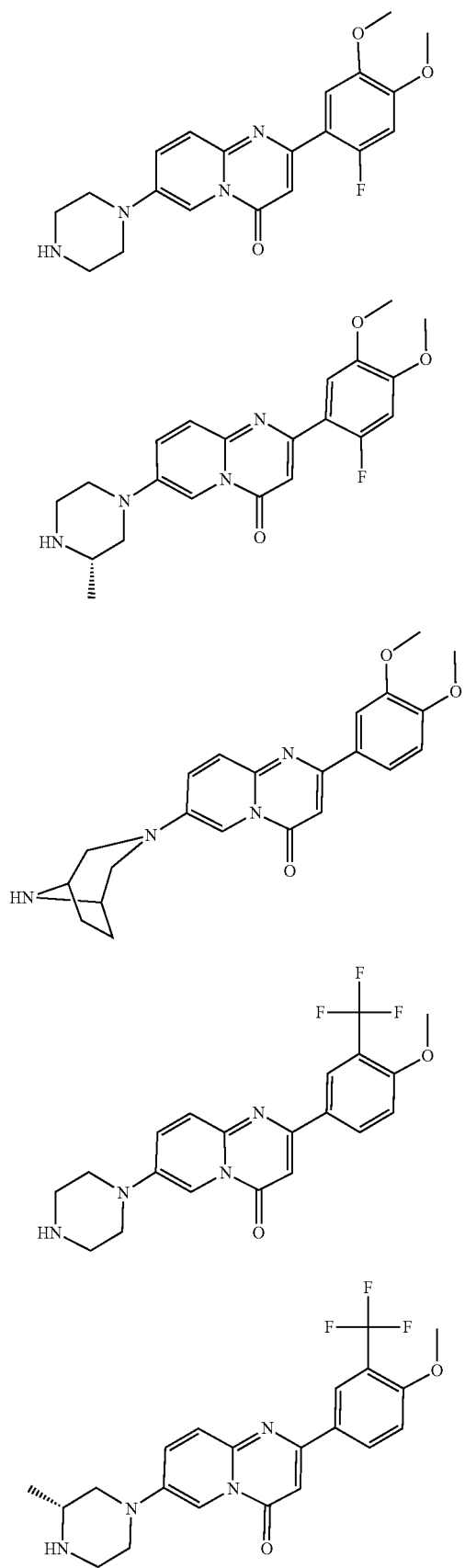
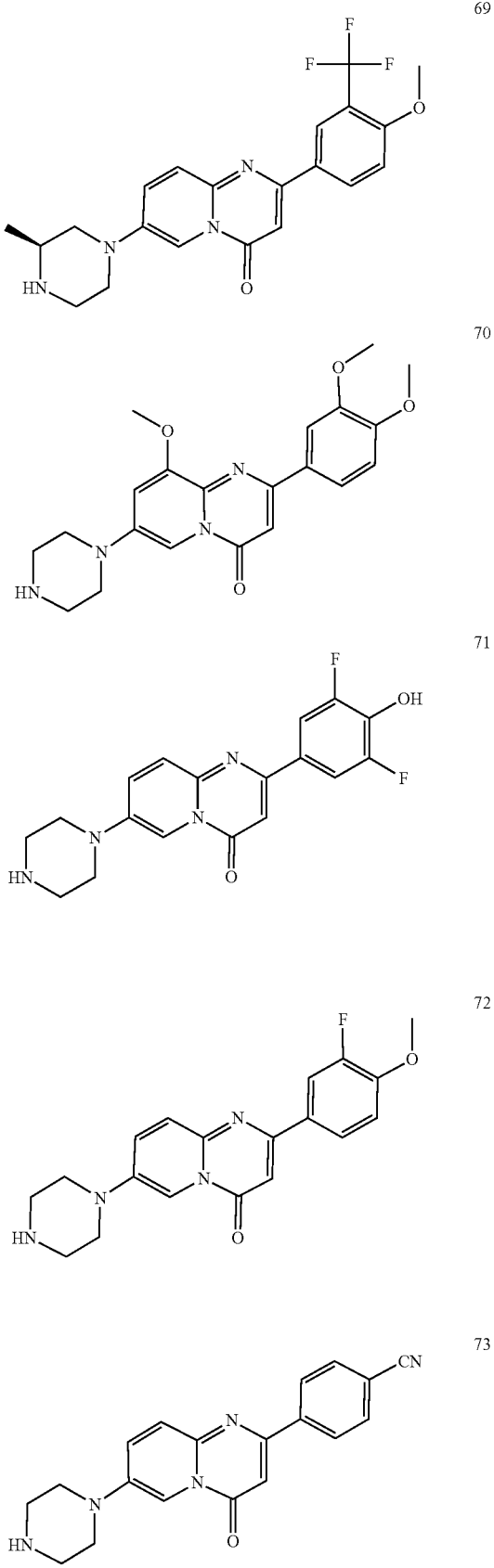

74 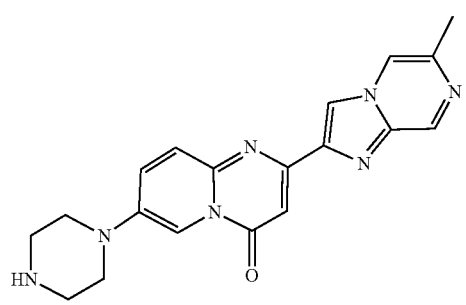
75 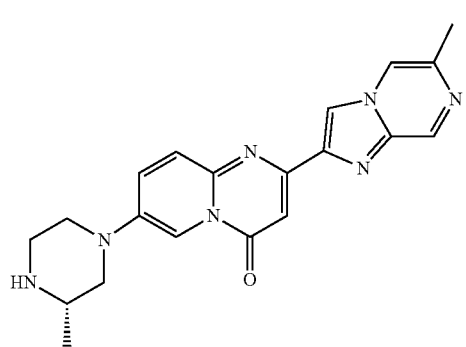
76 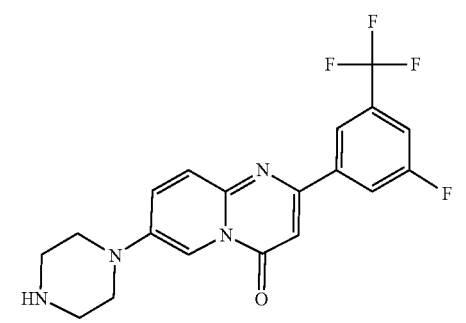
77 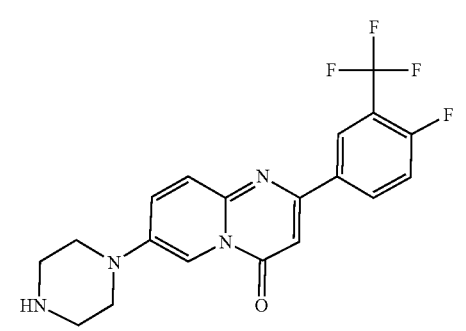
78 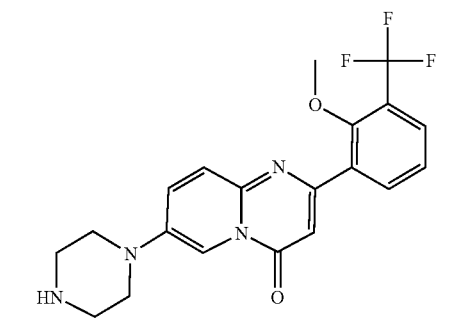
79 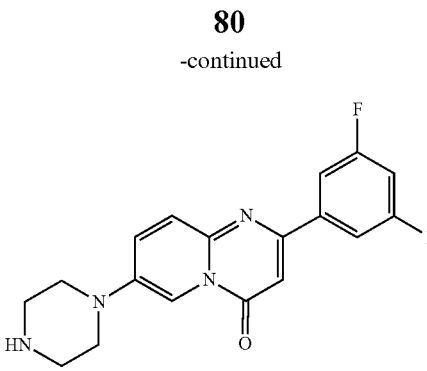
80 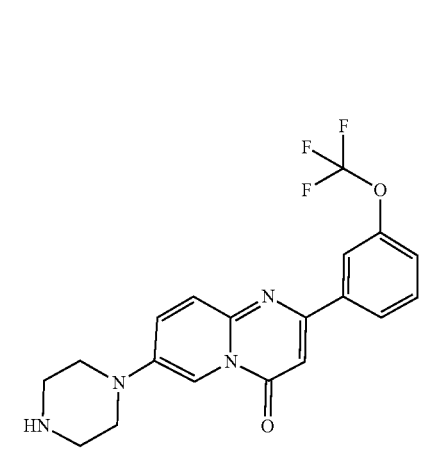
81 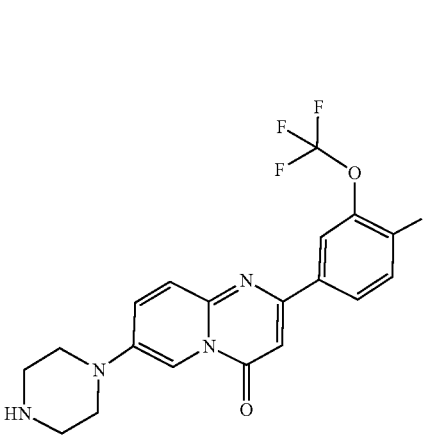
82 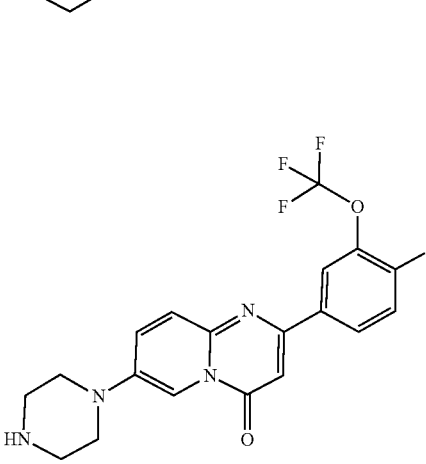

83
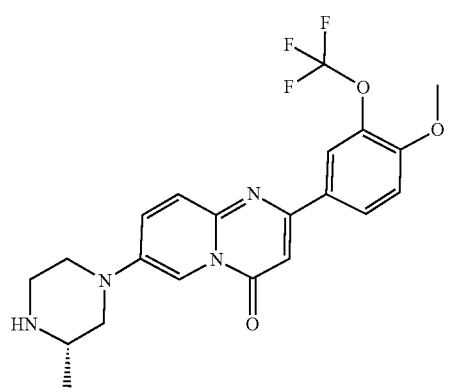
84
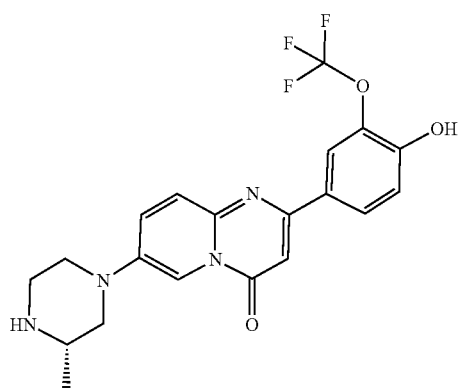
85
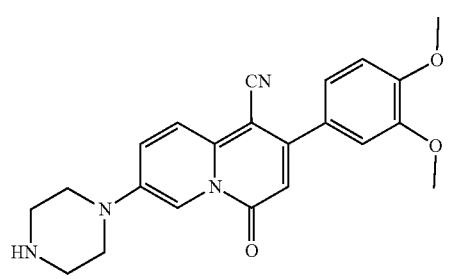
86
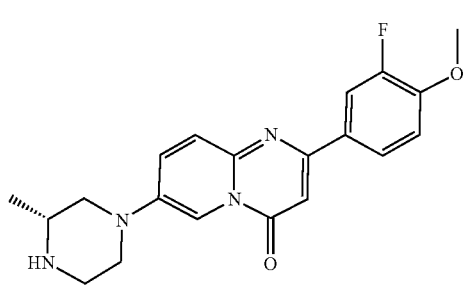
87
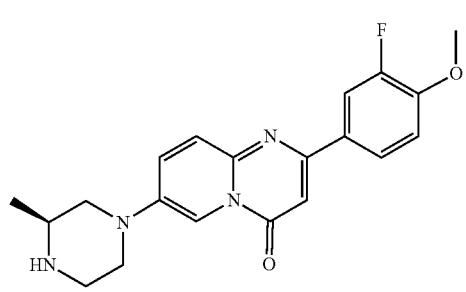
88
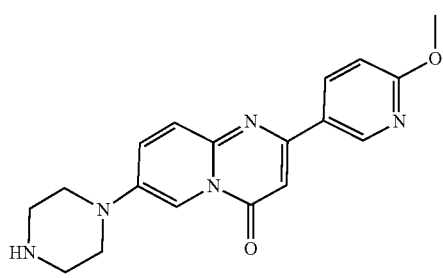
89
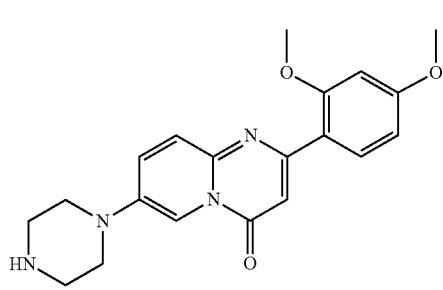
90
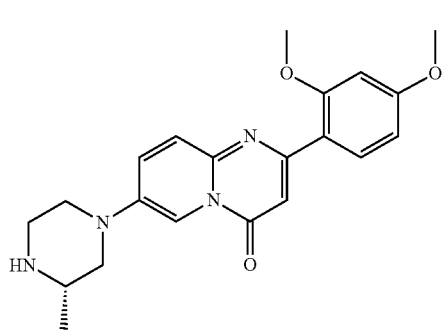
91
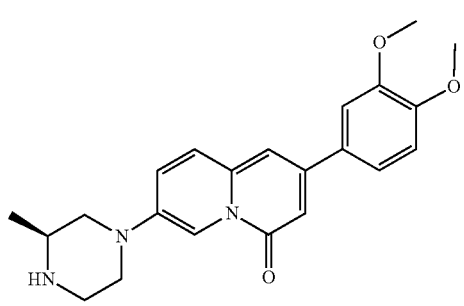
92
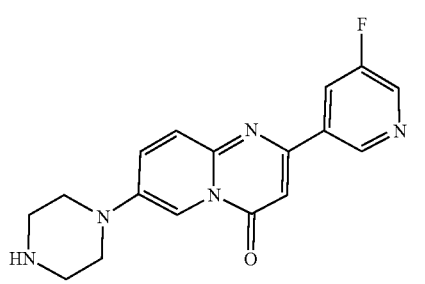

93
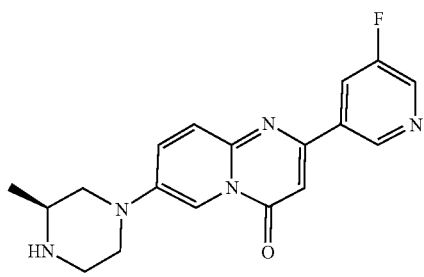
94
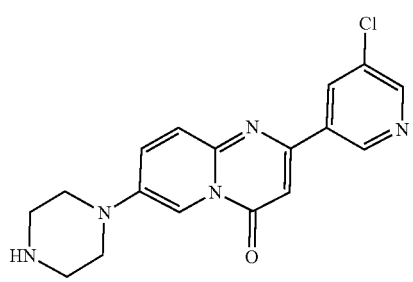
95
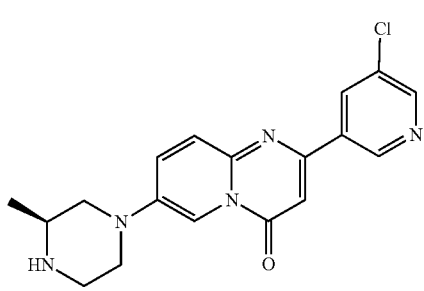
96
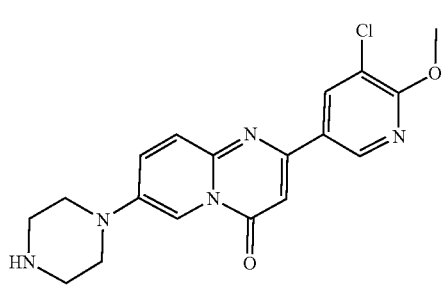
97
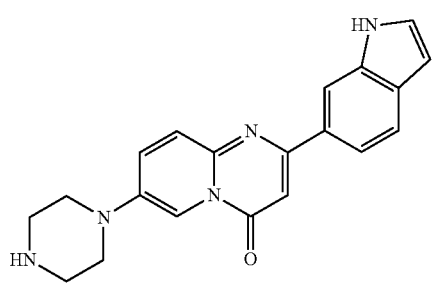
98
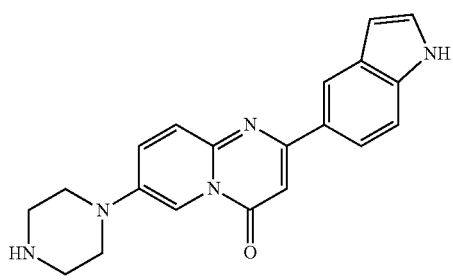
99
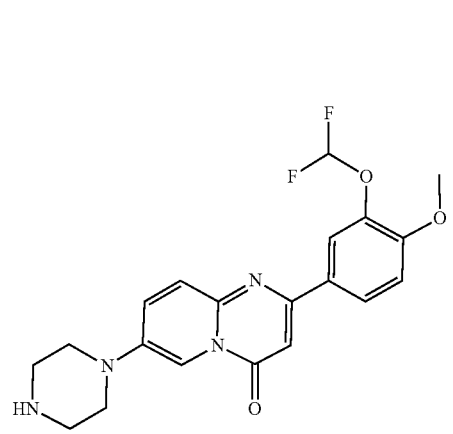
100
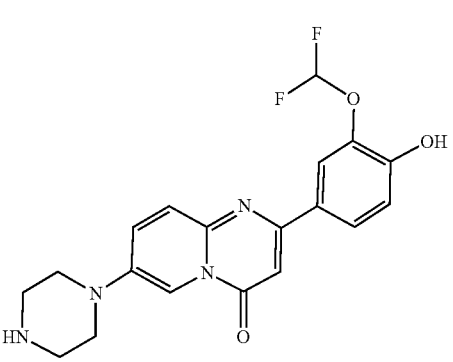
101
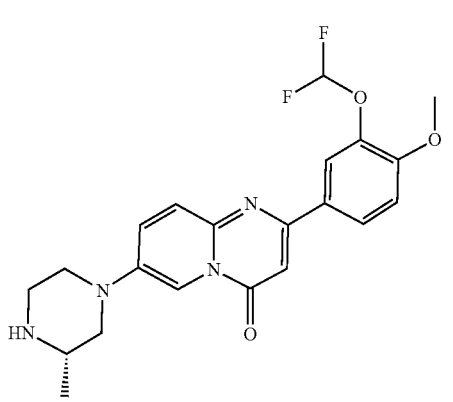

85
-continued
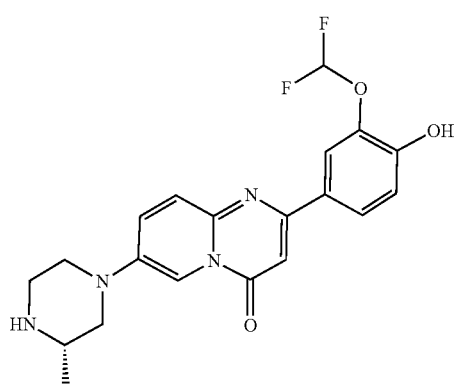
102
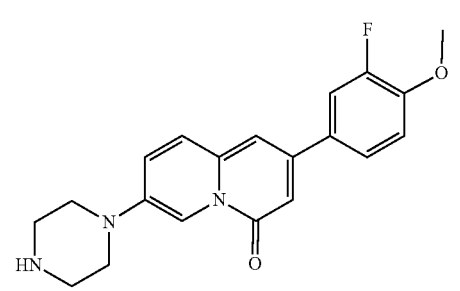
103
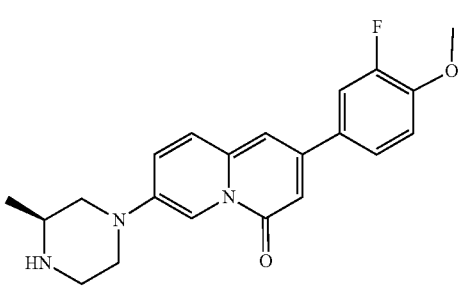
104
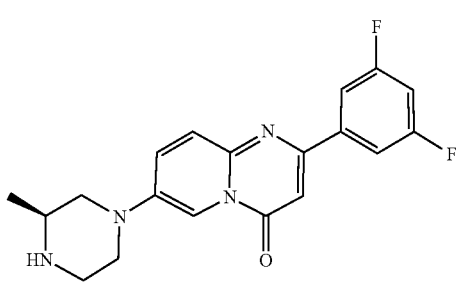
105
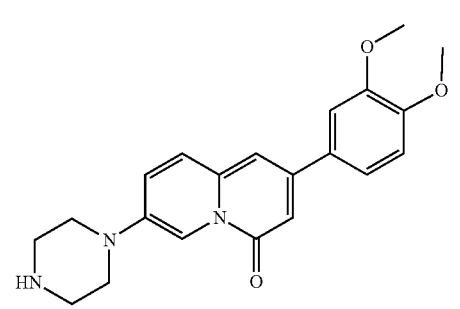
106
86
-continued
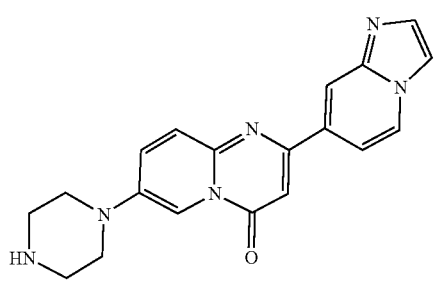
107
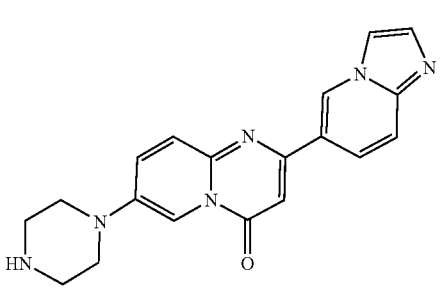
108
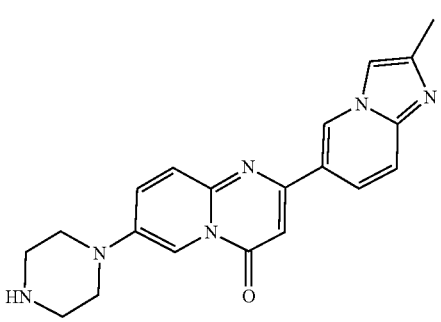
109
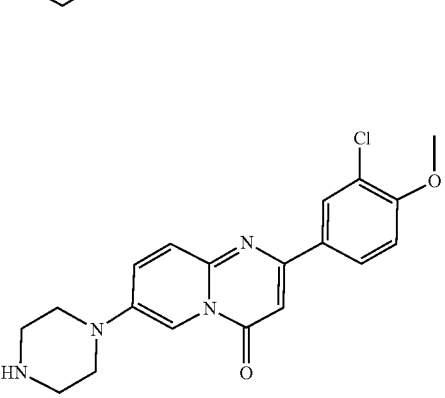
110
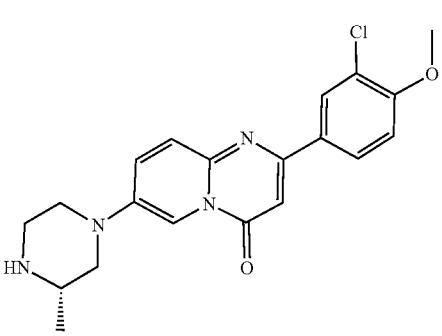
111

112
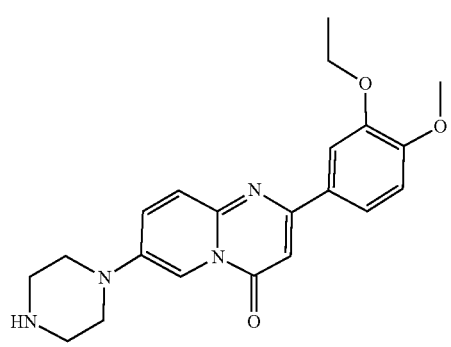
113
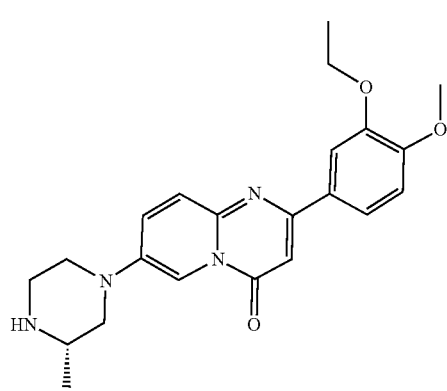
114
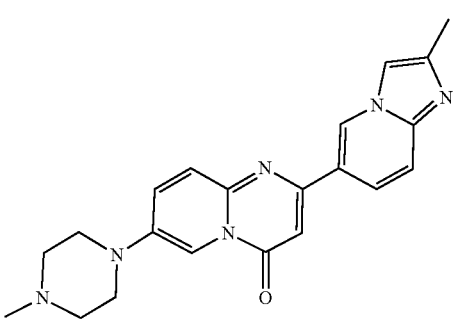
115
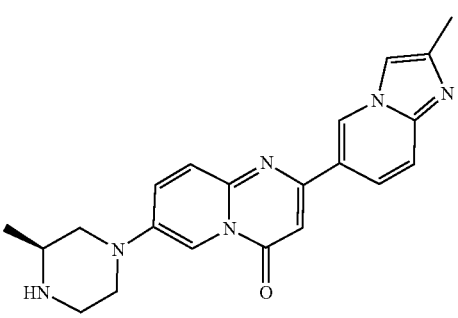
116
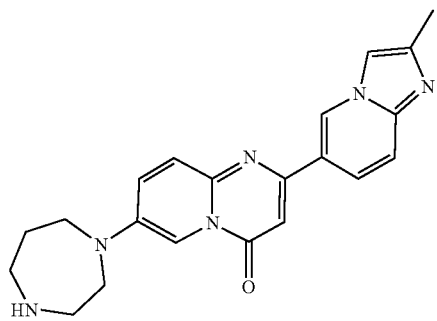
117
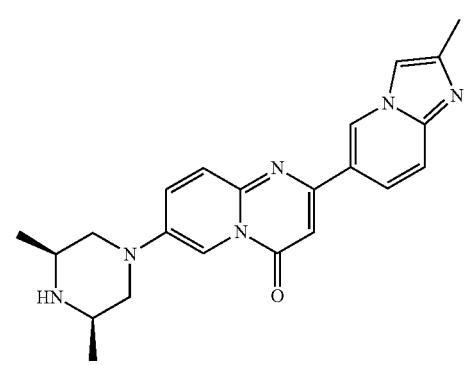
118
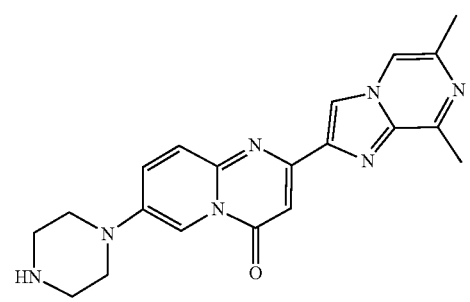
119
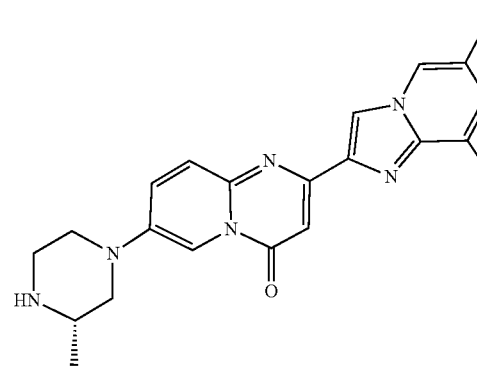
120
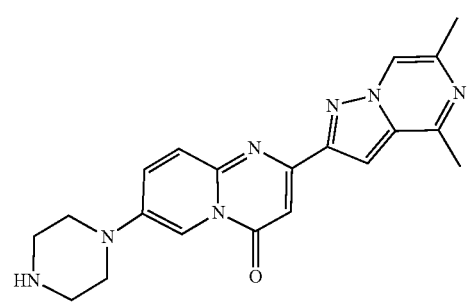

121 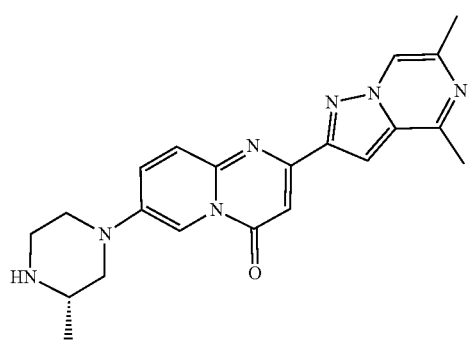
125 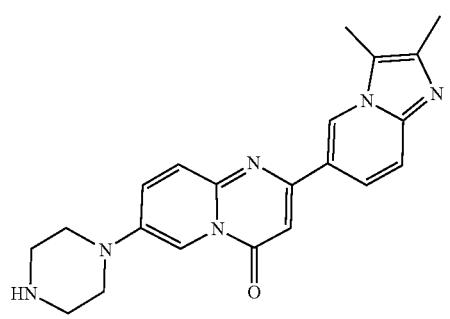
122 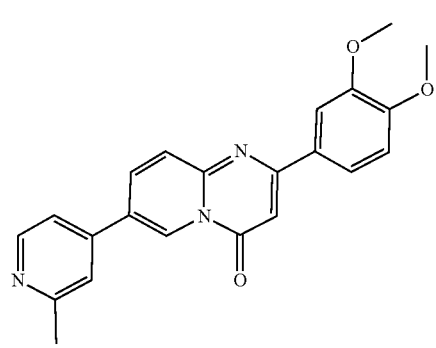
126 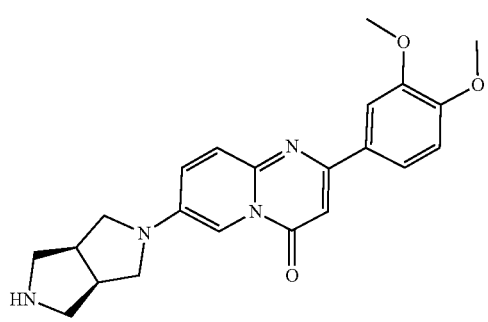
123 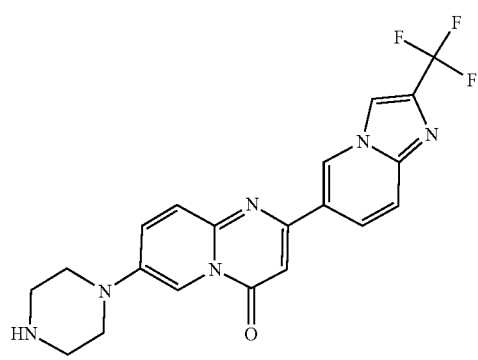
127 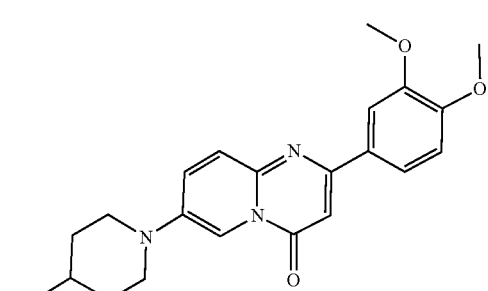
128
124 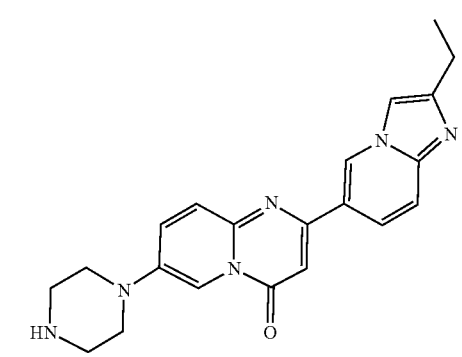
129 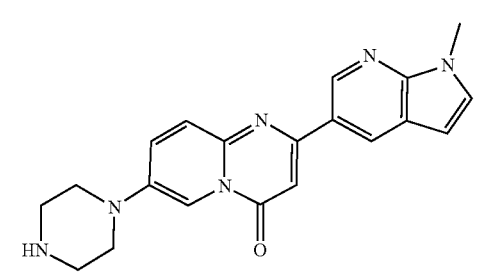

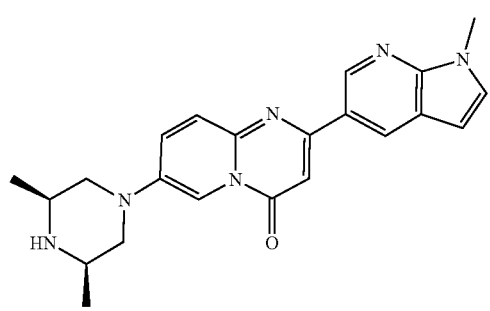
130
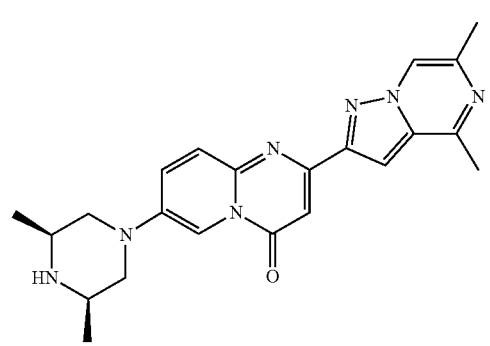
131
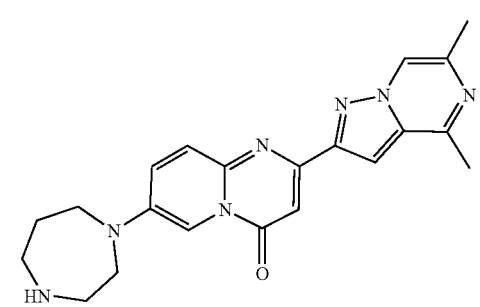
132
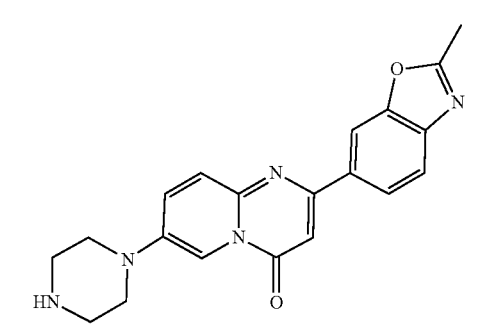
133
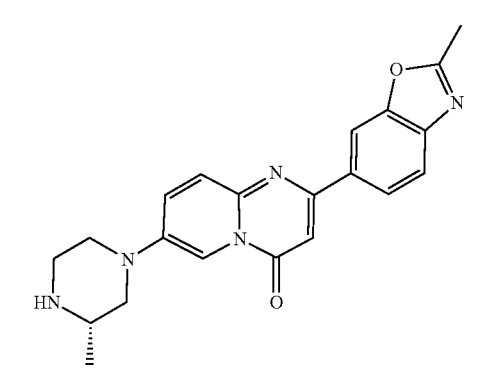
134
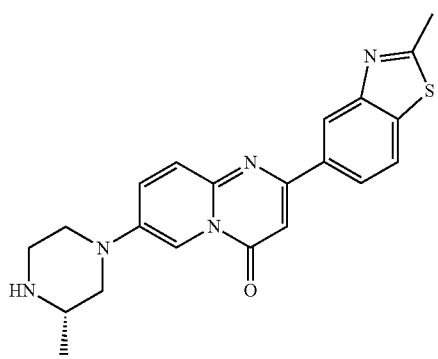
135
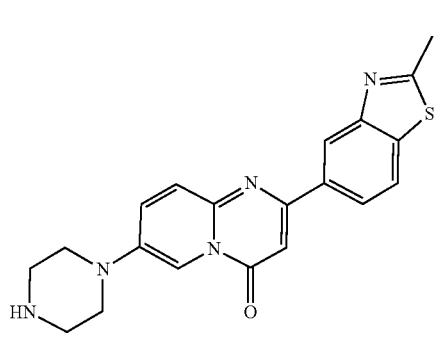
136
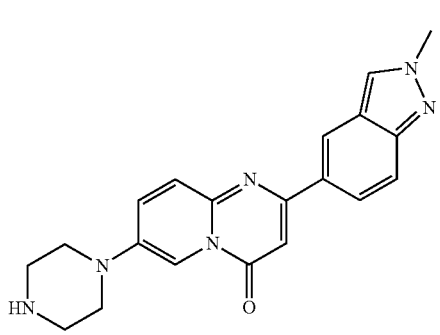
137
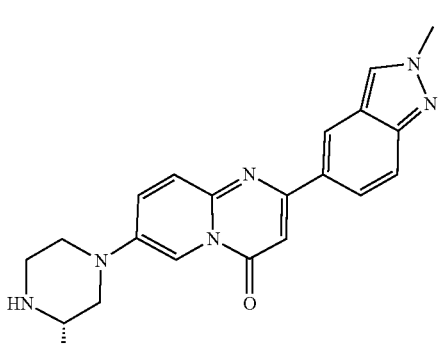
138

139 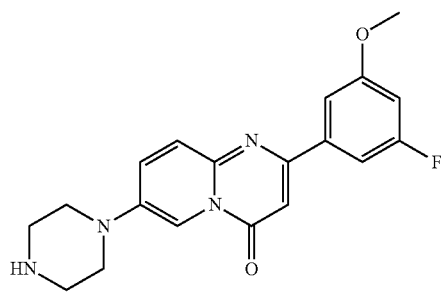
140 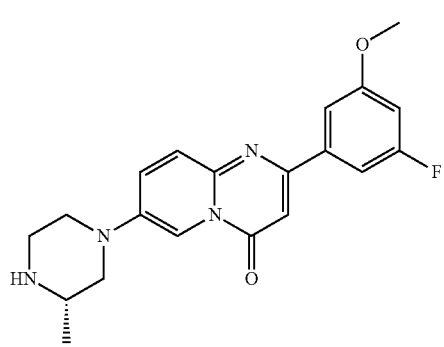
141 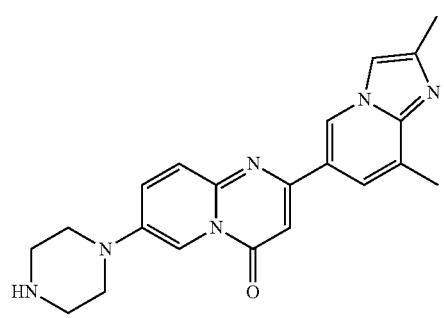
142 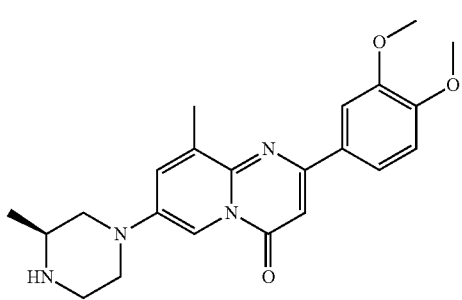
143 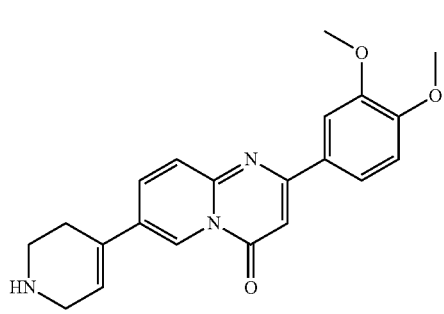
144 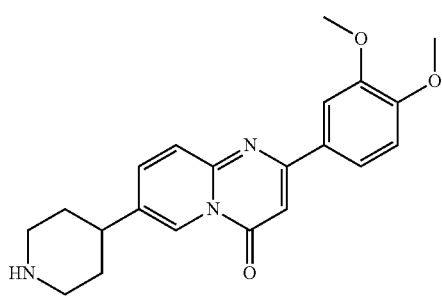
145 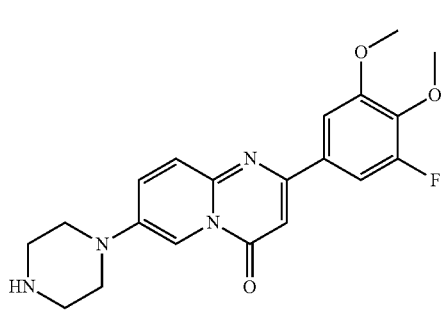
146 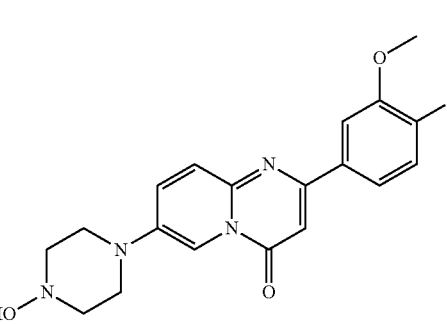
147 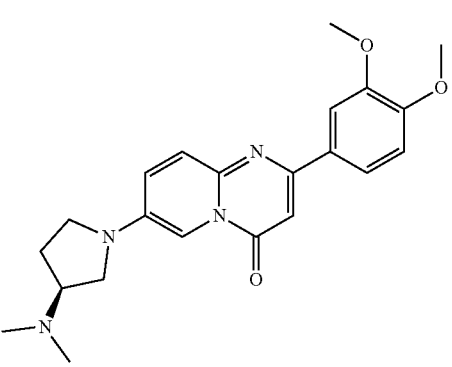
148 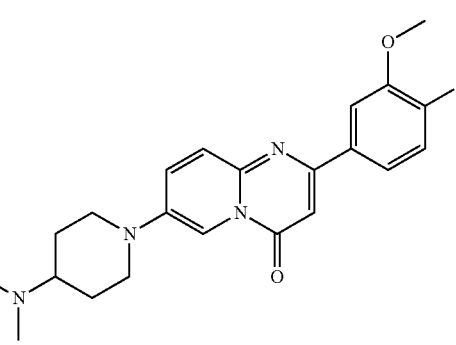

| | |
|---|---|
| 149 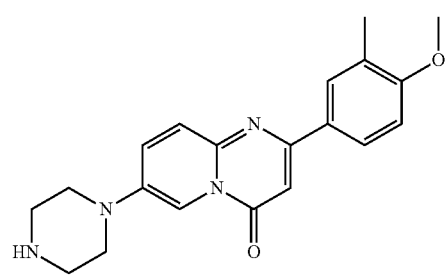 | 154 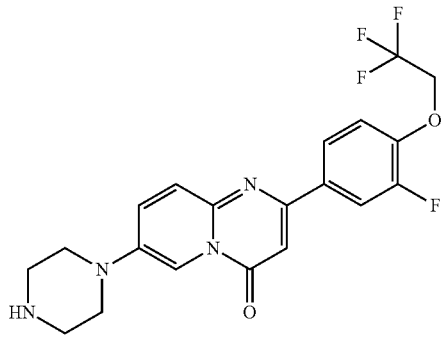 |
| 150 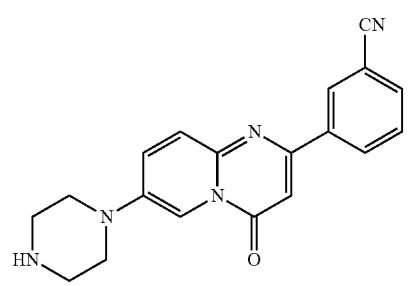 | 155 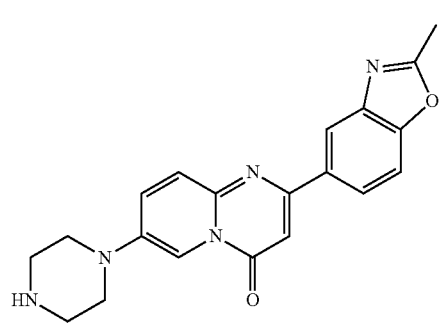 |
| 151 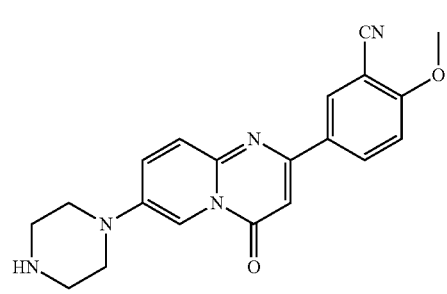 | 156 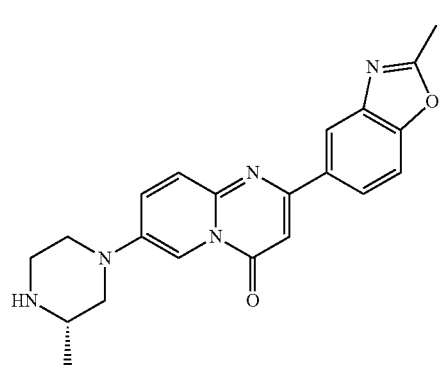 |
| 152 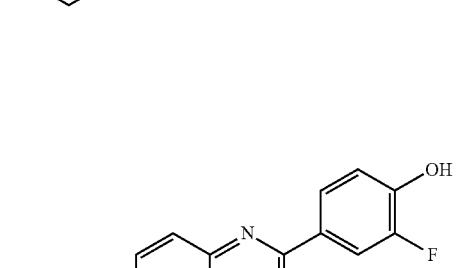 | 157 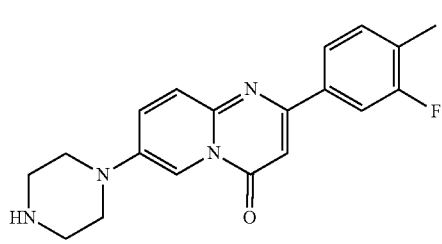 |
| 153 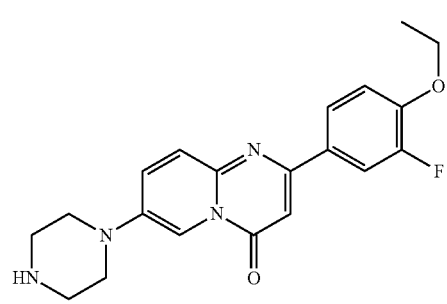 | 158 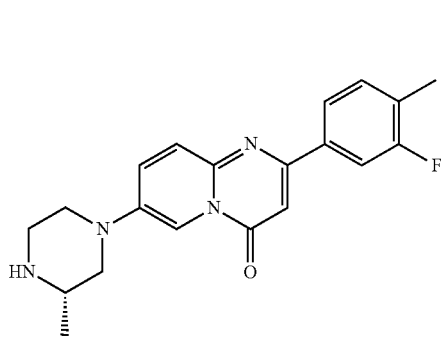 |

159
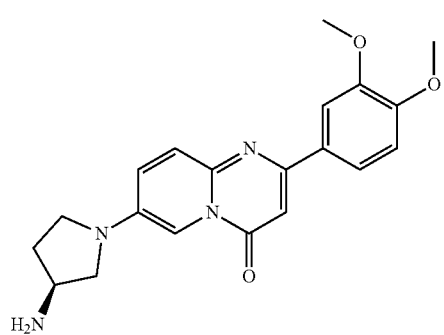
160
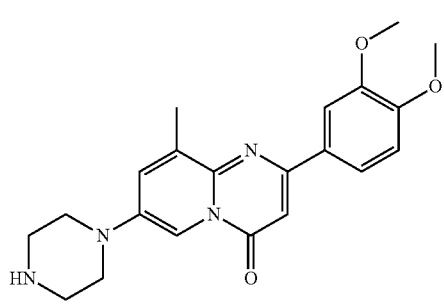
161
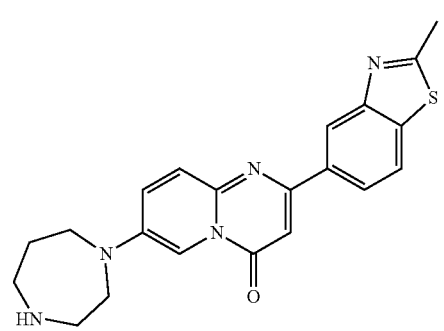
162
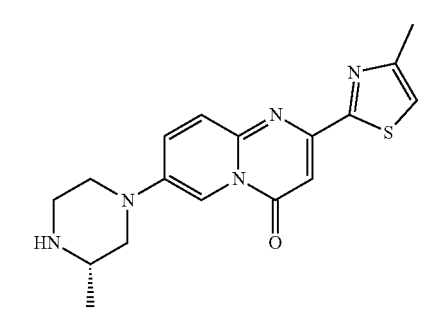
163
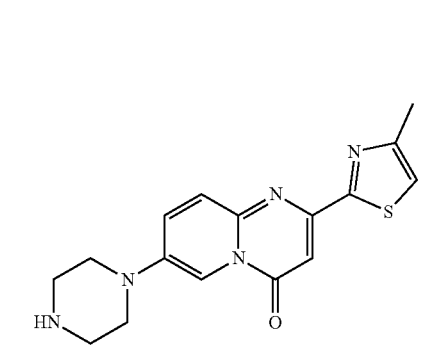
164
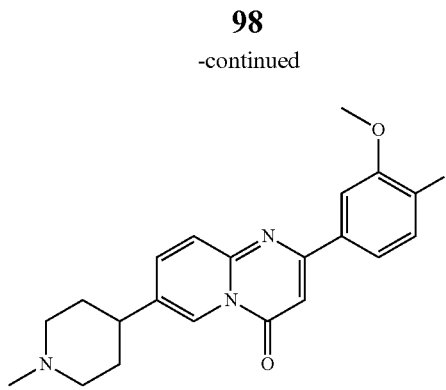
165
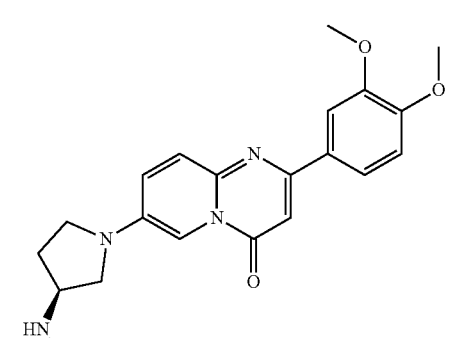
166
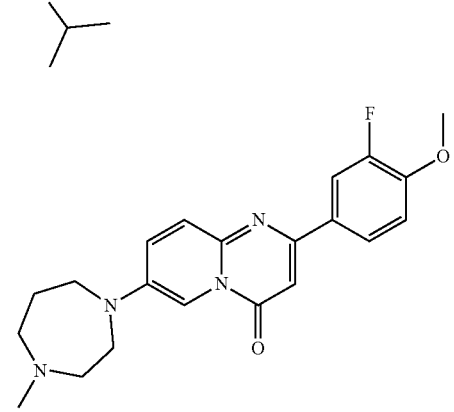
167
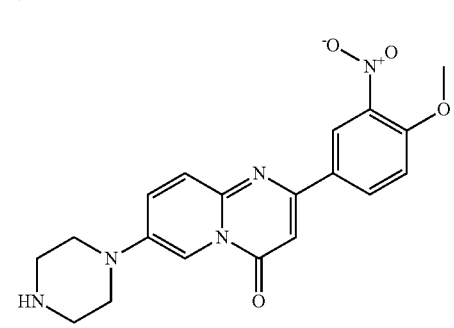
168
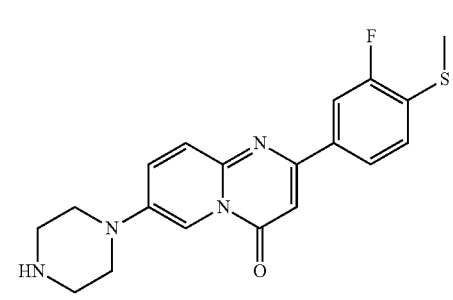

-continued
169
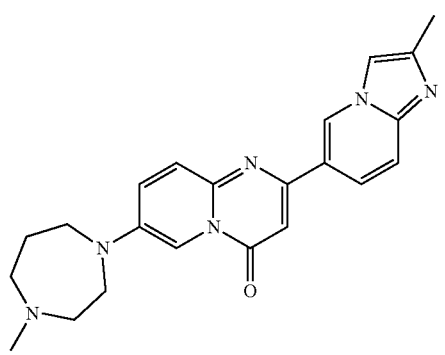
170
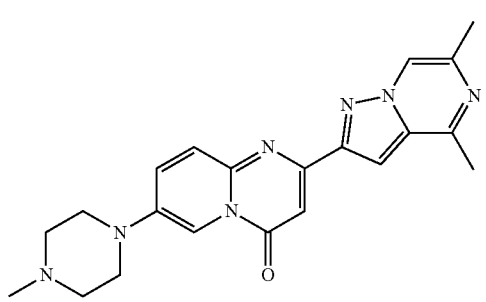
171
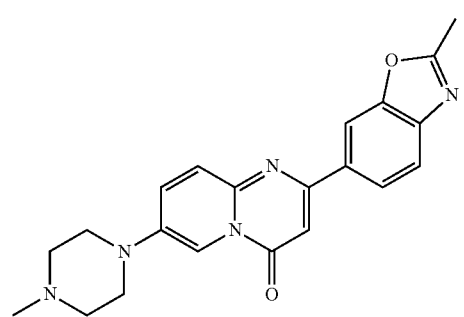
172
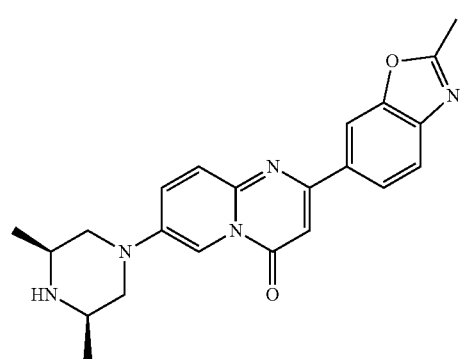
173
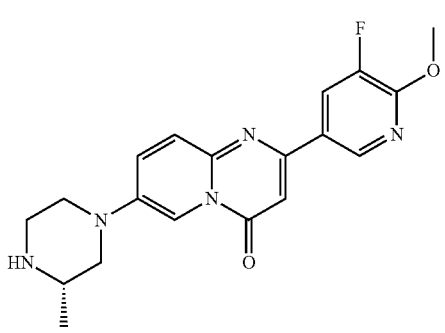
-continued
174
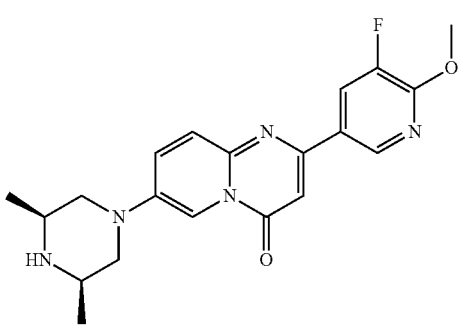
175
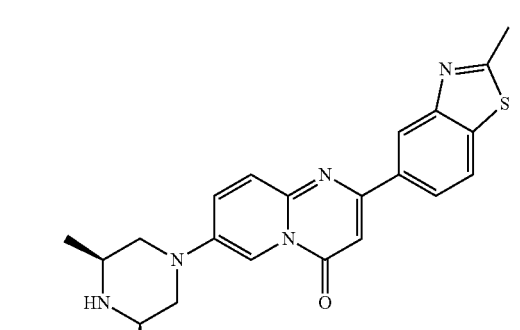
176
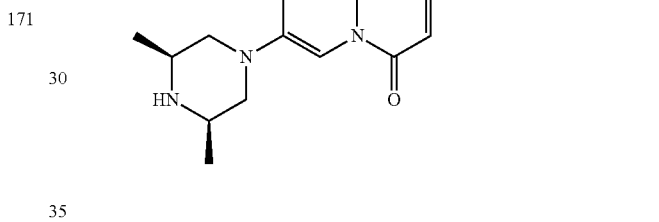
177
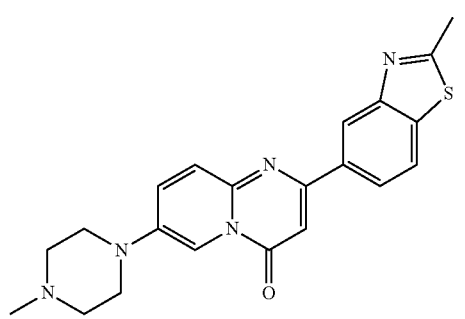
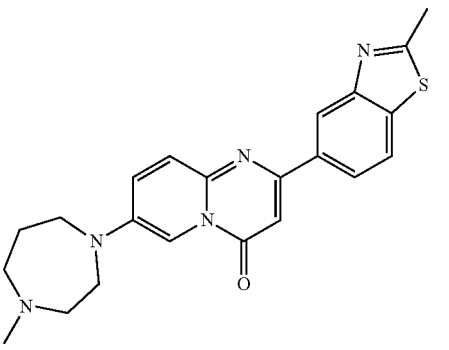

178 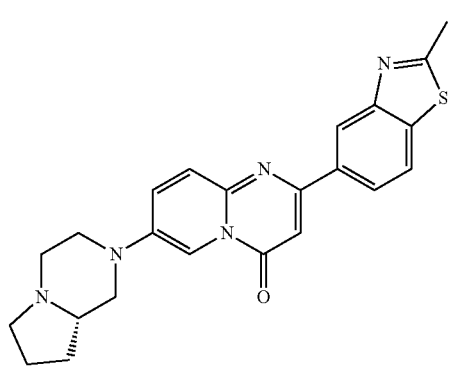
179 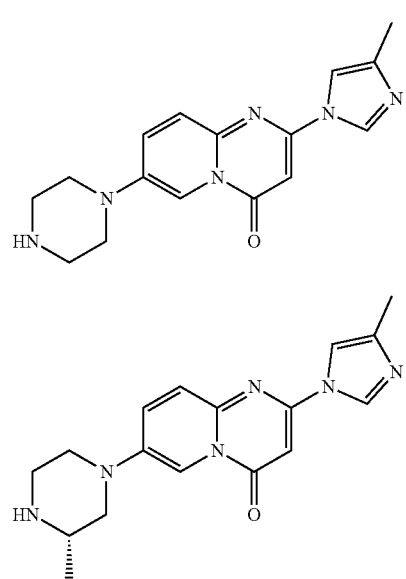
180 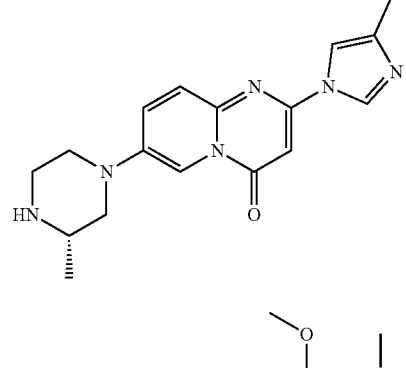
181 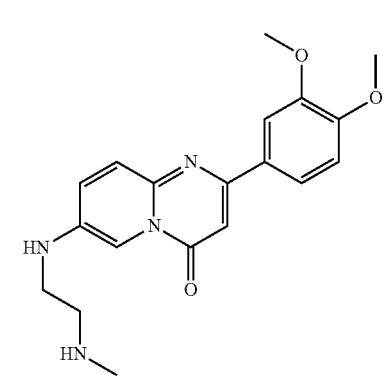
182 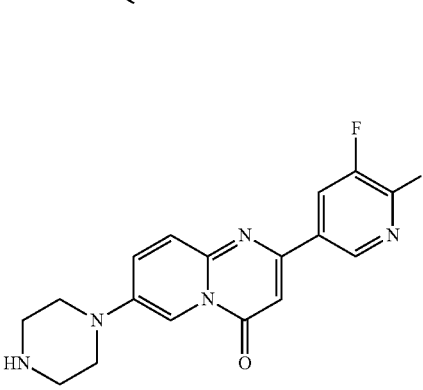
183 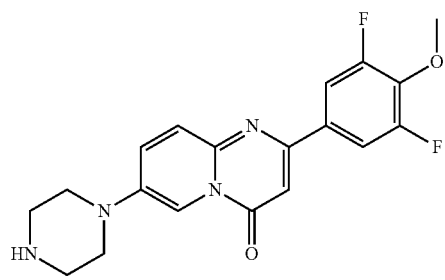
184 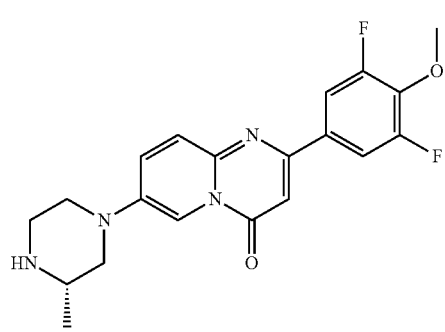
185 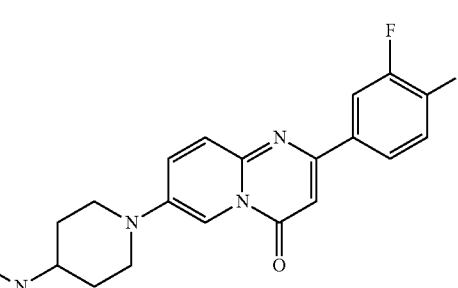
186 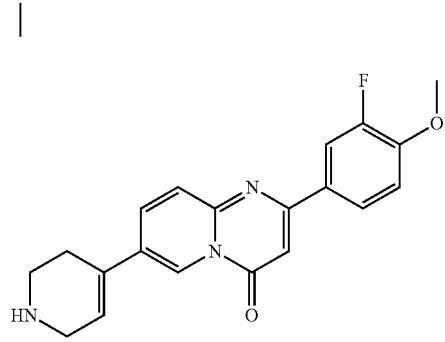
187 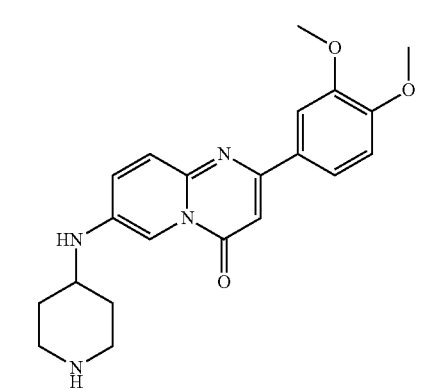

188
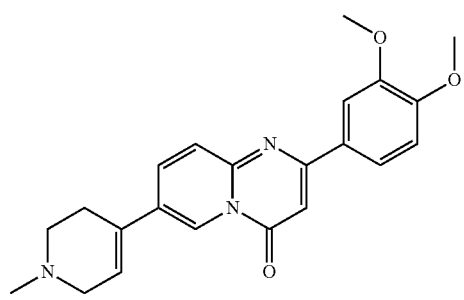
189
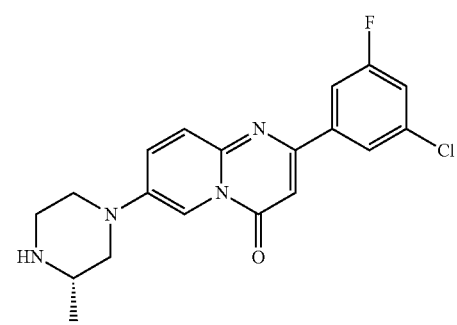
190
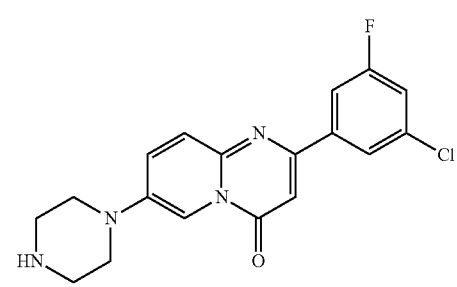
191
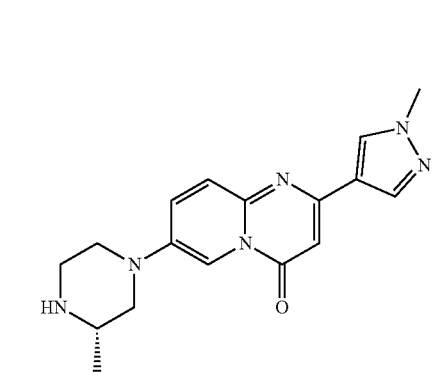
192
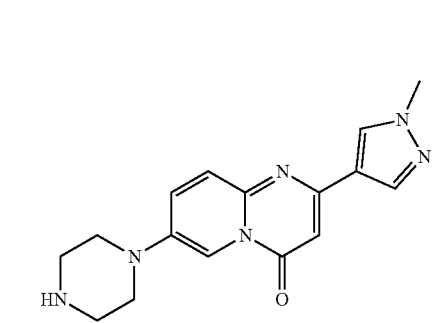
193
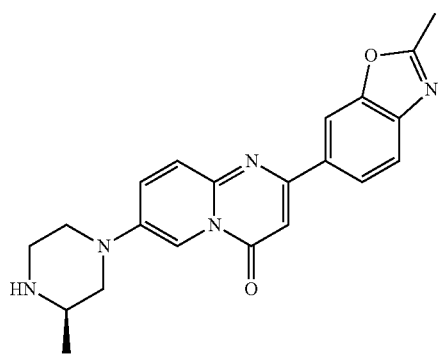
194
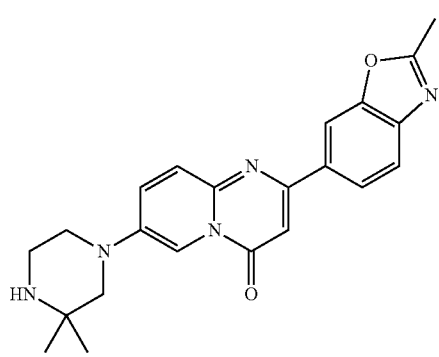
195
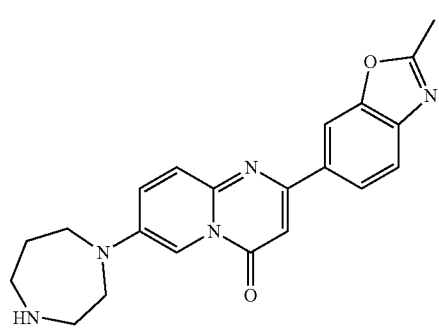
196
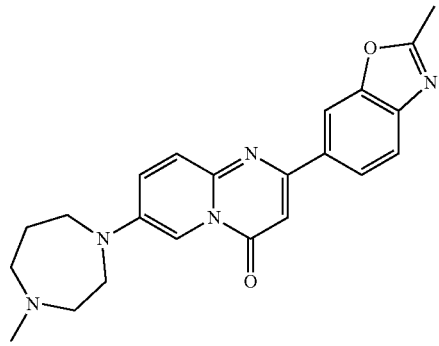

197 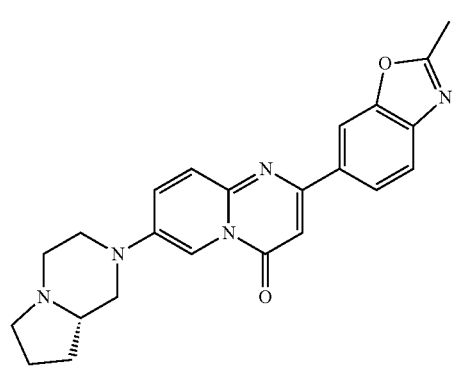
198 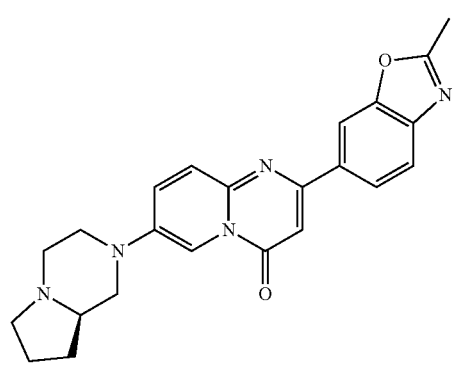
199 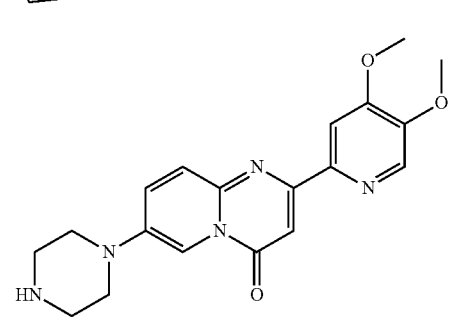
200 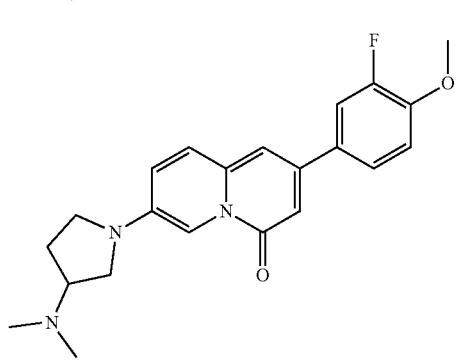
201 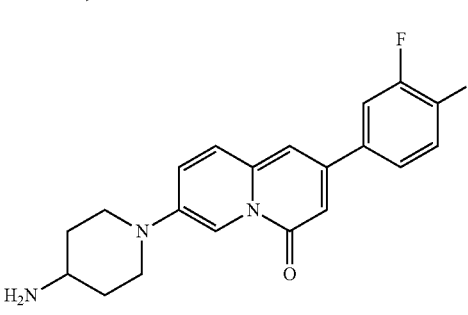
202 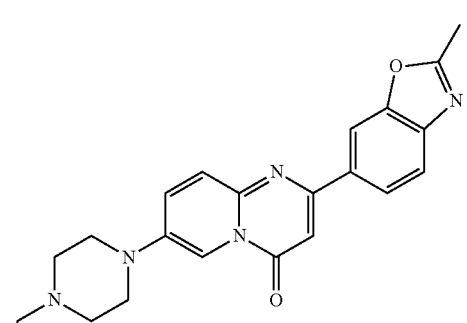
203 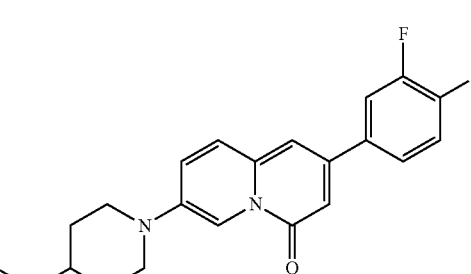
204 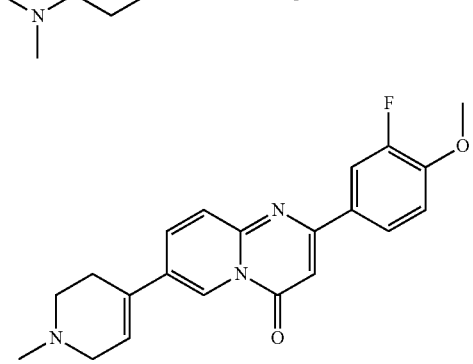
205 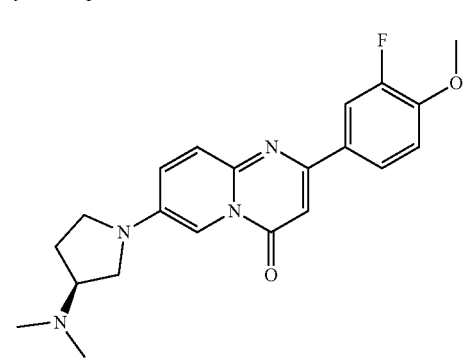
206 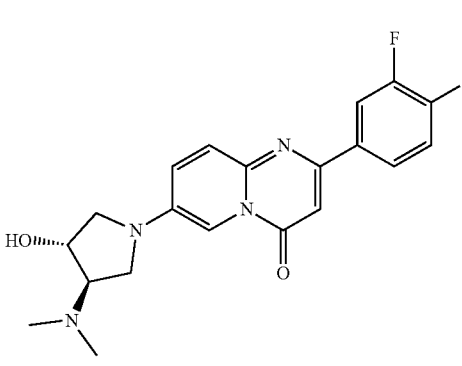

207
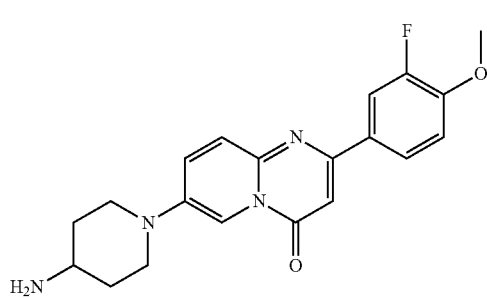
208
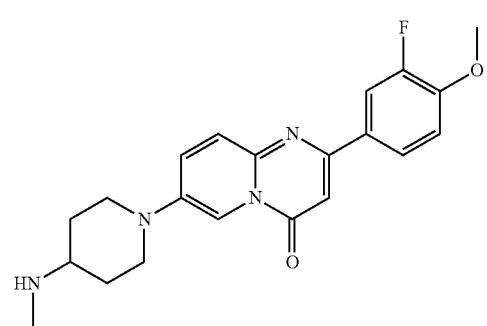
209
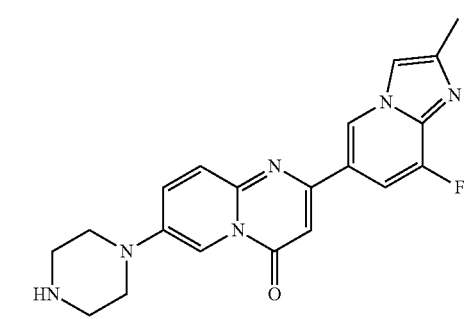
210
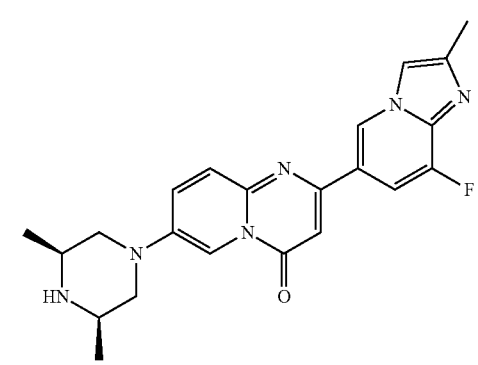
211
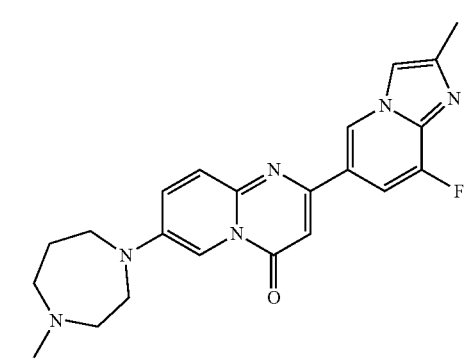
212
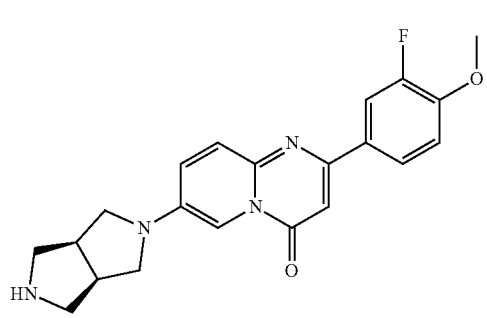
213
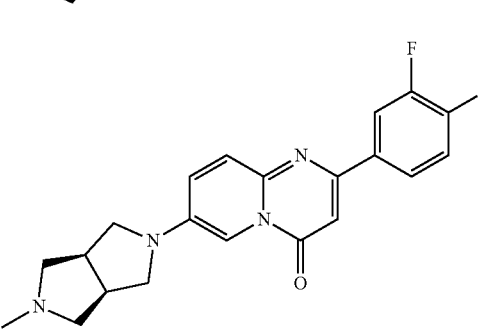
214
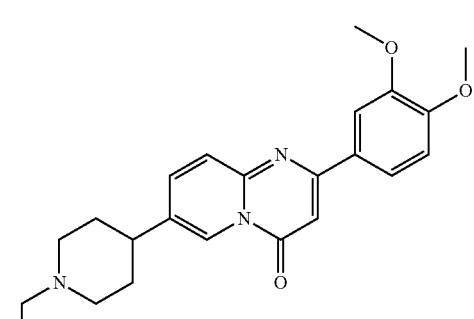
215
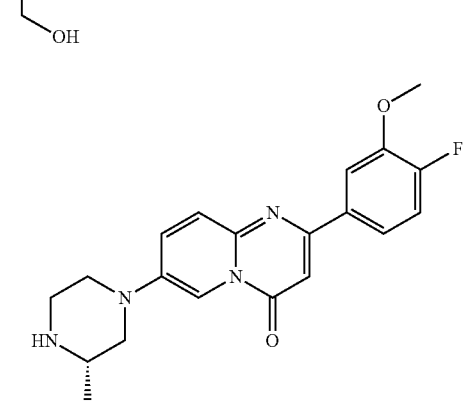
216
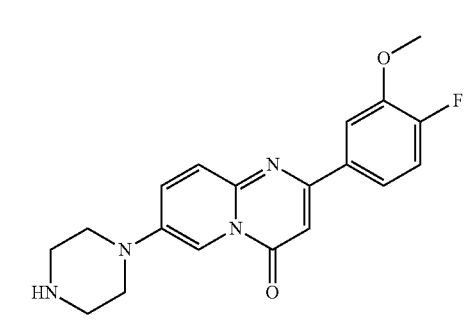

217 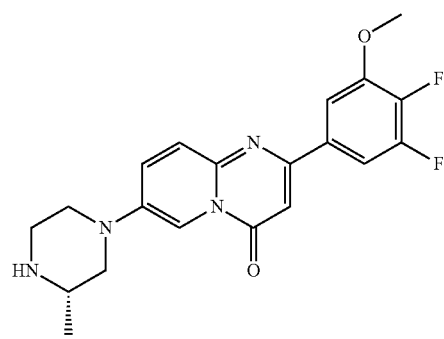
218 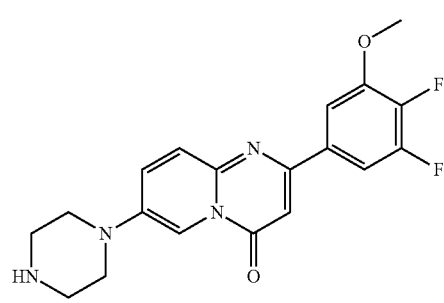
219 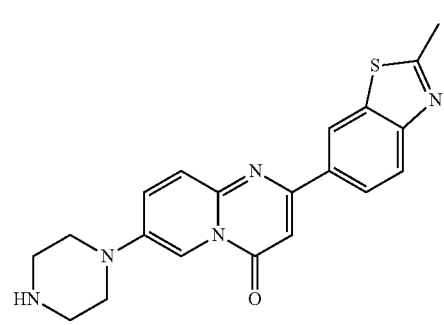
220 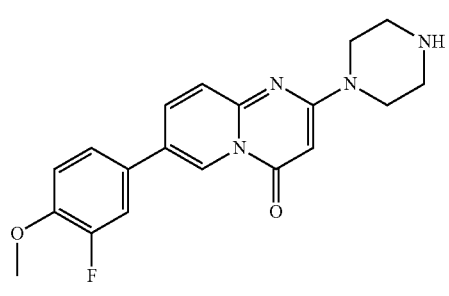
221 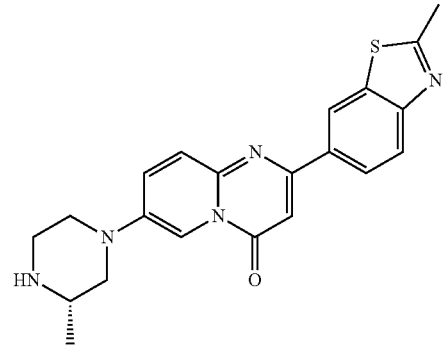
222 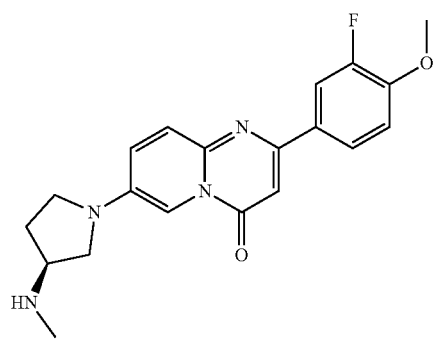
223 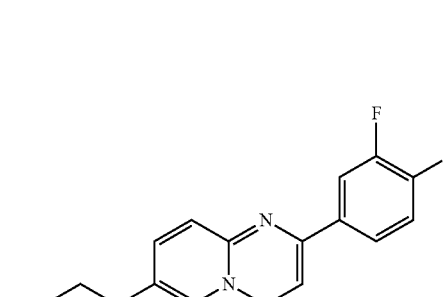
224 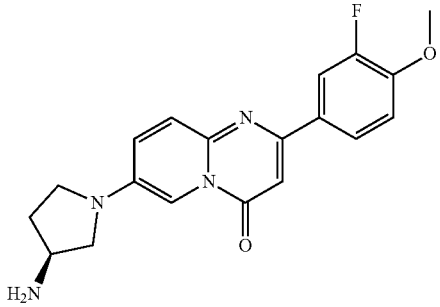
225 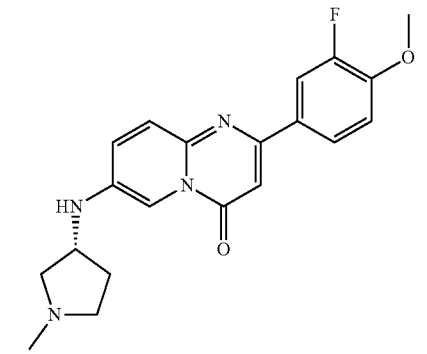

-continued
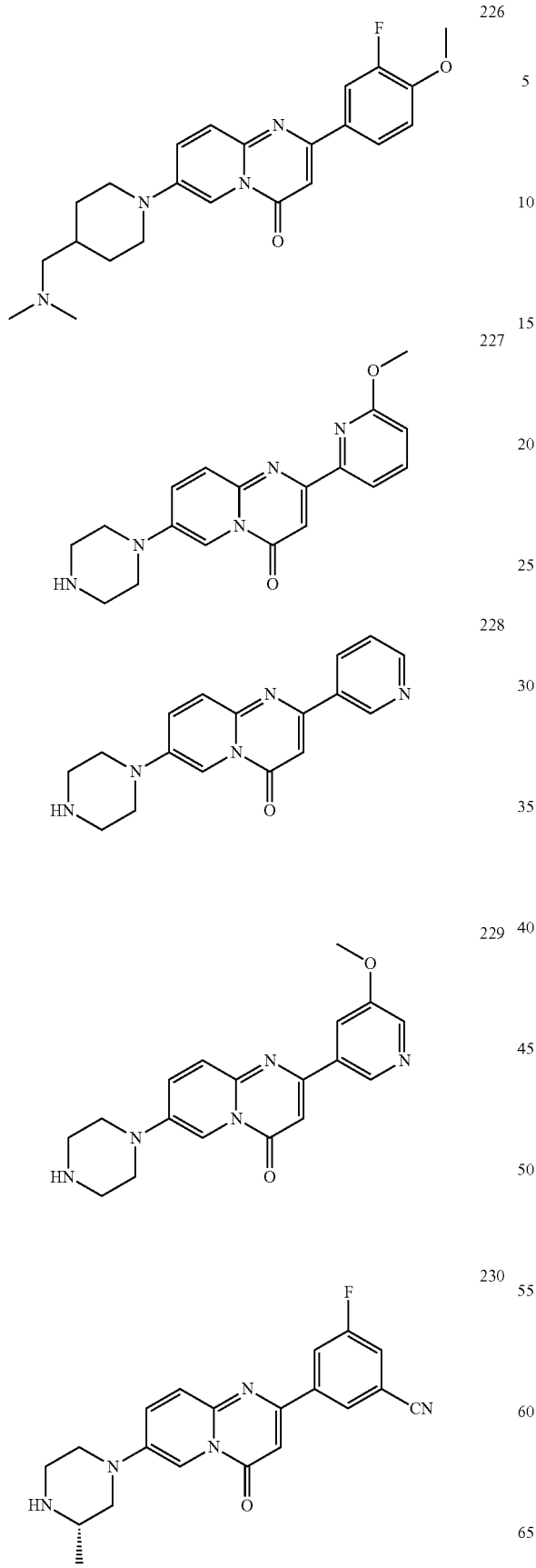
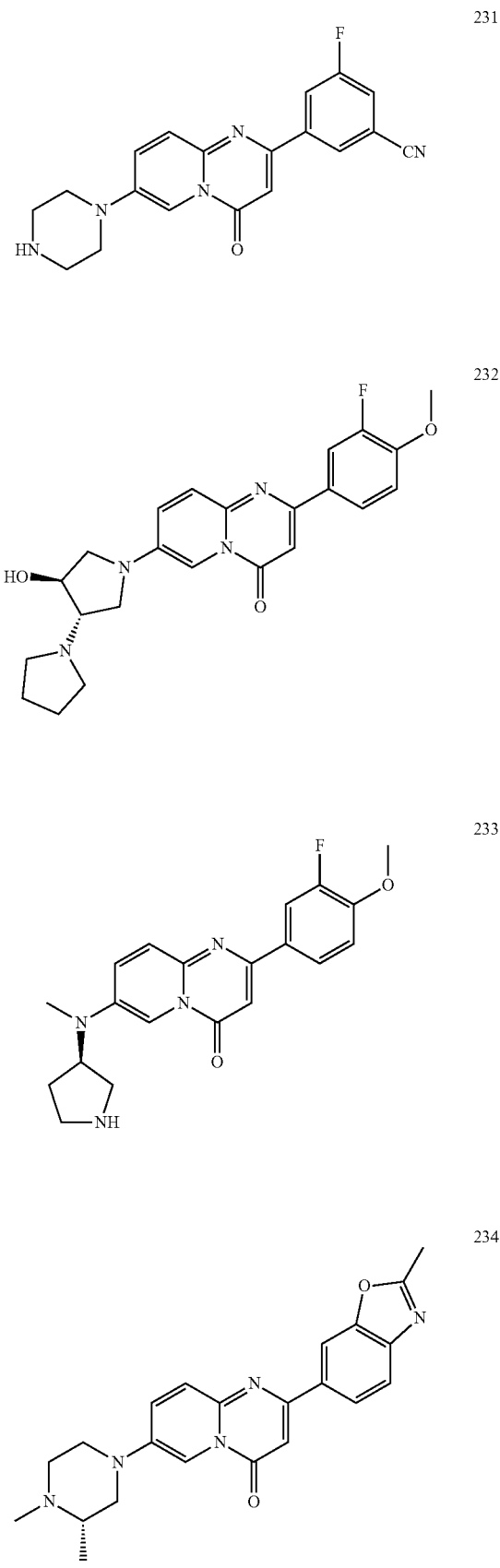

235 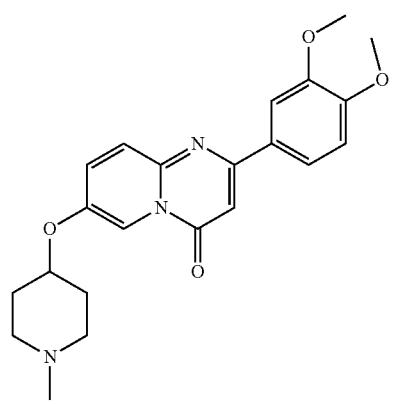
236 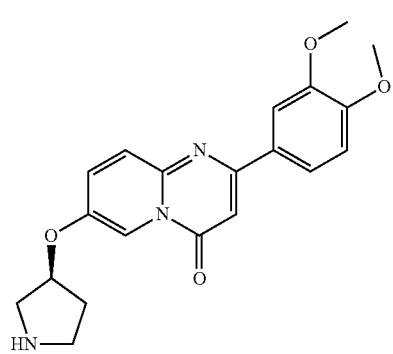
237 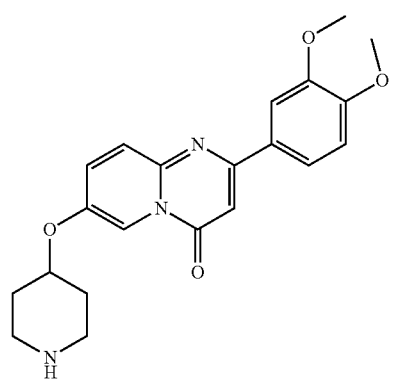
238 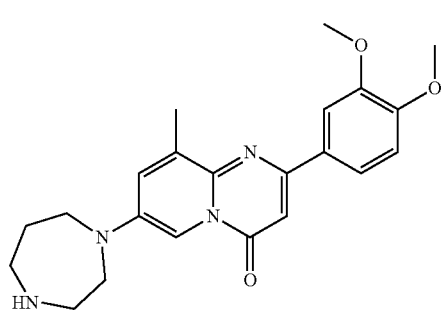
239 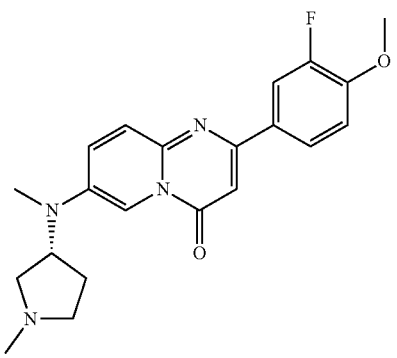
240 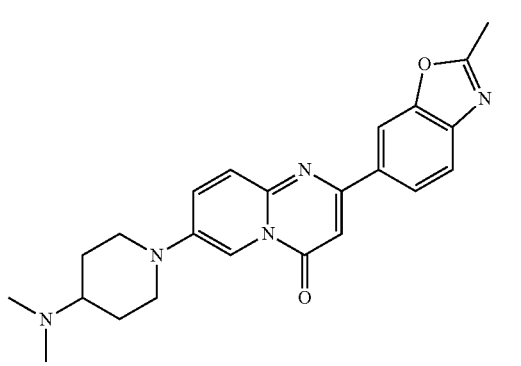
241 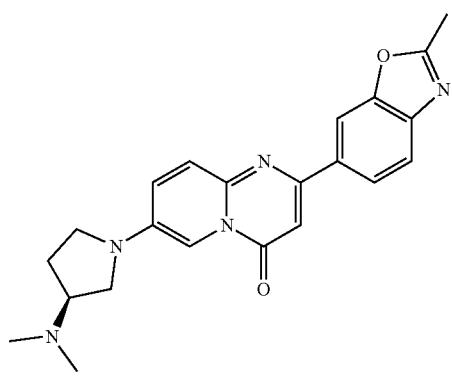
242 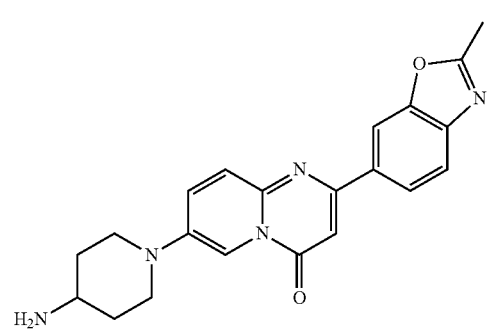

243 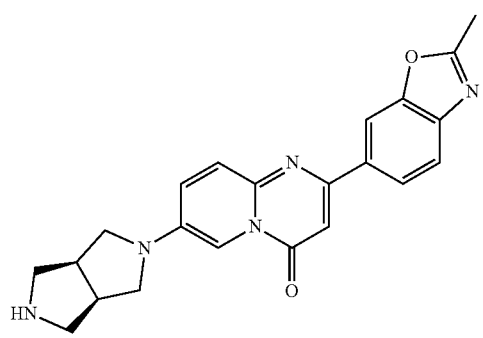
244 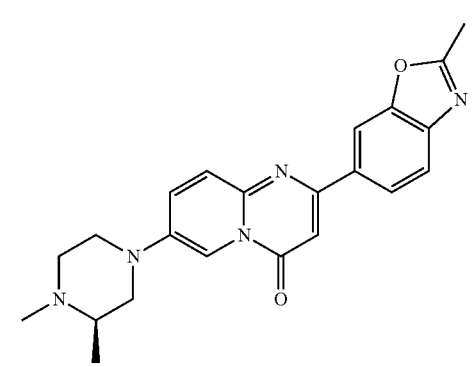
245 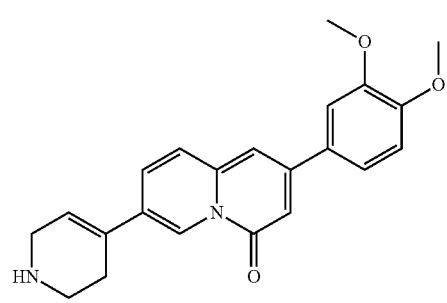
246 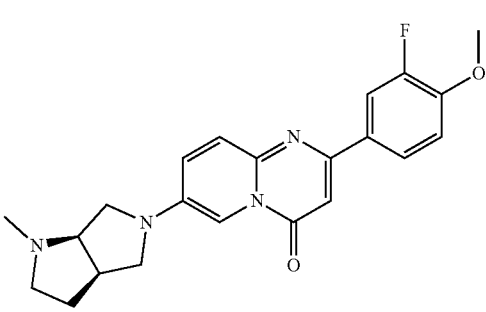
247 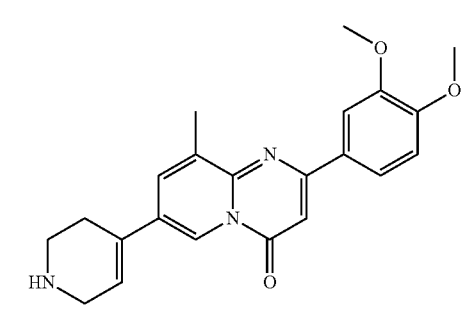
248 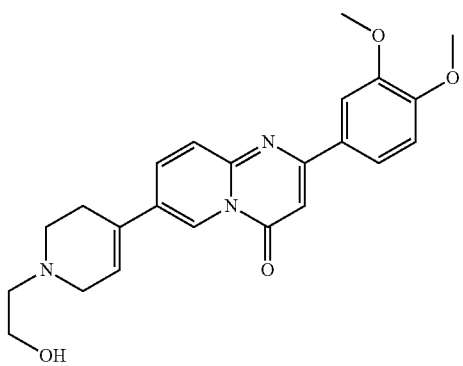
249 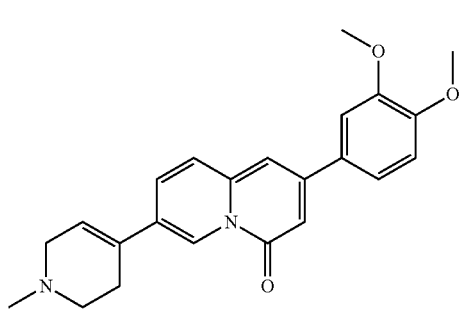
250 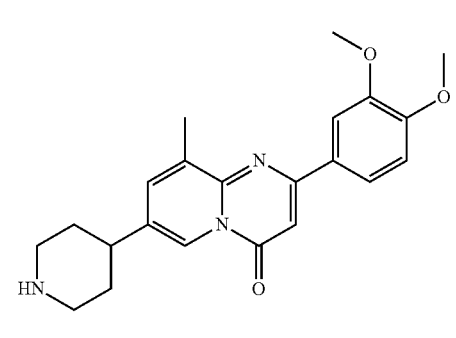
251 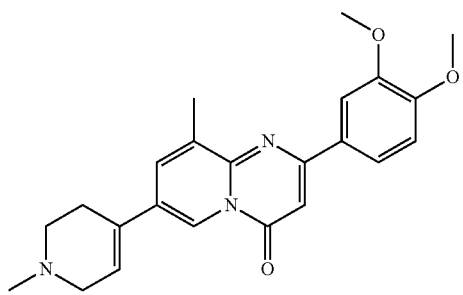
252 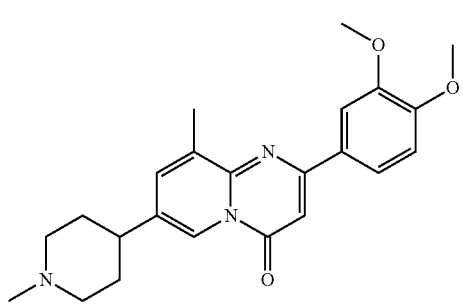

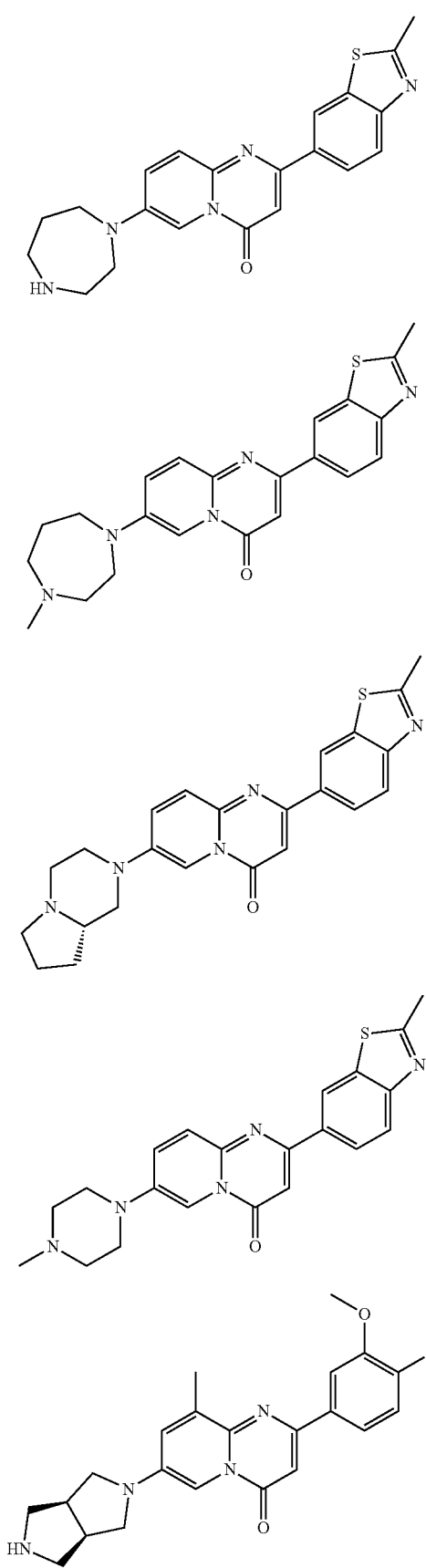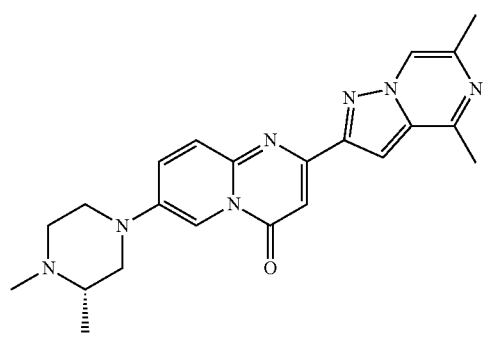

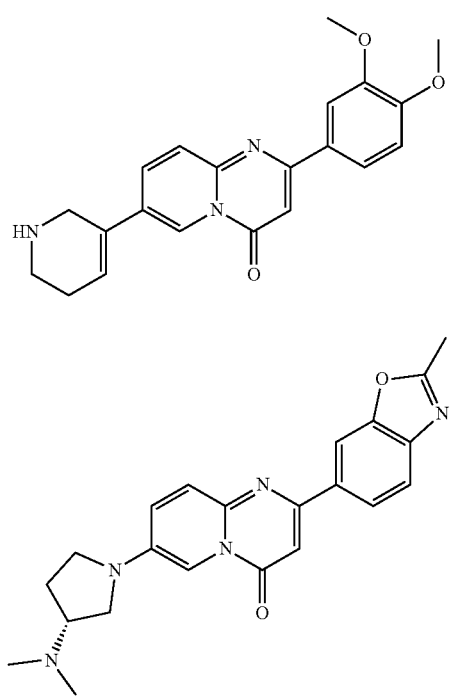
263
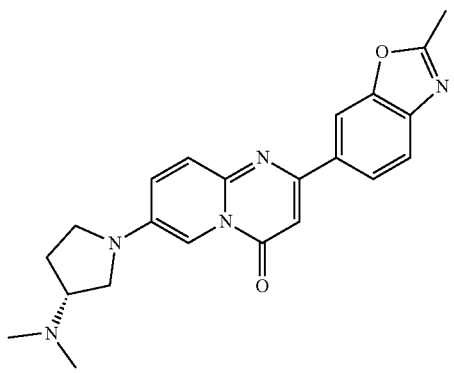
264
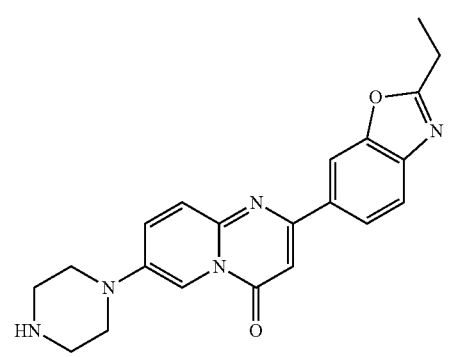
265
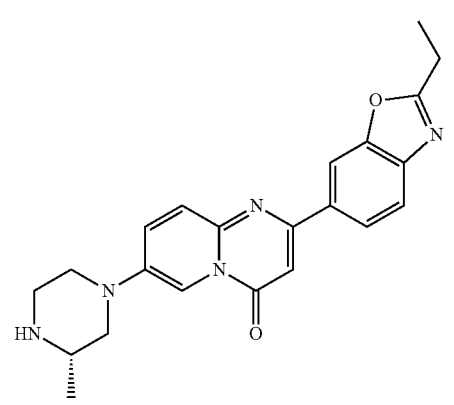
266
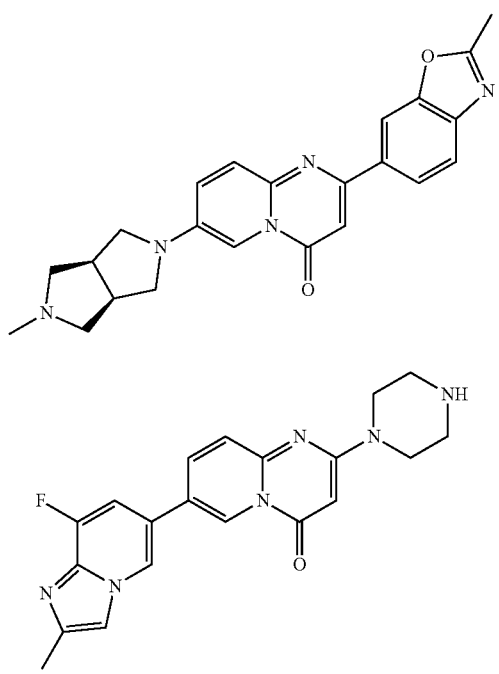
267
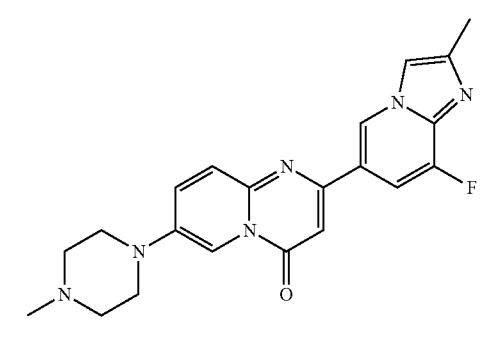
268
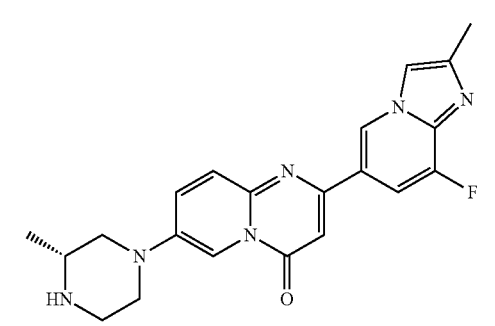
269
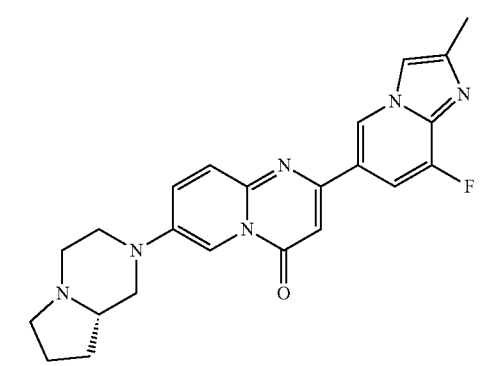
270
271

272
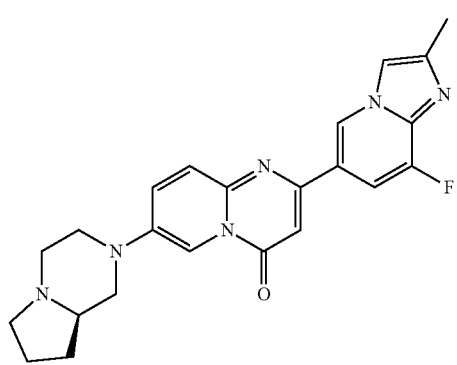
273
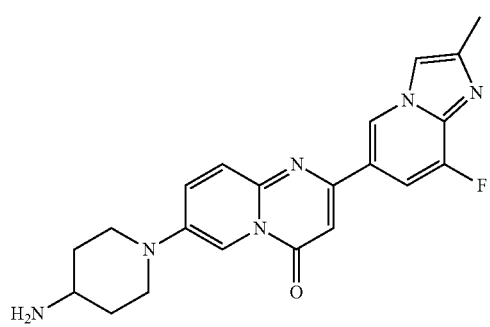
274
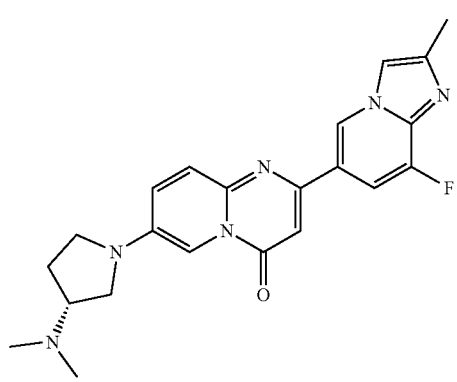
275
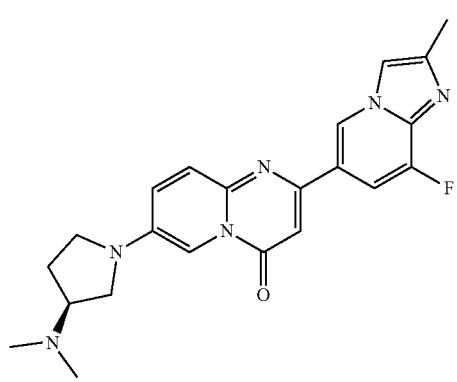
276
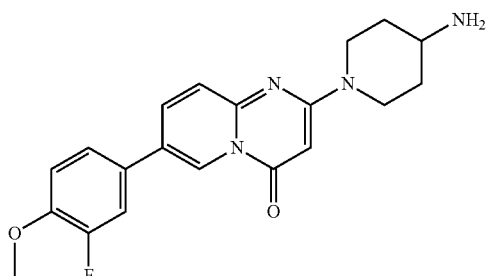
277
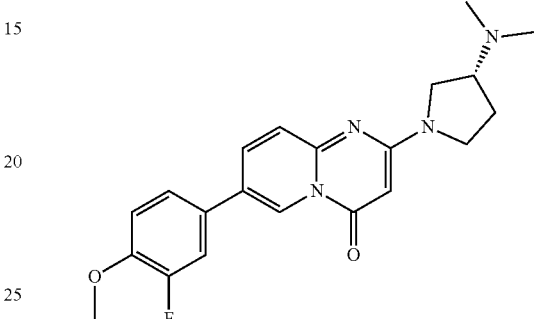
278
279
280
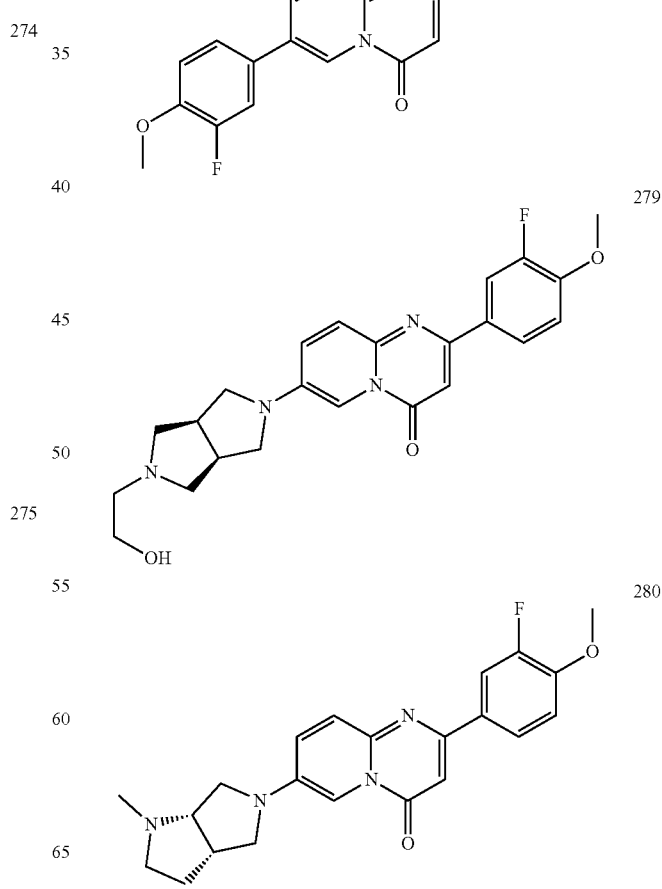

281
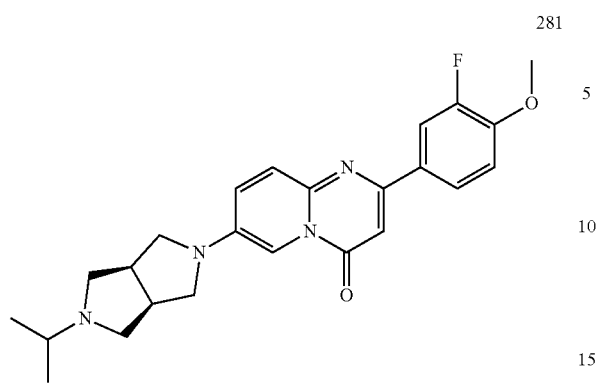
282
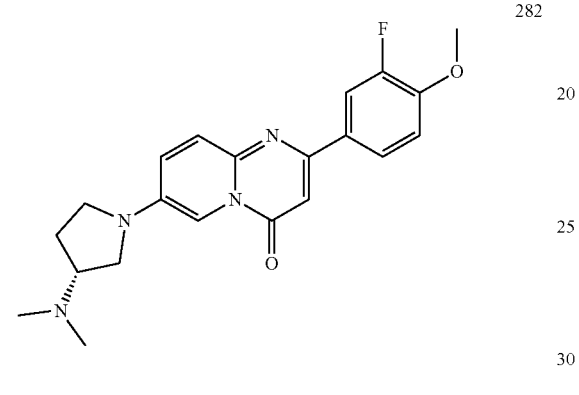
283
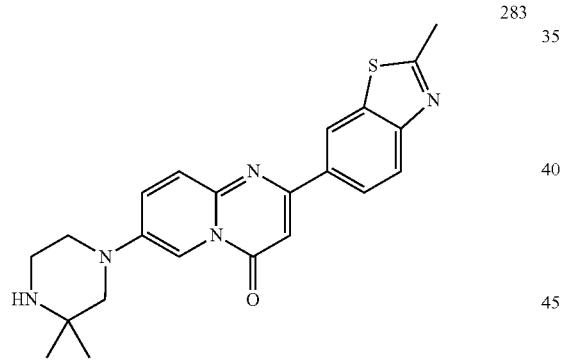
284
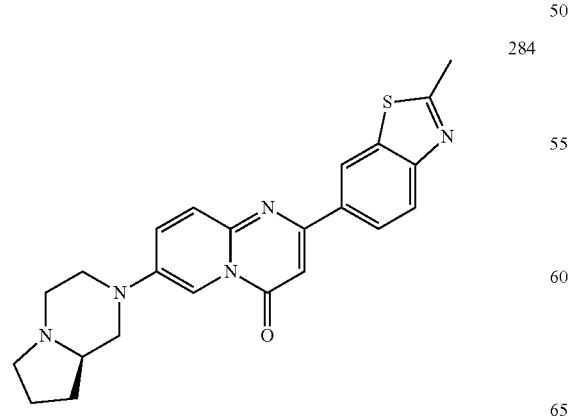
285
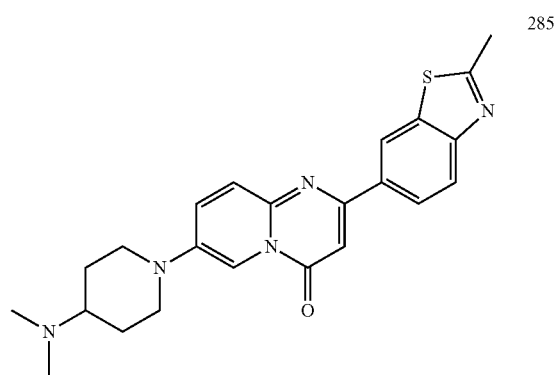
286
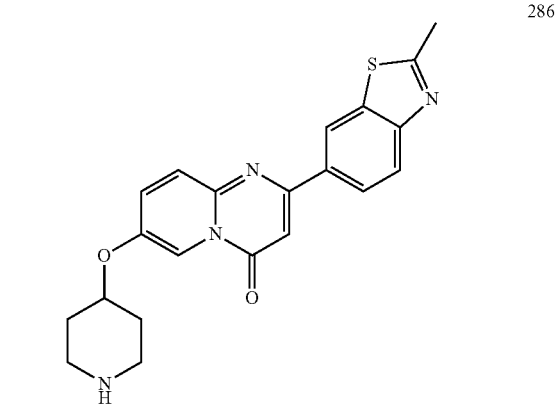
287
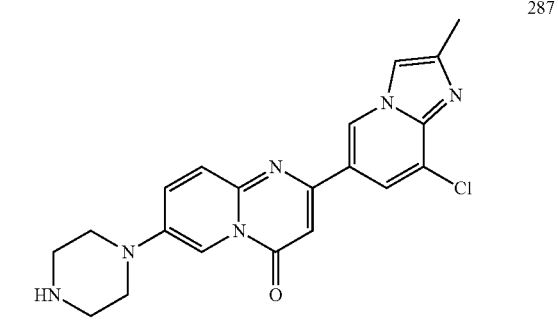
288
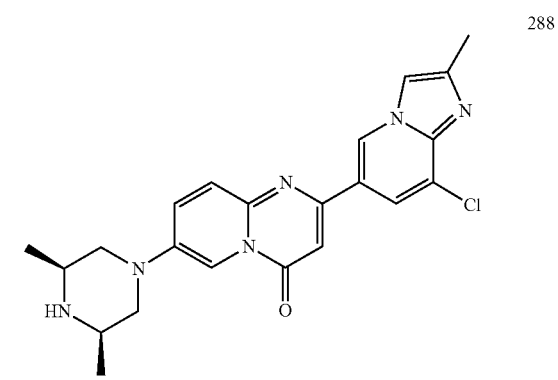

289
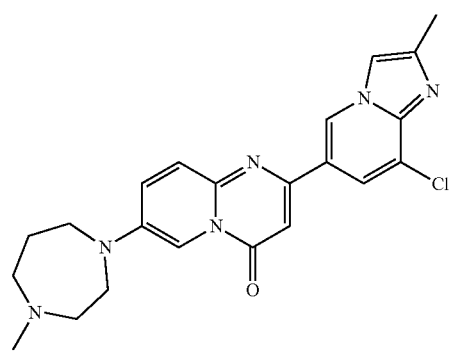
290
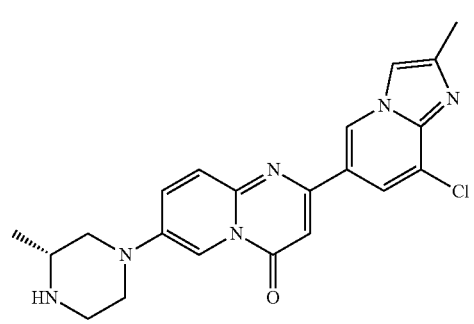
291
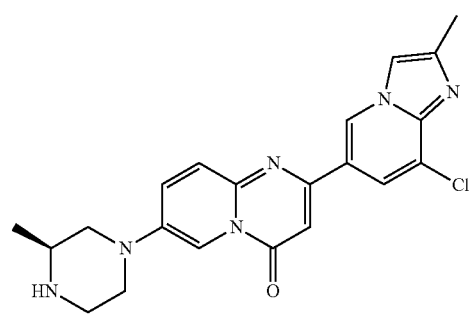
292
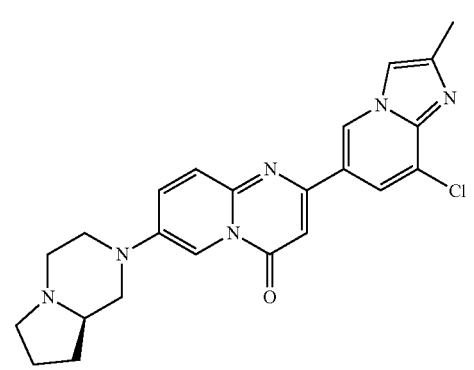
293
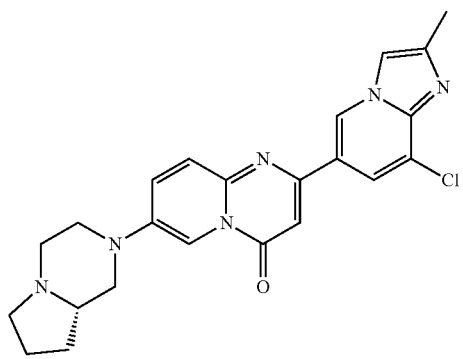
294
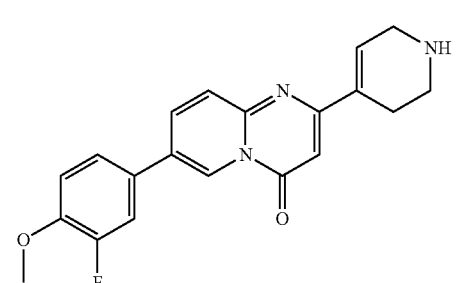
295
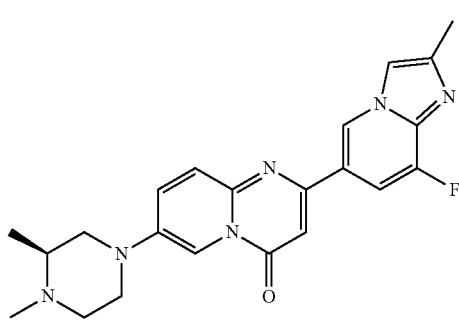
296
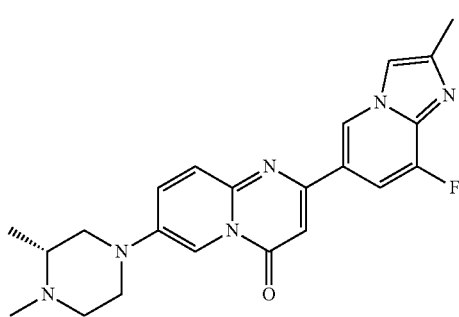
297
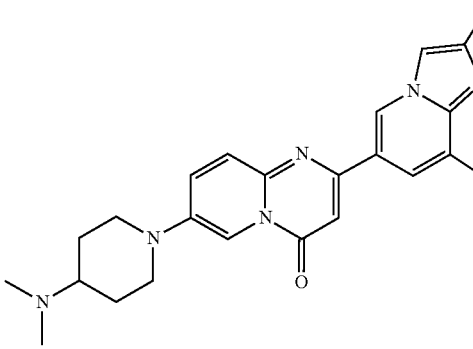

298
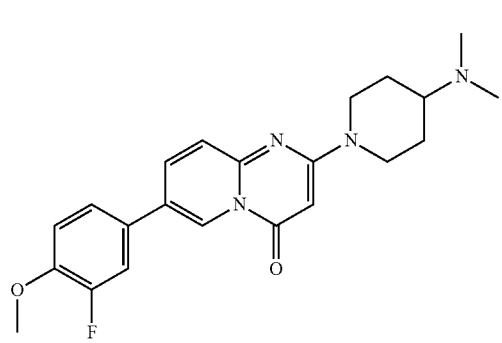
299
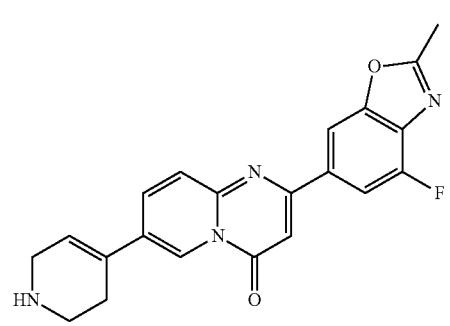
300
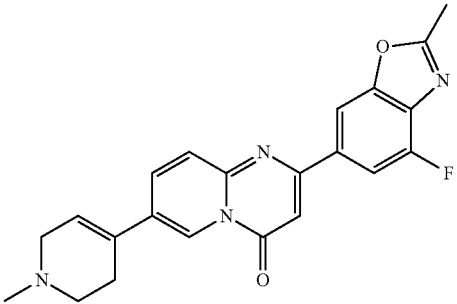
301
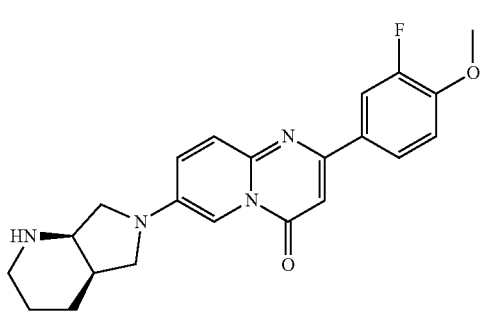
302
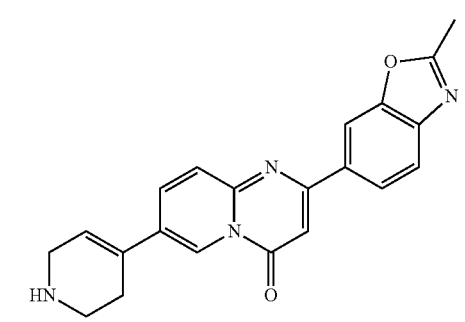
303
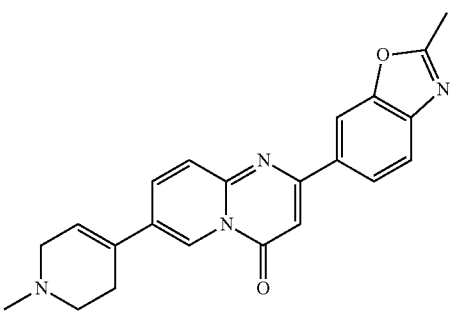
304
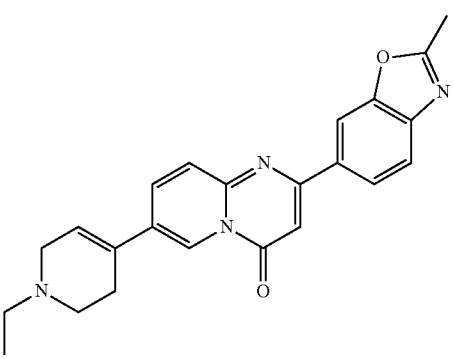
305
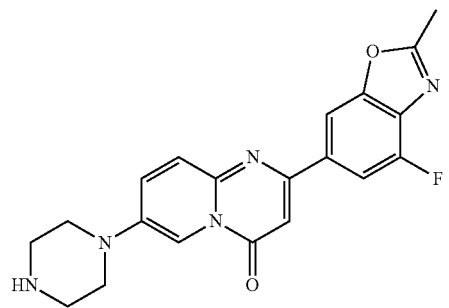
306
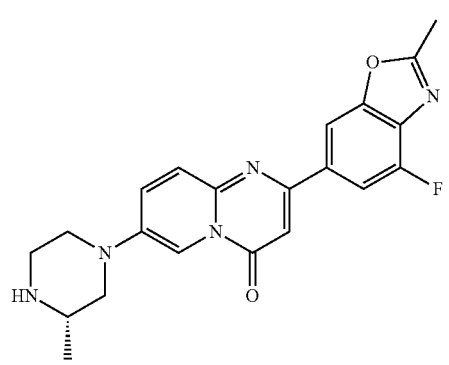

307
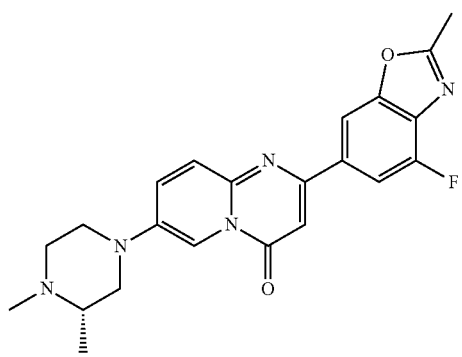
308
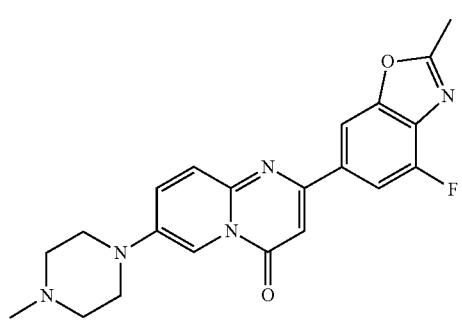
309
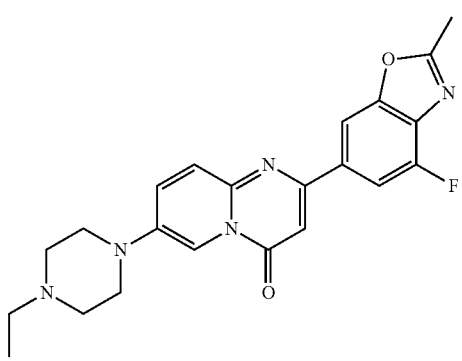
310
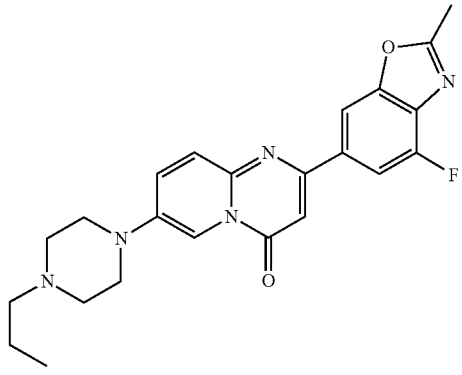
311
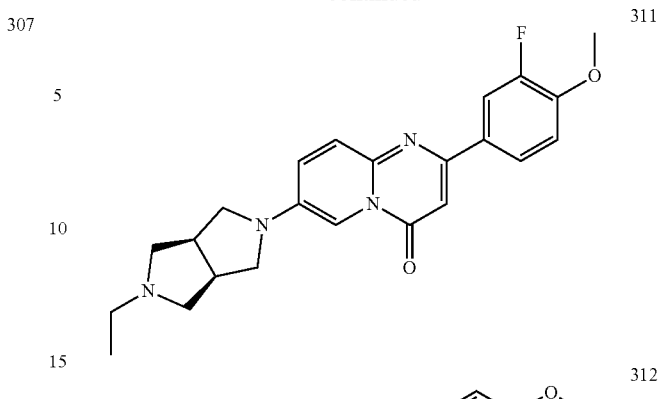
312
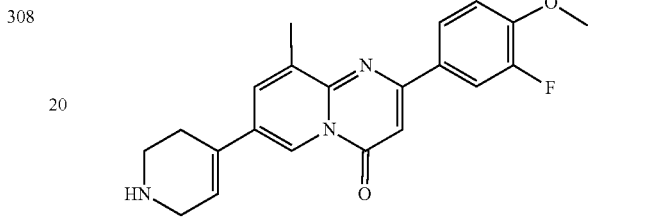
313
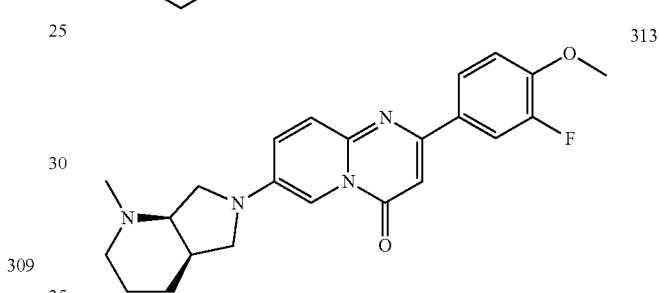
314
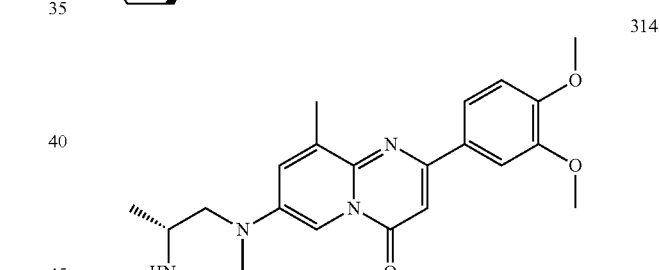
315
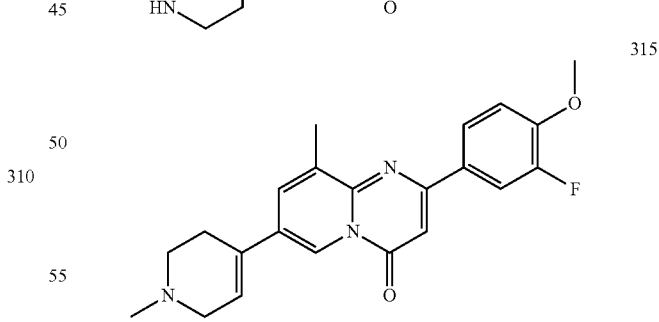
316
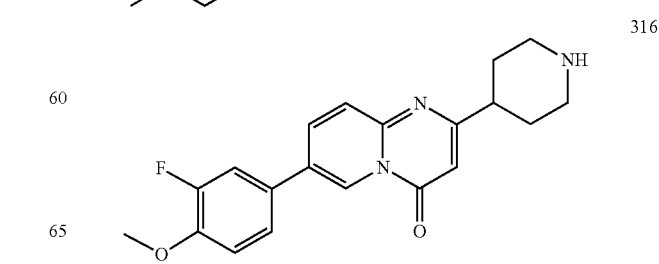

317 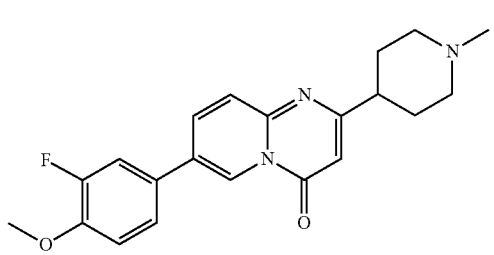
318 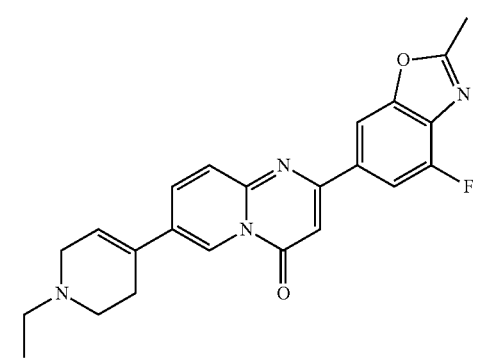
319 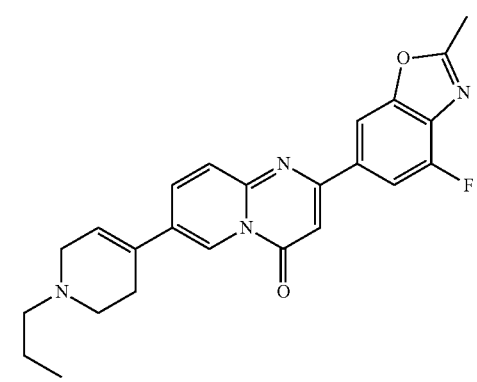
320 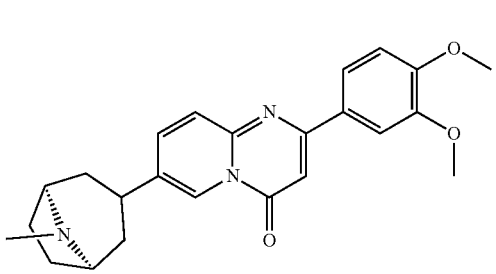
321 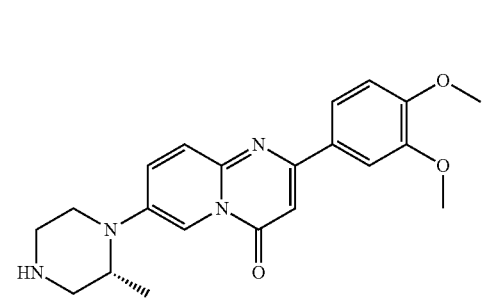
322 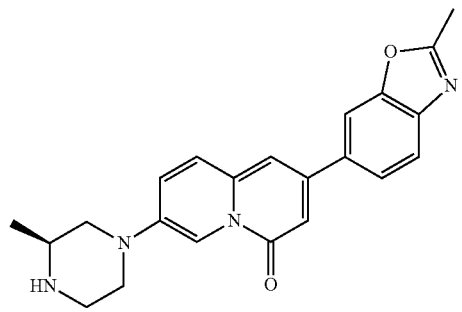
323 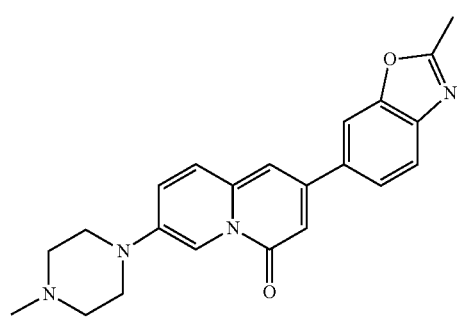
324 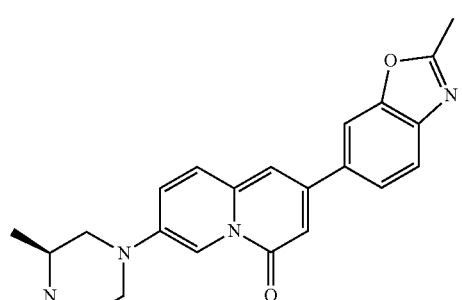
325 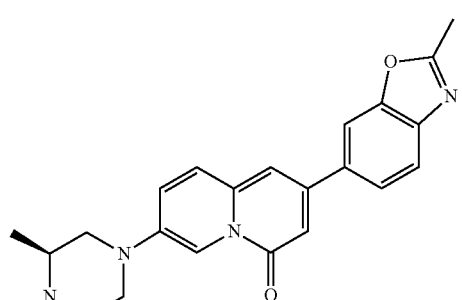
326 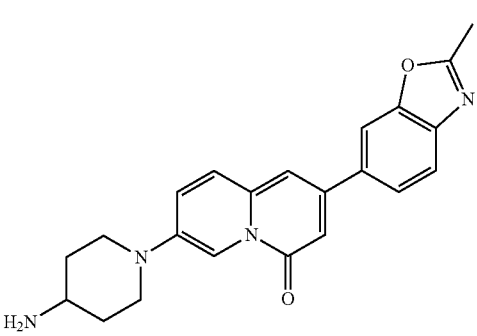

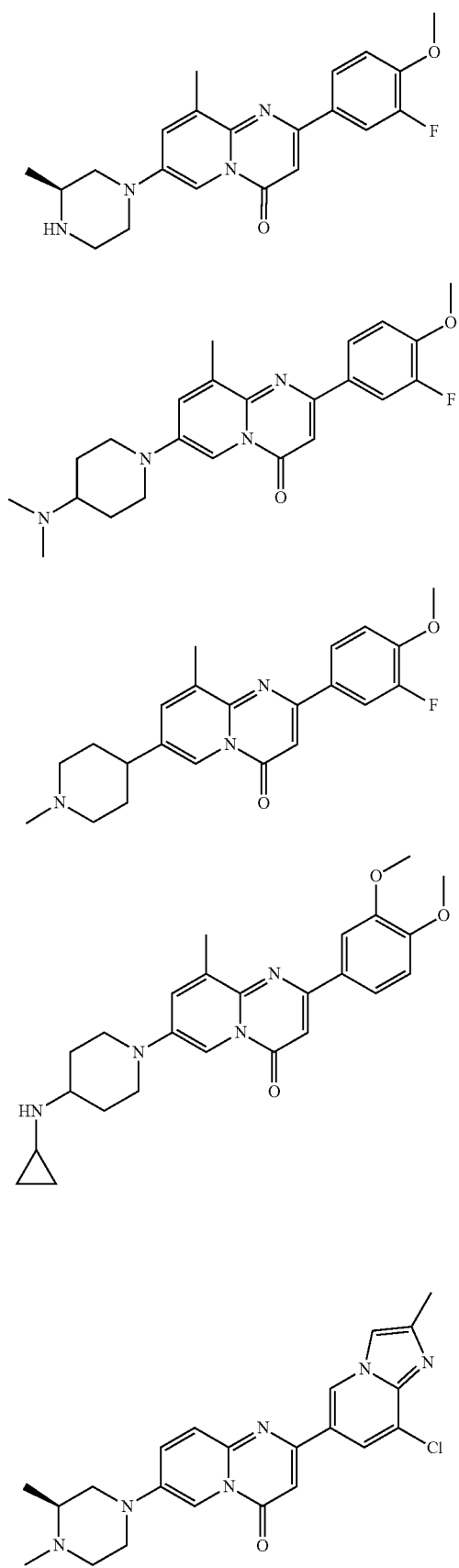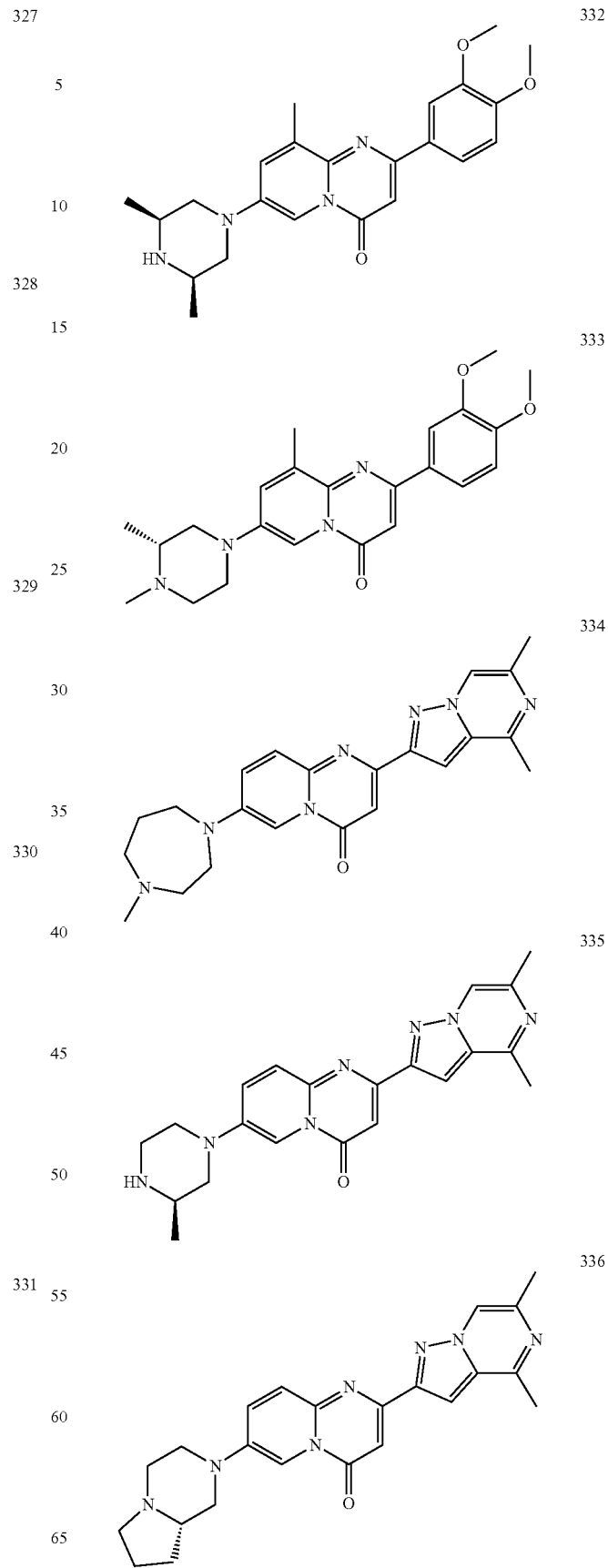

337 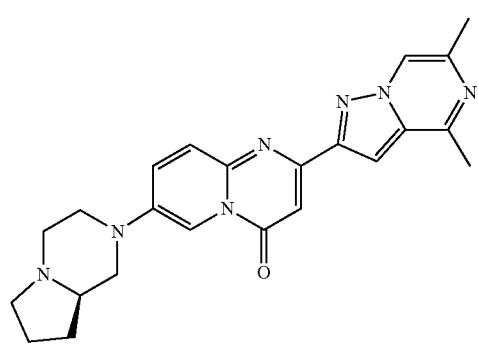
338 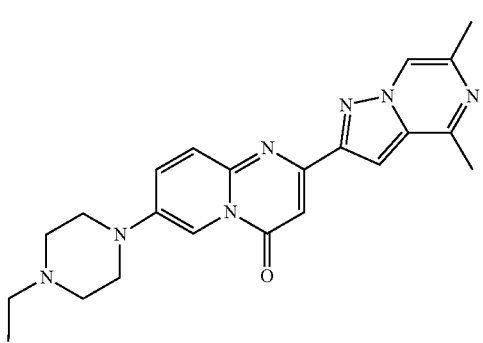
339 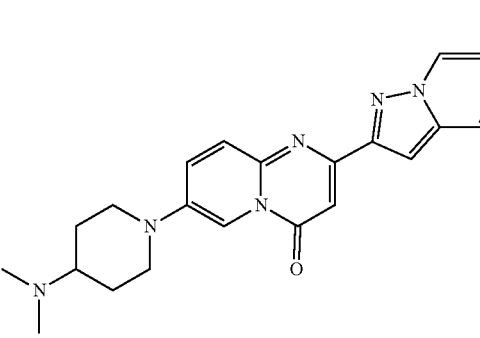
340 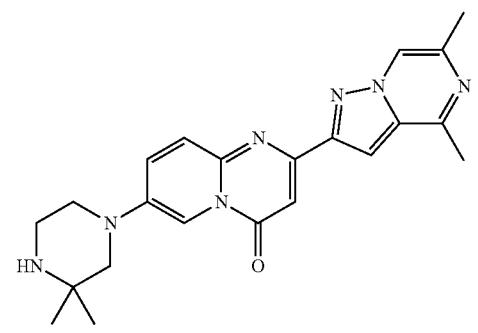
341 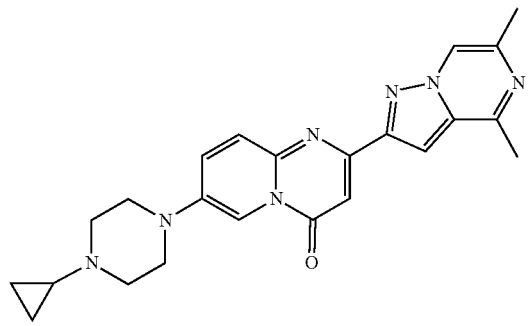
342 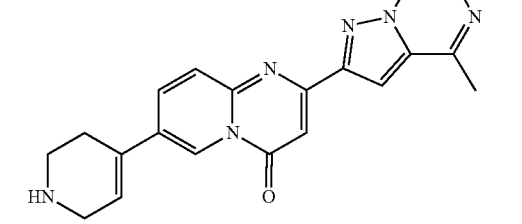
343 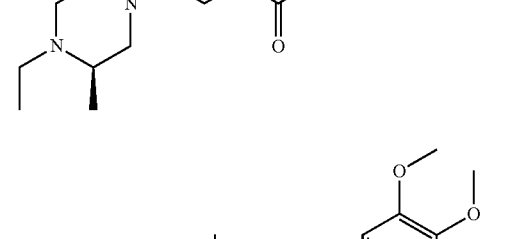
344 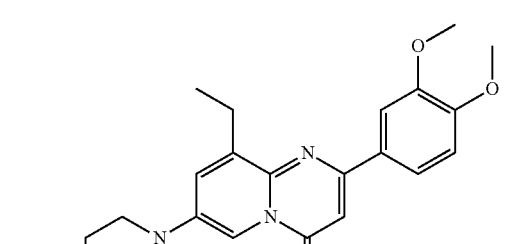
345 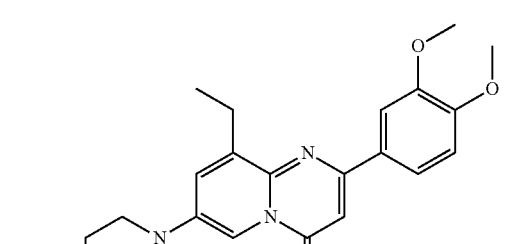

346 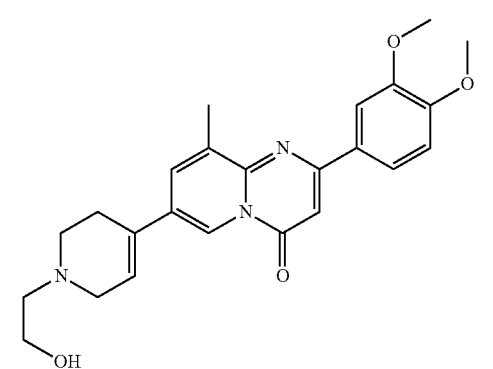
347 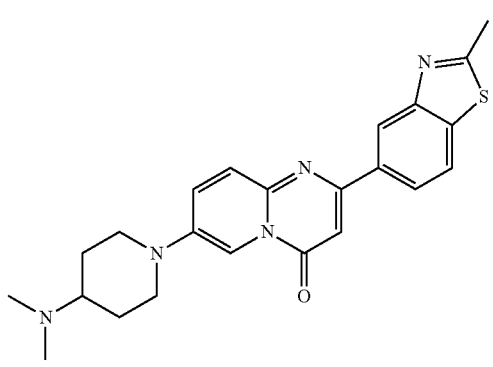
348 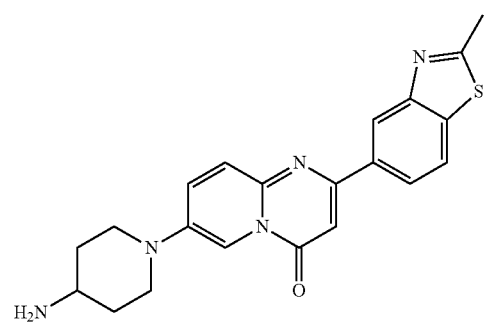
349 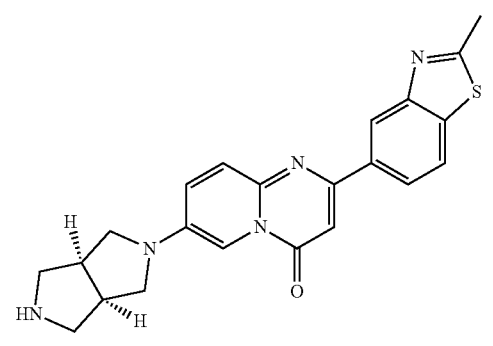
350 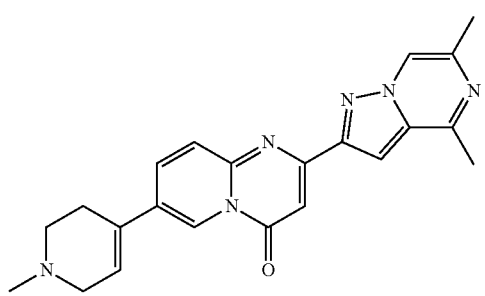
351 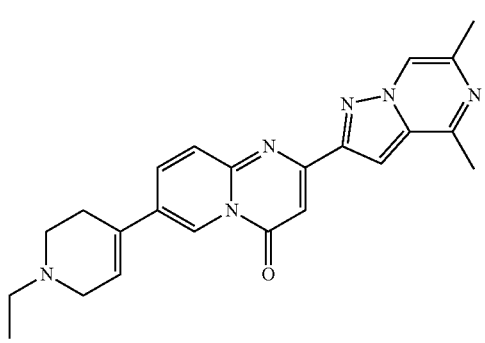
352 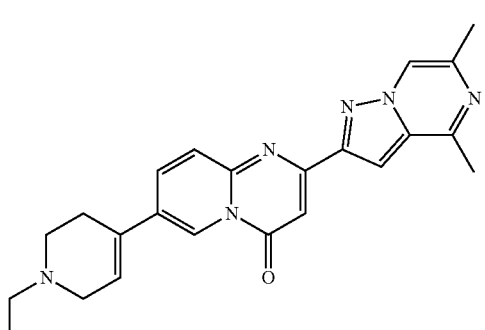
353 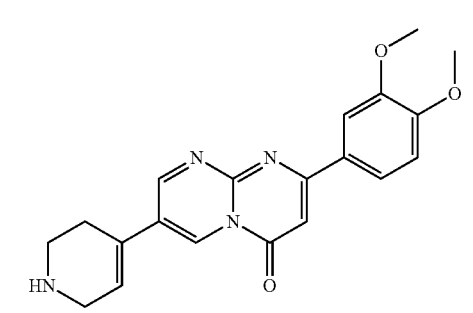
354 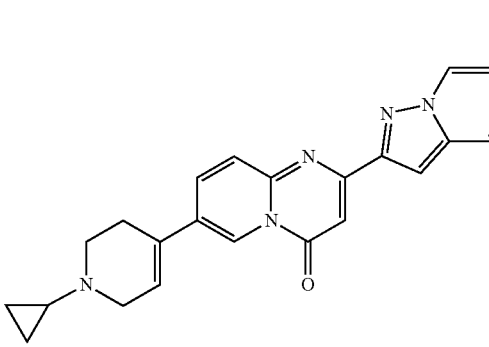

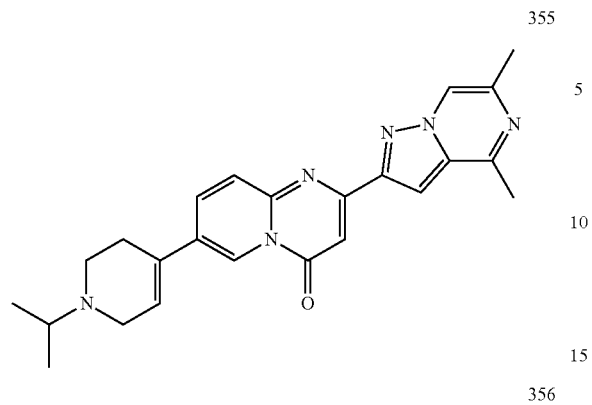
355
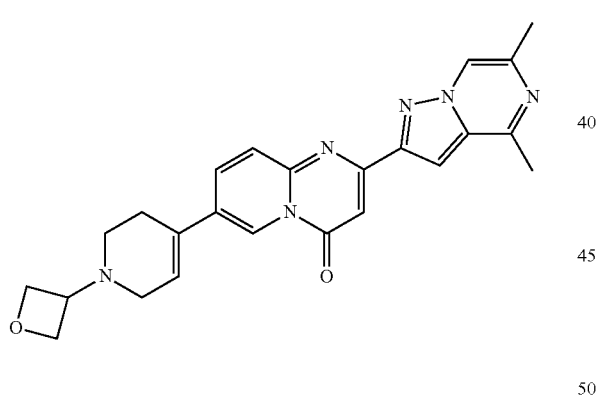
356
357
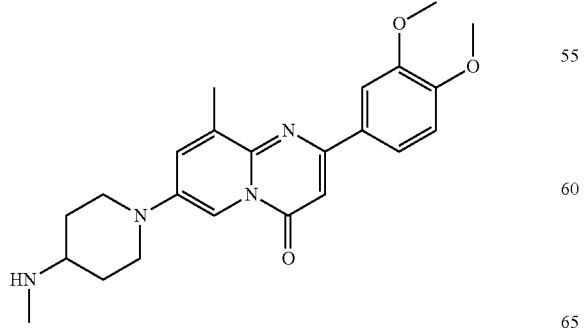
358
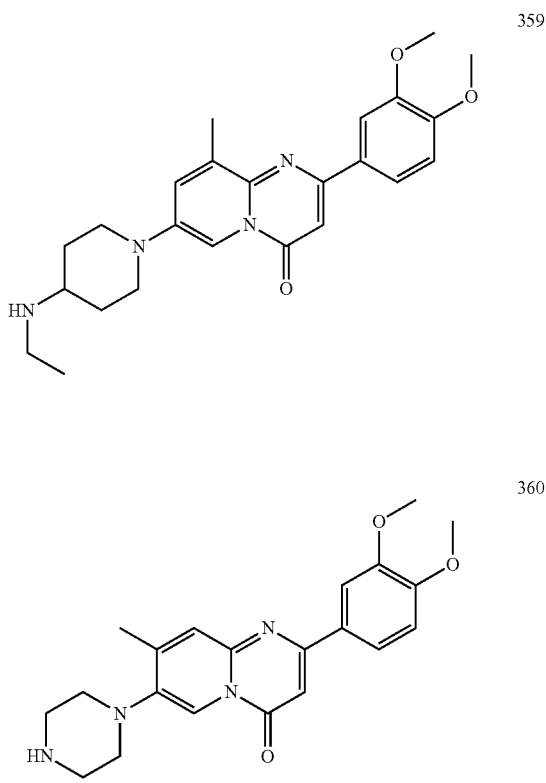
359
360
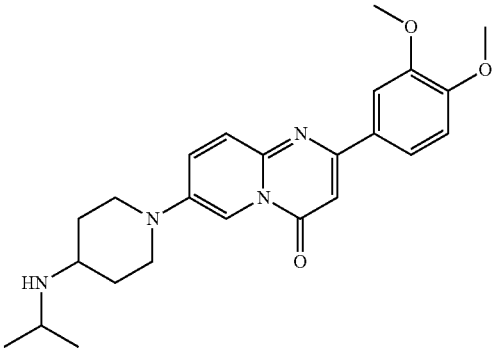
361
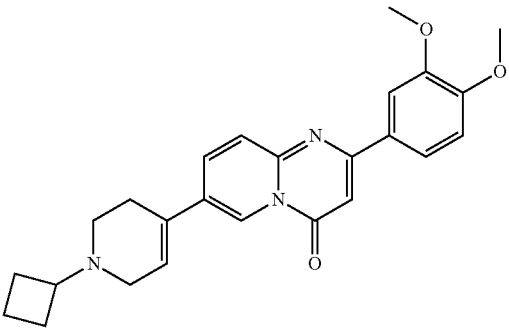
362

363 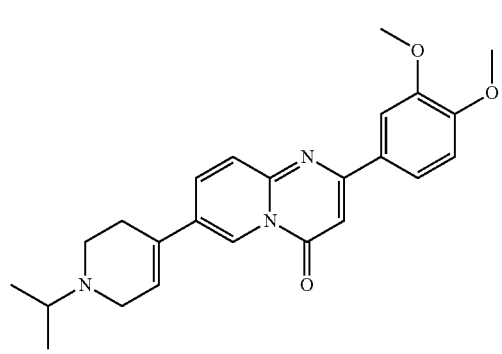
364 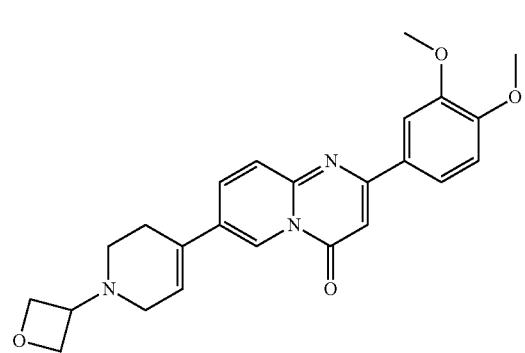
365 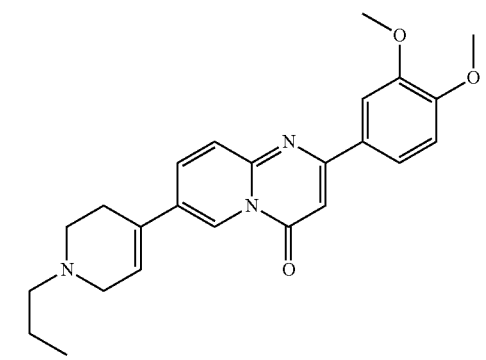
366 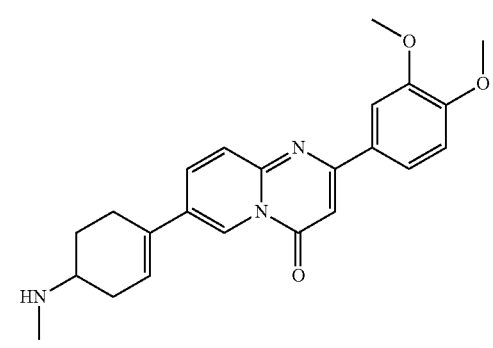
367 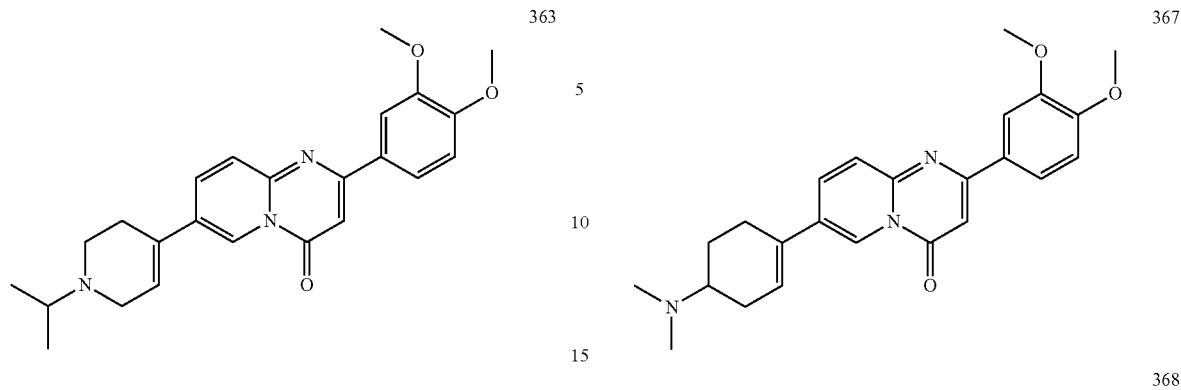
368
369
370

371 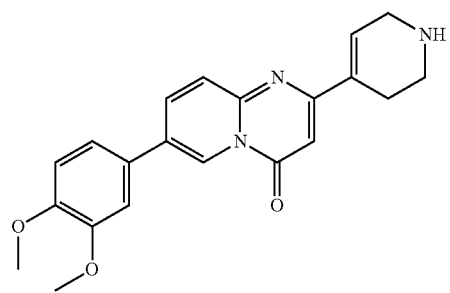
372 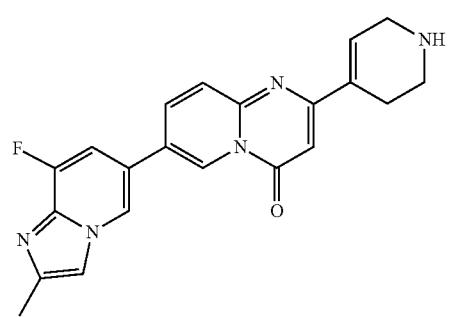
373 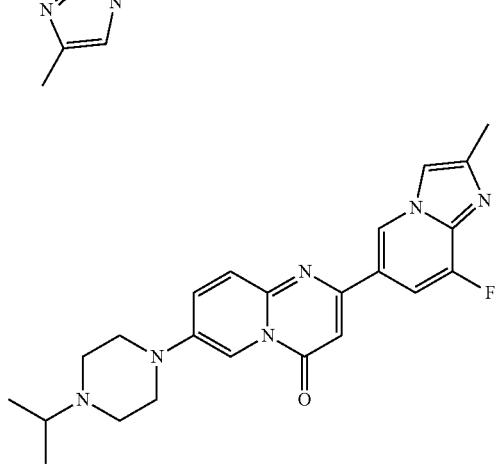
374 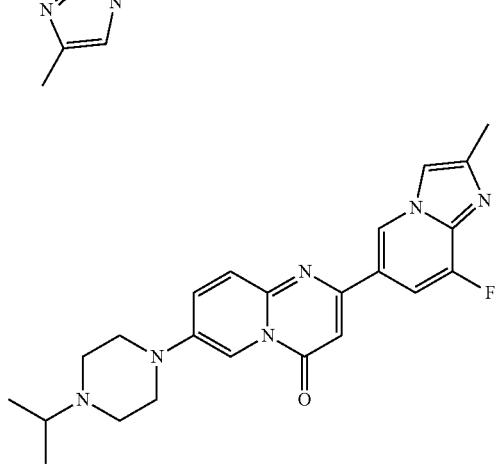
375 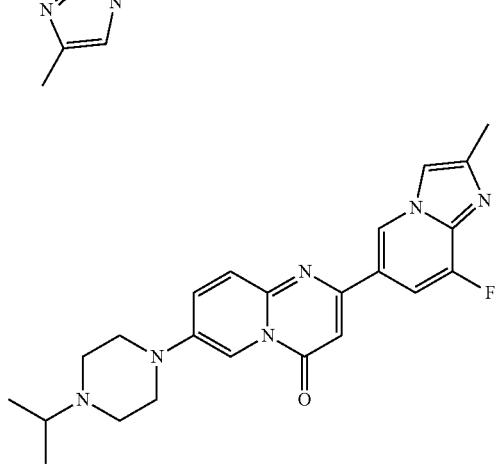
376 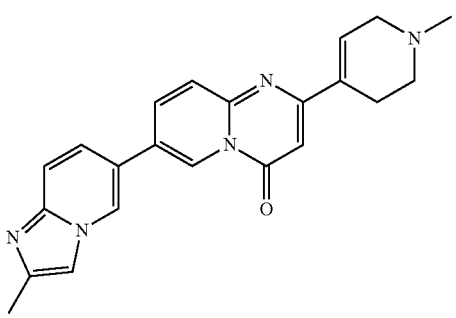
377 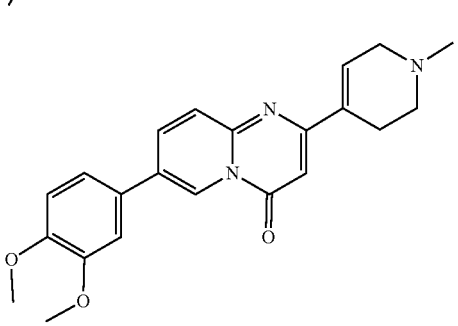
378 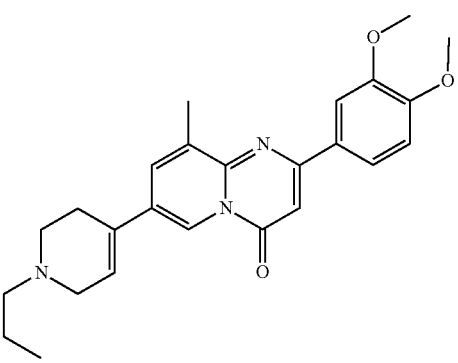
379 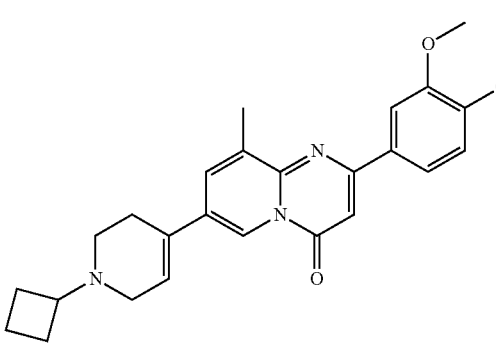
380 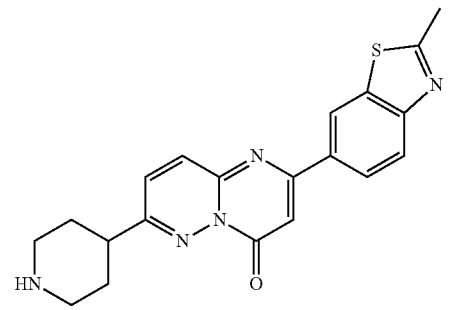

381 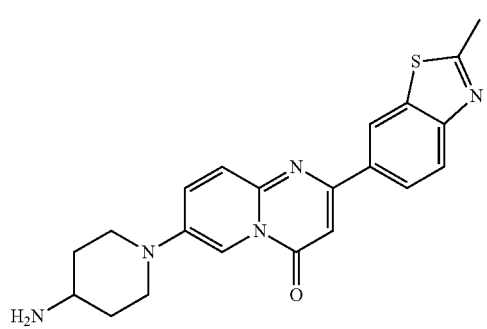
382 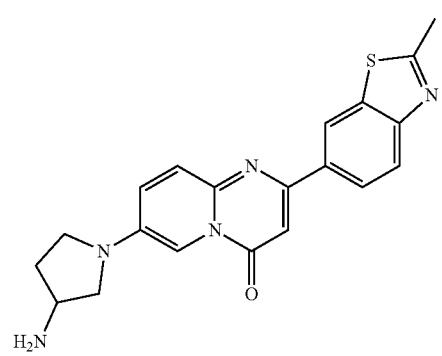
383 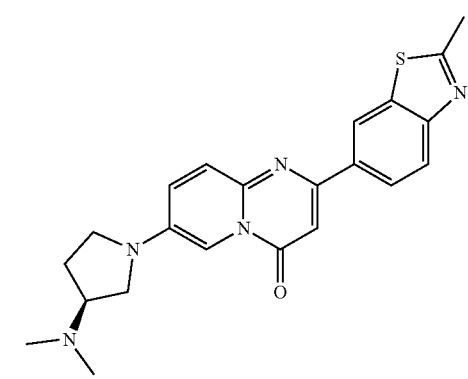
384 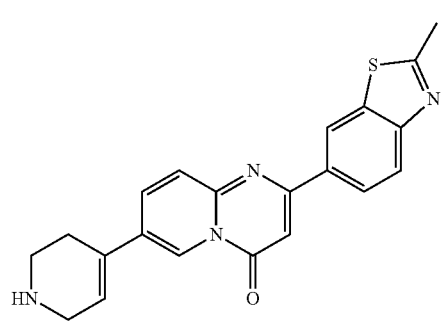
385 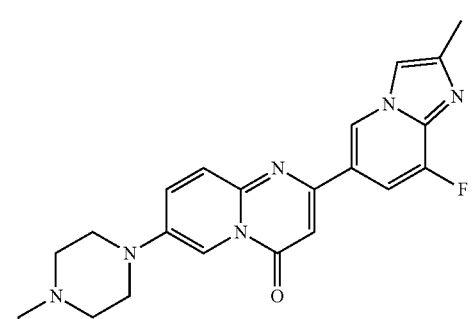
386 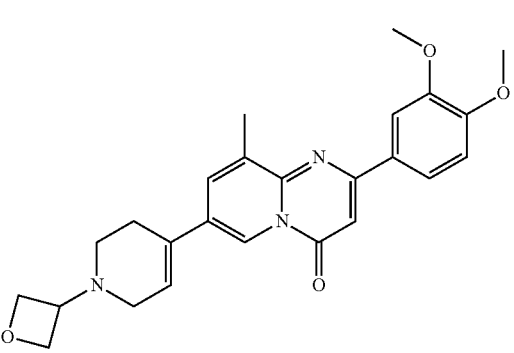
387 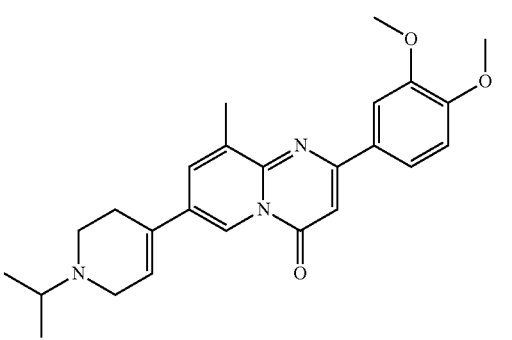
388 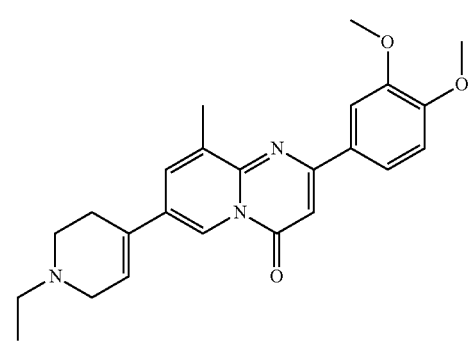

389
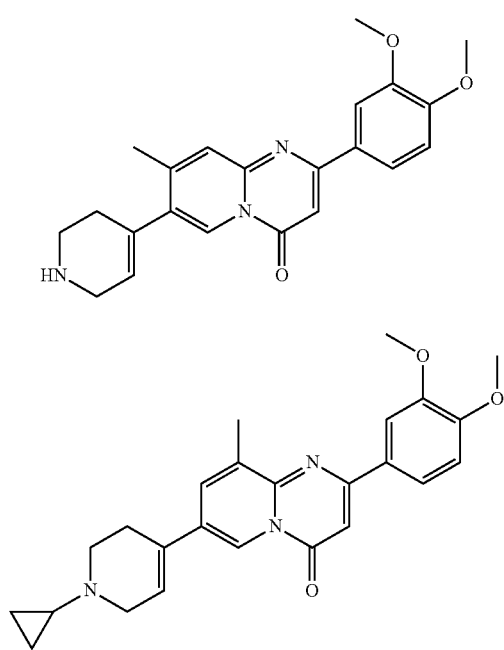
390
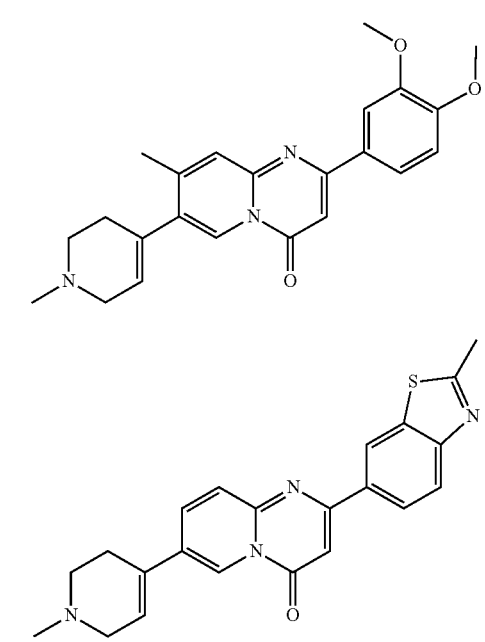
391
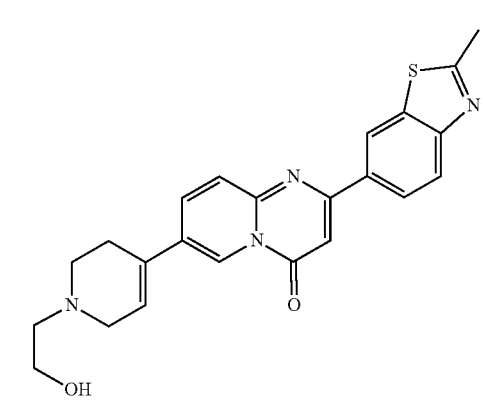
392
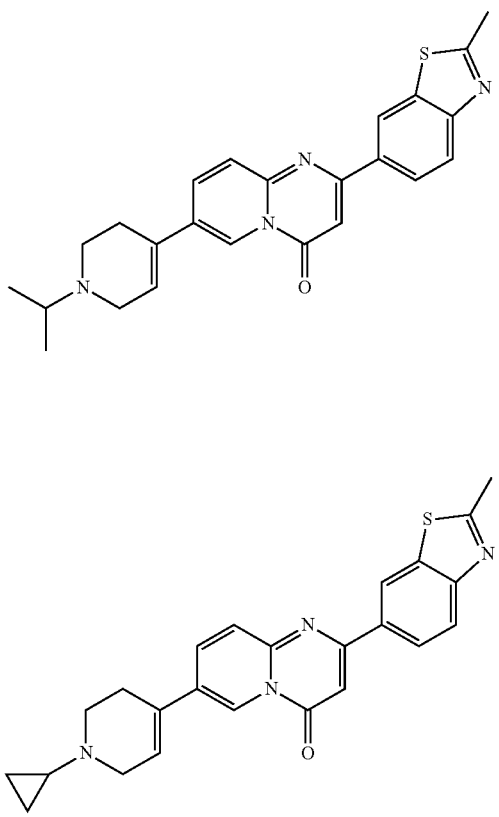
393
394
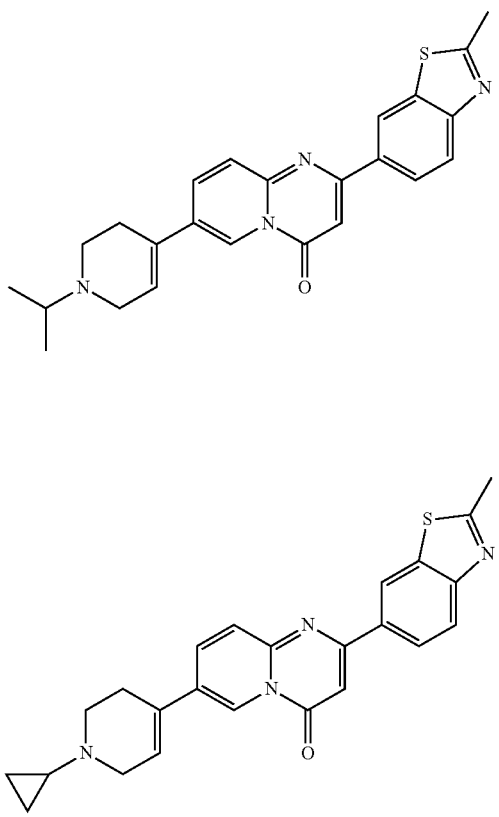
395
396
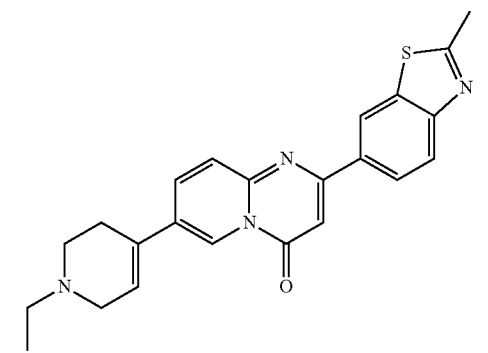
397
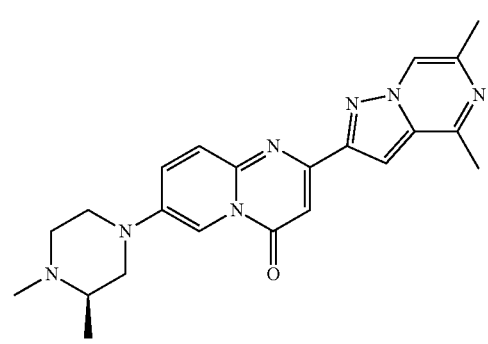

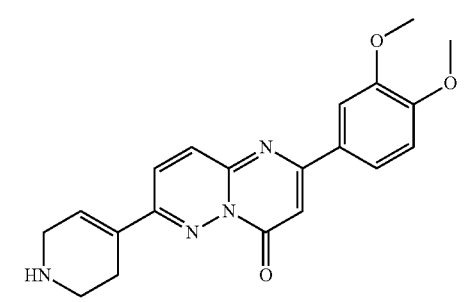 398
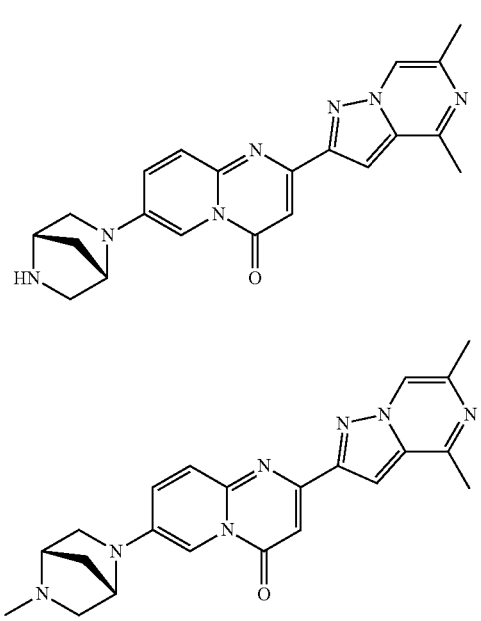 399
400
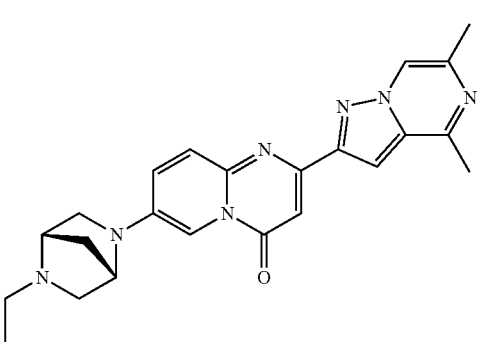 401
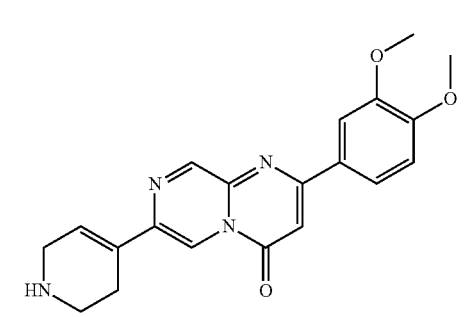 402
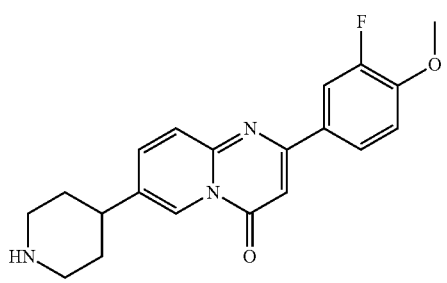 403
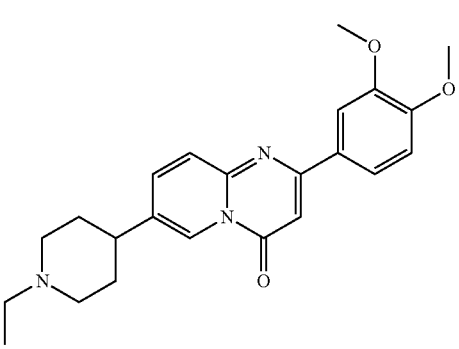 404
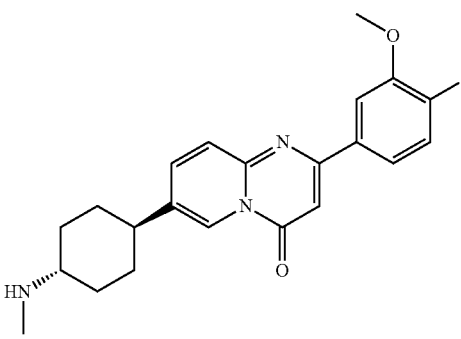 405
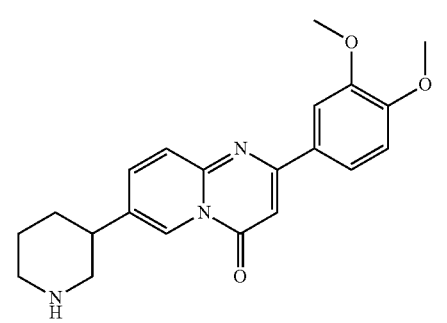 406

407
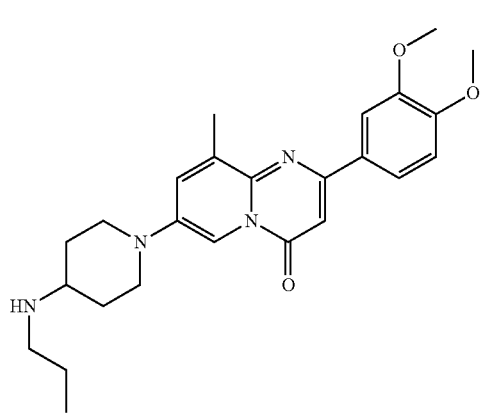
408
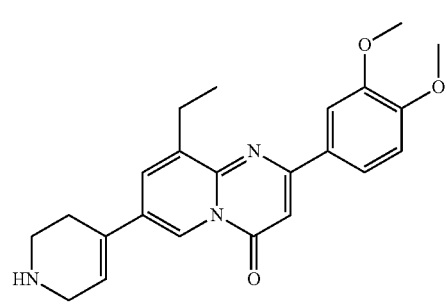
409
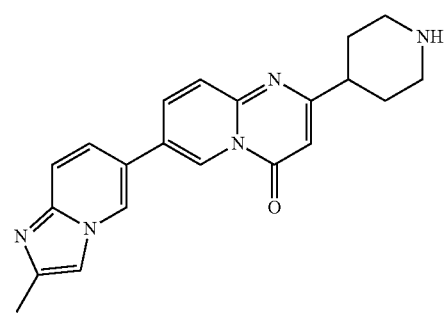
410
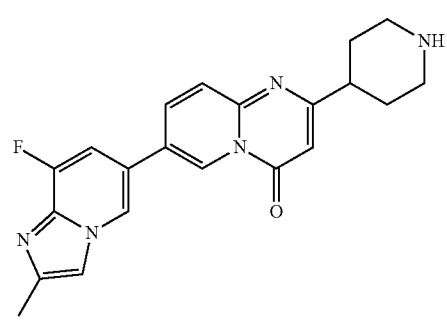
411
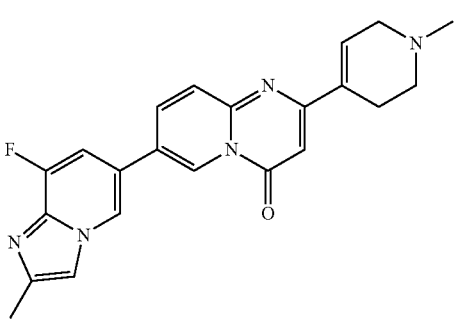
412
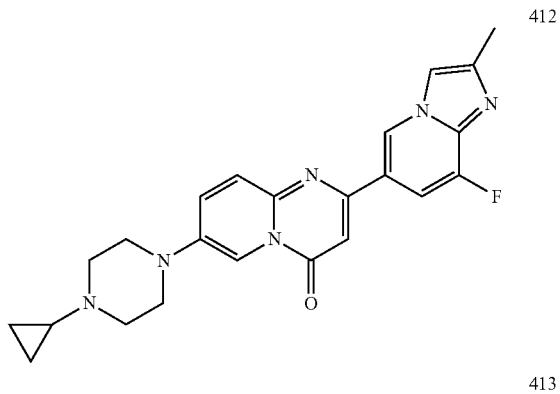
413
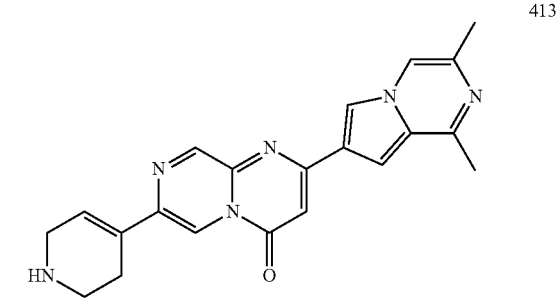
414
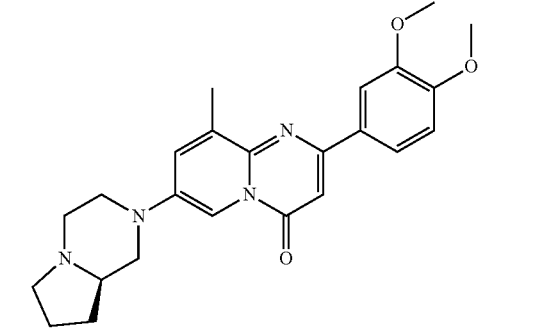
415
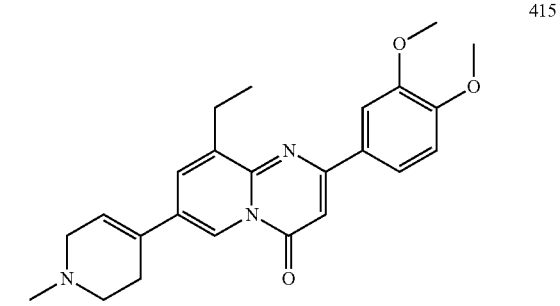
416
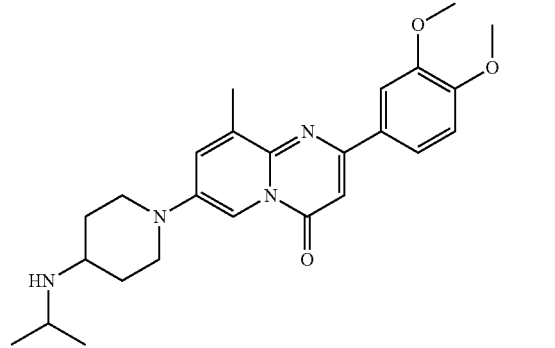

417
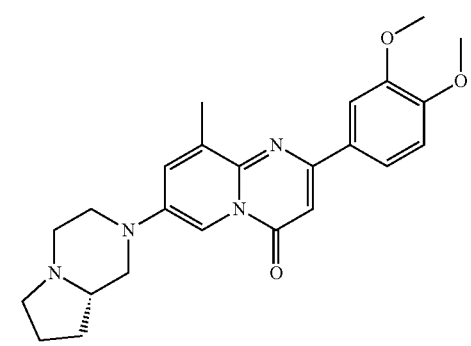
418
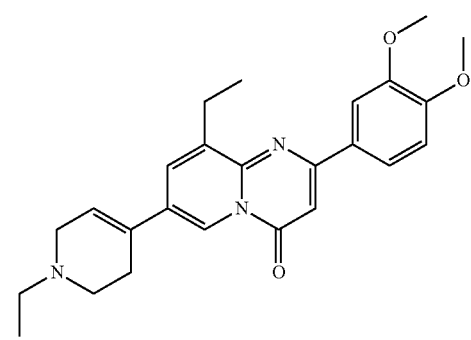
419
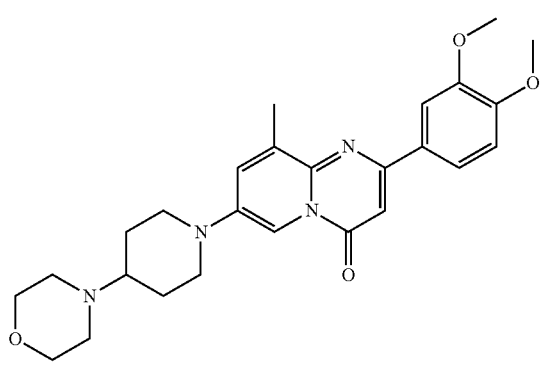
420
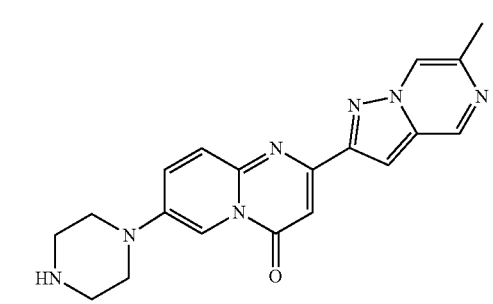
421
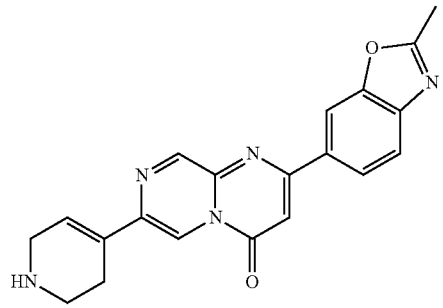
422
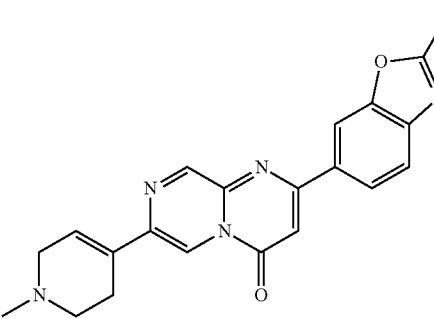
423
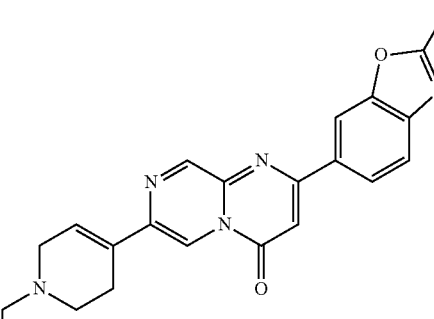
424
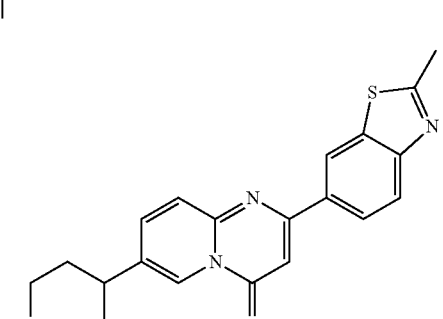
425
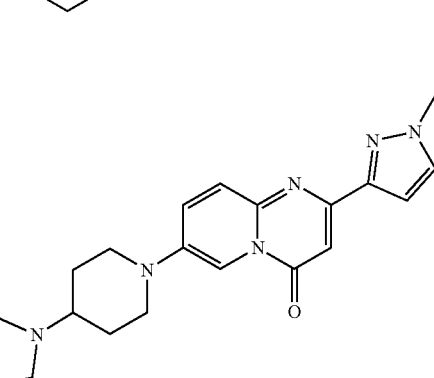

-continued
426
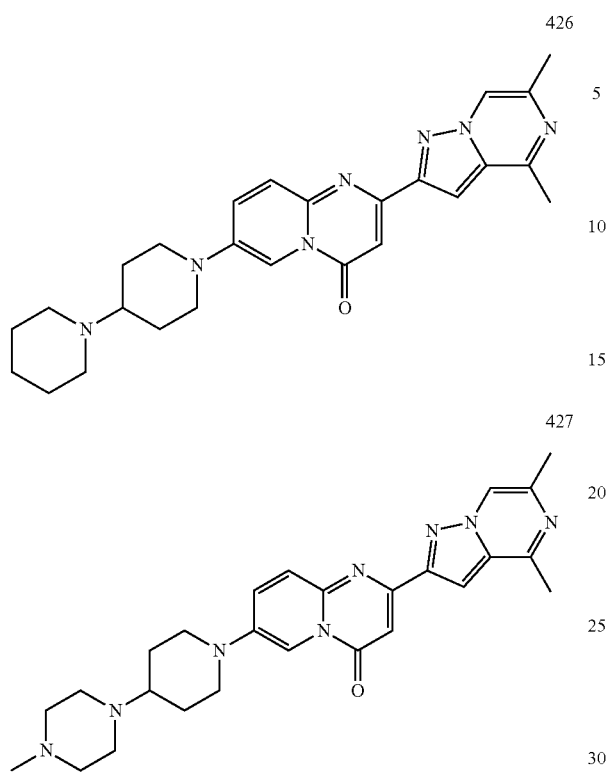
427
428
430
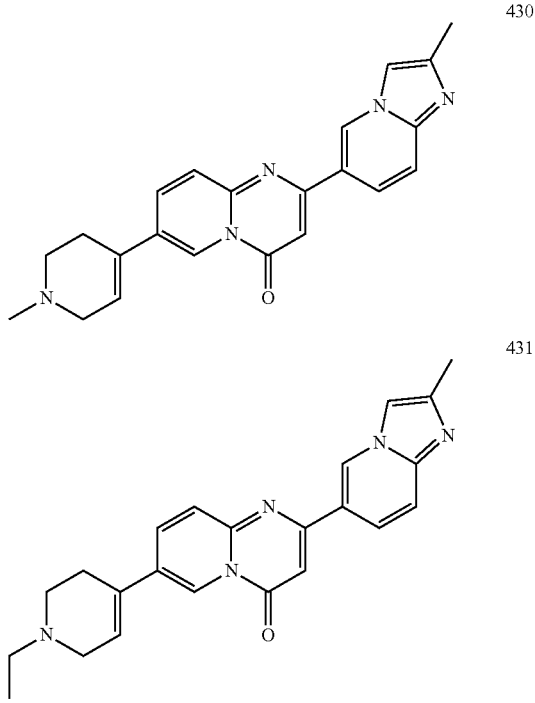
431
432
429
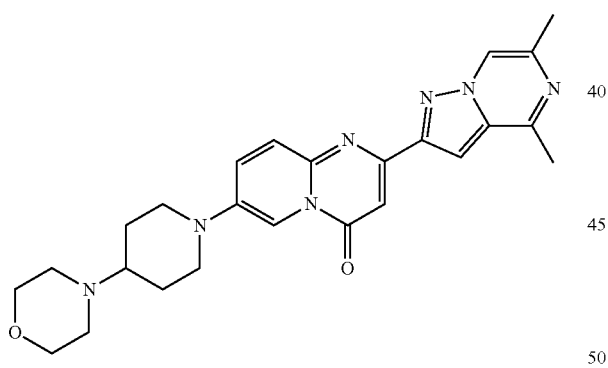
433
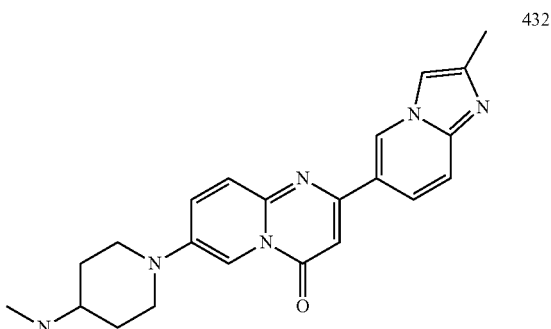
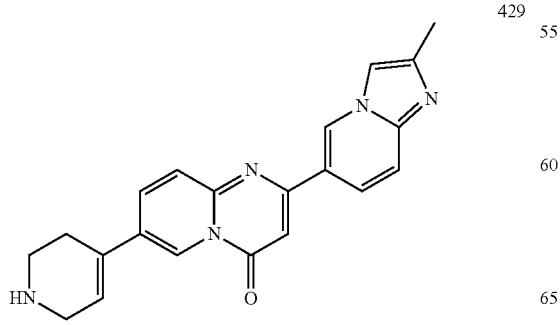
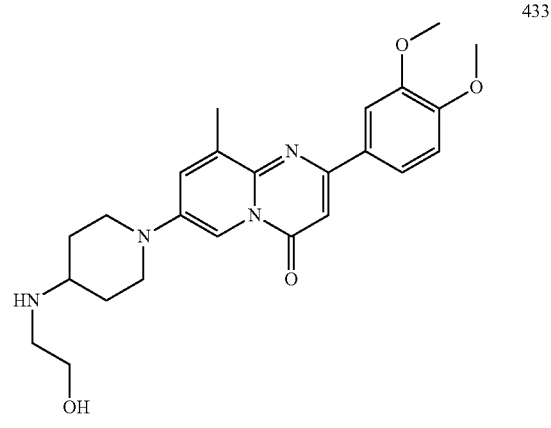

434 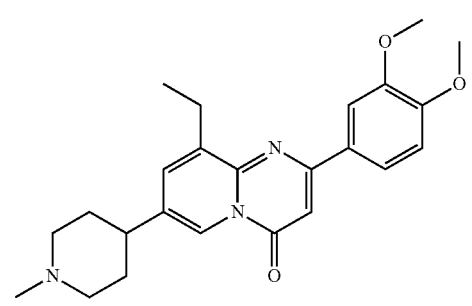
435 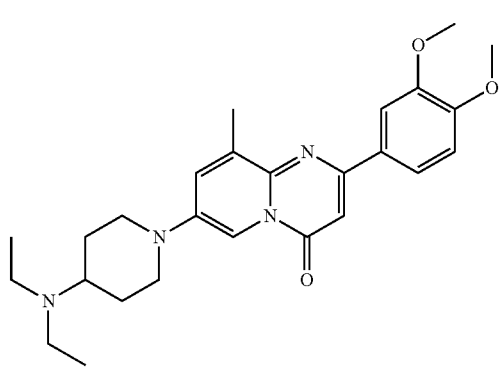
436 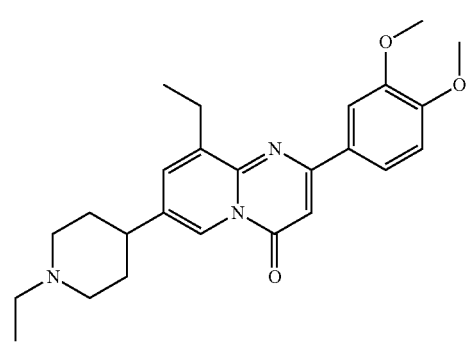
437 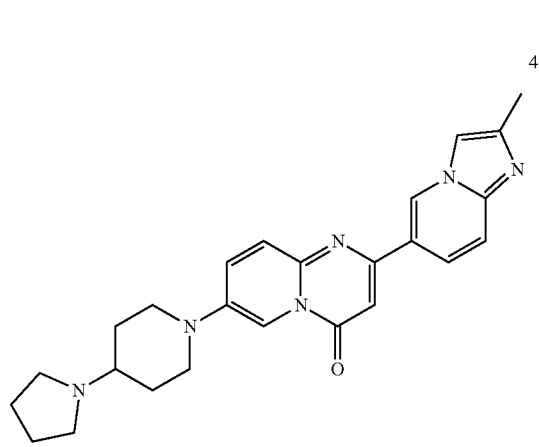
438 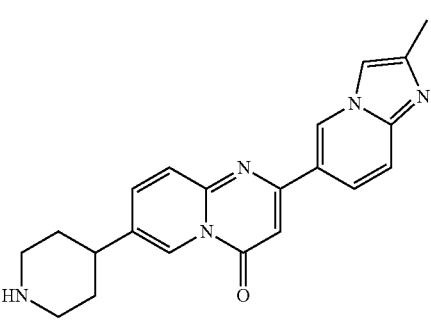
439 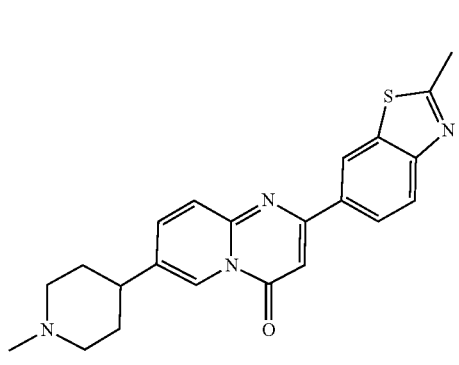
440 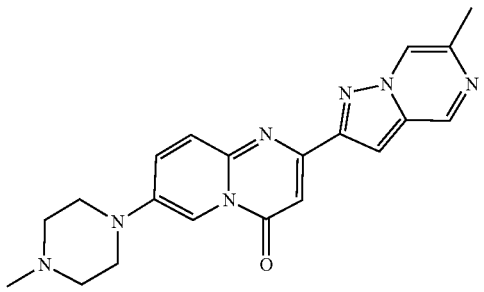
441 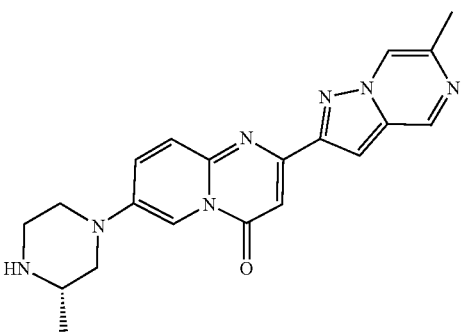

442
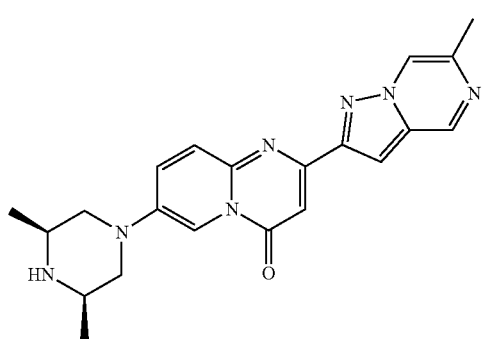
443
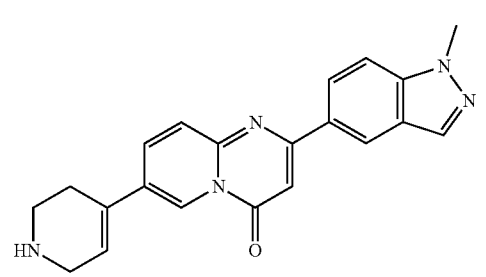
444
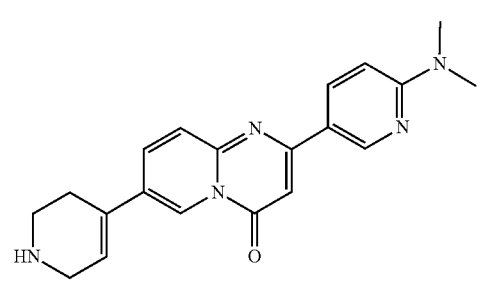
445
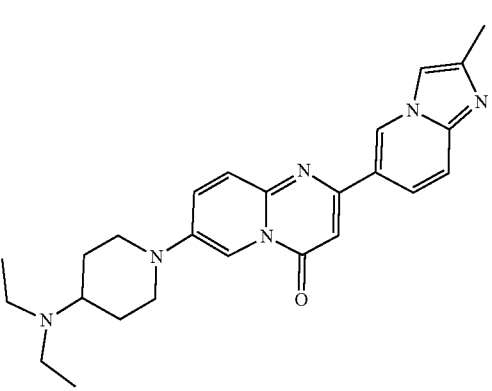
446
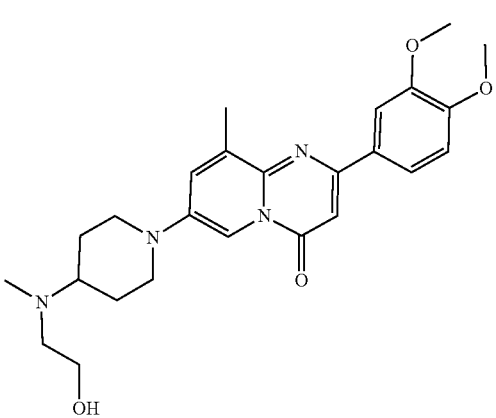
447
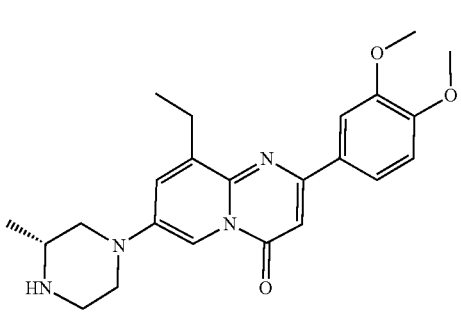
448
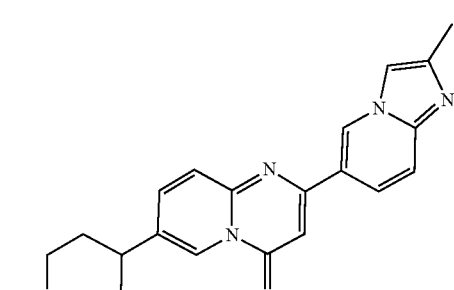
449
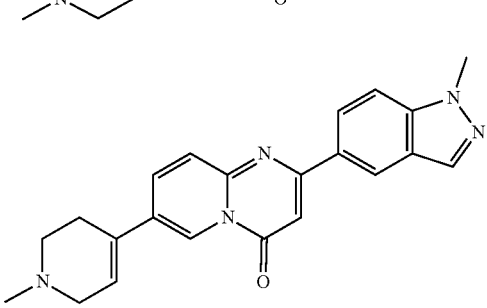
450
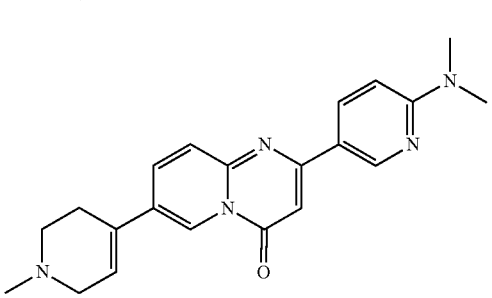
451
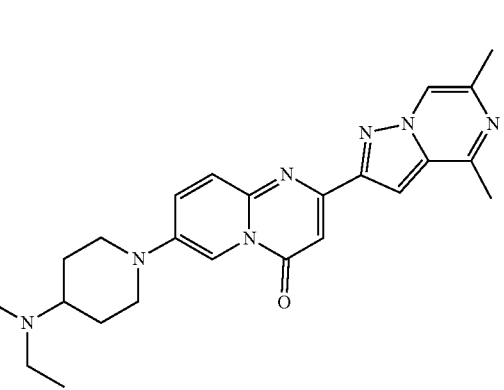

452 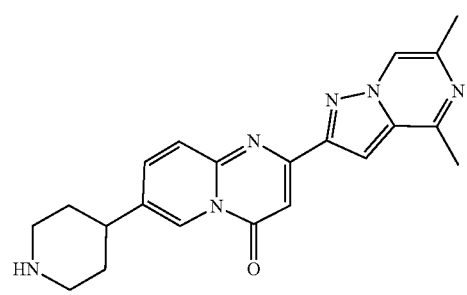
453 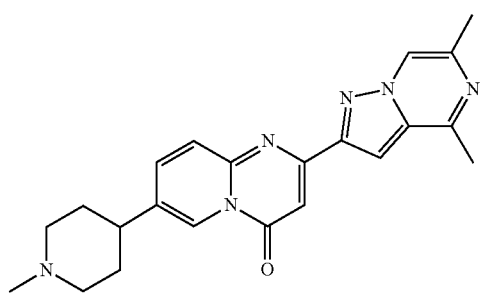
454 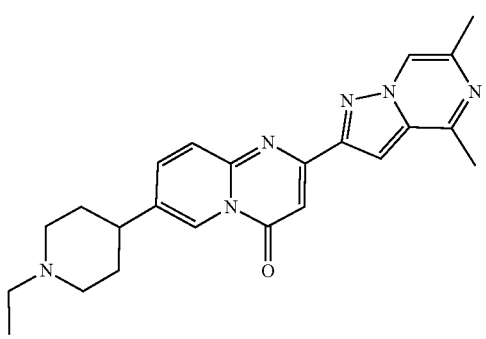
455 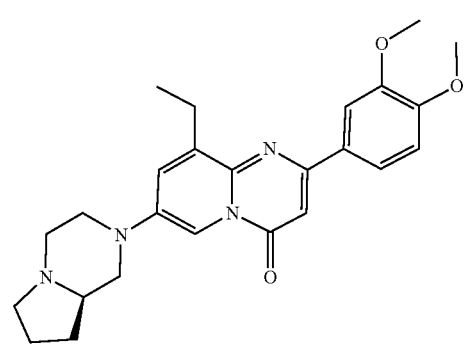
456 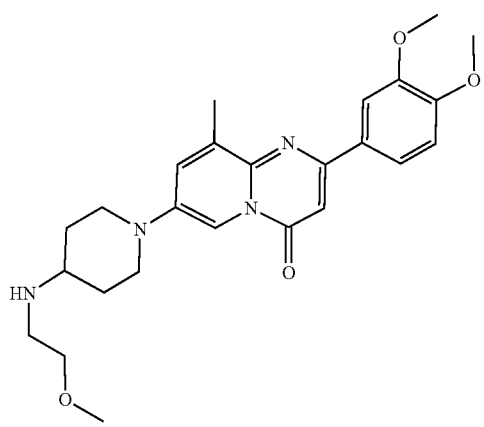
457 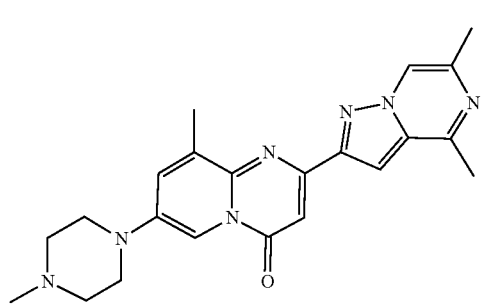
458 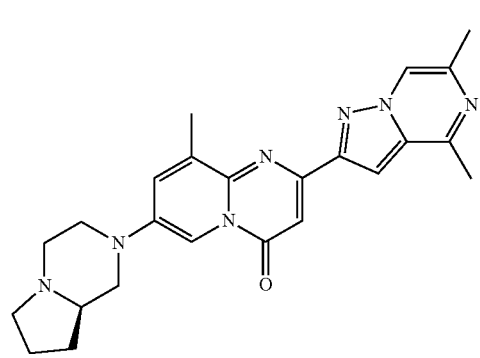
459 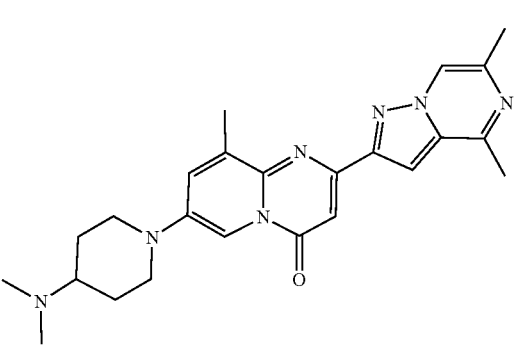

460
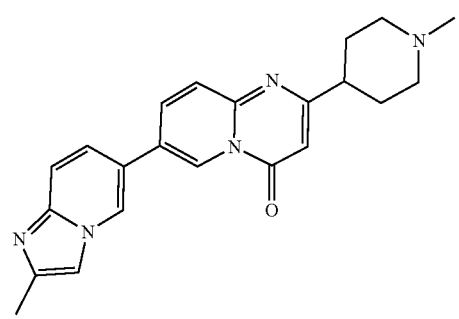
461
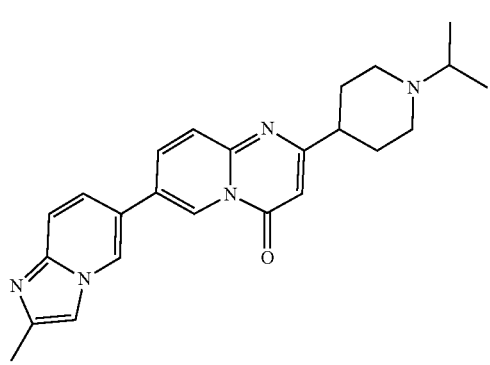
462
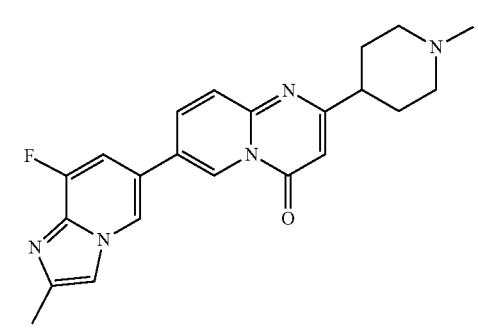
463
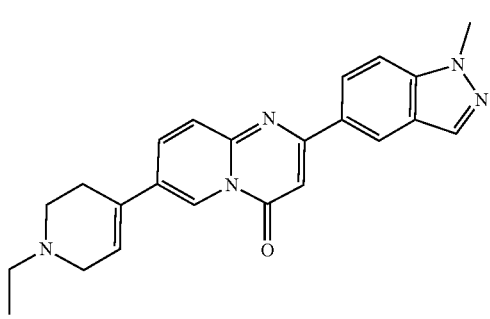
464
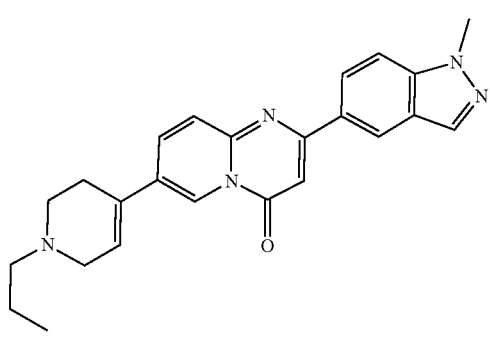
465
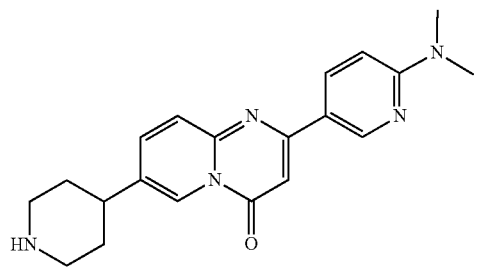
466
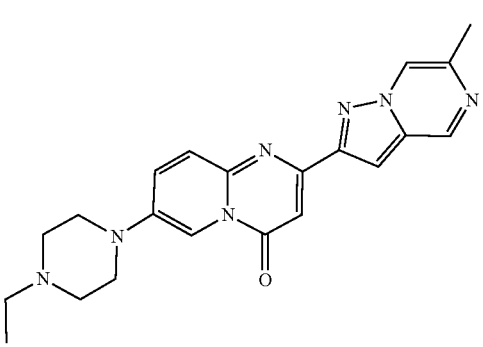
467
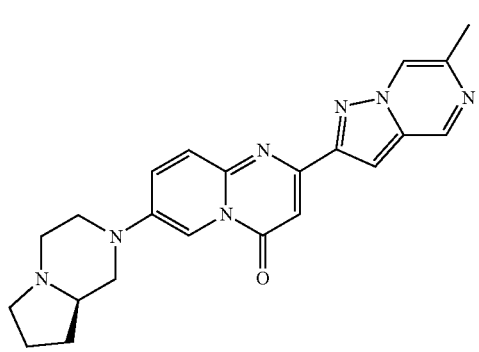
468
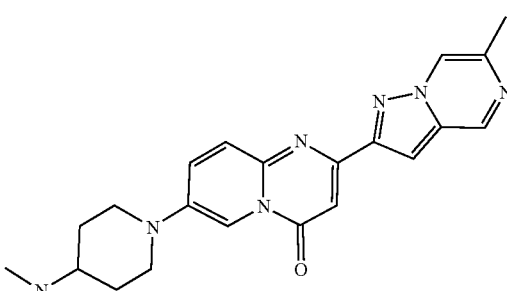
469
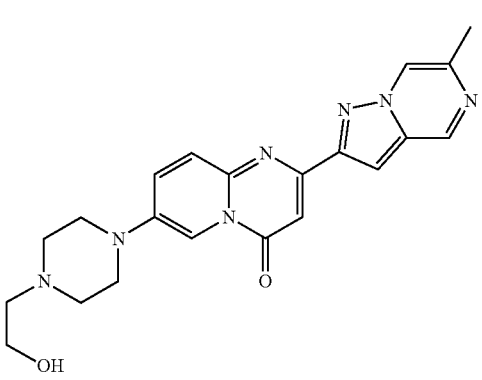

470 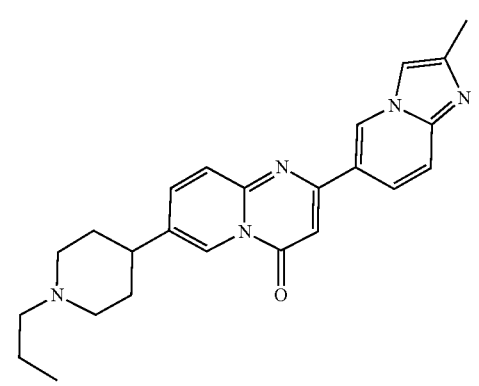
471 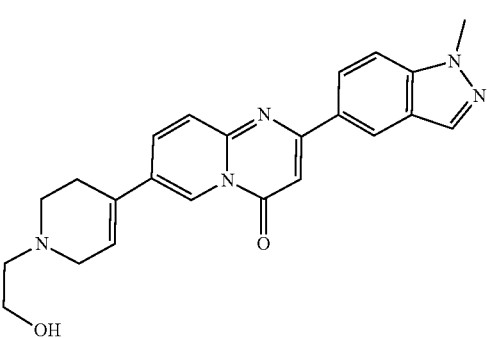
472 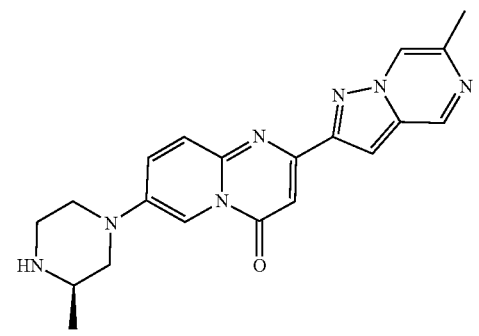
473 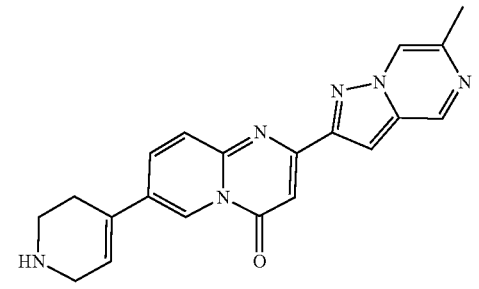
474 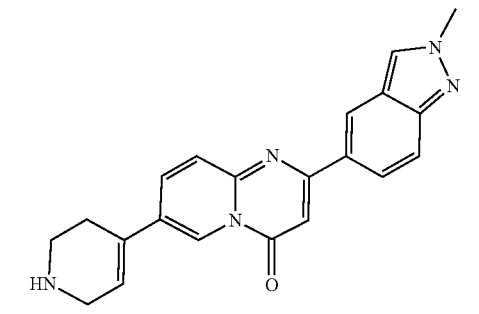
475 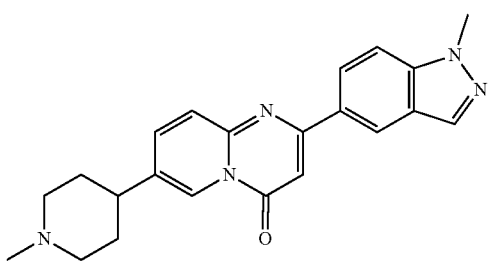
476 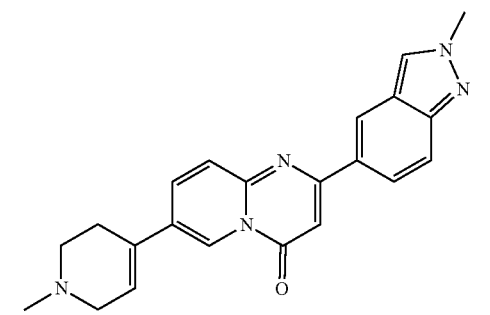
477 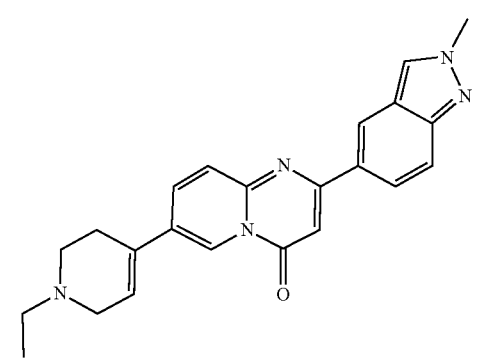
478 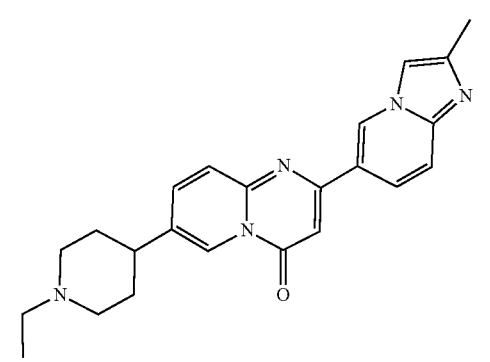
479 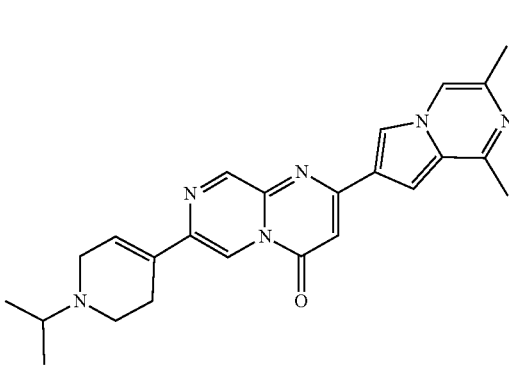

480 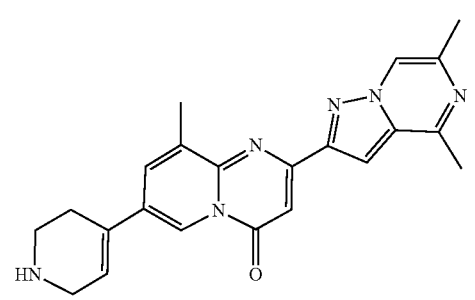
481 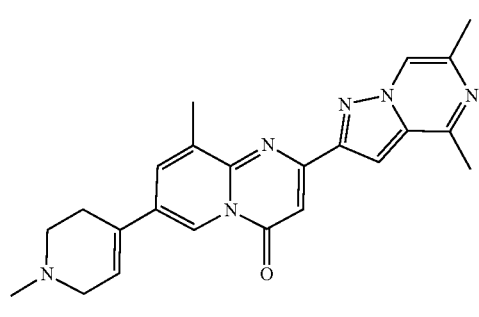
482 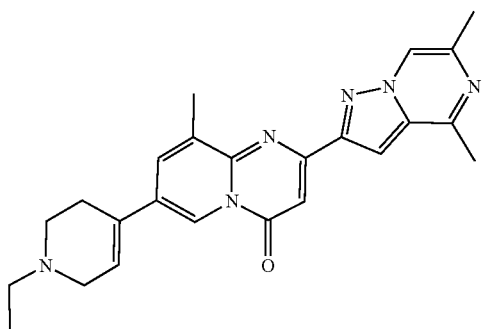
483 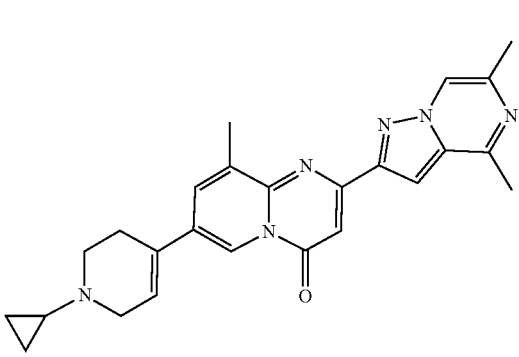
484 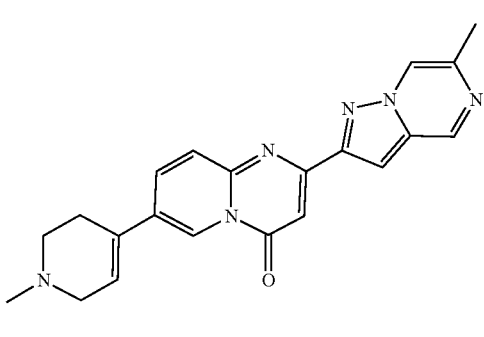
485 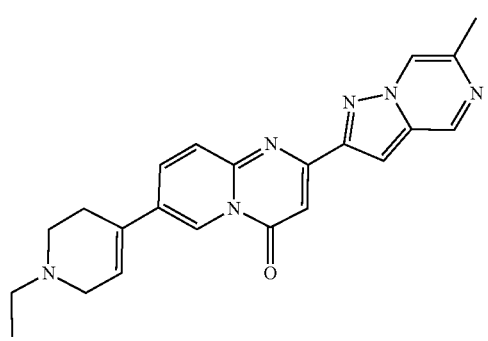
486 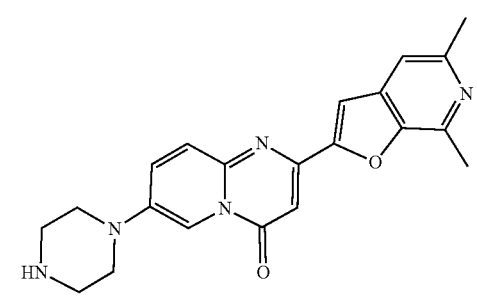
487 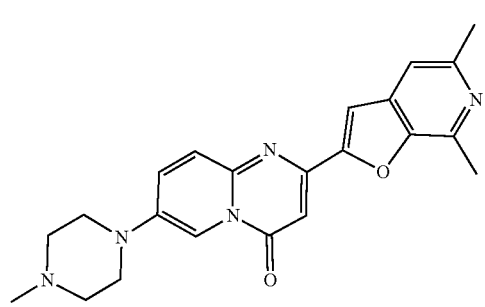
488 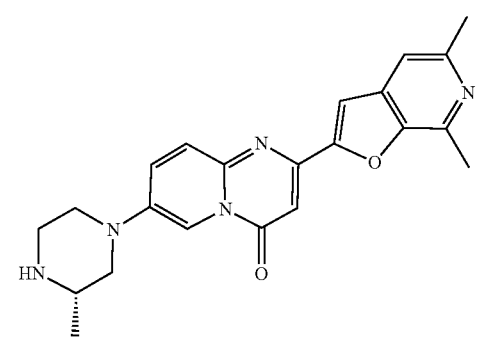
489 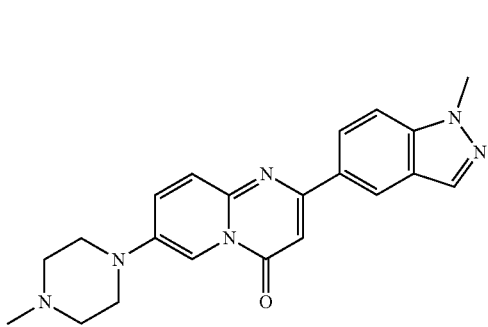

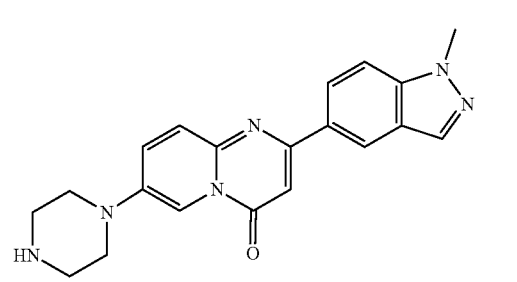
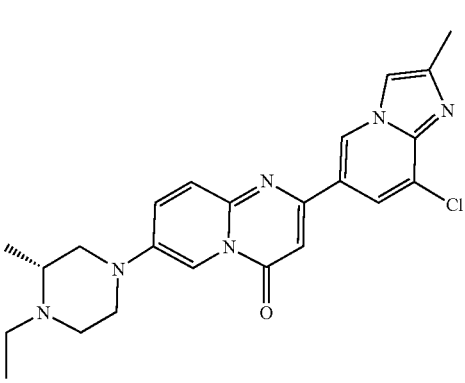
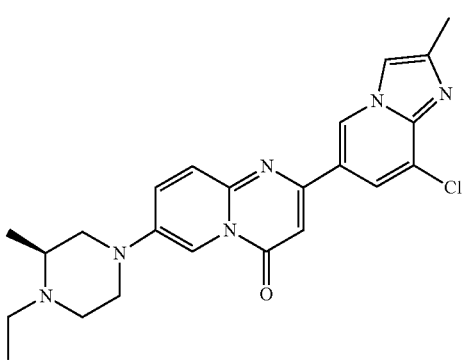
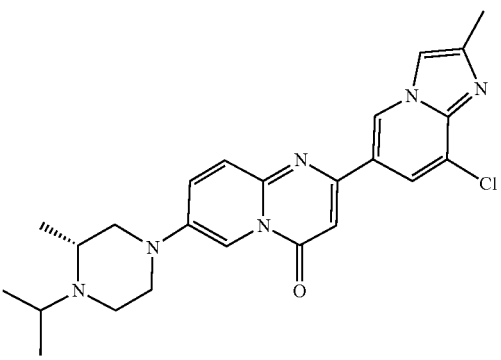
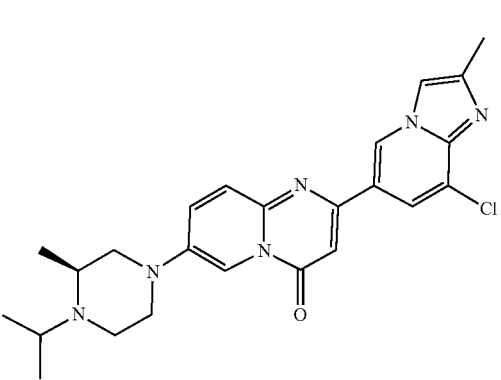

499
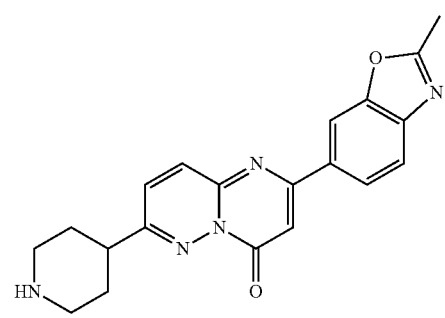
500
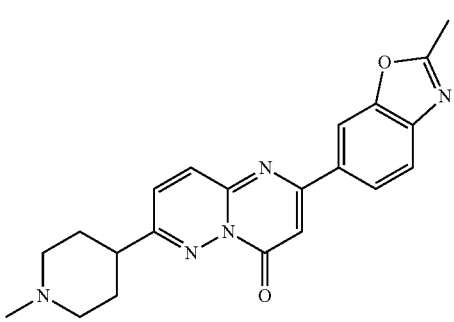
501
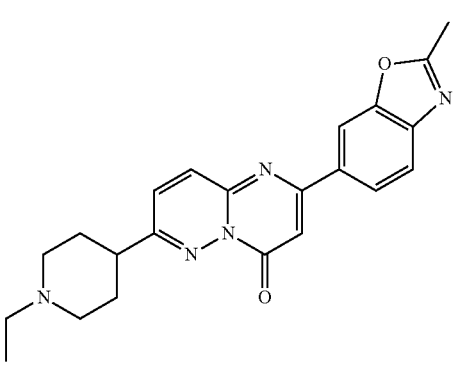
502
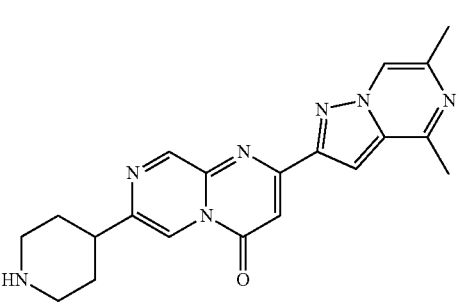
503
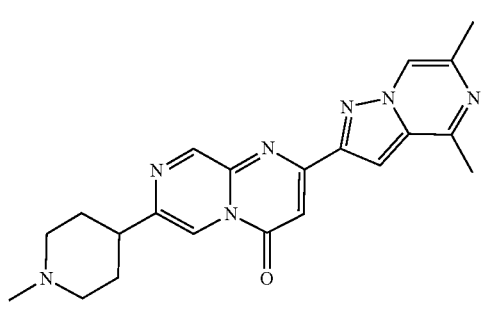
504
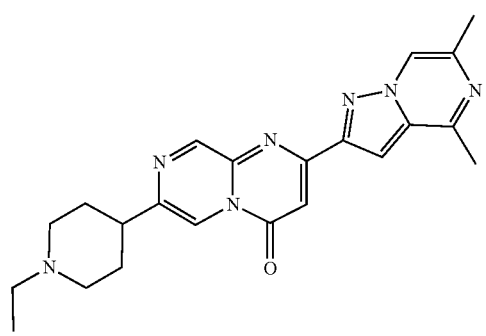
505
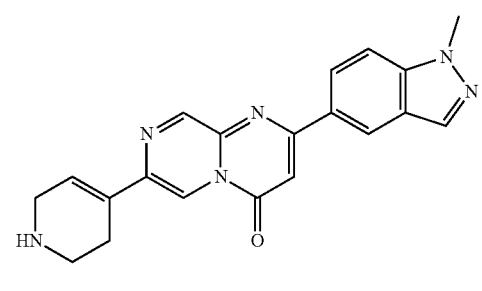
506
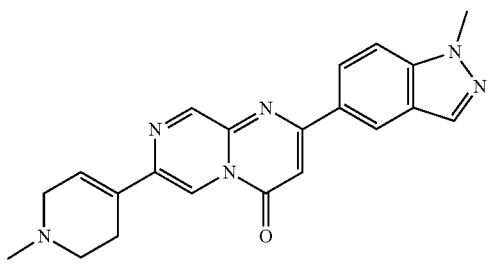
507
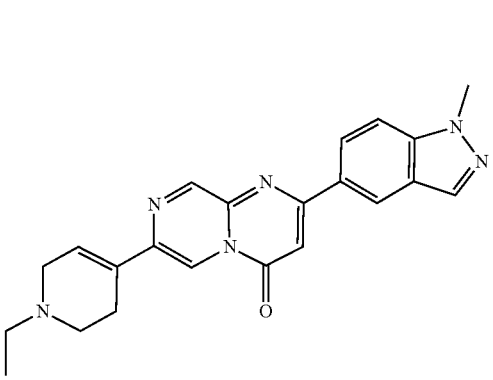
508
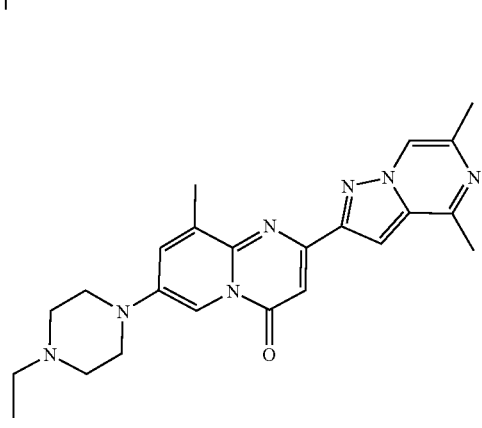

-continued
509
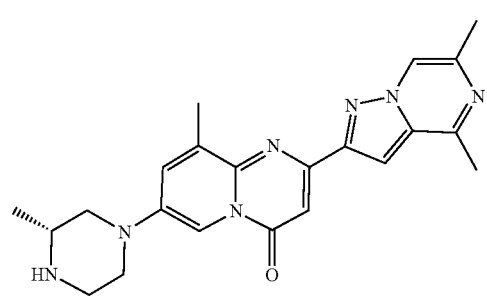
510
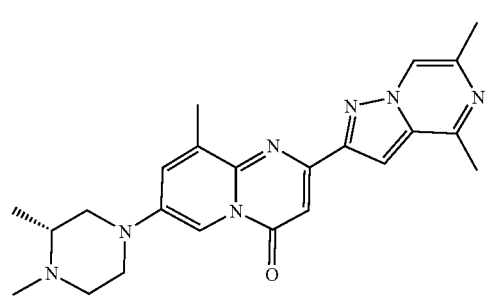
511
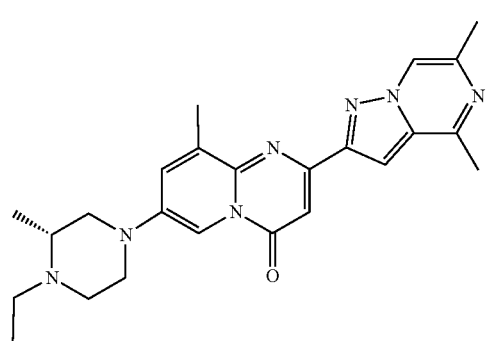
512
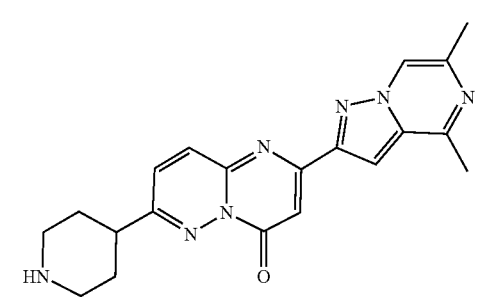
513
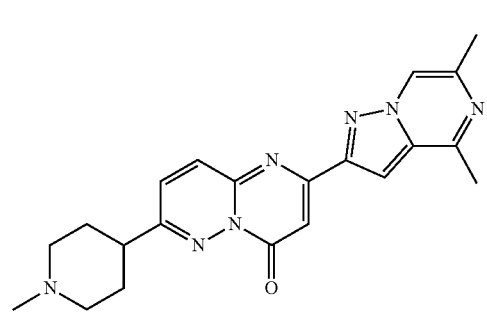
-continued
514
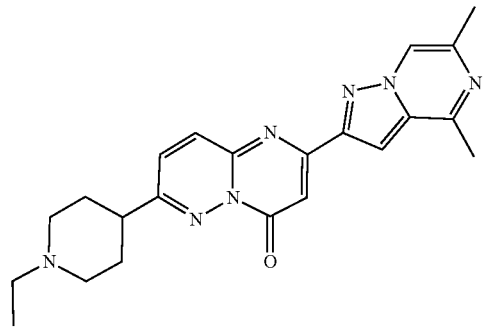
515
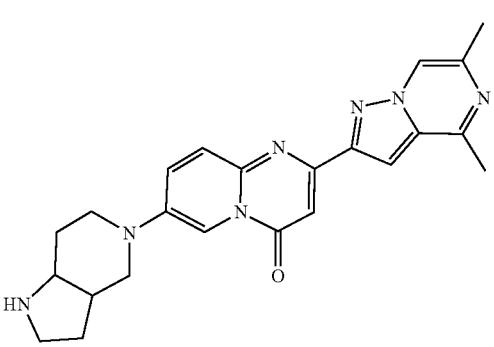
516
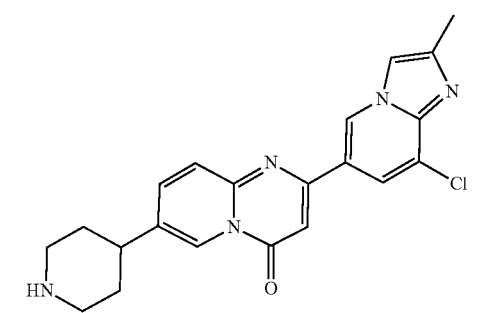
517
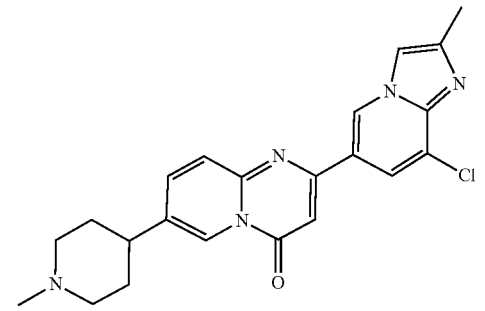
518
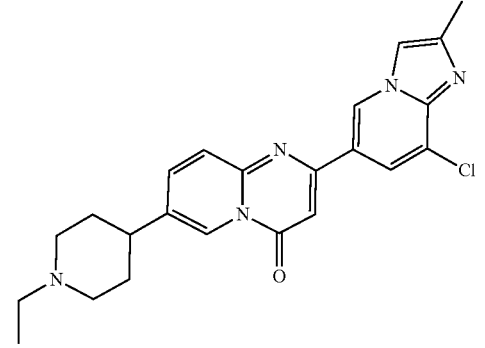

519
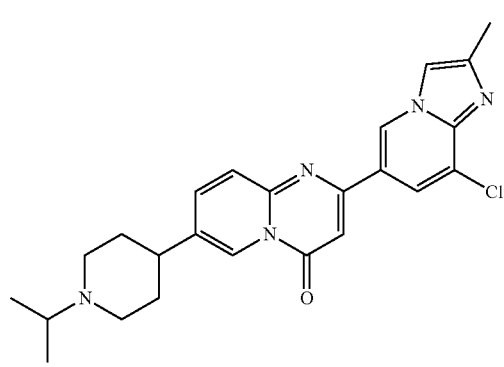
520
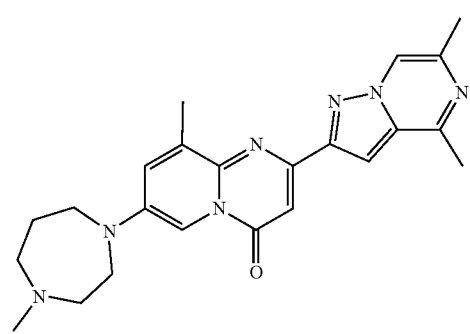
521
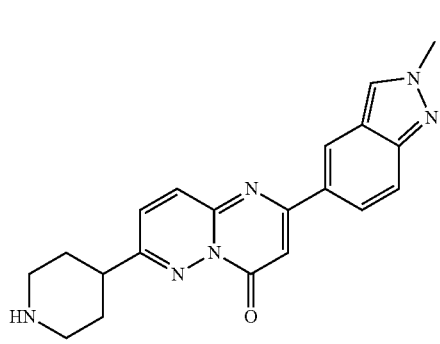
522
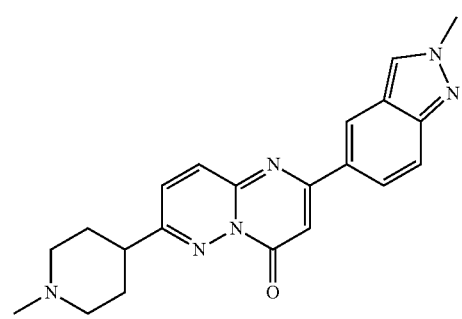
523
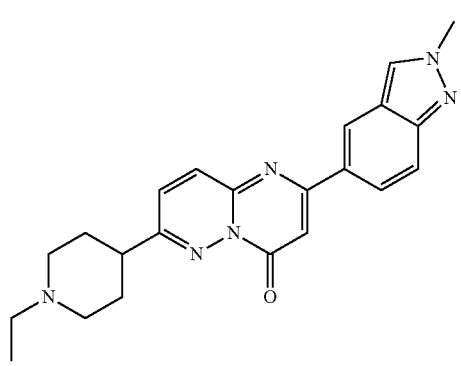
524
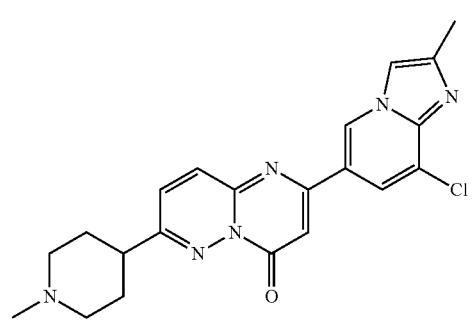
525
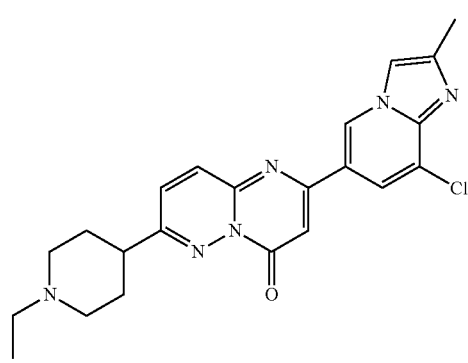
526
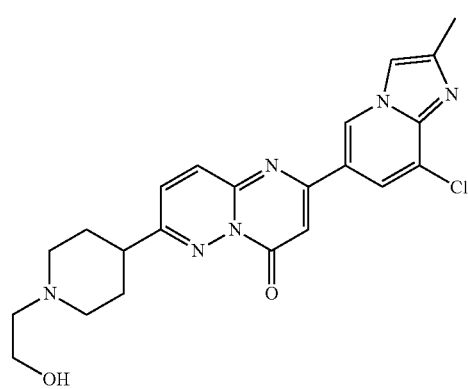

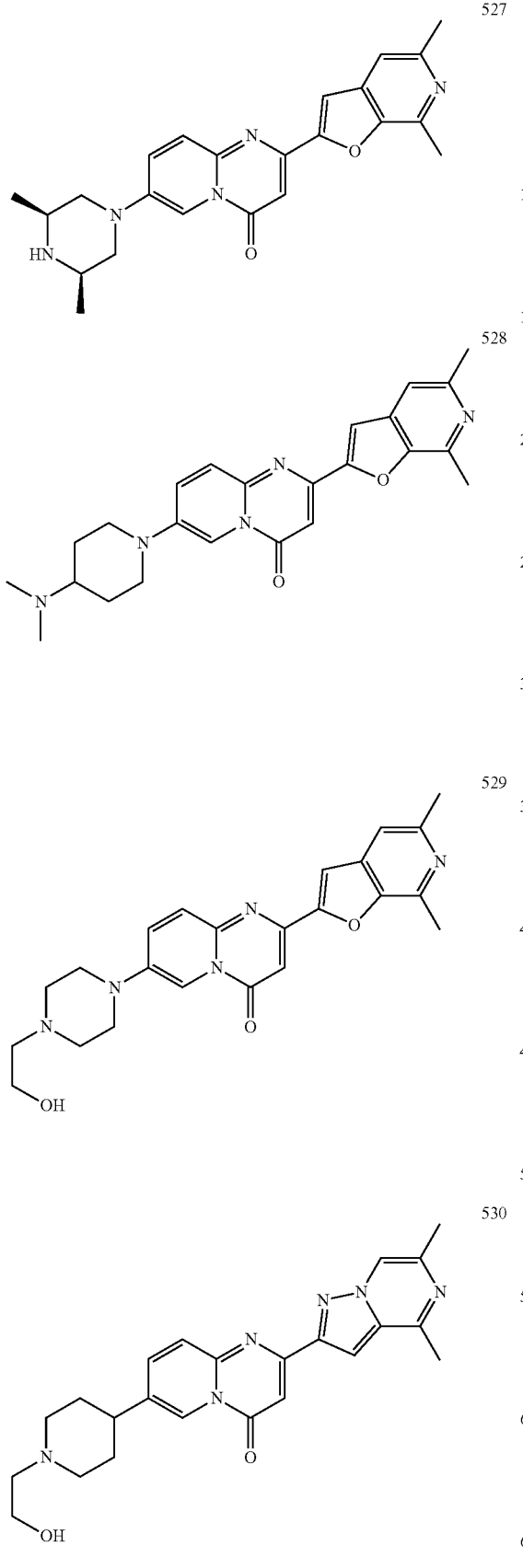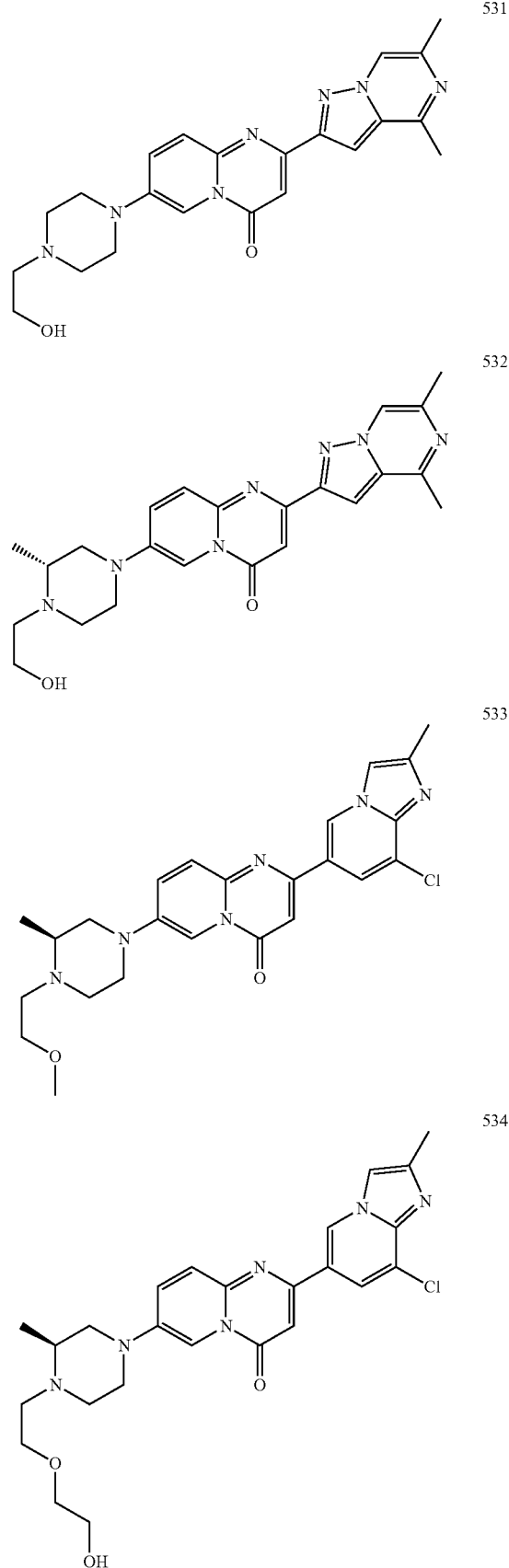

535
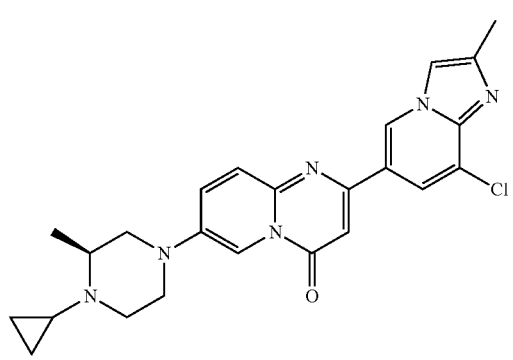
536
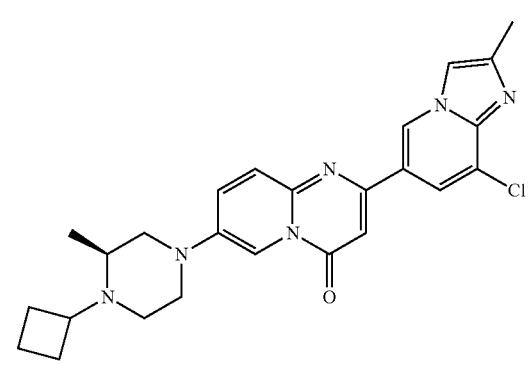
537
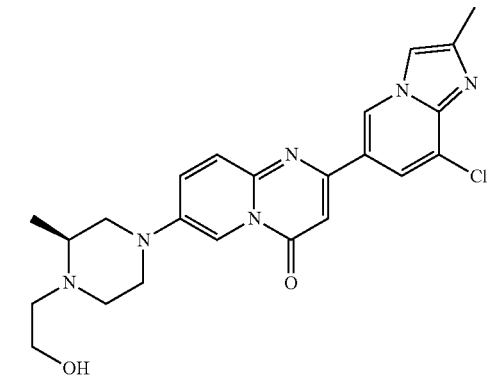
538
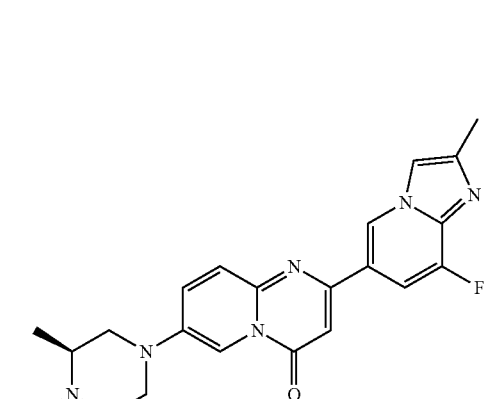
539
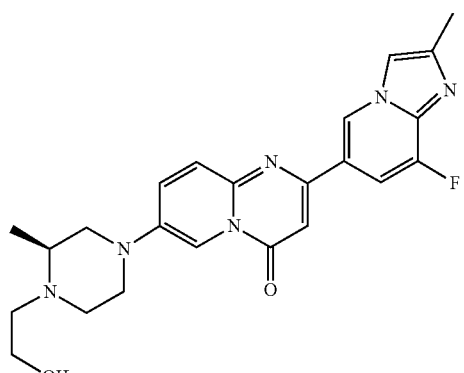
540
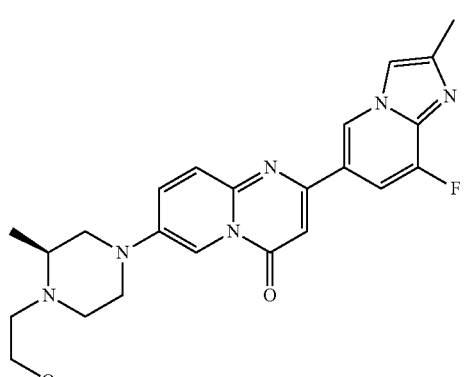
541
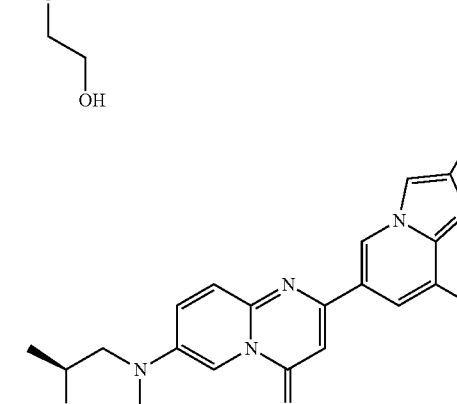
542
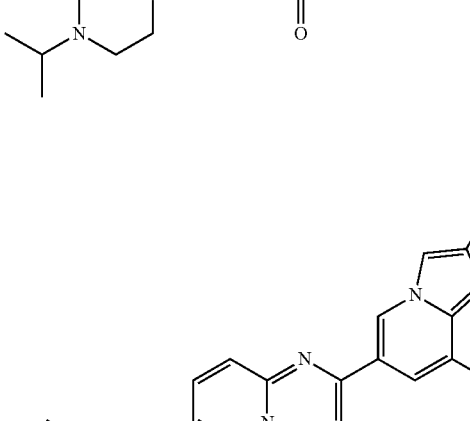

543 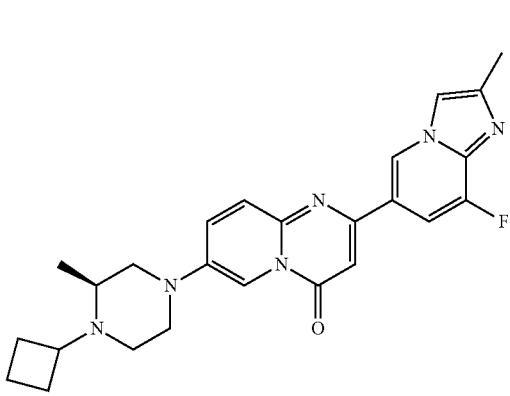
544 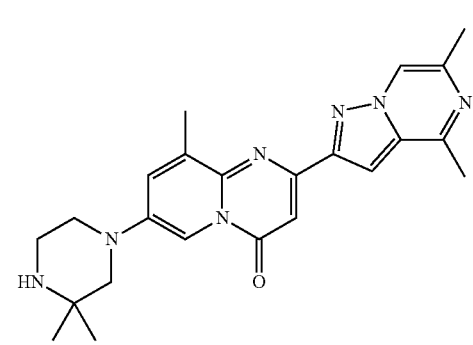
545 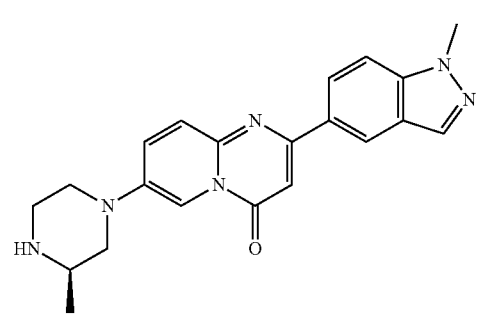
546 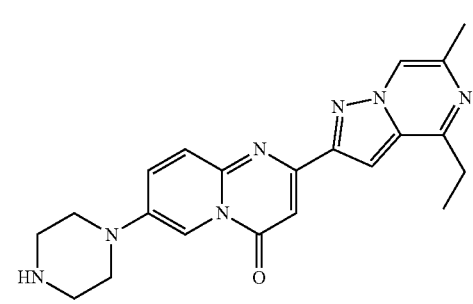
547 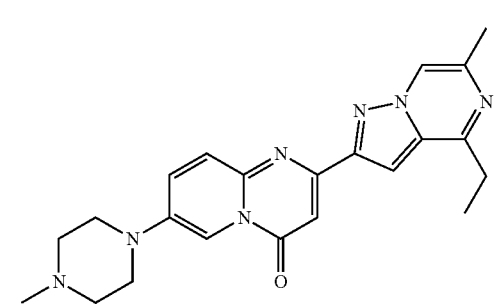
548 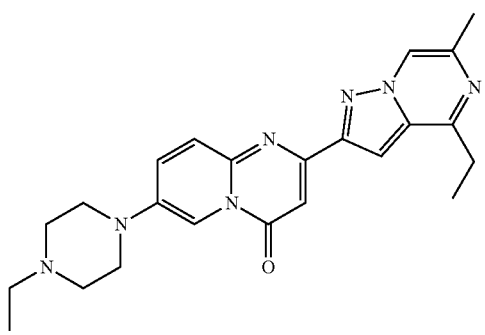
549 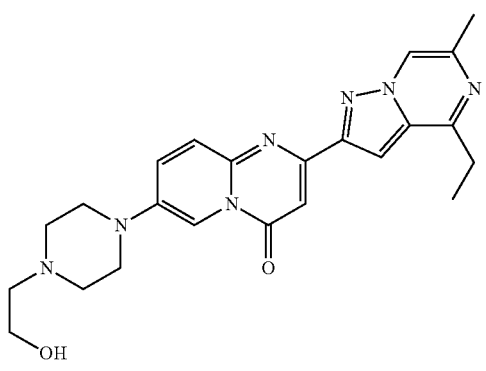
550 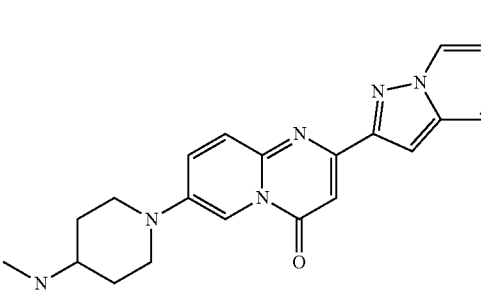
551 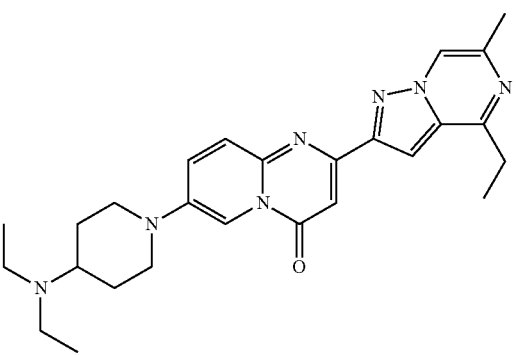

552
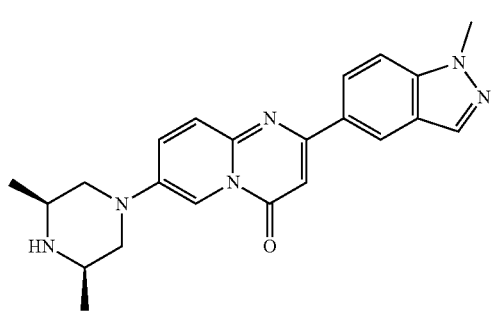
553
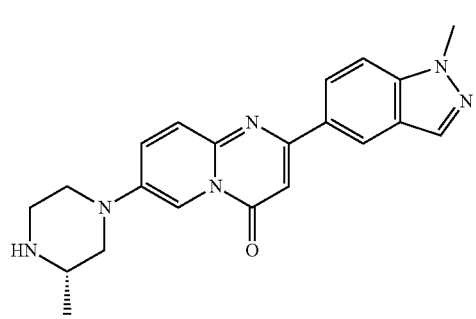
554
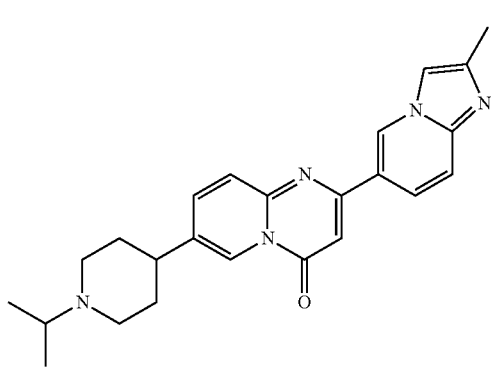
555
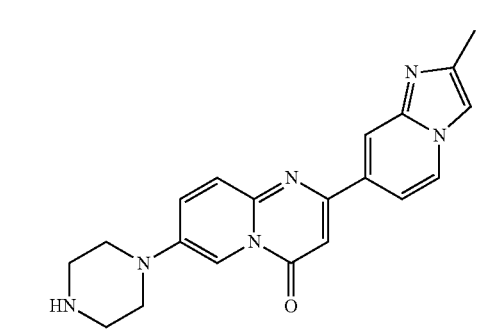
556
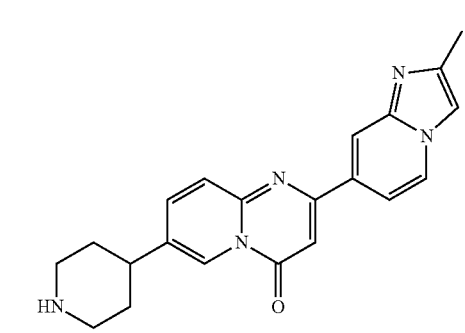
557
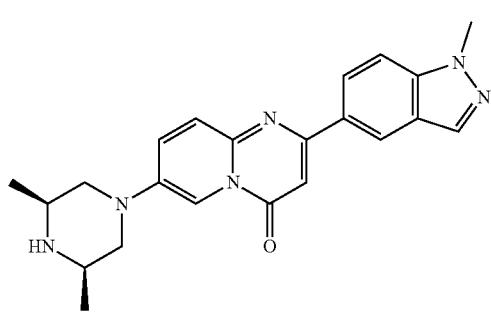
558
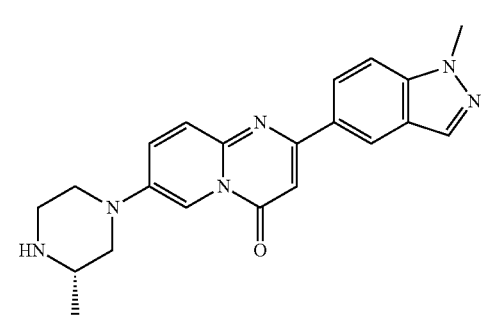
559
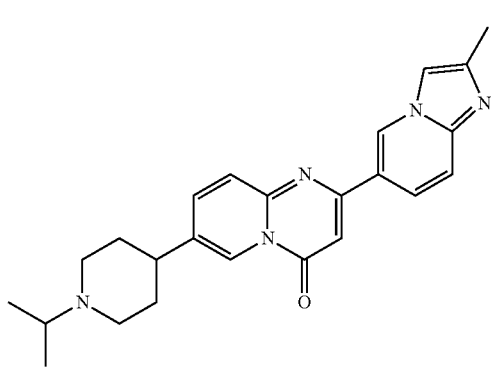
560
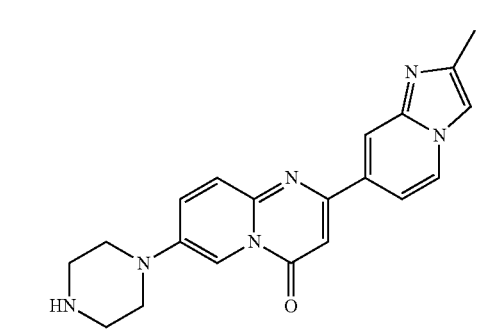
561
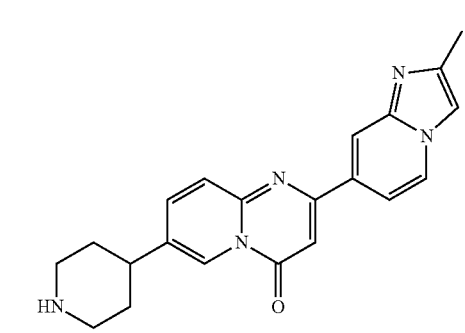

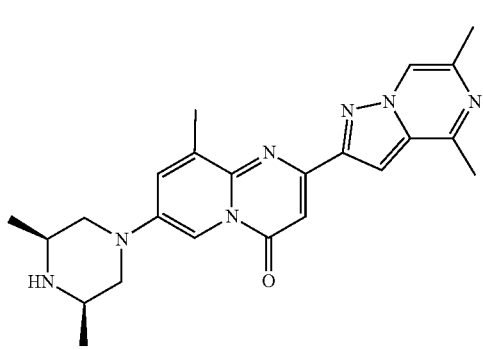
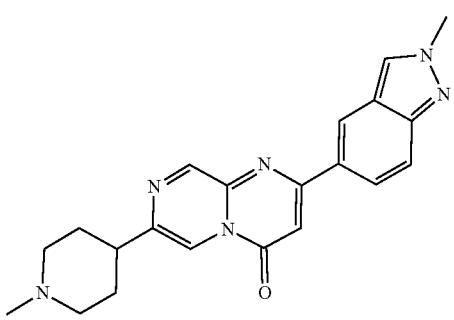
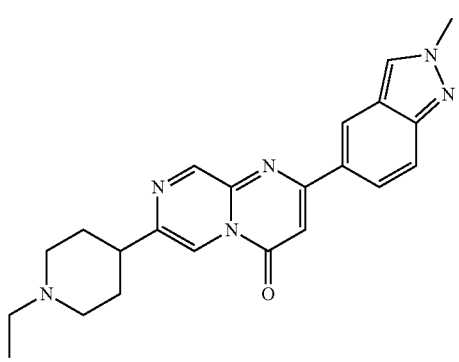
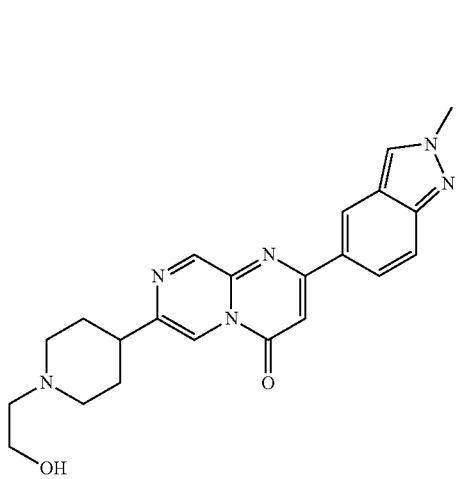
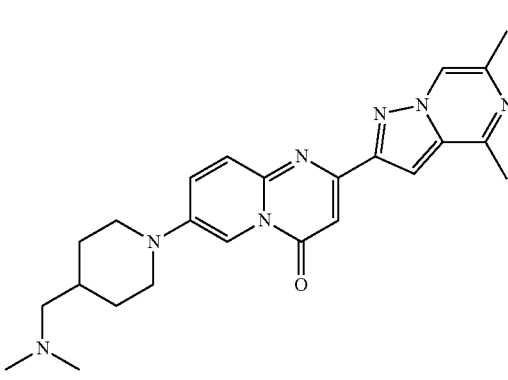

571
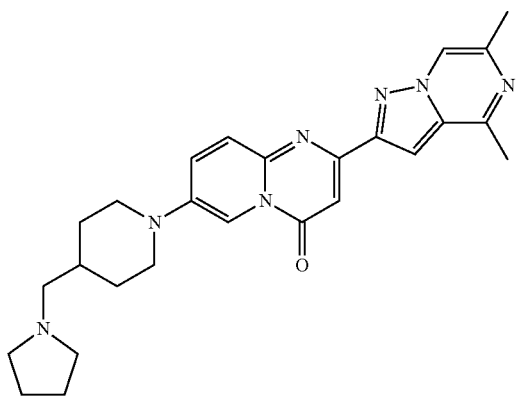
572
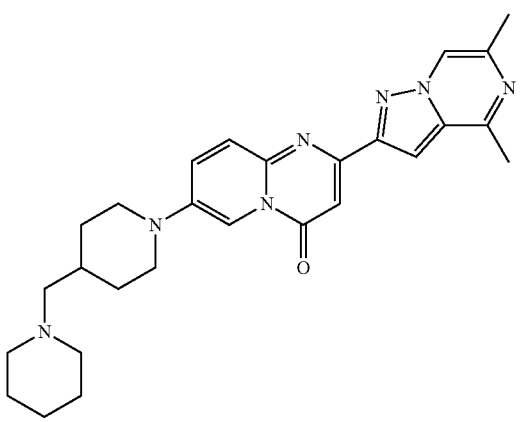
573
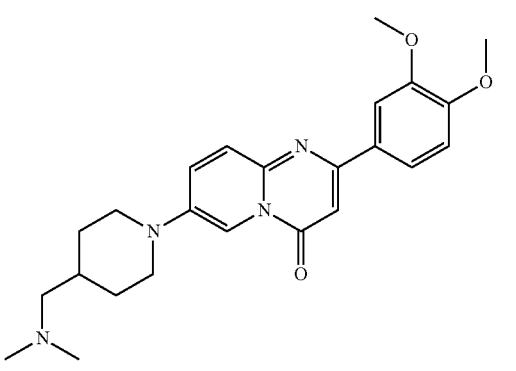
574
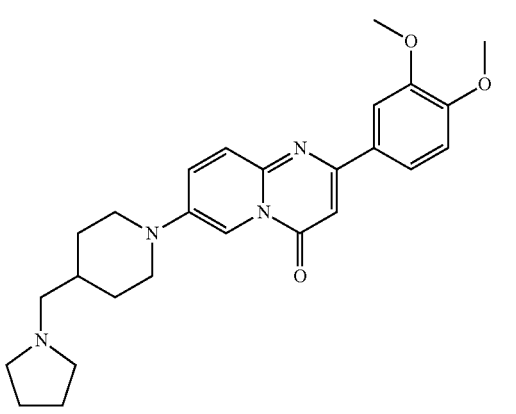
575
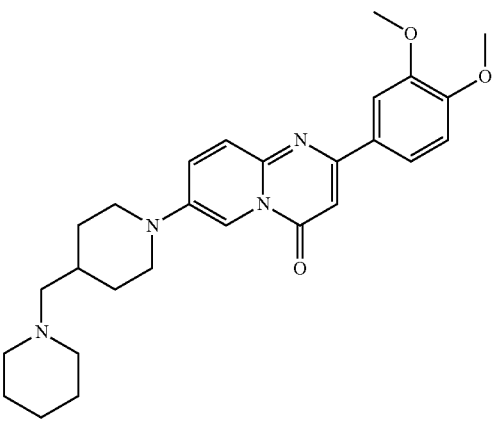
576
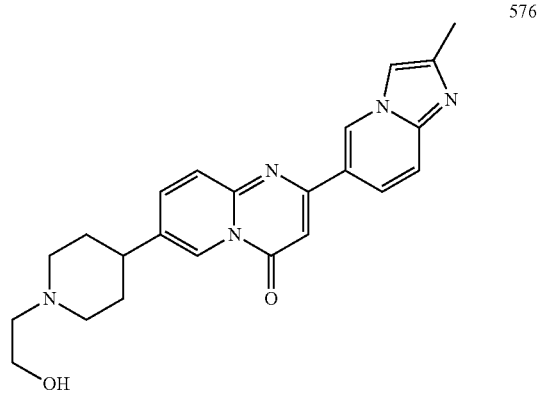
577
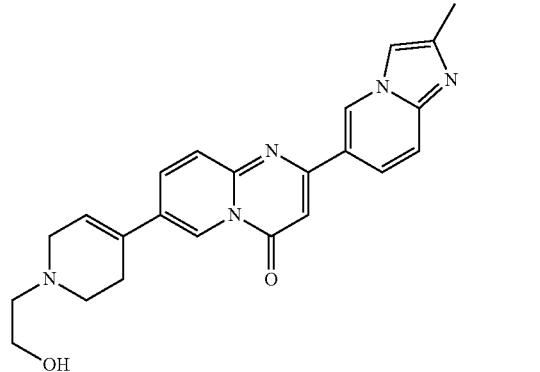
578
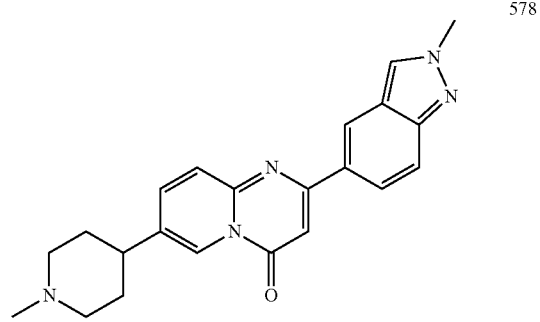

-continued
579
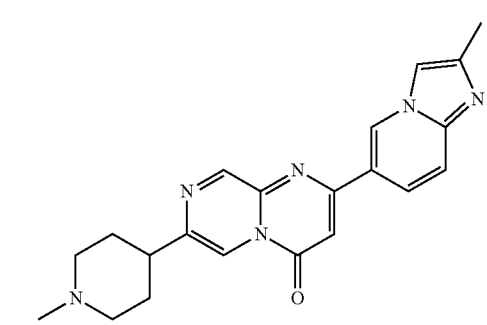
580
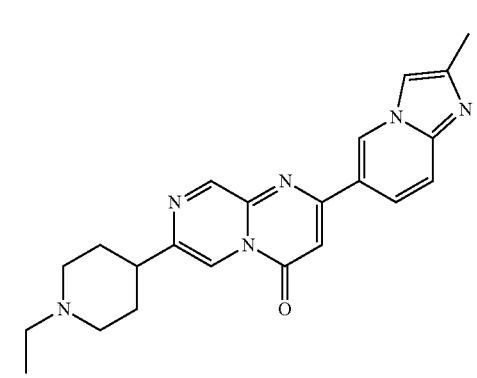
581
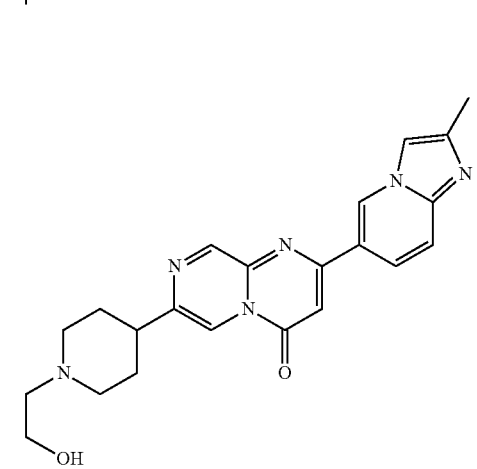
582
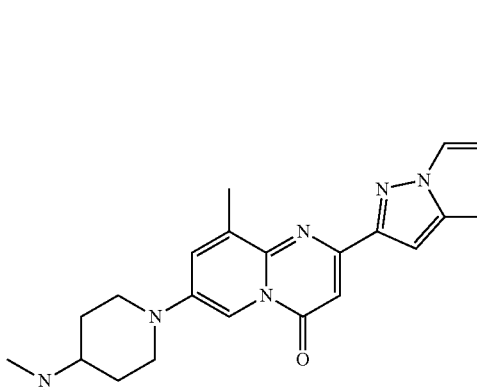
583
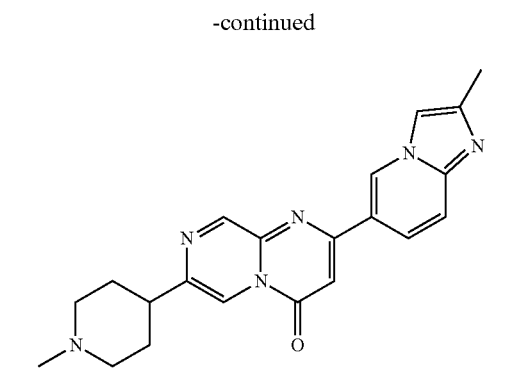
584
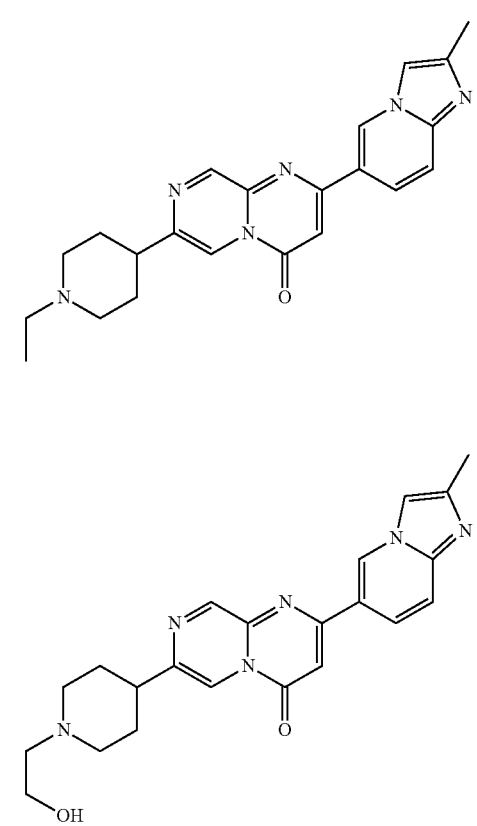
585
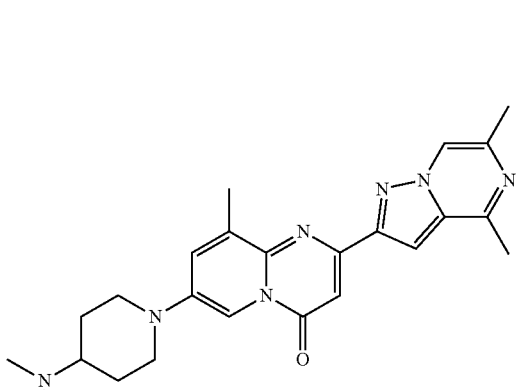
586
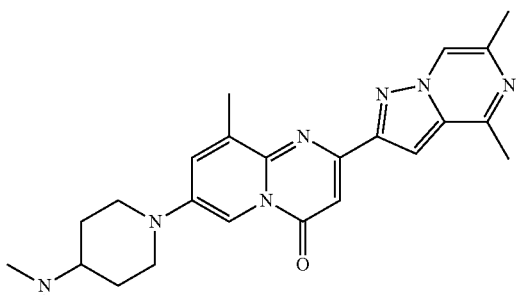
587

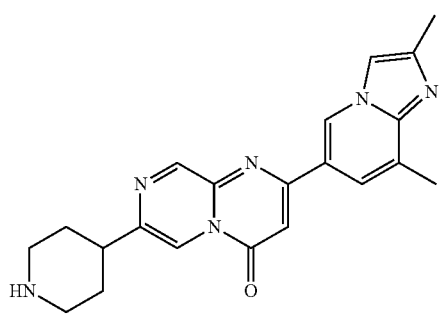
588
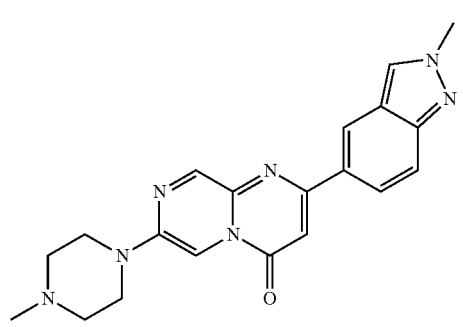
589
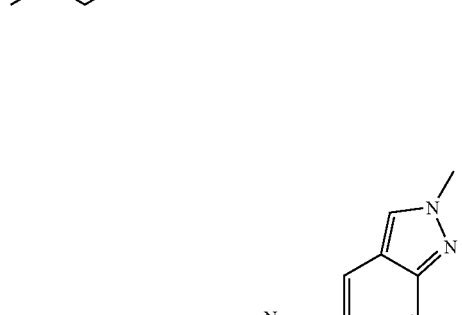
590
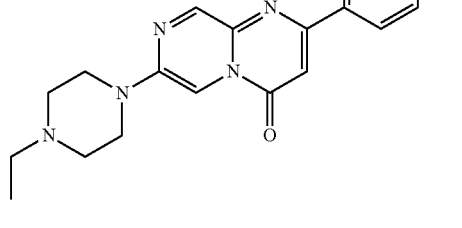
591
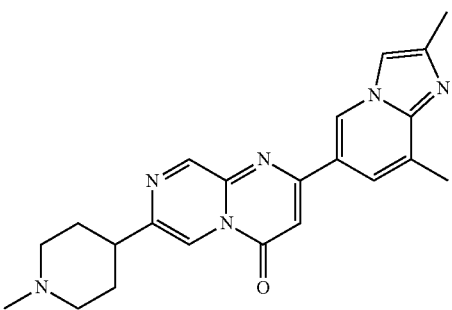
592
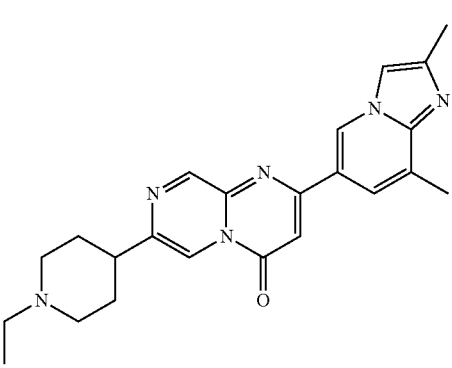
593
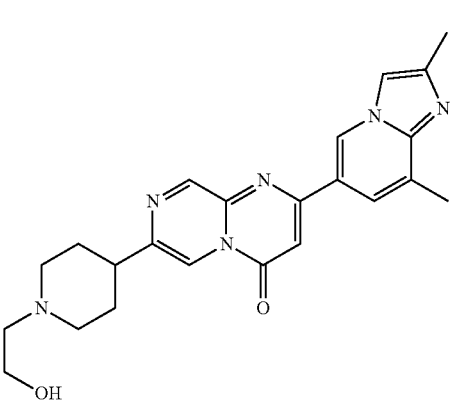
594
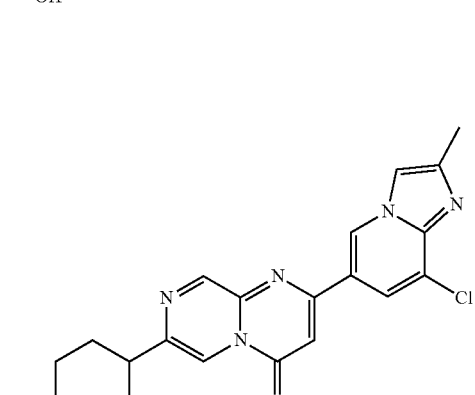
595

193
-continued
596
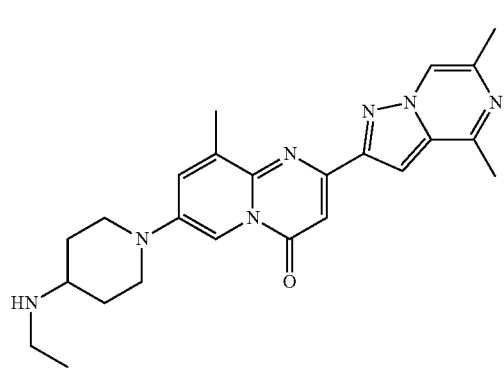
597
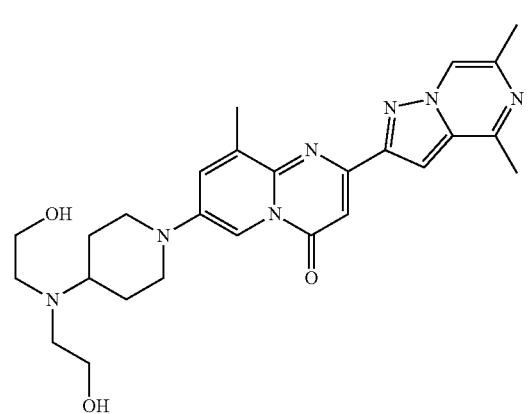
598
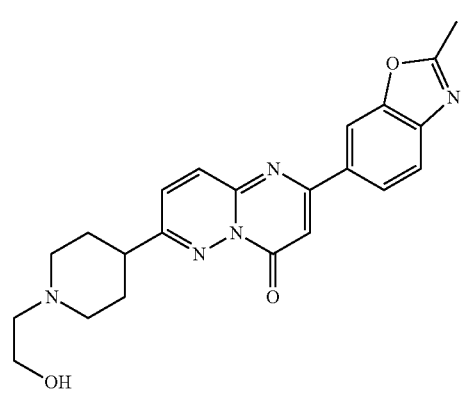
599
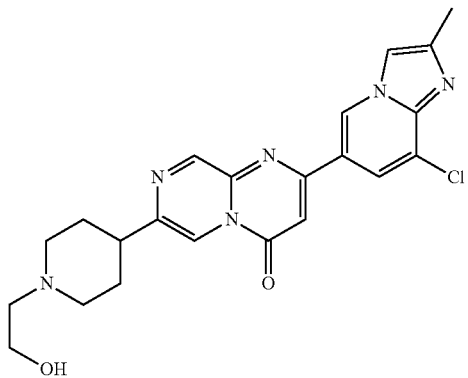
194
-continued
600
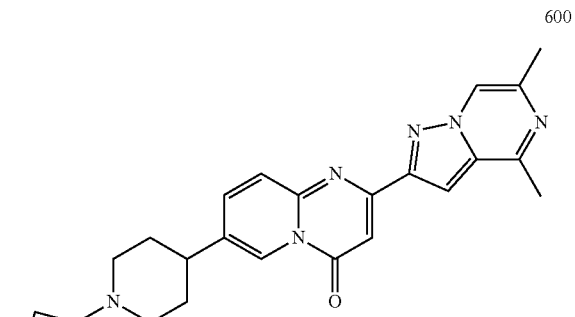
601
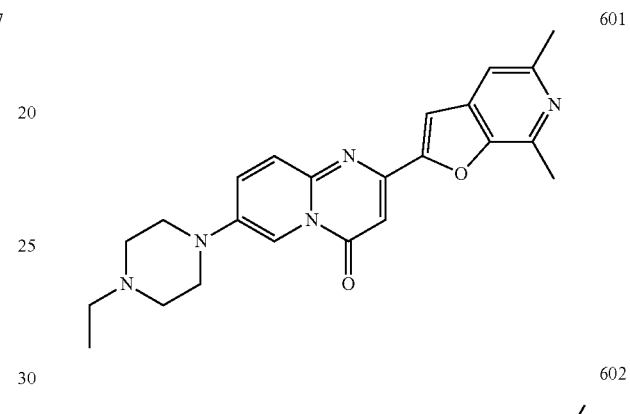
602
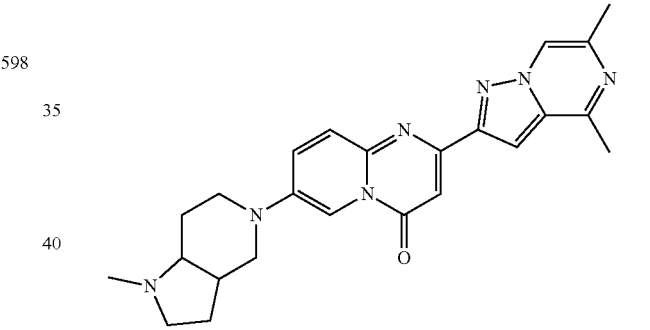
603
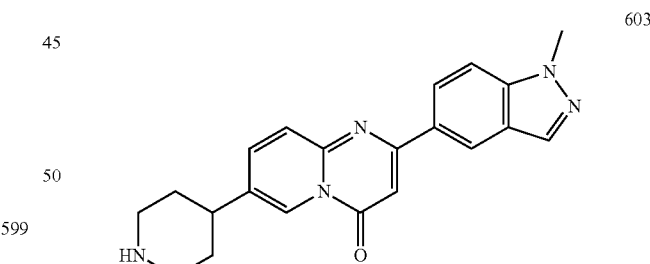
604
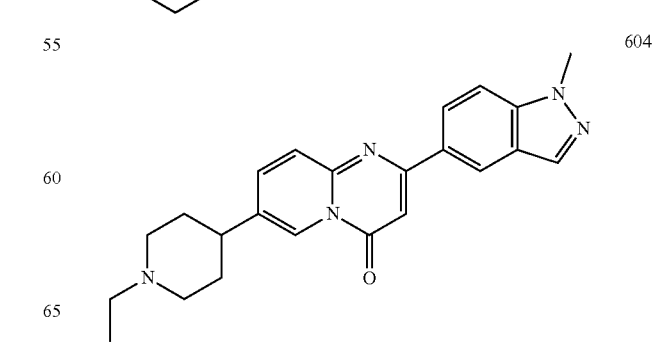

605
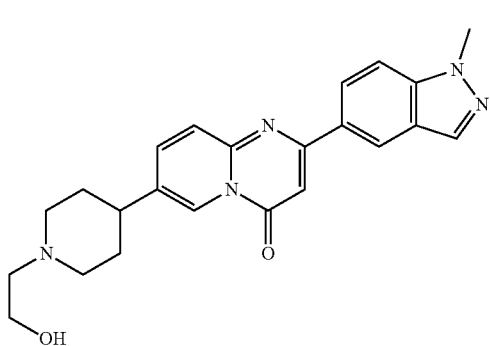
606
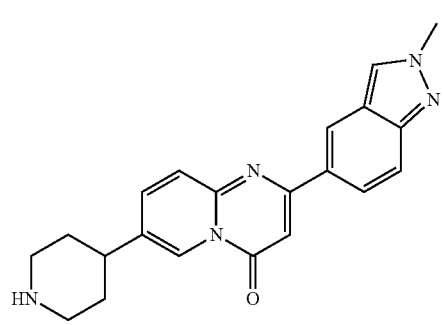
607
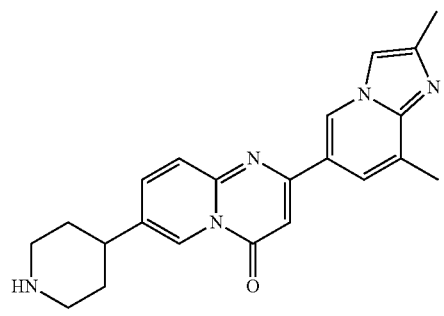
608
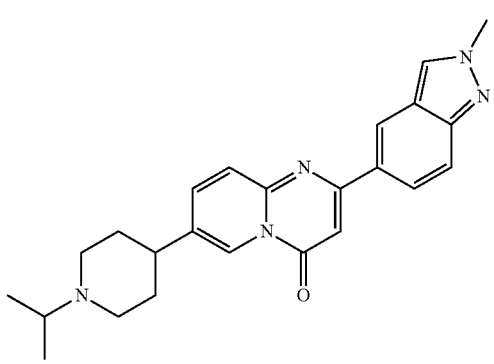
609
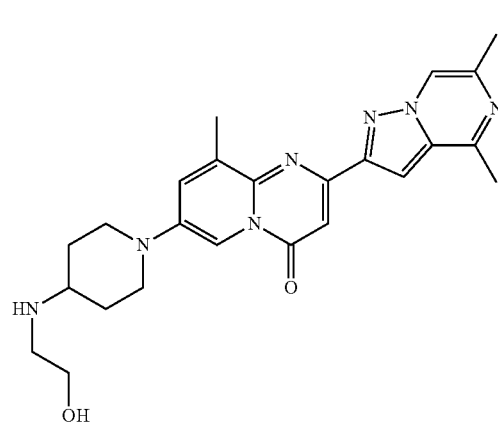
610
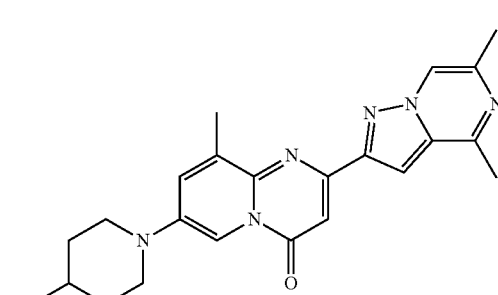
611
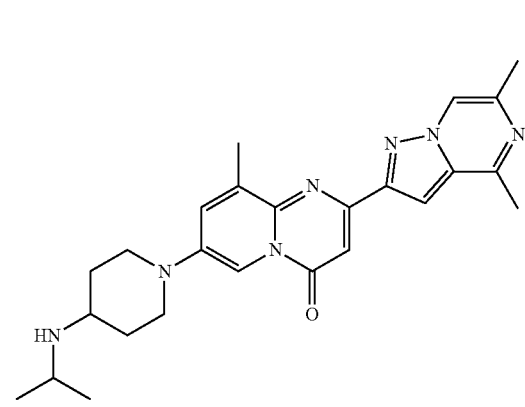
612
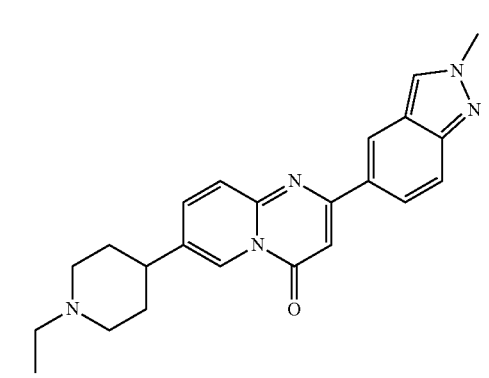

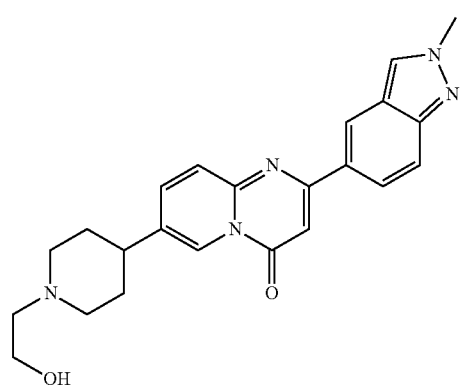
613
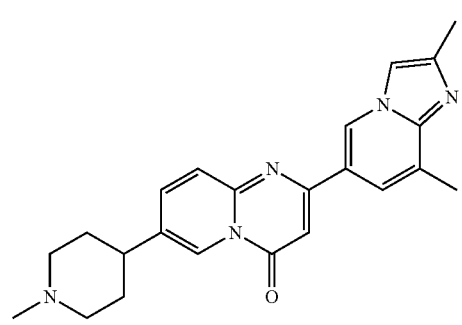
614
615
616
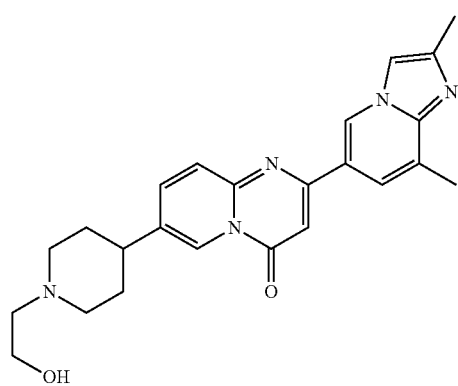
617
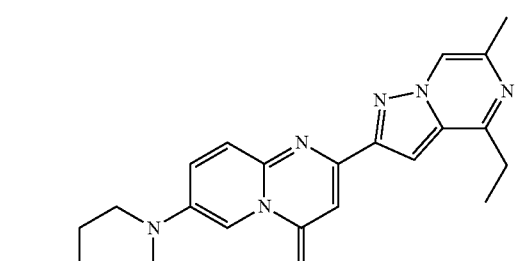
618
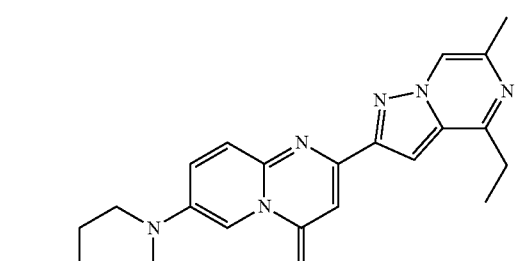
619
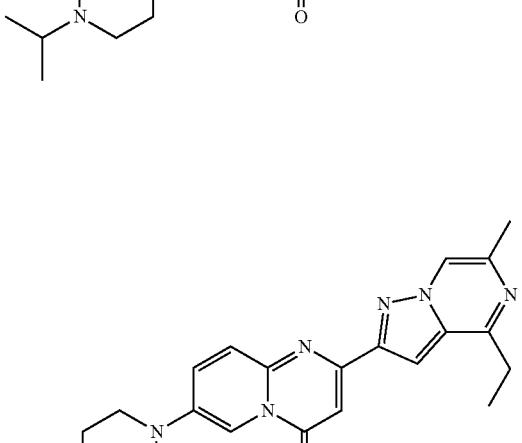
620

199
-continued
621
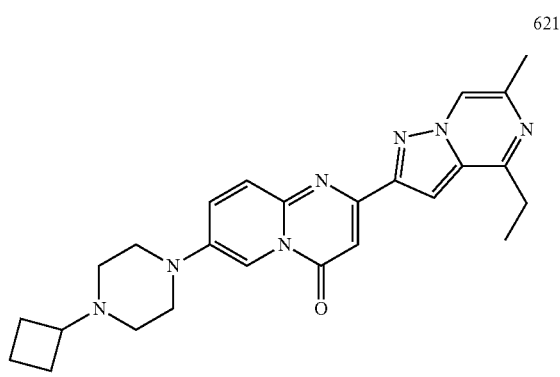
622
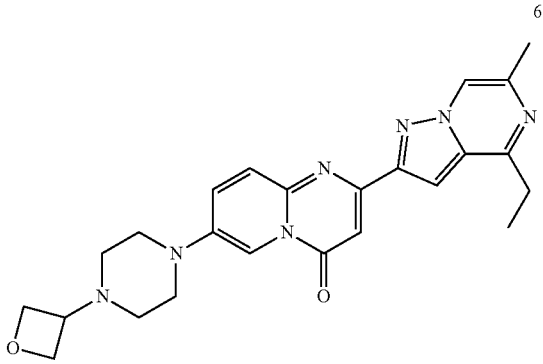
623
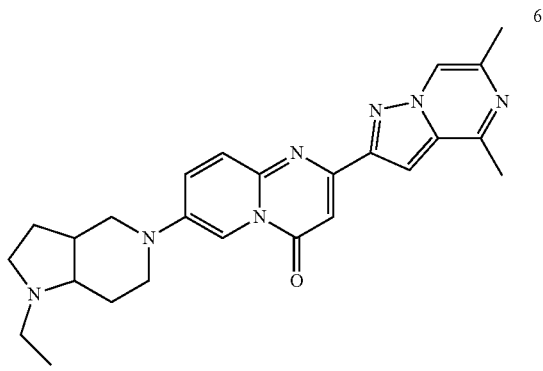
624
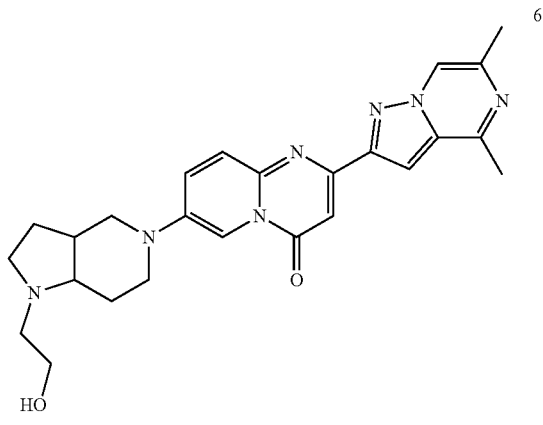
200
-continued
625
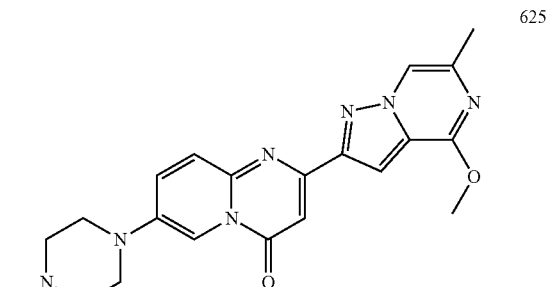
626
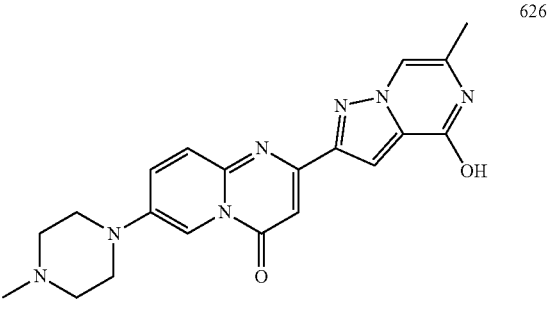
627
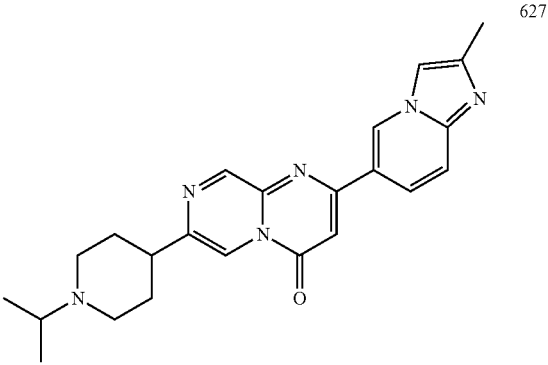
628
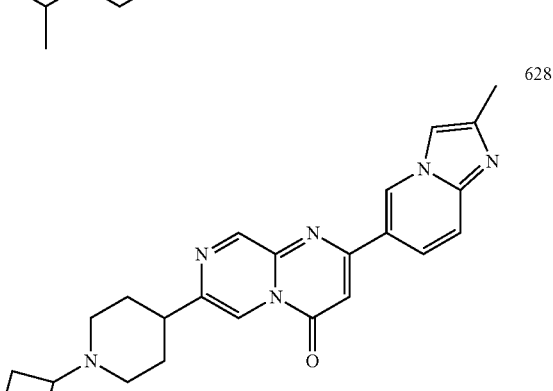
629
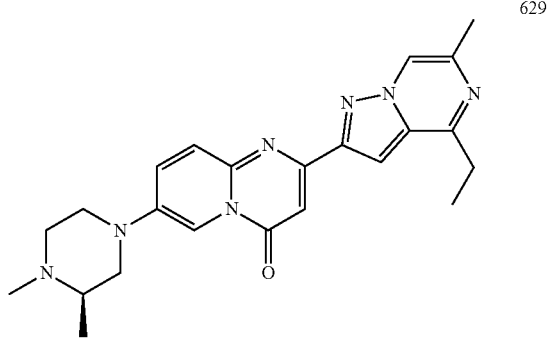

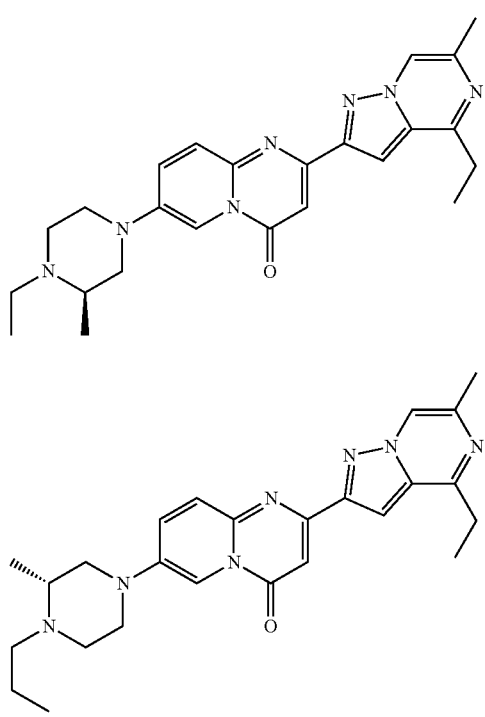
630
631
632
633
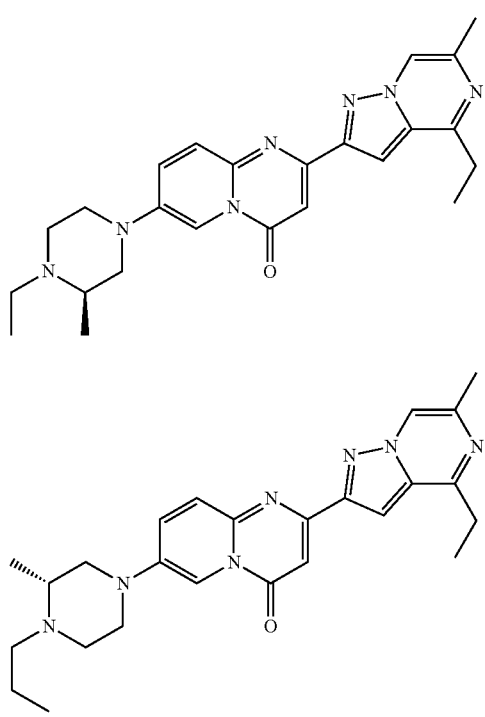
634
635
636
637
638

| 639 | 643 |
| 640 | 644 |
| 641 | 645 |
| 642 | 646 |

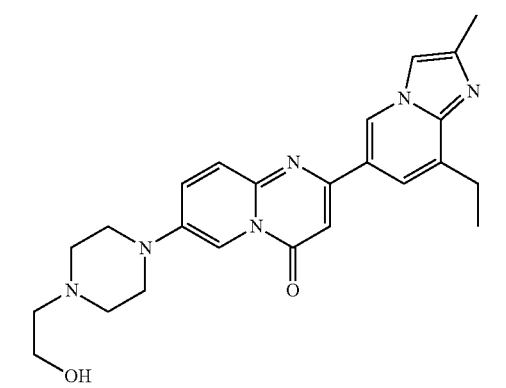
647
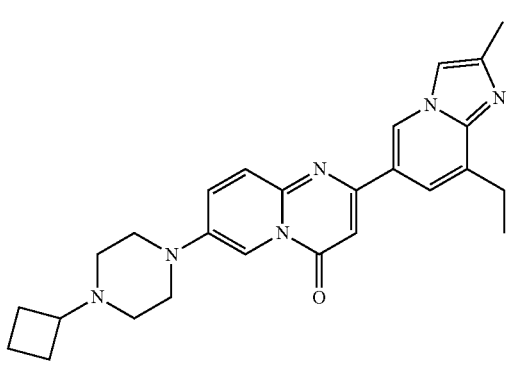
648
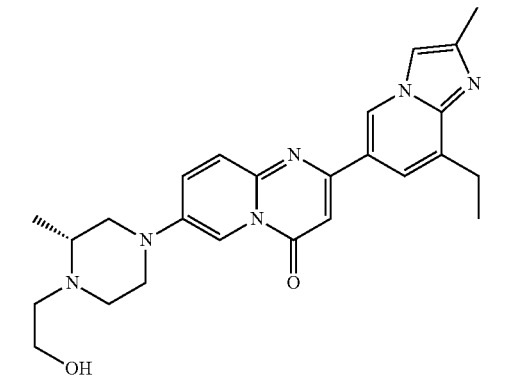
649
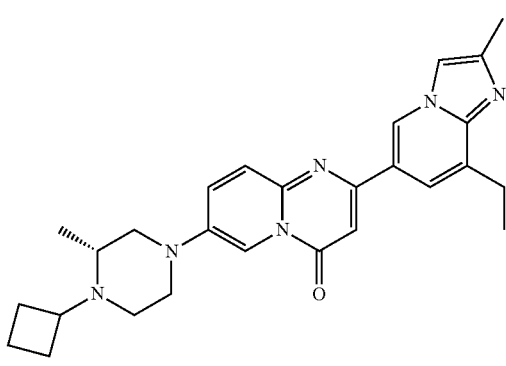
650
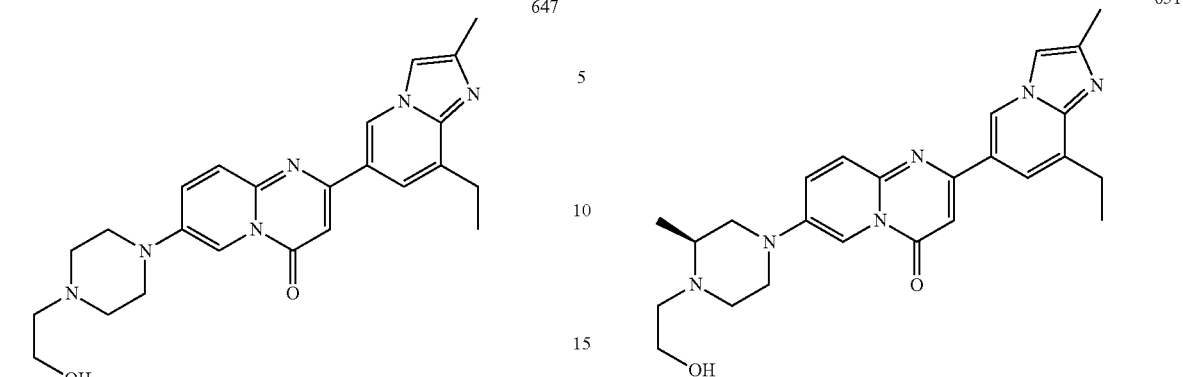
651
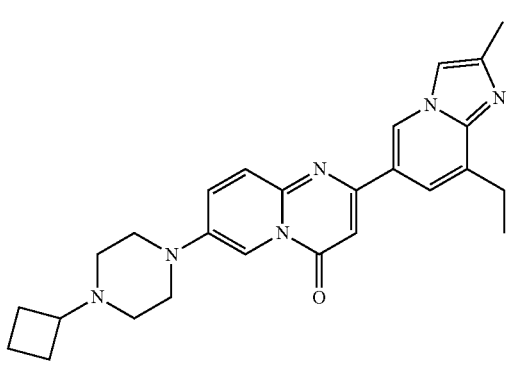
652
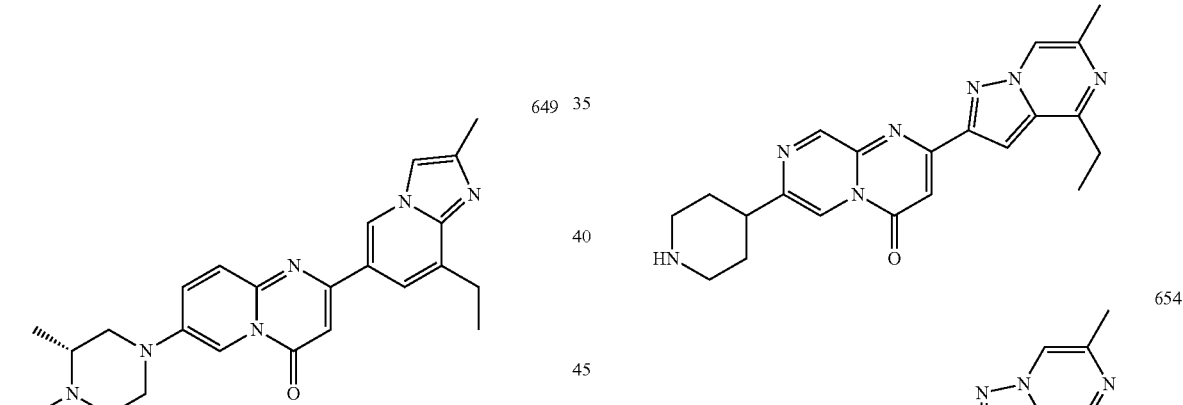
653
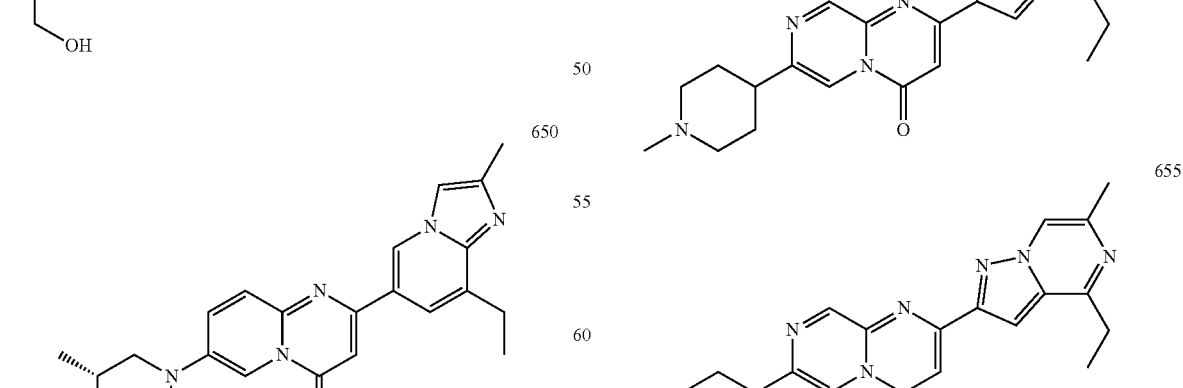
654
655

-continued
656 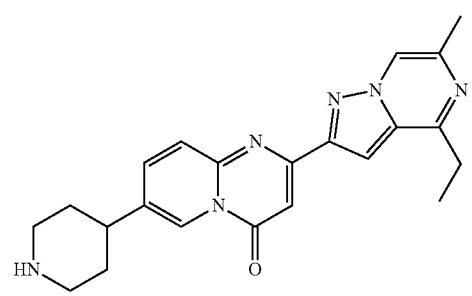
657 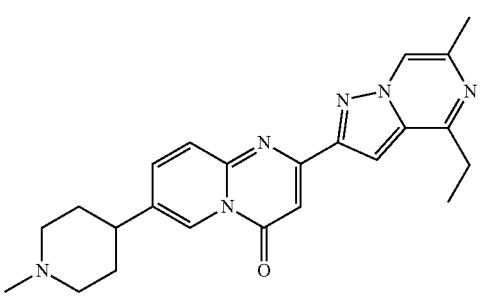
658 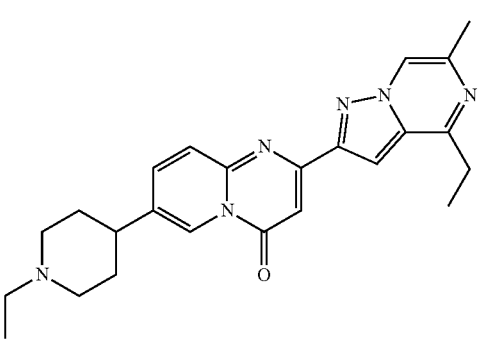
659 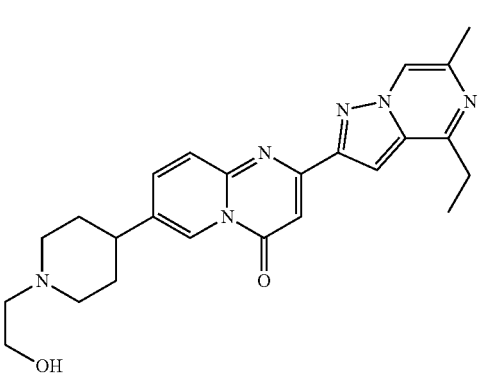
660 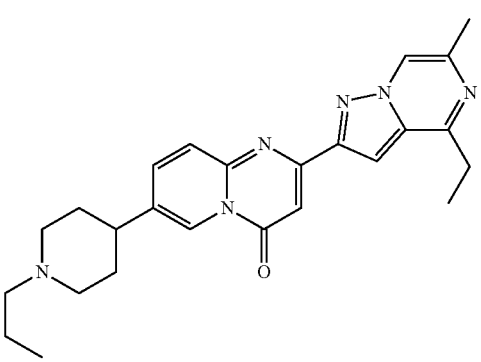
-continued
661 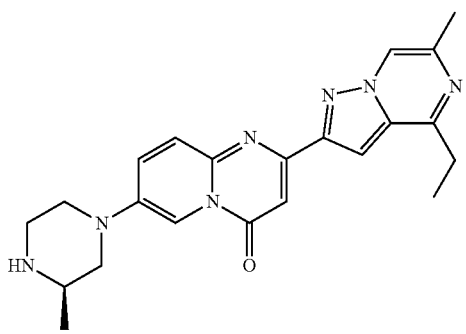
662 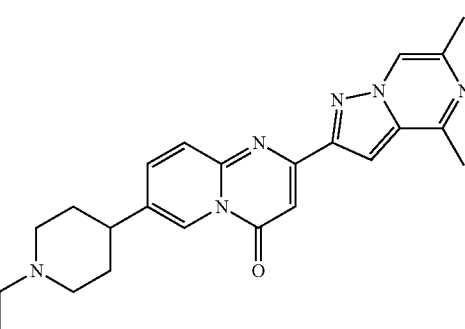
663 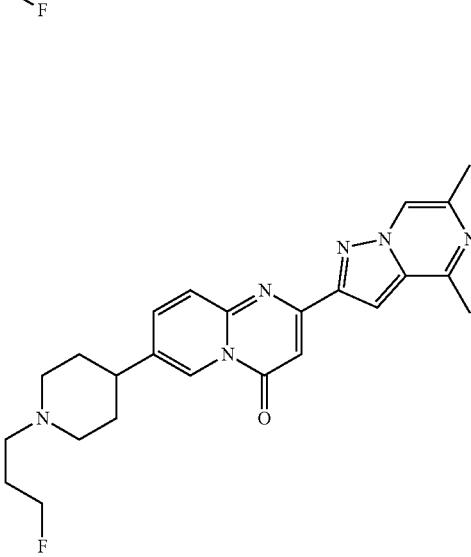
664 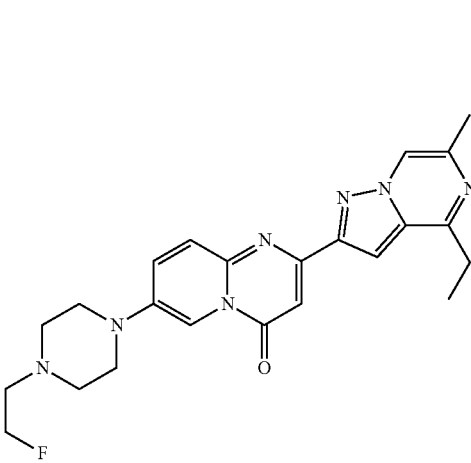

209
-continued
665
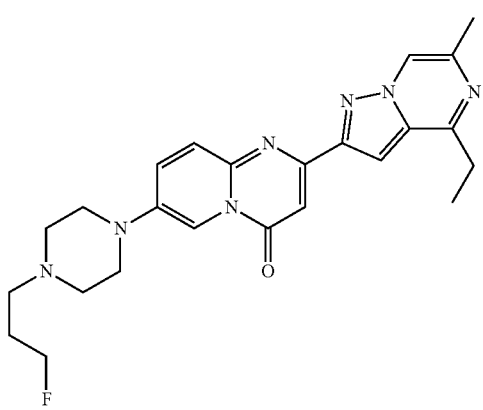
666
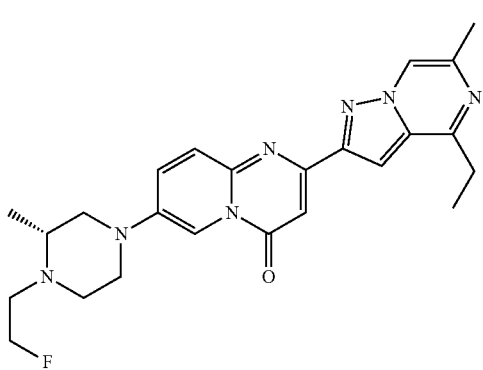
667
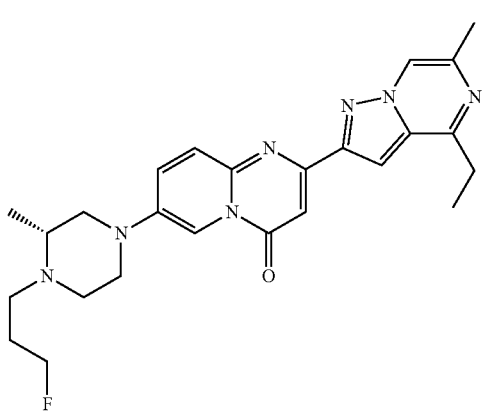
668
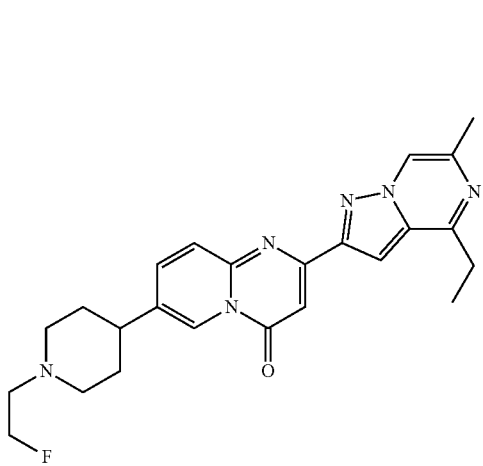
210
-continued
669
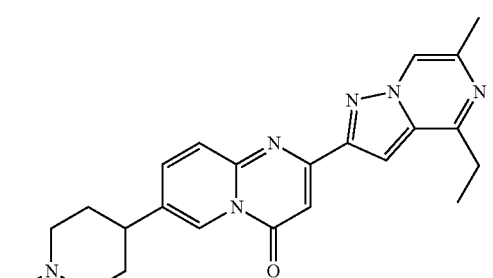
670
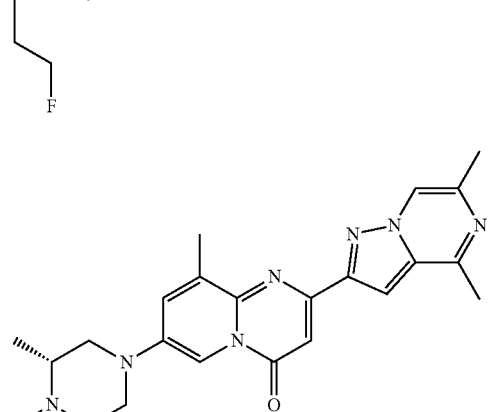
671
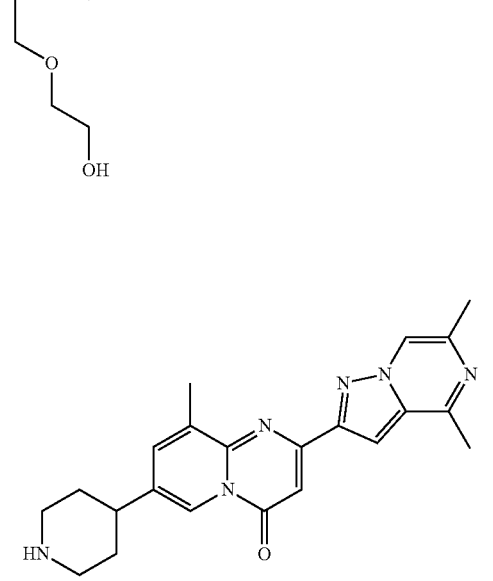
672
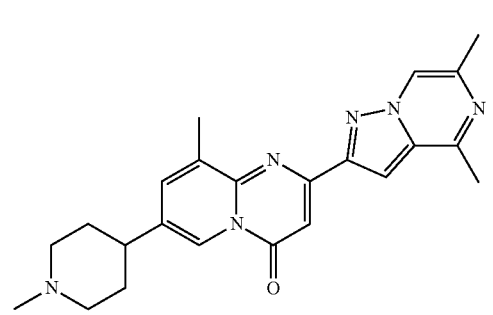

-continued
673
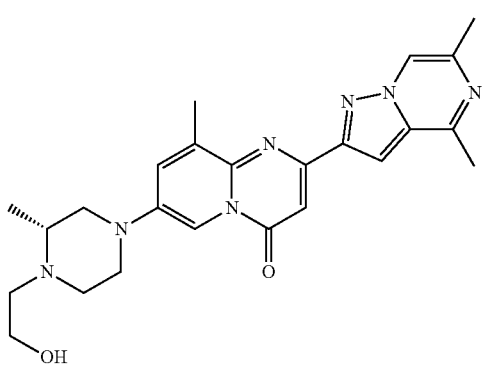
674
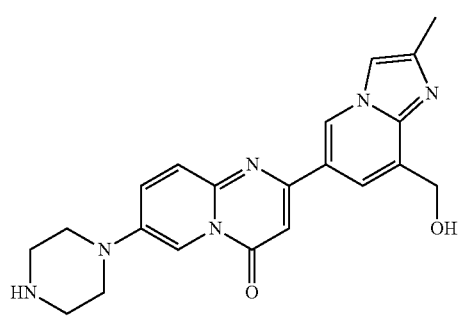
675
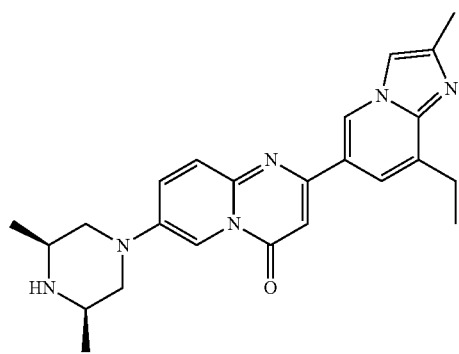
676
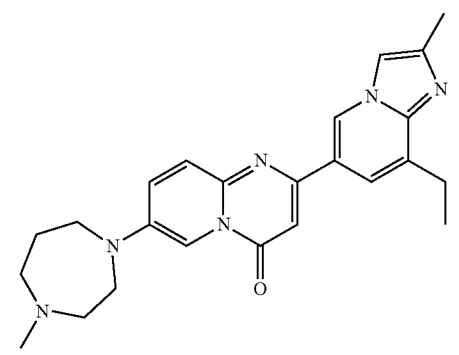
-continued
677
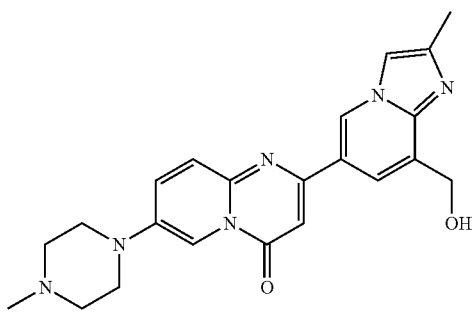
678
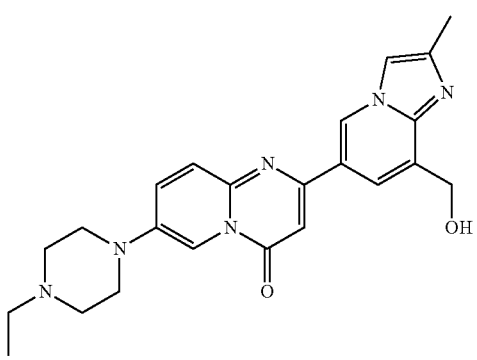
679
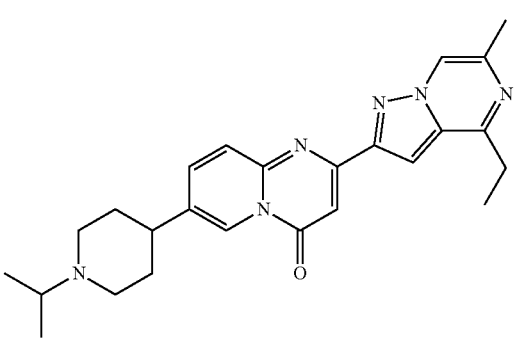
680
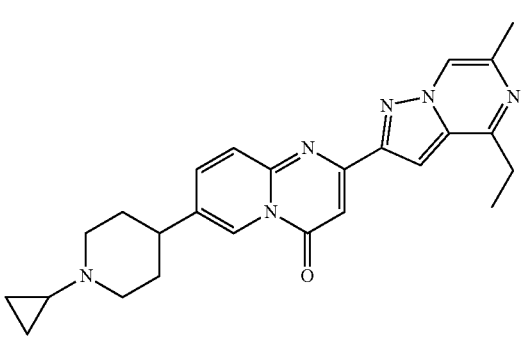

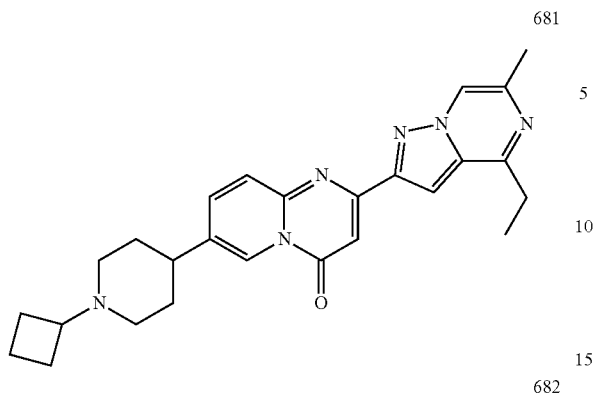
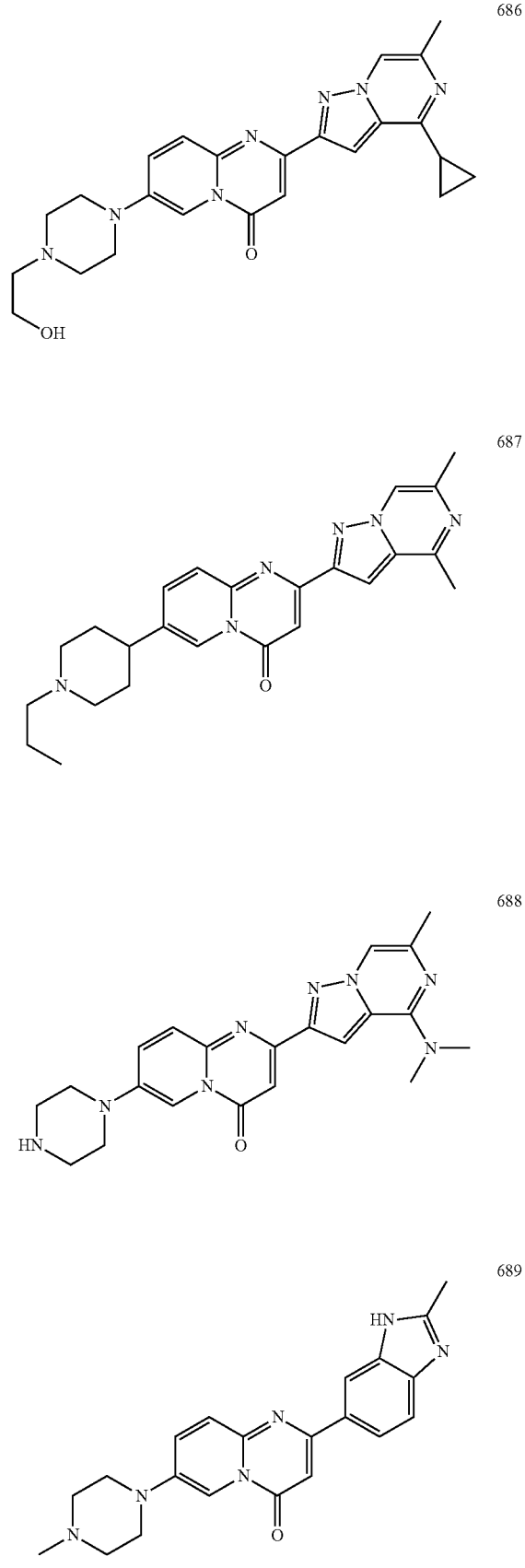

690
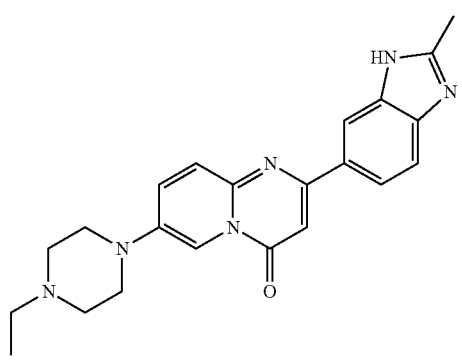
691
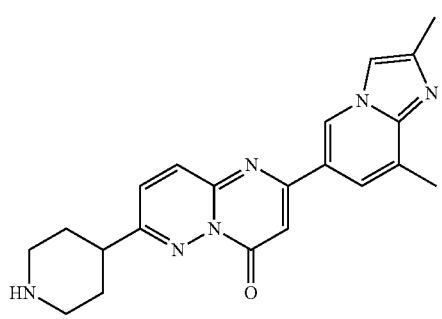
692
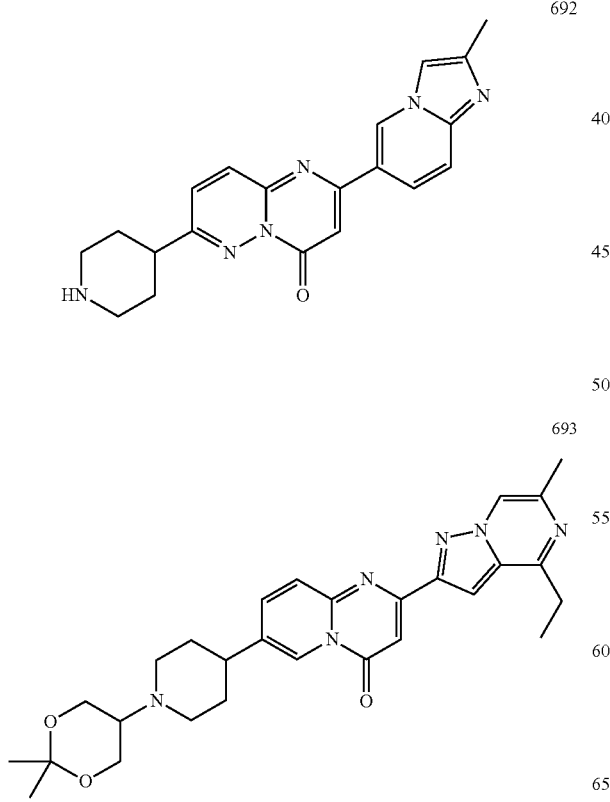
693
694
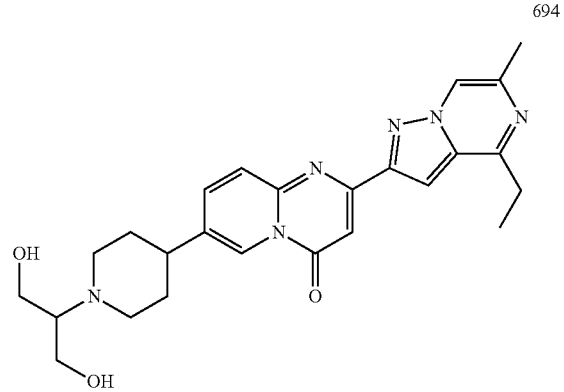
695
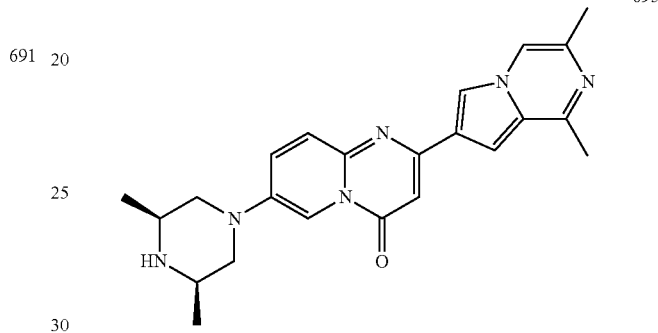
696
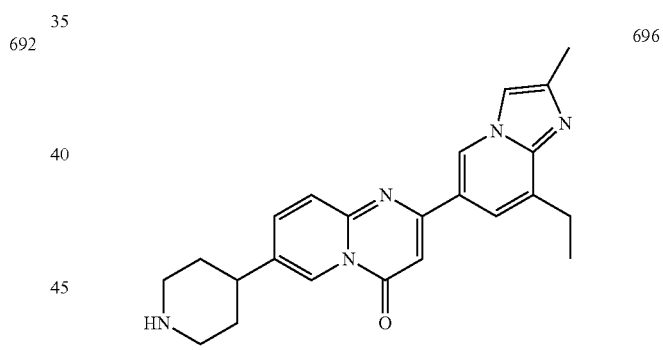
697
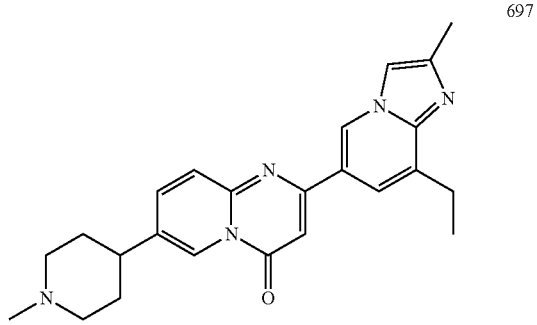

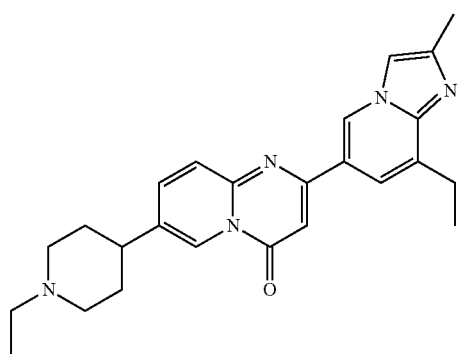
698
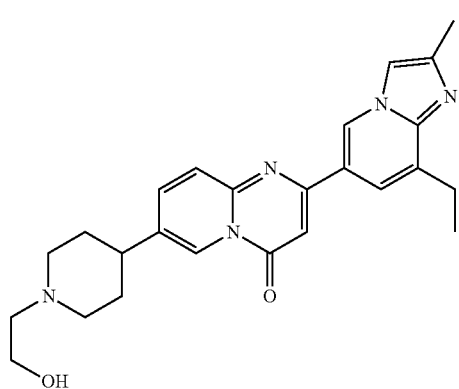
699
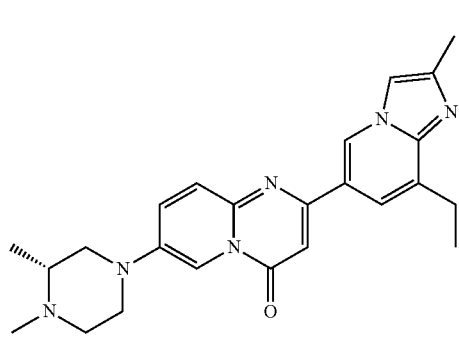
700
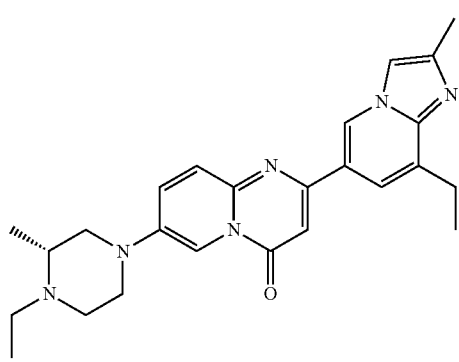
701
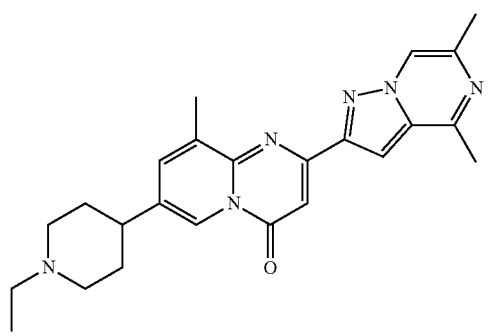
702
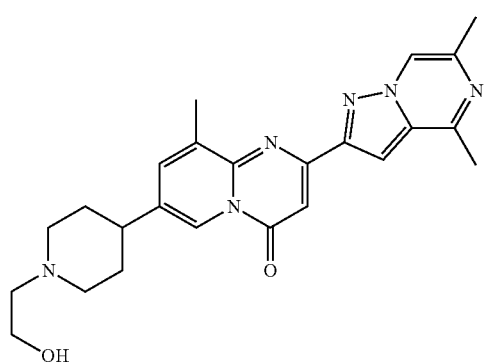
703
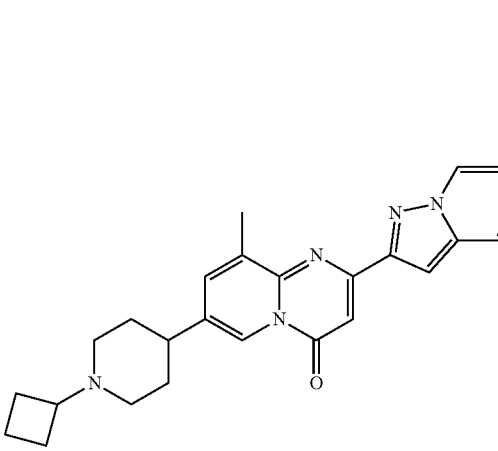
704
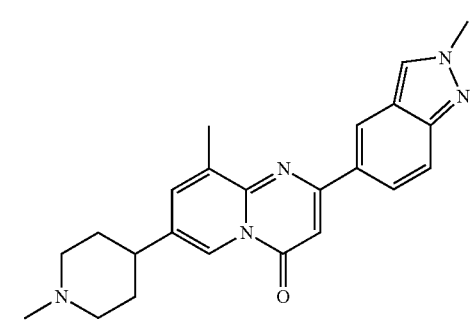
705

706
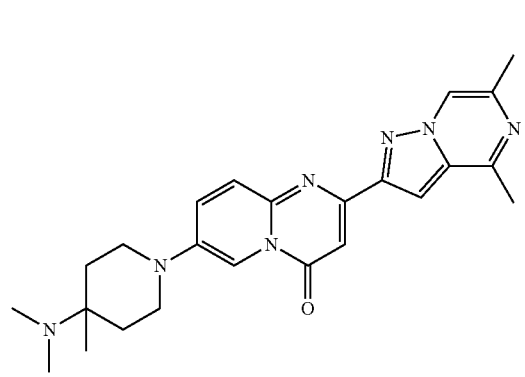
707
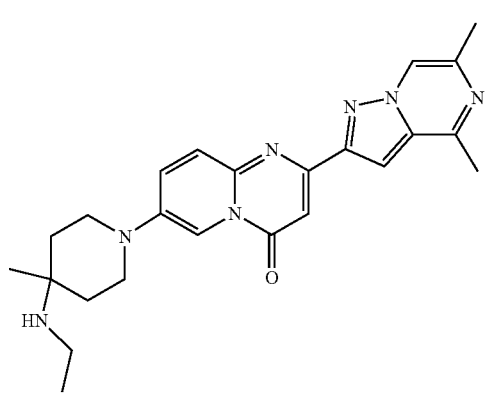
708
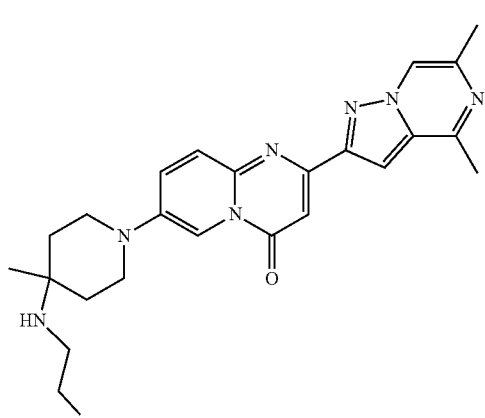
709
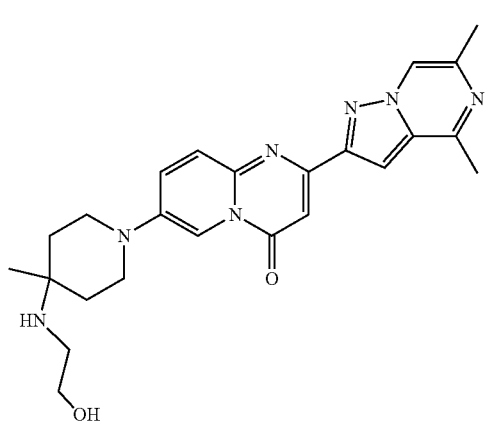
710
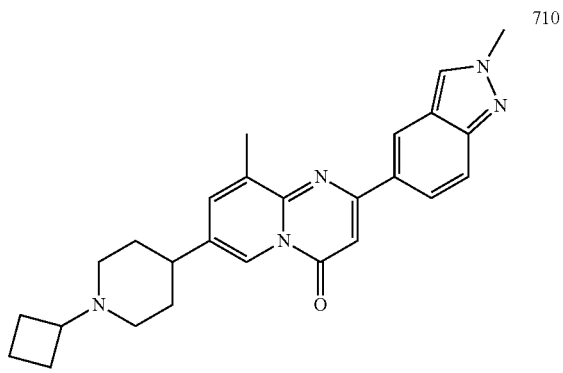
711
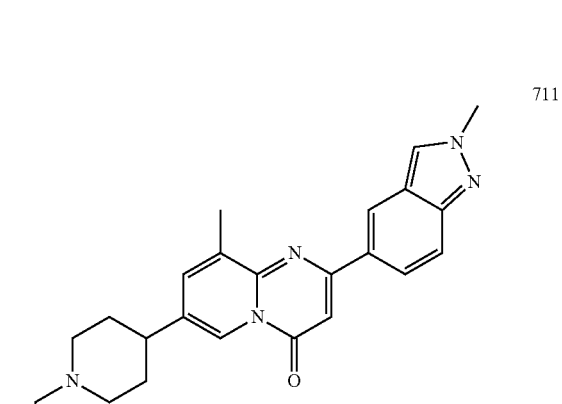
712
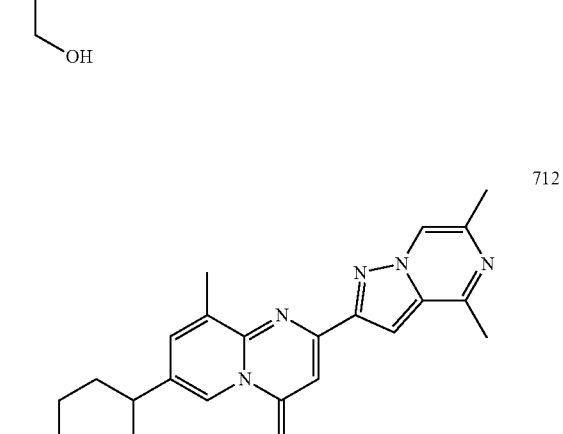
713
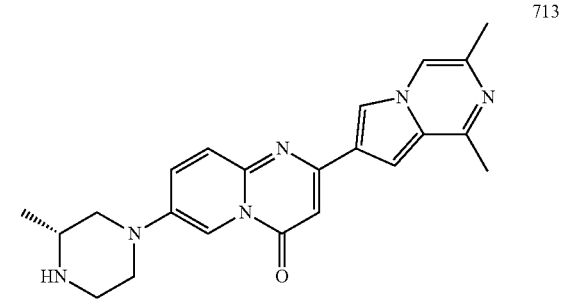

714 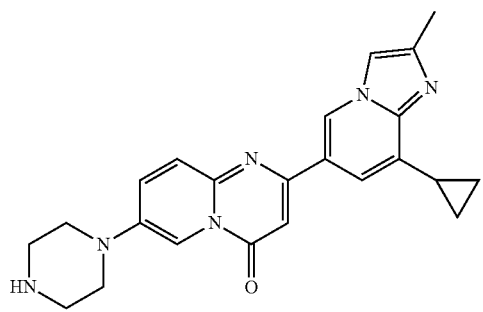
715 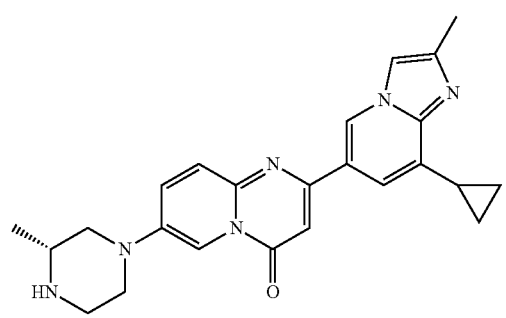
716 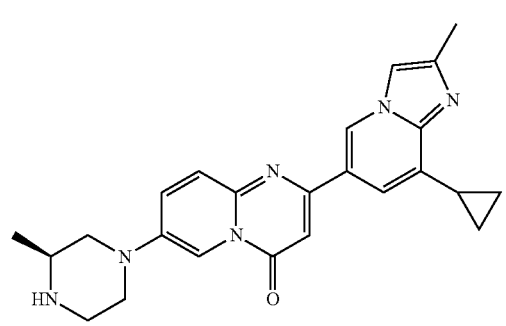
717 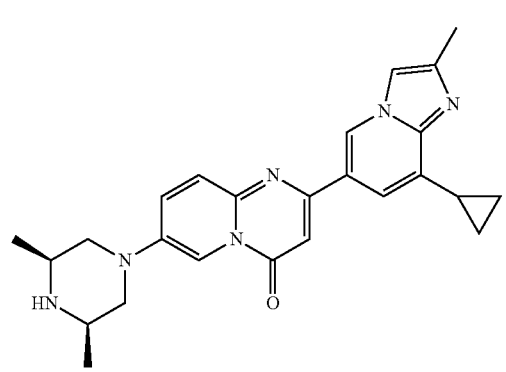
718 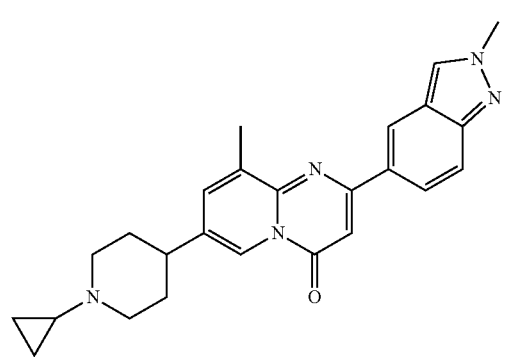
719 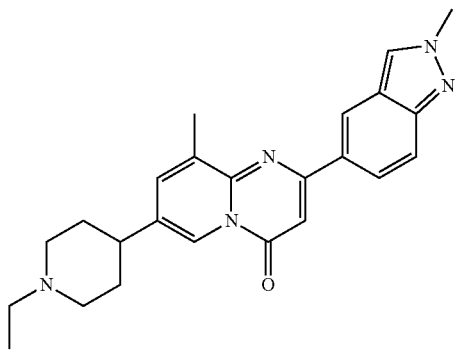
720 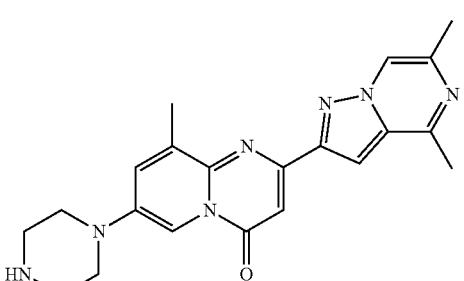
721 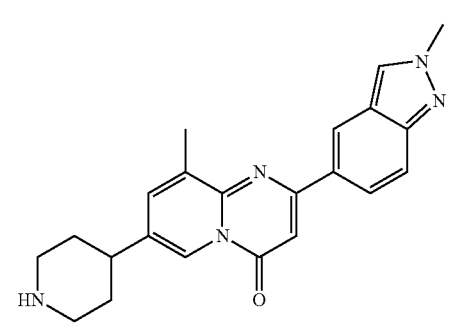
722 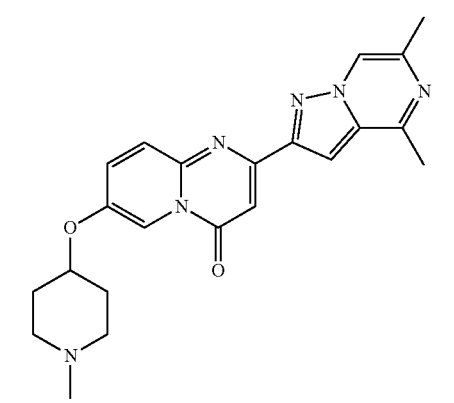
723 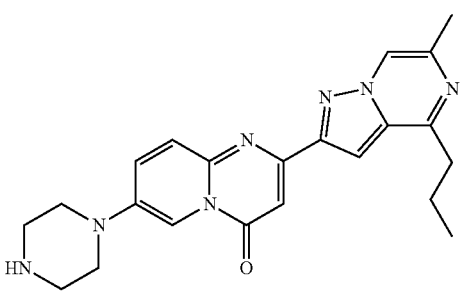

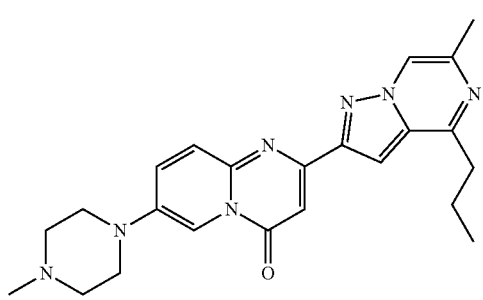
724
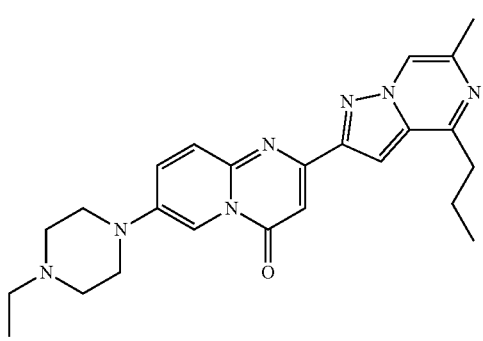
725
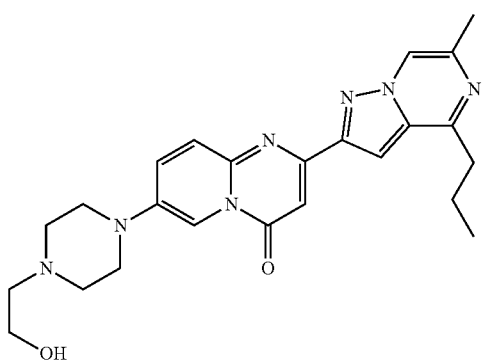
726
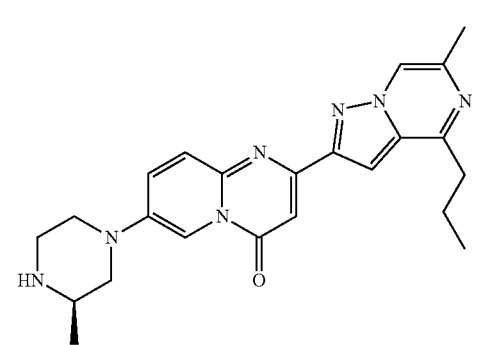
727
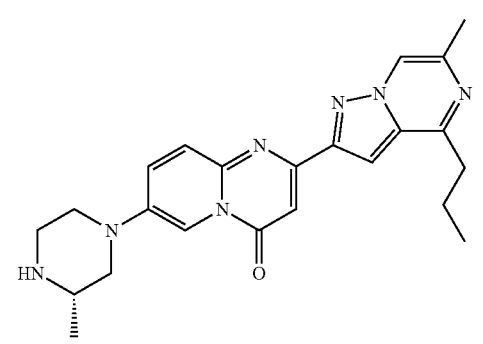
728
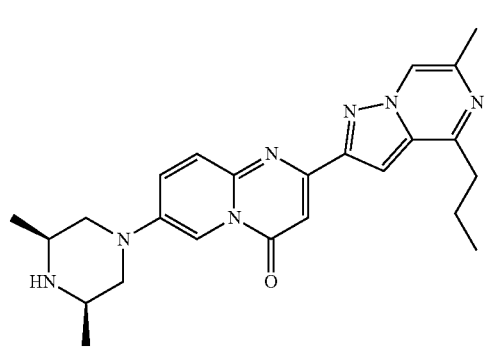
729
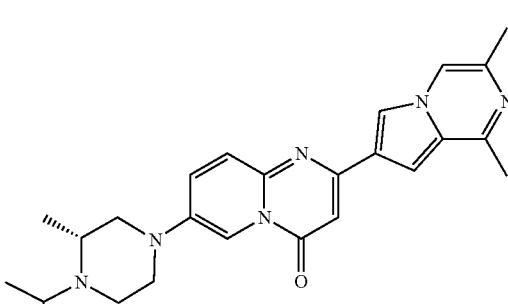
730
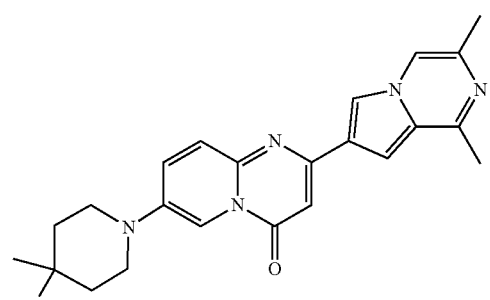
731
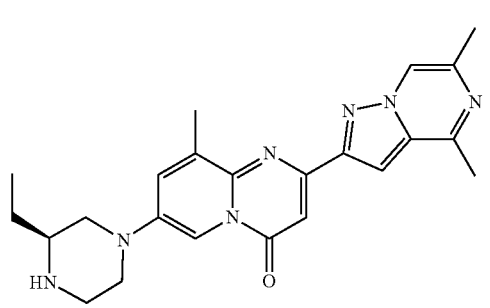
732

733
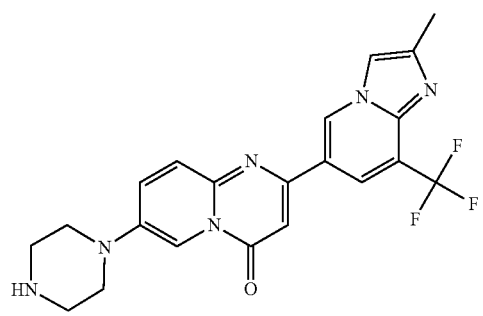
734
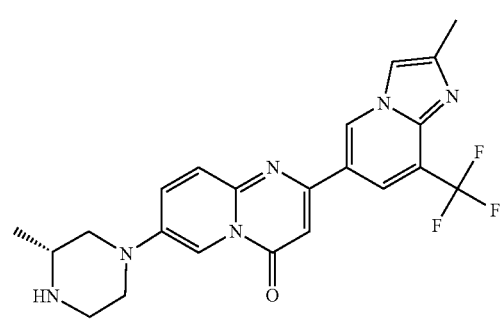
735
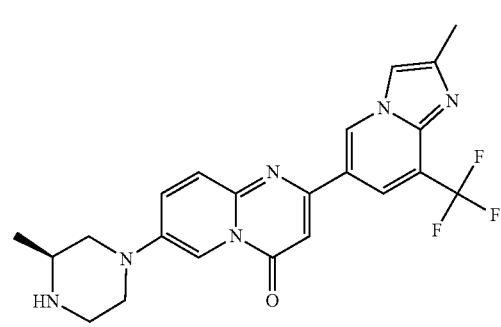
736
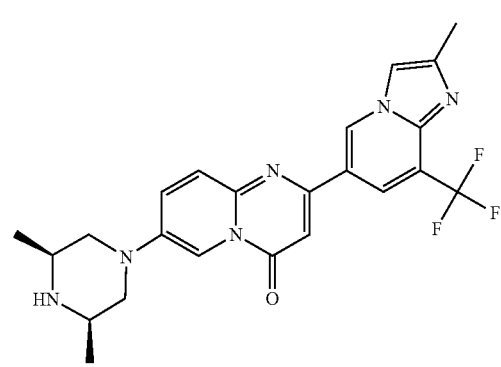
737
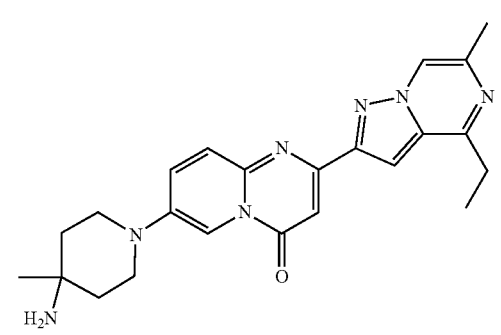
738
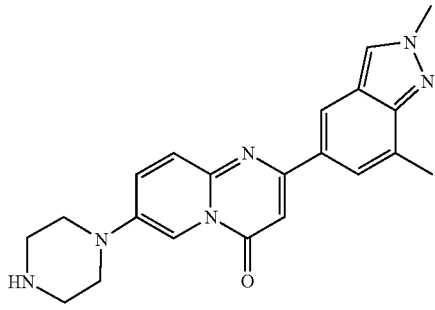
739
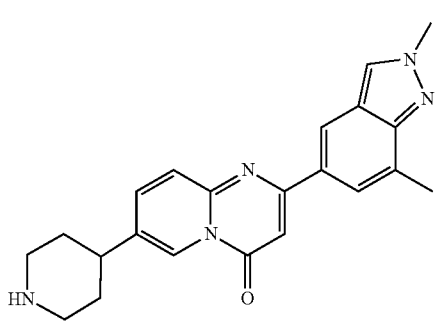
740
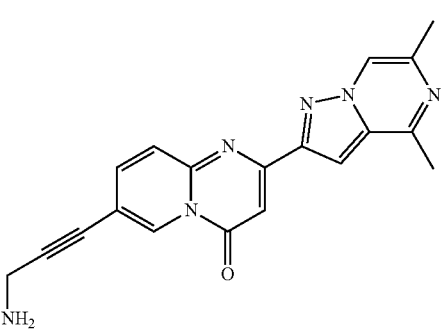
741
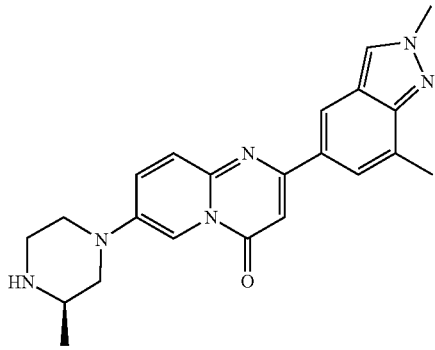
742
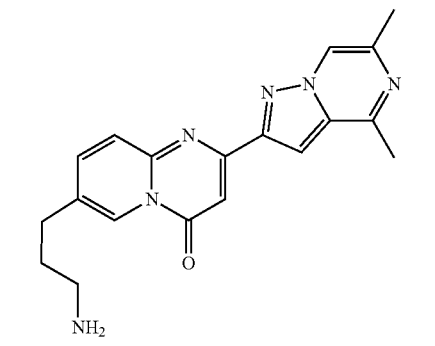

743 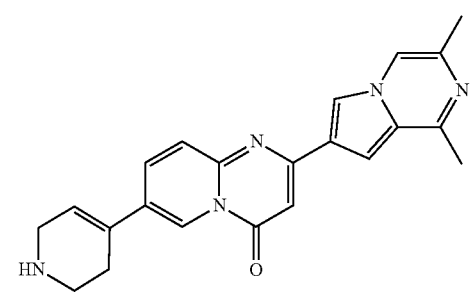
744 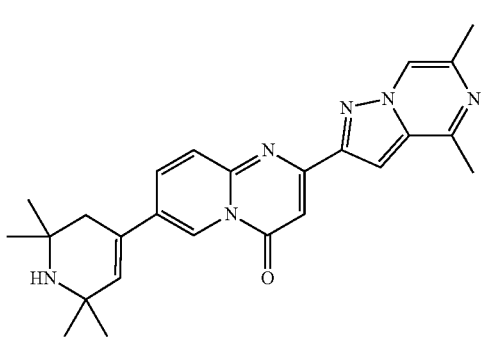
745 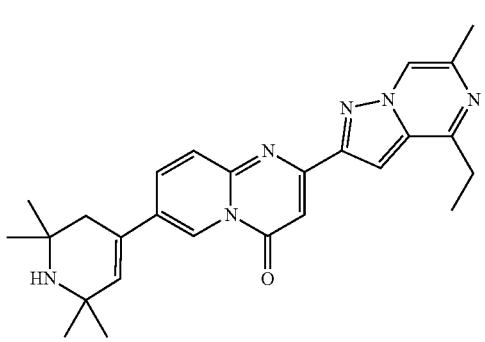
746 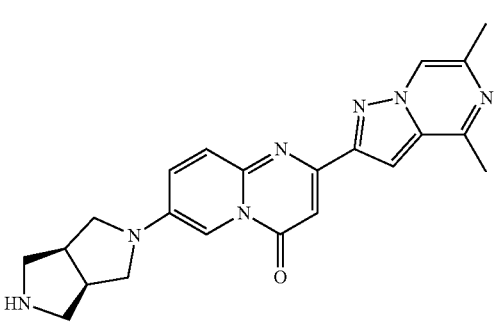
747 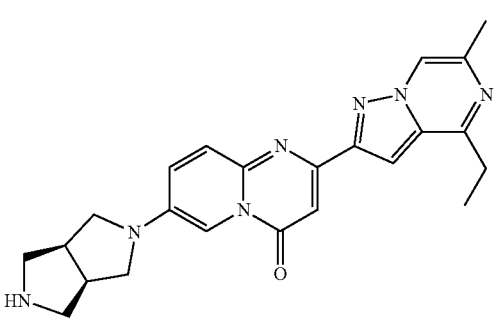
748 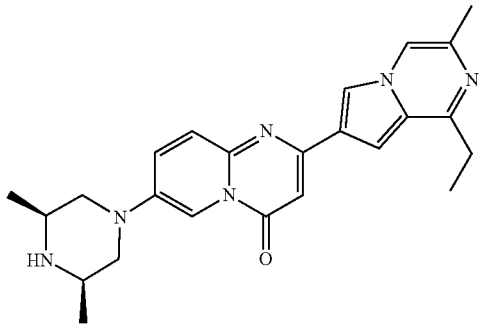
749 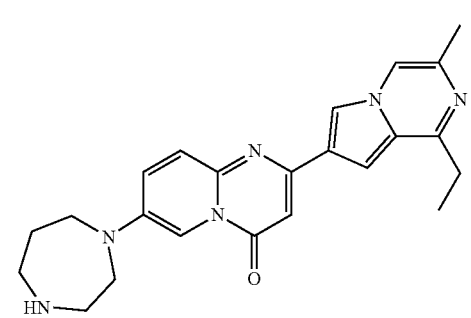
750 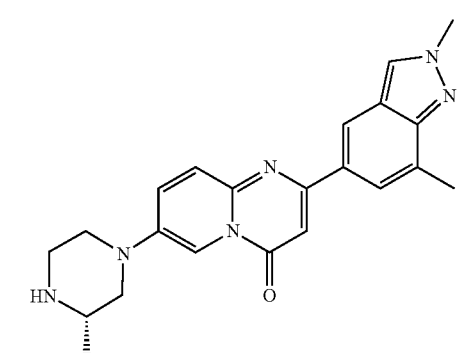
751 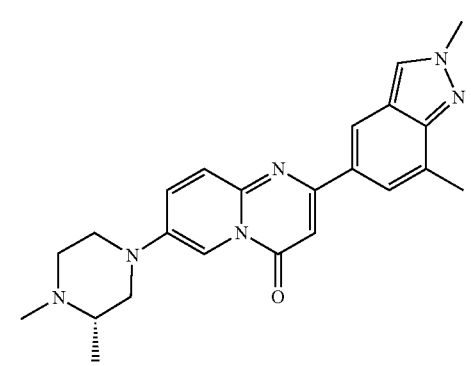
752 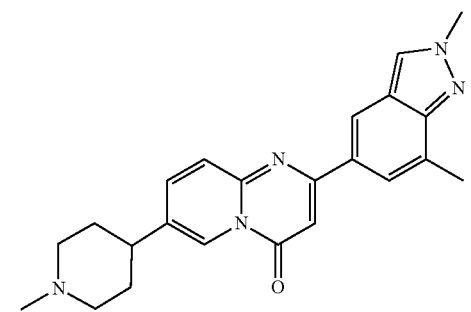

229
-continued
753
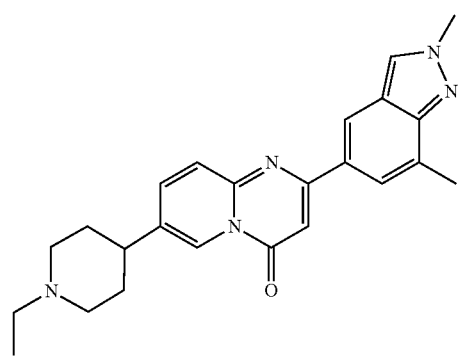
754
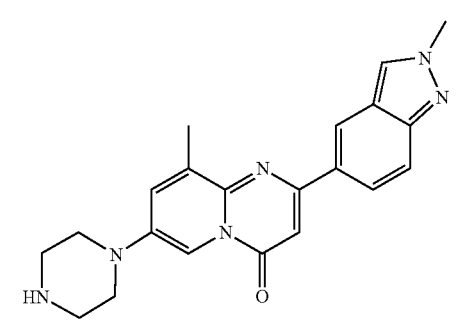
755
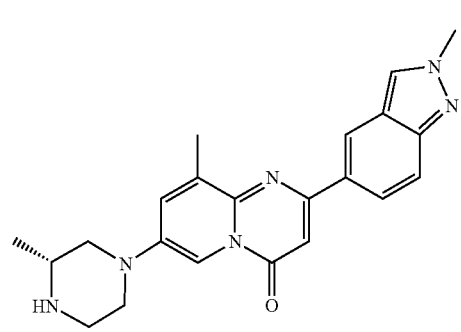
756
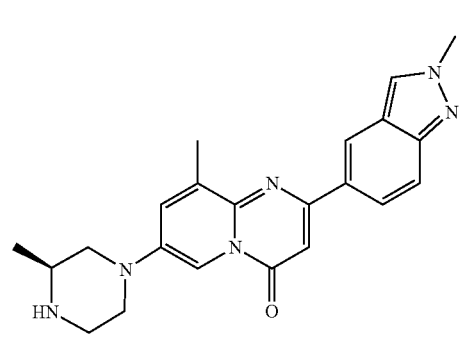
757
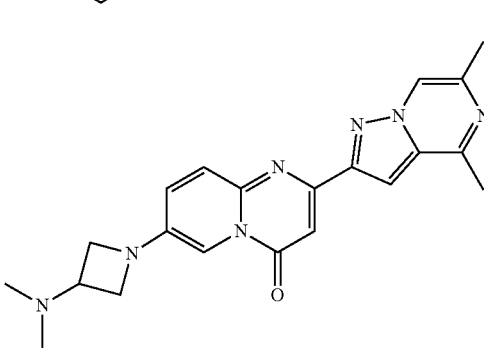
230
-continued
758
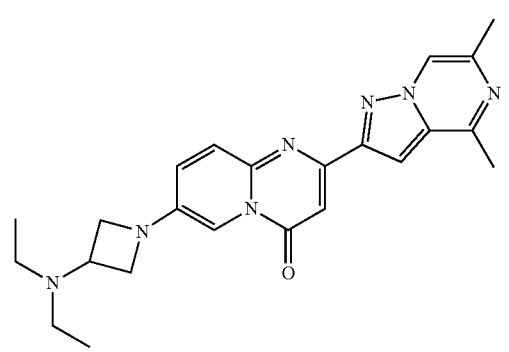
759
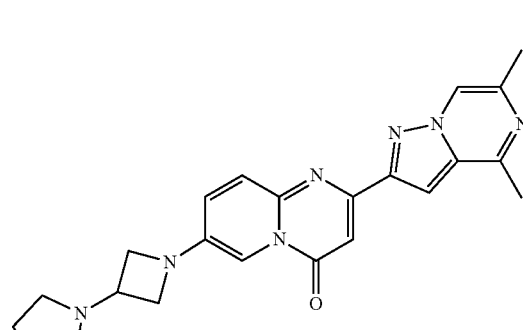
760
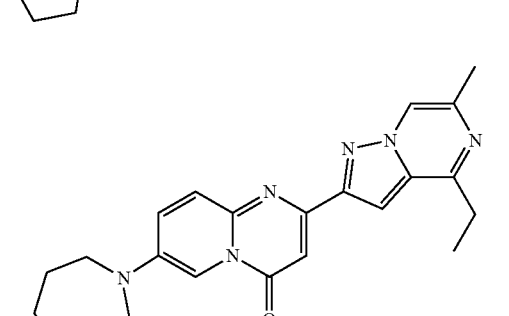
761
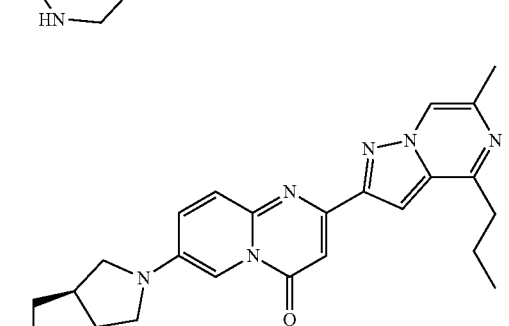
762
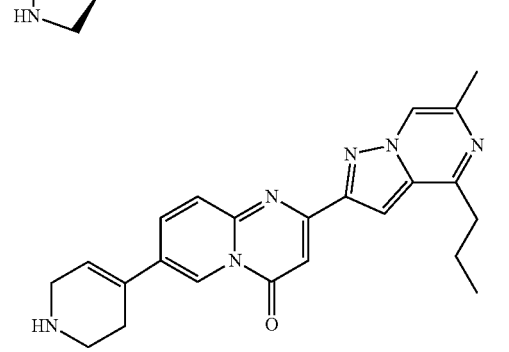

763 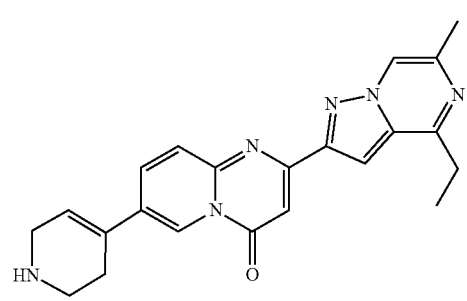
764 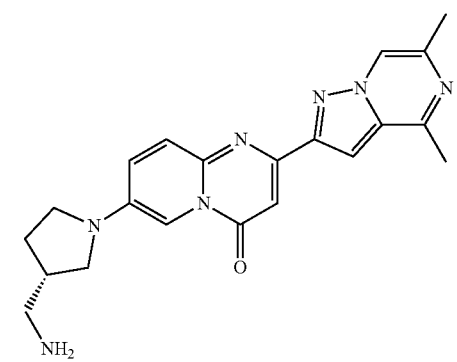
765 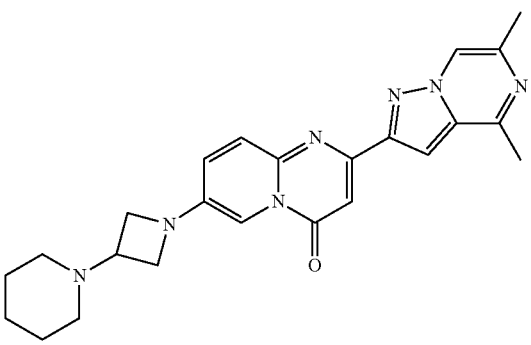
766 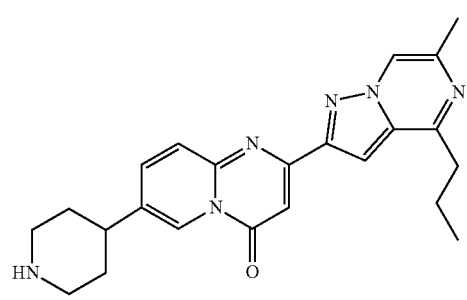
767 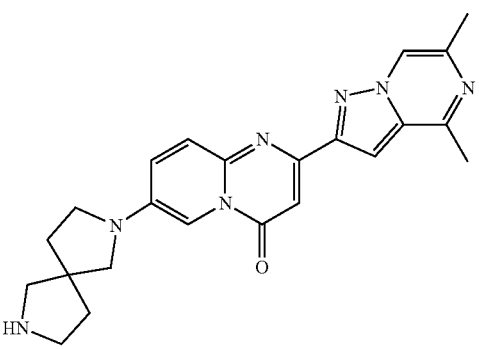
768 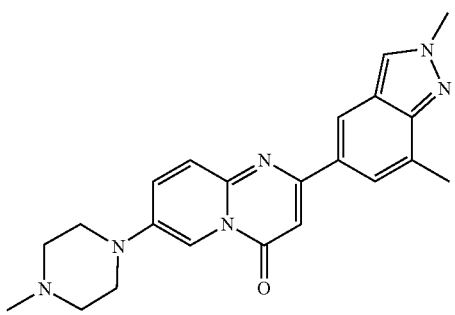
769 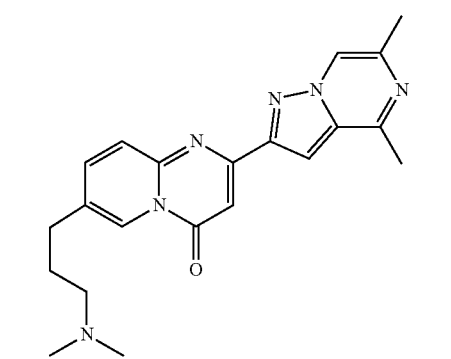
770 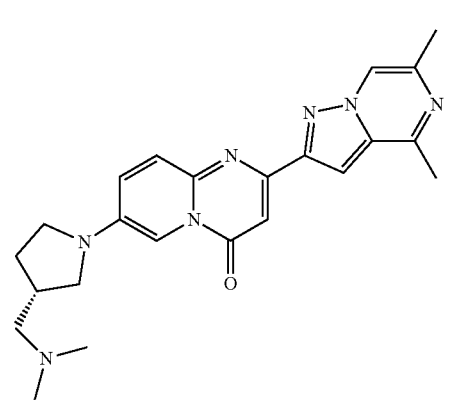
771 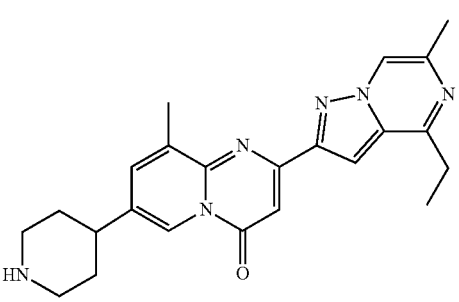
772 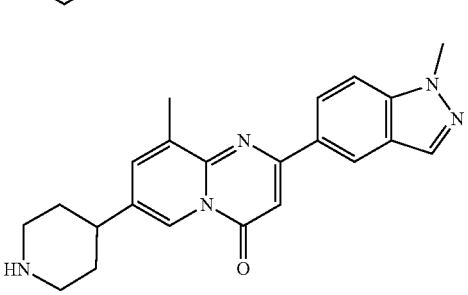

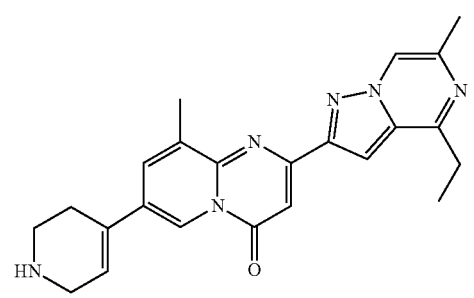
773
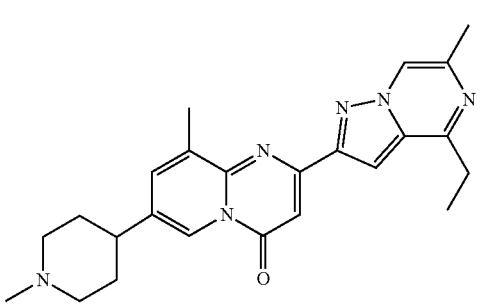
774
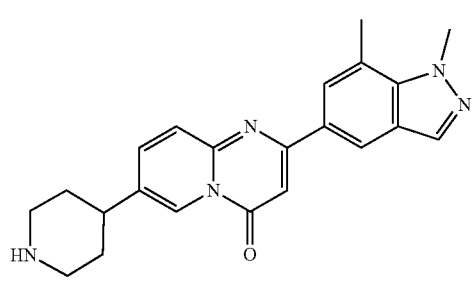
775
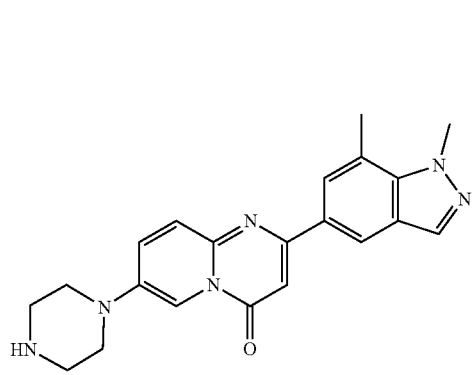
776
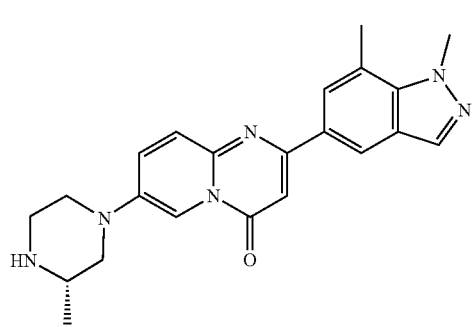
777
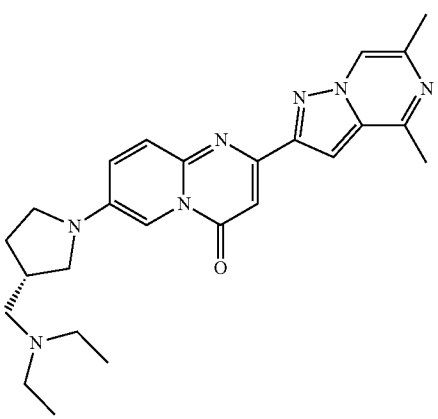
778
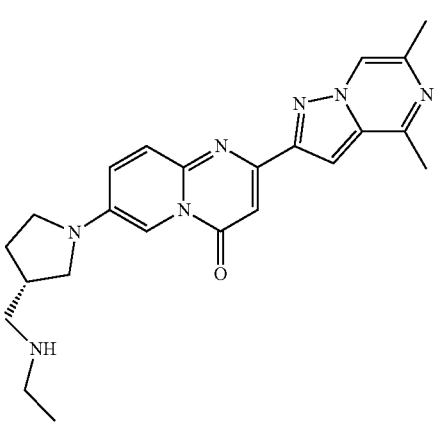
779
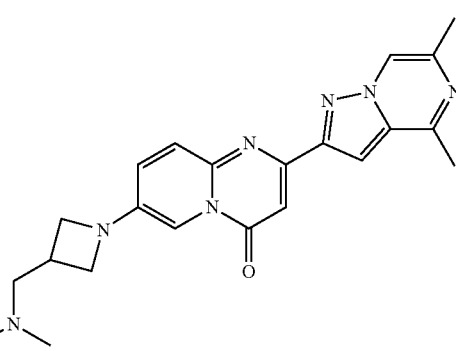
780
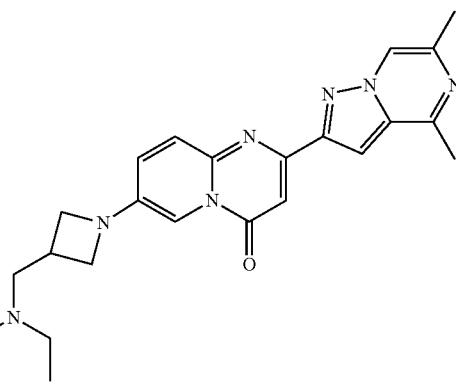
781

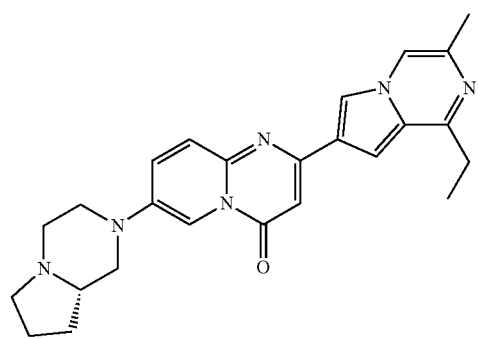
782
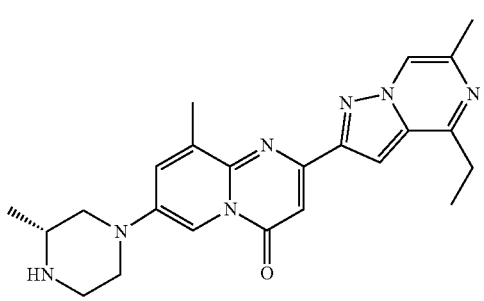
783
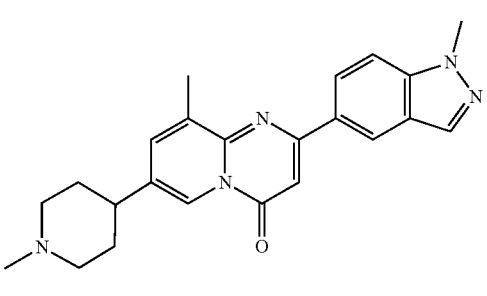
784
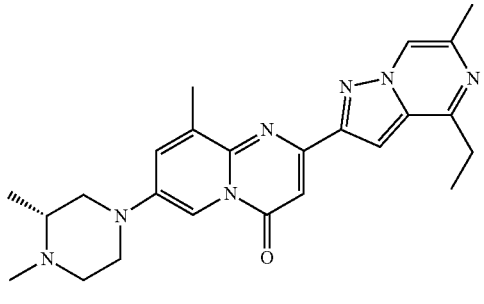
785
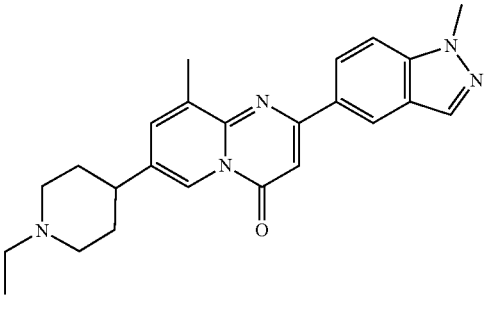
786
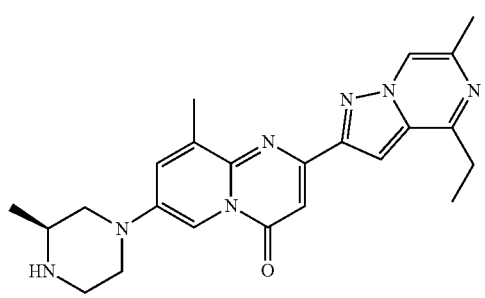
787
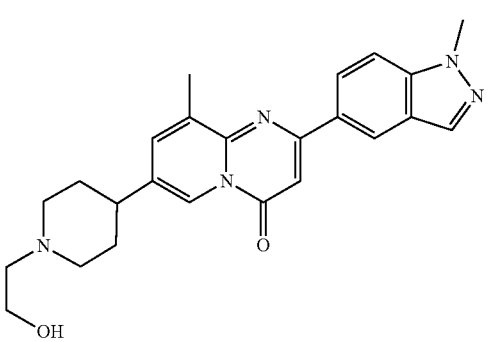
788
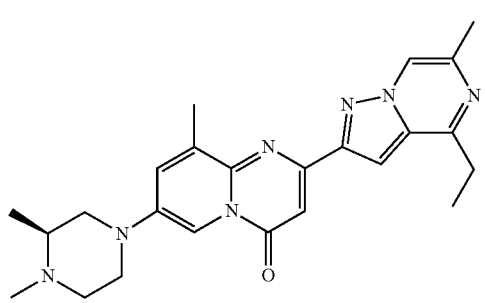
789
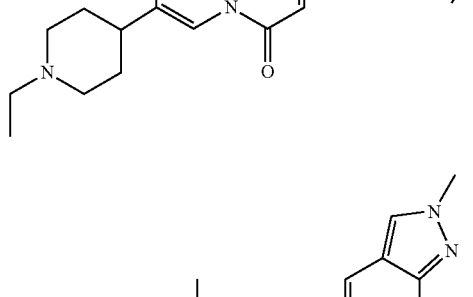
790
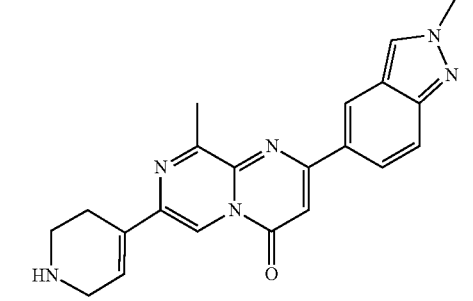
791

792
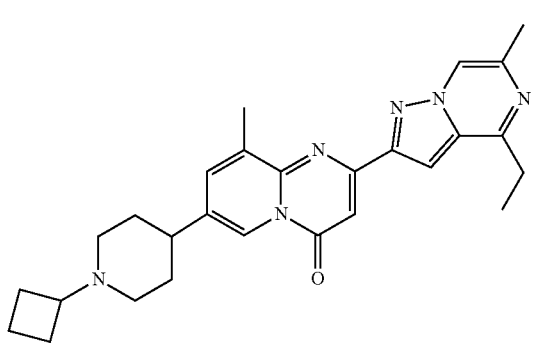
793
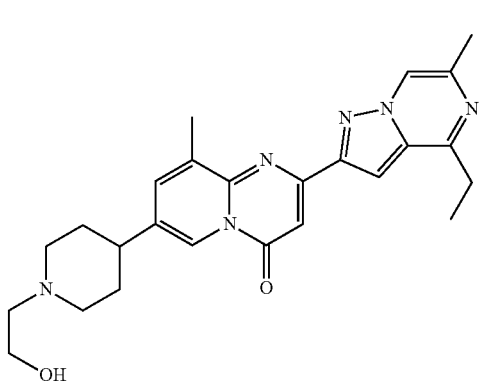
794
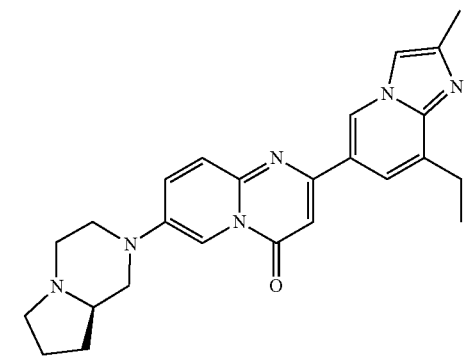
795
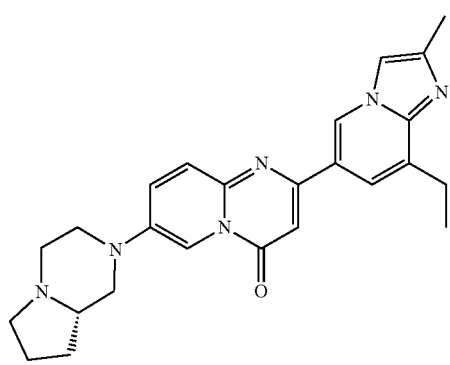
796
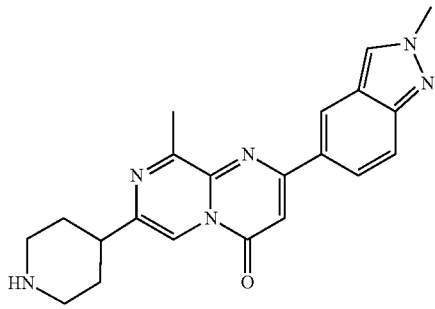
797
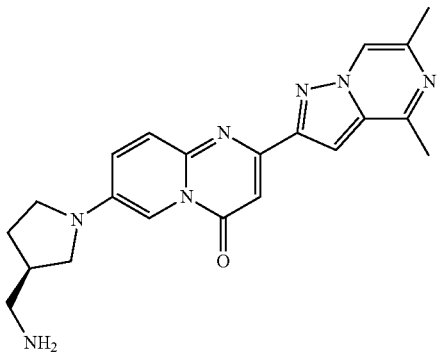
798
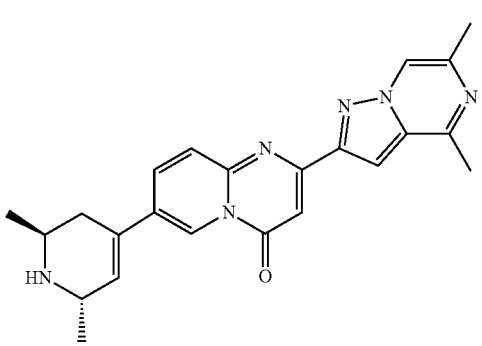
799
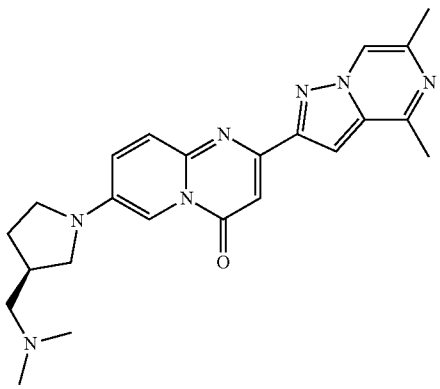

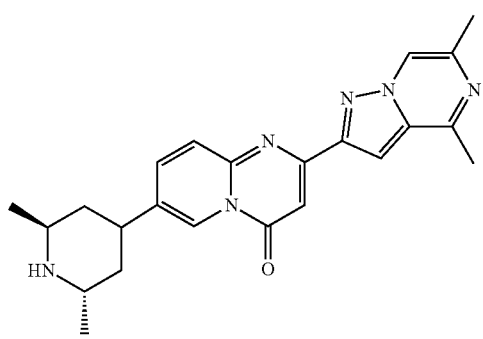
800
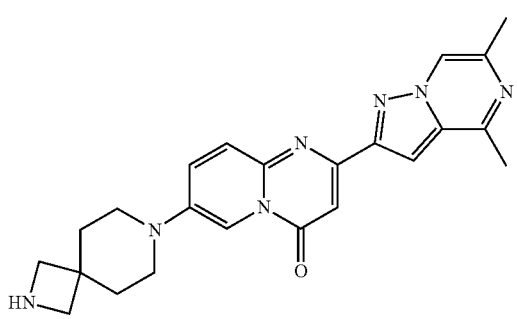
804
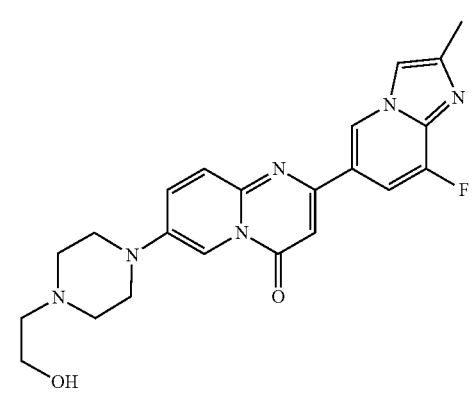
801
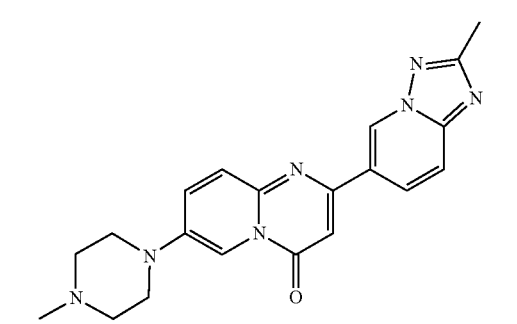
805
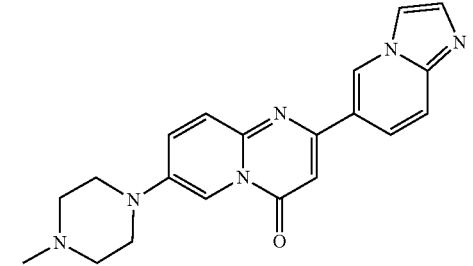
802
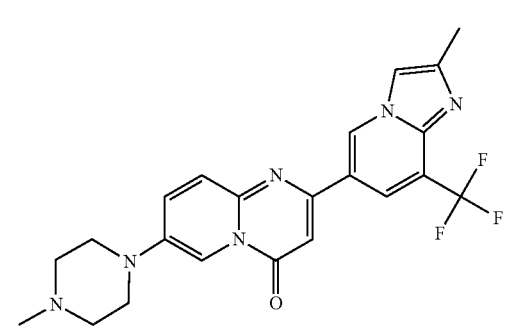
806
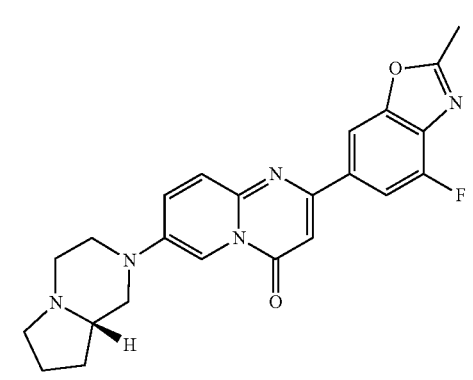
803
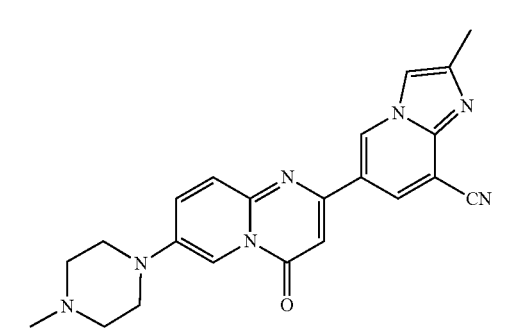
807
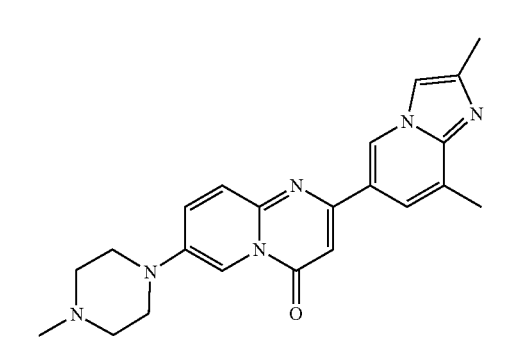
808

809
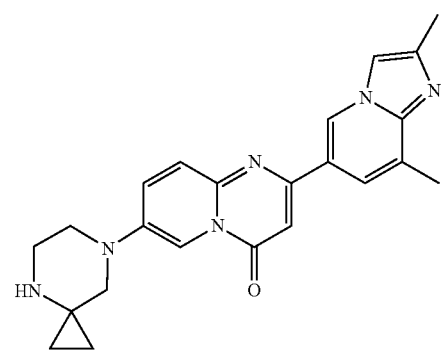
810
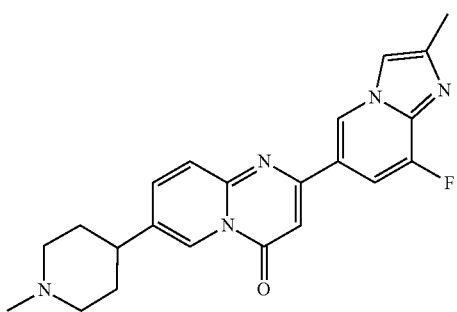
811
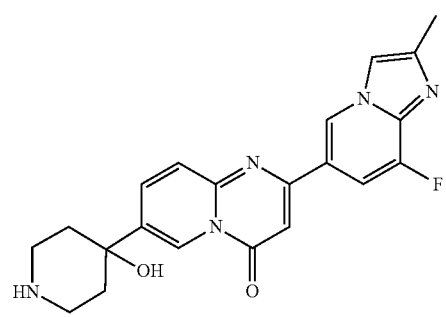
812
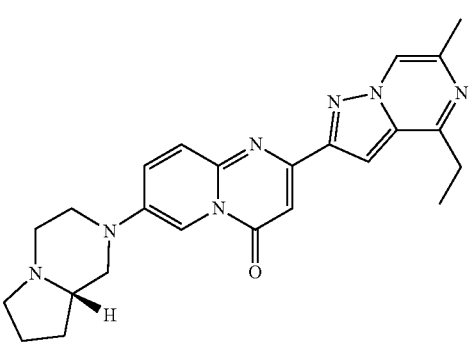
813
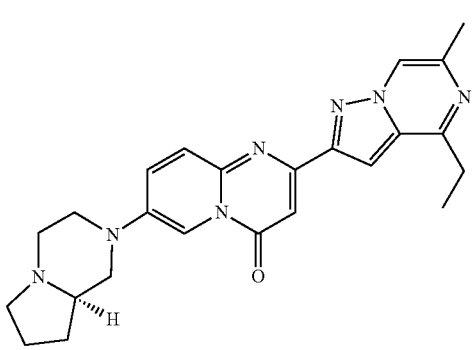
814
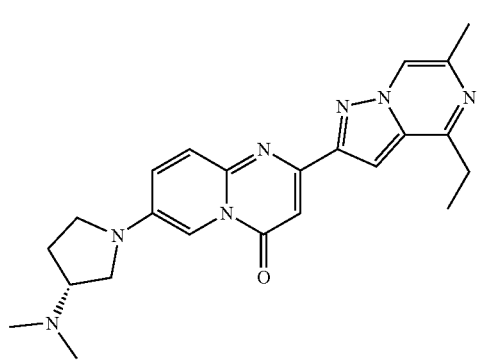
815
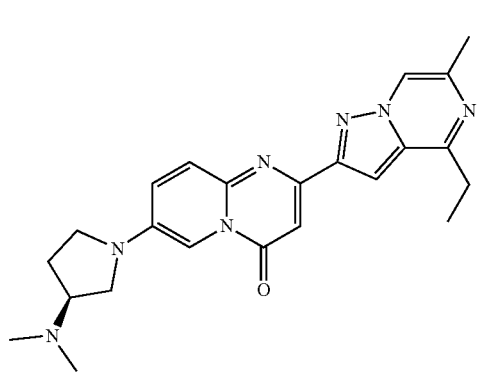
816
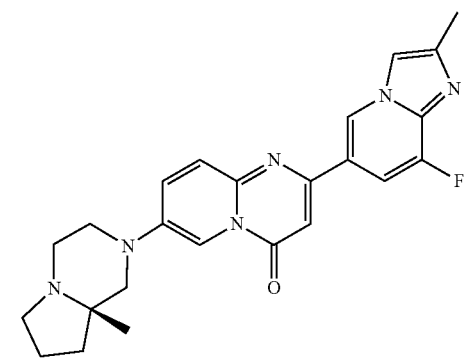
817
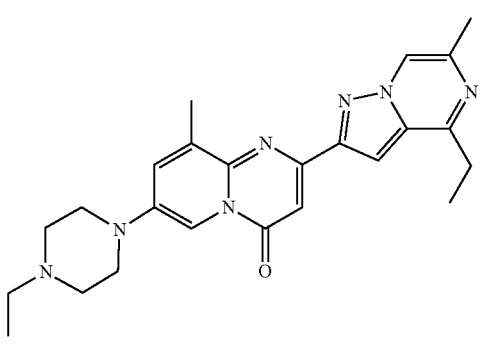

818 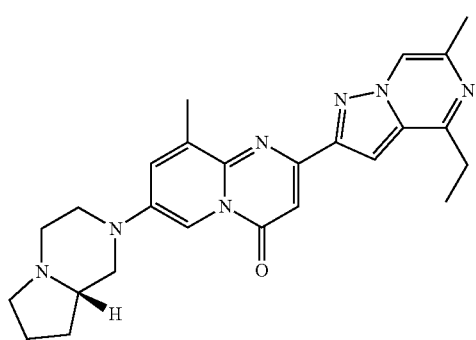
819 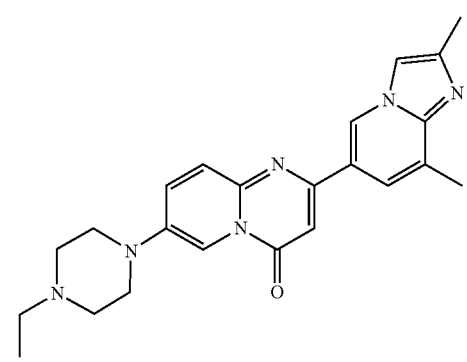
820 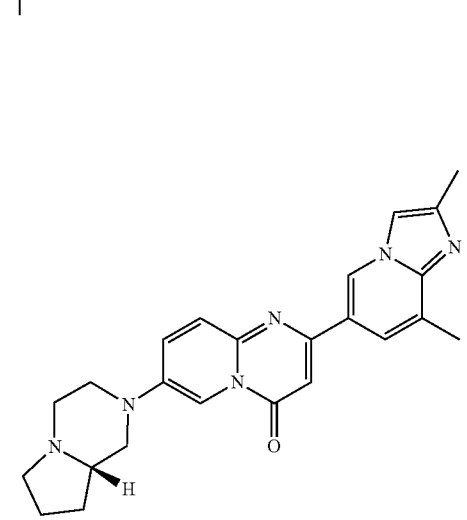
821 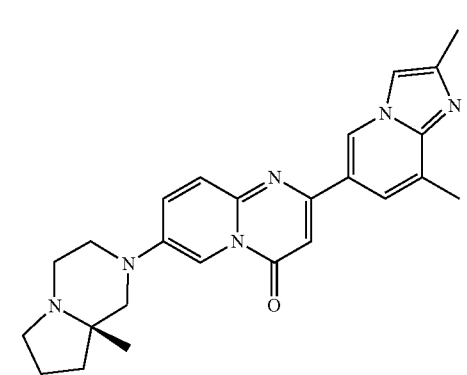
822 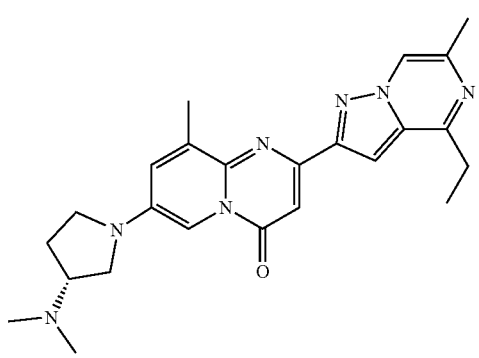
823 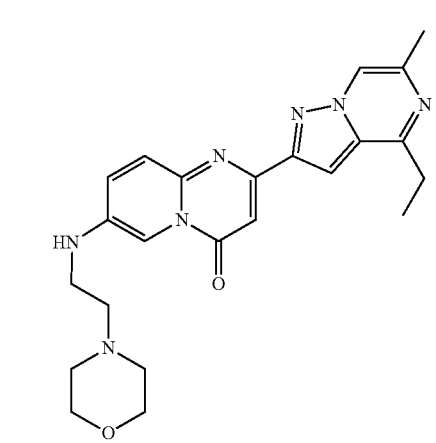
824 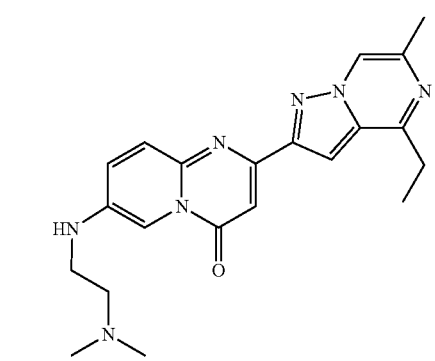
825 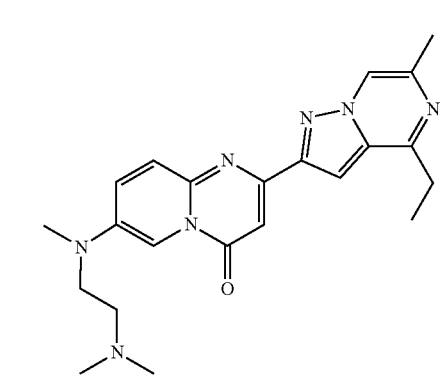

826
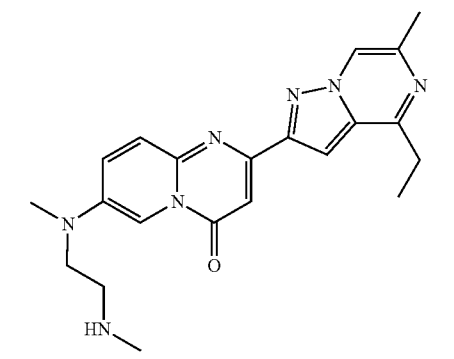
827
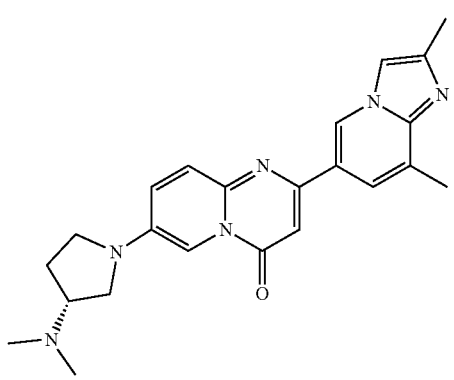
828
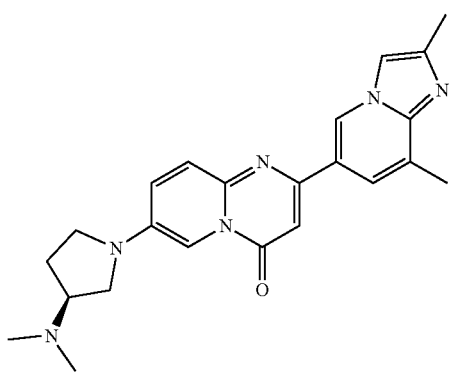
829
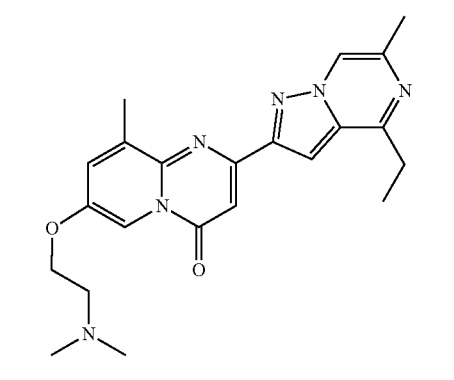
830
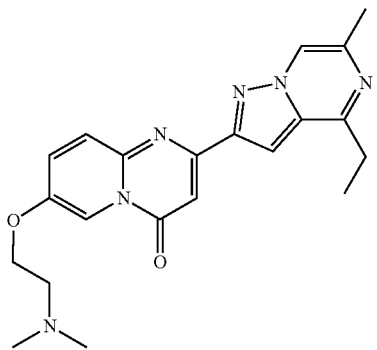
831
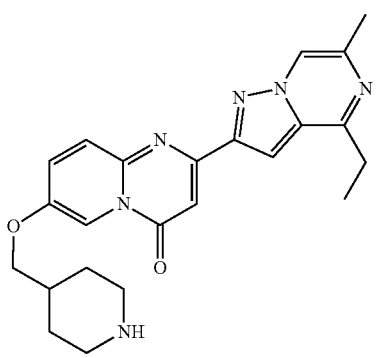
832
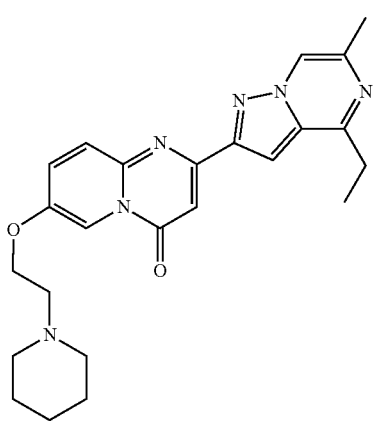
833
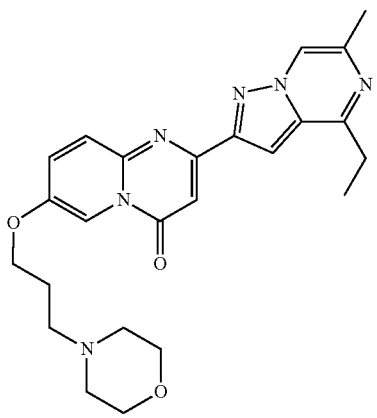

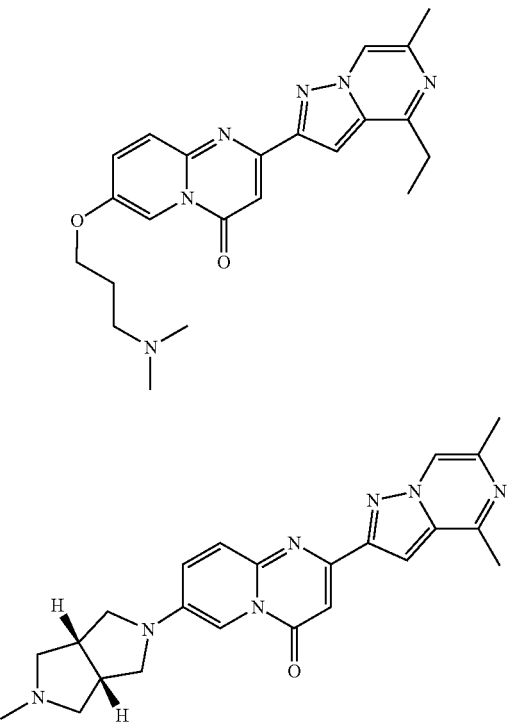

or a form thereof.

Terminology

The chemical terms used above and throughout the description herein, unless specifically defined otherwise, shall be understood by one of ordinary skill in the art to have the following indicated meanings.

As used herein, the term "$C_{1-8}$alkyl" generally refers to saturated hydrocarbon radicals having from one to eight carbon atoms in a straight or branched chain configuration, including, but not limited to, methyl, ethyl, n-propyl (also referred to as propyl or propanyl), isopropyl, n-butyl (also referred to as butyl or butanyl), isobutyl, sec-butyl, tert-butyl, n-pentyl (also referred to as pentyl or pentanyl), n-hexyl (also referred to as hexyl or hexanyl), n-heptyl (also referred to as heptyl or heptanyl), n-octyl and the like. In some embodiments, $C_{1-8}$alkyl includes, but is not limited to, $C_{1-6}$alkyl, $C_{1-4}$alkyl and the like. A $C_{1-8}$alkyl radical is optionally substituted with substituent species as described herein where allowed by available valences.

As used herein, the term "$C_{2-8}$alkenyl" generally refers to partially unsaturated hydrocarbon radicals having from two to eight carbon atoms in a straight or branched chain configuration and one or more carbon-carbon double bonds therein, including, but not limited to, ethenyl (also referred to as vinyl), allyl, propenyl and the like. In some embodiments, $C_{2-8}$alkenyl includes, but is not limited to, $C_{2-6}$alkenyl, $C_{2-4}$alkenyl and the like. A $C_{2-8}$alkenyl radical is optionally substituted with substituent species as described herein where allowed by available valences.

As used herein, the term "$C_{2-8}$alkynyl" generally refers to partially unsaturated hydrocarbon radicals having from two to eight carbon atoms in a straight or branched chain configuration and one or more carbon-carbon triple bonds therein, including, but not limited to, ethynyl, propynyl, butynyl and the like. In some embodiments, $C_{2-8}$alkynyl includes, but is not limited to, $C_{2-6}$alkynyl, $C_{2-4}$alkynyl and the like. A $C_{2-8}$alkynyl radical is optionally substituted with substituent species as described herein where allowed by available valences.

As used herein, the term "$C_{1-8}$alkoxy" generally refers to saturated hydrocarbon radicals having from one to eight carbon atoms in a straight or branched chain configuration of the formula: —O—$C_{1-8}$alkyl, including, but not limited to, methoxy, ethoxy, n-propoxy, isopropoxy, n-butoxy, isobutoxy, sec-butoxy, tert-butoxy, n-pentoxy, n-hexoxy and the like. In some embodiments, $C_{1-8}$alkoxy includes, but is not limited to, $C_{1-6}$alkoxy, $C_{1-4}$alkoxy and the like. A $C_{1-8}$alkoxy radical is optionally substituted with substituent species as described herein where allowed by available valences.

As used herein, the term "$C_{3-14}$cycloalkyl" generally refers to a saturated or partially unsaturated monocyclic, bicyclic or polycyclic hydrocarbon radical, including, but not limited to, cyclopropyl, cyclobutyl, cyclopentyl, cyclohexyl, cyclohexenyl, cycloheptyl, cyclooctyl, 1H-indanyl, indenyl, tetrahydro-naphthalenyl and the like. In some embodiments, $C_{3-14}$cycloalkyl includes, but is not limited to, $C_{3-8}$cycloalkyl, $C_{5-8}$cycloalkyl, $C_{3-10}$cycloalkyl and the like. A $C_{3-14}$cycloalkyl radical is optionally substituted with substituent species as described herein where allowed by available valences.

As used herein, the term "aryl" generally refers to a monocyclic, bicyclic or polycyclic aromatic carbon atom ring structure radical, including, but not limited to, phenyl, naphthyl, anthracenyl, fluorenyl, azulenyl, phenanthrenyl and the like. An aryl radical is optionally substituted with substituent species as described herein where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an O, S or N atom, including, but not limited to, furanyl (also referred to as furyl), thienyl (also referred to as thiophenyl), pyrrolyl, 2H-pyrrolyl, 3H-pyrrolyl, pyrazolyl, 1H-pyrazolyl, imidazolyl, 1H-imidazolyl, isoxazolyl, isothiazolyl, oxazolyl, 1,3-thiazolyl, triazolyl (such as 1H-1,2,3-triazolyl and the like), oxadiazolyl (such as 1,2,4-oxadiazolyl, 1,3,4-oxadiazolyl and the like), thiadiazolyl, tetrazolyl (such as 1H-tetrazolyl, 2H-tetrazolyl and the like), pyridinyl (also referred to as pyridyl), pyrimidinyl, pyrazinyl, pyridazinyl, triazinyl, indolyl, 1H-indolyl, indazolyl, 1H-indazolyl, 2H-indazolyl, indolizinyl, isoindolyl, benzofuranyl, benzothienyl (also referred to as benzothiophenyl), benzoimidazolyl, 1H-benzoimidazolyl, 1,3-benzothiazolyl, 1,3-benzoxazolyl (also referred to as 1,3-benzooxazolyl), purinyl, 9H-purinyl, quinolinyl, isoquinolinyl, quinazolinyl, quinoxalinyl, 1,3-diazinyl, 1,2-diazinyl, 1,2-diazolyl, 1,4-diazanaphthalenyl, acridinyl, furo[3,2-b]pyridinyl, furo[3,2-c]pyridinyl, furo[2,3-c]pyridinyl, 6H-thieno[2,3-b]pyrrolyl, thieno[3,2-c]pyridinyl, thieno[2,3-d]pyrimidinyl, 1H-pyrrolo[2,3-b]pyridinyl, 1H-pyrrolo[2,3-c]pyridinyl, 1H-pyrrolo[3,2-b]pyridinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, 3H-imidazo[4,5-b]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl, [1,2,4]triazolo[1,5-a]pyridinyl, [1,2,4]triazolo[4,3-a]pyridinyl and the like. A heteroaryl radical is optionally substituted on a carbon or nitrogen atom ring member with substituent species as described herein where allowed by available valences.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including, but not limited to, oxiranyl, oxetanyl, azetidinyl, tetrahydrofuranyl, pyrrolinyl, pyrrolidinyl, pyrazolinyl, pyrazolidinyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, pyranyl, dihydro-2H-pyranyl, thiopyranyl, 1,3-dioxanyl, 1,2,5,6-tetrahydropyridinyl, 1,2,3,6-tetrahydropyridinyl, piperidinyl, piperazinyl, morpholinyl, thiomorpholinyl, 1,4-diazepanyl, 1,3-benzodioxolyl (also referred to as benzo[d][1,3]dioxolyl), 1,4-benzodioxanyl, 2,3-dihydro-1,4-benzodioxinyl (also referred to as 2,3-dihydrobenzo[b][1,4]dioxinyl), hexahydropyrrolo[3,4-b]pyrrol-(1H)-yl, (3aS,6aS)-hexahydropyrrolo[3,4-b]pyrrol-(1H)-yl, (3aR,6aR)-hexahydropyrrolo[3,4-b]pyrrol-(1H)-yl, hexahydropyrrolo[3,4-b]pyrrol-(2H)-yl, (3aS,6aS)-hexahydropyrrolo[3,4-b]pyrrol-(2H)-yl, (3aR,6aR)-hexahydropyrrolo[3,4-b]pyrrol-(2H)-yl, hexahydropyrrolo[3,4-c]pyrrol-(1H)-yl, (3aR,6aS)-hexahydropyrrolo[3,4-c]pyrrol-(1H)-yl, (3aR,6aR)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(1H)-yl, (7R,8aS)-hexahydropyrrolo[1,2-a]pyrazin-(1H)-yl, (8aS)-hexahydropyrrolo[1,2-a]pyrazin-(1H)-yl, (8aR)-hexahydropyrrolo[1,2-a]pyrazin-(1H)-yl, (8aS)-octahydropyrrolo[1,2-a]pyrazin-(1H)-yl, (8aR)-octahydropyrrolo[1,2-a]pyrazin-(1H)-yl, hexahydropyrrolo[1,2-a]pyrazin-(2H)-one, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 2,5-diazabicyclo[2.2.2]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 2,6-diazaspiro[3.3]heptyl, 2,7-diazaspiro[3.5]nonyl, 5,8-diazaspiro[3.5]nonyl, 2,7-diazaspiro[4.4]nonyl, 6,9-diazaspiro[4.5]decyl and the like. A heterocyclyl radical is optionally substituted on a carbon or nitrogen atom ring member with substituent species as described herein where allowed by available valences.

As used herein, the term "$C_{1-8}$alkoxy-$C_{1-8}$alkyl" refers to a radical of the formula: —$C_{1-8}$alkyl-O—$C_{1-8}$alkyl.

As used herein, the term "$C_{1-8}$alkoxy-$C_{1-8}$alkyl-amino" refers to a radical of the formula: —NH—$C_{1-8}$alkyl-O—$C_{1-8}$alkyl.

As used herein, the term "($C_{1-8}$alkoxy-$C_{1-8}$alkyl)$_2$-amino" refers to a radical of the formula: —N($C_{1-8}$alkyl-O—$C_{1-8}$alkyl)$_2$.

As used herein, the term "$C_{1-8}$alkoxy-$C_{1-8}$alkyl-amino-$C_{1-8}$alkoxy" refers to a radical of the formula: —O—$C_{1-8}$alkyl-NH—$C_{1-8}$alkyl-O—$C_{1-8}$alkyl.

As used herein, the term "($C_{1-8}$alkoxy-$C_{1-8}$alkyl)$_2$-amino-$C_{1-8}$alkoxy" refers to a radical of the formula: —O—$C_{1-8}$alkyl-N($C_{1-8}$alkyl-O—$C_{1-8}$alkyl)$_2$.

As used herein, the term "($C_{1-8}$alkoxy-$C_{1-8}$alkyl)($C_{1-8}$alkyl)amino-$C_{1-8}$alkoxy" refers to a radical of the formula: —O—$C_{1-8}$alkyl-N($C_{1-8}$alkyl)($C_{1-8}$alkyl-O—$C_{1-8}$alkyl).

As used herein, the term "$C_{1-8}$alkoxy-$C_{1-8}$alkyl-amino-$C_{1-8}$alkyl" refers to a radical of the formula: —$C_{1-8}$alkyl-NH—$C_{1-8}$alkyl-O—$C_{1-8}$alkyl.

As used herein, the term "($C_{1-8}$alkoxy-$C_{1-8}$alkyl)$_2$-amino-$C_{1-8}$alkyl" refers to a radical of the formula: —$C_{1-8}$alkyl-N($C_{1-8}$alkyl-O—$C_{1-8}$alkyl)$_2$.

As used herein, the term "($C_{1-8}$alkoxy-$C_{1-8}$alkyl)($C_{1-8}$alkyl)amino-$C_{1-8}$alkyl" refers to a radical of the formula: —$C_{1-8}$alkyl-N($C_{1-8}$alkyl)($C_{1-8}$alkyl-O—$C_{1-8}$alkyl).

As used herein, the term "$C_{1-8}$alkoxy-carbonyl" refers to a radical of the formula: —C(O)—O—$C_{1-8}$alkyl.

As used herein, the term "$C_{1-8}$alkoxy-carbonyl-$C_{2-8}$alkenyl" refers to a radical of the formula: —$C_{2-8}$alkenyl-C(O)—O—$C_{1-8}$alkyl.

As used herein, the term "$C_{1-8}$alkoxy-carbonyl-amino" refers to a radical of the formula: —NH—C(O)—O—$C_{1-8}$alkyl.

As used herein, the term "$C_{1-8}$alkyl-amino" refers to a radical of the formula: —NH—$C_{1-8}$alkyl.

As used herein, the term "($C_{1-8}$alkyl)$_2$-amino" refers to a radical of the formula: —N($C_{1-8}$alkyl)$_2$.

As used herein, the term "$C_{1-8}$alkyl-amino-$C_{2-8}$alkenyl" refers to a radical of the formula: —$C_{2-8}$alkenyl-NH—$C_{1-8}$alkyl.

As used herein, the term "($C_{1-8}$alkyl)$_2$-amino-$C_{2-8}$alkenyl" refers to a radical of the formula: —$C_{2-8}$alkenyl-N($C_{1-8}$alkyl)$_2$.

As used herein, the term "$C_{1-8}$alkyl-amino-$C_{1-8}$alkoxy" refers to a radical of the formula: —O—$C_{1-8}$alkyl-NH—$C_{1-8}$alkyl.

As used herein, the term "($C_{1-8}$alkyl)$_2$-amino-$C_{1-8}$alkoxy" refers to a radical of the formula: —O—$C_{1-8}$alkyl-N($C_{1-8}$alkyl)$_2$.

As used herein, the term "$C_{1-8}$alkyl-amino-$C_{1-8}$alkyl" refers to a radical of the formula: —$C_{1-8}$alkyl-NH—$C_{1-8}$alkyl.

As used herein, the term "($C_{1-8}$alkyl)$_2$-amino-$C_{1-8}$alkyl" refers to a radical of the formula: —$C_{1-8}$alkyl-N($C_{1-8}$alkyl)$_2$.

As used herein, the term "$C_{1-8}$alkyl-amino-$C_{1-8}$alkyl-amino" refers to a radical of the formula: —NH—$C_{1-8}$alkyl-NH—$C_{1-8}$alkyl.

As used herein, the term "($C_{1-8}$alkyl)$_2$-amino-$C_{1-8}$alkyl-amino" refers to a radical of the formula: —NH—$C_{1-8}$alkyl-N($C_{1-8}$alkyl)$_2$.

As used herein, the term "($C_{1-8}$alkyl-amino-$C_{1-8}$alkyl)$_2$-amino" refers to a radical of the formula: —N($C_{1-8}$alkyl-NH—$C_{1-8}$alkyl)$_2$.

As used herein, the term "[($C_{1-8}$alkyl)$_2$-amino-$C_{1-8}$alkyl]$_2$-amino" refers to a radical of the formula: —N[$C_{1-8}$alkyl-N($C_{1-8}$alkyl)$_2$]$_2$.

As used herein, the term "($C_{1-8}$alkyl-amino-$C_{1-8}$alkyl)($C_{1-8}$alkyl)amino" refers to a radical of the formula: —N($C_{1-8}$alkyl)($C_{1-8}$alkyl-NH—$C_{1-8}$alkyl).

As used herein, the term "[($C_{1-8}$alkyl)$_2$-amino-$C_{1-8}$alkyl]($C_{1-8}$alkyl)amino" refers to a radical of the formula: —N($C_{1-8}$alkyl)[$C_{1-8}$alkyl-N($C_{1-8}$alkyl)$_2$].

As used herein, the term "$C_{1-8}$alkyl-amino-$C_{2-8}$alkynyl" refers to a radical of the formula: —$C_{2-8}$alkynyl-NH—$C_{1-8}$alkyl.

As used herein, the term "($C_{1-8}$alkyl)$_2$-amino-$C_{2-8}$alkynyl" refers to a radical of the formula: —$C_{2-8}$alkynyl-N($C_{1-8}$alkyl)$_2$.

As used herein, the term "$C_{1-8}$alkyl-carbonyl" refers to a radical of the formula: —C(O)—$C_{1-8}$alkyl.

As used herein, the term "$C_{1-8}$alkyl-carbonyl-amino" refers to a radical of the formula: —NH—C(O)—$C_{1-8}$alkyl.

As used herein, the term "$C_{1-8}$alkyl-thio" refers to a radical of the formula: —S—$C_{1-8}$alkyl.

As used herein, the term "amino-$C_{2-8}$alkenyl" refers to a radical of the formula: —$C_{2-8}$alkenyl-$NH_2$.

As used herein, the term "amino-$C_{1-8}$alkoxy" refers to a radical of the formula: —O—$C_{1-8}$alkyl-$NH_2$.

As used herein, the term "amino-$C_{1-8}$alkyl" refers to a radical of the formula: —$C_{1-8}$alkyl-$NH_2$.

As used herein, the term "amino-$C_{1-8}$alkyl-amino" refers to a radical of the formula: —NH—$C_{1-8}$alkyl-$NH_2$.

As used herein, the term "(amino-$C_{1-8}$alkyl)$_2$-amino" refers to a radical of the formula: —N($C_{1-8}$alkyl-$NH_2$)$_2$.

As used herein, the term "(amino-$C_{1-8}$alkyl)($C_{1-8}$alkyl) amino" refers to a radical of the formula: —N($C_{1-8}$alkyl) ($C_{1-8}$alkyl-$NH_2$).

As used herein, the term "amino-$C_{2-8}$alkynyl" refers to a radical of the formula: —$C_{2-8}$alkynyl-$NH_2$.

As used herein, the term "aryl-$C_{1-8}$alkoxy-carbonyl" refers to a radical of the formula: —C(O)—O—$C_{1-8}$alkyl-aryl.

As used herein, the term "aryl-$C_{1-8}$alkyl" refers to a radical of the formula: —$C_{1-8}$alkyl-aryl.

As used herein, the term "aryl-$C_{1-8}$alkyl-amino" refers to a radical of the formula: —NH—$C_{1-8}$alkyl-aryl.

As used herein, the term "(aryl-$C_{1-8}$alkyl)$_2$-amino" refers to a radical of the formula: —N($C_{1-8}$alkyl-aryl)$_2$.

As used herein, the term "(aryl-$C_{1-8}$alkyl)($C_{1-8}$alkyl) amino" refers to a radical of the formula: —N($C_{1-8}$alkyl) ($C_{1-8}$alkyl-aryl).

As used herein, the term "aryl-$C_{1-8}$alkyl-amino-$C_{1-8}$alkyl" refers to a radical of the formula: —$C_{1-8}$alkyl-NH—$C_{1-8}$alkyl-aryl.

As used herein, the term "(aryl-$C_{1-8}$alkyl)$_2$-amino-$C_{1-8}$alkyl" refers to a radical of the formula: —$C_{1-8}$alkyl-N($C_{1-8}$alkyl-aryl)$_2$.

As used herein, the term "(aryl-$C_{1-8}$alkyl)($C_{1-8}$alkyl) amino-$C_{1-8}$alkyl" refers to a radical of the formula: —$C_{1-8}$alkyl-N($C_{1-8}$alkyl)($C_{1-8}$alkyl-aryl).

As used herein, the term "aryl-amino" refers to a radical of the formula: —NH-aryl.

As used herein, the term "aryl-amino-carbonyl" refers to a radical of the formula: —C(O)—NH-aryl.

As used herein, the term "aryl-sulfonyloxy-$C_{1-8}$alkyl" refers to a radical of the formula: —$C_{1-8}$alkyl-O—$SO_2$-aryl.

As used herein, the term "benzoxy-carbonyl" refers to a radical of the formula: —C(O)—O—$CH_2$-phenyl.

As used herein, the term "$C_{3-14}$cycloalkyl-$C_{1-8}$alkyl" refers to a radical of the formula: —$C_{1-8}$alkyl-$C_{3-14}$cycloalkyl.

As used herein, the term "$C_{3-14}$cycloalkyl-amino" refers to a radical of the formula: —NH—$C_{3-14}$cycloalkyl.

As used herein, the term "$C_{3-14}$cycloalkyl-oxy" refers to a radical of the formula: —O—$C_{3-14}$cycloalkyl.

As used herein, the term "halo" or "halogen" generally refers to a halogen atom radical, including fluoro, chloro, bromo and iodo.

As used herein, the term "halo-$C_{1-8}$alkoxy" refers to a radical of the formula: —O—$C_{1-8}$alkyl-halo, wherein $C_{1-8}$alkyl is partially or completely substituted with one or more halogen atoms where allowed by available valences.

As used herein, the term "halo-$C_{1-8}$alkyl" refers to a radical of the formula: —$C_{1-8}$alkyl-halo, wherein $C_{1-8}$alkyl is partially or completely substituted with one or more halogen atoms where allowed by available valences.

As used herein, the term "halo-$C_{1-8}$alkyl-amino" refers to a radical of the formula:

As used herein, the term "(halo-$C_{1-8}$alkyl)($C_{1-8}$alkyl) amino" refers to a radical of the formula: —N($C_{1-8}$alkyl) ($C_{1-8}$alkyl-halo).

As used herein, the term "(halo-$C_{1-8}$alkyl)$_2$-amino" refers to a radical of the formula: —N($C_{1-8}$alkyl-halo)$_2$.

As used herein, the term "heteroaryl-$C_{1-8}$alkoxy" refers to a radical of the formula: —O—$C_{1-8}$alkyl-heteroaryl.

As used herein, the term "heteroaryl-$C_{1-8}$alkyl" refers to a radical of the formula: —$C_{1-8}$alkyl-heteroaryl.

As used herein, the term "heteroaryl-$C_{1-8}$alkyl-amino" refers to a radical of the formula: —NH—$C_{1-8}$alkyl-heteroaryl.

As used herein, the term "(heteroaryl-$C_{1-8}$alkyl)$_2$-amino" refers to a radical of the formula: —N($C_{1-8}$alkyl-heteroaryl)$_2$.

As used herein, the term "(heteroaryl-$C_{1-8}$alkyl)($C_{1-8}$alkyl)amino" refers to a radical of the formula: —N($C_{1-8}$alkyl) ($C_{1-8}$alkyl-heteroaryl).

As used herein, the term "heteroaryl-$C_{1-8}$alkyl-amino-$C_{1-8}$alkyl" refers to a radical of the formula: —$C_{1-8}$alkyl-NH—$C_{1-8}$alkyl-heteroaryl.

As used herein, the term "(heteroaryl-$C_{1-8}$alkyl)$_2$-amino-$C_{1-8}$alkyl" refers to a radical of the formula: —$C_{1-8}$alkyl-N ($C_{1-8}$alkyl-heteroaryl)$_2$.

As used herein, the term "(heteroaryl-$C_{1-8}$alkyl)($C_{1-8}$alkyl)amino-$C_{1-8}$alkyl" refers to a radical of the formula: —$C_{1-8}$alkyl-N($C_{1-8}$alkyl)($C_{1-8}$alkyl-heteroaryl).

As used herein, the term "heteroaryl-amino" refers to a radical of the formula: —NH-heteroaryl.

As used herein, the term "heterocyclyl-$C_{1-8}$alkoxy" refers to a radical of the formula: —O—$C_{1-8}$alkyl-heterocyclyl.

As used herein, the term "heterocyclyl-$C_{1-8}$alkyl" refers to a radical of the formula: —$C_{1-8}$alkyl-heterocyclyl.

As used herein, the term "heterocyclyl-$C_{1-8}$alkyl-amino" refers to a radical of the formula: —NH—$C_{1-8}$alkyl-heterocyclyl.

As used herein, the term "(heterocyclyl-$C_{1-8}$alkyl)$_2$-amino" refers to a radical of the formula: —N($C_{1-8}$alkyl-heterocyclyl)$_2$.

As used herein, the term "(heterocyclyl-$C_{1-8}$alkyl) ($C_{1-8}$alkyl)amino" refers to a radical of the formula: —N($C_{1-8}$alkyl)($C_{1-8}$alkyl-heterocyclyl).

As used herein, the term "heterocyclyl-$C_{1-8}$alkyl-amino-$C_{1-8}$alkyl" refers to a radical of the formula: —$C_{1-8}$alkyl-NH—$C_{1-8}$alkyl-heterocyclyl.

As used herein, the term "(heterocyclyl-$C_{1-8}$alkyl)$_2$-amino-$C_{1-8}$alkyl" refers to a radical of the formula: —$C_{1-8}$alkyl-N($C_{1-8}$alkyl-heterocyclyl)$_2$.

As used herein, the term "(heterocyclyl-$C_{1-8}$alkyl) ($C_{1-8}$alkyl)amino-$C_{1-8}$alkyl" refers to a radical of the formula: —$C_{1-8}$alkyl-N($C_{1-8}$alkyl)($C_{1-8}$alkyl-heterocyclyl).

As used herein, the term "heterocyclyl-amino" refers to a radical of the formula: —NH-heterocyclyl.

As used herein, the term "(heterocyclyl)($C_{1-8}$alkyl) amino" refers to a radical of the formula: —N($C_{1-8}$alkyl) (heterocyclyl).

As used herein, the term "heterocyclyl-amino-$C_{1-8}$alkyl" refers to a radical of the formula: —$C_{1-8}$alkyl-NH-heterocyclyl.

As used herein, the term "heterocyclyl-carbonyl" refers to a radical of the formula: —C(O)-heterocyclyl.

As used herein, the term "heterocyclyl-carbonyl-oxy" refers to a radical of the formula: —O—C(O)-heterocyclyl.

As used herein, the term "heterocyclyl-oxy" refers to a radical of the formula: —O-heterocyclyl.

As used herein, the term "hydroxy" refers to a radical of the formula: —OH.

As used herein, the term "hydroxy-$C_{1-8}$alkoxy-$C_{1-8}$alkyl" refers to a radical of the formula: —$C_{1-8}$alkyl-O—$C_{1-8}$alkyl-OH.

As used herein, the term "hydroxy-$C_{1-8}$alkyl" refers to a radical of the formula: —$C_{1-8}$alkyl-OH, wherein $C_{1-8}$alkyl is partially or completely substituted with one or more hydroxy radicals where allowed by available valences.

As used herein, the term "hydroxy-$C_{1-8}$alkyl-amino" refers to a radical of the formula: —NH—$C_{1-8}$alkyl-OH.

As used herein, the term "(hydroxy-$C_{1-8}$alkyl)$_2$-amino" refers to a radical of the formula: —N($C_{1-8}$alkyl-OH)$_2$.

As used herein, the term "(hydroxy-$C_{1-8}$alkyl)($C_{1-8}$alkyl) amino" refers to a radical of the formula: —N($C_{1-8}$alkyl) ($C_{1-8}$alkyl-OH).

As used herein, the term "hydroxy-$C_{1-8}$alkyl-amino-$C_{1-8}$alkyl" refers to a radical of the formula: —$C_{1-8}$alkyl-NH—$C_{1-8}$alkyl-OH.

As used herein, the term "(hydroxy-$C_{1-8}$alkyl)$_2$-amino-$C_{1-8}$alkyl" refers to a radical of the formula: —$C_{1-8}$alkyl-N($C_{1-8}$alkyl-OH)$_2$.

As used herein, the term "(hydroxy-$C_{1-8}$alkyl)($C_{1-8}$alkyl) amino-$C_{1-8}$alkyl" refers to a radical of the formula: —$C_{1-8}$alkyl-N($C_{1-8}$alkyl)($C_{1-8}$alkyl-OH).

As used herein, the term "hydroxy-$C_{1-8}$alkyl-amino-$C_{1-8}$alkoxy" refers to a radical of the formula: —O—$C_{1-8}$alkyl-NH—$C_{1-8}$alkyl-OH.

As used herein, the term "(hydroxy-$C_{1-8}$alkyl)$_2$-amino-$C_{1-8}$alkoxy" refers to a radical of the formula: —O—$C_{1-8}$alkyl-N($C_{1-8}$alkyl-OH)$_2$.

As used herein, the term "(hydroxy-$C_{1-8}$alkyl)($C_{1-8}$alkyl) amino-$C_{1-8}$alkoxy" refers to a radical of the formula: —O—$C_{1-8}$alkyl-N($C_{1-8}$alkyl)($C_{1-8}$alkyl-OH).

As used herein, the term "hydroxy-$C_{1-8}$alkyl-amino-$C_{1-8}$alkyl-amino" refers to a radical of the formula: —NH—$C_{1-8}$alkyl-NH—$C_{1-8}$alkyl-OH.

As used herein, the term "(hydroxy-$C_{1-8}$alkyl-amino-$C_{1-8}$alkyl)$_2$-amino" refers to a radical of the formula: —N($C_{1-8}$alkyl-NH—$C_{1-8}$alkyl-OH)$_2$.

As used herein, the term "(hydroxy-$C_{1-8}$alkyl)$_2$-amino-$C_{1-8}$alkyl-amino" refers to a radical of the formula: —NH—$C_{1-8}$alkyl-N($C_{1-8}$alkyl-OH)$_2$.

As used herein, the term "(hydroxy-$C_{1-8}$alkyl-amino-$C_{1-8}$alkyl)($C_{1-8}$alkyl)amino" refers to a radical of the formula: —N($C_{1-8}$alkyl)($C_{1-8}$alkyl-NH—$C_{1-8}$alkyl-OH).

As used herein, the term "[(hydroxy-$C_{1-8}$alkyl)$_2$-amino-$C_{1-8}$alkyl]($C_{1-8}$alkyl)amino" refers to a radical of the formula: —N($C_{1-8}$alkyl)[$C_{1-8}$alkyl-N($C_{1-8}$alkyl-OH)$_2$].

As used herein, the term "(hydroxy-$C_{1-8}$alkyl)($C_{1-8}$alkyl) amino-$C_{1-8}$alkyl-amino" refers to a radical of the formula: —NH—$C_{1-8}$alkyl-N($C_{1-8}$alkyl, $C_{1-8}$alkyl-OH).

As used herein, the term "[(hydroxy-$C_{1-8}$alkyl)($C_{1-8}$alkyl) amino-$C_{1-8}$alkyl]($C_{1-8}$alkyl)amino" refers to a radical of the formula: —N($C_{1-8}$alkyl)[$C_{1-8}$alkyl-N($C_{1-8}$alkyl)($C_{1-8}$alkyl-OH)].

As used herein, the term "substituent" means positional variables on the atoms of a core molecule that are attached at a designated atom position, replacing one or more hydrogen atoms on the designated atom, provided that the atom of attachment does not exceed the available valence or shared valences, such that the substitution results in a stable compound. Accordingly, combinations of substituents and/or variables are permissible only if such combinations result in stable compounds. It should also be noted that any carbon as well as heteroatom with a valence level that appears to be unsatisfied as described or shown herein is assumed to have a sufficient number of hydrogen atom(s) to satisfy the valences described or shown.

For the purposes of this description, where one or more substituent variables for a compound of Formula (I) encompass functionalities incorporated into a compound of Formula (I), each functionality appearing at any location within the disclosed compound may be independently selected, and as appropriate, independently and/or optionally substituted.

As used herein, the terms "independently selected," or "each selected" refer to functional variables in a substituent list that may be attached more than once on the structure of a core molecule, where the pattern of substitution at each occurrence is independent of the pattern at any other occurrence. Further, the use of a generic substituent on a core structure for a compound provided herein is understood to include the replacement of the generic substituent with specie substituents that are included within the particular genus, e.g., aryl may be independently replaced with phenyl or naphthalenyl (also referred to as naphthyl) and the like, such that the resulting compound is intended to be included within the scope of the compounds described herein.

As used herein, the term "each instance of" when used in a phrase such as " . . . aryl, aryl-$C_{1-8}$alkyl, heterocyclyl and heterocyclyl-$C_{1-8}$alkyl, wherein each instance of aryl and heterocyclyl is optionally substituted with one or two substituents . . . " is intended to include optional, independent substitution on each of the aryl and heterocyclyl rings and on the aryl and heterocyclyl portions of aryl-$C_{1-8}$alkyl and heterocyclyl-$C_{1-8}$alkyl.

As used herein, the term "optionally substituted" means that the specified substituent variables, groups, radicals or moieties represent the scope of the genus and may be independently chosen as needed to replace one or more hydrogen atoms on the designated atom of attachment of a core molecule.

As used herein, the terms "stable compound" or "stable structure" mean a compound that is sufficiently robust to be isolated to a useful degree of purity from a reaction mixture and formulations thereof into an efficacious therapeutic agent.

Compound names provided herein were obtained using ACD Labs Index Name software provided by ACD Labs and/or ChemDraw Ultra software provided by CambridgeSoft®. When the compound name disclosed herein conflicts with the structure depicted, the structure shown will supercede the use of the name to define the compound intended. Nomenclature for substituent radicals defined herein may differ slightly from the chemical name from which they are derived; one skilled in the art will recognize that the definition of the substituent radical is intended to include the radical as found in the chemical name.

The term "SMN," unless otherwise specified herein, refers to the human SMN1 gene, DNA or RNA, and/or human SMN2 gene, DNA or RNA. In a specific embodiment, the term "SMN1" refers to the human SMN1 gene, DNA or RNA. In another specific embodiment, the term "SMN2" refers to the human SMN2 gene, DNA or RNA.

Nucleic acid sequences for the human SMN1 and SMN2 genes are known in the art. For nucleic acid sequences of human SMN1, see, e.g., GenBank Accession Nos. DQ894095, NM_000344, NM_022874, and BC062723. For nucleic acid sequences of human SMN2, see, e.g., NM_022875, NM_022876, NM_022877, NM_017411, DQ894734 (Life Technologies, Inc. (formerly Invitrogen), Carlsbad, Calif.), BC000908, BC070242, CR595484, CR598529, CR609539, U21914, and BC015308.

The SMN1 gene can be found on the forward strand of human chromosome 5 from approximately nucleotide 70,220,768 to approximately nucleotide 70,249,769. The approximate locations of exons 6, 7 and 8 and introns 6 and 7 of SMN1 on human chromosome 5 are as follows:
  70,241,893 to 70,242,003 exon 6;
  70,242,004 to 70,247,767 intron 6;
  70,247,768 to 70,247,821 exon 7;
  70,247,822 to 70,248,265 intron 7; and,
  70,248,266 to 70,248,839 exon 8.

The SMN2 gene can be found on the forward strand of human chromosome 5 from approximately nucleotide 69,345,350 to approximately nucleotide 69,374,349.

The approximate locations of exons 6, 7 and 8 and introns 6 and 7 of SMN2 on human chromosome 5 are as follows:
  69,366,468 to 69,366,578 exon 6;
  69,366,579 to 69,372,347 intron 6;
  69,372,348 to 69,372,401 exon 7;
  69,372,402 to 69,372,845 intron 7; and,
  69,372,846 to 69,373,419 exon 8.

In specific embodiments, the nucleotide sequences delineated above for exons 6, 7 and 8 and introns 6 and 7 of SMN1 are used in the SMN1 minigene nucleic acid constructs described herein. In other specific embodiments, the nucleotide sequences of exons 6, 7 and 8 and introns 6 and 7 of SMN2 in the examples provided herein are used in the SMN2 minigene nucleic acid constructs described herein.

The term "Smn" or "Smn protein," unless otherwise specified herein, refers to a human Smn protein that contains the amino acid residues encoded by exons 1 through 7 of the SMN1 gene and/or SMN2 gene. In a specific embodiment, the Smn protein is stable and functional in vitro and/or in vivo as assessed by methods known to one of skill in the art. In another specific embodiment, the Smn protein is the full-length protein encoded by the human SMN1 gene and/or SMN2 gene. In another specific embodiment, the Smn protein has the amino acid sequence found at GenBank Accession No. NP_000335, AAC50473.1, AAA66242.1, or NP_059107.

As used herein, the term "enhances the inclusion of exon 7 of SMN2 into mRNA that is transcribed from the SMN2 gene," and analogous terms, unless otherwise specified herein, refers to the inclusion of the complete, intact, non-truncated sequence of exon 7 of SMN2 into the mature mRNA that is transcribed from the SMN2 gene (i.e., resulting in the production of full-length SMN2 mRNA) in vitro and/or in vivo, as assessed by methods known to one of skill in the art, such that increased levels of Smn protein are produced from the SMN2 gene in vitro and/or in vivo, as assessed by methods known to one of skill in the art; or, that increased expression of stable and functional Smn protein is produced from the SMN2 gene in vitro and/or in vivo, as assessed by methods known to one of skill in the art; or, that expression of the fusion protein encoded by the minigene is increased in vitro and/or in vivo, as assessed by methods known to one of skill in the art; or, that expression of Smn protein produced from the SMN2 gene in a subject (e.g., an animal model for SMA or a human subject or an SMA patient) in need thereof is increased.

As used herein, the term "enhances the inclusion of exon 7 of SMN1 into mRNA that is transcribed from the SMN1 gene," and analogous terms, unless otherwise specified herein, refers to the inclusion of the complete, intact, non-truncated sequence of exon 7 of SMN1 into the mature mRNA that is transcribed from the SMN1 gene (i.e., resulting in the production of full-length SMN1 mRNA) in vitro and/or in vivo, as assessed by methods known to one of skill in the art, such that increased levels of Smn protein are produced from the SMN1 gene in vitro and/or in vivo, as assessed by methods known to one of skill in the art; or, that increased expression of stable and functional Smn protein is produced from the SMN1 gene in vitro and/or in vivo, as assessed by methods known to one of skill in the art; or, that expression of the fusion protein encoded by the minigene is increased in vitro and/or in vivo, as assessed by methods known to one of skill in the art; or, that expression of Smn protein produced from the SMN1 gene in a subject (e.g., an animal model for SMA or a human subject) in need thereof is increased.

As used herein, the term "substantial change" in the context of the amount of mRNA means that the amount of mRNA does not change by a statistically significant amount, e.g., a p value less than a value selected from 0.1, 0.05, 0.01, 0.005, 0.001, 0.0005, 0.0001, 0.00005 or 0.00001.

As used herein, the terms "subject" and "patient" are used interchangeably to refer to an animal or any living organism having sensation and the power of voluntary movement, and which requires for its existence oxygen and organic food. Nonlimiting examples include members of the human, equine, porcine, bovine, rattus, murine, canine and feline species. In some embodiments, the subject is a mammal or a warm-blooded vertebrate animal. In certain embodiments, the subject is a non-human animal. In specific embodiments, the subject is a human. In one specific embodiment, the subject is a human SMA patient.

As used herein, the term "elderly human" refers to a human 65 years old or older.

As used herein, the term "human adult" refers to a human that is 18 years or older.

As used herein, the term "human child" refers to a human that is 1 year to 18 years old.

As used herein, the term "human infant" refers to a newborn to 1 year old year human.

As used herein, the term "human toddler" refers to a human that is 1 year to 3 years old.

Compound Forms

As used herein, the terms "a compound of Formula (Ia)," "a compound of Formula (Ia1)," "a compound of Formula (Ia2)," "a compound of Formula (Ia3)," "a compound of Formula (Ia4)," "a compound of Formula (II)," "a compound of Formula (IIa)," "a compound of Formula (IIa1)," "a compound of Formula (IIa2)," "a compound of Formula (IIa3)," "a compound of Formula (IIa4)," "a compound of Formula (III)," "a compound of Formula (IIIa)," "a compound of Formula (IIIa1)," "a compound of Formula (IIIa2)," "a compound of Formula (IIIa3)," "a compound of Formula (IIIa4)," "a compound of Formula (IV)," "a compound of Formula (IVa)," "a compound of Formula (IVa1)," "a compound of Formula (IVa2)," "a compound of Formula (V)," "a compound of Formula (Va)," "a compound of Formula (Va1)," "a compound of Formula (Va2)," "a compound of Formula (VI)," "a compound of Formula (VIa)," "a compound of Formula (VIa1)," "a compound of Formula (VIa2)," "a compound of Formula (VIa3)," "a compound of Formula (VIa4)," "a compound of Formula (VII)," "a compound of Formula (VIIa)," "a compound of Formula (VIIa1)," "a compound of Formula (VIIa2)," "a compound of Formula (VIII)," "a compound of Formula (VIIIa)," "a compound of Formula (VIIIa1)," "a compound of Formula (VIIIa2)," "a compound of Formula (IX)," "a compound of Formula (IXa)," "a compound of Formula (IXa1)," "a compound of Formula (IXa2)," "a compound of Formula (IXa3)," "a compound of Formula (IXa4)," "a compound of Formula (X)," "a compound of Formula (Xa)," "a compound of Formula (Xa1)," "a compound of Formula (Xa2)," "a compound of Formula (XI)," "a compound of Formula (XIa)," "a compound of Formula (XIa1)," "a compound of Formula (XIa2)," "a compound of Formula (XII)," "a compound of Formula (XIIa)," "a compound of Formula (XIIa1)," "a compound of Formula (XIIa2)," "a compound of Formula (XIIa3)," "a compound of Formula (XIIa4)," "a compound of Formula (XIII)," "a compound of Formula (XIIIa)," "a compound of Formula (XIIIa1)," "a compound of Formula (XIIIa2)," "a compound of Formula (XIV)," "a compound of Formula (XIVa)," "a compound of Formula (XIVa1)," and "a compound of Formula (XIVa2)," each refer to subgenera of the compound of Formula (I) or a form thereof.

Rather than repeat embodiments for the various subgenera of the compound of Formula (I), in certain embodiments, the term "a compound of Formula (I) or a form thereof" is used to inclusively to refer to a compound of Formula (Ia) or a form thereof, a compound of Formula (Ia1) or a form thereof, a compound of Formula (Ia2) or a form thereof, a compound of Formula (Ia3) or a form thereof, a compound of Formula (Ia4) or a form thereof, a compound of Formula (II) or a form thereof, a compound of Formula (IIa) or a form thereof, a compound of Formula (IIa1) or a form thereof, a compound of Formula (IIa2) or a form thereof, a compound of Formula (IIa3) or a form thereof, a compound of Formula (IIa4) or a form thereof, a compound of Formula (III) or a form thereof, a compound of Formula (IIIa) or a form thereof, a compound of Formula (IIIa1) or a form thereof, a compound of Formula (IIIa2) or a form thereof, a compound of Formula (IIIa3) or a form thereof, a compound of Formula (IIIa4) or a form thereof, a compound of Formula (IV) or a form thereof, a compound of Formula (IVa) or a form thereof, a compound of Formula (IVa1) or a form thereof, a compound of Formula (IVa2) or a form thereof, a compound of Formula (V) or a form thereof, a compound of Formula (Va) or a form thereof, a compound of Formula (Va1) or a form thereof, a compound of Formula (Va2) or a form thereof, a compound of Formula (VI) or a form thereof, a compound of Formula (VIa) or a form thereof, a compound of Formula (VIa1) or a form thereof, a compound of Formula (VIa2) or a form thereof, a compound of Formula (VIa3) or a form thereof, a compound of Formula (VIa4) or a form thereof, a compound of Formula (VII) or a form thereof, a compound of Formula (VIIa) or a form thereof, a compound of Formula (VIIa1) or a form thereof, a compound of Formula (VIIa2) or a form thereof, a compound of Formula (VIII) or a form thereof, a compound of Formula (VIIIa) or a form thereof, a compound of Formula (VIIIa1) or a form thereof, a compound of Formula (VIIIa2) or a form thereof, a compound of Formula (IX) or a form thereof, a compound of Formula (IXa) or a form thereof, a compound of Formula (IXa1) or a form thereof, a compound of Formula (IXa2) or a form thereof, a compound of Formula (IXa3) or a form thereof, a compound of Formula (IXa4) or a form thereof, a compound of Formula (X) or a form thereof, a compound of Formula (Xa) or a form thereof, a compound of Formula (Xa1) or a form thereof, a compound of Formula (Xa2) or a form thereof, a compound of Formula (XI) or a form thereof, a compound of Formula (XIa) or a form thereof, a compound of Formula (XIa1) or a form thereof, a compound of Formula (XIa2) or a form thereof, a compound of Formula (XII) or a form thereof, a compound of Formula (XIIa) or a form thereof, a compound of Formula (XIIa1) or a form thereof, a compound of Formula (XIIa2) or a form thereof, a compound of Formula (XIIa3) or a form thereof, a compound of Formula (XIIa4) or a form thereof, a compound of Formula (XIII) or a form thereof, a compound of Formula (XIIIa) or a form thereof, a compound of Formula (XIIIa1) or a form thereof, a compound of Formula (XIIIa2) or a form thereof, a compound of Formula (XIV) or a form thereof, a compound of Formula (XIVa) or a form thereof, a compound of Formula (XIVa1) or a form thereof or a compound of Formula (XIVa2) or a form thereof, either separately or together.

Thus, embodiments and references to "a compound of Formula (I)" are intended to be inclusive of compounds of Formula (Ia), Formula (Ia1), Formula (Ia2), Formula (Ia3), Formula (Ia4), Formula (II), Formula (IIa), Formula (IIa1), Formula (IIa2), Formula (IIa3), Formula (IIa4), Formula (III), Formula (IIIa), Formula (IIIa1), Formula (IIIa2), Formula (IIIa3), Formula (IIIa4), Formula (IV), Formula (IVa), Formula (IVa1), Formula (IVa2), Formula (V), Formula (Va), Formula (Va1), Formula (Va2), Formula (VI), Formula (VIa), Formula (VIa1), Formula (VIa2), Formula (VIa3), Formula (VIa4), Formula (VII), Formula (VIIa), Formula (VIIa1), Formula (VIIa2), Formula (VIII), Formula (VIIIa), Formula (VIIIa1), Formula (VIIIa2), Formula (IX), Formula (IXa), Formula (IXa1), Formula (IXa2), Formula (IXa3), Formula (IXa4), Formula (X), Formula (Xa), Formula (Xa1), Formula (Xa2), Formula (XI), Formula (XIa), Formula (XIa1), Formula (XIa2), Formula (XII), Formula (XIIa), Formula (XIIa1), Formula (XIIa2), Formula (XIIa3), Formula (XIIa4), Formula (XIII), Formula (XIIIa), Formula (XIIIa1), Formula (XIIIa2), Formula (XIV), Formula (XIVa), Formula (XIVa1) and Formula (XIVa2).

As used herein, the term "form" means a compound of Formula (I) selected from a free acid, free base, salt, isotopologue, stereoisomer, racemate, enantiomer, diastereomer, or tautomer thereof.

In certain embodiments described herein, the form of the compound of Formula (I) is a selected from a salt, isotopologue, stereoisomer, racemate, enantiomer, diastereomer or tautomer thereof.

In certain embodiments described herein, the form of the compound of Formula (I) is a selected from a free acid, isotopologue, stereoisomer, racemate, enantiomer, diastereomer or tautomer thereof.

In certain embodiments described herein, the form of the compound of Formula (I) is a selected from a free base, isotopologue, stereoisomer, racemate, enantiomer, diastereomer or tautomer thereof.

In certain embodiments described herein, the form of the compound of Formula (I) is a free acid, free base or salt thereof.

In certain embodiments described herein, the form of the compound of Formula (I) is an isotopologue thereof.

In certain embodiments described herein, the form of the compound of Formula (I) is a stereoisomer, racemate, enantiomer or diastereomer thereof.

In certain embodiments described herein, the form of the compound of Formula (I) is a tautomer thereof.

In certain embodiments described herein, the form of the compound of Formula (I) is a pharmaceutically acceptable form.

In certain embodiments described herein, the compound of Formula (I) or a form thereof is isolated for use.

As used herein, the term "isolated" means the physical state of a compound of Formula (I) or a form thereof after being isolated and/or purified from a synthetic process (e.g., from a reaction mixture) or natural source or combination thereof according to an isolation or purification process or processes described herein or which are well known to the skilled artisan (e.g., chromatography, recrystallization and the like) in sufficient purity to be characterizable by standard analytical techniques described herein or well known to the skilled artisan.

As used herein, the term "protected" means that a functional group on a compound of Formula (I) is in a form modified to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

Prodrugs of a compound of Formula (I) or a form thereof are also contemplated herein.

As used herein, the term "prodrug" means that a functional group on a compound of Formula (I) is in a form (e.g., acting as an active or inactive drug precursor) that is transformed in vivo to yield an active or more active compound of Formula (I) or a form thereof. The transformation may occur by various mechanisms (e.g., by metabolic and/or non-metabolic chemical processes), such as, for example, by hydrolysis and/or metabolism in blood, liver and/or other organs and tissues. A discussion of the use of prodrugs is provided by V. J. Stella, et. al., "Biotechnology: Pharmaceutical Aspects, Prodrugs: Challenges and Rewards," American Association of Pharmaceutical Scientists and Springer Press, 2007.

In one example, when a compound of Formula (I) or a form thereof contains a carboxylic acid functional group, a prodrug can comprise an ester formed by the replacement of the hydrogen atom of the acid group with a functional group such as alkyl and the like. In another example, when a compound of Formula (I) or a form thereof contains an alcohol functional group, a prodrug can be formed by the replacement of the hydrogen atom of the alcohol group with a functional group such as alkyl or substituted carbonyl and the like. In another example, when a compound of Formula (I) or a form thereof contains an amine functional group, a prodrug can be formed by the replacement of one or more amine hydrogen atoms with a functional group such as alkyl or substituted carbonyl. In another example, when a compound of Formula (I) or a form thereof contains a hydrogen substituent, a prodrug can be formed by the replacement of one or more hydrogen atoms with an alkyl substituent.

Pharmaceutically acceptable prodrugs of compounds of Formula (I) or a form thereof include those compounds substituted with one or more of the following groups: carboxylic acid esters, sulfonate esters, amino acid esters phosphonate esters, mono-, di- or triphosphate esters or alkyl substituents where appropriate. As described herein, it is understood by a person of ordinary skill in the art that one or more of such substituents may be used to provide a compound of Formula (I) or a form thereof for use as a prodrug.

The compounds of Formula (I) can form salts which are intended to be included within the scope of this description. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein.

The term "pharmaceutically acceptable salt(s)", as used herein, means those salts of compounds described herein that are safe and effective (i.e., non-toxic, physiologically acceptable) for use in mammals and that possess biological activity, although other salts are also useful. Salts of the compounds of Formula (I) may be formed, for example, by reacting a compound of Formula (I) with an amount of acid or base, such as an equivalent or stoichiometric amount, in a medium such as one in which the salt precipitates or in an aqueous medium followed by lyophilization.

Pharmaceutically acceptable salts include one or more salts of acidic or basic groups present in compounds described herein. Embodiments of acid addition salts include, but are not limited to, an acetate, diacetate, acid phosphate, ascorbate, benzoate, benzenesulfonate, bisulfate, bitartrate, borate, butyrate, chloride, citrate, camphorate, camphorsulfonate, ethanesulfonate, formate, fumarate, gentisinate, gluconate, glucaronate, glutamate, hydrobromide, hydrochloride, dihydrochloride, trihydrochloride, hydroiodide, isonicotinate, lactate, maleate, methanesulfonate, naphthalenesulfonate, nitrate, oxalate, pamoate, pantothenate, phosphate, propionate, saccharate, salicylate, succinate, sulfate, tartrate, thiocyanate, toluenesulfonate (also known as tosylate), trifluoroacetate, trifluoroacetic acid salt and the like. One or more embodiments of acid addition salts include chloride, hydrobromide, hydrochloride, dihydrochloride, trihydrochloride, acetate, diacetate, trifluoroacetate, trifluoroacetic acid salt and the like. More particular embodiments include a chloride, hydrobromide, hydrochloride, dihydrochloride, trifluoroacetate, trifluoroacetic acid salt and the like.

Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33, 201-217; Anderson et al, *The Practice of Medicinal Chemistry* (1996), Academic Press, New York; and in *The Orange Book* (see, website for Food & Drug Administration, Washington, D.C.). These disclosures are incorporated herein by reference thereto.

Suitable basic salts include, but are not limited to, aluminum, ammonium, calcium, lithium, magnesium, potassium, sodium, zinc, and diethanolamine salts. Certain compounds described herein can also form pharmaceutically acceptable salts with organic bases (for example, organic amines) such as, but not limited to, dicyclohexylamines, tert-butyl amines and the like, and with various amino acids such as, but not limited to, arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the description herein and all such acid and base salts are considered equivalent to the free forms of the corresponding compounds for the purposes described herein.

Compounds of Formula I and forms thereof may further exist in a tautomeric form. All such tautomeric forms are contemplated herein as part of the present description.

The compounds of Formula (I) may contain asymmetric or chiral centers, and, therefore, may exist in different stereoisomeric forms. The present description is intended to include all stereoisomeric forms of the compounds of Formula (I) as well as mixtures thereof, including racemic mixtures.

The compounds of Formula (I) described herein may include one or more chiral centers, and as such may exist as racemic mixtures (R/S) or as substantially pure enantiomers and diastereomers. The compounds may also exist as substantially pure (R) or (S) enantiomers (when one chiral center is present). In one embodiment, the compounds of Formula (I) described herein are (S) isomers and may exist as enantiomerically pure compositions substantially comprising only the (S) isomer. In another embodiment, the compounds of Formula (I) described herein are (R) isomers and may exist as enantiomerically pure compositions substantially comprising only the (R) isomer. As one of skill in the art will recognize, when more than one chiral center is present, the compounds of Formula (I) described herein may also include portions described as an (R,R), (R,S), (S,R) or (S,S) isomer, as defined by IUPAC Nomenclature Recommendations.

As used herein, the term "substantially pure" refers to compounds consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect, a compound of Formula (I) is a substantially pure (S) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect, a compound of Formula (I) is a substantially pure (R) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, a "racemate" is any mixture of isometric forms that are not "enantiomerically pure", including mixtures such as, without limitation, in a ratio of about 50/50, about 60/40, about 70/30, about 80/20, about 85/15 or about 90/10.

In addition, the present description embraces all geometric and positional isomers. For example, if a compound of Formula (I) incorporates a double bond or a fused ring, both the cis- and trans-forms, as well as mixtures, are embraced within the scope of the description herein.

Diastereomeric mixtures can be separated into their individual diastereomers on the basis of their physical chemical differences by methods well known to those skilled in the art, such as, for example, by chromatography and/or fractional crystallization. Enantiomers can be separated by use of chiral HPLC column or other chromatographic methods known to those skilled in the art.

Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered part of this description.

All stereoisomer forms (for example, geometric isomers, optical isomers, positional isomers and the like) of the present compounds (including salts, solvates, esters and prodrugs and transformed prodrugs thereof) which may exist due to asymmetric carbons on various substituents, including enantiomeric forms (which may exist even in the absence of asymmetric carbons), rotameric forms, atropisomers, diastereomeric forms and regioisomeric forms are contemplated within the scope of the description herein. For example, if a compound of Formula (I) incorporates a double bond or a fused ring, both the cis- and trans-forms, as well as mixtures thereof, are embraced within the scope of the description herein. Also, for example, all keto-enol and imine-enamine tautomeric forms of the compounds are included in the description herein. Individual stereoisomers of the compounds of Formula (I) described herein may, for example, be substantially free of other isomers, or may be present in a racemic mixture, as described supra.

The use of the terms "salt," "prodrug" and "transformed prodrug" are intended to equally apply to the salts, prodrugs and transformed prodrugs of all contemplated isotopologues, stereoisomers, racemates or tautomers of the instant compounds.

The term "isotopologue" refers to isotopically-enriched compounds which are identical to those recited herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, fluorine and chlorine, such as $H^2$, $H^3$, $C^{13}$, $C^{14}$, $N^{15}$, $O^{18}$, $O^{17}$, $P^{31}$, $P^{32}$, $S^{35}$, $F^{18}$, $Cl^{35}$ and $Cl^{36}$, respectively, each of which is also within the scope of this description.

Certain isotopically-enriched compounds described herein (e.g., those labeled with $H^3$ and $C^{14}$) are useful in compound and/or substrate tissue distribution assays. Tritiated (i.e., $H^3$) and carbon-14 (i.e., $C^{14}$) isotopes are particularly preferred for their ease of preparation and detectability. Further, substitution with heavier isotopes such as deuterium (i.e., "deuterium enriched") may afford certain therapeutic advantages resulting from greater metabolic stability (e.g., increased in vivo half-life or reduced dosage requirements) and hence may be preferred in some circumstances. Isotopically-enriched compounds of Formula (I) can generally be prepared using procedures known to persons of ordinary skill in the art by substituting an appropriate isotopically-enriched reagent for a non-isotopically-enriched reagent.

When the compounds are enriched with deuterium, the deuterium-to-hydrogen ratio on the deuterated atoms of the molecule substantially exceeds the naturally occurring deuterium-to-hydrogen ratio.

An embodiment described herein may include an isotopologue form of the compound of Formula (I), wherein the isotopologue is substituted on one or more atom members of the compound of Formula (I) with one or more deuterium atoms in place of one or more hydrogen atoms.

An embodiment described herein may include a compound of Formula (I) and forms thereof, wherein a carbon atom may have from 1 to 3 hydrogen atoms optionally replaced with deuterium.

One or more compounds described herein may exist in unsolvated as well as solvated forms with pharmaceutically acceptable solvents such as water, ethanol, and the like, and the description herein is intended to embrace both solvated and unsolvated forms.

As used herein, the term "solvate" means a physical association of a compound described herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

One or more compounds described herein may optionally be converted to a solvate. Preparation of solvates is generally known. A typical, non-limiting process involves dissolving a compound in a desired amount of the desired solvent (organic or water or mixtures thereof) at a higher than ambient temperature, and cooling the solution at a rate sufficient to form crystals which are then isolated by standard methods. Analytical techniques such as, for example infrared spectroscopy, show the presence of the solvent (or water) in the crystals as a solvate (or hydrate).

As used herein, the term "hydrate" means a solvate wherein the solvent molecule is water.

Polymorphic crystalline and amorphous forms of the compounds of Formula (I), and of the salts, solvates, esters and prodrugs of the compounds of Formula (I), are further intended to be included in the scope of the compounds described herein.

Compound Uses

Compounds of Formula (I) or a form thereof that enhance inclusion of exon 7 of SMN2 into mRNA that is transcribed from the SMN2 gene are described herein. Such compounds of Formula (I) or a form thereof have been shown to enhance the inclusion of exon 7 of SMN2 into mRNA that is transcribed from the SMN2 gene using the assays described herein (see Biological example section, infra). Accordingly, compounds of Formula (I) or a form thereof have utility as enhancers for the inclusion of exon 7 of SMN2 into mRNA that is transcribed from the SMN2 gene.

Compounds of Formula (I) or a form thereof for enhancing inclusion of exon 7 of SMN1 into mRNA that is transcribed from the SMN1 gene are described herein. Such compounds of Formula (I) or a form thereof may enhance inclusion of exon 7 of SMN1 into mRNA that is transcribed from the SMN1 gene using, e.g., an SMN1 minigene assay. Accordingly, compounds of Formula (I) or a form thereof may have utility as enhancers for the inclusion of exon 7 of SMN1 into mRNA that is transcribed from the SMN1 gene.

In one aspect, provided herein are methods for modulating the inclusion of exon 7 of SMN2 into RNA transcribed from the SMN2 gene, comprising contacting a human cell with a compound of Formula (I) or a form thereof. In a specific embodiment, provided herein are methods for modulating the inclusion of exon 7 of SMN2 into RNA transcribed from the SMN2 gene, comprising contacting a human cell with a compound of Formula (I) or a form thereof that modulates the expression of an SMN2 minigene described herein or in International Publication No. WO2009/151546 or U.S. Patent Application Publication No. 2011/0086833, each of which is incorporated herein by reference in its entirety. In one embodiment, the minigene is a minigene described in the Examples of International Publication No. WO2009/151546 or U.S. Patent Application Publication No. 2011/0086833. In another embodiment, the minigene is the minigene described in Biological Example 1, infra. The human cell can be contacted with a compound of Formula (I) or a form thereof in vitro and/or in vivo, e.g., in a non-human animal or in a human. In a specific embodiment, the human cell is from or in a human. In another specific embodiment, the human cell is from or in a human SMA patient. In another specific embodiment, the human cell is from or in a human SMA patient, wherein SMA is caused by an inactivating mutation or deletion in the SMN1 gene on both chromosomes, resulting in a loss of SMN1 gene function. In another embodiment, the human cell is a human cell from a human SMA patient. In certain embodiments, the human cell is from a cell line, such as GM03813, GM00232, GM09677, and/or GM23240 (available from Coriell Institute). In one embodiment, the compound is a compound of Formula (I) or a form thereof.

In a specific embodiment, provided herein is a method for enhancing the inclusion of exon 7 of SMN2 into mRNA that is transcribed from the SMN2 gene, comprising contacting a human cell with a compound of Formula (I) or a form thereof. In another embodiment, provided herein is a method for enhancing the inclusion of exon 7 of SMN2 into mRNA that is transcribed from the SMN2 gene, comprising contacting a human cell with a compound of Formula (I) or a form thereof that enhances the expression of an SMN2 minigene described herein or in International Publication No. WO2009/151546 or U.S. Patent Application Publication No. 2011/0086833, each of which is incorporated herein by reference in its entirety. In one embodiment, the minigene is a minigene described in the Examples of International Publication No. WO2009/151546 or U.S. Patent Application Publication No. 2011/0086833. In another embodiment, the minigene is the minigene described in Biological Example 1, infra. The human cell can be contacted with a compound of Formula (I) or a form thereof in vitro and/or in vivo, e.g., in a non-human animal or in a human. In a specific embodiment, the human cell is from or in a human. In another specific embodiment, the human cell is from or in a human SMA patient. In another specific embodiment, the human cell is from or in a human SMA patient, wherein SMA is caused by an inactivating mutation or deletion in the SMN1 gene on both chromosomes, resulting in a loss of SMN1 gene function. In another embodiment, the human cell is a human cell from a human SMA patient. In certain embodiments, the human cell is from a cell line, such as GM03813, GM00232, GM09677, and/or GM23240 (available from Coriell Institute). In one embodiment, the compound is a compound of Formula (I) or a form thereof.

In another aspect, provided herein are methods for enhancing the inclusion of exon 7 of SMN1 into RNA transcribed from the SMN1 gene, comprising contacting a human cell with a compound of Formula (I) or a form thereof. In a specific embodiment, provided herein are methods for enhancing the inclusion of exon 7 of SMN1 into RNA transcribed from the SMN1 gene, comprising contacting a human cell with a compound of Formula (I) or a form thereof. In another specific embodiment, provided herein are methods for enhancing the inclusion of exon 7 of SMN1 into RNA transcribed from the SMN1 gene, comprising contacting a human cell with a compound of Formula (I) or a form thereof that modulates the expression of an SMN1 minigene described in International Publication No. WO2009/151546 or U.S. Patent Application Publication No. 2011/0086833, each of which is incorporated herein by reference in its entirety. In one embodiment, the minigene is a minigene described in the Examples of International Publication No. WO2009/151546 or U.S. Patent Application Publication No. 2011/0086833. The human cell can be contacted with a compound of Formula (I) or a form thereof in vitro and/or in vivo, e.g., in a non-human animal or in a human. In a specific embodiment, the human cell is from or in a human. In another specific embodiment, the human cell is from or in a human SMA patient. In one embodiment, the compound is a compound of Formula (I) or a form thereof.

In specific embodiments, provided herein are methods for enhancing the inclusion of exon 7 of SMN1 and SMN2 into RNA transcribed from the SMN1 and SMN2 genes, comprising contacting a human cell with a compound of Formula (I) or a form thereof. The human cell can be contacted with a compound of Formula (I) or a form thereof in vitro and/or in vivo, e.g., in a non-human animal or in a human. In a specific embodiment, the human cell is from or in a human. In another specific embodiment, the human cell is from or in a human SMA patient. In one embodiment, the compound is a compound of Formula (I) or a form thereof.

In another aspect, provided herein is a method for modulating the inclusion of exon 7 of SMN2 into RNA transcribed from the SMN2 gene, comprising administering to a non-human animal model for SMA a compound of Formula (I) or a form thereof. In a specific embodiment, provided herein is a method for modulating the inclusion of exon 7 of SMN2 into RNA transcribed from the SMN2 gene, comprising administering to a non-human animal model for SMA a compound of Formula (I) or a form thereof that modulates the expression of an SMN2 minigene described herein or in International Publication No. WO2009/151546 or U.S. Patent Application Publication No. 2011/0086833, each of which is incorporated herein by reference in its entirety. In one embodiment, the minigene is a minigene described in the Examples of International Publication No. WO2009/151546 or U.S. Patent Application Publication No. 2011/0086833. In another embodiment, the minigene is the minigene described in Biological Example 1, infra. In a specific embodiment, the compound is a compound of Formula (I) or a form thereof.

In a specific embodiment, provided herein is a method for enhancing the inclusion of exon 7 of SMN2 into mRNA that is transcribed from the SMN2 gene, comprising administering to a non-human animal model for SMA a compound of Formula (I) or a form thereof. In another specific embodiment, provided herein is a method for enhancing the inclusion of exon 7 of SMN2 into mRNA that is transcribed from the SMN2 gene, comprising administering to a non-human animal model for SMA a compound of Formula (I) or a form thereof that enhances the expression of an SMN2 minigene described herein or in International Publication No. WO2009/151546 or U.S. Patent Application Publication No. 2011/0086833, each of which is incorporated herein by reference in its entirety. In one embodiment, the minigene is a minigene described in the Examples of International Publication No. WO2009/151546 or U.S. Patent Application Publication No. 2011/0086833. In another embodiment, the minigene is the minigene described in Biological Example 1, infra. In a specific embodiment, the compound is a compound of Formula (I) or a form thereof.

In another aspect, provided herein is a method for enhancing the inclusion of exon 7 of SMN1 into RNA transcribed from the SMN1 gene, comprising administering to a non-human animal model for SMA a compound of Formula (I) or a form thereof. In a specific embodiment, provided herein is a method for enhancing the inclusion of exon 7 of SMN1 into RNA transcribed from the SMN1 gene, comprising administering to a non-human animal model for SMA a compound of Formula (I) or a form thereof that modulates the expression of an SMN1 minigene described herein or in International Publication No. WO2009/151546 or U.S. Patent Application Publication No. 2011/0086833, each of which is incorporated herein by reference in its entirety. In one embodiment, the minigene is a minigene described in the Examples of International Publication No. WO2009/151546 or U.S. Patent Application Publication No. 2011/0086833. In a specific embodiment, the compound is a compound of Formula (I) or a form thereof.

In specific embodiments, provided herein is a method for enhancing the inclusion of exon 7 of SMN1 and SMN2 into RNA transcribed from the SMN1 and SMN2 genes, comprising administering to a non-human animal model for SMA a compound of Formula (I) or a form thereof. In a specific embodiment, the compound is a compound of Formula (I) or a form thereof.

In another aspect, provided herein is a method for increasing the amount of Smn protein, comprising contacting a human cell with a compound of Formula (I) or a form thereof. In a specific embodiment, provided herein is a method for increasing the amount of Smn protein, comprising contacting a human cell with a compound of Formula (I) that enhances the inclusion of exon 7 of SMN2 into mRNA that is transcribed from the SMN2 gene. In another specific embodiment, provided herein is a method for increasing the amount of Smn protein, comprising contacting a human cell with a compound of Formula (I) that enhances the inclusion of exon 7 of SMN1 and/or SMN2 into mRNA that is transcribed from the SMN1 and/or SMN2 gene. The human cell can be contacted with a compound of Formula (I) or a form thereof in vitro and/or in vivo, e.g., in a non-human animal or in a human. In a specific embodiment, the human cell is from or in a human. In another specific embodiment, the human cell is from or in a human SMA patient. In another specific embodiment, the human cell is from or in a human SMA patient, wherein SMA is caused by an inactivating mutation or deletion in the SMN1 gene on both chromosomes, resulting in a loss of SMN1 gene function. In another embodiment, the human cell is a human cell from a human SMA patient. In certain embodiments, the human cell is from a cell line, such as GM03813, GM00232, GM09677, and/or GM23240 (available from Coriell Institute). In one embodiment, the compound is a compound of Formula (I) or a form thereof.

In another aspect, provided herein is a method for increasing the amount of Smn protein, comprising administering to a non-human animal model for SMA a compound of Formula (I) or a form thereof. In a specific embodiment, provided herein is a method for increasing the amount of Smn protein, comprising administering to a non-human animal model for SMA a compound of Formula (I) that enhances the inclusion of exon 7 of SMN2 into mRNA that is transcribed from the SMN2 gene in, e.g., a cell-based or cell-free assay, such as described in the Biological Examples, infra. In another specific embodiment, provided herein is a method for increasing the amount of Smn protein, comprising administering to a non-human animal model for SMA a compound of Formula (I) that enhances the inclusion of exon 7 of SMN1 and/or SMN2 into mRNA that is transcribed from the SMN1 and/or SMN2 gene in, e.g., a cell-based or cell-free assay.

In one embodiment, the compound of Formula (I) enhances the expression of a minigene described herein or in International Publication No. WO2009/151546 or U.S. Patent Application Publication No. 2011/0086833, each of which is incorporated herein by reference in its entirety. In a specific embodiment, the compound of Formula (I) enhances the expression of a minigene described in the Examples of International Publication No. WO2009/151546 or U.S. Patent Application Publication No. 2011/0086833. In another specific embodiment, the compound of Formula (I) enhances the expression of a minigene described in Biological Example 1, infra. In one embodiment, the compound is a compound of Formula (I) or a form thereof.

In one embodiment, provided herein is the use of a compound of Formula (I) or a form thereof for the preparation of a medicament that enhances the inclusion of exon 7 of SMN2 into mRNA that is transcribed from the SMN2 gene. In another embodiment, provided herein is the use of a compound of Formula (I) or a form thereof for the preparation of a medicament that enhances the inclusion of exon 7 of SMN2 into mRNA that is transcribed from the SMN2 gene, thereby increasing expression of Smn protein in a human subject in need thereof. In a particular embodiment, the compound of Formula (I) or a form thereof enhances the inclusion of exon 7 of SMN2 into mRNA that is transcribed from the SMN2 gene in an assay described herein (see, e.g., the Biological Examples, infra). In a specific embodiment, the compound is a compound of Formula (I) or a form thereof.

In one embodiment, provided herein is the use of a compound of Formula (I) or a form thereof for the preparation of a medicament that enhances the inclusion of exon 7 of SMN1 and/or SMN2 into mRNA that is transcribed from the SMN1 and/or SMN2 gene. In another embodiment, provided herein is the use of a compound of Formula (I) or a form thereof for the preparation of a medicament that enhances the inclusion of exon 7 of SMN1 and/or SMN2 into mRNA that is transcribed from the SMN1 and/or SMN2 gene, thereby increasing expression of Smn protein in a human subject in need thereof. In a specific embodiment, the compound is a compound of Formula (I) or a form thereof.

In another aspect, provided herein are methods for enhancing the inclusion of exon 7 of SMN2 into mRNA that is transcribed from the SMN2 gene in a human subject in need thereof, comprising administering to the human subject an effective amount of a compound of Formula (I) or a form thereof. In a specific embodiment, provided herein is a method for enhancing the inclusion of exon 7 of SMN2 into mRNA that is transcribed from the SMN2 gene in a human subject in need thereof, comprising administering to the human subject an effective amount a compound of Formula (I) or a form thereof that enhances the inclusion of exon 7 of SMN2 into mRNA that is transcribed from the SMN2 gene as determined in an assay described herein (see, e.g., the Biological Examples, infra). In specific embodiments, the effective amount of the compound of Formula (I) or a form thereof is administered to the human subject in a pharmaceutical composition comprising a pharmaceutically acceptable carrier, excipient or diluent. In a particular embodiment, the compound of Formula (I) or a form thereof enhances the inclusion of exon 7 of SMN2 into mRNA that is transcribed from the SMN2 gene in an assay described herein (see, e.g., the Biological Examples, infra). In a specific embodiment, the human subject is a human SMA patient. In another specific embodiment, the human subject is a human SMA patient, wherein SMA is caused by an inactivating mutation or deletion in the SMN1 gene on both chromosomes, resulting in a loss of SMN1 gene function. In one embodiment, the compound is a compound of Formula (I) or a form thereof.

In another aspect, provided herein are methods for enhancing the inclusion of exon 7 of SMN1 into mRNA that is transcribed from the SMN1 gene in a human subject in need thereof, comprising administering to the human subject an effective amount of a compound of Formula (I) or a form thereof. In a particular embodiment, the compound of Formula (I) or a form thereof enhances the inclusion of exon 7 of SMN1 into mRNA that is transcribed from the SMN1 gene in an assay described in International Publication No. WO2009/151546 or U.S. Patent Application Publication No. 2011/0086833. In specific embodiments, the effective amount of the compound of Formula (I) or a form thereof is administered to the human subject in a pharmaceutical composition comprising a pharmaceutically acceptable carrier, excipient or diluent. In a specific embodiment, the human subject is a human SMA patient. In one embodiment, the compound is a compound of Formula (I) or a form thereof.

In another aspect, provided herein is a method for enhancing the inclusion of exon 7 of SMN1 and SMN2 into mRNA that is transcribed from the SMN1 and SMN2 genes in a human subject in need thereof, comprising administering to the human subject an effective amount a compound of Formula (I) or a form thereof. In a particular embodiment, the compound of Formula (I) or a form thereof enhances the inclusion of exon 7 of SMN1 into mRNA that is transcribed from the SMN1 gene in an assay(s) described in International Publication No. WO2009/151546 or U.S. Patent Application Publication No. 2011/0086833 (see, e.g., the Examples in those publications), each of which is incorporated herein by reference in its entirety. In specific embodiments, the effective amount of the compound of Formula (I) or a form thereof is administered to the human subject in a pharmaceutical composition comprising a pharmaceutically acceptable carrier, excipient or diluent. In a specific embodiment, the human subject is a human SMA patient. In another specific embodiment, the human subject is a human SMA patient, wherein SMA is caused by an inactivating mutation or deletion in the SMN1 gene on both chromosomes, resulting in a loss of SMN1 gene function. In one embodiment, the compound is a compound of Formula (I) or a form thereof.

In another aspect, provided herein are methods for enhancing the expression of Smn protein in a human subject in need thereof, comprising administering to the human subject an effective amount of a compound of Formula (I) or a form thereof. In a specific embodiment, provided herein is a method for enhancing the expression of Smn protein in a human subject in need thereof, comprising administering to the human subject an effective amount a compound of Formula (I) or a form thereof that enhances the inclusion of exon 7 of SMN2 into mRNA that is transcribed from the SMN2 gene. In another specific embodiment, provided herein is a method for enhancing the expression of Smn protein in a human subject in need thereof, comprising administering to the human subject an effective amount a compound of Formula (I) or a form thereof that enhances the inclusion of exon 7 of SMN1 and/or SMN2 into mRNA that is transcribed from the SMN1 and/or SMN2 gene. In specific embodiments, the effective amount of the compound of Formula (I) or a form thereof is administered to the human subject in a pharmaceutical composition comprising a pharmaceutically acceptable carrier, excipient or diluent. In a particular embodiment, the compound of Formula (I) or a form thereof enhances the inclusion of exon 7 of SMN1 and/or SMN2 into mRNA that is transcribed from the SMN1 and/or SMN2 gene in an assay described herein (see, e.g., the Biological Examples, infra) or in International Publication No. WO2009/151546 or U.S. Patent Application Publication No. 2011/0086833 (see, e.g., the Examples in those publications), each of which is incorporated herein by reference in its entirety.

In a specific embodiment, the human subject is a human SMA patient. In another specific embodiment, the human subject is a human SMA patient, wherein SMA is caused by an inactivating mutation or deletion in the teleomeric copy of the SMN1 gene in both chromosomes, resulting in a loss of SMN1 gene function. In one embodiment, the compound is a compound of Formula (I) or a form thereof.

In another embodiment, provided herein is the use of a compound of Formula (I) or a form thereof for the preparation of a medicament that enhances expression of Smn protein in a human subject in need thereof. In a particular embodiment, the compound of Formula (I) or a form thereof enhances the inclusion of exon 7 of SMN2 into mRNA that is transcribed from the SMN2 gene as determined in an assay described herein (see, e.g., the Biological Examples, infra). In another embodiment, the compound of Formula (I) or a form thereof enhances the inclusion of exon 7 of SMN1 and/or SMN2 into mRNA that is transcribed from the SMN1 and/or SMN2 gene as determined in an assay described herein (see, e.g., the Biological Examples, infra) or in International Publication No. WO2009/151546 or U.S. Patent Application Publication No. 2011/0086833 (see, e.g., the Examples in those publications), each of which is incorporated herein by reference in its entirety. In a specific embodiment, the compound is a compound of Formula (I) or a form thereof.

In another aspect, provided herein are methods for treating spinal muscular atrophy (SMA), comprising administering to a subject an effective amount of a compound of Formula (I) or a form thereof. In a specific embodiment, provided herein is a method for treating SMA in a human subject in need thereof, comprising administering to the subject an effective amount of a compound of Formula (I) or a form thereof. In another specific embodiment, provided herein is a method for treating SMA in a human subject in need thereof, comprising administering to the subject a pharmaceutical composition comprising an effective amount of a compound of Formula (I) or a form thereof, and a pharmaceutically acceptable carrier, excipient or diluent. In one embodiment, the compound is a compound of Formula (I) or a form thereof.

In another embodiment, provided herein is a method for treating SMA in a human subject in need thereof, comprising administering to the subject an effective amount of a compound of Formula (I) or a form thereof that enhances the inclusion of exon 7 of SMN2 into mRNA that is transcribed from the SMN2 gene. In a specific embodiment, provided herein is a method for treating SMA in a human subject in need thereof, comprising administering to the subject a pharmaceutical composition comprising an effective amount of a compound of Formula (I) or a form thereof that enhances the inclusion of exon 7 of SMN2 into mRNA that is transcribed from the SMN2 gene, and a pharmaceutically acceptable carrier, excipient or diluent. In another specific embodiment, provided herein is a method for treating SMA in a human subject in need thereof, comprising administering to the subject a pharmaceutical composition comprising an effective amount of a compound of Formula (I) or a form thereof that enhances the inclusion of exon 7 of SMN1 and/or SMN2 into mRNA that is transcribed from the SMN1 and/or SMN2 gene, and a pharmaceutically acceptable carrier, excipient or diluent. In a particular embodiment, the compound of Formula (I) or a form thereof enhances the inclusion of exon 7 of SMN2 into mRNA that is transcribed from the SMN2 gene in an assay described herein (see, e.g., the Biological Examples, infra). In another embodiment, the compound of Formula (I) or a form thereof enhances the inclusion of exon 7 of SMN1 and/or SMN2 into mRNA that is transcribed from the SMN1 and/or SMN2 gene as determined in an assay described herein (see, e.g., the Biological Examples, infra) or in International Publication No. WO2009/151546 or U.S. Patent Application Publication No. 2011/0086833 (see, e.g., the Examples in those publications), each of which is incorporated herein by reference in its entirety. In a specific embodiment, the compound is a compound of Formula (I) or a form thereof.

In another embodiment, provided herein is the use of a compound of Formula (I) or a form thereof in the manufacture of a medicament for treating SMA in a human subject in need thereof. In a particular embodiment, the compound of Formula (I) or a form thereof enhances the inclusion of exon 7 of SMN2 into mRNA that is transcribed from the SMN2 gene as determined in an assay described herein (see, e.g., the Biological Examples, infra). In another embodiment, the compound of Formula (I) or a form thereof enhances the inclusion of exon 7 of SMN1 and/or SMN2 into mRNA that is transcribed from the SMN1 and/or SMN2 gene as determined in an assay described herein (see, e.g., the Biological Examples, infra) or in International Publication No. WO2009/151546 or U.S. Patent Application Publication No. 2011/0086833 (see, e.g., the Examples in those publications), each of which is incorporated herein by reference in its entirety. In a specific embodiment, the compound is a compound of Formula (I) or a form thereof.

In an embodiment of a use or method provided herein, compounds of Formula (I) or a form thereof are used in combination with one or more additional agents. A compound(s) of Formula (I) or a form thereof can be administered to a subject or contacted with a cell prior to, concurrently with, or subsequent to administering to the subject or contacting the cell with an additional agent(s). A compound(s) of Formula (I) or a form thereof and an additional agent(s) can be administered to a subject or contacted with a cell in single composition or different compositions. In a specific embodiments, a compound(s) of Formula (I) or a form thereof is used in combination with gene replacement of SMN1 (using, e.g., viral delivery vectors). In another specific embodiments, a compound(s) of Formula (I) or a form thereof are used in combination with cell replacement using differentiated SMN1$^{+/+}$ and/or SMN2$^{+/+}$ stem cells. In another specific embodiments, a compound(s) of Formula (I) or a form thereof are used in combination with cell replacement using differentiated SMN1$^{+/+}$ stem cells. In another specific embodiments, a compound(s) of Formula (I) or a form thereof are used in combination with cell replacement using differentiated SMN2$^{+/+}$ stem cells. In another specific embodiment, a compound(s) of Formula (I) or a form thereof are used in combination with aclarubicin. In another specific embodiment, a compound(s) of Formula (I) or a form thereof are used in combination with a transcription activator such as a histone deacetylase ("HDAC") inhibitor (e.g., butyrates, valproic acid, and hydroxyurea), and mRNA stabilizers (e.g., mRNA decapping inhibitor RG3039 from Repligen).

In one embodiment, provided herein is the use of compounds of Formula (I) or a form thereof in combination with supportive therapy, including respiratory, nutritional or rehabilitation care.

In certain embodiments, treating SMA with a compound of Formula (I) or a form thereof (alone or in combination with an additional agent) has a therapeutic effect and/or beneficial effect. In a specific embodiment, treating SMA with a compound of Formula (I) or a form thereof (alone or in combination with an additional agent) results in one, two or more of the following effects: (i) reduces or ameliorates the severity of SMA; (ii) delays onset of SMA; (iii) inhibits the progression of SMA; (iv) reduces hospitalization of a subject; (v) reduces hospitalization length for a subject; (vi)

increases the survival of a subject; (vii) improves the quality of life of a subject; (viii) reduces the number of symptoms associated with SMA; (ix) reduces or ameliorates the severity of a symptom(s) associated with SMA; (x) reduces the duration of a symptom associated with SMA; (xi) prevents the recurrence of a symptom associated with SMA; (xii) inhibits the development or onset of a symptom of SMA; and/or (xiii) inhibits of the progression of a symptom associated with SMA.

Symptoms of SMA include muscle weakness, poor muscle tone, weak cry, weak cough, limpness or a tendency to flop, difficulty sucking or swallowing, difficulty breathing, accumulation of secretions in the lungs or throat, clenched fists with sweaty hand, flickering/vibrating of the tongue, head often tilted to one side, even when lying down, legs that tend to be weaker than the arms, legs frequently assuming a "frog legs" position, feeding difficulties, increased susceptibility to respiratory tract infections, bowel/bladder weakness, lower-than-normal weight, inability to sit without support, failure to walk, failure to crawl, and hypotonia, areflexia, and multiple congenital contractures (arthrogryposis) associated with loss of anterior horn cells.

In a specific embodiment, treating SMA with a compound of Formula (I) or a form thereof (alone or in combination with an additional agent) results in one, two or more of the following effects: (i) a reduction in the loss of muscle strength; (ii) an increase in muscle strength; (iii) a reduction in muscle atrophy; (iv) a reduction in the loss of motor function; (v) an increase in motor neurons; (vii) a reduction in the loss of motor neurons; (viii) protection of SMN deficient motor neurons from degeneration; (ix) an increase in motor function; (x) an increase in pulmonary function; and/or (xi) a reduction in the loss of pulmonary function.

In another embodiment, treating SMA with a compound of Formula (I) or a form thereof (alone or in combination with an additional agent) results in the functional ability or helps retain the functional ability for a human infant or a human toddler to sit up. In another embodiment, treating SMA with a compound of Formula (I) or a form thereof (alone or in combination with an additional agent) results in the functional ability or helps retain the functional ability for a human infant, a human toddler, a human child or a human adult to stand up unaided. In another embodiment, treating SMA with a compound of Formula (I) or a form thereof (alone or in combination with an additional agent) results in the functional ability or helps retain the functional ability for a human infant, a human toddler, a human child or a human adult to walk unaided. In another embodiment, treating SMA with a compound of Formula (I) or a form thereof (alone or in combination with an additional agent) results in the functional ability or helps retain the functional ability for a human infant, a human toddler, a human child or a human adult to run unaided. In another embodiment, treating SMA with a compound of Formula (I) or a form thereof (alone or in combination with an additional agent) results in the functional ability or helps retain the functional ability for a human infant, a human toddler, a human child or a human adult to breathe unaided. In another embodiment, treating SMA with a compound of Formula (I) or a form thereof (alone or in combination with an additional agent) results in the functional ability or helps retain the functional ability for a human infant, a human toddler, a human child or a human adult to turn during sleep unaided. In another embodiment, treating SMA with a compound of Formula (I) or a form thereof (alone or in combination with an additional agent) results in the functional ability or helps retain the functional ability for a human infant, a human toddler, a human child or a human adult to swallow unaided.

In certain embodiments, a primer and/or probe described below in the Biological Examples (e.g., SMN primers such as SEQ ID NO. 1, 7, 8, 11 or 13 and/or SEQ ID NO. 2, 9 or 12, and SMN probes such as a SEQ ID NO. 3 or 10) is used in an assay, such as RT-PCR, RT-qPCR, endpoint RT-PCR, PCR, qPCR, rolling circle amplification, Northern blot or Southern blot, to determine whether a compound of Formula (I) or a form thereof enhances the inclusion of exon 7 of SMN1 and/or SMN2 into mRNA that is transcribed from an SMN1 and/or SMN2 gene. In some embodiments, a primer and/or probe described below in the Biological Examples (e.g., SMN primers such as SEQ ID NO. 1, 7, 8, 11 or 13 and/or SEQ ID NO. 2, 9 or 12, and SMN probes such as a SEQ ID NO. 3 or 10) is used in an assay, such as RT-PCR, RT-qPCR, endpoint RT-PCR, PCR, qPCR, rolling circle amplification, Northern blot or Southern blot, or a pharmaceutical or assay kit as described infra, to monitor patient responses to a compound of Formula (I) or a form thereof.

In one embodiment, a compound of Formula (I):

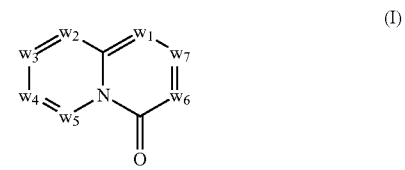

(I)

or a form thereof is used as described herein, wherein:
$w_1$ and $w_5$ are independently C—$R_a$ or N;
$w_2$ is C—$R_b$ or N;
$w_3$, $w_4$ and $w_7$ are independently C—$R_1$, C—$R_2$, C—$R_a$ or N;
$w_6$ is C—$R_1$, C—$R_2$, C—$R_c$ or N;
wherein one of $w_3$, $w_4$, $w_6$ and $w_7$ is C—$R_1$ and one other of $w_3$, $w_4$, $w_6$ and $w_7$ is C—$R_2$, provided that,
when $w_3$ is C—$R_1$, then $w_6$ is C—$R_2$ and $w_4$ and $w_7$ are independently C—$R_a$ or N; or,
when $w_3$ is C—$R_2$, then $w_6$ is C—$R_1$ and $w_4$ and $w_7$ are independently C—$R_a$ or N; or,
when $w_4$ is C—$R_1$, then $w_7$ is C—$R_2$ and $w_3$ is C—$R_a$ or N and $w_6$ is C—$R_c$ or N; or,
when $w_4$ is C—$R_2$, then $w_7$ is C—$R_1$ and $w_3$ is C—$R_a$ or N and $w_6$ is C—$R_c$ or N; and,
wherein any one, two or three of $w_1$, $w_2$, $w_3$, $w_4$, $w_5$, $w_6$ and $w_7$ may optionally be N;
$R_1$ is $C_{1-8}$alkyl, amino, $C_{1-8}$alkyl-amino, $(C_{1-8}$alkyl$)_2$-amino, $C_{1-8}$alkoxy-$C_{1-8}$alkyl-amino, $(C_{1-8}$alkoxy-$C_{1-8}$alkyl$)_2$-amino, $(C_{1-8}$alkoxy-$C_{1-8}$alkyl$)(C_{1-8}$alkyl$)$amino, amino-$C_{1-8}$alkyl, $C_{1-8}$alkyl-amino-$C_{1-8}$alkyl, $(C_{1-8}$alkyl$)_2$-amino-$C_{1-8}$alkyl, $C_{1-8}$alkoxy-$C_{1-8}$alkyl-amino-$C_{1-8}$alkyl, $(C_{1-8}$alkoxy-$C_{1-8}$alkyl$)_2$-amino-$C_{1-8}$alkyl, $(C_{1-8}$alkoxy-$C_{1-8}$alkyl$)(C_{1-8}$alkyl$)$amino-$C_{1-8}$alkyl, amino-$C_{1-8}$alkyl-amino, (amino-$C_{1-8}$alkyl$)_2$-amino, (amino-$C_{1-8}$alkyl$)(C_{1-8}$alkyl$)$amino, $C_{1-8}$alkyl-amino-$C_{1-8}$alkyl-amino, $(C_{1-8}$alkyl-amino-$C_{1-8}$alkyl$)_2$-amino, $(C_{1-8}$alkyl-amino-$C_{1-8}$alkyl$)(C_{1-8}$alkyl$)$amino, $(C_{1-8}$alkyl$)_2$-amino-$C_{1-8}$alkyl-amino, $[(C_{1-8}$alkyl$)_2$-amino-$C_{1-8}$alkyl$](C_{1-8}$alkyl$)$amino, amino-$C_{1-8}$alkoxy, $C_{1-8}$alkyl-amino-$C_{1-8}$alkoxy, $(C_{1-8}$alkyl$)_2$-amino-$C_{1-8}$alkoxy, $C_{1-8}$alkoxy-$C_{1-8}$alkyl-amino-$C_{1-8}$alkoxy, $C_{1-8}$alkoxy-$C_{1-8}$alkyl-amino-$C_{1-8}$alkoxy, $(C_{1-8}$alkoxy-$C_{1-8}$alkyl$)(C_{1-8}$alkyl$)$amino-$C_{1-8}$alkoxy, amino-$C_{2-8}$alkenyl, $C_{1-8}$alkyl-amino-$C_{2-8}$alkenyl, $(C_{1-8}$ alkyl)$_2$-amino-C$_{2-8}$alkenyl, amino-C$_{2-8}$alkynyl, C$_{1-8}$alkyl-amino-C$_{2-8}$alkynyl, (C$_{1-8}$alkyl)$_2$-amino-C$_{2-8}$alkynyl, halo-C$_{1-8}$alkyl-amino, (halo-C$_{1-8}$alkyl)$_2$-amino, (halo-C$_{1-8}$alkyl)(C$_{1-8}$alkyl)amino, hydroxy-C$_{1-8}$alkyl, hydroxy-C$_{1-8}$alkoxy-C$_{1-8}$alkyl, hydroxy-C$_{1-8}$alkyl-amino, (hydroxy-C$_{1-8}$alkyl)$_2$-amino, (hydroxy-C$_{1-8}$alkyl)(C$_{1-8}$alkyl)amino, hydroxy-C$_{1-8}$alkyl-amino-C$_{1-8}$alkyl, (hydroxy-C$_{1-8}$alkyl)$_2$-amino-C$_{1-8}$alkyl, (hydroxy-C$_{1-8}$alkyl)(C$_{1-8}$alkyl)amino-C$_{1-8}$alkyl, hydroxy-C$_{1-8}$alkyl-amino-C$_{1-8}$alkoxy, (hydroxy-C$_{1-8}$alkyl)$_2$-amino-C$_{1-8}$alkoxy, (hydroxy-C$_{1-8}$alkyl)(C$_{1-8}$alkyl)amino-C$_{1-8}$alkoxy, hydroxy-C$_{1-8}$alkyl-amino-C$_{1-8}$alkyl-amino, (hydroxy-C$_{1-8}$alkyl-amino-C$_{1-8}$alkyl)$_2$-amino, (hydroxy-C$_{1-8}$alkyl)$_2$-amino-C$_{1-8}$alkyl-amino, (hydroxy-C$_{1-8}$alkyl-amino-C$_{1-8}$alkyl)(C$_{1-8}$alkyl)amino, (hydroxy-C$_{1-8}$alkyl)(C$_{1-8}$alkyl)amino-C$_{1-8}$alkyl-amino, [(hydroxy-C$_{1-8}$alkyl)$_2$-amino-C$_{1-8}$alkyl](C$_{1-8}$alkyl)amino, [(hydroxy-C$_{1-8}$alkyl)(C$_{1-8}$alkyl)amino-C$_{1-8}$alkyl](C$_{1-8}$alkyl)amino, heterocyclyl, heterocyclyl-C$_{1-8}$alkyl, heterocyclyl-C$_{1-8}$alkoxy, heterocyclyl-amino, (heterocyclyl)(C$_{1-8}$alkyl)amino, heterocyclyl-amino-C$_{1-8}$alkyl, heterocyclyl-C$_{1-8}$alkyl-amino, (heterocyclyl-C$_{1-8}$alkyl)$_2$-amino, (heterocyclyl-C$_{1-8}$alkyl)(C$_{1-8}$alkyl)amino, heterocyclyl-C$_{1-8}$alkyl-amino-C$_{1-8}$alkyl, (heterocyclyl-C$_{1-8}$alkyl)$_2$-amino-C$_{1-8}$alkyl, (heterocyclyl-C$_{1-8}$alkyl)(C$_{1-8}$alkyl)amino-C$_{1-8}$alkyl, heterocyclyl-oxy, heterocyclyl-carbonyl, heterocyclyl-carbonyl-oxy, C$_{3-14}$cycloalkyl, aryl-C$_{1-8}$alkyl-amino, (aryl-C$_{1-8}$alkyl)$_2$-amino, (aryl-C$_{1-8}$alkyl)(C$_{1-8}$alkyl)amino, aryl-C$_{1-8}$alkyl-amino-C$_{1-8}$alkyl, (aryl-C$_{1-8}$alkyl)$_2$-amino-C$_{1-8}$alkyl, (aryl-C$_{1-8}$alkyl)(C$_{1-8}$alkyl)amino-C$_{1-8}$alkyl, heteroaryl, heteroaryl-C$_{1-8}$alkyl, heteroaryl-C$_{1-8}$alkoxy, heteroaryl-amino, heteroaryl-C$_{1-8}$alkyl-amino, (heteroaryl-C$_{1-8}$alkyl)$_2$-amino, (heteroaryl-C$_{1-8}$alkyl)(C$_{1-8}$alkyl)amino, heteroaryl-C$_{1-8}$alkyl-amino-C$_{1-8}$alkyl, (heteroaryl-C$_{1-8}$alkyl)$_2$-amino-C$_{1-8}$alkyl or (heteroaryl-C$_{1-8}$alkyl)(C$_{1-8}$alkyl)amino-C$_{1-8}$alkyl;

wherein, each instance of heterocyclyl, C$_{3-14}$cycloalkyl, aryl and heteroaryl is optionally substituted with one, two or three R$_3$ substituents and optionally, with one additional R$_4$ substituent; or, wherein, each instance of heterocyclyl, C$_{3-14}$cycloalkyl, aryl and heteroaryl is optionally substituted with one, two, three or four R$_3$ substituents;

R$_2$ is aryl, aryl-amino, aryl-amino-carbonyl, heterocyclyl, heteroaryl or heteroaryl-amino;

wherein, each instance of aryl, heterocyclyl and heteroaryl is optionally substituted with one, two or three R$_6$ substituents and optionally, with one additional R$_7$ substituent;

R$_a$ is, in each instance, independently selected from hydrogen, halogen or C$_{1-8}$alkyl;

R$_b$ is hydrogen, halogen, C$_{1-8}$alkyl or C$_{1-8}$alkoxy;

R$_3$ is, in each instance, independently selected from cyano, halogen, hydroxy, oxo, C$_{1-8}$alkyl, halo-C$_{1-8}$alkyl, C$_{1-8}$alkyl-carbonyl, C$_{1-8}$alkoxy, halo-C$_{1-8}$alkoxy, C$_{1-8}$alkoxy-C$_{1-8}$alkyl, C$_{1-8}$alkoxy-carbonyl, amino, C$_{1-8}$alkyl-amino, (C$_{1-8}$alkyl)$_2$-amino, amino-C$_{1-8}$alkyl, C$_{1-8}$alkyl-amino-C$_{1-8}$alkyl, (C$_{1-8}$alkyl)$_2$-amino-C$_{1-8}$alkyl, amino-C$_{1-8}$alkyl-amino, C$_{1-8}$alkyl-amino-C$_{1-8}$alkyl-amino, (C$_{1-8}$alkyl-amino-C$_{1-8}$alkyl)$_2$-amino, (C$_{1-8}$alkyl)$_2$-amino-C$_{1-8}$alkyl-amino, [(C$_{1-8}$alkyl)$_2$-amino-C$_{1-8}$alkyl]2-amino, (C$_{1-8}$alkyl-amino-C$_{1-8}$alkyl)(C$_{1-8}$alkyl)amino, [(C$_{1-8}$alkyl)$_2$-amino-C$_{1-8}$alkyl](C$_{1-8}$alkyl)amino, C$_{1-8}$alkoxy-C$_{1-8}$alkyl-amino, (C$_{1-8}$alkoxy-C$_{1-8}$alkyl)$_2$-amino, (C$_{1-8}$alkoxy-C$_{1-8}$alkyl) (C$_{1-8}$alkyl)amino, C$_{1-8}$alkyl-carbonyl-amino, C$_{1-8}$alkoxy-carbonyl-amino, hydroxy-C$_{1-8}$alkyl, hydroxy-C$_{1-8}$alkoxy-C$_{1-8}$alkyl, hydroxy-C$_{1-8}$alkyl-amino, (hydroxy-C$_{1-8}$alkyl)$_2$-amino or (hydroxy-C$_{1-8}$alkyl)(C$_{1-8}$alkyl)amino;

R$_4$ is C$_{3-14}$ cycloalkyl, C$_{3-14}$cycloalkyl-C$_{1-8}$alkyl, C$_{3-14}$cycloalkyl-amino, aryl-C$_{1-8}$alkyl, aryl-C$_{1-8}$ alkoxy-carbonyl, aryl-sulfonyloxy-C$_{1-8}$alkyl, heterocyclyl or heterocyclyl-C$_{1-8}$alkyl; wherein, each instance of C$_{3-14}$cycloalkyl, aryl and heterocyclyl is optionally substituted with one, two or three R$_5$ substituents;

R$_5$ is, in each instance, independently selected from halogen, hydroxy, cyano, nitro, C$_{1-8}$alkyl, halo-C$_{1-8}$alkyl, C$_{1-8}$alkoxy, halo-C$_{1-8}$alkoxy, amino, C$_{1-8}$alkyl-amino, (C$_{1-8}$alkyl)$_2$-amino or C$_{1-8}$alkyl-thio;

R$_6$ is, in each instance, independently selected from halogen, hydroxy, cyano, nitro, C$_{1-8}$alkyl, C$_{2-8}$alkenyl, halo-C$_{1-8}$alkyl, hydroxy-C$_{1-8}$alkyl, C$_{1-8}$alkoxy, halo-C$_{1-8}$alkoxy, C$_{1-8}$alkoxy-C$_{1-8}$alkyl, amino, C$_{1-8}$alkyl-amino, (C$_{1-8}$alkyl)$_2$-amino or C$_{1-8}$alkyl-thio; and, R$_7$ is C$_{3-14}$cycloalkyl, C$_{3-14}$cycloalkyl-oxy, aryl, heterocyclyl or heteroaryl.

An embodiment of the use of the compound of Formula (I) is the use of a compound selected from Formula (II), Formula (III), Formula (IV), Formula (V), Formula (VI), Formula (VII), Formula (VIII), Formula (IX), Formula (X), Formula (XI), Formula (XII), Formula (XIII) or Formula (XIV):

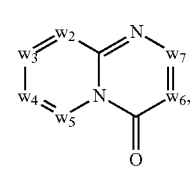

(II)

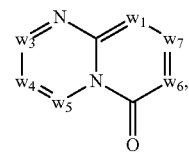

(III)

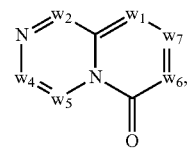

(IV)

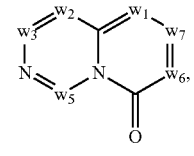

(V)

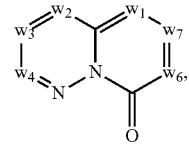

(VI)

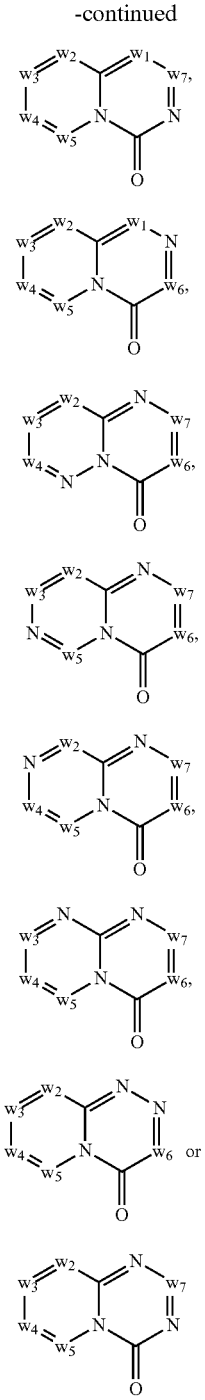

or a form thereof.

In an embodiment of the use of the compound of Formula (I), $w_3$ is C—$R_1$, $w_6$ is C—$R_2$, $w_1$, $w_4$, $w_5$ and $w_7$ are independently C—$R_a$ or N and $w_2$ is C—$R_b$ or N.

In another embodiment of the use of the compound of Formula (I), $w_3$ is C—$R_2$, $w_6$ is C—$R_1$, $w_1$, $w_4$, $w_5$ and $w_7$ are independently C—$R_a$ or N and $w_2$ is C—$R_b$ or N.

In another embodiment of the use of the compound of Formula (I), $w_4$ is C—$R_1$, $w_7$ is C—$R_2$, $w_1$, $w_3$ and $w_5$ are independently C—$R_a$ or N, $w_2$ is C—$R_b$ or N and $w_6$ is C—$R_c$ or N.

In another embodiment of the use of the compound of Formula (I), $w_4$ is C—$R_2$, $w_7$ is C—$R_1$, $w_1$, $w_3$ and $w_5$ are independently C—$R_a$ or N, $w_2$ is C—$R_b$ or N and $w_6$ is C—$R_c$ or N.

In an embodiment of the use of the compound of Formula (II), $w_3$ is C—$R_1$, $w_6$ is C—$R_2$, $w_4$, $w_5$ and $w_7$ are independently C—$R_a$ or N and $w_2$ is C—$R_b$ or N.

In another embodiment of the use of the compound of Formula (II), $w_3$ is C—$R_2$, $w_6$ is C—$R_1$, $w_4$, $w_5$ and $w_7$ are independently C—$R_a$ or N and $w_2$ is C—$R_b$ or N.

In another embodiment of the use of the compound of Formula (II), $w_4$ is C—$R_1$, $w_7$ is C—$R_2$, $w_3$ and $w_5$ are independently C—$R_a$ or N, $w_2$ is C—$R_b$ or N and $w_6$ is C—$R_c$ or N.

In another embodiment of the use of the compound of Formula (II), $w_4$ is C—$R_2$, $w_7$ is C—$R_1$, $w_3$ and $w_5$ are independently C—$R_a$ or N, $w_2$ is C—$R_b$ or N and $w_6$ is C—$R_c$ or N.

In an embodiment of the use of the compound of Formula (III), $w_3$ is C—$R_1$, $w_6$ is C—$R_2$ and $w_1$, $w_4$, $w_5$ and $w_7$ are independently C—$R_a$ or N.

In another embodiment of the use of the compound of Formula (III), $w_3$ is C—$R_2$, $w_6$ is C—$R_1$ and $w_1$, $w_4$, $w_5$ and $w_7$ are independently C—$R_a$ or N.

In another embodiment of the use of the compound of Formula (III), $w_4$ is C—$R_1$, $w_7$ is C—$R_2$, $w_1$, $w_3$ and $w_5$ are independently C—$R_a$ or N and $w_6$ is C—$R_c$ or N.

In another embodiment of the use of the compound of Formula (III), $w_4$ is C—$R_2$, $w_7$ is C—$R_1$, $w_1$, $w_3$ and $w_5$ are independently C—$R_a$ or N and $w_6$ is C—$R_c$ or N.

In an embodiment of the use of the compound of Formula (IV), $w_4$ is C—$R_1$, $w_7$ is C—$R_2$, $w_1$ and $w_5$ are independently C—$R_a$ or N, $w_2$ is C—$R_b$ or N and $w_6$ is C—$R_c$ or N.

In another embodiment of the use of the compound of Formula (IV), $w_4$ is C—$R_2$, $w_7$ is C—$R_1$, $w_1$ and $w_5$ are independently C—$R_a$ or N, $w_2$ is C—$R_b$ or N and $w_6$ is C—$R_c$ or N.

In an embodiment of the use of the compound of Formula (V), $w_3$ is C—$R_1$, $w_6$ is C—$R_2$, $w_1$, $w_5$ and $w_7$ are independently C—$R_a$ or N and $w_2$ is C—$R_b$ or N.

In another embodiment of the use of the compound of Formula (V), $w_3$ is C—$R_2$, $w_6$ is C—$R_1$, $w_1$, $w_5$ and $w_7$ are independently C—$R_a$ or N and $w_2$ is C—$R_b$ or N.

In an embodiment of the use of the compound of Formula (VI), $w_3$ is C—$R_1$, $w_6$ is C—$R_2$, $w_1$, $w_4$ and $w_7$ are independently C—$R_a$ or N and $w_2$ is C—$R_b$ or N.

In another embodiment of the use of the compound of Formula (VI), $w_3$ is C—$R_2$, $w_6$ is C—$R_1$, $w_1$, $w_4$ and $w_7$ are independently C—$R_a$ or N and $w_2$ is C—$R_b$ or N.

In another embodiment of the use of the compound of Formula (VI), $w_4$ is C—$R_1$, $w_7$ is C—$R_2$, $w_1$ and $w_3$ are independently C—$R_a$ or N, $w_2$ is C—$R_b$ or N and $w_6$ is C—$R_c$ or N.

In another embodiment of the use of the compound of Formula (VI), $w_4$ is C—$R_2$, $w_7$ is C—$R_1$, $w_1$ and $w_3$ are independently C—$R_a$ or N, $w_2$ is C—$R_b$ or N and $w_6$ is C—$R_c$ or N.

In another embodiment of the use of the compound of Formula (VII), $w_4$ is C—$R_1$, is C—$R_2$, $w_1$, $w_3$ and $w_5$ are C—$R_a$ or N and $w_2$ is C—$R_b$ or N.

In another embodiment of the use of the compound of Formula (VII), $w_4$ is C—$R_2$, is C—$R_1$, $w_1$, $w_3$ and $w_5$ are C—$R_a$ or N and $w_2$ is C—$R_b$ or N.

In another embodiment of the use of the compound of Formula (VIII), $w_3$ is C—$R_1$, $w_6$ is C—$R_2$, $w_1$, $w_4$ and $w_5$ are C—$R_a$ or N and $w_2$ is C—$R_b$ or N.

In another embodiment of the use of the compound of Formula (VIII), $w_3$ is C—$R_2$, $w_6$ is C—$R_1$, $w_1$, $w_4$ and $w_5$ are C—$R_a$ or N and $w_2$ is C—$R_b$ or N.

In an embodiment of the use of the compound of Formula (IX), $w_3$ is C—$R_1$, $w_6$ is C—$R_2$, $w_4$ and $w_7$ are independently C—$R_a$ or N and $w_2$ is C—$R_b$ or N.

In another embodiment of the use of the compound of Formula (IX), $w_3$ is C—$R_2$, $w_6$ is C—$R_1$, $w_4$ and $w_7$ are independently C—$R_a$ or N and $w_2$ is C—$R_b$ or N.

In another embodiment of the use of the compound of Formula (IX), $w_4$ is C—$R_1$, $w_7$ is C—$R_2$, $w_2$ is C—$R_b$ or N, $w_3$ is C—$R_a$ or N and $w_6$ is C—$R_c$ or N.

In another embodiment of the use of the compound of Formula (IX), $w_4$ is C—$R_2$, $w_7$ is C—$R_1$, $w_2$ is C—$R_b$ or N, $w_3$ is C—$R_a$ or N and $w_6$ is C—$R_c$ or N.

In an embodiment of the use of the compound of Formula (X), $w_3$ is C—$R_1$, $w_6$ is C—$R_2$, $w_2$ is C—$R_b$ or N and $w_5$ and $w_7$ are independently C—$R_a$ or N.

In another embodiment of the use of the compound of Formula (X), $w_3$ is C—$R_2$, $w_6$ is C—$R_1$, $w_2$ is C—$R_b$ or N and $w_5$ and $w_7$ are independently C—$R_a$ or N.

In an embodiment of the use of the compound of Formula (XI), $w_4$ is C—$R_1$, $w_7$ is C—$R_2$, $w_2$ is C—$R_b$ or N, $w_5$ is C—$R_a$ or N and $w_6$ is C—$R_c$ or N.

In another embodiment of the use of the compound of Formula (XI), $w_4$ is C—$R_2$, $w_7$ is C—$R_1$, $w_2$ is C—$R_b$ or N, $w_5$ is C—$R_a$ or N and $w_6$ is C—$R_c$ or N.

In an embodiment of the use of the compound of Formula (XII), $w_3$ is C—$R_1$, $w_6$ is C—$R_2$ and $w_4$, $w_5$ and $w_7$ are independently C—$R_a$ or N.

In another embodiment of the use of the compound of Formula (XII), $w_3$ is C—$R_2$, $w_6$ is C—$R_1$ and $w_4$, $w_5$ and $w_7$ are independently C—$R_a$ or N.

In another embodiment of the use of the compound of Formula (XII), $w_4$ is C—$R_1$, $w_7$ is C—$R_2$, $w_3$ and $w_5$ are independently C—$R_a$ or N and $w_6$ is C—$R_c$ or N.

In another embodiment of the use of the compound of Formula (XII), $w_4$ is C—$R_2$, $w_7$ is C—$R_1$, $w_3$ and $w_5$ are independently C—$R_a$ or N and $w_6$ is C—$R_c$ or N.

In an embodiment of the use of the compound of Formula (XIII), $w_3$ is C—$R_1$, $w_6$ is C—$R_2$, $w_2$ is C—$R_b$ or N and $w_4$ and $w_5$ are independently C—$R_a$ or N.

In another embodiment of the use of the compound of Formula (XIII), $w_3$ is C—$R_2$, $w_6$ is C—$R_1$, $w_2$ is C—$R_b$ or N and $w_4$ and $w_5$ are independently C—$R_a$ or N.

In an embodiment of the use of the compound of Formula (XIV), $w_4$ is C—$R_1$, $w_7$ is C—$R_2$, $w_2$ is C—$R_b$ or N and $w_3$ and $w_5$ are independently C—$R_a$ or N.

In another embodiment of the use of the compound of Formula (XIV), $w_4$ is C—$R_2$, is C—$R_1$, $w_2$ is C—$R_b$ or N and $w_3$ and $w_5$ are independently C—$R_a$ or N.

Another embodiment of the use of the compound of Formula (I) is the use of the compound selected from Formula (II), Formula (III), Formula (IX), Formula (XI) or Formula (XII):

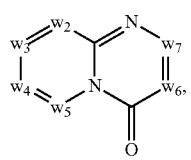
(II)

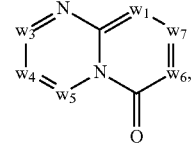
(III)

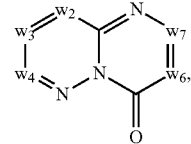
(IX)

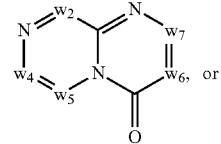
(XI)

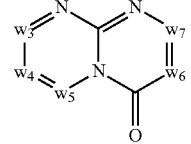
(XII)

or a form thereof.

Another embodiment of the use of the compound of Formula (I) is the use of the compound of Formula (II):

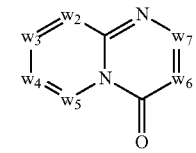
(II)

or a form thereof.

Another embodiment of the use of the compound of Formula (I) is the use of the compound of Formula (III):

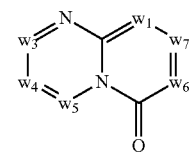
(III)

or a form thereof.

Another embodiment of the use of the compound of Formula (I) is the use of the compound of Formula (IV):

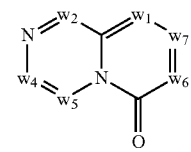
(IV)

or a form thereof.

Another embodiment of the use of the compound of Formula (I) is the use of the compound of Formula (V):

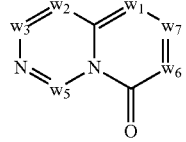
(V)

or a form thereof.

Another embodiment of the use of the compound of Formula (I) is the use of the compound of Formula (VI):

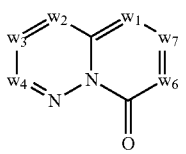
(VI)

or a form thereof.

Another embodiment of the use of the compound of Formula (I) is the use of the compound of Formula (VII):

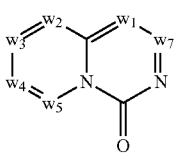
(VII)

or a form thereof.

Another embodiment of the use of the compound of Formula (I) is the use of the compound of Formula (VIII):

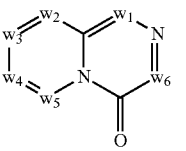
(VIII)

or a form thereof.

Another embodiment of the use of the compound of Formula (I) is the use of the compound of Formula (IX):

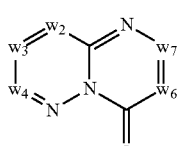
(IX)

or a form thereof.

Another embodiment of the use of the compound of Formula (I) is the use of the compound of Formula (X):

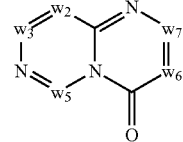
(X)

or a form thereof.

Another embodiment of the use of the compound of Formula (I) is the use of the compound of Formula (XI):

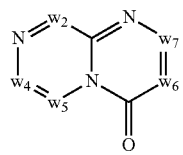
(XI)

or a form thereof.

Another embodiment of the compound of Formula (I) is the use of the compound of Formula (XII):

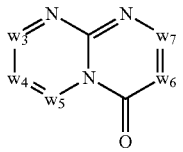
(XII)

or a form thereof.

Another embodiment of the use of the compound of Formula (I) is the use of the compound of Formula (XIII):

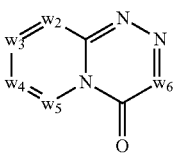
(XIII)

or a form thereof.

Another embodiment of the use of the compound of Formula (I) is the use of the compound of Formula (XIV):

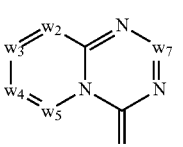
(XIV)

or a form thereof.

An embodiment of the use of the compound of Formula (I), Formula (II), Formula (III), Formula (IV), Formula (V), Formula (VI), Formula (VII), Formula (VIII), Formula (IX), Formula (X), Formula (XI), Formula (XII), Formula (XIII) or Formula (XIV) is the use of a compound selected from Formula (Ia), Formula (IIa), Formula (IIIa), Formula (IVa), Formula (Va), Formula (VIa), Formula (VIIa), Formula (VIIIa), Formula (IXa), Formula (Xa), Formula (XIa), Formula (XIIa), Formula (XIIIa) or Formula (XIVa), respectively:

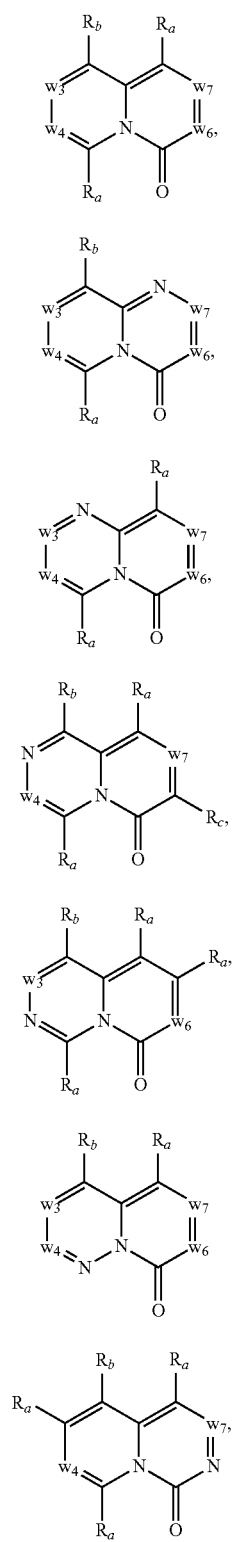

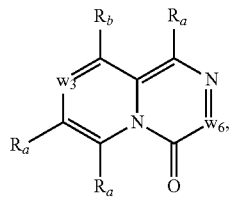

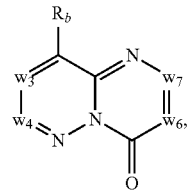

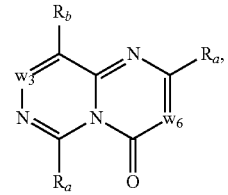

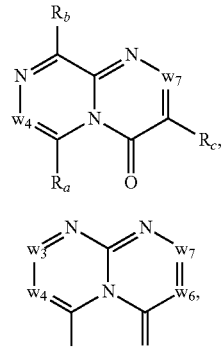

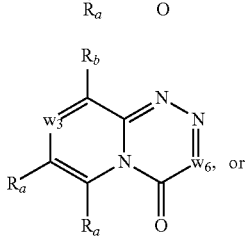

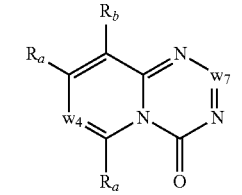

or a form thereof.

In an embodiment of the use of the compound of Formula (Ia), one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—$R_c$ or N.

In an embodiment of the use of the compound of Formula (IIa), one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—$R_c$ or N.

In an embodiment of the use of the compound of Formula (IIIa), one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—$R_c$ or N.

In an embodiment of the use of the compound of Formula (IVa), one of $w_4$ and $w_7$ is C—$R_1$ and the other is C—$R_2$, provided that, when $w_4$ is C—$R_1$, then $w_7$ is C—$R_2$; or, when $w_4$ is C—$R_2$, then $w_7$ is C—$R_1$.

In an embodiment of the use of the compound of Formula (Va), one of $w_3$ and $w_6$ is C—$R_1$ and the other is C—$R_2$, provided that, when $w_3$ is C—$R_1$, then $w_6$ is C—$R_2$; or, when $w_3$ is C—$R_2$, then $w_6$ is C—$R_1$.

In an embodiment of the use of the compound of Formula (VIa), one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—$R_c$ or N.

In an embodiment of the use of the compound of Formula (VIIa), one of $w_4$ and $w_7$ is C—$R_1$ and the other is C—$R_2$, provided that, when $w_4$ is C—$R_1$, then $w_7$ is C—$R_2$; or, when $w_4$ is C—$R_2$, then $w_7$ is C—$R_1$.

In an embodiment of the use of the compound of Formula (VIIIa), one of $w_3$ and $w_6$ is C—$R_1$ and the other is C—$R_2$, provided that, when $w_3$ is C—$R_1$, then $w_6$ is C—$R_2$; or, when $w_3$ is C—$R_2$, then $w_6$ is C—$R_1$.

In an embodiment of the use of the compound of Formula (IXa), one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—$R_c$ or N.

In an embodiment of the use of the compound of Formula (Xa), one of $w_3$ and $w_6$ is C—$R_1$ and the other is C—$R_2$, provided that, when $w_3$ is C—$R_1$, then $w_6$ is C—$R_2$; or, when $w_3$ is C—$R_2$, then $w_6$ is C—$R_1$.

In an embodiment of the use of the compound of Formula (XIa), one of $w_4$ and $w_7$ is C—$R_1$ and the other is C—$R_2$, provided that, when $w_4$ is C—$R_1$, then $w_7$ is C—$R_2$; or, when $w_4$ is C—$R_2$, then $w_7$ is C—$R_1$.

In an embodiment of the use of the compound of Formula (XIIa), one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—$R_c$ or N.

In an embodiment of the use of the compound of Formula (XIIIa), one of $w_3$ and $w_6$ is C—$R_1$ and the other is C—$R_2$, provided that, when $w_3$ is C—$R_1$, then $w_6$ is C—$R_2$; or, when $w_3$ is C—$R_2$, then $w_6$ is C—$R_1$.

In an embodiment of the use of the compound of Formula (XIVa), one of $w_4$ and $w_7$ is C—$R_1$ and the other is C—$R_2$, provided that, when $w_4$ is C—$R_1$, then $w_7$ is C—$R_2$; or, when $w_4$ is C—$R_2$, then $w_7$ is C—$R_1$.

An embodiment of the use of the compound of Formula (I), Formula (II), Formula (III), Formula (IX), Formula (XI) or Formula (XII) is the use of the compound selected from Formula (Ia), Formula (IIa), Formula (IIIa), Formula (IXa), Formula (XIa) or Formula (XIIa), respectively:

(Ia)

(IIa)

(IIIa)

(IXa)

-continued

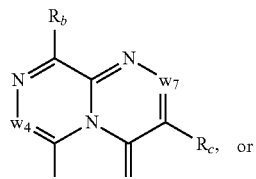
(XIa)

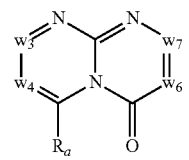
(XIIa)

or a form thereof.

Another embodiment of the use of the compound of Formula (I) is the use of the compound of Formula (Ia):

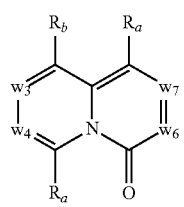
(Ia)

or a form thereof.

Another embodiment of the use of the compound of Formula (II) is the use of the compound of Formula (IIa):

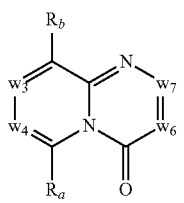
(IIa)

or a form thereof.

Another embodiment of the use of the compound of Formula (III) is the use of the compound of Formula (IIIa):

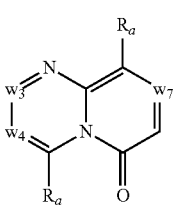
(IIIa)

or a form thereof.

Another embodiment of the use of the compound of Formula (IV) is the use of the compound of Formula (IVa):

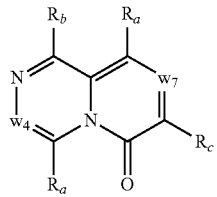
(IVa)

or a form thereof.

Another embodiment of the use of the compound of Formula (V) is the use of the compound of Formula (Va):

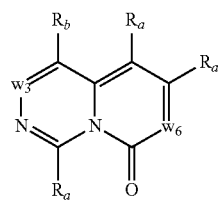
(Va)

or a form thereof.

Another embodiment of the use of the compound of Formula (VI) is the use of the compound of Formula (VIa):

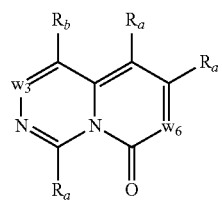
(VIa)

or a form thereof.

Another embodiment of the use of the compound of Formula (VII) is the use of the compound of Formula (VIIa):

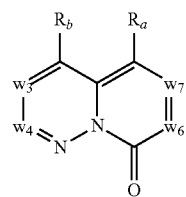
(VIIa)

or a form thereof.

Another embodiment of the use of the compound of Formula (VIII) is the use of the compound of Formula (VIIIa):

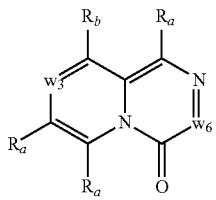
(VIIIA)

or a form thereof.

Another embodiment of the use of the compound of Formula (IX) is the use of the compound of Formula (IXa):

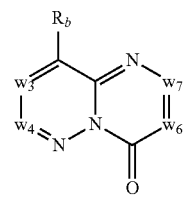
(IXa)

or a form thereof.

Another embodiment of the use of the compound of Formula (X) is the use of the compound of Formula (Xa):

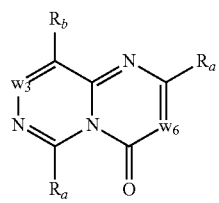
(Xa)

or a form thereof.

Another embodiment of the use of the compound of Formula (XI) is the use of the compound of Formula (XIa):

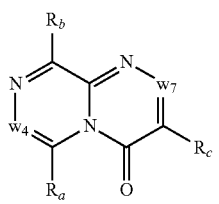
(XIa)

or a form thereof.

Another embodiment of the use of the compound of Formula (XII) is the use of the compound of Formula (XIIa):

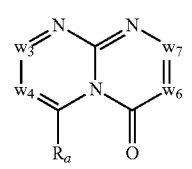
(XIIa)

or a form thereof.

Another embodiment of the use of the compound of Formula (XIII) is the use of the compound of Formula (XIIIa):

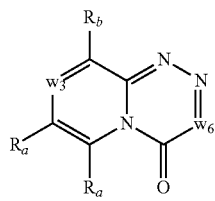
(XIIIa)

or a form thereof.

Another embodiment of the use of the compound of Formula (XIV) is the use of the compound of Formula (XIVa):

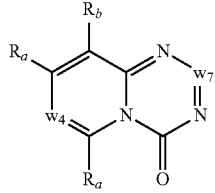
(XIVa)

or a form thereof.

An embodiment of the use of the compound of Formula (Ia) is the use of a compound of Formula (Ia1), Formula (Ia2), Formula (Ia3) or Formula (Ia4):

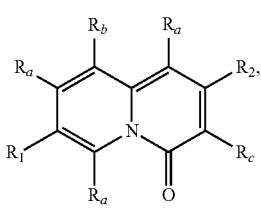
(Ia1)

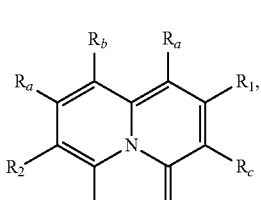
(Ia2)

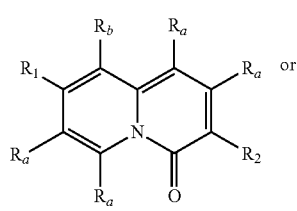
(Ia3)

(Ia4)

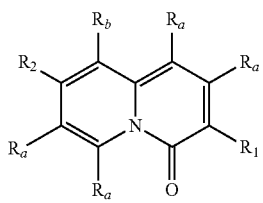

or a form thereof.

An embodiment of the use of the compound of Formula (IIa) is the use of a compound of Formula (IIa1), Formula (IIa2), Formula (IIa3) or Formula (IIa4):

(IIa1)

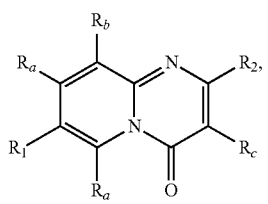

(IIa2)

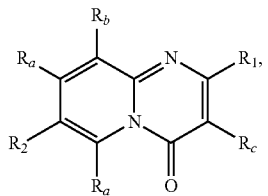

(IIa3)

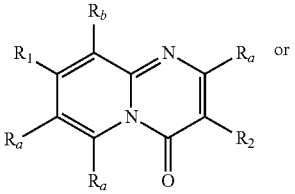

(IIa4)

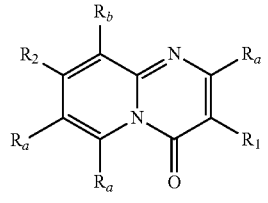

or a form thereof.

An embodiment of the use of the compound of Formula (IIIa) is the use of a compound of Formula (IIIa1), Formula (IIIa2), Formula (IIIa3) or Formula (IIIa4):

(IIIa1)

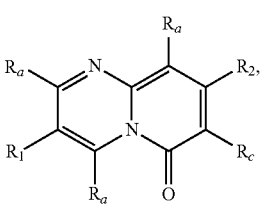

(IIIa2)

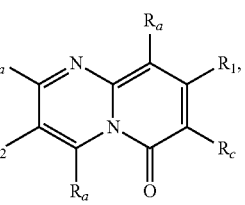

(IIIa3)

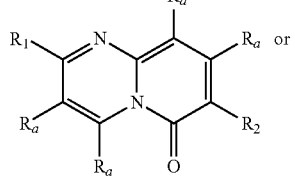

(IIIa4)

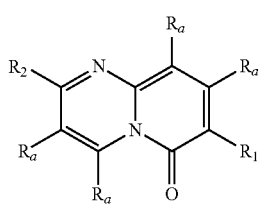

or a form thereof.

An embodiment of the use of the compound of Formula (IVa) is the use of a compound of Formula (IVa1) or Formula (IVa2):

(IVa1)

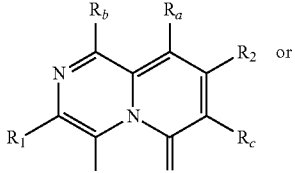

(IVa2)

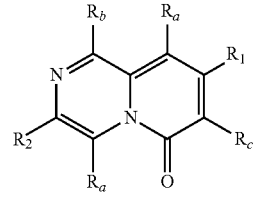

or a form thereof.

An embodiment of the use of the compound of Formula (Va) is the use of a compound of Formula (Va1) or Formula (Va2):

(Va1)

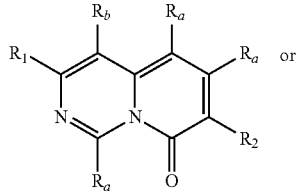

(Va2)

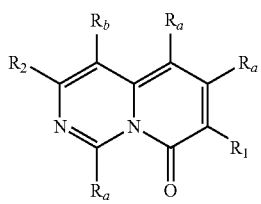

or a form thereof.

An embodiment of the use of the compound of Formula (VIa) is the use of a compound of Formula (VIa1), Formula (VIa2), Formula (VIa3) or Formula (VIa2):

(VIa1)

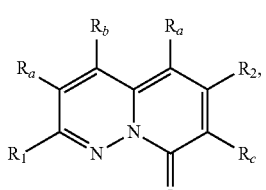

(VIa2)

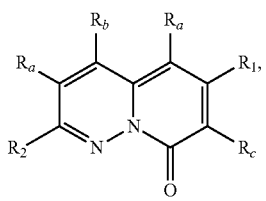

(VIa3)

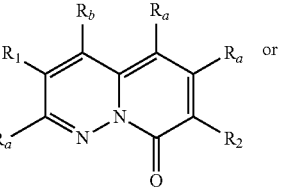

(VIa4)

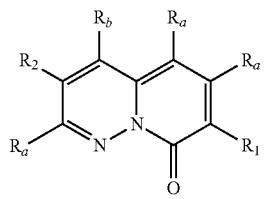

or a form thereof.

An embodiment of the use of the compound of Formula (VIIa) is the use of a compound of Formula (VIIa1) or Formula (VIIa2):

(VIIa1)

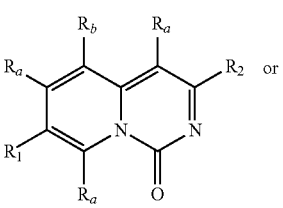 or (VIIa2)

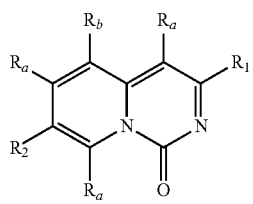

or a form thereof.

An embodiment of the use of the compound of Formula (VIIIa) is the use of a compound of Formula (VIIIa1) or Formula (VIIIa2):

(VIIIa1)

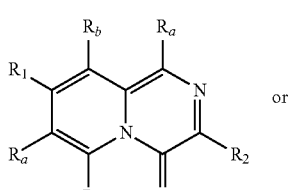 or (VIIIa2)

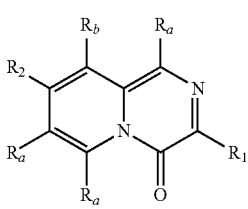

or a form thereof.

An embodiment of the use of the compound of Formula (IXa) is the use of a compound of Formula (IXa1), Formula (IXa2), Formula (IXa3) or Formula (IXa4):

(IXa1)

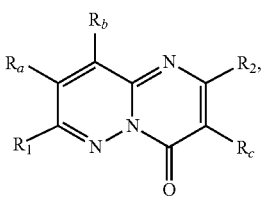

(IXa2)

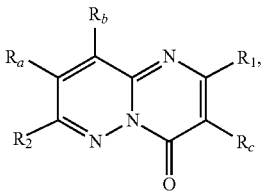

(IXa3)

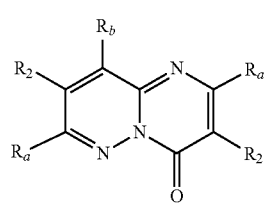 or

-continued

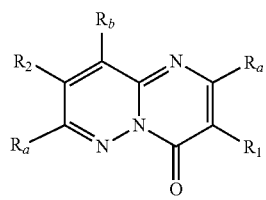
(IXa4)

or a form thereof.

An embodiment of the use of the compound of Formula (Xa) is the use of a compound of Formula (Xa1) or Formula (Xa2):

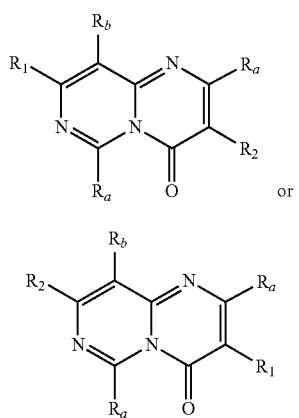
(Xa1)

or (Xa2)

or a form thereof.

An embodiment of the use of the compound of Formula (XIa) is the use of a compound of Formula (XIa1) or Formula (XIa2):

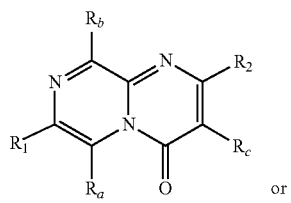
(XIa1)

or

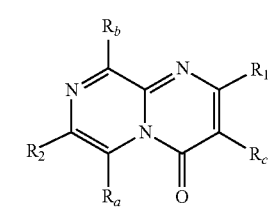
(XIa2)

or a form thereof.

An embodiment of the use of the compound of Formula (XIIa) is the use of a compound of Formula (XIIa1), Formula (XIIa2), Formula (XIIa3) or Formula (XIIa4):

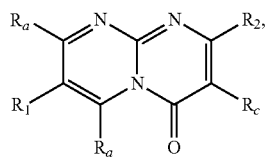
(XIIa1)

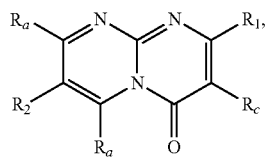
(XIIa2)

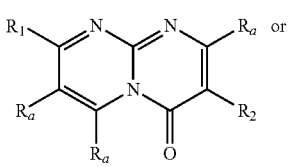
(XIIa3) or

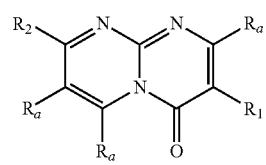
(XIIa4)

or a form thereof.

An embodiment of the use of the compound of Formula (XIIIa) is the use of a compound of Formula (XIIIa1) or Formula (XIIIa2):

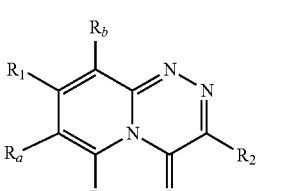
(XIIIa1)

or

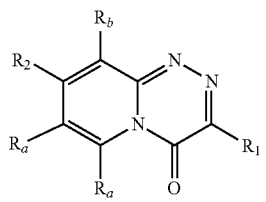
(XIIIa2)

or a form thereof.

An embodiment of the use of the compound of Formula (XIVa) is the use of a compound of Formula (XIVa1) or Formula (XIVa2):

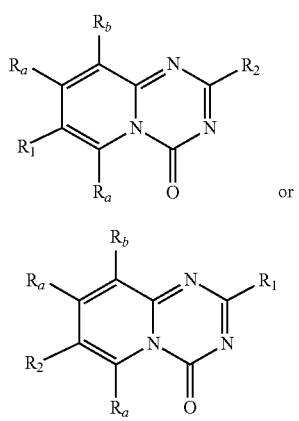

(XIVa1)

or (XIVa2)

or a form thereof.

An embodiment of the use of the compound of Formula (Ia) is the use of the compound of Formula (Ia1):

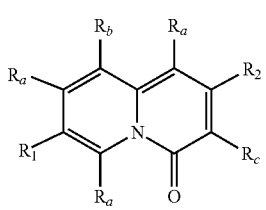

(Ia1)

or a form thereof.

An embodiment of the use of the compound of Formula (Ia) is the use of the compound of Formula (Ia2):

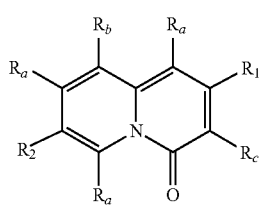

(Ia2)

or a form thereof.

An embodiment of the use of the compound of Formula (Ia) is the use of the compound of Formula (Ia3):

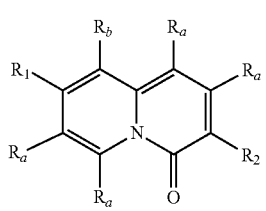

(Ia3)

or a form thereof.

An embodiment of the use of the compound of Formula (Ia) is the use of the compound of Formula (Ia4):

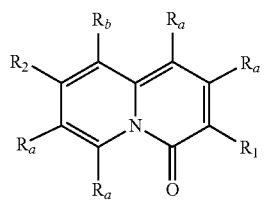

(Ia4)

or a form thereof.

An embodiment of the use of the compound of Formula (IIa) is the use of the compound of Formula (IIa1):

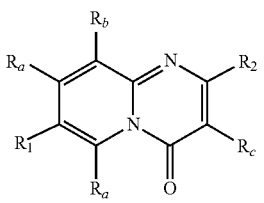

(IIa1)

or a form thereof.

An embodiment of the use of the compound of Formula (IIa) is the use of the compound of Formula (IIa2):

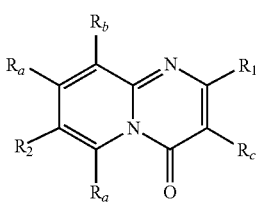

(IIa2)

or a form thereof.

An embodiment of the use of the compound of Formula (IIa) is the use of the compound of Formula (IIa3):

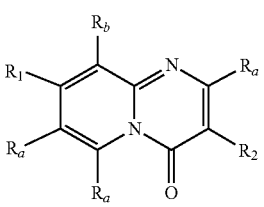

(IIa3)

or a form thereof.

An embodiment of the use of the compound of Formula (IIa) is the use of the compound of Formula (IIa4):

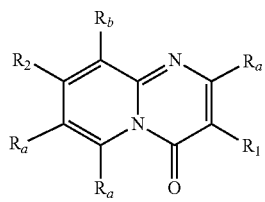

(IIa4)

or a form thereof.

An embodiment of the use of the compound of Formula (IIIa) is the use of the compound of Formula (IIIa1):

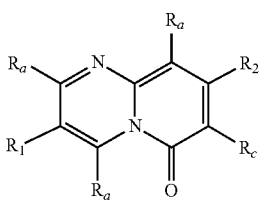

(IIIa1)

or a form thereof.

An embodiment of the use of the compound of Formula (IIIa) is the use of the compound of Formula (IIIa2):

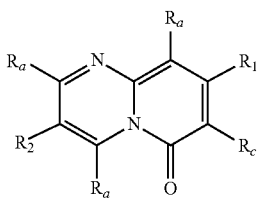

(IIIa2)

or a form thereof.

An embodiment of the use of the compound of Formula (IIIa) is the use of the compound of Formula (IIIa3):

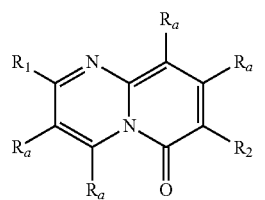

(IIIa3)

or a form thereof.

An embodiment of the use of the compound of Formula (IIIa) is the use of the compound of Formula (IIIa4):

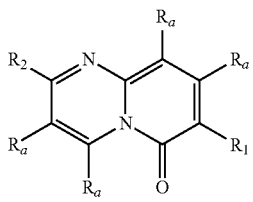

(IIIa4)

or a form thereof.

An embodiment of the use of the compound of Formula (IVa) is the use of the compound of Formula (IVa1):

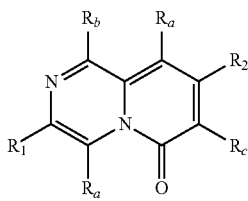

(IVa1)

or a form thereof.

An embodiment of the use of the compound of Formula (IVa) is the use of the compound of Formula (IVa2):

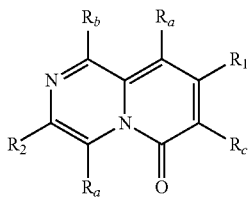

(IVa2)

or a form thereof.

An embodiment of the use of the compound of Formula (Va) is the use of the compound of Formula (Va1):

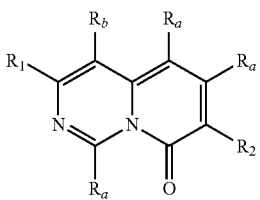

(Va1)

or a form thereof.

An embodiment of the use of the compound of Formula (Va) is the use of the compound of Formula (Va2):

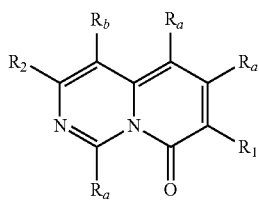
(Va2)

or a form thereof.

An embodiment of the use of the compound of Formula (VIa) is the use of the compound of Formula (VIa1):

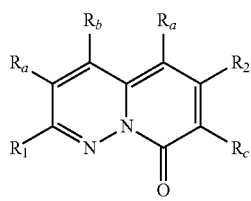
(VIa1)

or a form thereof.

An embodiment of the use of the compound of Formula (VIa) is the use of the compound of Formula (VIa2):

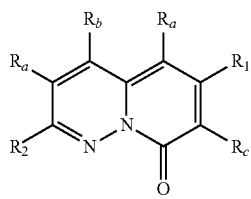
(VIa2)

or a form thereof.

An embodiment of the use of the compound of Formula (VIa) is the use of the compound of Formula (VIa3):

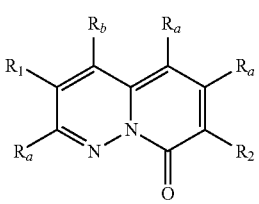
(VIa3)

or a form thereof.

An embodiment of the use of the compound of Formula (VIa) is the use of the compound of Formula (VIa4):

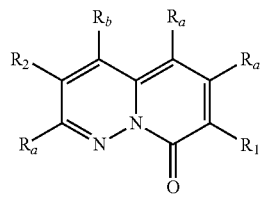
(VIa4)

or a form thereof.

An embodiment of the use of the compound of Formula (VIIa) is the use of the compound of Formula (VIIa1):

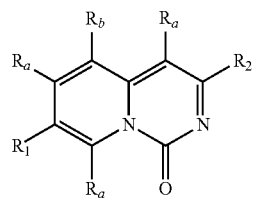
(VIIa1)

or a form thereof.

An embodiment of the use of the compound of Formula (VIIa) is the use of the compound of Formula (VIIa2):

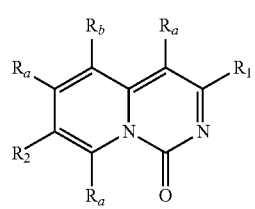
(VIIa2)

or a form thereof.

An embodiment of the use of the compound of Formula (VIIIa) is the use of the compound of Formula (VIIIa1):

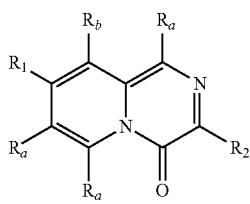
(VIIIa1)

or a form thereof.

An embodiment of the use of the compound of Formula (VIIIa) is the use of the compound of Formula (VIIIa2):

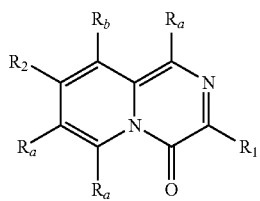
(VIIIa2)

or a form thereof.

An embodiment of the use of the compound of Formula (IXa) is the use of the compound of Formula (IXa1):

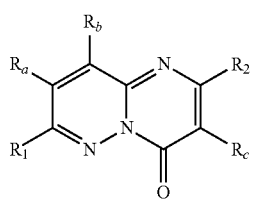
(IXa1)

or a form thereof.

An embodiment of the use of the compound of Formula (IXa) is the use of the compound of Formula (IXa2):

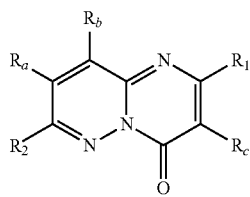
(IXa2)

or a form thereof.

An embodiment of the use of the compound of Formula (IXa) is the use of the compound of Formula (IXa3):

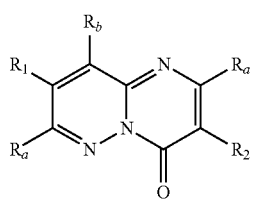
(IXa3)

or a form thereof.

An embodiment of the use of the compound of Formula (IXa) is the use of the compound of Formula (IXa4):

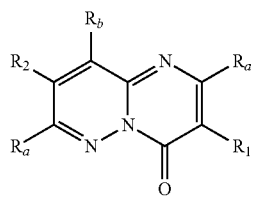
(IXa4)

or a form thereof.

An embodiment of the use of the compound of Formula (Xa) is the use of the compound of Formula (Xa1):

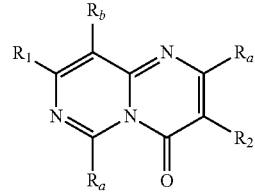
(Xa1)

or a form thereof.

An embodiment of the use of the compound of Formula (Xa) is the use of the compound of Formula (Xa2):

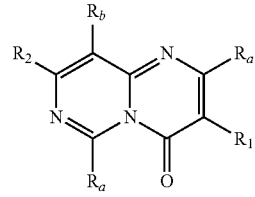
(Xa2)

or a form thereof.

An embodiment of the use of the compound of Formula (XIa) is the use of the compound of Formula (XIa1):

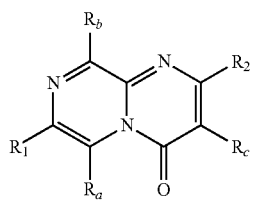
(XIa1)

or a form thereof.

An embodiment of the use of the compound of Formula (XIa) is the use of the compound of Formula (XIa2):

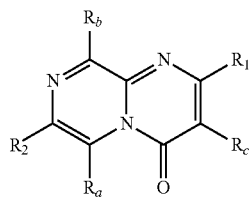

(XIa2)

or a form thereof.

An embodiment of the use of the compound of Formula (XIIa) is the use of the compound of Formula (XIIa1):

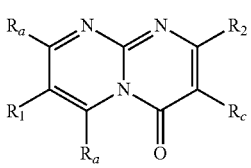

(XIIa1)

or a form thereof.

An embodiment of the use of the compound of Formula (XIIa) is the use of the compound of Formula (XIIa2):

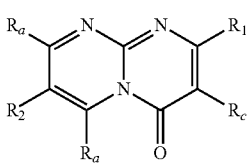

(XIIa2)

or a form thereof.

An embodiment of the use of the compound of Formula (XIIa) is the use of the compound of Formula (XIIa3):

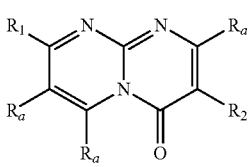

(XIIa3)

or a form thereof.

An embodiment of the use of the compound of Formula (XIIa) is the use of the compound of Formula (XIIa4):

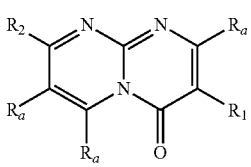

(XIIa4)

or a form thereof.

An embodiment of the use of the compound of Formula (XIIIa) is the use of the compound of Formula (XIIIa1):

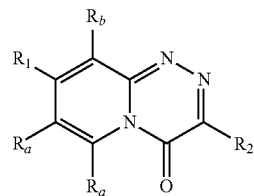

(XIIIa1)

or a form thereof.

An embodiment of the use of the compound of Formula (XIIIa) is the use of the compound of Formula (XIIIa2):

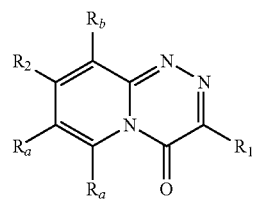

(XIIIa2)

or a form thereof.

An embodiment of the use of the compound of Formula (XIVa) is the use of the compound of Formula (XIVa1):

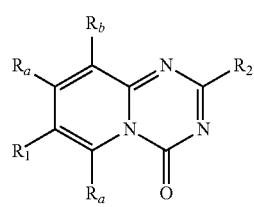

(XIVa1)

or a form thereof.

An embodiment of the use of the compound of Formula (XIVa) is the use of the compound of Formula (XIVa2):

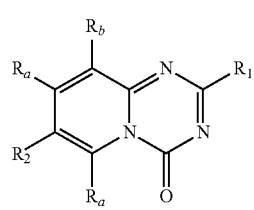

(XIVa2)

or a form thereof.

Patient Population

In some embodiments, a compound of Formula (I) or a form thereof, or a pharmaceutical composition thereof is administered to a subject suffering from SMA. In other embodiments, a compound of Formula (I) or a form thereof, is administered to a subject predisposed or susceptible to SMA. In a specific embodiment, a compound of Formula (I) or a form thereof, or a pharmaceutical composition thereof is administered to a human subject having SMA, wherein SMA is caused by an inactivating mutation or deletion in the SMN1 gene on both chromosomes, resulting in a loss of SMN1 gene function. In certain embodiments, the human subject is genotyped prior to administration of a compound of Formula (I) or a form thereof, or a pharmaceutical composition thereof to determine whether the subject has an inactivating mutation or deletion in the teleomeric copy of the SMN1 gene in both chromosomes, which results in a loss of SMN1 gene function. In some embodiments, a compound of Formula (I) or a form thereof, or pharmaceutical composition thereof is administered to a subject with Type 0 SMA. In some embodiments, a compound of Formula (I) or a form thereof, or a pharmaceutical composition thereof is administered to a subject with Type 1 SMA. In other embodiments, a compound of Formula (I) or a form thereof, or a pharmaceutical composition thereof is administered to a subject with Type 2 SMA. In other embodiments, a compound of Formula (I) or a form thereof, or a pharmaceutical composition thereof is administered to a subject with Type 3 SMA. In some embodiments, a compound of Formula (I) or a form thereof, or a pharmaceutical composition thereof is administered to a subject with Type 4 SMA. In certain embodiments, the human subject is an SMA patient.

In certain embodiments, a compound of Formula (I) or a form thereof, or a pharmaceutical composition thereof is administered to a subject that will or might benefit from enhanced inclusion of exon 7 of SMN1 and/or SMN2 into mRNA that is transcribed from the SMN1 and/or SMN2 gene. In specific embodiments, a compound of Formula (I) or a form thereof, or a pharmaceutical composition thereof is administered to a subject that will or may benefit from enhanced Smn protein expression.

In certain embodiments, a compound of Formula (I) or a form thereof, or a pharmaceutical composition thereof is administered to a human that has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In some embodiments, a compound of Formula (I) or a form thereof, or a pharmaceutical composition thereof is administered to a human infant. In other embodiments, a compound of Formula (I) or a form thereof, or a pharmaceutical composition thereof is administered to a human toddler. In other embodiments, a compound of Formula (I) or a form thereof, or a pharmaceutical composition thereof is administered to a human child. In other embodiments, a compound of Formula (I) or a form thereof, or a pharmaceutical composition thereof is administered to a human adult. In yet other embodiments, a compound of Formula (I) or a form thereof, or a pharmaceutical composition thereof is administered to an elderly human.

In some embodiments, a compound of Formula (I) or a form thereof, or a pharmaceutical composition thereof, is administered to a patient to prevent the onset of SMA in a patient at risk of developing SMA. In other embodiments, an effective amount of a compound of Formula (I) or a form thereof, or a pharmaceutical composition thereof, is administered to a patient to prevent the onset of SMA in a patient at risk of developing SMA. In other embodiments, a prophylactically effective amount of a compound of Formula (I) or a form thereof, or a pharmaceutical composition thereof, is administered to a patient to prevent the onset of SMA in a patient at risk of developing SMA. In other embodiments, a therapeutically effective amount of a compound of Formula (I) or a form thereof, or a pharmaceutical composition thereof, is administered to a patient to prevent the onset of SMA in a patient at risk of developing SMA.

In some embodiments, a compound of Formula (I) or a form thereof, or a pharmaceutical composition thereof, is administered to an SMA patient to treat or ameliorate SMA. In other embodiments, an effective amount of a compound of Formula (I) or a form thereof, or a pharmaceutical composition thereof, is administered to an SMA patient to treat or ameliorate SMA. In other embodiments, a prophylactically effective amount of a compound of Formula (I) or a form thereof, or a pharmaceutical composition thereof, is administered to an SMA patient to prevent advancement of SMA. In other embodiments, a therapeutically effective amount of a compound of Formula (I) or a form thereof, or a pharmaceutical composition thereof, is administered to an SMA patient to treat or ameliorate SMA.

In some embodiments, a compound of Formula (I) or a form thereof, or a medicament thereof is administered to a subject suffering from SMA. In other embodiments, a compound of Formula (I) or a form thereof, is administered to a subject predisposed or susceptible to SMA. In a specific embodiment, a compound of Formula (I) or a form thereof, or a medicament thereof is administered to a human subject having SMA, wherein SMA is caused by an inactivating mutation or deletion in the SMN1 gene on both chromosomes, resulting in a loss of SMN1 gene function. In certain embodiments, the human subject is genotyped prior to administration of a compound of Formula (I) or a form thereof, or a medicament thereof to determine whether the subject has an inactivating mutation or deletion in the teleomeric copy of the SMN1 gene in both chromosomes, which results in a loss of SMN1 gene function. In some embodiments, a compound of Formula (I) or a form thereof, or medicament thereof is administered to a subject with Type 0 SMA. In some embodiments, a compound of Formula (I) or a form thereof, or a medicament thereof is administered to a subject with Type 1 SMA. In other embodiments, a compound of Formula (I) or a form thereof, or a medicament thereof is administered to a subject with Type 2 SMA. In other embodiments, a compound of Formula (I) or a form thereof, or a medicament thereof is administered to a subject with Type 3 SMA. In some embodiments, a compound of Formula (I) or a form thereof, or a medicament thereof is administered to a subject with Type 4 SMA. In certain embodiments, the human subject is an SMA patient.

In certain embodiments, a compound of Formula (I) or a form thereof, or a medicament thereof is administered to a subject that will or might benefit from enhanced inclusion of exon 7 of SMN1 and/or SMN2 into mRNA that is transcribed from the SMN1 and/or SMN2 gene. In specific embodiments, a compound of Formula (I) or a form thereof, or a medicament thereof is administered to a subject that will or may benefit from enhanced Smn protein expression.

In certain embodiments, a compound of Formula (I) or a form thereof, or a medicament thereof is administered to a human that has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In some embodiments, a compound of Formula (I) or a form thereof, or a medicament thereof is administered to a human infant. In other embodiments, a compound of Formula (I) or a form thereof, or a medicament thereof is administered to a human toddler. In other embodiments, a compound of Formula (I) or a form thereof, or a medicament thereof is administered to a human child. In other embodiments, a compound of Formula (I) or a form thereof, or a medicament thereof is administered to a human adult. In yet other embodiments, a compound of Formula (I) or a form thereof, or a medicament thereof is administered to an elderly human.

In some embodiments, a compound of Formula (I) or a form thereof, or a medicament thereof is administered to a patient to prevent the onset of SMA in a patient at risk of developing SMA. In other embodiments, an effective amount of a compound of Formula (I) or a form thereof, or a medicament thereof, is administered to a patient to prevent the onset of SMA in a patient at risk of developing SMA. In other embodiments, a prophylactically effective amount of a compound of Formula (I) or a form thereof, or a medicament thereof, is administered to a patient to prevent the onset of SMA in a patient at risk of developing SMA. In other embodiments, a therapeutically effective amount of a compound of Formula (I) or a form thereof, or a medicament thereof, is administered to a patient to prevent the onset of SMA in a patient at risk of developing SMA.

In some embodiments, a compound of Formula (I) or a form thereof, or a medicament thereof, is administered to an SMA patient to treat or ameliorate SMA. In other embodiments, an effective amount of a compound of Formula (I) or a form thereof, or a medicament thereof, is administered to an SMA patient to treat or ameliorate SMA. In other embodiments, a prophylactically effective amount of a compound of Formula (I) or a form thereof, or a medicament thereof, is administered to an SMA patient to prevent advancement of SMA. In other embodiments, a therapeutically effective amount of a compound of Formula (I) or a form thereof, or a medicament thereof, is administered to an SMA patient to treat or ameliorate SMA.

Mode of Administration

When administered to a patient, a compound of Formula (I) or a form thereof is preferably administered as a component of a composition that optionally comprises a pharmaceutically acceptable carrier, excipient or diluent. The composition can be administered orally, or by any other convenient route, for example, by infusion or bolus injection, by absorption through epithelial or mucocutaneous linings (e.g., oral mucosa, rectal, and intestinal mucosa) and may be administered together with another biologically active agent. Administration can be systemic or local. Various delivery systems are known, e.g., encapsulation in liposomes, microparticles, microcapsules, capsules, and can be used to administer the compound.

Methods of administration include but are not limited to parenteral, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of a compound into the bloodstream. In a specific embodiment, a compound is administered orally.

Dosage and Dosage Forms

The amount of a compound of Formula (I) or a form thereof that will be effective in the treatment of SMA depend, e.g., on the route of administration, the type of SMA, the general health of the subject, ethnicity, age, weight, and gender of the subject, diet, time, and the severity of SMA, and should be decided according to the judgment of the practitioner and each patient's or subject's circumstances.

In specific embodiments, an "effective amount," "prophylactically effective amount" or "therapeutically effective amount" in the context of the administration of a compound of Formula (I) or a form thereof, or composition or medicament thereof refers to an amount of a compound of Formula (I) which has a therapeutic effect and/or beneficial effect. In certain specific embodiments, an "effective amount," "prophylactically effective amount" or "therapeutically effective amount" in the context of the administration of a compound of Formula (I) or a form thereof, or composition or medicament thereof results in one, two or more of the following effects: (i) reduces or ameliorates the severity of SMA; (ii) delays onset of SMA; (iii) inhibits the progression of SMA; (iv) reduces hospitalization of a subject; (v) reduces hospitalization length for a subject; (vi) increases the survival of a subject; (vii) improves the quality of life of a subject; (viii) reduces the number of symptoms associated with SMA; (ix) reduces or ameliorates the severity of a symptom(s) associated with SMA; (x) reduces the duration of a symptom associated with SMA; (xi) prevents the recurrence of a symptom associated with SMA; (xii) inhibits the development or onset of a symptom of SMA; and/or (xiii) inhibits of the progression of a symptom associated with SMA. In certain embodiments, an effective amount of a compound of Formula (I) or a form thereof is an amount effective to enhance inclusion of exon 7 of SMN2 into SMN2 mRNA that is transcribed from the SMN2 gene and increases the levels of Smn protein produced from the SMN2 gene and thus producing a desired beneficial effect in a subject in need thereof. In some instances, the desired effect can be determined by analyzing or quantifying: (1) the inclusion of exon 7 of SMN2 into mRNA that is transcribed from the SMN2 gene; or (2) the levels of Smn protein produced from the SMN2 gene. Non-limiting examples of effective amounts of a compound of Formula (I) or a form thereof are described herein.

For example, the effective amount may be the amount required to treat SMA in a human subject in need thereof, or the amount required to enhance inclusion of exon 7 of SMN2 into mRNA that is transcribed from the SMN2 gene in a human subject in need thereof, or the amount required to increase levels of Smn protein produced from the SMN2 gene in a human subject in need thereof. In a specific embodiment, the human subject is an SMA patient.

In general, the effective amount will be in a range of from about 0.001 mg/kg/day to about 500 mg/kg/day for a patient or subject having a weight in a range of between about 1 kg to about 200 kg. The typical adult subject is expected to have a median weight in a range of between about 70 and about 100 kg.

Within the scope of the present description, the "effective amount" of a compound of Formula (I) or a form thereof for use in the manufacture of a medicament, the preparation of a pharmaceutical kit or in a method for treating SMA in a human subject in need thereof, is intended to include an amount in a range of from about 0.001 mg to about 35,000 mg. In a specific embodiment, the human subject is an SMA patient.

The compositions described herein are formulated for administration to the subject via any drug delivery route known in the art. Nonlimiting examples include oral, ocular, rectal, buccal, topical, nasal, ophthalmic, subcutaneous, intramuscular, intravenous (bolus and infusion), intracerebral, transdermal, and pulmonary routes of administration.

Pharmaceutical Compositions

Embodiments described herein include the use of a compound of Formula (I) or a form thereof in a pharmaceutical composition. In a specific embodiment, described herein is the use of a compound of Formula (I) or a form thereof in a pharmaceutical composition for treating SMA in a human subject in need thereof comprising administering an effective amount of a compound of Formula (I) or a form thereof in admixture with a pharmaceutically acceptable excipient. In a specific embodiment, the human subject is an SMA patient.

A compound of Formula (I) or a form thereof may optionally be in the form of a composition comprising the compound or a form thereof and an optional carrier, excipient or diluent. Other embodiments provided herein include pharmaceutical compositions comprising an effective amount of a compound of Formula (I) or a form thereof and a pharmaceutically acceptable carrier, excipient, or diluent. In a specific embodiment, the pharmaceutical compositions are suitable for veterinary and/or human administration. The pharmaceutical compositions provided herein can be in any form that allows for the composition to be administered to a subject.

In a specific embodiment and in this context, the term "pharmaceutically acceptable carrier, excipient or diluent" means a carrier, excipient or diluent approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which a therapeutic agent is administered. Such pharmaceutical carriers can be sterile liquids, such as water and oils, including those of petroleum, animal, vegetable or synthetic origin, such as peanut oil, soybean oil, mineral oil, sesame oil and the like. Water is a specific carrier for intravenously administered pharmaceutical compositions. Saline solutions and aqueous dextrose and glycerol solutions can also be employed as liquid carriers, particularly for injectable solutions.

Typical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. Further provided herein are anhydrous pharmaceutical compositions and dosage forms comprising one or more compounds of Formula (I) or a form thereof as described herein. The compositions and single unit dosage forms can take the form of solutions or syrups (optionally with a flavoring agent), suspensions (optionally with a flavoring agent), emulsions, tablets (e.g., chewable tablets), pills, capsules, granules, powder (optionally for reconstitution), taste-masked or sustained-release formulations and the like.

Pharmaceutical compositions provided herein that are suitable for oral administration can be presented as discrete dosage forms, such as, but are not limited to, tablets, caplets, capsules, granules, powder, and liquids. Such dosage forms contain predetermined amounts of active ingredients, and may be prepared by methods of pharmacy well known to those skilled in the art.

Examples of excipients that can be used in oral dosage forms provided herein include, but are not limited to, binders, fillers, disintegrants, and lubricants.

Biomarkers

In certain embodiments, the amount of mRNA that is transcribed from the SMN1 gene and/or SMN2 gene and includes exon 7 of SMN1 and/or SMN2 is used as a biomarker for SMA. In certain embodiments, the amount of mRNA that is transcribed from the SMN1 gene and/or SMN2 gene and does not include exon 7 of SMN1 and/or SMN2 is used as a biomarker for SMA. In other embodiments, the amount of mRNA that is transcribed from the SMN1 and/or SMN2 gene and includes exon 7 of SMN1 and/or SMN2 is used as a biomarker for an SMA patient being treated with a compound, such as disclosed herein. In other embodiments, the amount of mRNA that is transcribed from the SMN1 and/or SMN2 gene and does not include exon 7 of SMN1 and/or SMN2 is used as a biomarker for an SMA patient being treated with a compound, such as disclosed herein. In some embodiments, a change in the amount of mRNA that is transcribed from the SMN1 and/or SMN2 gene and includes exon 7 of SMN1 and/or SMN2 and a corresponding change in the amount of mRNA that is transcribed from the SMN1 and/or SMN2 gene and does not include exon 7 of SMN1 and/or SMN2 is a biomarker for a patient being treated with a compound, such as disclosed herein. In a specific embodiment, the patient is an SMA patient.

In a specific embodiment, an increase in the amount of mRNA that is transcribed from the SMN1 and/or SMN2 gene and includes exon 7 of SMN1 and/or SMN2 and a corresponding decrease in the amount of mRNA that is transcribed from the SMN1 and/or SMN2 gene and does not include exon 7 of SMN1 and/or SMN2 after the administration of a compound (e.g., a compound of Formula (I) disclosed herein) indicates that the compound may be effective to treat SMA. In another specific embodiment, a decrease in the amount of mRNA that is transcribed from the SMN2 gene and includes exon 7 of SMN2 and a corresponding increase in the amount of mRNA that is transcribed from the SMN2 gene and does not include exon 7 of SMN2 after the administration of a compound (e.g., a compound of Formula (I) disclosed herein) indicates that the compound will not be effective to treat SMA. In accordance with these embodiments, an SMN primer(s) and/or an SMN probe described below can be used in assays, such as PCR (e.g., qPCR) and RT-PCR (e.g., RT-qPCR or endpoint RT-PCR) to assess and/or quantify the amount of mRNA that is transcribed from the SMN1 gene and/or SMN2 gene and does or does not include exon 7 of SMN1 and/or SMN2.

In one embodiment, provided herein are SMN primers and/or SMN probes (e.g., a forward primer having the nucleotide sequence of SEQ ID NO. 1, 7, 8, 11 or 13; and/or a reverse primer having the nucleotide sequence of SEQ ID NO. 9 or 12; and/or an SMN probe such as a SEQ ID NO. 3 or 10) for amplifying nucleic acids encoding or encoded by human SMN1 and/or SMN2. These primers can be used as primers in, e.g., RT-PCR (such as RT-PCR, endpoint RT-PCR and/or RT-qPCR as described herein or as known to one skilled in the art), PCR (such as qPCR) or rolling circle amplification, and as probes in hybridization assays, such as a Northern blot and/or a Southern blot assay. As utilized in the Biological Examples herein, endpoint RT-PCR is a reverse transcription-polymerase chain reaction that is carried out for a certain number of amplification cycles (or until starting materials are exhausted) following by a quantification of each of the DNA products using, e.g., gel electrophoretic separation, staining with a fluorescent dye, quantification of fluorescence and the like.

SEQ ID NO. 1 hybridizes to DNA or RNA comprising nucleotides corresponding to nucleotides 22 to 40 of exon 7 of SMN1 and/or SMN2, SEQ ID NO. 2 hybridizes to DNA or RNA comprising nucleotides corresponding to nucleotides 4 to 26 of the firefly luciferase coding sequence; SEQ ID NO. 7 hybridizes to nucleic acid sequences (e.g., the sense strand of DNA) comprising nucleotides corresponding to nucleotides 32 to 54 of exon 7 of SMN1 and/or SMN2 and nucleotides 1 to 4 of exon 8 of SMN1 and/or SMN2, SEQ ID NO. 8 hybridizes to nucleic acid sequences (e.g., the sense strand of DNA) comprising nucleotides corresponding, in order, to nucleotides 87 to 111 of exon 7 of SMN1 and/or SMN2 and nucleotides 1 to 3 of exon 8 of SMN1 and/or SMN2, SEQ ID NO. 9 hybridizes to nucleic acid sequences (e.g., the antisense strand of DNA or RNA) comprising nucleotides corresponding to nucleotides 39 to 62 of exon 8 of SMN1 and/or SMN2, SEQ ID NO. 11 hybridizes to nucleic acid sequences (e.g., the sense strand of DNA) comprising nucleotides corresponding to nucleotides 43 to 63 of exon 6 of SMN1 and/or SMN2, SEQ ID NO. 12 hybridizes to nucleic acid sequences (e.g., the antisense strand of DNA or RNA) comprising nucleotides corresponding to nucleotides 51 to 73 of exon 8 of SMN1 and/or SMN2, and SEQ ID NO. 13 hybridizes to nucleic acid sequence (e.g., the sense strand of DNA) comprising nucleotides corresponding to nucleotides 22 to 46 of exon 6 of SMN1 and/or SMN2.

Accordingly, an oligonucleotide corresponding to SEQ ID NO. 9, 11, 12 and/or 13 can be used in an amplification reaction to amplify nucleic acids encoding or encoded by human SMN1 and/or SMN2 lacking exon 7 of human SMN1 and/or SMN2 and nucleic acid encoding or encoded by human SMN1 and/or SMN2 and includes exon 7 of human SMN1 and/or SMN2. In contrast, an oligonucleotide corresponding to SEQ ID NO. 8 in conjunction with a downstream reverse primer (e.g., SEQ ID NO. 9 or 12) can be used to amplify nucleic acids encoding or encoded by human SMN1 and/or SMN2 lacking exon 7 of human SMN1 and/or SMN2 and an oligonucleotide corresponding to SEQ ID NO. 1 and 7 in conjunction with a downstream reverse primer (e.g., SEQ ID NO. 9 or 12) can be used to amplify nucleic acids encoding or encoded by human SMN1 and/or human SMN2 and includes exon 7 of SMN1 and/or SMN2.

SEQ ID NO. 3 hybridizes to nucleic acid sequences (e.g., the sense strand of DNA) comprising nucleotides corresponding, in order, to nucleotides 50 to 54 of exon 7 of human SMN1 and/or SMN2 and nucleotides 1 to 21 of exon 8 of human SMN1 and/or SMN2, and SEQ ID NO. 10 hybridizes to nucleic acid sequences (e.g., the sense strand of DNA) comprising nucleotides corresponding to nucleotides 7 to 36 of exon 8 of human SMN1 and/or SMN2. SEQ ID NO. 3 is useful as a probe to detect mRNA that is transcribed from the minigene and includes exon 7 of SMN1 and/or SMN2, described herein or described in International Publication No. WO 2009/151546 or U.S. Patent Application Publication No. 2011/0086833 (each of which is incorporated herein by reference in its entirety) and to detect mRNA that is transcribed from human SMN1 and/or SMN2 and includes exon 7 of SMN1 and/or SMN2. In addition, SEQ ID NO. 10 is useful as a probe to detect mRNA that is transcribed from the minigene and does or does not include exon 7 of SMN1 and/or SMN2 and to detect mRNA that is transcribed from human SMN1 and/or SMN2, described herein or as described in International Publication No. WO 2009/151546 or U.S. Patent Application Publication No. 2011/0086833, each of which is incorporated herein by reference in its entirety.

In a specific embodiment, a primer and/or probe described below in the Biological Examples (e.g., SMN primers such as SEQ ID NO. 1, 7, 11 or 13 and/or SEQ ID NO. 2, 9 or 12, and/or SMN probes such as a SEQ ID NO. 3 or 10) is used in an assay, such as RT-PCR, RT-qPCR, endpoint RT-PCR, PCR, qPCR, rolling circle amplification and, as applicable, Northern blot or Southern blot (e.g., an assay such as described below in the Biological Examples), to determine whether a compound (e.g., a compound of Formula (I) or a form thereof) enhances the inclusion of exon 7 of SMN1 and/or SMN2 into mRNA that is transcribed from an SMN1 and/or SMN2 gene.

In another embodiment, a primer and/or probe described below in the Biological Examples (e.g., SMN primers such as SEQ ID NO. 1, 7, 11 or 13 and/or SEQ ID NO. 9 or 12, and/or SMN probes such as a SEQ ID NO. 3 or 10) is used in an assay, such as RT-PCR, RT-qPCR, endpoint RT-PCR, PCR, qPCR, rolling circle amplification and, as applicable, Northern blot or Southern blot (e.g., an assay such as described below in the Biological Examples), to monitor the amount of mRNA that is transcribed from the SMN1 and/or SMN2 gene and includes exon 7 of SMN1 and/or SMN2 in a patient sample. In a specific embodiment, the patient is an SMA patient.

In another embodiment, a primer and/or probe described below in the Biological Examples (e.g., SMN primers such as SEQ ID NO. 1, 7, 11 or 13 and/or SEQ ID NO. 9 or 12, and/or SMN probes such as a SEQ ID NO. 3 or 10) is used in an assay, such as RT-PCR, RT-qPCR, endpoint RT-PCR, PCR, qPCR, rolling circle amplification and, as applicable, Northern blot or Southern blot (e.g., an assay such as described below in the Biological Examples), to monitor a patient's response to a compound (e.g., a compound of Formula (I) or a form thereof). In a specific embodiment, the patient is an SMA patient.

A sample (e.g., a blood sample, PBMC sample, or tissue sample, such as a skin or muscle tissue sample) from a patient can be obtained using techniques known to one skilled in the art and the primers and/or probes described in the Biological Examples below can be used in assays (e.g., PCR, RT-PCR, RT-qPCR, qPCR, endpoint RT-PCR, rolling circle amplification, Northern blot and Southern blot) to determine the amount of mRNA that is transcribed from the SMN1 and/or SMN2 genes (e.g., the amount of mRNA that includes exon 7 of SMN2 transcribed from the SMN2 gene).

A sample derived from a patient refers to a sample that is processed and/or manipulated after being obtained from the patient using techniques known to one skilled in the art. For example, a sample from a patient can be processed to, e.g., extract RNA, using techniques known to one of skill in the art. A sample from a patient can be processed to, e.g., extract RNA and the RNA is reversed transcribed to produce cDNA. In a specific embodiment, the patient is an SMA patient.

In a specific embodiment, provided herein is a method for detecting the amount of mRNA that is transcribed from the SMN1 and/or SMN2 gene and includes exon 7 of SMN1 and/or SMN2, comprising: (a) contacting a patient sample (e.g., blood sample or tissue sample) or a sample derived from a patient (e.g., a blood sample or tissue sample that has been processed to extract RNA) with a forward SMN primer described below (e.g., SEQ ID NO. 1, 7, 11 or 13) and/or a reverse SMN primer described herein (e.g., SEQ ID NO. 9 or 12) along with applicable components for, e.g., an RT-PCR (e.g., endpoint RT-PCR and/or RT-qPCR), PCR (e.g., qPCR) or rolling circle amplification; and (b) detecting the amount of mRNA that is transcribed from the SMN1 and/or SMN2 gene and includes exon 7 of SMN1 and/or SMN2. In certain embodiments, the sample is from or derived from a patient administered a compound, such as a compound of Formula (I) or a form thereof as described herein. In a specific embodiment, the patient is an SMA patient.

In another specific embodiment, provided herein is a method for detecting the amount of mRNA that is transcribed from the SMN1 and SMN2 genes, comprising: (a) contacting a patient sample (e.g., blood sample or tissue sample) or a sample derived from a patient (e.g., a blood sample or tissue sample that has been processed to extract RNA) with a forward SMN primer described below (e.g., SEQ ID NO. 1, 7, 11 or 13) and/or a reverse SMN primer described herein (e.g., SEQ ID NO. 9 or 12) along with applicable components for, e.g., an RT-PCR (e.g., endpoint RT-PCR and/or RT-qPCR), PCR (e.g., qPCR) or rolling circle amplification; and (b) detecting the amount of mRNA that is transcribed from the SMN1 and SMN2 genes. In certain embodiments, the sample is from or derived from a patient administered a compound, such as a compound of Formula (I) or a form thereof as described herein. In a specific embodiment, the patient is an SMA patient.

The amount of mRNA that is transcribed from the human SMN1 and SMN2 genes that includes exon 7 of SMN1 and SMN2 and the amount of mRNA that is transcribed from the human SMN1 and SMN2 genes and does not include exon 7 of SMN1 and SMN2 can be differentiated from each other by, e.g., size of the RNA or DNA fragment generated from SMN1 and SMN2 mRNA that includes exon 7 of SMN1 and SMN2 and from SMN1 and SMN2 mRNA that do not include exon 7 of SMN1 and SMN2.

In another specific embodiment, provided herein is a method for detecting the amount of mRNA that is transcribed from the SMN1 and/or SMN2 gene and does not include exon 7 of SMN1 and/or SMN2, comprising: (a) contacting a patient sample (e.g., blood sample or tissue sample) or a sample derived from a patient (e.g., a blood sample or tissue sample that has been processed to extract RNA) with a forward SMN primer described below (e.g., SEQ ID NO. 8, 11 or 13) and/or a reverse SMN primer described herein (e.g., SEQ ID NO. 9 or 12) along with applicable components for, e.g., an RT-PCR (e.g., endpoint RT-PCR and/or RT-qPCR), PCR (e.g., qPCR) or rolling circle amplification; and (b) detecting the amount of mRNA that is transcribed from the SMN1 and/or SMN2 gene and does not include exon 7 of SMN1 and/or SMN2. In certain embodiments, the sample is from or derived from a patient administered a compound, such as a compound of Formula (I) or a form thereof as described herein. In a specific embodiment, the patient is an SMA patient.

In another specific embodiment, provided herein is a method for detecting the amount of mRNA that is transcribed from the SMN1 and/or SMN2 gene and includes exon 7 of SMN1 and/or SMN2, comprising: (a) contacting a patient sample (e.g., blood sample or tissue sample) or a sample derived from a patient (e.g., a blood sample or tissue sample that has been processed to extract RNA) with an SMN probe described below (e.g., SEQ ID NO. 3 or 10) along with applicable components, e.g., of an RT-PCR (e.g., endpoint RT-PCR and/or RT-qPCR), PCR (e.g., qPCR), rolling circle amplification and, as applicable, Northern blot or Southern blot; and (b) detecting the amount of mRNA that is transcribed from the SMN1 and/or SMN2 gene and includes exon 7 of SMN1 and/or SMN2. In certain embodiments, the sample is from or derived from a patient administered a compound, such as a compound of Formula (I) or a form thereof as described herein. In a specific embodiment, the patient is an SMA patient.

In another specific embodiment, provided herein is a method for detecting the amount of mRNA that is transcribed from the SMN1 and SMN2 genes, comprising: (a) contacting a patient sample (e.g., blood sample or tissue sample) or a sample derived from a patient (e.g., a blood sample or tissue sample that has been processed to extract RNA) with an SMN probe described below (e.g., SEQ ID NO. 3 or 10) along with applicable components for, e.g., an RT-PCR (e.g., endpoint RT-PCR and/or RT-qPCR), PCR (e.g., qPCR), rolling circle amplification and, as applicable, Northern blot or Southern blot; and (b) detecting the amount of mRNA that is transcribed from the SMN1 and SMN2 genes.

The amount of mRNA that is transcribed from the human SMN1 and SMN2 genes that includes exon 7 of SMN1 and SMN2 and the amount of mRNA that is transcribed from the human SMN1 and SMN2 genes and does not include exon 7 of SMN1 and SMN2 can be differentiated from each other by, e.g., size of the RNA or DNA fragment generated from SMN1 and SMN2 mRNA that includes exon 7 of SMN1 and SMN2 and from SMN1 and SMN2 mRNA that do not include exon 7 of SMN1 and SMN2. In certain embodiments, the sample is from or derived from a patient administered a compound, such as a compound of Formula (I) or a form thereof as described herein. In a specific embodiment, the patient is an SMA patient.

In another specific embodiment, provided herein is a method for detecting the amount of mRNA that is transcribed from the SMN1 and/or SMN2 gene and does not include exon 7 of SMN1 and/or SMN2, comprising: (a) contacting a patient sample (e.g., blood sample or tissue sample) or a sample derived from a patient (e.g., a blood sample or tissue sample that has been processed to extract RNA) with an SMN probe described below (e.g., SEQ ID NO. 10) along with applicable components for, e.g., an RT-PCR (e.g., endpoint RT-PCR and/or RT-qPCR), PCR (e.g., qPCR), rolling circle amplification, or Northern blot or Southern blot; and (b) detecting the amount of mRNA that is transcribed from the SMN1 and/or SMN2 gene and does not include exon 7 of SMN1 and/or SMN2. In certain embodiments, the sample is from or derived from a patient administered a compound, such as a compound of Formula (I) or a form thereof as described herein. In a specific embodiment, the patient is an SMA patient.

In a specific embodiment, provided herein is a method for detecting the amount of mRNA that is transcribed from the SMN1 and/or SMN2 gene and includes exon 7 of SMN1 and/or SMN2, comprising: (a) contacting a patient sample (e.g., blood sample or tissue sample) or a sample derived from a patient (e.g., a blood sample or tissue sample that has been processed to extract RNA) with a forward SMN primer described below (e.g., SEQ ID NO. 1, 7, 11 or 13) and/or a reverse SMN primer described herein (e.g., SEQ ID NO. 9 or 12) and/or an SMN probe described herein (e.g., SEQ ID NO. 3 or 10) along with applicable components for e.g., an RT-PCR (e.g., endpoint RT-PCR and/or RT-qPCR), PCR (e.g., qPCR) or rolling circle amplification; and (b) detecting the amount of mRNA that is transcribed from the SMN1 and/or SMN2 gene and includes exon 7 of SMN1 and/or SMN2. In certain embodiments, the sample is from or derived from a patient administered a compound, such as a compound of Formula (I) or a form thereof as described herein. In a specific embodiment, the patient is an SMA patient.

In a specific embodiment, provided herein is a method for detecting the amount of mRNA that is transcribed from the SMN1 and SMN2 genes, comprising: (a) contacting a patient sample (e.g., blood sample or tissue sample) or a sample derived from a patient (e.g., a blood sample or tissue sample that has been processed to extract RNA) with a forward SMN primer described below (e.g., SEQ ID NO. 1, 7, 8, 11 or 13) and/or a reverse SMN primer described herein (e.g., SEQ ID NO. 9 or 12) and/or an SMN probe described herein (e.g., SEQ ID NO. 3 or 10) along with applicable components for e.g., an RT-PCR (e.g., endpoint RT-PCR and/or RT-qPCR), PCR (e.g., qPCR) or rolling circle amplification, as applicable; and (b) detecting the amount of mRNA that is transcribed from the SMN1 and SMN2 genes. In a specific embodiment, the patient is an SMA patient.

The amount of mRNA that is transcribed from the human SMN1 and SMN2 genes that includes exon 7 of SMN1 and SMN2 and the amount of mRNA that is transcribed from the human SMN1 and SMN2 genes that do not include exon 7 of SMN1 and SMN2 can be differentiated from each other by, e.g., size of the RNA or DNA fragment generated from SMN1 and SMN2 mRNA that includes exon 7 of SMN1 and SMN2 and from SMN1 and SMN2 mRNA that does not include exon 7 of SMN1 and SMN2. In certain embodiments, the sample is from or derived from a patient administered a compound, such as a compound of Formula (I) or a form thereof as described herein. In a specific embodiment, the patient is an SMA patient.

In a specific embodiment, provided herein is a method for detecting the amount of mRNA that is transcribed from the SMN1 and/or SMN2 gene and does not include exon 7 of SMN1 and/or SMN2, comprising: (a) contacting a patient sample (e.g., blood sample or tissue sample) or a sample derived from a patient (e.g., a blood sample or tissue sample that has been processed to extract RNA) with a forward SMN primer described below (e.g., SEQ ID NO. 8) and/or a reverse SMN primer described herein (e.g., SEQ ID NO. 9 or 12) and/or an SMN probe described herein (e.g., SEQ ID NO. 10) along with applicable components for e.g., an RT-PCR (e.g., endpoint RT-PCR and/or RT-qPCR), PCR (e.g., qPCR) or rolling circle amplification; and (b) detecting the amount of mRNA that is transcribed from the SMN1 and/or SMN2 gene and does not include exon 7 of SMN1 and/or SMN2. In certain embodiments, the sample is from or derived from a patient administered a compound, such as a compound of Formula (I) or a form thereof as described herein. In a specific embodiment, the patient is an SMA patient.

In a specific embodiment, provided herein is a method for assessing an SMA patient's response to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 1, 7, 11 or 13) and/or a reverse SMN primer described herein (e.g., SEQ ID NO. 9 or 12) along with applicable components for e.g., RT-PCR (e.g., endpoint RT-PCR and/or RT-qPCR), PCR (e.g., qPCR) or rolling circle amplification, wherein the sample is from or derived from an SMA patient administered a compound (e.g., a compound described herein); and (b) detecting the amount of mRNA that is transcribed from the SMN1 and/or SMN2 gene and includes exon 7 of SMN1 and/or SMN2, wherein (1) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound indicates that the patient is responsive to the compound and that the compound may be or is beneficial and/or of therapeutic value to the patient; and (2) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound indicates that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In another specific embodiment, provided herein is a method for assessing an SMA patient's response to a compound, comprising: (a) administering a compound to an SMA patient; (b) contacting a sample (e.g., blood sample or tissue sample) obtained or derived from the patient with a forward SMN primer described below (e.g., SEQ ID NO. 1, 7, 11 or 13) and/or a reverse SMN primer described herein (e.g., SEQ ID NO. 9 or 12) along with applicable components for e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and includes exon 7 of SMN2, wherein (1) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound indicates that the patient is responsive to the compound and that the compound may be or is beneficial and/or of therapeutic value to the patient; and (2) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound indicates that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In a specific embodiment, provided herein is a method for assessing an SMA patient's response to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 1, 7, 11 or 13) and/or a reverse SMN primer described herein (e.g., SEQ ID NO. 9 or 12) and/or an SMN probe (e.g., SEQ ID NO. 3 or 10) along with applicable components for e.g., RT-PCR (e.g., endpoint RT-PCR and/or RT-qPCR), PCR (e.g., qPCR) or rolling circle amplification, wherein the sample is from or derived from an SMA patient administered a compound (e.g., a compound of Formula (I) or a form thereof as described herein); and (b) detecting the amount of mRNA that is transcribed from the SMN1 and/or SMN2 gene and includes exon 7 of SMN1 and/or SMN2, wherein (1) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound indicates that the patient is responsive to the compound and that the compound may be or is beneficial and/or of therapeutic value to the patient; and (2) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound indicates that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In another specific embodiment, provided herein is a method for assessing an SMA patient's response to a compound, comprising: (a) administering a compound to an SMA patient; (b) contacting a sample (e.g., blood sample or tissue sample) obtained or derived from the patient with a forward SMN primer described below (e.g., SEQ ID NO. 1, 7, 11 or 13) and/or a reverse SMN primer described herein (e.g., SEQ ID NO. 9 or 12) and/or an SMN probe (e.g., SEQ ID NO. 3 or 10) along with applicable components for e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and includes exon 7 of SMN1 and/or SMN2, wherein (1) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound indicates that the patient is responsive to the compound and that the compound may be or is beneficial and/or of therapeutic value to the patient; and (2) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound indicates that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In a specific embodiment, provided herein is a method for assessing an SMA patient's response to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 8, 11 or 13) and/or a reverse SMN primer described herein (e.g., SEQ ID NO. 9 or 12) along with applicable components for e.g., RT-PCR (e.g., endpoint RT-PCR and/or RT-qPCR), PCR (e.g., qPCR) or rolling circle amplification, wherein the sample is from or derived from an SMA patient administered a compound (e.g., a compound of Formula (I) or a form thereof as described herein); and (b) detecting the amount of mRNA that is transcribed from the SMN1 and/or SMN2 gene and does not include exon 7 of SMN1 and/or SMN2, wherein (1) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound indicates that the patient is responsive to the compound and that the compound may be or is beneficial and/or of therapeutic value to the patient; and (2) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound indicates that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In another specific embodiment, provided herein is a method for assessing an SMA patient's response to a compound, comprising: (a) administering a compound to an SMA patient; (b) contacting a sample (e.g., blood sample or tissue sample) obtained or derived from the patient with a forward SMN primer described below (e.g., SEQ ID NO. 8, 11 or 13) and/or a reverse SMN primer described herein (e.g., SEQ ID NO. 9 or 12) along with applicable components for e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and does not include exon 7 of SMN1 and/or SMN2, wherein (1) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound indicates that the patient is responsive to the compound and that the compound may be or is beneficial and/or of therapeutic value to the patient; and (2) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound indicates that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In a specific embodiment, provided herein is a method for assessing an SMA patient's response to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 8, 11 or 13) and/or a reverse SMN primer described herein (e.g., SEQ ID NO. 9 or 12) and/or an SMN probe (e.g., SEQ ID NO. 10) along with applicable components for e.g., RT-PCR (e.g., endpoint RT-PCR and/or RT-qPCR), PCR (e.g., qPCR) or rolling circle amplification, wherein the sample is from or derived from an SMA patient administered a compound (e.g., a compound of Formula (I) or a form thereof as described herein); and (b) detecting the amount of mRNA that is transcribed from the SMN1 and/or SMN2 gene and does not include exon 7 of SMN1 and/or SMN2, wherein (1) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound indicates that the patient is responsive to the compound and that the compound may be or is beneficial and/or of therapeutic value to the patient; and (2) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound indicates that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In another specific embodiment, provided herein is a method for assessing an SMA patient's response to a compound, comprising: (a) administering a compound to an SMA patient; (b) contacting a sample (e.g., blood sample or tissue sample) obtained or derived from the patient with a forward SMN primer described below (e.g., SEQ ID NO. 8, 11 or 13) and/or a reverse SMN primer described herein (e.g., SEQ ID NO. 9 or 12) and/or an SMN probe (e.g., SEQ ID NO. 10) along with applicable components for e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and does not include exon 7 of SMN1 and/or SMN2, wherein (1) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound indicates that the patient is responsive to the compound and that the compound may be or is beneficial and/or of therapeutic value to the patient; and (2) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound indicates that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In a specific embodiment, provided herein is a method for assessing an SMA patient's response to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 11 or 13) and/or a reverse SMN primer described herein (e.g., SEQ ID NO. 9 or 12) along with applicable components for e.g., RT-PCR (e.g., endpoint RT-PCR and/or RT-qPCR), PCR (e.g., qPCR) or rolling circle amplification, wherein the sample is from or derived from an SMA patient administered a compound (e.g., a compound of Formula (I) or a form thereof as described herein); and (b) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1)(i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound, indicate that the patient is responsive to the compound and that the compound may be or is beneficial and/or of therapeutic value to the patient; and (2)(i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., the same type of tissue sample) from the patient prior to administration of the compound, indicates that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In another specific embodiment, provided herein is a method for assessing an SMA patient's response to a compound, comprising: (a) administering a compound to an SMA patient; (b) contacting a sample (e.g., blood sample or tissue sample) obtained or derived from the patient with a forward SMN primer described below (e.g., SEQ ID NO. 11 or 13) and/or a reverse SMN primer described herein (e.g., SEQ ID NO. 9 or 12) along with applicable components for e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1)(i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound, indicate that the patient is responsive to the compound and that the compound may be or is beneficial and/or of therapeutic value to the patient; and (2)(i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., the same type of tissue sample) from the patient prior to administration of the compound, indicate that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In a specific embodiment, provided herein is a method for assessing an SMA patient's response to a compound, comprising: (a) contacting an SMA patient sample (e.g., blood sample or tissue sample) or a sample derived from an SMA patient (e.g., a blood sample or tissue sample that has been processed to extract RNA) with an SMN probe (e.g., SEQ ID NO. 10) along with applicable components for e.g., RT-PCR (e.g., endpoint RT-PCR and/or RT-qPCR), PCR (e.g., qPCR) or rolling circle amplification, wherein the sample is from or derived from an SMA patient administered a compound (e.g., a compound of Formula (I) or a form thereof as described herein); and (b) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1)(i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound, indicate that the patient is responsive to the compound and that the compound may be or is beneficial and/or of therapeutic value to the patient; and (2)(i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., the same type of tissue sample) from the patient prior to administration of the compound, indicate that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In another specific embodiment, provided herein is a method for assessing an SMA patient's response to a compound, comprising: (a) administering a compound to an SMA patient; (b) contacting a sample (e.g., blood sample or tissue sample) obtained or derived from the patient with an SMN probe (e.g., SEQ ID NO. 10) along with applicable components for e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1)(i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound, indicate that the patient is responsive to the compound and that the compound may be or is beneficial and/or of therapeutic value to the patient; and (2)(i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., the same type of tissue sample) from the patient prior to administration of the compound, indicate that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In a specific embodiment, provided herein is a method for assessing an SMA patient's response to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 11 or 13) and/or a reverse SMN primer described herein (e.g., SEQ ID NO. 9 or 12) and/or an SMN probe (e.g., SEQ ID NO. 10) along with applicable components for e.g., RT-PCR (e.g., endpoint RT-PCR and/or RT-qPCR) or PCR (e.g., qPCR), wherein the sample is from or derived from an SMA patient administered a compound (e.g., a compound of Formula (I) or a form thereof as described herein); and (b) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1)(i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound, indicate that the patient is responsive to the compound and that the compound may be or is beneficial and/or of therapeutic value to the patient; and (2)(i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., the same type of tissue sample) from the patient prior to administration of the compound, indicate that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In another specific embodiment, provided herein is a method for assessing an SMA patient's response to a compound, comprising: (a) administering a compound to an SMA patient; (b) contacting a sample (e.g., blood sample or tissue sample) obtained or derived from the patient with a forward SMN primer described below (e.g., SEQ ID NO. 11 or 13) and/or a reverse SMN primer described herein (e.g., SEQ ID NO. 9 or 12) and/or an SMN probe (e.g., SEQ ID NO. 10) along with applicable components for, e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1)(i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound, indicate that the SMN1 and/or patient is responsive to the compound and that the compound may be or is beneficial and/or of therapeutic value to the patient; and (2)(i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., the same type of tissue sample) from the patient prior to administration of the compound, indicate that the patient is not responsive to the compound and that the compound is not beneficial and/or of therapeutic value to the patient. In certain embodiments, the patient's response is assessed 1 hour, 2 hours, 4 hours, 8 hours, 12 hours, 16 hours, 20 hours, 1 day, 2 days, 3 days, 5 days, 7 days, 14 days, 28 days, 1 month, 2 months, 3 months, 6 months, 9 months, 12 months or more after administration of a compound, such as a compound of Formula (I) or a form thereof as described herein.

In a specific embodiment, provided herein is a method for monitoring an SMA patient's responsiveness to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 1, 7, 11 or 13) and/or a reverse SMN primer described herein (e.g., SEQ ID NO. 9 or 12) along with applicable components for e.g., RT-PCR (e.g., endpoint RT-PCR and/or RT-qPCR), PCR (e.g., qPCR) or rolling circle amplification, wherein the sample is from or derived from an SMA patient administered a compound (e.g., a compound of Formula (I) or a form thereof as described herein); and (b) detecting the amount of mRNA that is transcribed from the SMN1 and/or SMN2 gene and includes exon 7 of SMN1 and/or SMN2, wherein (1) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to the administration of the compound or a certain number of doses of the compound, or a certain earlier date indicates that the patient is responsive to the compound and that the compound may be or is beneficial and/or of therapeutic value to the patient; and (2) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to the administration of the compound or a certain number of doses of the compound, or a certain earlier date indicates that the patient is not responsive to the compound and that the compound is not beneficial and/or of therapeutic value to the patient. In certain embodiments, the patient's response is monitored 1 hour, 2 hours, 4 hours, 8 hours, 12 hours, 16 hours, 20 hours, 1 day, 2 days, 3 days, 4 days, 5 days, 7 days, 14 days, 28 days, 1 month, 2 months, 3 months, 6 months, 9 months, 12 months or more after administration of a compound, such as of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein. In some embodiments, the patient's response is monitored over a period of days, weeks, months or years during or after the continuous administration of a compound, such as a compound of Formula (I) or a form thereof as described herein.

In another specific embodiment, provided herein is a method for monitoring an SMA patient's responsiveness to a compound, comprising: (a) administering a compound to an SMA patient; (b) contacting a sample (e.g., blood sample or tissue sample) obtained or derived from the patient with a forward SMN primer described below (e.g., SEQ ID NO. 1, 7, 11 or 13) and/or a reverse SMN primer described herein (e.g., SEQ ID NO. 9 or 12) along with applicable components for, e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and includes exon 7 of SMN1 and/or SMN2, wherein (1) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to the administration of the compound or a certain number of doses of the compound, or a certain earlier date indicates that the patient is responsive to the compound and that the compound may be or is beneficial and/or of therapeutic value to the patient; and (2) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to the administration of the compound or a certain number of doses of the compound, or a certain earlier date indicates that the patient is not responsive to the compound and that the compound is not beneficial and/or of therapeutic value to the patient. In certain embodiments, the patient's response is monitored 1 hour, 2 hours, 4 hours, 8 hours, 12 hours, 16 hours, 20 hours, 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein. In some embodiments, the patient's response is monitored over a period of days, weeks, months or years during or after the continuous administration of a compound, such as a compound of Formula (I) or a form thereof as described herein.

In a specific embodiment, provided herein is a method for monitoring an SMA patient's responsiveness to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 1, 7, 11 or 13) and/or a reverse SMN primer described herein (e.g., SEQ ID NO. 9 or 12) and/or an SMN probe (e.g., SEQ ID NO. 3 or 10) along with applicable components for e.g., RT-PCR (e.g., endpoint RT-PCR and/or RT-qPCR), PCR (e.g., qPCR) or rolling circle amplification, wherein the sample is from or derived from an SMA patient administered a compound (e.g., a compound of Formula (I) or a form thereof as described herein); and (b) detecting the amount of mRNA that is transcribed from the SMN1 and/or SMN2 gene and includes exon 7 of SMN1 and/or SMN2, wherein (1) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to the administration of the compound or a certain number of doses of the compound, or a certain earlier date indicates that the patient is responsive to the compound and that the compound may be or is beneficial and/or of therapeutic value to the patient; and (2) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to the administration of the compound or a certain number of doses of the compound, or a certain earlier date indicates that the patient is not responsive to the compound and that the compound is not beneficial and/or of therapeutic value to the patient. In certain embodiments, the patient's response is monitored 1 hour, 2 hours, 4 hours, 8 hours, 12 hours, 16 hours, 20 hours, 1 day, 2 days, 3 days, 4 days, 5 days, 7 days, 14 days, 28 days, 1 month, 2 months, 3 months, 6 months, 9 months, 12 months or more after administration of a compound, such as of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein. In some embodiments, the patient's response is monitored over a period of days, weeks, months or years during or after the continuous administration of a compound, such as a compound of Formula (I) or a form thereof as described herein.

In another specific embodiment, provided herein is a method for monitoring an SMA patient's responsiveness to a compound, comprising: (a) administering a compound to an SMA patient; (b) contacting a sample (e.g., blood sample or tissue sample) obtained or derived from the patient with a forward SMN primer described below (e.g., SEQ ID NO. 1, 7, 11 or 13) and/or a reverse SMN primer described herein (e.g., SEQ ID NO. 9 or 12) and/or an SMN probe (e.g., SEQ ID NO. 3 or 10) along with applicable components for, e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and includes exon 7 of SMN1 and/or SMN2, wherein (1) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to the administration of the compound or a certain number of doses of the compound, or a certain earlier date indicates that the patient is responsive to the compound and that the compound may be or is beneficial and/or of therapeutic value to the patient; and (2) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to the administration of the compound or a certain number of doses of the compound, or a certain earlier date indicates that the patient is not responsive to the compound and that the compound is not beneficial and/or of therapeutic value to the patient. In certain embodiments, the patient's response is monitored 1 hour, 2 hours, 4 hours, 8 hours, 12 hours, 16 hours, 20 hours, 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein. In some embodiments, the patient's response is monitored over a period of days, weeks, months or years during or after the continuous administration of a compound, such as a compound of Formula (I) or a form thereof as described herein.

In a specific embodiment, provided herein is a method for monitoring an SMA patient's responsiveness to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 8, 11 or 13) and/or a reverse SMN primer described herein (e.g., SEQ ID NO. 9 or 12) along with applicable components for, e.g., RT-PCR (e.g., endpoint RT-PCR and/or RT-qPCR), PCR (e.g., qPCR) or rolling circle amplification, wherein the sample is from or derived from an SMA patient administered a compound (e.g., a compound of Formula (I) or a form thereof as described herein); and (b) detecting the amount of mRNA that is transcribed from the SMN1 and/or SMN2 gene and does not include exon 7 of SMN1 and/or SMN2, wherein (1) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to the administration of the compound or a certain number of doses of the compound, or a certain earlier date indicates that the patient is responsive to the compound and that the compound may be or is beneficial and/or of therapeutic value to the patient; and (2) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to the administration of the compound or a certain number of doses of the compound, or a certain earlier date indicates that the patient is not responsive to the compound and that the compound is not beneficial and/or of therapeutic value to the patient. In certain embodiments, the patient's response is monitored 1 hour, 2 hours, 4 hours, 8 hours, 12 hours, 16 hours, 20 hours, 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein. In some embodiments, the patient's response is monitored over a period of days, weeks, months or years during or after the continuous administration of a compound, such as a compound of Formula (I) or a form thereof as described herein.

In another specific embodiment, provided herein is a method for monitoring an SMA patient's responsiveness to a compound, comprising: (a) administering a compound to an SMA patient; (b) contacting a sample (e.g., blood sample or tissue sample) obtained or derived from the patient with a forward SMN primer described below (e.g., SEQ ID NO. 8, 11 or 13) and/or a reverse SMN primer described herein (e.g., SEQ ID NO. 9 or 12) along with applicable components for, e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and does not include exon 7 of SMN1 and/or SMN2, wherein (1) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to the administration of the compound or a certain number of doses of the compound, or a certain earlier date indicates that the patient is responsive to the compound and that the compound may be or is beneficial and/or of therapeutic value to the patient; and (2) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to the administration of the compound or a certain number of doses of the compound, or a certain earlier date indicates that the patient is not responsive to the compound and that the compound is not beneficial and/or of therapeutic value to the patient. In certain embodiments, the patient's response is monitored 1 hour, 2 hours, 4 hours, 8 hours, 12 hours, 16 hours, 20 hours, 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein. In some embodiments, the patient's response is monitored continuous administration of a compound over a period of days, weeks, months or years, such as a compound of Formula (I) or a form thereof as described herein.

In a specific embodiment, provided herein is a method for monitoring an SMA patient's responsiveness to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 8, 11 or 13) and/or a reverse SMN primer described herein (e.g., SEQ ID NO. 9 or 12) and/or an SMN probe (e.g., SEQ ID NO. 10) along with applicable components for, e.g., RT-PCR (e.g., endpoint RT-PCR and/or RT-qPCR), PCR (e.g., qPCR) or rolling circle amplification, wherein the sample is from or derived from a patient administered a compound (e.g., a compound of Formula (I) or a form thereof as described herein); and (b) detecting the amount of mRNA that is transcribed from the SMN1 and/or SMN2 gene and does not include exon 7 of SMN1 and/or SMN2, wherein (1) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to the administration of the compound or a certain number of doses of the compound, or a certain earlier date indicates that the patient is responsive to the compound and that the compound may be or is beneficial and/or of therapeutic value to the patient; and (2) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to the administration of the compound or a certain number of doses of the compound, or a certain earlier date indicates that the patient is not responsive to the compound and that the compound is not beneficial and/or of therapeutic value to the patient. In certain embodiments, the patient's response is monitored 1 hour, 2 hours, 4 hours, 8 hours, 12 hours, 16 hours, 20 hours, 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein. In some embodiments, the patient's response is monitored over a period of days, weeks, months or years during or after the continuous administration of a compound, such as a compound of Formula (I) or a form thereof as described herein.

In another specific embodiment, provided herein is a method for monitoring an SMA patient's responsiveness to a compound, comprising: (a) administering a compound to an SMA patient; (b) contacting a sample (e.g., blood sample or tissue sample) obtained or derived from the patient with a forward SMN primer described below (e.g., SEQ ID NO. 8, 11 or 13) and/or a reverse SMN primer described herein (e.g., SEQ ID NO. 9 or 12) and/or an SMN probe (e.g., SEQ ID NO. 10) along with applicable components for, e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and does not include exon 7 of SMN1 and/or SMN2, wherein (1) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to the administration of the compound or a certain number of doses of the compound, or a certain earlier date indicates that the patient is responsive to the compound and that the compound may be or is beneficial and/or of therapeutic value to the patient; and (2) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to the administration of the compound or a certain number of doses of the compound, or a certain earlier date indicates that the patient is not responsive to the compound and that the compound is not beneficial and/or of therapeutic value to the patient. In certain embodiments, the patient's response is monitored 1 hour, 2 hours, 4 hours, 8 hours, 12 hours, 16 hours, 20 hours, 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein. In some embodiments, the patient's response is monitored over a period of days, weeks, months or years during or after the continuous administration of a compound, such as a compound of Formula (I) or a form thereof as described herein.

In a specific embodiment, provided herein is a method for monitoring an SMA patient's response to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 11 or 13) and/or a reverse SMN primer described herein (e.g., SEQ ID NO. 9 or 12) along with applicable components for, e.g., RT-PCR (e.g., endpoint RT-PCR and/or RT-qPCR), PCR (e.g., qPCR) or rolling circle amplification, wherein the sample is from or derived from an SMA patient administered a compound (e.g., a compound of Formula (I) or a form thereof as described herein); and (b) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1)(i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound or a certain number of doses of the compound, or a certain earlier date, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound or a certain number of doses of the compound, or a certain earlier date, indicate that the patient is responsive to the compound and that the compound may be or is beneficial and/or of therapeutic value to the patient; and (2)(i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound or a certain number of doses of the compound, or a certain earlier date, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., the same type of tissue sample) from the patient prior to administration of the compound or a certain number of doses of the compound, or a certain earlier date, indicate that the patient is not responsive to the compound and that the compound is not beneficial and/or of therapeutic value to the patient. In certain embodiments, the patient's response is monitored 1 hour, 2 hours, 4 hours, 8 hours, 12 hours, 16 hours, 20 hours, 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein. In some embodiments, the patient's response is monitored over a period of days, weeks, months or years during or after the continuous administration of a compound, such as a compound of Formula (I) or a form thereof as described herein.

In another specific embodiment, provided herein is a method for monitoring an SMA patient's response to a compound, comprising: (a) administering a compound to an SMA patient; (b) contacting a sample (e.g., blood sample or tissue sample) obtained or derived from the patient with a forward SMN primer described below (e.g., SEQ ID NO. 11 or 13) and/or a reverse SMN primer described herein (e.g., SEQ ID NO. 9 or 12) along with applicable components for, e.g., RT-PCR (e.g., endpoint RT-PCR and/or RT-qPCR), PCR (e.g., qPCR), or rolling circle amplification; and (c) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1)(i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound or a certain number of doses of the compound, or a certain earlier date, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound or a certain number of doses of the compound, or a certain earlier date, indicate that the patient is responsive to the compound and that the compound may be or is beneficial and/or of therapeutic value to the patient; and (2)(i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound or a certain number of doses of the compound, or a certain earlier date, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., the same type of tissue sample) from the patient prior to administration of the compound or a certain number of doses of the compound, or a certain earlier date, indicate that the patient is not responsive to the compound and that the compound is not beneficial and/or of therapeutic value to the patient. In certain embodiments, the patient's response is monitored 1 hour, 2 hours, 4 hours, 8 hours, 12 hours, 16 hours, 20 hours, 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein. In some embodiments, the patient's response is monitored over a period of days, weeks, months or years during or after the continuous administration of a compound, such as a compound of Formula (I) or a form thereof as described herein.

In a specific embodiment, provided herein is a method for monitoring an SMA patient's response to a compound, comprising: (a) contacting an SMA patient sample (e.g., blood sample or tissue sample) or a sample derived from an SMA patient (e.g., a blood sample or tissue sample that has been processed to extract RNA) with an SMN probe (e.g., SEQ ID NO. 10) along with applicable components for, e.g., RT-PCR (e.g., endpoint RT-PCR and/or RT-qPCR), PCR (e.g., qPCR) or rolling circle amplification, wherein the sample is from or derived from an SMA patient administered a compound (e.g., a compound of Formula (I) or a form thereof as described herein); and (b) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1)(i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of S SMN1 and/or MN2 in an analogous sample (e.g., from the same type of tissue sample) from the patient prior to administration of the compound or a certain number of doses of the compound, or a certain earlier date, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound or a certain number of doses of the compound, or a certain earlier date, indicate that the patient is responsive to the compound and that the compound may be or is beneficial and/or of therapeutic value to the patient; and (2)(i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound or a certain number of doses of the compound, or a certain earlier date, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., the same type of tissue sample) from the patient prior to administration of the compound or a certain number of doses of the compound, or a certain earlier date, indicate that the patient is not responsive to the compound and that the compound is not beneficial and/or of therapeutic value to the patient. In certain embodiments, the patient's response is monitored 1 hour, 2 hours, 4 hours, 8 hours, 12 hours, 16 hours, 20 hours, 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein. In some embodiments, the patient's response is monitored over a period of days, weeks, months or years during or after the continuous administration of a compound, such as a compound of Formula (I) or a form thereof as described herein.

In another specific embodiment, provided herein is a method for monitoring an SMA patient's response to a compound, comprising: (a) administering a compound to an SMA patient; (b) contacting a sample (e.g., blood sample or tissue sample) obtained or derived from the patient with an SMN probe (e.g., SEQ ID NO. 10) along with applicable components for, e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1)(i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound or a certain number of doses of the compound, or a certain earlier date, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound or a certain number of doses of the compound, or a certain earlier date, indicate that the patient is responsive to the compound and that the compound may be or is beneficial and/or of therapeutic value to the patient; and (2)(i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound or a certain number of doses of the compound, or a certain earlier date, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., the same type of tissue sample) from the patient prior to administration of the compound or a certain number of doses of the compound, or a certain earlier date, indicate that the patient is not responsive to the compound and that the compound is not beneficial and/or of therapeutic value to the patient. In certain embodiments, the patient's response is monitored 1 hour, 2 hours, 4 hours, 8 hours, 12 hours, 16 hours, 20 hours, 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein. In some embodiments, the patient's response is monitored over a period of days, weeks, months or years during or after the continuous administration of a compound, such as a compound of Formula (I) or a form thereof as described herein.

In a specific embodiment, provided herein is a method for monitoring an SMA patient's response to a compound, comprising: (a) contacting an SMA patient sample (e.g., blood sample or tissue sample) or a sample derived from an SMA patient (e.g., a blood sample or tissue sample that has been processed to extract RNA) with a forward SMN primer described below (e.g., SEQ ID NO. 11 or 13) and/or a reverse SMN primer described herein (e.g., SEQ ID NO. 9 or 12) and/or an SMN probe (SEQ ID NO. 10) along with applicable components for, e.g., RT-PCR (e.g., endpoint RT-PCR and/or RT-qPCR), PCR (e.g., qPCR) or rolling circle amplification, wherein the sample is from or derived from an SMA patient administered a compound (e.g., a compound of Formula (I) or a form thereof as described herein); and (b) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1)(i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN2 in an analogous sample (e.g., from the same type of tissue sample) from the patient prior to administration of the compound or a certain number of doses of the compound, or a certain earlier date, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound or a certain number of doses of the compound, or a certain earlier date, indicate that the patient is responsive to the compound and that the compound may be or is beneficial and/or of therapeutic value to the patient; and (2)(i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound or a certain number of doses of the compound, or a certain earlier date, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., the same type of tissue sample) from the patient prior to administration of the compound or a certain number of doses of the compound, or a certain earlier date, indicate that the patient is not responsive to the compound and that the compound is not beneficial and/or of therapeutic value to the patient. In certain embodiments, the patient's response is monitored 1 hour, 2 hours, 4 hours, 8 hours, 12 hours, 16 hours, 20 hours, 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein. In some embodiments, the patient's response is monitored over a period of days, weeks, months or years during or after the continuous administration of a compound, such as a compound of Formula (I) or a form thereof as described herein.

In another specific embodiment, provided herein is a method for monitoring an SMA patient's response to a compound, comprising: (a) administering a compound to an SMA patient; (b) contacting a sample (e.g., blood sample or tissue sample) obtained or derived from the patient with a forward SMN primer described below (e.g., SEQ ID NO. 11 or 13) and/or a reverse SMN primer described herein (e.g., SEQ ID NO. 9 or 12) and/or an SMN probe (SEQ ID NO. 10) along with applicable components for, e.g., RT-PCR (e.g., endpoint RT-PCR and/or RT-qPCR), PCR (e.g., qPCR) or rolling circle amplification; and (c) detecting the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, wherein (1)(i) an increase in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., from the same type of tissue sample) from the patient prior to administration of the compound or a certain number of doses of the compound, or a certain earlier date, and (ii) a decrease in the amount of mRNA that is transcribed from the SMN1 and/or SMN2 gene and does not include exon 7 of SMN1 and/or SMN2 in the patient sample relative to the amount of mRNA that is transcribed from the SMN1 and/or SMN2 gene and does not include exon 7 of SMN1 and/or SMN2 in an analogous sample (e.g., from the same type of tissue sample) from the patient prior to administration of the compound or a certain number of doses of the compound, or a certain earlier date, indicate that the patient is responsive to the compound and that the compound may be or is beneficial and/or of therapeutic value to the patient; and (2)(i) no change or no substantial change in the amount of mRNA that is transcribed from the SMN1 and/or SMN2 gene and includes exon 7 of SMN1 and/or SMN2 in the patient sample relative to the amount of mRNA that is transcribed from the SMN1 and/or SMN2 gene and includes exon 7 of SMN1 and/or SMN2 in an analogous sample (e.g., the same type of tissue sample) from the patient prior to administration of the compound or a certain number of doses of the compound, or a certain earlier date, and (ii) no change or no substantial change in the amount of mRNA that is transcribed from the SMN1 and/or SMN2 gene and does not include exon 7 of SMN1 and/or SMN2 in the patient sample relative to the amount of mRNA that is transcribed from the SMN2 gene and does not include exon 7 of SMN1 and/or SMN2 in an analogous sample (e.g., the same type of tissue sample) from the patient prior to administration of the compound or a certain number of doses of the compound, or a certain earlier date, indicate that the patient is not responsive to the compound and that the compound is not beneficial and/or of therapeutic value to the patient. In certain embodiments, the patient's response is monitored 1 hour, 2 hours, 4 hours, 8 hours, 12 hours, 16 hours, 20 hours, 1 day, 2 days, 3 days, 4 days, 5 days, 7 days, 14 days, 28 days, 1 month, 2 months, 3 months, 6 months, 9 months, 12 months or more after administration of a compound, such as a compound of Formula (I) or a form thereof as described herein. In some embodiments, the patient's response is monitored after the patient has received 1, 2, 3, 4, 5, 6, 7, 8, 9, 10, 11, 12, 13, 14, 15, 16, 17, 18, 19, 20, 21, 22, 23, 24, 25 or more doses of a compound, such as a compound of Formula (I) or a form thereof as described herein. In some embodiments, the patient's response is monitored after the administration of 1-5, 5-10, 10-15, 15-20, 20-30, 30-40, 40-50, or 50-100 doses of a compound, such as a compound of Formula (I) or a form thereof as described herein. In some embodiments, the patient's response is monitored over a period of days, weeks, months or years during or after the continuous administration of a compound, such as a compound of Formula (I) or a form thereof as described herein.

In specific embodiments, SMA in a patient is caused by an inactivating mutation or deletion in the SMN1 gene on both chromosomes, resulting in a loss of SMN1 gene function.

Kits

In one aspect, provided herein are pharmaceutical or assay kits comprising an SMN primer or probe described herein, in one or more containers, and instructions for use. In one embodiment, a pharmaceutical or assay kit comprises, in a container, one or more SMN reverse primers (e.g., SEQ ID NO. 2, 9 and/or 12) and/or one or more SMN forward primers (SEQ ID NO. 1, 7, 8, 11 and/or 13)) and instructions for use. In another embodiment, a pharmaceutical or assay kit comprises, in one container, an SMN reverse primer (e.g., SEQ ID NO. 2, 9 or 12), an SMN forward primer (SEQ ID NO. 1, 7, 8, 11 or 13)) and instructions for use.

In one embodiment, a pharmaceutical or assay kit comprises, in separate containers, one SMN reverse primer (e.g., SEQ ID NO. 2, 9 or 12) in one container, another SMN forward primer (e.g., SEQ ID NO. 1, 7, 8, 11 or 13)) in another container, and instructions for use.

In certain embodiments, applicable components needed for a PCR (e.g., qPCR), RT-PCR (e.g., endpoint RT-PCR and/or RT-qPCR) or rolling circle amplification, such as polymerase, deoxynucleoside triphosphates, etc., are included in such kits. In some embodiments, components needed for hybridization are included in such kits. A pharmaceutical or assay kit containing such primers can be used in PCR and RT-PCR to, e.g.: (i) assess whether a therapeutic agent (e.g., a compound of Formula (I) or a form thereof) enhances inclusion of exon 7 of SMN1 and/or SMN2 into mRNA that is transcribed from the SMN1 and/or SMN2 gene, (ii) monitor the amount of mRNA that is transcribed from the SMN1 and/or SMN2 gene and includes exon 7 of SMN1 and/or SMN2 and the amount of mRNA that is transcribed from the SMN1 and/or SMN2 gene and does not include exon 7 of SMN1 and/or SMN2, and/or (iii) monitor a subject's response to a therapeutic agent (e.g., a compound of Formula (I) or a form thereof). In other embodiments, the subject is a human subject. In other embodiments, the human subject is a human patient. In certain other embodiments, the human patient is a human SMA patient.

In a specific embodiment, a pharmaceutical or assay kit comprises the forward primer with the sequence found in SEQ ID NO. 1, in a container, and the reverse primer with the sequence found in SEQ ID NO. 2, in another container. In certain embodiments, these primers are used in RT-PCR (e.g., endpoint RT-PCR and/or RT-qPCR), PCR (e.g., qPCR) or rolling circle amplification for amplifying nucleotide sequences encoded by a human SMN1 minigene or human SMN2 minigene, such as described those described herein or in International Publication No. WO 2009/151546 or U.S. Patent Application Publication No. 2011/0086833, each of which is incorporated herein by reference in its entirety. In other embodiments, these primers are used as probes in, e.g., hybridization assays, such as Southern blot or Northern blot.

In a specific embodiment, a pharmaceutical or assay kit comprises the forward primer with the nucleotide sequence found in SEQ ID NO. 7, in a container, and the reverse primer with the nucleotide sequence found in SEQ ID NO. 9, in another container. In certain embodiments, these primers are used in RT-PCR (e.g., endpoint RT-PCR and/or RT-qPCR), PCR (e.g., qPCR) or rolling circle amplification for amplifying nucleotide sequences encoded by endogenous human SMN1 and SMN2 genes. In other embodiments, these primers are used as probes in, e.g., hybridization assays, such as Southern blot or Northern blot.

In another specific embodiment, a pharmaceutical or assay kit comprises the forward primer with the nucleotide sequence found in SEQ ID NO. 8, in a container, and the reverse primer with the nucleotide sequence found in SEQ ID NO. 9, in another container. In certain embodiments, these primers are used in RT-PCR (e.g., endpoint RT-PCR and/or RT-qPCR), PCR (e.g., qPCR) or rolling circle amplification for amplifying nucleotide sequences encoded by the endogenous human SMN2 gene. In other embodiments, these primers are used as probes in, e.g., hybridization assays, such as Southern blot or Northern blot.

In a specific embodiment, a pharmaceutical or assay kit comprises the forward primer with the nucleotide sequence found in SEQ ID NO. 7, in a container, the forward primer with the nucleotide sequence found in SEQ ID NO. 8, in another container, and the reverse primer with the nucleotide sequence found in SEQ ID NO. 9, in another container. In certain embodiments, these primers are used in RT-PCR (e.g., endpoint RT-PCR and/or RT-qPCR), PCR (e.g., qPCR) or rolling circle amplification for amplifying nucleotide sequences encoded by endogenous human SMN1 and SMN2 genes. In other embodiments, these primers are used as probes in, e.g., hybridization assays, such as Southern blot or Northern blot.

In a specific embodiment, a pharmaceutical or assay kit comprises the forward primer with the nucleotide sequence found in SEQ ID NO. 11, in a container, and the reverse primer with the nucleotide sequence found in SEQ ID NO. 12, in another container. In certain embodiments, these primers are used in RT-PCR (e.g., endpoint RT-PCR and/or RT-qPCR), PCR (e.g., qPCR) or rolling circle amplification for amplifying nucleotide sequences encoded by endogenous human SMN1 and SMN2 genes. In other embodiments, these primers are used as probes in, e.g., hybridization assays, such as Southern blot or Northern blot.

In a specific embodiment, a pharmaceutical or assay kit comprises the forward primer with the nucleotide sequence found in SEQ ID NO. 11, in a container, and the reverse primer with the nucleotide sequence found in SEQ ID NO. 9, in another container. In certain embodiments, these primers are used in RT-PCR (e.g., endpoint RT-PCR and/or RT-qPCR), PCR (e.g., qPCR) or rolling circle amplification for amplifying nucleotide sequences encoded by endogenous human SMN1 and SMN2 genes. In other embodiments, these primers are used as probes in, e.g., hybridization assays, such as Southern blot or Northern blot.

In a specific embodiment, a pharmaceutical or assay kit comprises the forward primer with the nucleotide sequence found in SEQ ID NO. 13, in a container, and the reverse primer with the nucleotide sequence found in SEQ ID NO. 12, in another container. In certain embodiments, these primers are used in RT-PCR (e.g., endpoint RT-PCR and/or RT-qPCR), PCR (e.g., qPCR) or rolling circle amplification for amplifying nucleotide sequences encoded by endogenous human SMN1 and SMN2 genes. In other embodiments, these primers are used as probes in, e.g., hybridization assays, such as Southern blot or Northern blot.

In a specific embodiment, a pharmaceutical or assay kit comprises the forward primer with the nucleotide sequence found in SEQ ID NO. 13, in a container, and the reverse primer with the nucleotide sequence found in SEQ ID NO. 9, in another container. In certain embodiments, these primers are used in RT-PCR (e.g., endpoint RT-PCR and/or RT-qPCR), PCR (e.g., qPCR) or rolling circle amplification for amplifying nucleotide sequences encoded by endogenous human SMN1 and SMN2 genes. In other embodiments, these primers are used as probes in, e.g., hybridization assays, such as Southern blot or Northern blot.

In a specific embodiment, a pharmaceutical or assay kit comprises the forward primer with the nucleotide sequence found in SEQ ID NO. 1, in a container, and the reverse primer with the nucleotide sequence found in SEQ ID NO. 9, in another container. In certain embodiments, these primers are used in RT-PCR (e.g., endpoint RT-PCR and/or RT-qPCR), PCR (e.g., qPCR) or rolling circle amplification for amplifying nucleotide sequences encoded by endogenous human SMN1 and SMN2 genes. In other embodiments, these primers are used as probes in, e.g., hybridization assays, such as Southern blot or Northern blot.

In a specific embodiment, a pharmaceutical or assay kit comprises the forward primer with the nucleotide sequence found in SEQ ID NO. 1, in a container, and the reverse primer with the nucleotide sequence found in SEQ ID NO. 12, in another container. In certain embodiments, these primers are used in RT-PCR (e.g., endpoint RT-PCR and/or RT-qPCR), PCR (e.g., qPCR) or rolling circle amplification for amplifying nucleotide sequences encoded by endogenous human SMN1 and SMN2 genes. In other embodiments, these primers are used as probes in, e.g., hybridization assays, such as Southern blot or Northern blot.

In another embodiment, a pharmaceutical or assay kit comprises an SMN probe described herein (e.g., SEQ ID NO. 3 or 10), in one container. In other embodiments, the probe is used in, e.g., a hybridization assay, such as a Southern blot or Northern blot. In a specific embodiment, the probe is used in RT-qPCR or qPCR. In certain embodiments, components needed for a PCR (e.g., qPCR), RT-PCR (e.g., endpoint RT-PCR and/or RT-qPCR) or rolling circle amplification, such as polymerase, deoxynucleoside triphosphates, primers, etc., are included in such kits. In some embodiments, components needed for hybridization are included in such kits.

In one embodiment, a pharmaceutical or assay kit comprises an SMN reverse primer (e.g., SEQ ID NO. 2, 9 or 12) in one container, an SMN forward primer (e.g., SEQ ID NO. 1, 7, 8, 11 or 13) in another container, and an SMN probe (e.g., SEQ ID NO. 3 or 10) in another container, and instructions for use. In another embodiment, a pharmaceutical or assay kit comprises one or more SMN reverse primers (e.g., SEQ ID NO. 2, 9 and/or 12) in one container, one or more SMN forward primers (e.g., SEQ ID NO. 1, 7, 8, 11 and/or 13) in another container, and one or more SMN probe (e.g., SEQ ID NO. 3 and/or 10) in another container, and instructions for use.

In certain embodiments, components needed to run a PCR, RT-PCR or rolling circle amplification, such as polymerase, deoxynucleoside triphosphates, etc., are included in such kits. A pharmaceutical or assay kit containing such probes and/or primers can be used in PCR and RT-PCR to, e.g.: (i) assess whether a therapeutic agent (e.g., a compound of Formula (I) or a form thereof) enhances inclusion of exon 7 of SMN1 and/or SMN2 into mRNA that is transcribed from the SMN1 and/or SMN2 gene, (ii) monitor the amount of mRNA that is transcribed from the SMN1 and/or SMN2 gene and includes exon 7 and the amount of mRNA that is transcribed from the SMN1 and/or SMN2 gene and does not include exon 7 of SMN1 and/or SMN2, and/or (iii) monitor a subject's response to a therapeutic agent (e.g., a compound of Formula (I) or a form thereof). In other embodiments, the subject is a human subject. In other embodiments, the human subject is a human patient. In certain other embodiments, the human patient is a human SMA patient.

In another aspect, provided herein is a pharmaceutical kit comprising a compound of Formula (I) or a form thereof, in a container, and instructions for use of the compound or form thereof. In a specific embodiment, provided herein is a pharmaceutical kit comprising a pharmaceutical composition comprising a compound of Formula (I) or a form thereof and a pharmaceutically acceptable carrier, excipient or diluent, and instructions for use. In another specific embodiment, provided herein is a pharmaceutical kit comprising a pharmaceutical composition comprising an effective amount of a compound of Formula (I) or a form thereof and a pharmaceutically acceptable carrier, excipient or diluent, and instructions for use. In one embodiment, the instructions for use explain one, two or more of the following: the dose, route of administration, frequency of administration and side effects of administration of a compound of Formula (I) or a form thereof to a subject. In other embodiments, the subject is a human subject. In other embodiments, the human subject is a human patient. In certain other embodiments, the human patient is a human SMA patient.

As disclosed herein, general methods for preparing the compounds of Formula (I) or a form thereof as described herein are available via standard, well-known synthetic methodology. Many of the starting materials are commercially available or, when not available, can be prepared using the routes described below using techniques known to those skilled in the art. The synthetic schemes provided herein comprise multiple reaction steps, each of which is intended to stand on its own and can be carried out with or without any preceding or succeeding step(s). In other words, each of the individual reaction steps of the synthetic schemes provided herein in isolation is contemplated.

General Synthetic Methods

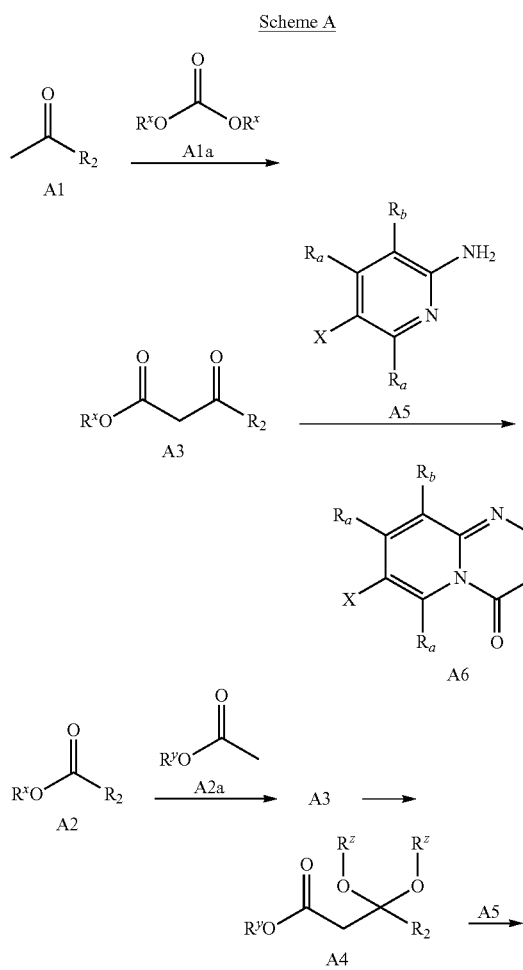

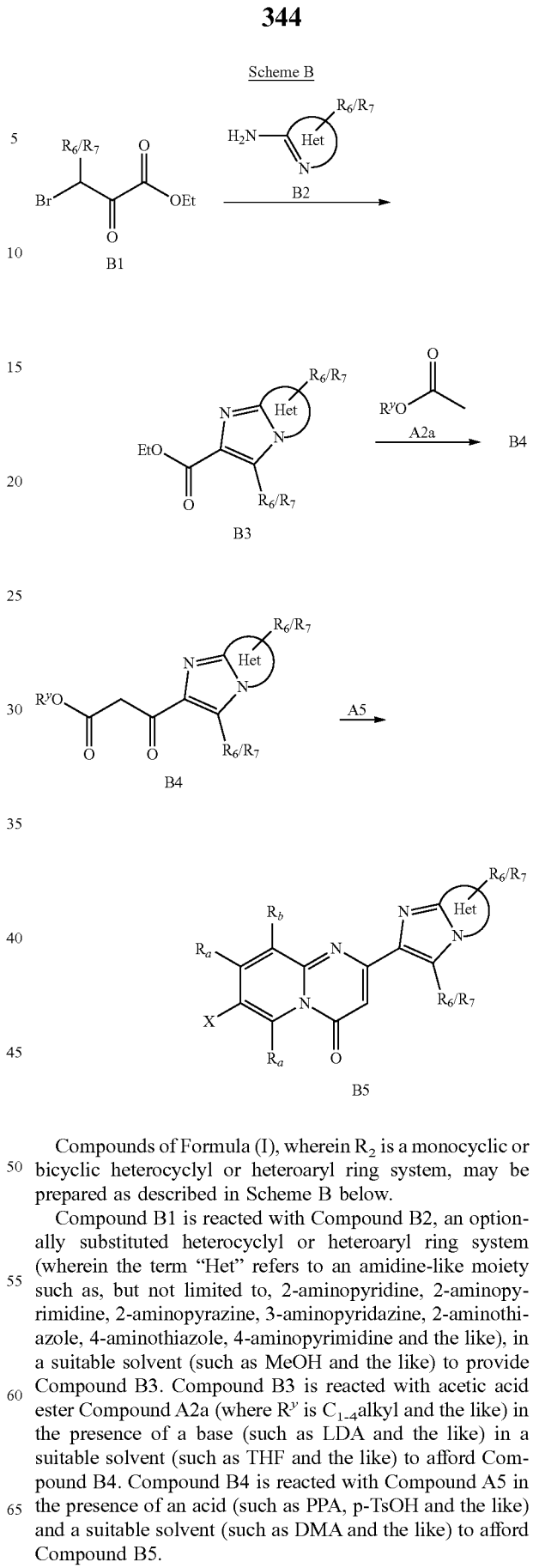

Compounds of Formula (I), wherein $R_2$ is a monocyclic or bicyclic aryl, heterocyclyl or heteroaryl ring system, may be prepared as described in Scheme A below.

Methyl ketone Compound A1 is reacted with dialkyl carbonate Compound A1a (where $R^x$ is $C_{1-4}$alkyl and the like) in the presence of a base (such as NaH and the like) in a suitable solvent (such as THF and the like) to provide Compound A3. Alternatively, ester Compound A2 is reacted with acetic acid ester Compound A2a (where $R^y$ is $C_{1-4}$alkyl and the like) in the presence of a base (such as LDA and the like) in a suitable solvent (such as THF and the like) to provide Compound A3. Compound A3 is further reacted in the presence of an alcohol (such as MeOH and the like) and an acid catalyst (such as p-TsOH and the like) to provide acetal Compound A4 (where $R^z$ is $C_{1-4}$alkyl and the like). Either Compound A3 or Compound A4 is reacted with Compound A5 (where X represents various reactive groups, which may be used to provide a plurality of $R_1$ functional group substituents by reacting suitable starting materials with Compound A5 or Compound A6 using techniques known to a person of ordinary skill in the art) in the presence of an acid (such as PPA, p-TsOH and the like) and a suitable solvent (such as DMA and the like) to afford Compound A6.

Compounds of Formula (I), wherein $R_2$ is a monocyclic or bicyclic heterocyclyl or heteroaryl ring system, may be prepared as described in Scheme B below.

Compound B1 is reacted with Compound B2, an optionally substituted heterocyclyl or heteroaryl ring system (wherein the term "Het" refers to an amidine-like moiety such as, but not limited to, 2-aminopyridine, 2-aminopyrimidine, 2-aminopyrazine, 3-aminopyridazine, 2-aminothiazole, 4-aminothiazole, 4-aminopyrimidine and the like), in a suitable solvent (such as MeOH and the like) to provide Compound B3. Compound B3 is reacted with acetic acid ester Compound A2a (where $R^y$ is $C_{1-4}$alkyl and the like) in the presence of a base (such as LDA and the like) in a suitable solvent (such as THF and the like) to afford Compound B4. Compound B4 is reacted with Compound A5 in the presence of an acid (such as PPA, p-TsOH and the like) and a suitable solvent (such as DMA and the like) to afford Compound B5.

Scheme C

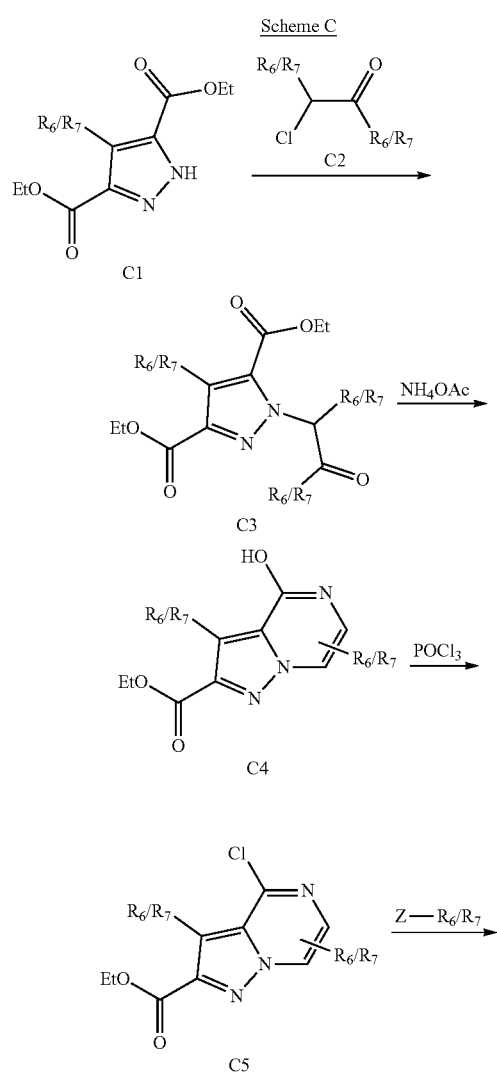

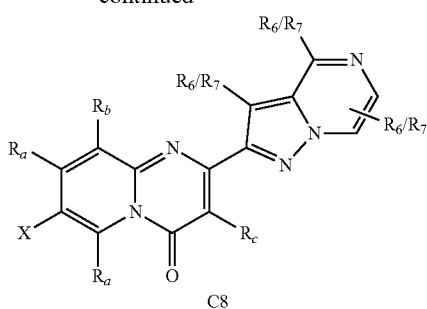

Compounds of Formula (I), wherein $R_2$ is a monocyclic or bicyclic heteroaryl ring system, may be prepared as described in Scheme C below.

A 2,4-diester pyrazole Compound C1 is reacted with an α-chloro ketone Compound C2 in the presence of a base (such as $K_2CO_3$ and the like) and a suitable solvent (such as acetone and the like) to afford Compound C3. Compound C3 is treated with ammonium acetate in a suitable solvent (such as AcOH and the like) to provide Compound C4. Compound C4 is treated with a chlorinating reagent (such as $POCl_3$ and the like) to provide Compound C5. Compound C5 is reacted with an alkyl boronic acid (where Z is $B(OH)_2$ and $R^z$ is $C_{1-4}$alkyl and the like) or an alkyl boronic acid ester (where Z is B2(pin)$_2$ also referred to as bis(pinacolato)diboron and $R^z$ is $C_{1-4}$alkyl and the like) in the presence of a catalyst (such as $Pd(dppf)Cl_2$ and the like) and a base (such as $K_2CO_3$ and the like) in a suitable solvent (such as DMF and the like), undergoing Suzuki cross coupling to give Compound C6. Compound C6 is reacted with acetic acid ester Compound A2a (where $R^y$ is $C_{1-4}$alkyl and the like) in the presence of a base (such as LDA and the like) in a suitable solvent (such as THF and the like) to afford Compound C7. Compound C7 is reacted with Compound A5 in the presence of an acid (such as p-TsOH, PPTs and the like) and a suitable solvent to afford Compound C8.

Scheme D

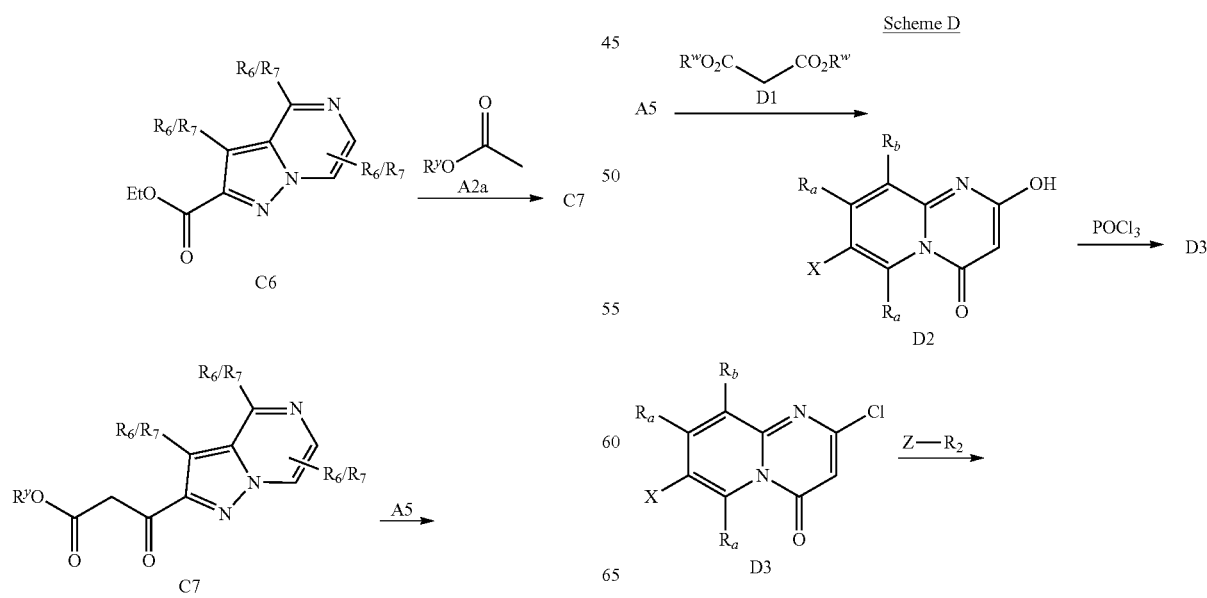

Scheme D -continued

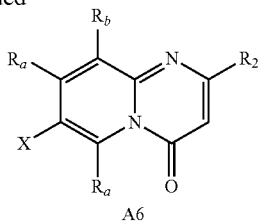

A6

Compounds of Formula (I), wherein $R_2$ is a monocyclic or bicyclic aryl or heteroaryl ring system, may be prepared as described in Scheme D below.

Compound A5 is reacted with malonic ester Compound D1 (where $R^w$ is $C_{1-4}$alkyl, 2,4,6-trichlorophenyl and the like) to afford Compound D2. Compound D2 is treated with a chlorinating reagent (such as $POCl_3$ and the like) to provide Compound D3. Compound D3 is reacted with an $R_2$ substituted alkyl boronic acid (where Z is $B(OH)_2$) or an alkyl boronic acid ester (where Z is $B_2(pin)_2$), wherein $R_2$ is aryl or heteroaryl, in the presence of a catalyst (such as $Pd(dppf)Cl_2$ and the like) and a base (such as $K_2CO_3$ and the like) in a suitable solvent (such as DMF and the like), undergoing Suzuki cross coupling to give Compound A6.

Scheme E

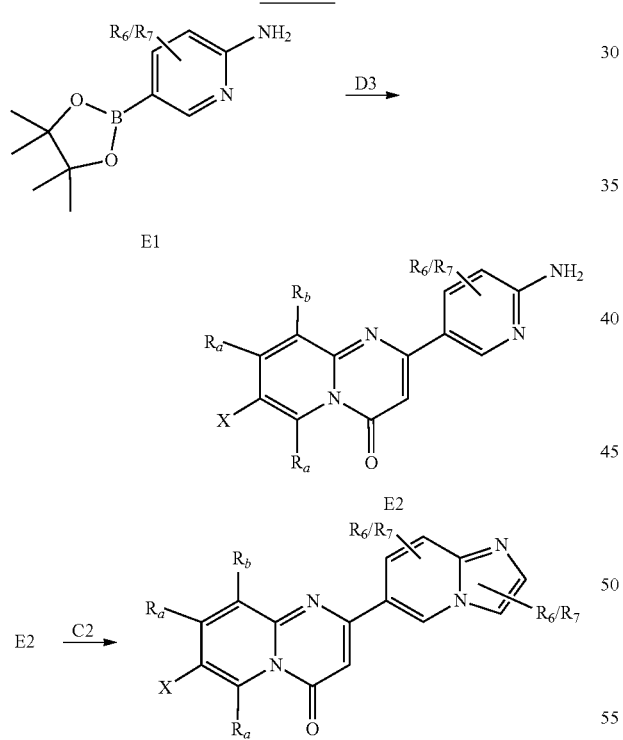

Compounds of Formula (I), wherein $R_2$ is a monocyclic or bicyclic heteroaryl ring system, may be prepared as described in Scheme E below.

Compound E1 is reacted with Compound D3 in the presence of a catalyst (such as $Pd(dppf)Cl_2$ and the like) and a base (such as $K_2CO_3$ and the like) in a suitable solvent (such as DMF and the like), undergoing Suzuki cross coupling to give Compound E2. Compound E2 is reacted with Compound C2 in a suitable solvent (such as DMSO and the like) to afford Compound E3.

Scheme F

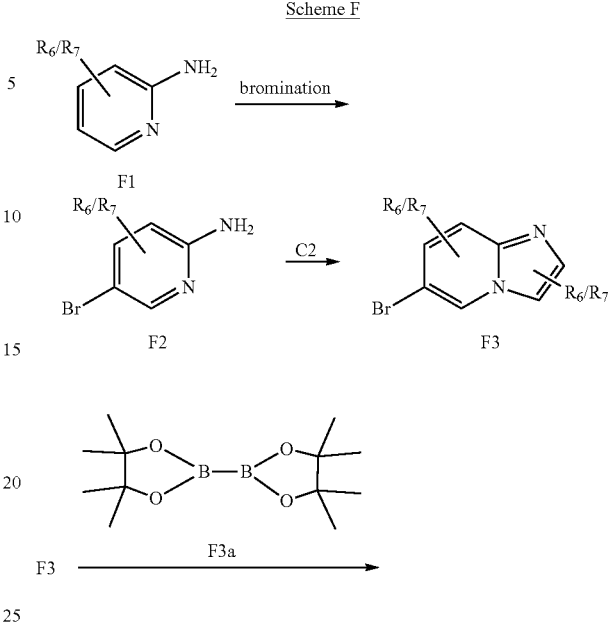

Compounds of Formula (I), wherein $R_2$ is a monocyclic or bicyclic heteroaryl ring system, may be prepared as described in Scheme F below.

An optionally substituted 2-aminopyridine Compound F1 is reacted with a brominating reagent (such as $Br_2$ and NBS and the like) to provide Compound F2. Compound F2 is reacted with Compound C2 in a suitable solvent (such as DMSO and the like) to afford Compound F3. Compound F3 is reacted with Compound F3a in the presence of a catalyst (such as $Pd(dppf)Cl_2$ and the like) and a base (such as KOAc and the like) in a suitable solvent (such as acetonitrile and the like) to provide Compound F4. Compound F4 is reacted with Compound D3 in the presence of a catalyst (such as $Pd(dppf)Cl_2$ and the like) and a base (such as $K_2CO_3$ and the like) in a suitable solvent (such as DMF and the like), undergoing Suzuki cross coupling to give Compound F5.

Scheme G

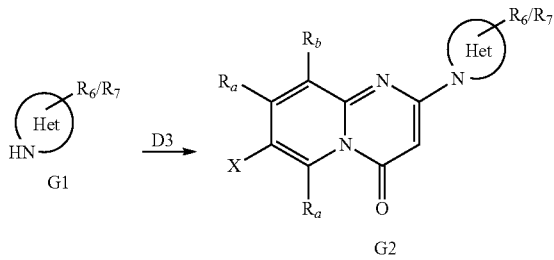

Compounds of Formula (I), wherein $R_2$ is a monocyclic or bicyclic heteroaryl ring system, may be prepared as described in Scheme G below.

An optionally substituted azole Compound G1 (wherein the term "Het" refers to the azole ring system optionally further containing one, two or three additional nitrogen ring members where allowed by available valences) is reacted with Compound D3 in a suitable solvent (such as DMSO and the like) to provide Compound G2.

Scheme H

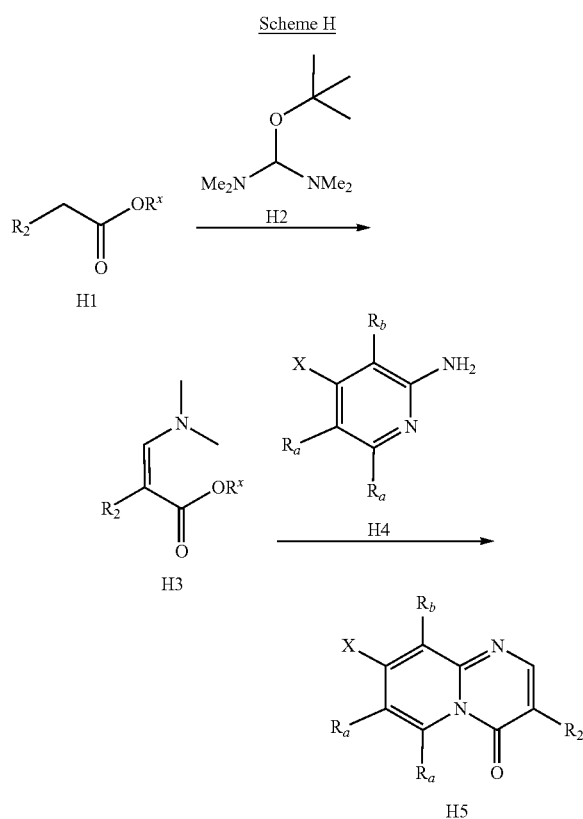

Compounds of Formula (I), wherein $R_2$ is a monocyclic or bicyclic aryl, heterocyclyl or heteroaryl ring system, may be prepared as described in Scheme H below.

Compound H1 (where $R_2$ is a monocyclic or bicyclic aryl, heterocyclyl or heteroaryl ring system) is reacted with Bredereck's reagent Compound 112 (or DMF-DMA and the like) to form Compound 113. Compound 113 is reacted with Compound 114 (where X represents various reactive groups, which may be used to provide a plurality of $R_1$ functional group substituents by reacting suitable starting materials with Compound 114 or Compound 115 using techniques known to a person of ordinary skill in the art) to provide Compound 115.

Compounds of Formula (I), wherein $R_2$ is a monocyclic or bicyclic aryl or heteroaryl ring system, may be prepared as described in Scheme I below.

Scheme I

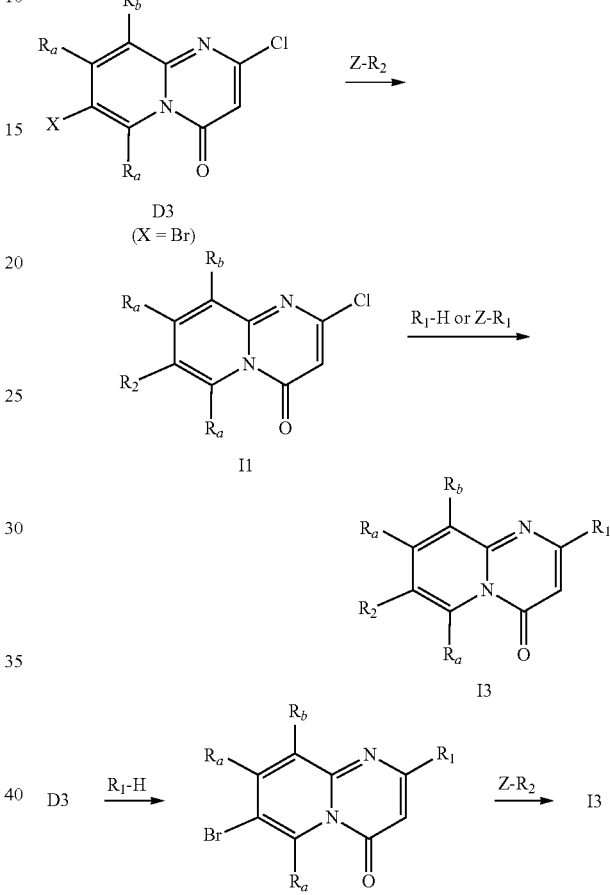

Compound D3 (where X is bromo and the like) is reacted with an $R_2$ substituted alkyl boronic acid (where Z is $B(OH)_2$) or an alkyl boronic acid ester (where Z is $B_2(pin)_2$), wherein $R_2$ is a monocyclic or bicyclic aryl or heteroaryl ring system and the like, in the presence of a catalyst (such as $Pd(dppf)Cl_2$ and the like) and a base (such as $K_2CO_3$ and the like) in a suitable solvent (such as DMF and the like), undergoing Suzuki cross coupling to provide Compound I1. Compound I1 is reacted with $R_1$—H (wherein $R_1$ contains a nucleophilic amino or hydroxyl group and the like) in a suitable solvent (such as DMSO and the like) to provide Compound I3.

Compound I1 may also be reacted with an $R_1$ substituted alkyl boronic acid (where Z is $B(OH)_2$) or an alkyl boronic acid ester (where Z is $B_2(pin)_2$) in the presence of a palladium catalyst (such as $Pd(dppf)Cl_2$ and the like) and a base (such as $K_2CO_3$ and the like) in a suitable solvent (such as DMF and the like) undergoing Suzuki coupling to provide Compound I3.

Alternatively, Compound D3 (where X is bromo and the like) may be reacted with $R_1$—H (wherein $R_1$ contains a nucleophilic amino or hydroxyl group and the like) in a suitable solvent (such as DMSO and the like) to provide Compound I2. Compound I2 is reacted with an $R_2$ substituted alkyl boronic acid (where Z is $B(OH)_2$) or an alkyl boronic acid ester (where Z is $B_2(pin)_2$) in the presence of a catalyst (such as $Pd(dppf)Cl_2$ and the like) and a base (such as $K_2CO_3$ and the like) in a suitable solvent (such as DMF and the like), undergoing Suzuki cross coupling to give Compound I3.

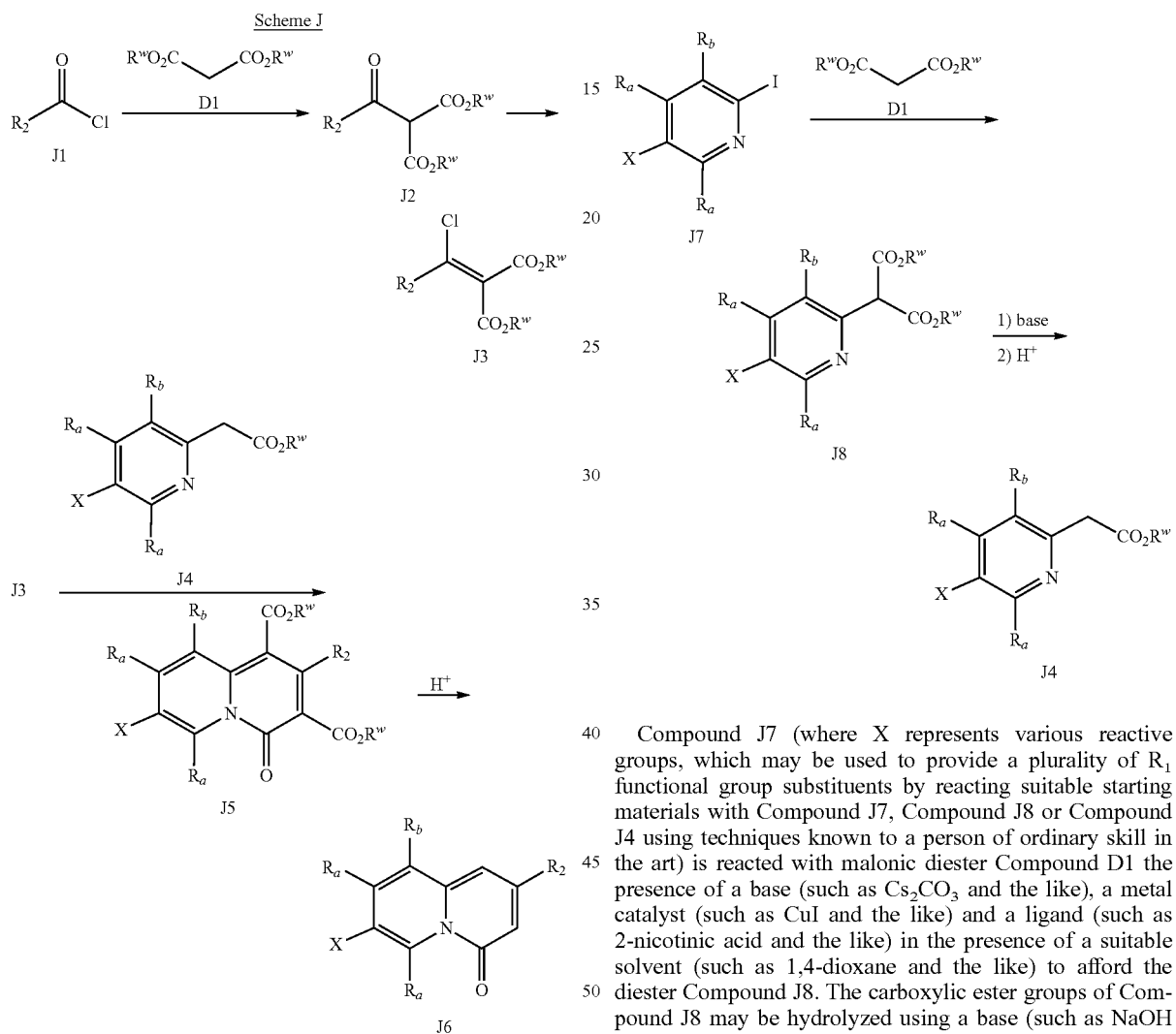

Compounds of Formula (I), wherein $R_2$ is a monocyclic or bicyclic aryl, heterocyclyl or heteroaryl ring system, may be prepared as described in Scheme J below.

Compound J1 (where $R_2$ is a monocyclic or bicyclic aryl, heterocyclyl or heteroaryl ring system) is reacted with malonic ester Compound D1 in the presence of a base (such as TEA or DIEA and the like), a Lewis acid (such as $MgCl_2$ and the like) and a suitable solvent (such as ACN and the like) to provide Compound J2. Compound J2 is treated with a chlorinating reagent (such as $POCl_3$ and the like) in the presence of a base (such as Hünig's base and the like) to provide Compound J3.

Compound J3 is reacted with Compound J4 (where X represents various reactive groups, which may be used to provide a plurality of $R_1$ functional group substituents by reacting suitable starting materials with Compound J4, Compound J5 or Compound J6 using techniques known to a person of ordinary skill in the art) in the presence of a base (such as NaH and the like) and a suitable solvent (such as DMF and the like) to afford Compound J5. The carboxylic ester groups of Compound J5 may be hydrolyzed and decarboxylated under acidic conditions (such as TFA and the like) in a suitable solvent (such as water and the like) to give Compound J6.

Compound J7 (where X represents various reactive groups, which may be used to provide a plurality of $R_1$ functional group substituents by reacting suitable starting materials with Compound J7, Compound J8 or Compound J4 using techniques known to a person of ordinary skill in the art) is reacted with malonic diester Compound D1 the presence of a base (such as $Cs_2CO_3$ and the like), a metal catalyst (such as CuI and the like) and a ligand (such as 2-nicotinic acid and the like) in the presence of a suitable solvent (such as 1,4-dioxane and the like) to afford the diester Compound J8. The carboxylic ester groups of Compound J8 may be hydrolyzed using a base (such as NaOH and the like) in a suitable solvent system (such as MeOH and water and the like), then decarboxylated and acidified using an acid (such as HCl and the like) in a suitable solvent (such as water and the like) to give Compound J4.

SPECIFIC SYNTHETIC EXAMPLES

To describe in more detail and assist in understanding, the following non-limiting examples are offered to more fully illustrate the scope of compounds described herein and are not to be construed as specifically limiting the scope thereof. Such variations of the compounds described herein that may be now known or later developed, which would be within the purview of one skilled in the art to ascertain, are considered to fall within the scope of the compounds as described herein and hereinafter claimed. These examples illustrate the preparation of certain compounds. Those of skill in the art will understand that the techniques described in these examples represent techniques, as described by those of ordinary skill in the art, that function well in synthetic practice, and as such constitute preferred modes for the practice thereof. However, it should be appreciated that those of skill in the art should, in light of the present disclosure, appreciate that many changes can be made in the specific methods that are disclosed and still obtain a like or similar result without departing from the spirit and scope of the present description.

Other than in the following examples of the embodied compounds, unless indicated to the contrary, all numbers expressing quantities of ingredients, reaction conditions, experimental data, and so forth used in the specification and claims are to be understood as being modified by the term "about". Accordingly, all such numbers represent approximations that may vary depending upon the desired properties sought to be obtained by a reaction or as a result of variable experimental conditions. Therefore, within an expected range of experimental reproducibility, the term "about" in the context of the resulting data, refers to a range for data provided that may vary according to a standard deviation from the mean. As well, for experimental results provided, the resulting data may be rounded up or down to present data consistently, without loss of significant figures. At the very least, and not as an attempt to limit the application of the doctrine of equivalents to the scope of the claims, each numerical parameter should be construed in light of the number of significant digits and rounding techniques used by those of skill in the art.

While the numerical ranges and parameters setting forth the broad scope of the present description are approximations, the numerical values set forth in the examples set forth below are reported as precisely as possible. Any numerical value, however, inherently contains certain errors necessarily resulting from the standard deviation found in their respective testing measurements.

COMPOUND EXAMPLES

As used above, and throughout the present description, the following abbreviations, unless otherwise indicated, shall be understood to have the following meanings:

| Abbreviation | Meaning |
| --- | --- |
| Δ | heating (chemistry) or deletion (biology) |
| AcOH or HOAc | acetic acid |
| $Ac_2O$ | acetic anhydride |
| Ar | argon |
| ACN | acetonitrile |
| BINAP | 2,2'-bis(diphenylphosphino)-1,1'-binaphthalene |
| $B(OiPr)_3$ | triisopropyl borate |
| Boc | tert-butoxy-carbonyl |
| $Boc_2O$ | di-tert-butyl dicarbonate |
| BuOH | n-butanol |
| °C. | degrees Centigrade |
| CDI | 1,1-carbonyldiimidazole or N,N'-carbonyldiimidazole |
| $(CHO)_n$ or $(HCHO)_n$ | paraformaldehyde |
| d/h/hr/hrs/min/s | day(d)/hour(h, hr or hrs)/minute(min)/second(s) |
| DavePhos | 2-dicyclohexylphosphino-2'-(N,N-dimethylamino)biphenyl |
| DCE | 1,2-dichloroethane |
| DCM | dichloromethane ($CH_2Cl_2$) |
| DIAD | diisopropyl azodicarboxylate |
| DIEA or DIPEA | N,N-diisopropylethylamine |
| DMA | dimethylacetamide |
| DMAP | 4-(dimethylamino)pyridine |
| DME | 1,2-dimethoxyethane |
| DMF | dimethylformamide |
| DMSO | dimethylsulfoxide |
| EDC or EDCI | N-(3-dimethylaminopropyl)-N'-ethylcarbodiimide hydrochloride |
| EtOAc | ethyl acetate |
| EtOH | ethanol |
| $Et_2O$ | diethyl ether |
| HCOH | formaldehyde |
| iPrI | iodopropane |
| JohnPhos | (2-biphenyl)-di-t-butylphosphine |
| KOAc | potassium acetate |
| LAH | lithium aluminum hydride |
| LC/MS, LCMS or LC-MS | liquid chromatographic mass spectroscopy |
| LDA | lithium diisopropylamine |
| LiHMDS or LHMDS | lithium bis(trimethylsilyl)amide |
| MeOH | methanol |
| MeI | iodomethane |
| Me—THF | 2-methyltetrahydrofuran |
| $Me_2Zn$ | dimethylzinc |
| $MnO_2$ | manganese dioxide |
| MS | mass spectroscopy |
| NaH | sodium hydride |
| NaHS | sodium hydrosulfide |
| NaHMDS | sodium bis(trimethylsilyl)amide or sodium hexamethyldisilazide |
| NaI | sodium iodide |
| NaOAc | sodium acetate |
| NaOMe | sodium methoxide |

| Abbreviation | Meaning |
| --- | --- |
| NBS | N-bromosuccinimide |
| NMP | N-methylpyrrolidone |
| NMR | nuclear magnetic resonance |
| o/n | overnight |
| Pd | palladium |
| Pd/C | palladium on carbon |
| Pd(dba)$_2$ | bis(dibenzylideneacetone)palladium |
| Pd$_2$(dba)$_3$ or Pd$_2$dba$_3$ | tris(dibenzylideneacetone)dipalladium(0) |
| PdCl$_2$(PhCN)$_2$ | trans-bis(benzonitrile)dichloropalladium(II) |
| PdCl$_2$(dppf), PdCl$_2$dppf or Pd(dppf)Cl$_2$ | [1,1'-bis(diphenylphosphino)ferrocene]dichloropalladium(II) |
| Pd(OAc)$_2$ | palladium(II) acetate |
| Pd(PPh$_3$)$_4$ or Pd(Ph$_3$P)$_4$ | tetrakis(triphenylphosphine)palladium(0) |
| Pd(PPh$_3$)$_2$Cl$_2$, PdCl$_2$(PPh$_3$)$_2$ or PdCl$_2$(Ph$_3$P)$_2$ | bis(triphenylphosphine)palladium(II) dichloride |
| PHBu$_3$BF$_4$ or tBu$_3$PHBF$_4$ | tri-tert-butylphosphonium tetrafluoroborate |
| PhI | iodobenzene |
| PhI(OTFA)$_2$ | [bis(trifluoroacetoxy)iodo]benzene |
| PhMe | toluene |
| Ph-NTf2 or PhNTf$_2$ | N-phenyl triflimide, also referred to as N-phenyl-bis(trifluoromethanesulfonimide) |
| POCl$_3$ | phosphoryl chloride |
| PPh$_3$ | triphenylphosphine |
| PPA | polyphosphoric acid |
| PPTs | pyridinium p-toluenesulfonate |
| Psi | pounds per square inch pressure |
| PyBOP | (benzotriazol-1-yloxy)tripyrrolidinophosphonium hexafluorophosphate |
| rt | room temperature |
| S-Phos, SPhos or Sphos | 2-dicyclohexylphosphino-2',6'-dimethoxybiphenyl |
| T$_3$P | propylphosphonic anhydride |
| TEA, Et$_3$N or NEt$_3$ | triethylamine |
| Tf$_2$O | triflic anhydride |
| TFA | trifluoroacetic acid |
| THF | tetrahydrofuran |
| TLC | thin layer chromatography |
| TMS | trimethylsilane |
| TMSCl | trimethylchlorosilane or trimethylsilyl chloride |
| TMSOK | potassium trimethylsilanolate |
| t-Bu | tert-butyl |
| TsOH, p-TsOH or pTSA | tosylic acid or p-toluenesulfonic acid |
| xantphos | 4,5-bis(diphenylphosphino)-9,9-dimethylxanthene |

Example 1

Preparation of Cpd 72

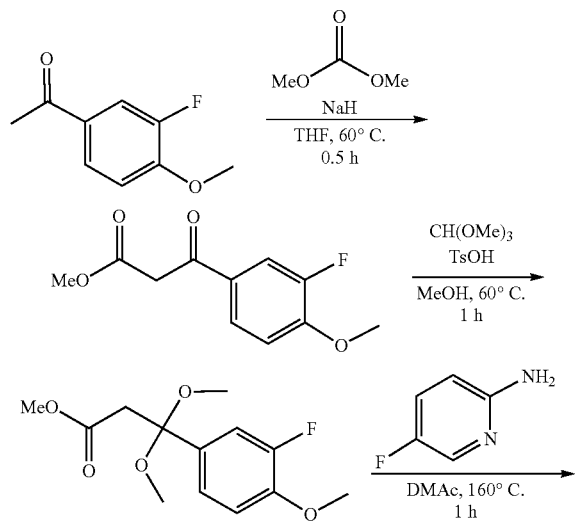

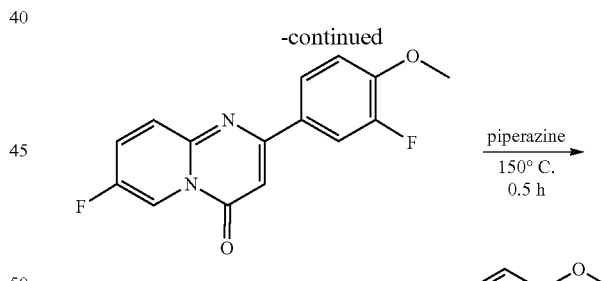

Step A: 3'-Fluoro-4'-methoxyacetophenone (336 mg, 2 mmol) was dissolved in THF (4 mL). To the solution was added dimethyl carbonate (0.42 mL, 5 mmol) and sodium hydride (200 mg, 5 mmol, 60% dispersion in mineral oil) sequentially. The mixture was heated to 60° C. for 30 minutes. After cooling the mixture to 0° C., the remaining sodium hydride was quenched with 1N aqueous HCl (20 mL). The mixture was extracted with EtOAc (20 mL). The organic layer was washed with brine, dried over Na₂SO₄, filtered and concentrated. The residue was eluted from silica gel with EtOAc (25%) in hexanes, affording methyl 3-(3-fluoro-4-methoxyphenyl)-3-oxopropanoate as a pale yellow oil (405 mg, 89%). MS m/z 227.2 [M+H]⁺; ¹H NMR (CDCl₃, 500 MHz): δ 7.76 (1H, dd, J=8.6 Hz, 2.1 Hz), 7.72 (1H, dd, J=11.7 Hz, 2.2 Hz), 7.04 (1H, t, J=8.4 Hz), 3.99 (3H, s), 3.97 (2H, s), 3.78 (3H, s).

Step B: methyl 3-(3-fluoro-4-methoxyphenyl)-3-oxopropanoate (405 mg, 1.8 mmol) was dissolved in methanol (1 mL). p-Toluenesulfonic acid monohydrate (17 mg, 0.09 mmol) was added to the solution, followed by trimethylorthoformate (0.30 mL, 2.7 mmol). The solution was stirred at 60° C. for 1 hour. Volatiles were removed with a stream of nitrogen providing crude methyl 3-(3-fluoro-4-methoxyphenyl)-3,3-dimethoxypropanoate. ¹H NMR (DMSO-d₆, 500 MHz): δ 7.18-7.15 (3H, m), 3.85 (3H, s), 3.38 (3H, s), 3.10 (6H, s), 2.98 (2H, s).

Step C: To the crude material (1.8 mmol) from Step B was added 5-fluoropyridin-2-amine (213 mg, 1.9 mmol). The mixture was heated neat to 160° C. for 1 hour to provide 7-fluoro-2-(3-fluoro-4-methoxyphenyl)-4H-pyrido[1,2-a]pyrimidin-4-one (Δ75 mg, 92%). MS m/z 289.2 [M+H]⁺; ¹H NMR (CDCl₃, 500 MHz): δ 8.99 (1H, m), 7.92 (1H, dd, J=12.5 Hz, 2.2 Hz), 7.90 (1H, d, 8.5 Hz), 7.88 (1H, m), 7.73 (1H, m), 7.10 (1H, t, J=8.5 Hz), 6.85 (1H, s), 3.99 (3H, s).

Step D: 7-Fluoro-2-(3-fluoro-4-methoxyphenyl)-4H-pyrido[1,2-a]pyrimidin-4-one (200 mg, 0.7 mmol) was combined with piperazine (430 mg, 3.5 mmol) in dimethylacetamide (0.5 mL). The mixture was stirred at 150° C. for 0.5 hours, then chromatographed on silica gel, eluting with 0% to 8% MeOH (3% NH₃) in CH₂Cl₂. The title compound was obtained as a yellow powder (175 mg, 71%). M.P. 191-195° C.; MS m/z 355.0 [M+H]⁺; ¹H NMR (DMSO-d₆, 500 MHz): δ 8.20 (1H, d, J=2.7 Hz), 8.07-8.02 (3H, m), 7.67 (1H, d, J=9.7 Hz), 7.28 (1H, t, J=8.7 Hz), 6.93 (1H, s), 3.13 (4H, m), 2.90 (3H, s), 2.88 (4H, m), 2.34 (1H, br s).

As shown in Table 1 below, additional compounds disclosed herein may be prepared according to Example 1 by substituting the appropriate starting materials, reagents and reaction conditions.

Example 2

Preparation of Cpd 239

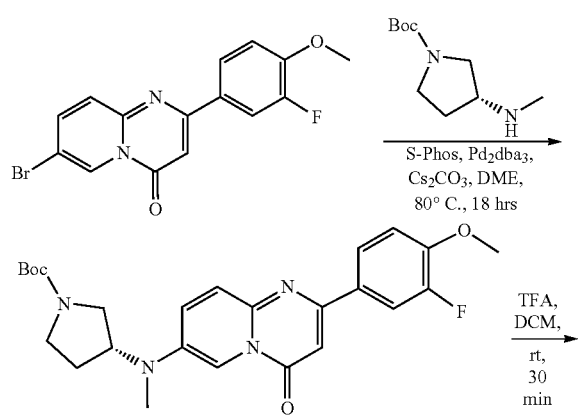

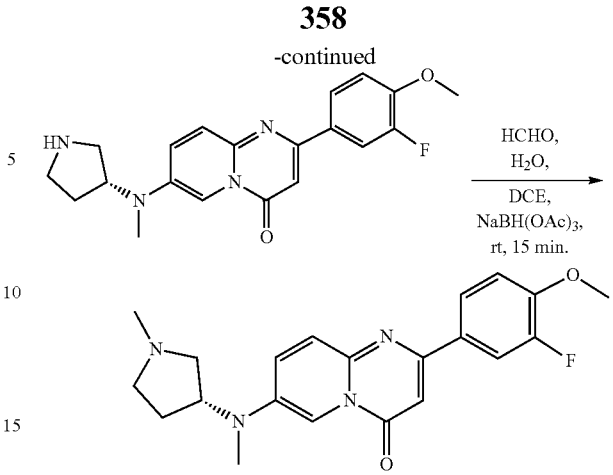

Step A: A mixture of 7-bromo-2-(3-fluoro-4-methoxyphenyl)-4H-pyrido[1,2-a]pyrimidin-4-one (250 mg, 0.72 mmol), (R)-tert-butyl 3-(methylamino)pyrrolidine-1-carboxylate (180 mg, 0.90 mmol), Pd₂dba₃ (61 mg, 0.065 mmol), dicyclohexyl(2',6'-dimethoxybiphenyl-2-yl)phosphine (SPhos, 78 mg, 0.19 mmol), Cs₂CO₃ (500 mg, 1.53 mmol), and 1,2-dimethoxyethane (DME, 2.0 mL) were stirred under an argon atmosphere at 80° C. for 18 hours. The reaction mixture was then diluted with CH₂Cl₂/MeOH (9:1) and was filtered to remove solids. The filtrate was concentrated under vacuum. Purification by silica gel chromatography (10% to 20% acetone in CH₂Cl₂), followed by an ether wash, yielded (R)-tert-butyl 3-((2-(3-fluoro-4-methoxyphenyl)-4-oxo-4H-pyrido[1,2-a]pyrimidin-7-yl)(methyl)amino)pyrrolidine-1-carboxylate (132 mg, 39%) as a light tan solid. MS m/z 469.0 [M+H]⁺.

Step B: A solution of (R)-tert-butyl 3-((2-(3-fluoro-4-methoxyphenyl)-4-oxo-4H-pyrido[1,2-a]pyrimidin-7-yl)(methyl)amino)pyrrolidine-1-carboxylate (130 mg, 0.28 mmol) in CH₂Cl₂ (2.0 mL) and TFA (500 µL) was stirred at room temperature for 30 minutes. The mixture was poured into 1N NaOH solution (50 mL). The product was extracted into CH₂Cl₂/EtOH (9:1). The organic layer was concentrated under vacuum. Purification by silica gel chromatography (CH₂Cl₂/MeOH/NH₄OH=9/1/0.1) yielded (R)-2-(3-fluoro-4-methoxyphenyl)-7-(methyl(pyrrolidin-3-yl)amino)-4H-pyrido[1,2-a]pyrimidin-4-one (82 mg, 79%) as a yellow solid. MS m/z 369.1 [M+H]⁺.

Step C: A mixture of (R)-2-(3-fluoro-4-methoxyphenyl)-7-(methyl(pyrrolidin-3-yl)amino)-4H-pyrido[1,2-a]pyrimidin-4-one (45 mg, 0.12 mmol), DCE (500 µL), formaldehyde (37% w/w in H₂O, 200 µL), and NaBH(OAc)₃ (85 mg, 0.40 mmol) was stirred at room temperature for 15 minutes. The reaction mixture was added to an aqueous K₂CO₃ solution, and the title product was extracted into CH₂Cl₂. The organic layer was concentrated under vacuum. Purification by silica gel chromatography (10% MeOH in CH₂Cl₂) yielded the title compound (39 mg, 85%) as an off-white solid. M.P. 143-149° C.; MS m/z 383.5 [M+H]⁺; ¹H NMR (500 MHz, DMSO-d₆): δ 8.13 (d, 1H, J=3 Hz), 8.0-8.1 (m, 3H), 7.69 (d, 1H, J=10 Hz), 7.29 (t, 1H, J=9.0 Hz), 6.90 (s, 1H), 4.58 (m, 1H), 3.92 (s, 3H), 2.93 (3H, s), 2.81 (m, 1H), 2.75 (m, 1H), 2.49 (m, 1H, obscured by DMSO-d₆), 2.20 (m, 2H), 2.28 (s, 3H), 1.76 (m, 1H).

As shown in Table 1 below, additional compounds disclosed herein may be prepared according to Example 2 by substituting the appropriate starting materials, reagents and reaction conditions.

Example 3

Preparation of Cpd 6

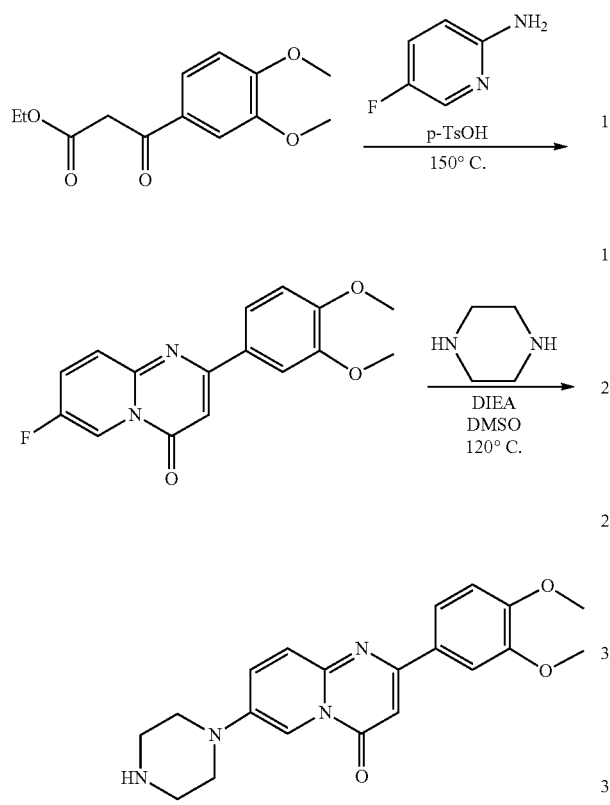

Step A: A mixture of ethyl 3-(3,4-dimethoxyphenyl)-3-oxopropanoate (2.02 g, 8.0 mmol), 2-amino-5-fluoropyridine (0.897 g, 8.0 mmol) and p-TsOH (152 mg, 0.8 mmol) was heated at 150° C. The mixture was melted and then solidified. After 1 hour, the mixture was cooled to room temperature and washed with MeCN to give 2-(3,4-dimethoxyphenyl)-7-fluoro-4H-pyrido[1,2-a]pyrimidin-4-one as a yellow solid (1.356 g, 56%). MS m/z 367.5 [M+H]$^+$; $^1$H NMR (500 MHz, DMSO-d$_6$): δ 8.92 (1H, dd, J=2.9 Hz, 4.8 Hz), 8.11-8.07 (1H, m), 7.85-7.82 (1H, m), 7.77 (1H, d, J=2.1 Hz), 7.09 (1H, d, J=8.6 Hz), 7.06 (1H, s), 6.93 (1H, s), 3.88 (3H, s), 3.84 (3H, s), Step B: A mixture of 2-(3,4-dimethoxyphenyl)-7-fluoro-4H-pyrido[1,2-a]pyrimidin-4-one (1.50 g, 5.0 mmol), piperazine (1.29 g, 15 mmol) and DIEA (1.3 mL, 7.5 mmol) in DMSO (10 mL) was heated at 120° C. After 15 hours, the volatiles were removed and the residue was washed with MeCN to give the title compound as a yellow solid (1.674 g, 91%). M.P. 182-184° C.; MS m/z 367.5 [M+H]$^+$; $^1$H NMR (500 MHz, DMSO-d$_6$): δ 8.20 (1H, d, J=2.7 Hz), 8.04 (1H, dd, J=2.8 Hz, 9.8 Hz), 7.79 (1H, dd, J=2.1 Hz, 8.5 Hz), 7.74 (1H, d, J=2.1 Hz), 7.67 (1H, d, J=9.7 Hz), 7.07 (1H, d, J=8.5 Hz), 6.93 (1H, s), 3.87 (3H, s), 3.83 (3H, s), 3.12 (4H, m), 2.88 (4H, m).

As shown in Table 1 below, additional compounds disclosed herein may be prepared according to Example 3 by substituting the appropriate starting materials, reagents and reaction conditions.

Example 4

Preparation of Cpd 1

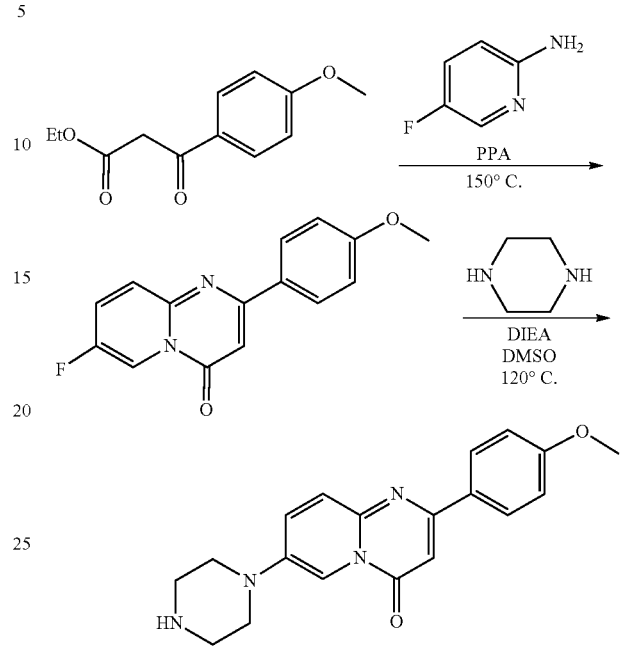

Step A: A mixture of ethyl 3-(3-methoxyphenyl)-3-oxopropanoate (2.68 mL, 14.0 mmol) and 2-amino-5-fluoropyridine (1.12 g, 10.0 mmol) in PPA (~5 g) was heated at 120° C. After 0.5 hours, the dark purple mixture was cooled to room temperature and treated with ice-water. The precipitate was filtered, washed with water and MeCN to give 2-(4-methoxyphenyl)-7-fluoro-4H-pyrido[1,2-a]pyrimidin-4-one as a slightly yellow solid (1.758 g, 65%). MS m/z 271.2 [M+H]$^+$.

Step B: Following the procedure in Example 3, Step B, 7-fluoro-2-(4-methoxyphenyl)-4H-pyrido[1,2-a]pyrimidin-4-one (81 mg, 0.3 mmol) and piperazine (129 mg, 1.5 mmol) in DMSO (1 mL) gave the title compound as a yellow solid (66 mg, 66%). M.P. 182-184° C.; MS m/z 337.3 [M+H]$^+$; $^1$H NMR (500 MHz, DMSO-d$_6$): δ 8.20 (1H, d, J=2.6 Hz), 8.16 (2H, dd, J=2.0 Hz, 7.0 Hz), 8.05 (1H, dd, J=2.7 Hz, 9.7 Hz), 7.67 (1H, d, J=9.7 Hz), 7.05 (2H, d, J=1.9 Hz, 7.0 Hz), 6.86 (1H, s), 3.83 (3H, s), 3.12 (4H, m), 2.87 (4H, m).

As shown in Table 1 below, additional compounds disclosed herein may be prepared according to Example 4 by substituting the appropriate starting materials, reagents and reaction conditions.

Example 5

Preparation of Cpd 81 and Cpd 82

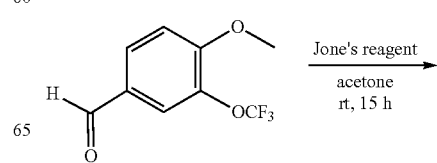

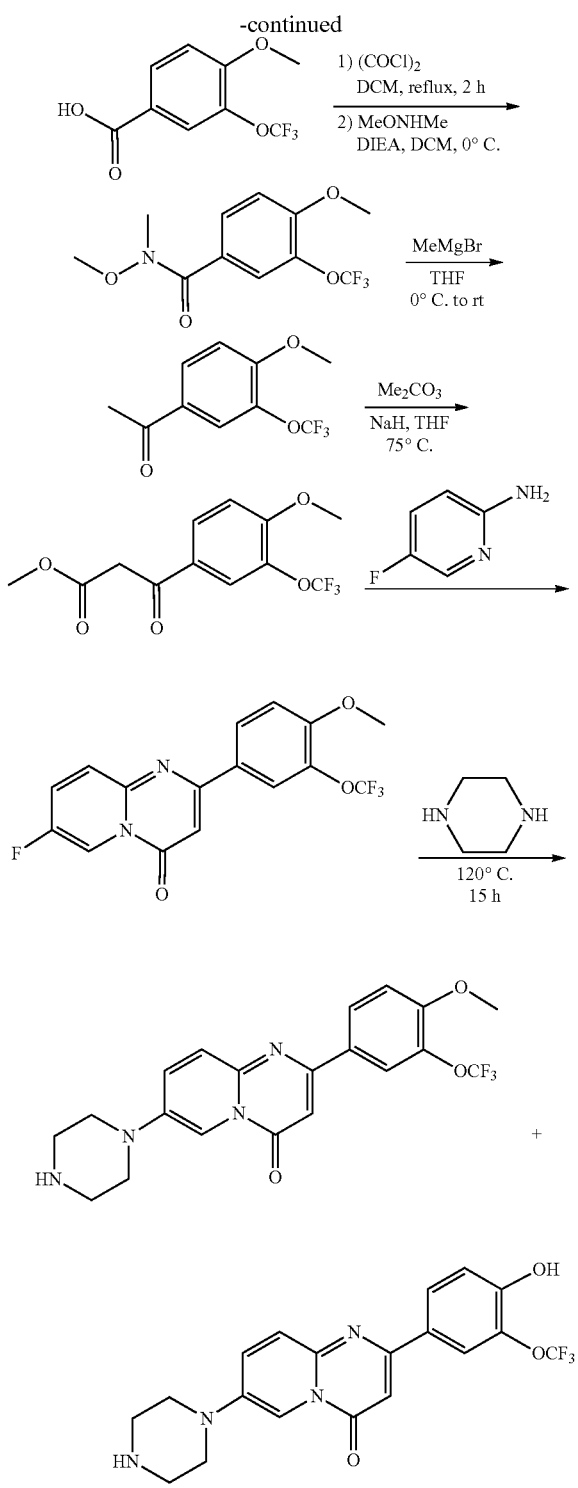

Step A: To a solution of 4-methoxy-3-(trifluoromethoxy) benzaldehyde (1.0 g, 4.5 mmol) in acetone (30 mL) was added Jone's reagent (5 mL). After stirring at room temperature for 15 hours, methanol (2 mL) was added and the mixture was filtered. The filtrate was concentrated, dissolved in EtOAc and washed with water. The organics were dried and concentrated to give 4-methoxy-3-(trifluoromethoxy)-benzoic acid as a white solid (1.02 g, 96%), MS m/z 235.2 [M−H]⁻.

Step B: To a solution of 4-methoxy-3-(trifluoromethoxy) benzoic acid (1.02 g, 4.32 mmol) in DCM (10 mL) was added oxalyl chloride (5 mL). After refluxing for 6 hours, the solution was concentrated to give 4-methoxy-3-(trifluoromethoxy)-benzoyl chloride. The crude acid chloride was dissolved in DCM (10 mL) and cooled to 0° C. Diisopropylethylamine (1.56 mL, 9.0 mmol) and N,O-dimethylhydroxylamine (0.658 g, 6.7 mmol) were added. After stirring at room temperature for 2 hours, the mixture was washed with water. The organics were dried, concentrated and chromatographed (5% EtOAc in CH₂Cl₂) to give 4-dimethoxy-N-methyl-3-(trifluoromethoxy)benzamide as an amber oil (0.58 g, 48%).

Step C: To a solution of 4-dimethoxy-N-methyl-3-(trifluoromethoxy)-benzamide (0.58 g, 2.08 mmol) in THF (8 mL) at 0° C. was added MeMgBr (3.0 M, 0.83 mL, 2.5 mmol). After stirring at room temperature for 15 hours, the solution was washed with water. The organics were dried and concentrated to give 11-(4-methoxy-3-(trifluoromethoxy)phenyl)ethanone as a white solid (0.45 g, 96%).

Step D: To a solution of the crude 1-(2-fluoro-4,5-dimethoxyphenyl)-ethanone (0.45 g, 2.0 mmol) and dimethyl carbonate (1.5 mL, 18.2 mmol) in THF (8 mL) at room temperature was added NaH (60%, 0.44 g, 10.9 mmol). After heating at 75° C. for 20 minutes, the mixture was quenched with NH₄Cl (satd.). The pH of the mixture was adjusted to neutral with 1N HCl. The mixture was extracted with EtOAc. The organics were dried and concentrated to give methyl 3-(4-methoxy-3-(trifluoromethoxy)phenyl)-3-oxopropanoate. MS m/z 299.1 [M+H]⁺. The crude product was used directly in the next step.

Step E: A solution of the crude methyl 3-(4-methoxy-3-(trifluoromethoxy)phenyl)-3-oxopropanoate (2 mmol) from step D, p-TsOH (38 mg, 0.2 mmol) and trimethoxymethane in MeOH (4 mL) was heated at 60° C. After 1 hour, the volatiles were removed and 2-amino-5-fluoropyridine (0.224 g, 2.0 mmol) was added. The mixture was heated at 150° C. for 1 hour, cooled to room temperature and washed with MeCN to give 7-fluoro-2-(4-methoxy-3-(trifluoromethoxy)phenyl)-4H-pyrido[1,2-a]pyrimidin-4-one (146 mg, 21%). MS m/z 355.1 [M+H]⁺.

Step F: A mixture of 7-fluoro-2-(4-methoxy-3-(trifluoromethoxy)phenyl)-4H-pyrido[1,2-a]pyrimidin-4-one (71 mg, 0.2 mmol), piperazine (38 mg, 0.4 mmol) and diisopropylethylamine (69 uL, 0.4 mmol) in DMSO (0.5 mL) was heated at 120° C. After 15 hours, the volatiles were removed and the residue was chromatographed (20% MeOH in DCM) to give two products:

Cpd 81 (8 mg, 9%) was obtained as a yellow solid. M.P. 158-162° C.; MS m/z 421.1 [M+H]⁺; ¹H NMR (500 MHz, DMSO-d₆): δ 8.26 (1H, d, J=2.6 Hz), 8.24 (1H, dd, J=2.2 Hz, 8.8 Hz), 8.19 (1H, m), 8.08 (1H, dd, J=2.8 Hz, 9.7 Hz), 7.75 (1H, d, J=9.7 Hz), 7.37 (1H, d, J=8.8 Hz), 6.99 (1H, s), 3.94 (3H, s), 3.07 (4H, m), 2.50 (4H, m, obscured by DMSO-d₆; and, Cpd 82 (9 mg, 11%) was obtained as a yellow solid. M.P. 245-248° C.; MS m/z 407.2 [M+H]⁺; ¹H NMR (500 MHz, DMSO-d₆): δ 8.21 (1H, d, J=2.7 Hz), 8.11 (1H, m), 8.07-8.03 (2H, m), 7.68 (1H, d, J=9.7 Hz), 7.11 (1H, d, J=8.6 Hz), 6.87 (1H, s), 3.14 (4H, m), 2.88 (4H, m).

As shown in Table 1 below, additional compounds disclosed herein may be prepared according to Example 5 by substituting the appropriate starting materials, reagents and reaction conditions.

Example 6

Preparation of Cpd 70

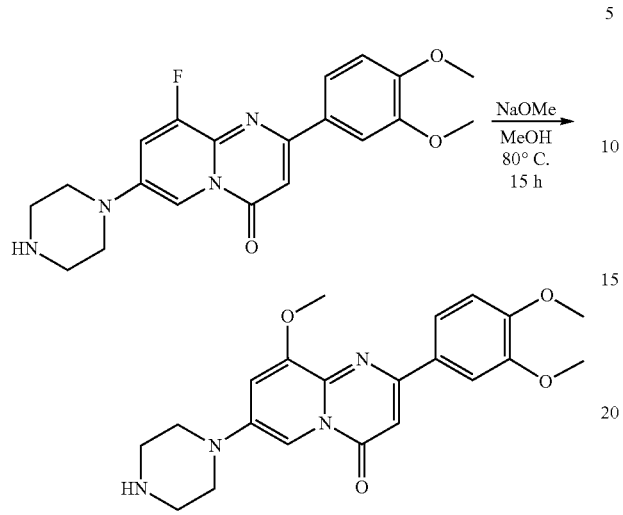

To a suspension of 2-(3,4-dimethoxyphenyl)-9-fluoro-7-(piperazin-1-yl)-4H-pyrido[1,2-a]pyrimidin-4-one (38 mg, 0.1 mmol, prepared by following the procedures in Example 3, Steps A and B in MeOH (0.5 mL) was added NaOMe (0.5 M in MeOH, 1 mL, 0.5 mmol). After heating at 80° C. for 15 hours, the volatiles were removed and the residue was chromatographed (10-15% MeOH/CH$_2$Cl$_2$) to give the title compound as a yellow solid (18 mg, 45%). M.P. 185-187° C.; MS m/z 397.3 [M+H]$^+$; $^1$H NMR (500 MHz, DMSO-d$_6$): δ 8.20 (1H, d, J=2.5 Hz), 7.80 (2H, m), 7.08 (1H, d, J=9.0 Hz), 7.00 (1H, s), 6.97 (1H, d, J=2.5 Hz), 3.89 (3H, s), 3.87 (3H, s), 3.83 (3H, s), 3.30 (4H, m), 2.98 (4H, m).

Example 7

Preparation of Cpd 74

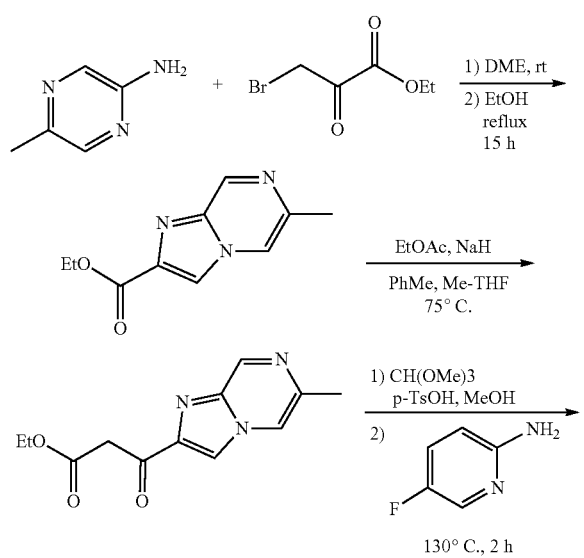

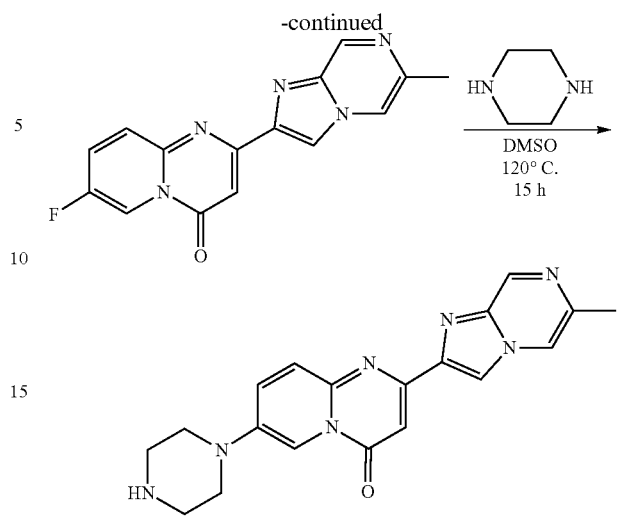

Step A: To a solution of 2-amino-5-methylpyrazine (1.09 g, 10 mmol) in DME (10 mL) was added ethyl 3-bromo-2-oxopropanoate (1.57 mL, 12.5 mmol). The mixture was stirred at room temperature for 45 minutes. The precipitate was filtered, washed with Et$_2$O and dried to give a yellow solid. The solid was suspended in EtOH (20 mL) and heated at 90° C. After 1.5 hours, the resulting brown solution was concentrated and adjusted to pH 7. The mixture was extracted with EtOAc. The organics were concentrated and the residue was triturated and washed with MeCN to give ethyl 6-methylimidazo[1,2-a]pyrazine-2-carboxylate as a brown solid (0.993 g, 48%). MS m/z 206.2 [M+H]$^+$.

Step B: To a solution of ethyl 6-methylimidazo[1,2-a]pyrazine-2-carboxylate (0.971 g, 4.73 mmol) and EtOAc (0.98 mL, 10 mmol) in toluene (2 mL) and Me-THF (8 mL) at room temperature was added NaH (60%, 0.503 mg, 12.6 mmol). After heating at 70° C. for 30 minutes, the mixture was cooled to room temperature, quenched with ice, adjusted to pH 7 with 1N HCl and extracted with EtOAc. The organics were combined, dried, concentrated and chromatographed to give ethyl 3-(6-methylimidazo[1,2-a]pyrazin-2-yl)-3-oxopropanoate as a brownish oil (0.93 g, 78%).

Step C: Following the procedure in Example 1 Step B, ethyl 3-(6-methylimidazo[1,2-a]pyrazin-2-yl)-3-oxopropanoate (0.913 g, 3.7 mmol), p-toluenesulfonic acid monohydrate (70 mg, 0.37 mmol) and trimethylorthoformate (0.81 mL, 7.4 mmol) in MeOH (10 mL) afforded the ketal which was used directly in the next step.

Step D: Following the procedure in Example 1 Step C, the crude dimethoxypropanoate (from Step C and 2-amino-5-fluoro-pyridine (0.422 g, 3.7 mmol) gave 7-fluoro-2-(6-methylimidazo[1,2-a]pyrazin-2-yl)-4H-pyrido[1,2-a]pyrimidin-4-one as a brownish solid (0.344 g, 31%). MS m/z 295.9 [M+H]$^+$; $^1$H NMR (500 MHz, DMSO-d$_6$): δ 9.09 (1H, s), 8.97-8.96 (1H, m), 8.67 (1H, s), 8.47 (1H, s), 8.15-8.11 (1H, m), 7.85-7.82 (1H, m), 7.08 (1H, s), 2.42 (3H, S).

Step E: Following the procedure in Example 3, Step B, 7-fluoro-2-(6-methylimidazo[1,2-a]pyrazin-2-yl)-4H-pyrido[1,2-a]pyrimidin-4-one (59 mg, 0.2 mmol) and piperazine (52 mg, 0.6 mmol) in DMSO (0.5 mL) gave the title compound as a yellow solid (28 mg, 39%). M.P. 221-225° C.; MS m/z 362.2 [M+H]$^+$; $^1$H NMR (500 MHz, DMSO-d$_6$): δ 9.07 (1H, s), 8.62 (1H, s), 8.46 (1H, s), 8.25 (1H, d, J=2.6 Hz), 8.09 (1H, d, J=2.7 Hz, 9.7 Hz), 7.67 (1H, d, J=9.7 Hz), 7.00 (1H, s), 3.16 (4H, m), 2.90 (4H, m), 2.44 (3H, s).

As shown in Table 1 below, additional compounds disclosed herein may be prepared according to Example 7 by substituting the appropriate starting materials, reagents and reaction conditions.

Example 8

Preparation of Cpd 29

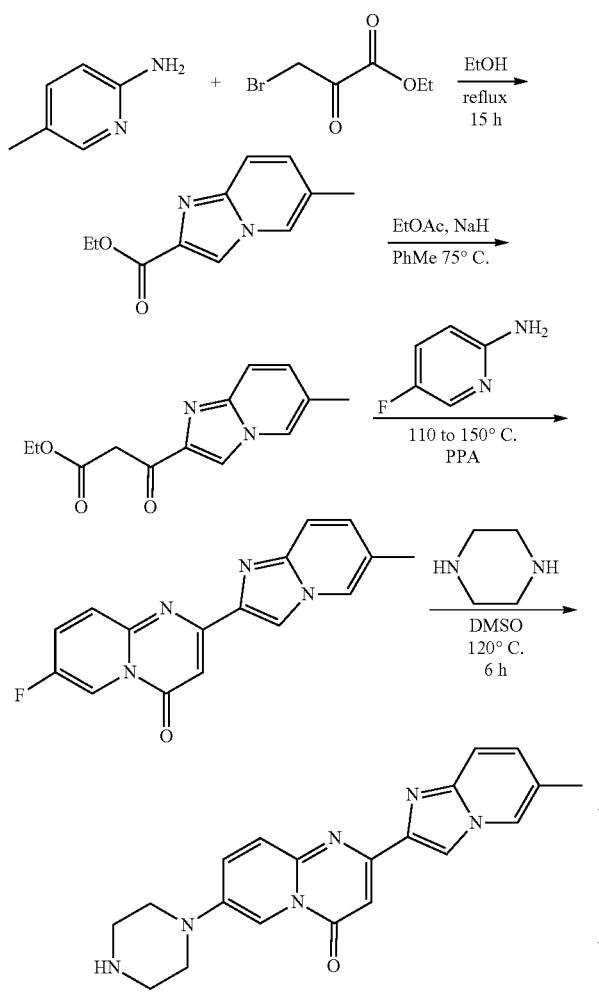

Step A: Following the procedure in Example 7, Step A, 2-amino-5-methylpyridine (5.41 g, 50 mmol) and ethyl 3-bromo-2-oxopropanoate (7.0 mL, 50 mmol) in MeOH (50 mL) gave ethyl 6-methylimidazo[1,2-a]pyridine-2-carboxylate as a yellowish solid (9.50 g, 93%), MS m/z 205.1 [M+H]$^+$.

Step B: Following the procedure in Example 7, Step B, ethyl 6-methylimidazo[1,2-a]pyridine-2-carboxylate (0.55 g, 2.5 mmol), EtOAc (0.29 mL, 5.0 mmol) and NaH (60%, 0.20 g, 5 mmol) in toluene (5 mL) gave ethyl 3-(6-methylimidazo[1,2-a]pyridin-2-yl)-3-oxopropanoate as a yellow solid (0.62 g, 100%), MS m/z 243.1 [M+H]$^+$.

Step C: Following the procedure in Example 4, Step A, ethyl 3-(6-methylimidazo[1,2-a]pyridin-2-yl)-3-oxopropanoate (246 mg, 1.0 mmol) and 2-amino-5-fluoropyridine (334 mg, 1.2 mmol) in PPA (~5 g) gave 7-fluoro-2-(6-methylimidazo[1,2-a]pyridin-2-yl)-4H-pyrido[1,2-a]pyrimidin-4-one as a yellow solid (17 mg, 6%), MS m/z 295.2 [M+H]$^+$.

Step D: Following the procedure in Example 3, Step B, 7-fluoro-2-(6-methylimidazo[1,2-a]pyridin-2-yl)-4H-pyrido[1,2-a]pyrimidin-4-one (17 mg, 0.06 mmol) and piperazine (30 mg, 0.3 mmol) in DMSO (10 mL) gave the title compound as a light brown solid (19 mg, 83%). M.P. 193-198° C.; MS m/z 361.3 [M+H]$^+$; $^1$H NMR (500 MHz, DMSO-d$_6$): δ 8.48 (1H, s), 8.41 (1H, s), 8.25 (1H, d, J=2.6 Hz), 8.06 (1H, dd, J=2.7 Hz, 9.7 Hz), 7.66 (1H, d, J=9.7 Hz), 7.55 (1H, d, 9.3 Hz), 7.18 (1H, d, J=9.3 Hz), 6.96 (1H, s), 3.23 (4H, m), 3.01 (4H, m), 2.29 (3H, s).

Example 9

Preparation of Cpd 170

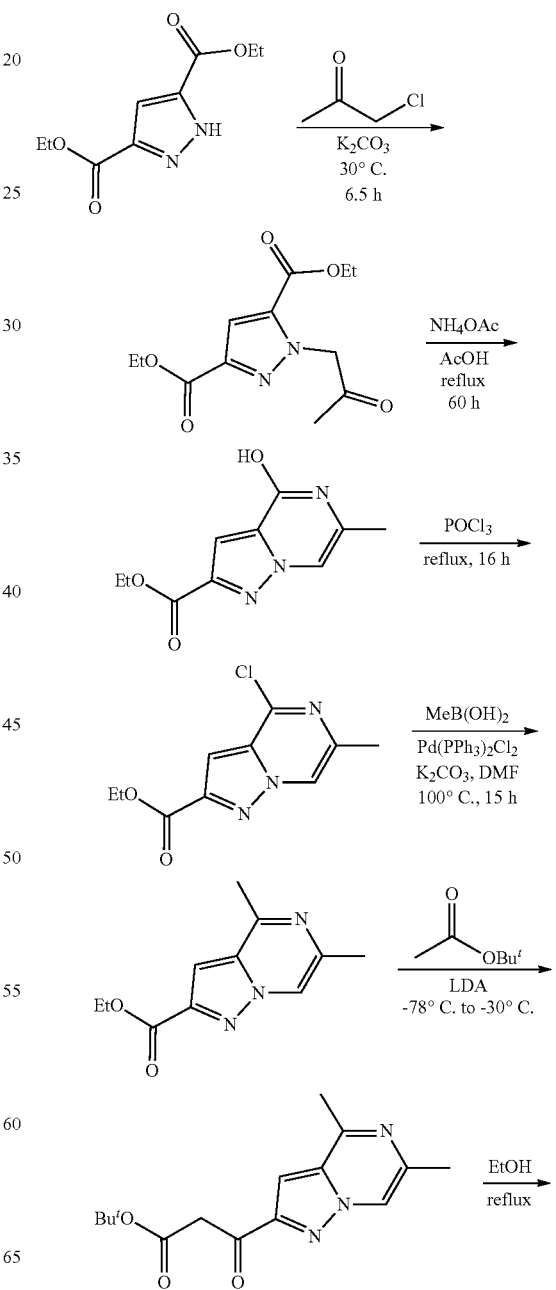

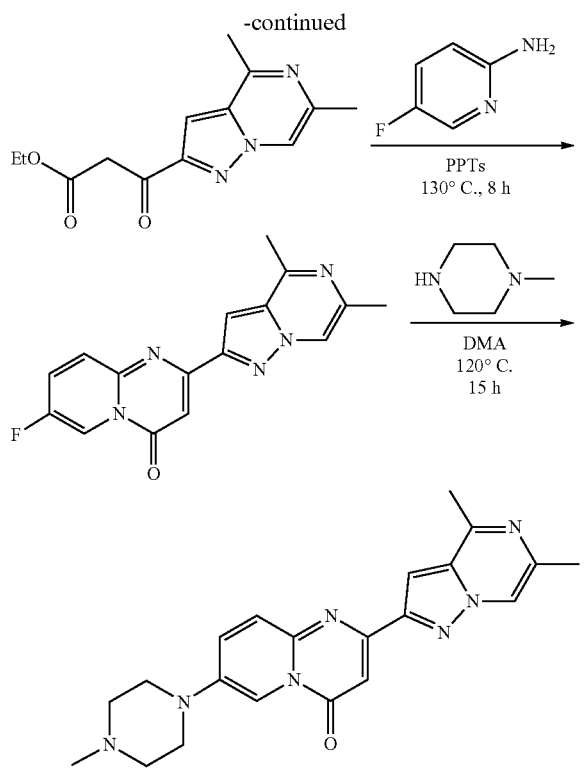

Step A: To a solution of diethyl 1H-pyrazole-3,5-dicarboxylate (10.0 g, Δ7 mmol) and chloroacetone (3.76 mL, Δ7 mmol) in acetone (200 mL) was added potassium carbonate (7.2 g, 52 mmol). After heating at 30° C. for 6 hours, the mixture was concentrated to remove the volatiles. The residue was taken into EtOAc and washed with water. The organics were dried over MgSO$_4$ and concentrated to give diethyl 1-(2-oxopropyl)-1H-pyrazole-3,5-dicarboxylate as a light brown solid, which was used directly in the next step, MS m/z 269.1 [M+H]$^+$.

Step B: To a solution of diethyl 1-(2-oxopropyl)-1H-pyrazole-3,5-dicarboxylate (~47 mmol) in acetic acid (300 mL) was added ammonium acetate (72 g, 940 mmol). After refluxing for 48 hours, the mixture was concentrated to minimum volume and diluted with water. The precipitate was filtered, washed with water and MeCN to give ethyl 4-hydroxy-6-methylpyrazolo[1,5-a]pyrazine-2-carboxylate as a tan solid (6.7 g, 64%), MS m/z 222.1 [M+H]$^+$.

Step C: A mixture of ethyl 4-hydroxy-6-methylpyrazolo[1,5-a]pyrazine-2-carboxylate (7.18 g, 32.5 mmol) in POCl$_3$ (80 mL) was refluxed for 15 hours. The dark mixture was concentrated and washed with MeCN to give ethyl 4-chloro-6-methylpyrazolo[1,5-a]pyrazine-2-carboxylate (5.197 g) as an off-white solid. The filtrate was concentrated and chromatographed to give an additional 1.42 g product (6.617 g, 85%) MS m/z 240.1 [M+H]$^+$, 242.1 [M+2+H]t Step D: A mixture of ethyl 4-chloro-6-methylpyrazolo[1,5-a]pyrazine-2-carboxylate (5.197 g, 21.7 mmol), MeB(OH)$_2$ (3.90 g, 65.1 mmol), K$_2$CO$_3$ (14.8 g, 107.5 mmol) and Pd(PPh$_3$)$_2$Cl$_2$ in (456 mg, 0.65 mmol) DMF (100 mL) was degassed and heated under N$_2$ for 15 hours. The mixture was concentrated on a rotovap to remove most of the DMF and washed with water. The residue was chromatographed (2% to 5% MeOH in CH$_2$Cl$_2$) to give ethyl 4,6-dimethylpyrazolo[1,5-a]pyrazine-2-carboxylate as a yellow solid (3.90 g, 82%), MS m/z 220.1 [M+H]$^+$; $^1$H NMR (500 MHz, DMSO-d$_6$): δ 8.54 (1H, s), 7.49 (1H, s), 4.36 (2H, q, J=7.2 Hz), 2.70 (3H, s), 2.42 (3H, s), 1.34 (3H, t, J=7.2 Hz).

Step E: To a solution of t-butyl acetate (1.63 mL, 12.1 mmol) in THF (50 mL) at −78° C. was added LDA (1.5 M, 0.97 mL, 14.5 mmol). After 0.5 hours, the solution was cannulated to a solution of ethyl 4,6-dimethylpyrazolo[1,5-a]pyrazine-2-carboxylate (1.33 g, 6.07 mmol) in THF (100 mL) at −30° C. After 1 hour, the mixture was quenched with saturated NH$_4$Cl, adjusted to pH 5-6 and extracted with EtOAc. The combined organics were dried and concentrated. The residue was chromatographed (2% to 4% MeOH/CH$_2$Cl$_2$) to give t-butyl 3-(4,6-dimethylpyrazolo[1,5-a]pyrazin-2-yl)-3-oxopropanoate as a yellow oil (1.696 g, 97%), MS m/z 290.2 [M+H]$^+$; $^1$H NMR (500 MHz, DMSO-d$_6$): δ 8.57 (1H, s), 7.50 (1H, s), 4.02 (2H, s), 2.70 (3H, s), 2.43 (3H, s), 1.38 (9H, s).

Step F: A solution of t-butyl 3-(4,6-dimethylpyrazolo[1,5-a]pyrazin-2-yl)-3-oxopropanoate (4.86 g, 16.8 mmol) in EtOH (30 mmol) was heated at 120° C. in a capped tube. After 1 hour, the solution was cooled to room temperature and the volatiles were removed to give ethyl 3-(4,6-dimethylpyrazolo[1,5-a]pyrazin-2-yl)-3-oxopropanoate as a yellow solid (4.44 g, 98%), MS m/z 262.2 [M+H]$^+$.

Step G: A mixture of 2-amino-5-fluoro-pyridine (134 mg, 1.2 mmol), ethyl 3-(4,6-dimethylpyrazolo[1,5-a]pyrazin-2-yl)-3-oxopropanoate (261 mg, 1.0 mmol) and PPTs (12.6 mg, 0.05 mmol) was heated at 130° C. After 8 hours, the mixture was cooled to room temperature and chromatographed to give 2-(4,6-dimethylpyrazolo[1,5-a]pyrazin-2-yl)-7-fluoro-4H-pyrido[1,2-a]pyrimidin-4-one as a yellow solid (220 mg, 71%). MS m/z 310.2 [M+H]$^+$; $^1$H NMR (500 MHz, DMSO-d$_6$): δ 8.97-8.95 (1H, m), 8.55 (1H, s), 8.16-8.12 (1H, m), 7.87-7.85 (1H, m), 7.56 (1H, s), 7.03 (1H, s), 2.73, (3H, s), 2.43 (3H, s).

Step H: Following the procedure in Example 3, Step B, 2-(4,6-dimethylpyrazolo[1,5-a]pyrazin-2-yl)-7-fluoro-4H-pyrido[1,2-a]pyrimidin-4-one (309 mg, 1.0 mmol) and piperazine (1.1 mL, 10 mmol) in DMA (1.0 mL) gave the title compound as a yellow solid (313 mg, 80%). M.P. 254-256° C.; MS m/z 390.4 [M+H]$^+$; $^1$H NMR (500 MHz, DMSO-d$_6$): δ 8.55 (1H, s), 8.27 (1H, d, J=2.7 Hz), 8.12 (1H, dd, J=2.8 Hz, 9.7 Hz), 7.71 (1H, d, J=9.7 Hz), 7.54 (1H, s), 6.95 (1H, s), 3.25 (4H, m), 2.72 (3H, s), 2.51 (4H, m, obscured by DMSO-d$_6$), 2.43 (3H, s), 2.25 (3H, s).

As shown in Table 1 below, additional compounds disclosed herein may be prepared according to Example 9 by substituting the appropriate starting materials, reagents and reaction conditions.

Example 10

Preparation of Cpd 163

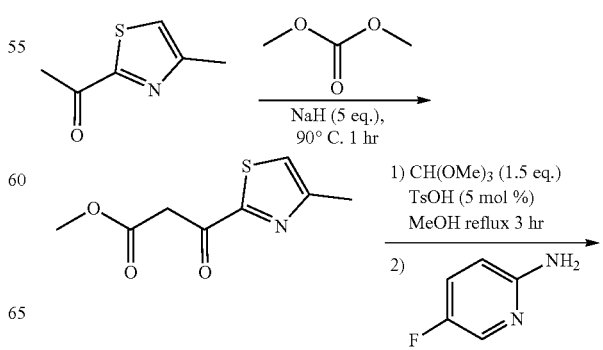

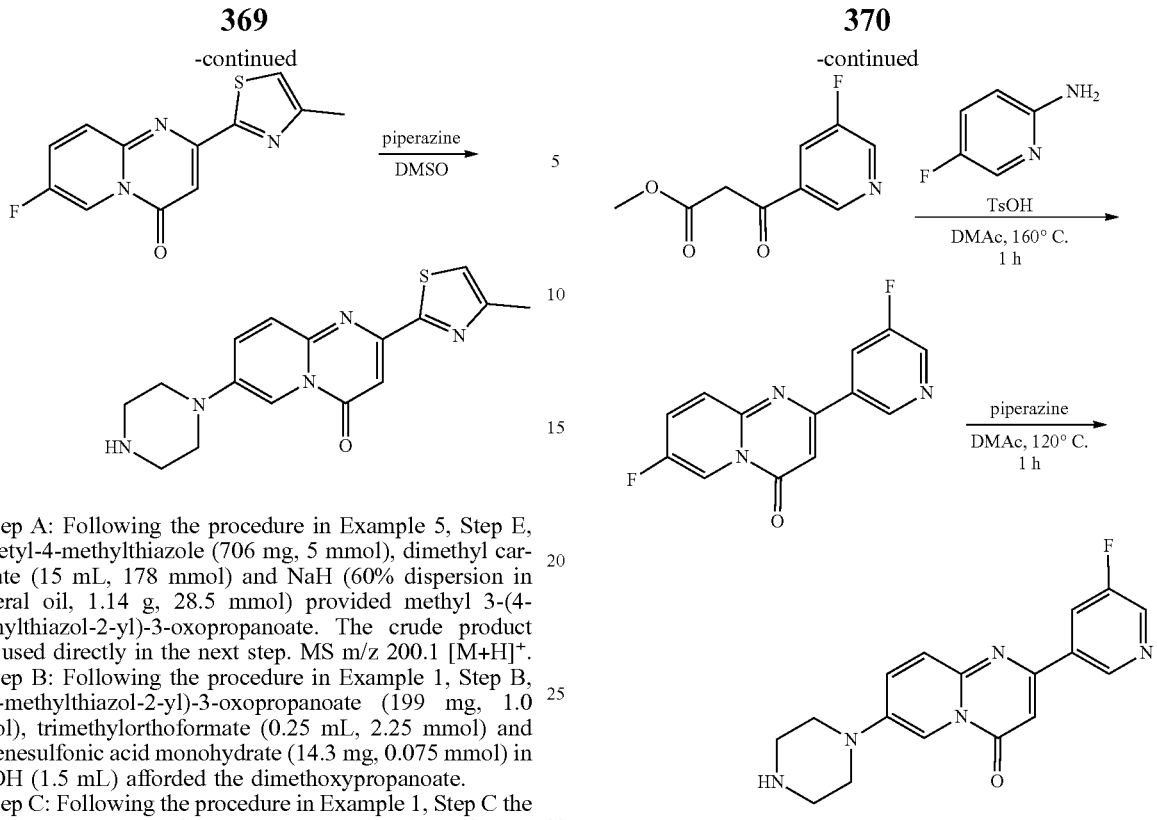

Step A: Following the procedure in Example 5, Step E, 2-acetyl-4-methylthiazole (706 mg, 5 mmol), dimethyl carbonate (15 mL, 178 mmol) and NaH (60% dispersion in mineral oil, 1.14 g, 28.5 mmol) provided methyl 3-(4-methylthiazol-2-yl)-3-oxopropanoate. The crude product was used directly in the next step. MS m/z 200.1 [M+H]+.

Step B: Following the procedure in Example 1, Step B, 3-(4-methylthiazol-2-yl)-3-oxopropanoate (199 mg, 1.0 mmol), trimethylorthoformate (0.25 mL, 2.25 mmol) and toluenesulfonic acid monohydrate (14.3 mg, 0.075 mmol) in MeOH (1.5 mL) afforded the dimethoxypropanoate.

Step C: Following the procedure in Example 1, Step C the dimethoxypropanoate from Step B and 2-amino-4-fluoropyridine (201.8 mg, 1.8 mmol) in DMA (1.5 mL) provided 7-fluoro-2-(4-methylthiazol-2-yl)-4H-pyrido[1,2-a]pyrimidin-4-one (175.5 mg, 67%). MS m/z 262.1 [M+H]+.

Step D: Following the procedure in Example 3, Step B, 7-fluoro-2-(4-methylthiazol-2-yl)-4H-pyrido[1,2-a]pyrimidin-4-one (52.2 mg, 0.2 mmol) and piperazine (86 mg, 1 mmol) in DMSO (0.8 mL) provided the title compound (20 mg, 30%). M.P. 142-147° C.; MS m/z 328.2 [M+H]+; 1H NMR (500 MHz, DMSO-d6): δ 8.27 (1H, dd, J=2.7 Hz, 18.6 Hz), 8.11-8.16 (1H, m), 7.73 (1H, t, J=9.2 Hz), 7.56 (1H, s), 6.88 (1H, d, J=3.2 Hz), 3.29-3.31 (2H, m), 3.16-3.18 (2H, m), 2.89-2.91 (2H, m), 2.67-2.69 (2H, m), 2.47 (3H, s).

As shown in Table 1 below, additional compounds disclosed herein may be prepared according to Example 10 by substituting the appropriate starting materials, reagents and reaction conditions.

Example 11

Preparation of Cpd 92

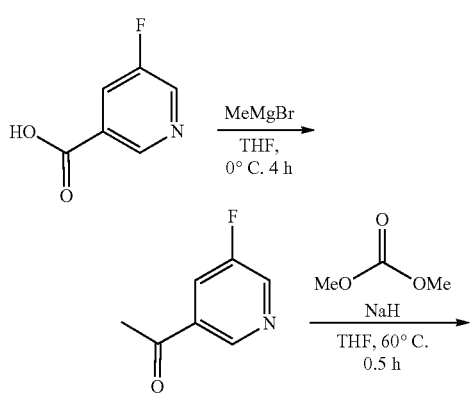

Step A: 5-Fluoronicotinic acid (1.0 g, 7.1 mmol) was dissolved in THF (10 mL) and cooled to 0° C. A 1.4 M solution of methylmagnesium bromide in THF:toluene (3:1) (11.2 mL, 15.6 mmol) was added drop wise to the solution. The solution was allowed to warm to room temperature. The solution was stirred at room temperature for 4 hours, upon which 1N aqueous HCl (50 mL) was slowly added. The mixture was partitioned into EtOAc (200 mL) and aqueous 1N NaOH (200 mL). The organic layer was washed with brine, dried over Na2SO4, filtered and concentrated. The residue was chromatographed on silica, eluting with EtOAc (0% to 50%) in hexanes to afford 1-(5-fluoropyridin-3-yl)ethanone as a white powder (290 mg, 29%).

Step B: Following the procedure in Example 5, Step D, the methyl ketone from Step A, dimethyl carbonate (0.44 mL, 5.25 mmol) and sodium hydride (210 mg, 60% dispersion in mineral oil, 5.25 mmol) in THF (6 mL) afforded methyl 3-(5-fluoropyridin-3-yl)-3-oxopropanoate as an off white powder (278 mg, 67%).

Step C: Methyl 3-(5-fluoropyridin-3-yl)-3-oxopropanoate (138 mg, 0.7 mmol) was combined with 5-fluoropyridin-2-amine (90 mg, 0.8 mmol) and toluenesulfonic acid monohydrate (6 mg, 0.03 mmol) in dimethylacetamide (0.5 mL). The mixture was heated to 160° C. for 1 hour. The mixture was cooled to 120° C., before adding piperazine (300 mg, 3.5 mmol). The mixture was stirred at 120° C. for 1 hour. The mixture was loaded onto silica in CH2Cl2 and eluted with 0% to 8% MeOH (3% NH3) in CH2Cl2. The title compound was obtained as a yellow powder (37 mg, 16%). M.P. 201-208° C.; MS m/z 326.2 [M+H]+; 1H NMR (DMSO-d6, 500 MHz): δ 9.25 (1H, s), 8.70 (1H, d, J=2.8 Hz), 8.42 (1H, d, J=10.2 Hz), 8.22 (1H, d, 2.7 Hz), 8.12 (1H, dd, J=9.8 Hz, 2.8 Hz), 7.74 (1H, d, J=9.7 Hz), 7.11 (1H, s), 3.16 (4H, m), 2.89 (4H, m), 2.37 (1H, br s).

As shown in Table 1 below, additional compounds disclosed herein may be prepared according to Example 11 by substituting the appropriate starting materials, reagents and reaction conditions.

Example 12

Preparation of Cpd 98

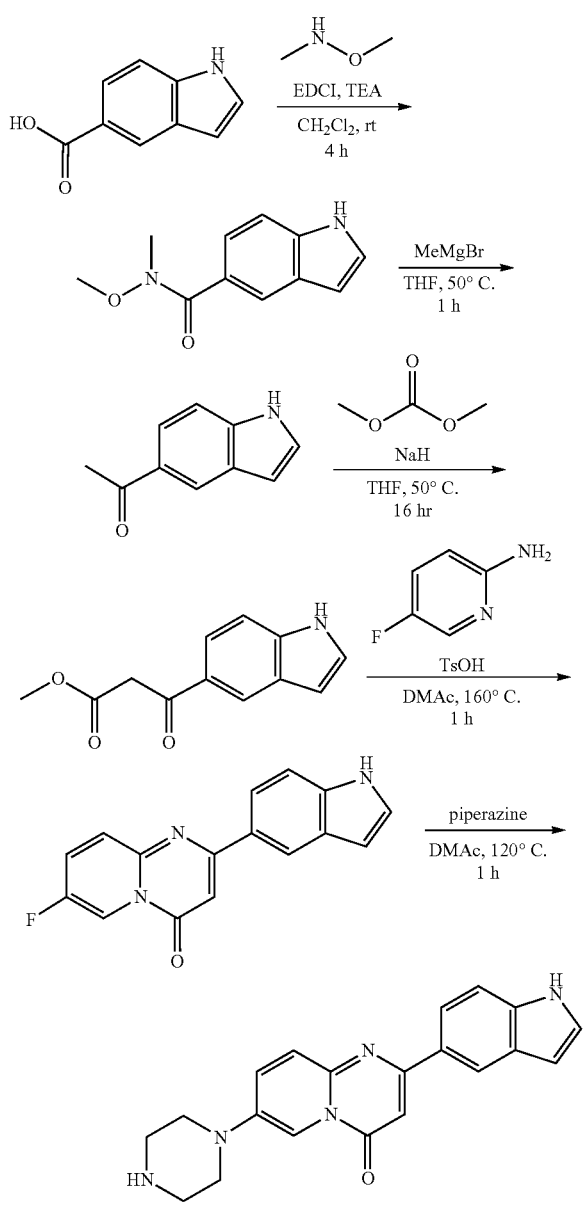

Step A: 1H-Indole-5-carboxylic acid (1.0 g, 6.2 mmol) was combined with N,O-dimethylhydroxylamine hydrochloride (907 mg, 9.3 mmol), N-(3-dimethylaminopropyl)-N'-ethylcarbodiimide hydrochloride (1.78 g, 9.3 mmol) and N,N-diisopropylethylamine (3.2 mL, 18.6 mmol) in $CH_2Cl_2$ (12 mL). After stirring for 4 hours at room temperature, the mixture was washed with aqueous HCl (1N, 20 mL). The organic layer was dried over $Na_2SO_4$ and concentrated. The crude product was used directly in the next step.

Step B: The crude product from Step A was dissolved in THF (20 mL). A 1.4 M solution of methylmagnesium bromide (11.2 mL, 15.6 mmol) in THF:toluene (3:1), was added drop wise to the solution. The solution was allowed to warm to room temperature. The solution was stirred at 50° C. for 1 hour, upon which 1N aqueous HCl (50 mL) was slowly added. The mixture was partitioned into EtOAc (200 mL) and aqueous 1N NaOH (200 mL). The organic layer was washed with brine, dried over $Na_2SO_4$, filtered and concentrated. The residue was chromatographed on silica, eluting with EtOAc (0% to 50%) in hexanes to afford 1-(1H-indol-5-yl)ethanone as a white powder (323 mg, 33%).

Step C: Following the procedure in Example 5, Step E, the methyl ketone from Step B, dimethyl carbonate (0.46 mL, 5.5 mmol) and sodium hydride (220 mg, 60% dispersion in mineral oil, 5.5 mmol) in THF (6 mL) afforded methyl methyl 3-(1H-indol-5-yl)-3-oxopropanoate as an off white powder (120 mg, 27%). MS m/z 216.1 [M−H]$^-$.

Step D: Following the procedure of Example 11, Step C, methyl 3-(1H-indol-5-yl)-3-oxopropanoate (98 mg, 0.45 mmol), 5-fluoropyridin-2-amine (56 mg, 0.5 mmol), toluenesulfonic acid monohydrate (9 mg, 0.05 mmol) and piperazine (194 mg, 2.25 mmol) in dimethylacetamide (0.5 mL) afforded the title compound as an off-white powder (40 mg, 26%). M.P. 266-272° C. MS m/z 346.2 [M+H]$^+$; $^1$H NMR (DMSO-d$_6$, 500 MHz): δ 11.3 (1H, s), 8.46 (1H, s), 8.22 (1H, d, J=2.8 Hz), 8.04 (1H, dd, J=9.7 Hz, 2.8 Hz), 7.95 (1H, d, J=8.7 Hz), 7.69 (1H, d, J=9.7 Hz), 7.49 (1H, d, J=8.6 Hz), 7.42 (1H, t, J=2.7 Hz), 6.90 (1H, s), 6.57 (1H, m), 3.14 (4H, m), 2.89 (4H, m), 2.36 (1H, br s).

As shown in Table 1 below, additional compounds disclosed herein may be prepared according to Example 12 by substituting the appropriate starting materials, reagents and reaction conditions.

Example 13

Preparation of Cpd 107

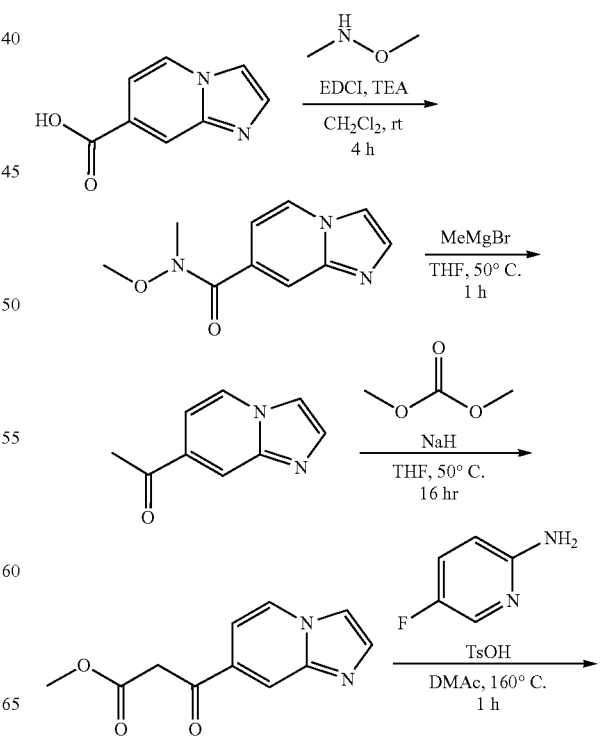

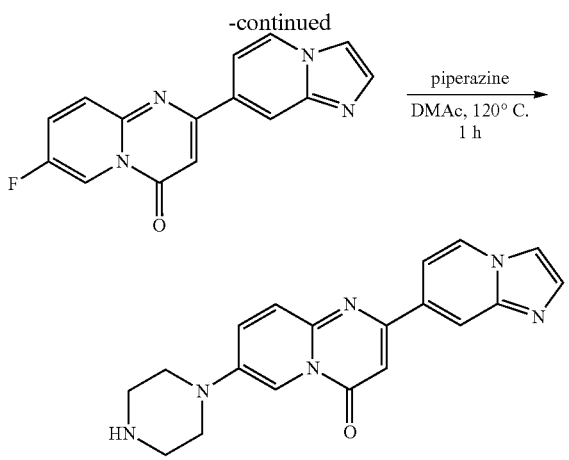

Step A: Following the procedure in Example 12, Step A, imidazo[1,2-a]pyridine-7-carboxylic acid (1.0 g, 6.2 mmol), N,O-dimethylhydroxylamine hydrochloride (907 mg, 9.3 mmol), N-(3-dimethylaminopropyl)-N'-ethylcarbodiimide hydrochloride (1.78 g, 9.3 mmol) and N,N-diisopropylethylamine (3.2 mL, 18.6 mmol) in $CH_2Cl_2$ (12 mL) gave N-methoxy-N-methylimidazo[1,2-a]pyridine-7-carboxamide (505 mg, 40%).

Step B: Following the procedure in Example 12, Step B, the product from Step A (505 mg, 2.5 mmol), methylmagnesium bromide (3.6 mmol) in THF (10 mL) afforded 1-(imidazo[1,2-a]pyridin-7-yl)ethanone (275 mg, 70%).

Step C: Following the procedure in Example 5, Step E, the methyl ketone from Step B (275 mg, 1.7 mmol), dimethyl carbonate (0.35 mL, 4.25 mmol) and sodium hydride (170 mg, 60% dispersion in mineral oil, 4.25 mmol) in THF (5 mL) afforded methyl 3-(imidazo[1,2-a]pyridin-7-yl)-3-oxopropanoate as an off-white powder (215 mg, 58%).

Step D: Following the procedure of Example 11, Step C, methyl 3-(imidazo[1,2-a]pyridin-7-yl)-3-oxopropanoate (215 mg, 1.0 mmol), 5-fluoropyridin-2-amine (123 mg, 1.1 mmol), toluenesulfonic acid monohydrate (19 mg, 0.1 mmol) and piperazine (430 mg, 5 mmol) in dimethylacetamide (1.0 mL) afforded the title compound as an off-white powder (40 mg, 12%). M.P. 258-270° C.; MS m/z 347.0 [M+H]$^+$; $^1$H NMR (DMSO-d$_6$, 500 MHz): δ 8.65 (1H, d, J=7.2 Hz), 8.46 (1H, s), 8.24 (1H, d, J=2.7 Hz), 8.11 (1H, dd, J=9.7 Hz, 2.7 Hz), 8.06 (1H, s), 7.75 (1H, d, J=9.7 Hz), 7.73 (1H, dd, J=7.2 Hz, 2.7 Hz), 7.71 (1H, s), 7.10 (1H, s), 3.16 (4H, m), 2.89 (4H, m), 2.34 (1H, br s).

Example 14

Preparation of Cpd 171

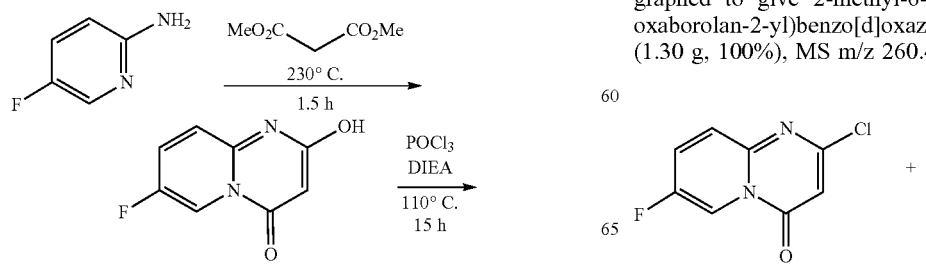

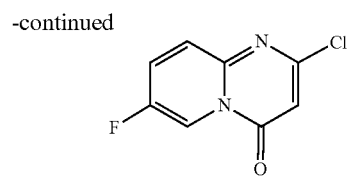

Part 1, Step A: A mixture of 2-amino-5-fluoropyridine (11.20 g, 0.10 mol) and dimethyl malonate (57.0 mL, 0.50 mol) was heated at 230° C. for 1.5 hours. After cooling to room temperature, the precipitate was filtered and washed with ACN (3×) to give 7-fluoro-2-hydroxy-4H-pyrido[1,2-a]pyrimidin-4-one as a dark solid (14 g), which was used directly in the next step. MS m/z 181.3 [M+H]$^+$.

Part 1, Step B: A dark mixture of crude 7-fluoro-2-hydroxy-4H-pyrido[1,2-a]pyrimidin-4-one (14 g, ~77 mmol) in POCl$_3$ (50 mL) and DIEA (13.3 mL, 77 mmol) was heated at 110° C. for 15 hours. The volatiles were removed and the dark residue was treated with ice-water, washed with water (3×) and dried to give a brown solid. The crude brown solid was chromatographed (5% MeOH in $CH_2Cl_2$) to give 2-chloro-7-fluoro-4H-pyrido[1,2-a]pyrimidin-4-one as a yellow solid (9.84 g, 50%, 2 steps), MS m/z 199.2 [M+H]$^+$; $^1$H NMR (500 MHz, DMSO-d$_6$): δ 8.99 (1H, dd, J=2.8 Hz, 4.7 Hz), 8.27-8.23 (1H, m), 7.85 (1H, dd, J=5.4 Hz, 9.8 Hz), 6.56 (1H, s).

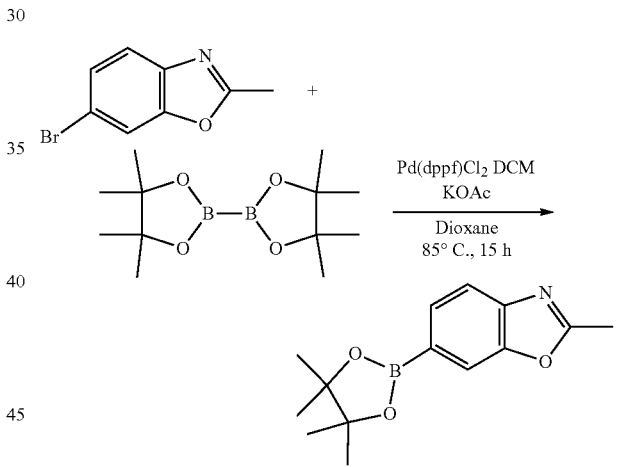

Part 2: A mixture of 6-bromo-2-methylbenzo[d]oxazole (1.06 g, 5.0 mmol), 4,4,4',4',5,5,5',5'-octamethyl-2,2'-bi(1,3,2-dioxaborolane) (1.40 g, 5.5 mmol), KOAc (1.47 g, 15 mmol) and Pd(dppf)Cl$_2$·$CH_2Cl_2$ (122 mg, 0.15 mmol) in dioxane (8 mL) was degassed and heated under N$_2$ at 85° C. After 15 hours, the mixture was diluted with EtOAc, filtered through celite and concentrated. The residue was chromatographed to give 2-methyl-6-(4,4,5,5-tetramethyl-1,3,2-dioxaborolan-2-yl)benzo[d]oxazole as a light orange solid (1.30 g, 100%), MS m/z 260.4 [M+H]$^+$.

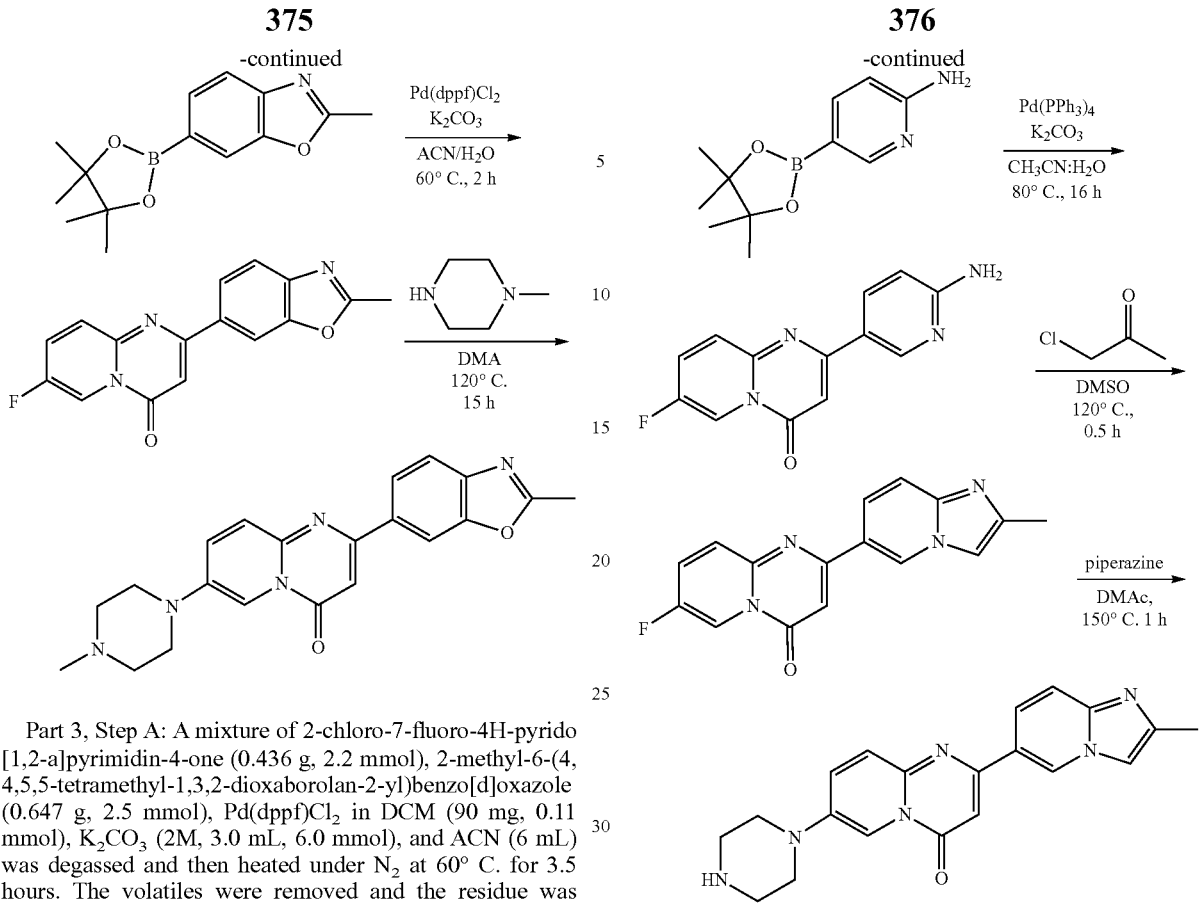

Part 3, Step A: A mixture of 2-chloro-7-fluoro-4H-pyrido[1,2-a]pyrimidin-4-one (0.436 g, 2.2 mmol), 2-methyl-6-(4,4,5,5-tetramethyl-1,3,2-dioxaborolan-2-yl)benzo[d]oxazole (0.647 g, 2.5 mmol), Pd(dppf)Cl$_2$ in DCM (90 mg, 0.11 mmol), K$_2$CO$_3$ (2M, 3.0 mL, 6.0 mmol), and ACN (6 mL) was degassed and then heated under N$_2$ at 60° C. for 3.5 hours. The volatiles were removed and the residue was chromatographed (2.5% MeOH/CH$_2$Cl$_2$) to give 7-fluoro-2-(2-methylbenzo[d]oxazol-6-yl)-4H-pyrido[1,2-a]pyrimidin-4-one as an off-white solid (0.64 g, 98%). MS m/z 296.4 [M+H]$^+$; $^1$H NMR (500 MHz, DMSO-d$_6$): δ 8.96-8.95 (1H, m), 8.51 (1H, d, J=1.6 Hz), 8.26 (1H, dd, J=8.5 Hz, 1.6 Hz), 8.16-8.12 (1H, m), 7.91-7.88 (1H, m), 7.78 (1H, d, J=8.4 Hz), 7.17 (1H, s), 2.67 (3H, s).

Part 3, Step B: A mixture of 7-fluoro-2-(2-methylbenzo[d]oxazol-6-yl)-4H-pyrido[1,2-a]pyrimidin-4-one (60 mg, 0.2 mmol) and 1-Methyl piperazine (0.11 mL, 1.0 mmol) in DMA (0.3 mL) was heated at 120° C. for 15 hours. The volatiles were removed and the residue was chromatographed to give the title compound as a yellow solid (46 mg, 61%). M.P. 178-183° C.; MS m/z 376.5 [M+H]$^+$; $^1$H NMR (500 MHz, DMSO-d$_6$): δ 8.47 (1H, d, J=1.5 Hz), 8.25 (1H, d, J=2.7 Hz), 8.23 (1H, dd, J=1.6 Hz, 8.4 Hz), 8.11 (1H, dd, J=2.8 Hz, 9.7 Hz), 7.76 (1H, d, J=8.6 Hz), 7.74 (1H, d, J=9.9 Hz), 7.06 (1H, s), 3.25 (4H, m), 2.66 (3H, s), 2.25 (3H, s).

As shown in Table 1 below, additional compounds disclosed herein may be prepared according to Example 14 by substituting the appropriate starting materials, reagents and reaction conditions.

Example 15

Preparation of 109

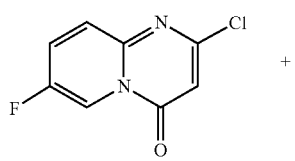

+

Step A: 2-Chloro-7-fluoro-4H-pyrido[1,2-a]pyrimidin-4-one (990 mg, 5 mmol, prepared according to the procedure in Example 14, Part 1) was combined with 2-aminopyridine-5-boronic acid pinacol ester (1.21 g, 5.5 mmol), tetrakis(triphenylphosphine) palladium(0) (281 mg, 0.25 mmol), CH$_3$CN (10 mL) and aqueous K$_2$CO$_3$ (1M, 10 mL). The mixture was heated to 80° C. for 6 hours. The mixture was cooled to room temperature, and then filtered. The collected precipitate was washed with CH$_3$CN and dried under vacuum, providing 2-(6-aminopyridin-3-yl)-7-fluoro-4H-pyrido[1,2-a]pyrimidin-4-one as a yellow powder (1.13 g, 88%). MS m/z 257.0 [M+H]$^+$; $^1$H NMR (DMSO-d$_6$, 500 MHz): δ 8.90 (1H, m), 8.83 (1H, d, J=2.1 Hz), 8.17 (1H, dd, J=8.8 Hz, 2.5 Hz), 8.07 (1H, m), 7.78 (1H, dd, J=9.8 Hz, 5.3 Hz), 6.87 (1H, s), 6.58 (2H, s), 6.53 (1H, d, 8.9 Hz).

Step B. 2-(6-Aminopyridin-3-yl)-7-fluoro-4H-pyrido[1,2-a]pyrimidin-4-one (254 mg, 1.0 mmol) was combined with chloroacetone (100 µL, 1.2 mmol) in DMSO (360 µL, 1.65 mmol). The mixture was heated to 120° C. for 30 minutes. After cooling to room temperature, the mixture was partitioned in CH$_2$Cl$_2$ and saturated aqueous NaHCO$_3$. The organic layer was concentrated. The residue was eluted from silica with MeOH (0% to 6%) in CH$_2$Cl$_2$, affording 7-fluoro-2-(2-methylimidazo[1,2-a]pyridin-6-yl)-4H-pyrido[1,2-a]pyrimidin-4-one as a tan powder (136 mg, 46%). MS m/z 295.0 [M+H]$^+$; $^1$H NMR (DMSO-d$_6$, 500 MHz): δ 9.40 (1H, s), 8.95 (1H, m), 8.14 (1H, m), 7.96 (1H, dd, J=9.5 Hz, 1.9 Hz), 7.85 (2H, m), 7.54 (1H, J=9.4), 7.08 (1H, s), 2.36 (3H, s).

Step C: 7-Fluoro-2-(2-methylimidazo[1,2-a]pyridin-6-yl)-4H-pyrido[1,2-a]pyrimidin-4-one (45 mg, 0.15 mmol) was combined with piperazine (65 mg, 0.75 mmol) in dimethylacetamide (0.5 mL). The mixture was heated to 150° C. for 1 hour. The mixture was loaded onto silica and eluted with 0% to 8% MeOH (3% NH₃) in CH₂Cl₂ to afford the title compound as a tan powder (33 mg, 61%). M.P. 259-267° C.; MS m/z 361.1 [M+H]⁺; ¹H NMR (DMSO-d₆, 500 MHz): δ 9.36 (1H, s), 8.23 (1H, d, J=2.7 Hz), 8.10 (1H, dd, J=9.7 Hz, 2.7 Hz), 7.94 (1H, dd, J=9.5 Hz, 1.8 Hz), 7.82 (1H, s), 7.70 (1H, d, J=9.7 Hz), 7.52 (1H, d, J=9.5 Hz), 6.96 (1H, s), 3.15 (4H, m), 2.89 (4H, m), 2.36 (3H, s).

As shown in Table 1 below, additional compounds disclosed herein may be prepared according to Example 15 by substituting the appropriate starting materials, reagents and reaction conditions.

Example 16

Preparation of Cpd 209

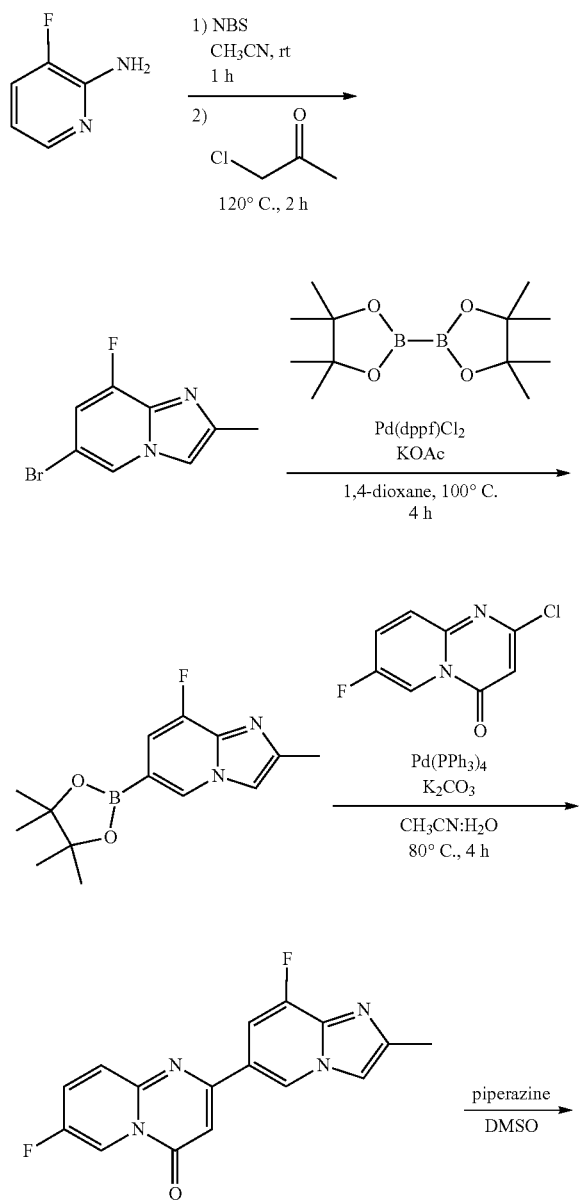

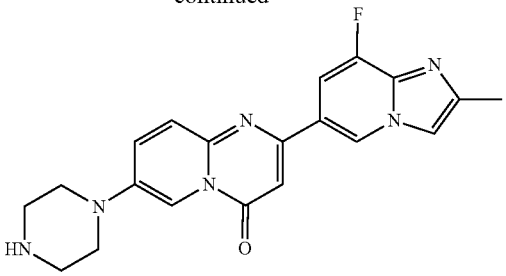

Step A: 3-Fluoropyridin-2-amine (5.0 g, 45 mmol) was combined with N-bromosuccinimide (8.0 g, 45 mmol) in CH₃CN (40 mL). The mixture was stirred at room temperature for 30 minutes. Chloroacetone (4.3 mL, 54 mmol) was added to the mixture. The mixture was heated to 100° C., allowing the CH₃CN to evaporate. After 1 hour, the temperature was raised to 120° C. for 2 hours. The mixture solidified upon cooling. The solid material was dissolved in H₂O (50 mL). To the aqueous solution was added 100 mL of saturated aqueous NaHCO₃. A precipitate formed, and was collected by vacuum filtration. The solid material was washed with H₂O and dried under vacuum. The material was loaded onto silica in CH₂Cl₂ and eluted with EtOAc (0% to 30%) in CH₂Cl₂, providing 6-bromo-8-fluoro-2-methylimidazo[1,2-a]pyridine as a tan powder (4.65 g, 45%). MS m/z 229.2 [M+H]⁺, 231.2 [M+2+H]⁺; ¹H NMR (DMSO-d₆, 500 MHz): δ 8.72 (1H, s), 7.79 (1H, s), 7.39 (1H, d, J=10.7 Hz), 2.35 (3H, s).

Step B: Following the procedure in Example 14, Part 2, 6-Bromo-8-fluoro-2-methylimidazo[1,2-a]pyridine (912 mg, 4 mmol), 4,4,4',4',5,5,5',5'-octamethyl-2,2'-bi(1,3,2-dioxaborolane) (1.32 g, 4.8 mmol), [1,1'-bis(diphenylphosphino)ferrocene]-dichloropalladium(II) (163 mg, 0.2 mmol) and potassium acetate (784 mg, 8 mmol) provided 8-fluoro-2-methyl-6-(4,4,5,5-tetramethyl-1,3,2-dioxaborolan-2-yl) imidazo[1,2-a]pyridine. The crude product was used directly in the next step.

Step C: Following the procedure in Example 14, Part 3, Step A, the crude product of 8-fluoro-2-methyl-6-(4,4,5,5-tetramethyl-1,3,2-dioxaborolan-2-yl)imidazo[1,2-a]pyridine from step A and 2-chloro-7-fluoro-4H-pyrido[1,2-a]pyrimidin-4-one (4 mmol, prepared in Example 14, Part 1, Step B), tetrakis(triphenylphosphine) palladium(0) (225 mg, 0.2 mmol) and aqueous K₂CO₃ (1M, 8 mL) provided 7-fluoro-2-(8-fluoro-2-methylimidazo[1,2-a]pyridin-6-yl)-4H-pyrido[1,2-a]pyrimidin-4-one as a tan powder (860 mg, 69%). MS m/z 313.0 [M+H]⁺.

Step D: Following the procedure in Example 14, Part 3, Step B, 7-Fluoro-2-(8-fluoro-2-methylimidazo[1,2-a]pyridin-6-yl)-4H-pyrido[1,2-a]pyrimidin-4-one (65 mg, 0.21 mmol) and piperazine (90 mg, 1.05 mmol) afforded the title compound as a tan powder (34 mg, 43%). M.P. 282-288° C.; MS m/z 379.4 [M+H]⁺; ¹H NMR (DMSO-d₆, 500 MHz): δ 9.26 (1H, s), 8.21 (1H, d, J=2.6 Hz), 8.10 (1H, dd, J=9.7 Hz, 2.7 Hz), 7.93 (1H, d, J=2.3 Hz), 7.84 (1H, d, J=12.7 Hz), 7.68 (1H, d, J=9.8 Hz), 6.98 (1H, s), 3.14 (4H, m), 2.88 (4H, m), 2.39 (3H, s), 2.35 (1H, br s).

As shown in Table 1 below, additional compounds disclosed herein may be prepared according to Example 16 by substituting the appropriate starting materials, reagents and reaction conditions.

Example 17

Preparation of Cpd 182

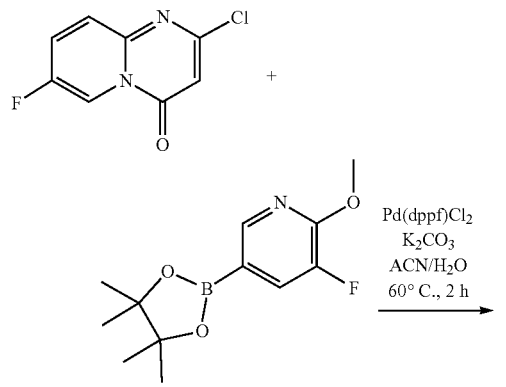

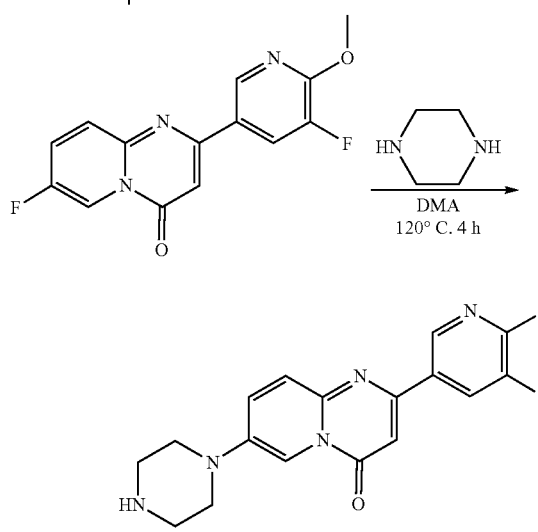

Step A: Following the procedure for Example 14, Part 3, Step A, 3-fluoro-2-methoxy-5-(4,4,5,5-tetramethyl-1,3,2-dioxaborolan-2-yl)pyridine (~4.85 mmol, crude product prepared by the procedure in Example 14, Part 2) and 2-chloro-7-fluoro-4H-pyrido[1,2-a]pyrimidin-4-one (0.64 g, 3.23 mmol, prepared in Example 14, Part 1) gave 7-fluoro-2-(5-fluoro-6-methoxypyridin-3-yl)-4H-pyrido[1,2-a]pyrimidin-4-one (1.0 g, 100%) as a brown solid, MS m/z 290.4 [M+H]+.

Step B: A mixture of 7-fluoro-2-(5-fluoro-6-methoxypyridin-3-yl)-4H-pyrido[1,2-a]pyrimidin-4-one (145 mg, 0.5 mmol) and piperazine (43 mg, 0.5 mmol) in DMA (1 mL) was heated at 120° C. After 4 hours, the volatiles were removed and the residue was chromatographed (20% MeOH/CH$_2$Cl$_2$) to give the title compound as a yellow solid (63 mg, 36%). M.P. 166-170° C.; MS m/z 356.4 [M+H]+; $^1$H NMR (500 MHz, DMSO-d$_6$): δ 8.83 (1H, d, J=1.9 Hz), 8.39 (1H, dd, J=1.9 Hz, 11.8 Hz), 8.23 (1H, d, J=2.6 Hz), 8.10 (1H, dd, J=2.7 Hz, 9.7 Hz), 7.71 (1H, d, J=9.7 Hz), 7.02 (1H, s), 4.03 (3H, s), 3.20 (4H, m), 2.94 (4H, m).

As shown in Table 1 below, additional compounds disclosed herein may be prepared according to Example 17 by substituting the appropriate starting materials, reagents and reaction conditions.

Example 18

Preparation of Cpd 191

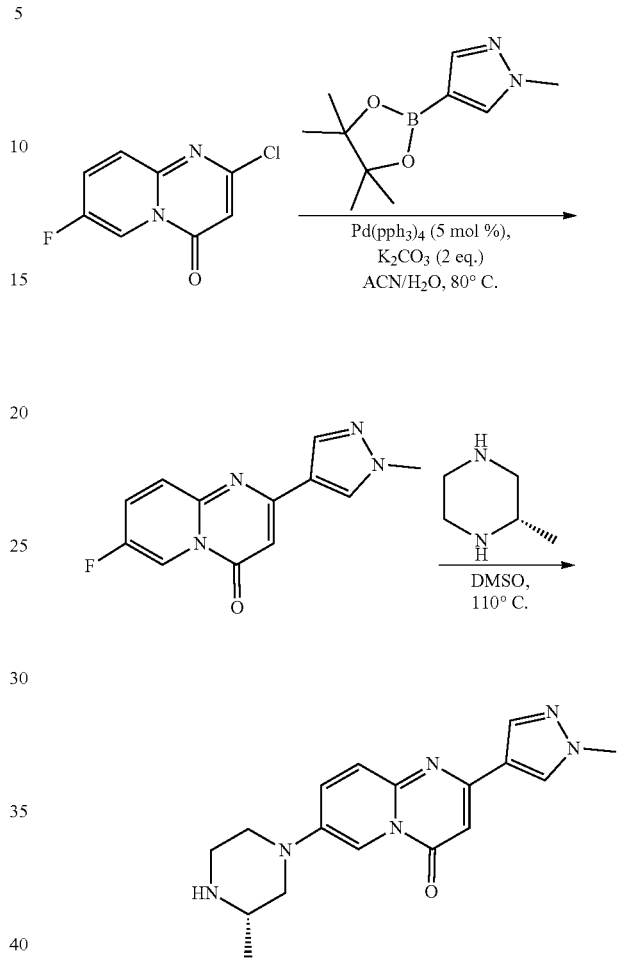

Step A: Following the procedure of Example 14, Part 3, Step A, 2-chloro-7-fluoro-4H-pyrido[1,2-a]pyrimidin-4-one (199 mg, 1 mmol, prepared in Example 14, Part 1), 1-methyl-4-(4,4,5,5-tetramethyl-1,3,2-dioxaborolan-2-yl)-1H-pyrazole (239.2 mg 1.15 mmol), Pd(PPh$_3$)$_4$ (57.8 mg, 0.05 mmol) and K$_2$CO$_3$ (276.4 mg, 2 mmol) in CH$_3$CN/H$_2$O (1.0 mL/1.0 mL) gave 7-fluoro-2-(1-methyl-1H-pyrazol-4-yl)-4H-pyrido[1,2-a]pyrimidin-4-one (97.6 mg, 40%). MS m/z 245.1 [M+H]+.

Step B: Following the procedure of Example 14, Part 3, Step B, 7-fluoro-2-(1-methyl-1H-pyrazol-4-yl)-4H-pyrido[1,2-a]pyrimidin-4-one (48.8 mg, 0.2 mmol) and (S)-2-methylpiperazine (100 mg, 1 mmol) in DMSO (0.5 mL) gave the title compound (32.1 mg, 49.5%). M.P. 168-170° C.; MS m/z 325.2 [M+H]+; $^1$H NMR (500 MHz, DMSO-d$_6$): δ 8.35 (1H, s), 8.18 (1H, d, J=2.8 Hz), 8.06 (1H, s), 8.02 (1H, dd, J=9.7 Hz, 2.6 Hz), 7.56 (1H, d, J=9.8 Hz), 6.63 (1H, s), 3.89 (3H, s), 3.54-3.57 (2H, m), 2.99-3.02 (1H, m), 2.80-2.85 (2H, m), 2.58-2.64 (1H, m), 2.24-2.28 (1H, m), 1.05 (3H, d, J=6.3 Hz).

As shown in Table 1 below, additional compounds disclosed herein may be prepared according to Example 18 by substituting the appropriate starting materials, reagents and reaction conditions.

Example 19

Preparation of Cpd 128

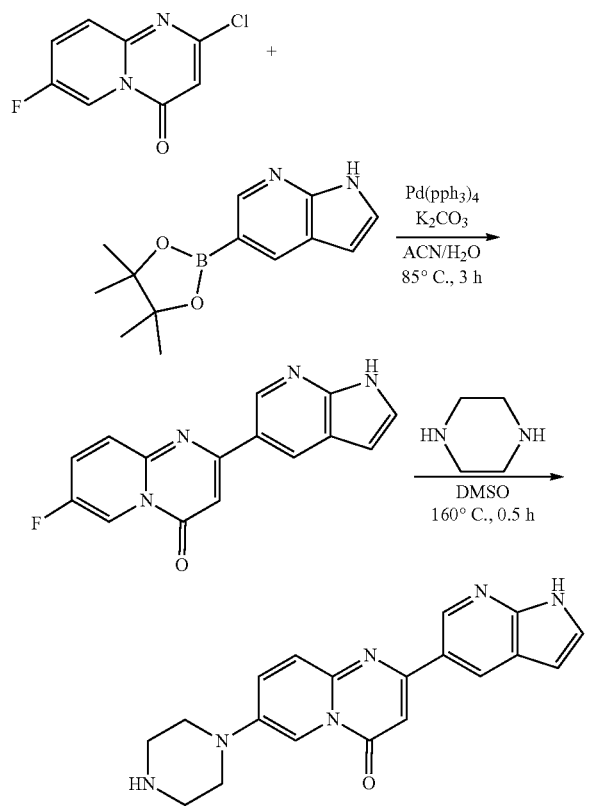

Step A: To a solution of 2-chloro-7-fluoro-4H-pyrido[1,2-a]pyrimidin-4-one (199 mg, 1.0 mmol, prepared in Example 14, Part 1) in 2 mL of acetonitrile were added 5-(4,4,5,5-tetramethyl-1,3,2-dioxaborolan-2-yl)-1H-pyrrolo[2,3-b]pyridine (293 mg, 1.2 mmol), tetrakistriphenylphosphine Pd (0) (57.8 mg, 0.05 mmol) and aqueous $K_2CO_3$ (1M in water, 2 mmol) at room temperature. The mixture was stirred at 85° C. for 3 hours and cooled to room temperature. The solid was filtered off and washed with dichloromethane, water and acetonitrile to give 7-fluoro-2-(1H-pyrrolo[2,3-b]pyridin-5-yl)-4H-pyrido[1,2-a]pyrimidin-4-one (249 mg, 89%). MS m/z 281.1 $[M+H]^+$.

Step B: A solution of 7-fluoro-2-(1H-pyrrolo[2,3-b]pyridin-5-yl)-4H-pyrido[1,2-a]pyrimidin-4-one (100 mg, 0.36 mmol) in DMSO (1 mL) was treated with piperazine (154 mg, 1.79 mmol) at room temperature. The solution was stirred at 160° C. for 30 minutes and cooled to room temperature. The reaction mixture was loaded on silica gel without concentration and eluted with MeOH (0% to 20%) in $CH_2Cl_2$ to provide the title compound (74.8 mg, 60%). M.P. 252-255° C.; MS m/z 347.1 $[M+H]^+$; $^1H$ NMR (DMSO-$d_6$, 500 MHz) δ 11.8 (1H, s), 8.95 (1H, d, J=2.0 Hz)), 8.64 (1H, d, J=1.7 Hz), 8.14 (1H, d, J=2.3 Hz), 8.0-7.9 (1H, m), 7.62 (1H, d, J=9.6 Hz), 7.45 (1H, m), 6.9 (1H, s), 6.48 (1H, br. m). 3.1 (4H, m), 2.85 (4H, m).

As shown in Table 1 below, additional compounds disclosed herein may be prepared according to Example 19 by substituting the appropriate starting materials, reagents and reaction conditions.

Example 20

Preparation of Cpd 153

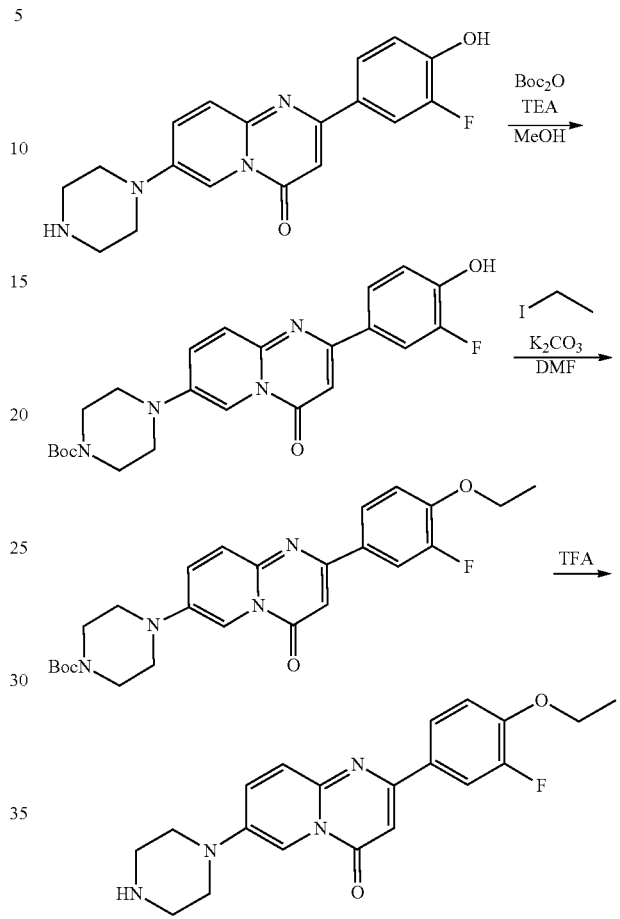

Step A: 2-(3-Fluoro-4-hydroxyphenyl)-7-(piperazin-1-yl)-4H-pyrido[1,2-a]pyrimidin-4-one (180 mg, 0.53 mmol), prepared by Suzuki coupling according to the procedure in Example 14, Part 3, Step A, was combined with di-tert-butyl dicarbonate (131 mg, 0.6 mmol) and triethylamine (85 μL, 0.6 mmol) in MeOH (4 mL). The mixture was stirred at 50° C. for 2 hours. The mixture was filtered, leaving a yellow powder, which was washed with MeOH and dried under vacuum, affording tert-butyl 4-(2-(3-fluoro-4-hydroxyphenyl)-4-oxo-4H-pyrido[1,2-a]pyrimidin-7-yl)piperazine-1-carboxylate (230 mg, 99%). MS m/z 441.0 $[M+H]^+$.

Step B: tert-Butyl 4-(2-(3-fluoro-4-hydroxyphenyl)-4-oxo-4H-pyrido[1,2-a]pyrimidin-7-yl)piperazine-1-carboxylate (60 mg, 0.14 mmol) was combined with $K_2CO_3$ (39 mg, 0.28 mmol) and iodoethane (48 μL, 0.21 mmol) in DMF (1 mL). The mixture was stirred at 50° C. for 1 hour. After cooling to room temperature, $H_2O$ (0.5 mL) was added dropwise to the mixture. The precipitate was collected, washed with $H_2O$, and dried under vacuum.

Step C: To the crude product from Step B was added trifluoroacetic acid (1 mL). After standing for 10 minutes, volatiles were removed. The residue was partitioned in $CH_2Cl_2$ (4 mL) and aqueous $K_2CO_3$ (1M, 2 mL). The organic layer was removed and concentrated, providing the title compound (36 mg, 70%). M.P. 180-186° C.; MS m/z 369.1 $[M+H]^+$; $^1H$ NMR (DMSO-$d_6$, 500 MHz): δ 8.21 (1H, d, J=2.7 Hz), 8.02 (3H, m), 7.68 (1H, d, J=9.7 Hz), 7.27 (1H, t, J=8.8 Hz), 6.93 (1H, s), 4.20 (2H, q, J=7.0 Hz), 3.14 (4H, m), 2.88 (4H, m), 2.36 (1H, br), 1.39 (3H, t, J=7.0 Hz).

As shown in Table 1 below, additional compounds disclosed herein may be prepared according to Example 20 by substituting the appropriate starting materials, reagents and reaction conditions.

Example 21

Preparation of Cpd 179

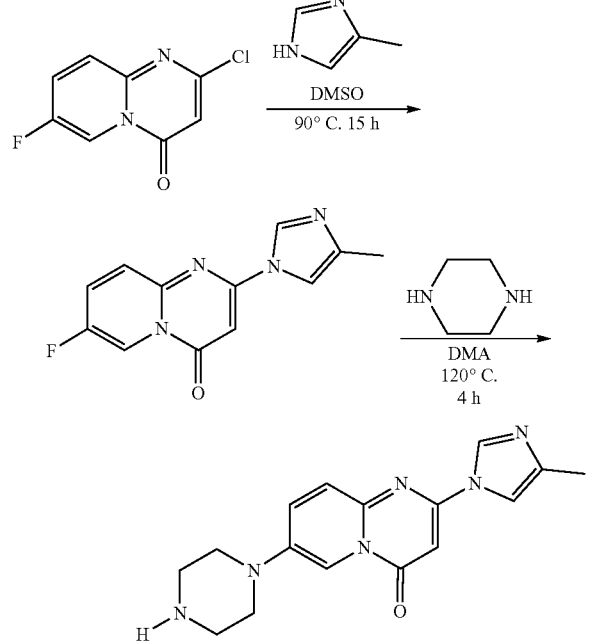

Step A: A mixture of 2-chloro-7-fluoro-4H-pyrido[1,2-a]pyrimidin-4-one (300 mg, 1.5 mmol) and 4-methyl-1H-imidazole (429 mg, 6.0 mmol) in DMSO (1.5 mL) was heated at 90° C. for 15 hours. The mixture was cooled to room temperature and diluted with CH₃CN. The precipitate was filtered, washed with CH₃CN (3×) and dried to give 2-(4-methyl-1H-imidazol-1-yl)-7-(piperazin-1-yl)-4H-pyrido[1,2-a]pyrimidin-4-one as an off-white solid (225 mg, 61%). MS m/z 345.4 [M+H]⁺.

Step B: A mixture of 2-(4-methyl-1H-imidazol-1-yl)-7-(piperazin-1-yl)-4H-pyrido[1,2-a]pyrimidin-4-one (73 mg, 0.3 mmol) and piperazine (129 mg, 1.5 mmol) in DMA (0.6 mL) was heated at 120° C. for 4 hours. The DMA was removed and the mixture was diluted with CH₃CN. The precipitate was filtered, washed with CH₃CN (3×) and dried to give the title compound as a yellow solid (310 mg, 95%). M.P. 204-206° C.; MS m/z 311.1 [M+H]⁺; ¹H NMR (500 MHz, DMSO-d₆): δ 8.47 (1H, d, J=1.2 Hz), 8.22 (1H, d, J=2.7 Hz), 8.13 (1H, dd, J=2.8 Hz, 9.6 Hz), 7.69 (1H, d, J=1.1 Hz), 7.63 (1H, d, J=9.6 Hz), 6.68 (1H, s), 3.14 (4H, m), 2.87 (4H, m), 2.16 (3H, s).

As shown in Table 1 below, additional compounds disclosed herein may be prepared according to Example 21 by substituting the appropriate starting materials, reagents and reaction conditions.

Example 22

Preparation of Cpd 143

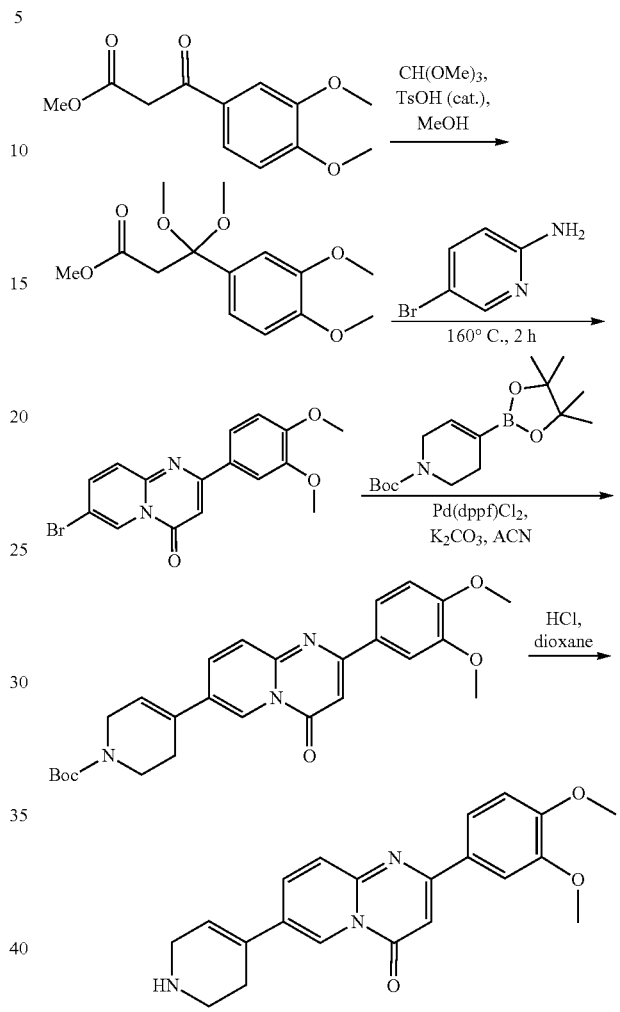

Step A: Following the procedure in Example 1, Step A, methyl 3-(3,4-dimethoxyphenyl)-3-oxopropanoate (5.0 gram, 20 mmol), trimethylorthoformate (3.5 mL, 30 mmol) and p-toluenesulfonic acid monohydrate (380 mg, 2 mmol) in methanol (50 mL) provided methyl 3-(3,4-dimethoxyphenyl)-3,3-dimethoxypropanoate. The crude product was used directly in the next step without purification. ¹H NMR (DMSO-d₆, 500 MHz): δ 6.93 (3H, m), 3.82 (2H, q, J=7.2 Hz), 3.75 (3H, s), 3.73 (3H, s), 3.12 (6H, s), 2.92 (2H, s), 0.92 (3H, t, J=7.1 Hz).

Step B: To the above ketal intermediate was added 5-bromopyridin-2-amine (3.5 g, 20 mmol). The mixture was heated to 150° C. for 2 hours, then cooled to room temperature. The crude product was triturated with acetonitrile and filtered to provide the title compound as a white solid (6.8 gram, 94%). MS m/z 360.9 [M+H]⁺, 362.9 [M+2+H]⁺.

Step C: Following the procedure in Example 14, Part 3, Step A, 7-bromo-2-(3,4-dimethoxyphenyl)-4H-pyrido[1,2-a]pyrimidin-4-one (181 mg, 0.5 mmol), tert-butyl 4-(4,4,5,5-tetramethyl-1,3,2-dioxaborolan-2-yl)-5,6-dihydropyridine-1(2H)-carboxylate (170 mg, 0.55 mmol), potassium carbonate (207 mg, 1.5 mmol) and Pd(dppf)Cl₂ (36.5 mg, 0.05 mmol) in acetonitrile (2 mL) provided tert-butyl 4-(2-

(3,4-dimethoxyphenyl)-4-oxo-4H-pyrido[1,2-a]pyrimidin-7-yl)-5,6-dihydropyridine-1(2H)-carboxylate as a white solid (0.22 mg, 95%). MS m/z 464.1 [M+H]$^+$; $^1$H NMR (500 MHz, DMSO-d$_6$) δ 8.82 (s, 1H), 8.24 (dd, J=1.5, 9 Hz, 1H), 7.85 (dd, J=2, 8.5 Hz, 1H), 7.78 (d, J=2 Hz, 1H), 7.73 (d, J=9.5 Hz, 1H), 7.10 (d, J=9 Hz, 1H), 7.05 (s, 1H), 6.54 (s, 1H), 4.09 (bs, 2H), 3.89 (s, 3H), 3.85 (s, 3H), 3.60-3.59 (m, 2H), 2.64-2.63 (m, 2H), 1.45 (s, 9H).

Step D: The intermediate obtained from Step A was suspended in a solution of HCl in dioxane (4M, 4 mL). The reaction mixture was stirred at room temperature for 2 hours. The mixture was concentrated and the residue was partitioned between dichloromethane and saturated aqueous sodium bicarbonate. The organics were dried, concentrated and chromatographed on a basic alumina column, eluting with dichloromethane with methanol (10%) to provide the title compound as a white solid (150 mg, 88%). M.P. 196-198° C.; MS m/z 364.1 [M+H]$^+$; $^1$H NMR (500 MHz, DMSO-d$_6$) δ 8.77 (d, J=2 Hz, 1H), 8.24 (dd, J=2, 9.5 Hz, 1H), 7.85 (dd, J=2, 8.5 Hz, 1H), 7.78 (d, J=2 Hz, 1H), 7.71 (d, J=9.5 Hz, 1H), 7.09 (d, J=8.5 Hz, 1H), 7.03 (s, 1H), 6.60 (s, 1H), 3.89 (s, 3H), 3.85 (s, 3H), 3.45 (d, J=2.5 Hz, 2H), 2.97 (t, J=5.5 Hz, 2H), 2.41 (bs, 2H).

As shown in Table 1 below, additional compounds disclosed herein may be prepared according to Example 22 by substituting the appropriate starting materials, reagents and reaction conditions.

Example 23

Preparation of Cpd 188

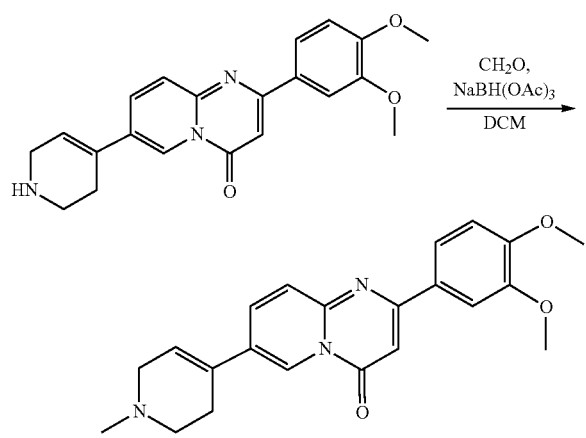

A mixture of 2-(3,4-dimethoxyphenyl)-7-(1,2,3,6-tetrahydropyridin-4-yl)-4H-pyrido[1,2-a]pyrimidin-4-one (30 mg, 0.08 mmol), formaldehyde (0.05 mL, 37%, ~0.8 mmol) and sodium triacetoxyborohydride (50 mg, 0.24 mmol) was stirred in dichloromethane (1 mL) for 2 hr. The reaction mixture was diluted with dichloromethane and neutralized with sodium bicarbonate. The organics were dried and concentrated to provide the title compound as a white solid (26 mg, 83%). M.P. 165-168° C.; MS m/z 378.4 [M+H]$^+$; $^1$H NMR (500 MHz, DMSO-d$_6$) δ 8.79 (d, J=2 Hz, 1H), 8.25 (dd, J=2, 9.5 Hz, 1H), 7.85 (dd, J=2, 8.5 Hz, 1H), 7.78 (d, J=2 Hz, 1H), 7.71 (d, J=9.5 Hz, 1H), 7.10 (d, J=8.5 Hz, 1H), 7.04 (s, 1H), 6.56 (s, 1H), 3.89 (s, 3H), 3.85 (s, 3H), 3.09 (bs, 2H), 2.64-2.61 (m, 2H), 2.56 (bs, 2H), 2.51 (s, 3H).

As shown in Table 1 below, additional compounds disclosed herein may be prepared according to Example 23 by substituting the appropriate starting materials, reagents and reaction conditions.

Example 24

Preparation of Cpd 144

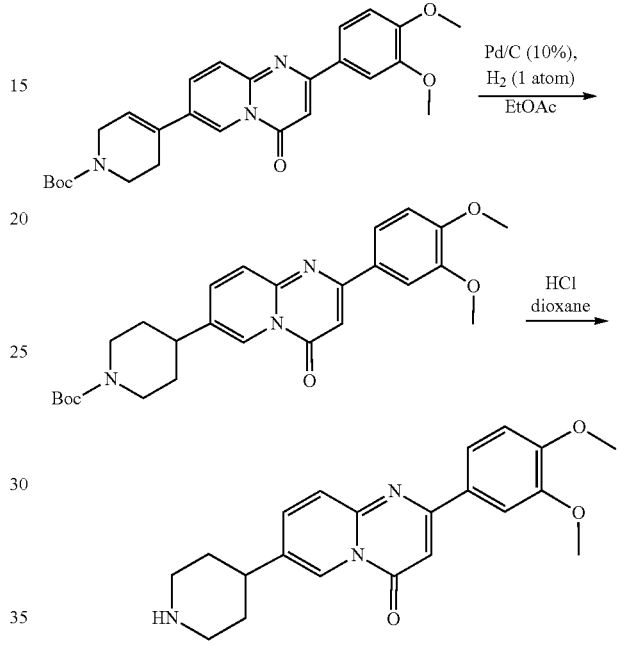

Step A: A mixture of tert-butyl 4-(2-(3,4-dimethoxyphenyl)-4-oxo-4H-pyrido[1,2-a]pyrimidin-7-yl)-5,6-dihydropyridine-1(2H)-carboxylate (100 mg, 0.22 mmol, prepared as depicted in Example 22, Step C) and Pd/C (10%) (10 mg) in ethyl acetate (25 mL) was stirred under 1 atmosphere of hydrogen overnight. The reaction mixture was filtered through celite, concentrated and chromatographed on a silica column, eluting with EtOAc/CH$_2$Cl$_2$ (30/70) to provide tert-butyl 4-(2-(3,4-dimethoxyphenyl)-4-oxo-4H-pyrido[1,2-a]pyrimidin-7-yl)piperidine-1-carboxylate as a white solid (75 mg, 75%), which was used directly in the next step without further purification. MS m/z 466.4 [M+H]$^+$; $^1$H NMR (500 MHz, DMSO-d$_6$) δ 8.57 (s, 1H), 7.80 (dd, J=2.5, 9.5 Hz, 1H), 7.64 (dd, J=2, 8.5 Hz, 1H), 7.57 (d, J=2 Hz, 1H), 7.53 (d, J=9 Hz, 1H), 6.9 (d, J=9 Hz, 1H), 6.82 (s, 1H), 3.92 (bs, 2H), 3.69 (s, 3H), 3.65 (s, 3H), 2.78-2.71 (m, 2H), 2.69-2.65 (1H, m), 1.69-1.67 (m, 2H), 1.41-1.38 (m, 2H), 1.24 (s, 9H).

Step B: Following the procedure in Example 22, Step D, the above product from Step A and HCl in dioxane (4M, 3 mL) provided the title compound as a white solid (49 mg, 83%). M.P. 214-217° C.; MS m/z 366.4 [M+H]$^+$; $^1$H NMR (500 MHz, DMSO-d$_6$) δ 8.88 (d, J=2 Hz, 1H), 8.09 (dd, J=2, 9.5 Hz, 1H), 7.98 (dd, J=2, 8.5 Hz, 1H), 7.91 (d, J=2 Hz, 1H), 7.88 (d, J=9 Hz, 1H), 7.23 (d, J=8.5 Hz, 1H), 7.15 (s, 1H), 4.02 (s, 3H), 3.98 (s, 3H), 3.30 (d, J=11.5 Hz, 2H), 3.01 (tt, J=2 Hz, 12 Hz, 1H), 2.87 (t, J=12 Hz, 2H), 2.02 (d, J=12.5 Hz, 2H), 1.80-1.73 (m, 2H).

Example 25

Preparation of Cpd 164

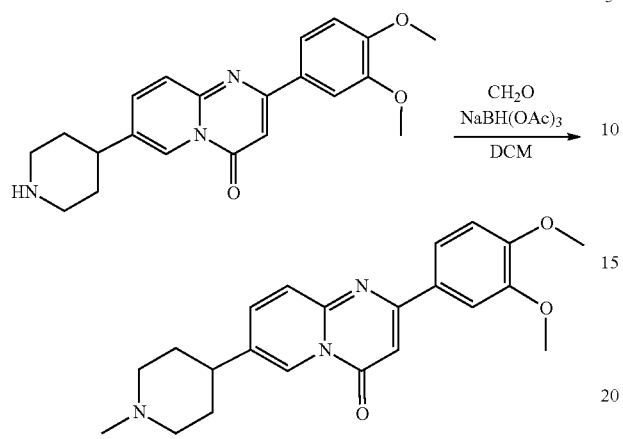

Following the procedure in Example 23, 2-(3,4-dimethoxyphenyl)-7-(piperidin-4-yl)-4H-pyrido[1,2-a]pyrimidin-4-one (10 mg, 0.027 mmol), formaldehyde (10 μL, 37%, 0.13 mmol) and sodium triacetoxyborohydride (17 mg, 5.7 mmol) in dichloromethane (0.5 mL) provided the title compound as a white solid (7.6 mg, 73%). M.P. 181-183° C.; MS m/z 380.1 [M+H]$^+$; $^1$H NMR (500 MHz, DMSO-d$_6$) δ 8.76 (d, J=2 Hz, 1H), 8.0 (dd, J=2, 9 Hz, 1H), 7.84 (dd, J=2, 8.5 Hz, 1H), 7.77 (d, J=2 Hz, 1H), 7.72 (d, J=9.5 Hz, 1H), 7.09 (d, J=8.5 Hz, 1H), 7.01 (s, 1H), 3.89 (s, 3H), 3.84 (s, 3H), 2.91 (d, J=9.5 Hz, 2H), 2.73-2.64 (m, 1H), 2.22 (s, 3H), 2.01 (t, J=8.5 Hz, 2H), 1.88-1.85 (m, 2H), 1.71-1.69 (m, 2H).

As shown in Table 1 below, additional compounds disclosed herein may be prepared according to Example 25 by substituting the appropriate starting materials, reagents and reaction conditions.

Example 26

Preparation of Cpd 263

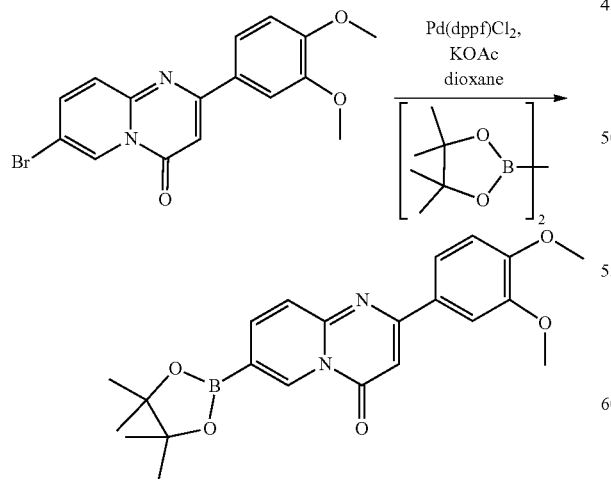

Part 1: Following the procedure in Example 14, Part 2, 7-Bromo-2-(3,4-dimethoxyphenyl)-4H-pyrido[1,2-a]pyrimidin-4-one (661 mg, 1.8 mmol), prepared in Example 22, Step B, KOAc (530 mg, 5.4 mmol), bis(pincolato)diboron (700 mg, 2.7 mmol), and Pd(dppf)Cl$_2$ (60 mg, 0.09 mmol) in dioxane (5 mL) provided 2-(3,4-dimethoxyphenyl)-7-(4,4,5,5-tetramethyl-1,3,2-dioxaborolan-2-yl)-4H-pyrido[1,2-a]pyrimidin-4-one as a white solid (560 mg, 76%). MS m/z 327.1 [M+H]$^+$ for boronic acid.

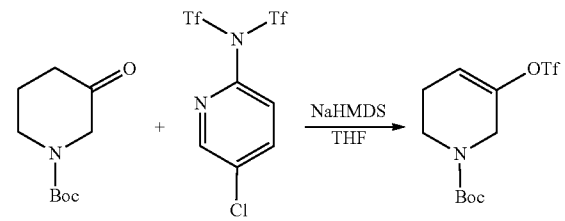

Part 2: To a solution of tert-butyl 3-oxopiperidine-1-carboxylate (482 mg, 2.4 mmol) in 2-methyltetrahydrofuran (2.5 mL) was added drop wise a solution of sodium bis(trimethylsilyl)amide (2.6 mL, 2.6 mmol, 1.0M in THF) at −78° C. under argon. The mixture was stirred at −78° C. for 1 hr, followed by the addition of a solution of N-(5-chloropyridin-2-yl)-1,1,1-trifluoro-N-(trifluoromethylsulfonyl)-methanesulfonamide (1.0 gram, 2.5 mmol) in 2-methyltetrahydrofuran (2.5 mL), and then the reaction was allowed to warm to room temperature over 2 hours. After stirring at room temperature overnight, the reaction was quenched with saturated aqueous sodium carbonate, diluted with ether, and the organics were washed with water, dried and concentrated. The crude product was chromatographed on a basic alumina column, eluting with 5% ethyl acetate in hexane to provide the title compound as a colorless oil (290 mg, 37%).

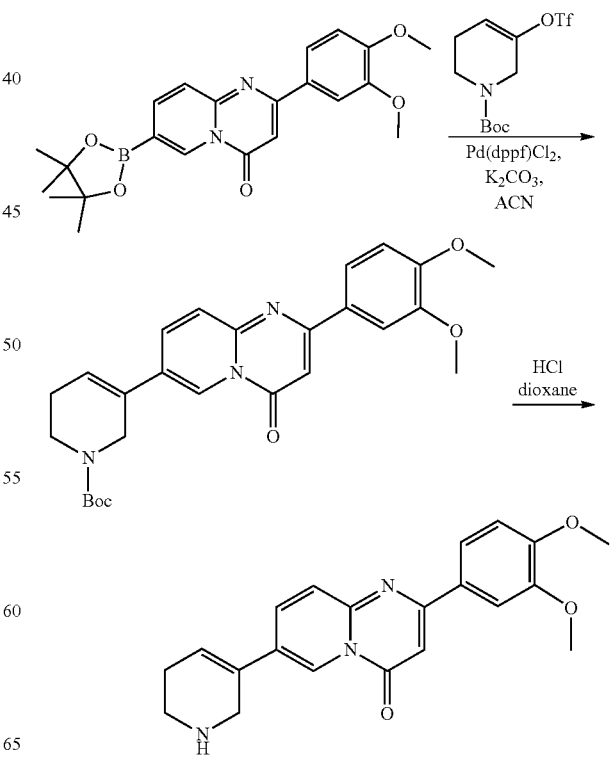

Part 3, Step A: Following the procedure of Example 14, Part 3, Step A, 2-(3,4-dimethoxyphenyl)-7-(4,4,5,5-tetramethyl-1,3,2-dioxaborolan-2-yl)-4H-pyrido[1,2-a]pyrimidin-4-one (370 mg, 0.91 mmol), tert-butyl 3-(trifluoromethylsulfonyloxy)-5,6-dihydropyridine-1(2H)-carboxylate (290 mg, 0.88 mmol), potassium carbonate (364 mg, 2.6 mmol) and Pd(dppf)Cl$_2$ (58 mg, 0.08 mmol) in acetonitrile (4 mL) provided tert-butyl 3-(2-(3,4-dimethoxyphenyl)-4-oxo-4H-pyrido[1,2-a]pyrimidin-7-yl)-5,6-dihydropyridine-1(2H)-carboxylate as a white solid (0.22 mg, 62%). MS m/z 464.3 [M+H]$^+$.

Part 3, Step B: Following the procedure in Example 22, Step B, tert-butyl 3-(2-(3,4-dimethoxyphenyl)-4-oxo-4H-pyrido[1,2-a]pyrimidin-7-yl)-5,6-dihydropyridine-1(2H)-carboxylate (220 mg, 0.47 mmol) and HCl in dioxane (4M, 5 mL) provided the title compound (160 mg, 79%). M.P. 146-150° C.; MS m/z 364.2 [M+H]$^+$; $^1$H NMR (500 MHz, DMSO-d$_6$) δ 8.73 (d, J=2 Hz, 1H), 8.23 (dd, J=2, 9.5 Hz, 1H), 7.85 (dd, J=2, 8.5 Hz, 1H), 7.78 (d, J=2.5 Hz, 1H), 7.71 (d, J=9.5 Hz, 1H), 7.10 (d, J=8.5 Hz, 1H), 7.05 (s, 1H), 6.60 (s, 1H), 3.89 (s, 3H), 3.85 (s, 3H), 3.29 (bs, 2H), 2.40-2.36 (m, 4H).

Example 27

Preparation of Cpd 237

Step B: tert-Butyl 4-(2-(3,4-dimethoxyphenyl)-4-oxo-4H-pyrido[1,2-a]pyrimidin-7-yloxy)piperidine-1-carboxylate was dissolved into CH$_2$Cl$_2$/TFA (0.5 mL/0.5 mL) at 0° C. The mixture was stirred at 0° C. for 2 hours, until the starting material disappeared. After most of the TFA was evaporated, ice cold saturated NaHCO$_3$ was added to the reaction mixture. The mixture was extracted with CH$_2$Cl$_2$. The organic layer was dried over MgSO$_4$ and concentrated to provide the title compound (57 mg, 74.8% for 2 steps). M.P. 221-224° C.; MS m/z 382.2 [M+H]$^+$; $^1$H NMR (500 MHz, DMSO-d$_6$): δ 8.58 (1H, d, J=2.9 Hz), 7.81-7.86 (2H, m), 7.73-7.78 (2H, m), 7.08 (1H, d, J=8.7 Hz), 7.01 (1H, s), 4.82-4.86 (1H, m), 3.87 (3H, s), 3.83 (3H, s), 3.23-3.27 (2H, m), 3.04-3.09 (2H, m), 2.13-2.18 (2H, m), 1.85-1.91 (2H, m).

As shown in Table 1 below, additional compounds disclosed herein may be prepared according to Example 27 by substituting the appropriate starting materials, reagents and reaction conditions.

Example 28

Preparation of Cpd 52

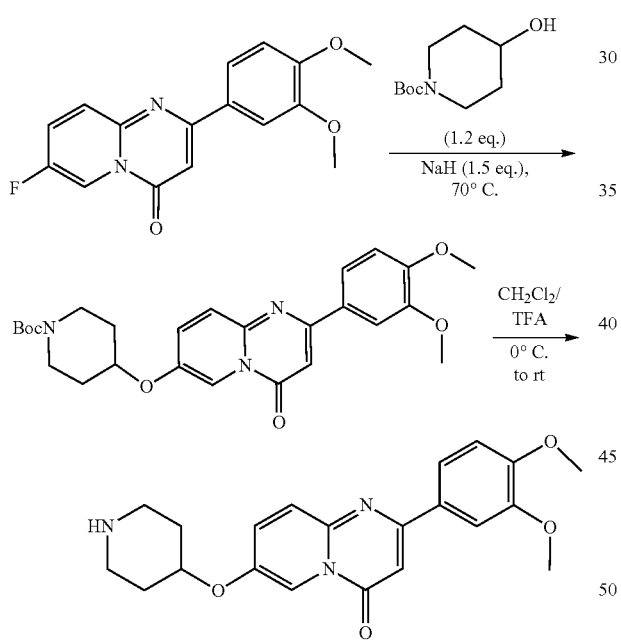

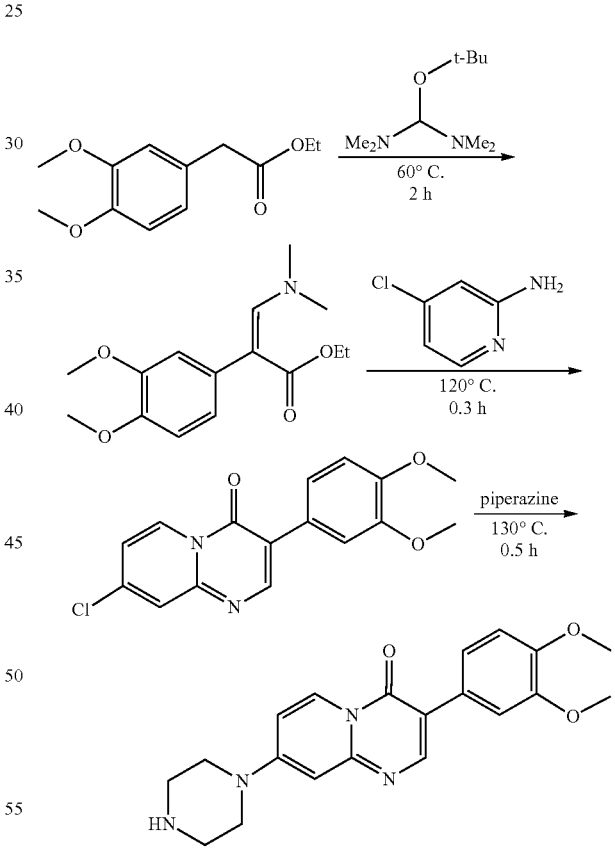

Step A: NaH (60% dispersion in mineral oil, 12 mg, 0.3 mmol) was added slowly to 1-Boc-4-hydroxypiperidine (48.3 mg, 0.24 mmol) in anhydrous THF at room temperature. The reaction mixture was stirred at room temperature for 10 minutes, and 2-(3,4-dimethoxyphenyl)-7-F-4H-pyrido[1,2-a]pyrimidin-4-one (60 mg, 0.2 mmol) was added. The reaction mixture was then heated at 70° C. for 3 hours. A small amount of ice water was added to quench the reaction. After most of the THF was evaporated, ether was added to the mixture, and the precipitate was filtered and dried to provide tert-butyl 4-(2-(3,4-dimethoxyphenyl)-4-oxo-4H-pyrido[1,2-a]pyrimidin-7-yloxy)piperidine-1-carboxylate, which was used in the next step without further purification.

Step A: Ethyl 2-(3,4-dimethoxyphenyl)acetate (673 mg, 3 mmol) was combined with 1-tert-butoxy-N,N,N',N'-tetramethylmethanediamine (0.68 mL, 3.3 mmol). The mixture was heated to 60° C. for 2 hours. The mixture was used directly in the next step without work-up.

Step B: 4-Chloropyridin-2-amine (424 mg, 3.3 mmol) was added directly to the mixture. The mixture was heated to 120° C. for 20 minutes. The mixture was used directly in the next step without work-up.

Step C: Piperazine (1.3 g, 15 mmol) was added to the mixture from Step B, which stirred for an additional 30 minutes at 120° C. The mixture was chromatographed on silica with 10% MeOH (1% triethylamine) in $CH_2Cl_2$ affording the title compound as a yellow powder (120 mg, 11%). M.P. 175-179° C.; MS m/z 367.2 [M+H]$^+$; $^1$H NMR (DMSO-d$_6$, 500 MHz): δ 8.84 (1H, d, J=8.2 Hz), 8.40 (1H, s), 7.44 (1H, d, J=2.1 Hz), 7.34 (1H, dd, J=8.4 Hz, 2.1 Hz), 7.28 (1H, dd, J=8.2 Hz, 2.8 Hz), 6.99 (1H, d, J=8.5 Hz), 6.73 (1H, d, J=2.8 Hz), 3.80 (3H, s), 3.78 (3H, s), 3.48 (4H, m), 2.82 (4H, m).

Example 29

Preparation of Cpd 220

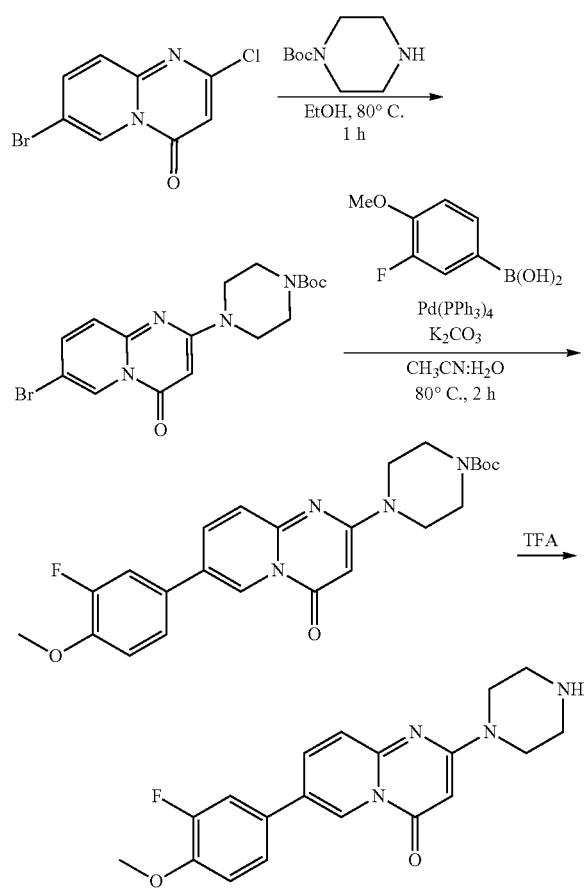

Step A: 7-Bromo-2-chloro-4H-pyrido[1,2-a]pyrimidin-4-one (130 mg, 0.5 mmol), prepared according to Example 14, Part 1, was combined with tert-butyl piperazine-1-carboxylate (140 mg, 0.75 mmol) and triethylamine (0.14 mL, 1.0 mmol) in EtOH (2 mL). The mixture was heated to 80° C. for 1 hour. The reaction mixture was cooled to room temperature, and then filtered. The collected material was chromatographed on silica with 0% to 50% EtOAc in $CH_2Cl_2$, providing tert-butyl 4-(7-bromo-4-oxo-4H-pyrido[1,2-a]pyrimidin-2-yl)piperazine-1-carboxylate (130 mg, 64%). MS m/z 409.4 [M+H]$^+$.

Step B: The intermediate (0.3 mmol) from Step A was combined with 3-fluoro-4-methoxyphenylboronic acid (77 mg, 0.45 mmol) and tetrakis(triphenylphosphine) palladium (0) (35 mg, 0.03 mmol) in $CH_3CN$ (2 mL) and aqueous $K_2CO_3$ (1M, 2 mL). The mixture was heated at 80° C. with vigorous stirring under argon for 2 hours. The organic layer was removed and concentrated. The residue was chromatographed on silica with 0% to 50% EtOAc in $CH_2Cl_2$.

Step C: The Boc-protected intermediate from Step B was dissolved in trifluoroacetic acid (1 mL). After 20 minutes, volatiles were removed. The residue was partitioned in $CH_2Cl_2$ and aqueous $K_2CO_3$ (1M). The organic layer was removed and concentrated, affording the title compound as a white powder (30 mg, 17%). M.P. 202-206° C.; MS m/z 355.0 [M+H]$^+$; $^1$H NMR (DMSO-d$_6$, 500 MHz): δ 8.93 (1H, d, J=2.0 Hz), 8.15 (1H, dd, J=9.3 Hz, 2.3 Hz), 7.67 (1H, dd, J=12.7 Hz, 2.3 Hz), 7.54 (1H, m), 7.37 (1H, d, J=9.2), 7.30 (1H, t, J=8.8 Hz), 5.62 (1H, s), 3.90 (3H, s), 3.57 (4H, m), 2.75 (4H, m), 2.42 (1H, br s).

As shown in Table 1 below, additional compounds disclosed herein may be prepared according to Example 29 by substituting the appropriate starting materials, reagents and reaction conditions.

Example 30

Preparation of Cpd 276

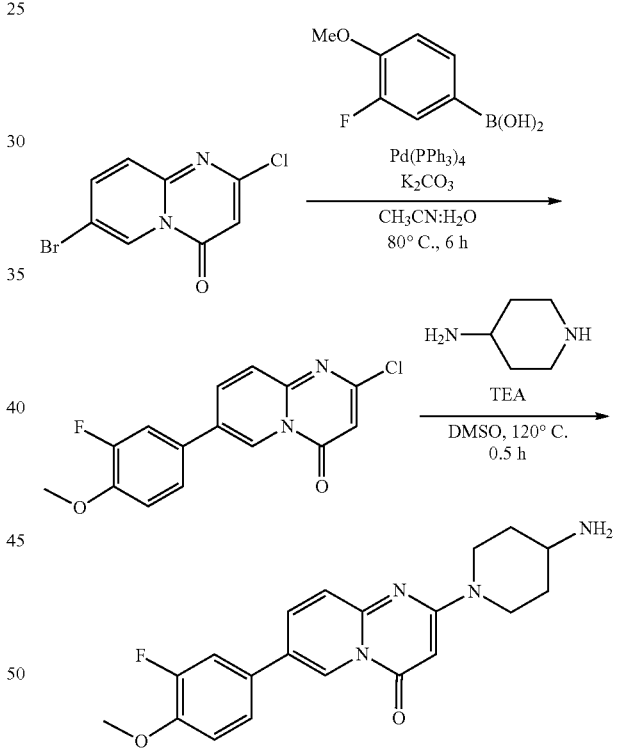

Step A. 7-Bromo-2-chloro-4H-pyrido[1,2-a]pyrimidin-4-one (1.29 g, 5 mmol) was combined with 3-fluoro-4-methoxyphenylboronic acid (850 mg, 5 mmol), tetrakis(triphenylphosphine) palladium(0) (281 mg, 0.25 mmol), $CH_3CN$ (10 mL) and aqueous $K_2CO_3$ (1M, 10 mL). The mixture was heated to 80° C. for 6 hours. After cooling to room temperature, the mixture was partitioned in $CH_2Cl_2$ (75 mL) and $H_2O$ (50 mL). The organic layer was collected and concentrated. The residue was chromatographed on silica, eluting with EtOAc (0% to 50%) in $CH_2Cl_2$, to afford 2-chloro-7-(3-fluoro-4-methoxyphenyl)-4H-pyrido[1,2-a]pyrimidin-4-one as a white powder (520 mg, 34%). MS m/z 305.0 [M+H]$^+$.

Step B. 2-Chloro-7-(3-fluoro-4-methoxyphenyl)-4H-pyrido[1,2-a]pyrimidin-4-one (180 mg, 0.6 mmol) was combined with 4-aminopiperidine (90 mg, 0.9 mmol) and triethylamine (165 µL, 1.2 mmol) in DMSO (0.75 mL). The mixture was heated to 120° C. for 30 minutes. After cooling to room temperature, CH$_3$CN (2 mL) was added to the mixture. The mixture was filtered. The collected material was washed with CH$_3$CN and dried under vacuum, affording the title compound as a white powder (115 mg, 52%). M.P. 268-283° C.; MS m/z 369.3 [M+H]$^+$; $^1$H NMR (DMSO-d$_6$, 500 MHz): δ 8.94 (1H, d, J=2.0 Hz), 8.16 (1H, dd, J=9.3 Hz, 2.3 Hz), 7.68 (1H, dd, J=12.7 Hz, 2.3 Hz), 7.55 (1H, d, J=8.5 Hz), 7.39 (1H, d, J=9.2), 7.30 (1H, t, J=8.9 Hz), 5.70 (1H, s), 5.20 (2H, br), 4.36 (2H, br), 3.92 (3H, s), 3.04 (3H, m), 1.87 (2H, m), 1.32 (2H, m).

As shown in Table 1 below, additional compounds disclosed herein may be prepared according to Example 30 by substituting the appropriate starting materials, reagents and reaction conditions.

Example 31

Preparation of Cpd 85

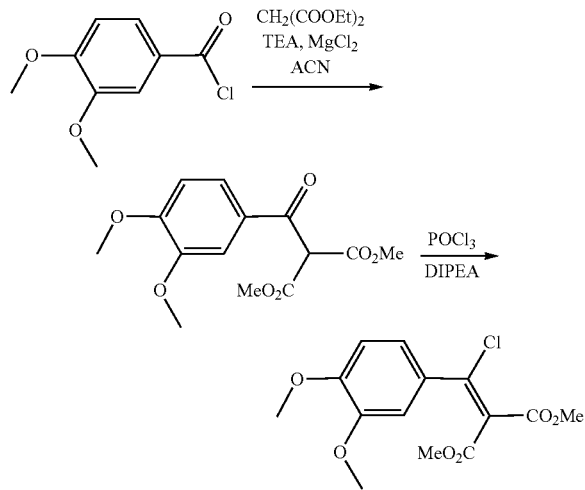

Part 1, Step A: To a suspension of MgCl$_2$ (2.85 g, 30 mmol) in acetonitrile (27 mL) at 0° C. was added dropwise diethyl malonate (3.4 mL, 30 mmol) and triethylamine (8.3 mL, 60 mmol). The mixture was stirred at 0° C. for 30 minutes. 3,4-dimethoxybenzoyl chloride (5.0 g, 25 mmol) was then added portionwise. The mixture was allowed to stir at room temperature overnight, after which it was treated with 1N HCl, extracted with ether, dried and evaporated. The residue was purified on silica with ethyl acetate (5% to 40%) in hexanes to give dimethyl 2-(3,4-dimethoxybenzoyl)malonate (7.38 g, 100%). MS m/z 297.1 [M+H]$^+$.

Part 1, Step B: To a solution of dimethyl 2-(3,4-dimethoxybenzoyl)malonate (2.96 g, 10 mmol) in POCl$_3$ (9.4 mL, 100 mmol) at room temperature was added DIPEA (2.75 mL, 16.7 mmol) dropwise. The mixture was then stirred at 100° C. for 3 hours. POCl$_3$ was removed under vacuum and the residue was treated with ice-water and extracted with ether. The organic layer was washed with 1N HCl, dried and evaporated. The residue was purified on silica with ethyl acetate (5% to 50%) in hexanes to give the title compound (2.0 g, 64%). MS m/z 282.9 [M+H]$^+$.

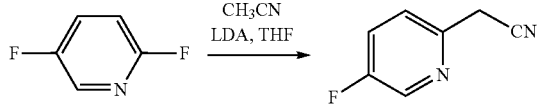 [SMILES: Fc1ccc(F)nc1 ; N#CCc1ccc(F)cn1]

Part 2: To a solution of LDA (1.5 M, 13.3 mL, 20 mmol) in THF (15 mL) at −78° C. was added dropwise a solution of 2,5-difluoropyridine (1.15 g, 10 mmol) in THF (10 mL). The temperature was then allowed to rise to room temperature, and the mixture was stirred at room temperature for 2 hours before the reaction was quenched with aqueous NH$_4$Cl. The mixture was extracted with ethyl acetate, dried, and evaporated. The residue was purified on silica with ethyl acetate (5% to 50%) in hexanes to give 2-(5-fluoropyridin-2-yl)acetonitrile (0.8 g, 59%). MS m/z 137.0 [M+H]$^+$.

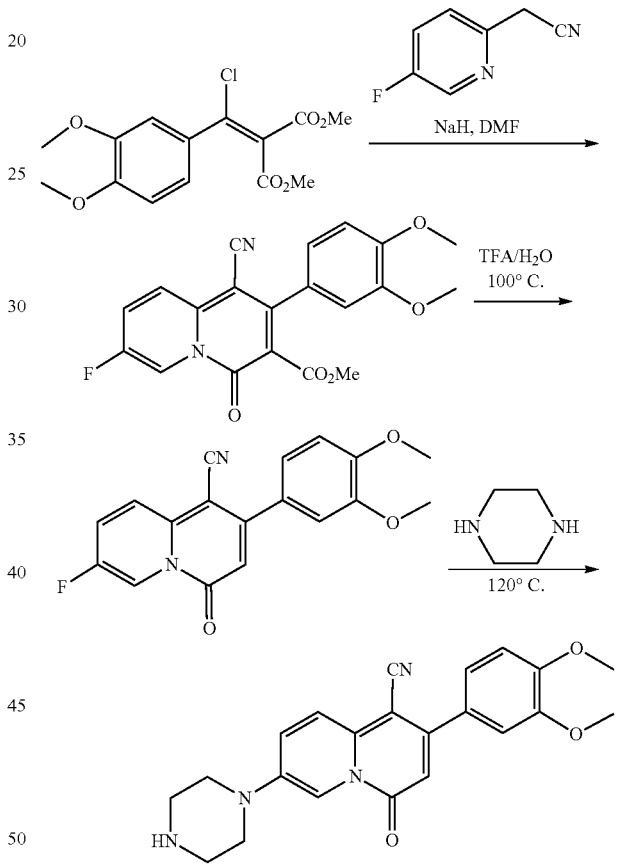

Part 3, Step A: To a solution of 2-(5-fluoropyridin-2-yl)acetonitrile (44 mg, 0.325 mmol) in DMF (0.5 mL) was added 60% NaH (20 mg, 0.325 mmol). The mixture was stirred at room temperature for 10 minutes and then treated with dimethyl 2-(chloro(3,4-dimethoxyphenyl)methylene)malonate (102 mg, 0.325 mmol). The mixture was stirred for 15 minutes, and the reaction was quenched with saturated NH$_4$Cl solution. The mixture was filtered. The solid was washed with water and used directly in the next step without further purification.

Part 3, Step B: The crude solid from Step A was treated with TFA (2.0 mL) and water (0.2 mL). The mixture was stirred at 100° C. overnight. The solvent was then removed under vacuum and the crude product was used in the next step without further purification.

Part 3, Step C: The crude product from Step B was heated with piperazine (86 mg, 1.0 mmol) in DMSO (1.0 mL) at 120° C. overnight. Removal of the solvent by $N_2$ followed by purification over silica with methanol (10%) in dichloromethane provided the title compound (30 mg, 25%). M.P. 199-202° C.; MS m/z 391.2 [M+H]$^+$; $^1$H NMR (500 MHz, CDCl$_3$) δ: 8.60 (1H, d, J=2.2 Hz), 7.98 (1H, d, J=9.8 Hz), 7.59 (1H, dd, J=9.5, 2.5 Hz), 7.20 (1H, dd, J=8.5, 2.2 Hz), 7.12 (1H, d, J=2.2 Hz), 6.93 (1H, d, J=8.2 Hz), 6.52 (1H, s), 3.89 (3H, s), 3.88 (3H, s), 3.23-3.21 (4H, m), 3.05-3.03 (4H, m).

Example 32

Preparation of Cpd 91

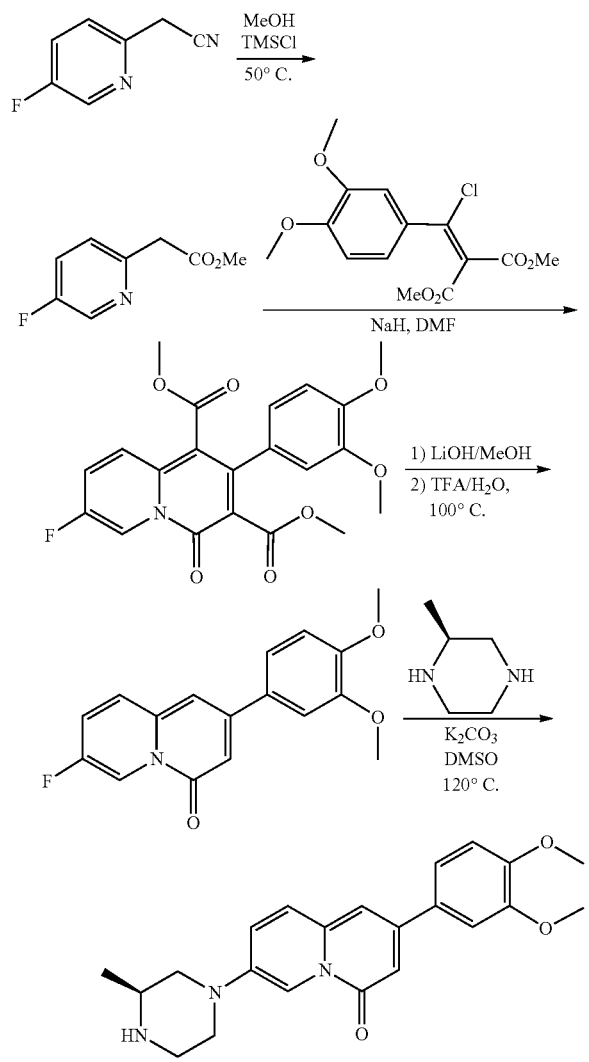

Step A: To a solution of 2-(5-fluoropyridin-2-yl)acetonitrile (0.78 g, 5.7 mmol) in MeOH (15 mL) was added trimethysilyl chloride (4.4 mL, 34.4 mmol) dropwise. The mixture was stirred at 50° C. overnight. Organic volatiles were removed under vacuum and the residue was partitioned between ether and aqueous sodium bicarbonate. The aqueous layer was extracted with ether. The ether extractions were combined, dried and evaporated to give methyl 2-(5-fluoropyridin-2-yl)acetate as an oil (0.9 g, 93%), which was used without further purification. MS m/z 170.1 [M+H]$^+$.

Step B: Following the procedure in Example 31, Part 3, Step A, methyl 2-(5-fluoropyridin-2-yl)acetate (0.34 g, 2.0 mmol), 60% NaH (176 mg, 4.4 mmol) and dimethyl 2-(chloro(3,4-dimethoxyphenyl)methylene)malonate (0.69 g, 2.2 mmol, prepared in Example 31, Part 1, Step B) in DMF (3.0 mL) provided the desired dimethyl 2-(3,4-dimethoxyphenyl)-7-fluoro-4-oxo-4H-quinolizine-1,3-dicarboxylate (0.2 g, 24%). MS m/z 416.1 [M+H]$^+$.

Step C: A solution of dimethyl 2-(3,4-dimethoxyphenyl)-7-fluoro-4-oxo-4H-quinolizine-1,3-dicarboxylate (0.2 g, 0.48 mmol) in methanol (6.0 mL) was treated with aqueous LiOH (2.0 N, 2.0 mL, 4.0 mmol) and stirred at 90° C. for 2 hours. Aqueous workup followed by evaporation provided a dark residue, which was treated with TFA (2.0 mL) and water (0.2 mL) and stirred at 100° C. for 1 hour. Removal of the solvents by $N_2$ followed by chromatography with ethyl acetate (25% to 75%) in hexanes provided 2-(3,4-dimethoxyphenyl)-7-fluoro-4H-quinolizin-4-one (30 mg, 21%). MS m/z 300.2 [M+H]$^+$.

Step D: A solution of 2-(3,4-dimethoxyphenyl)-7-fluoro-4H-quinolizin-4-one (30 mg, 0.1 mmol), (S)-2-methyl piperazine (30 mg, 0.3 mmol) and K$_2$CO$_3$ (27 mg, 0.2 mmol) in DMSO (0.2 mL) was stirred at 120° C. for 48 hours. Removal of the solvents by $N_2$ followed by purification by dichloromethane and methanol (10%) provided the title compound (24 mg, 63%). M.P. 243-245° C.; MS m/z 380.2 [M+H]$^+$; $^1$H NMR (500 MHz, CDCl$_3$) δ: 8.52 (1H, d, J=2.2 Hz), 7.46 (1H, d, J=9.8 Hz), 7.30 (2H, dt, J=10.4, 2.2 Hz), 7.22 (1H, d, J=1.9 Hz), 6.98 (1H, d, J=8.5 Hz), 6.84 (2H, s), 3.96 (3H, s), 3.95 (3H, s), 3.58-3.54 (2H, m), 3.50 (1H, s), 3.21-3.19 (1H, m), 3.12-3.04 (2H, m), 2.85-2.80 (1H, m), 2.49 (1H, t, J=11.1 Hz), 1.20 (3H, d, J=6.6 Hz).

Example 33

Preparation of Cpd 106

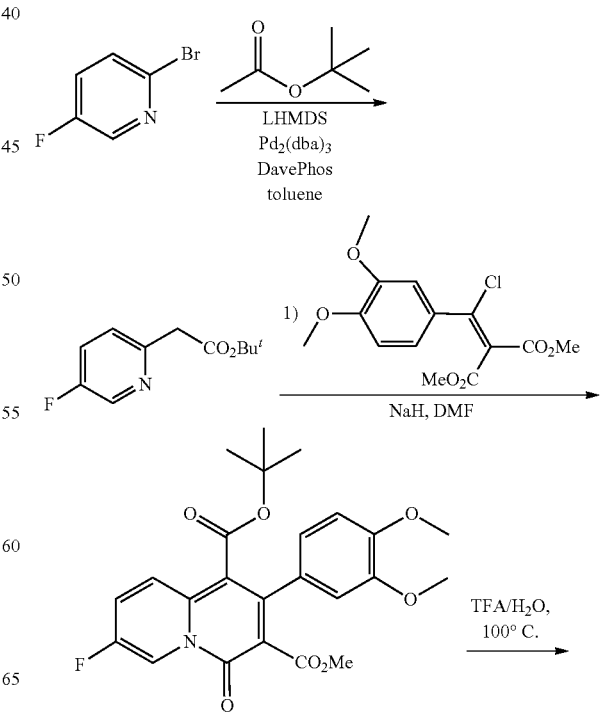

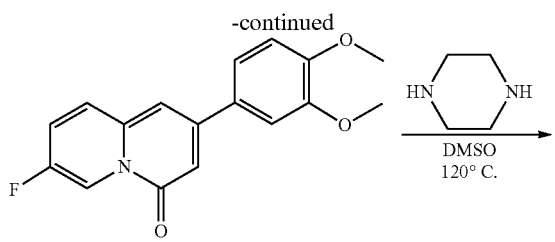

Step A: To a mixture of Pd$_2$(dba)$_3$ (0.55 g, 0.6 mmol) and DavePhos (0.50 g, 1.26 mmol) in toluene (40 mL) at room temperature under an argon atmosphere was added a solution of LHMDS in hexane (1.0 M×50 mL, 50 mmol) dropwise. The mixture was stirred for 10 minutes and then cooled to −10° C., into which tert-butyl acetate (6.2 mL, 46 mmol) was added and stirred for another 10 minutes. 2-Bromo-5-fluoropyridine (3.52 g, 20 mmol) was then added portionwise. Upon completion of the addition, the temperature was allowed to rise to room temperature and the mixture was stirred for another 1 hour. The reaction was then quenched by saturated NH$_4$Cl solution. Aqueous workup followed by chromatography with ethyl acetate (0% to 20%) in hexanes provided tert-butyl 2-(5-fluoropyridin-2-yl)acetate (2.6 g, 62%).

Step B: Following the procedure in Example 31 Part 3, Step A, tert-butyl 2-(5-fluoropyridin-2-yl)acetate, 60% NaH (80 mg, 2.0 mmol) and dimethyl 2-(chloro(3,4-dimethoxyphenyl)-methylene)malonate (0.32 g, 1.0 mmol, prepared in Example 31, Part 2, Step B) in DMF (1.0 mL) provided 1-tert-butyl 3-methyl 2-(3,4-dimethoxyphenyl)-7-fluoro-4-oxo-4H-quinolizine-1,3-dicarboxylate. The crude solid was used directly in the next step without purification.

Step C: Following the procedure in Example 31 Part 3, Step B, The crude solid from Step B, TFA (5 mL) and water (2 mL) provided 2-(3,4-dimethoxyphenyl)-7-fluoro-4H-quinolizin-4-one (145 mg, 48%). MS m/z 300.2 [M+H]$^+$.

Step D: Following the procedure in Example 31 Part 3, Step C, dimethoxyphenyl)-7-fluoro-4H-quinolizin-4-one (75 mg, 0.25 mmol) and piperazine (75 mg, 0.87 mmol) in DMSO (0.5 mL) provided the title compound (30 mg, 33%). M.P. 170-172° C.; MS m/z 366.1 [M+H]$^+$; $^1$H NMR (500 MHz, CDCl$_3$) δ: 8.53 (1H, d, J=2.2 Hz), 7.46 (1H, d, J=9.5 Hz), 7.32-7.27 (2H, m), 7.22 (1H, d, J=1.9 Hz), 6.97 (1H, d, J=8.5 Hz), 6.84 (2H, s), 3.98 (3H, s), 3.95 (3H, s), 3.25-3.20 (4H, m), 3.13-3.07 (4H, m).

As shown in Table 1 below, additional compounds disclosed herein may be prepared according to Example 33 by substituting the appropriate starting materials, reagents and reaction conditions.

Example 34

Preparation of Cpd 245

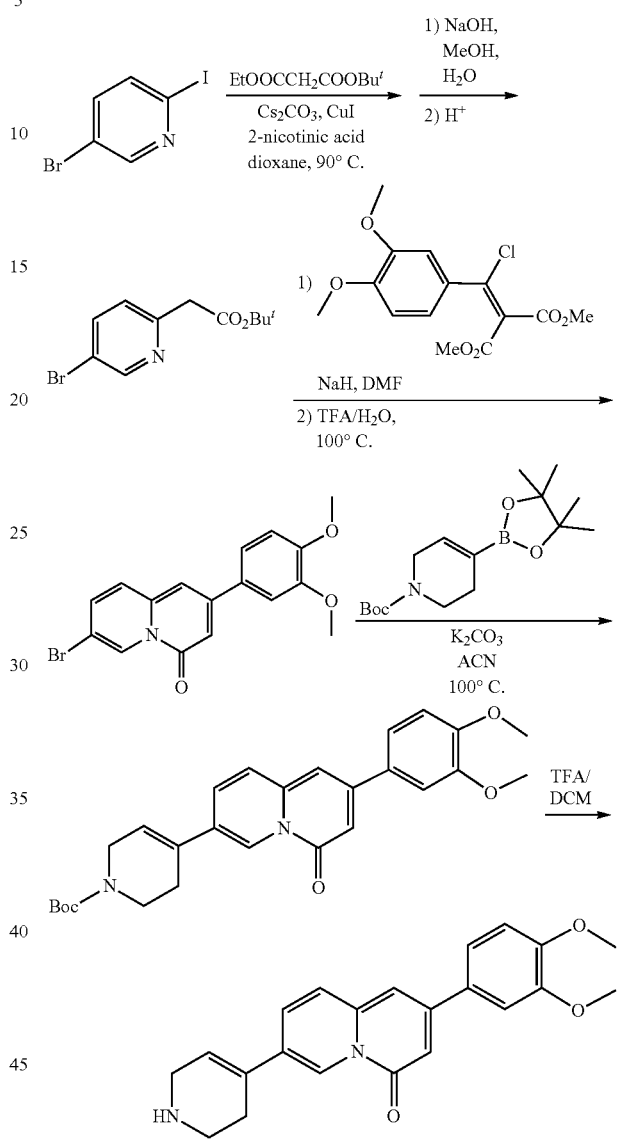

Step A: A mixture of 5-bromo-2-iodopyridine (2.84 g, 10 mmol), tert-butyl ethyl malonate (3.76 g, 20 mmol), Cs$_2$CO$_3$ (9.77 g, 30 mmol), CuI (0.19 g, 1.0 mmol) and 2-nicotinic acid (0.246 g, 2.0 mmol) in dioxane (20 mmol) was stirred at 90° C. overnight under nitrogen atmosphere. The mixture was then treated with water, extracted with ethyl acetate, dried and evaporated. The residue was dissolved in MeOH (100 mL) and water (40 mL) and NaOH (1.2 g, 30 mmol) were added. The mixture was stirred at room temperature for 3 hours, then acidified with 1N HCl to pH 4, extracted with ethyl acetate, dried and chromatographed with ethyl acetate (10% to 50%) in hexanes to give tert-butyl 2-(5-bromopyridin-2-yl)acetate (1.2 g, 44%).

Step B: Following the procedure in Example 33, Step B and C, tert-butyl 2-(5-bromopyridin-2-yl)acetate (0.54 g, 2.0 mmol) was treated with NaH (60% in mineral oil, 0.16 g, 4.0 mmol) in DMF (2.0 mL) followed by reaction with 2-(chloro(3,4-dimethoxyphenyl)methylene)malonate (2.0 mmol).

Deprotection and decarboxylation in TFA (5.0 mL) and water (2.0 mL) at 100° C. afforded 7-bromo-2-(3,4-dimethoxyphenyl)-4H-quinolizin-4-one (0.17 g, 68%). MS m/z 360.1 [M+H]$^+$, 362.0 [M+2+H]t Step C: A mixture of 7-bromo-2-(3,4-dimethoxyphenyl)-4H-quinolizin-4-one (0.17 g, 0.47 mmol), tert-butyl 4-(4,4,5,5-tetramethyl-1,3,2-dioxaborolan-2-yl)-5,6-dihydropyridine-1(2H)-carboxylate (0.18 g, 0.57 mmol), PdCl$_2$dppf (38 mg, 0.047 mmol), K$_2$CO$_3$ (2.0 M×0.75 mL, 1.5 mmol) in acetonitrile (1.5 mL) was stirred at 100° C. for 16 hours. The mixture was then treated with water, extracted with dichloromethane, dried and chromatographed with ethyl acetate (20% to 100%) in dichloromethane to give tert-butyl 4-(2-(3,4-dimethoxyphenyl)-4-oxo-4H-quinolizin-7-yl)-5,6-dihydropyridine-1(2H)-carboxylate (0.16 g, 73%). MS m/z 463.3 [M+H]$^+$.

Step D: tert-butyl 4-(2-(3,4-dimethoxyphenyl)-4-oxo-4H-quinolizin-7-yl)-5,6-dihydropyridine-1(2H)-carboxylate (80 mg, 0.17 mmol) was treated with dichloromethane (1.0 mL) and TFA (1.0 mL) and stirred at room temperature for 1 hour. The mixture was then evaporated, treated with dichloromethane and washed with saturated aqueous sodium bicarbonate solution. The organic layer was dried and evaporated to give the title compound (63 mg, 100%). M.P. 174-176° C.; MS m/z 363.2 [M+H]$^+$; $^1$H NMR (500 MHz, CDCl$_3$) δ: 9.04 (1H, s), 7.53 (1H, dd, J=9.2, 1.9 Hz), 7.47 (1H, d, J=9.2 Hz), 7.31 (1H, dd, J=8.5, 2.2 Hz), 7.23 (1H, d, J=2.2 Hz), 6.99 (1H, J=8.2 Hz), 6.86 (2H, br s), 6.36 (1H, s), 3.99 (3H, s), 3.97 (3H, s), 3.67-3.60 (2H, m), 3.24-3.13 (2H, m), 2.62-2.55 (2H, m), 2.21 (1H, br s).

Example 35

Preparation of Cpd 249

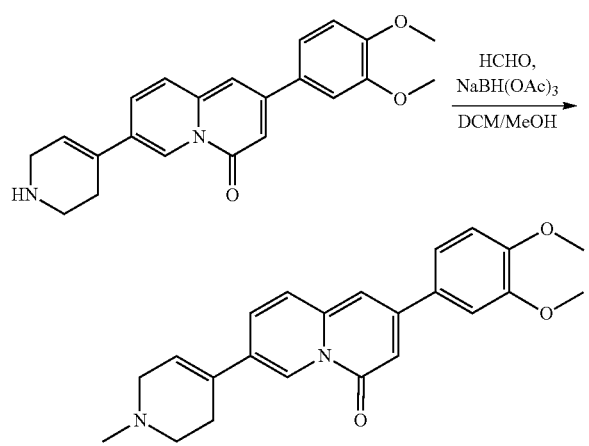

Following the procedure in Example 23, 2-(3,4-dimethoxyphenyl)-7-(1,2,3,6-tetrahydropyridin-4-yl)-4H-quinolizin-4-one (30 mg, 0.083 mmol), sodium triacetoxyborohydride (53 mg, 0.25 mmol) and aqueous solution of formaldehyde (30%, 14 μL, 0.166 mmol) in 10% methanol in dichloromethane (1.0 mL) gave the title compound (26 mg, 83%). M.P. 194-196° C.; MS m/z 377.2 [M+H]$^+$; $^1$H NMR (500 MHz, CDCl$_3$) δ: 9.03 (1H, s), 7.51-7.44 (2H, m), 7.29 (1H, dd, J=8.5, 2.2 Hz), 7.21 (1H, d, J=1.9 Hz), 6.98 (1H, J=8.2 Hz), 6.87-6.82 (2H, m), 6.26 (1H, s), 3.98 (3H, s), 3.95 (3H, s), 3.48 (2H, br s), 3.06-2.97 (2H, m), 2.90-2.80 (2H, m), 2.65 (3H, s).

Example 36

Preparation of Cpd 306

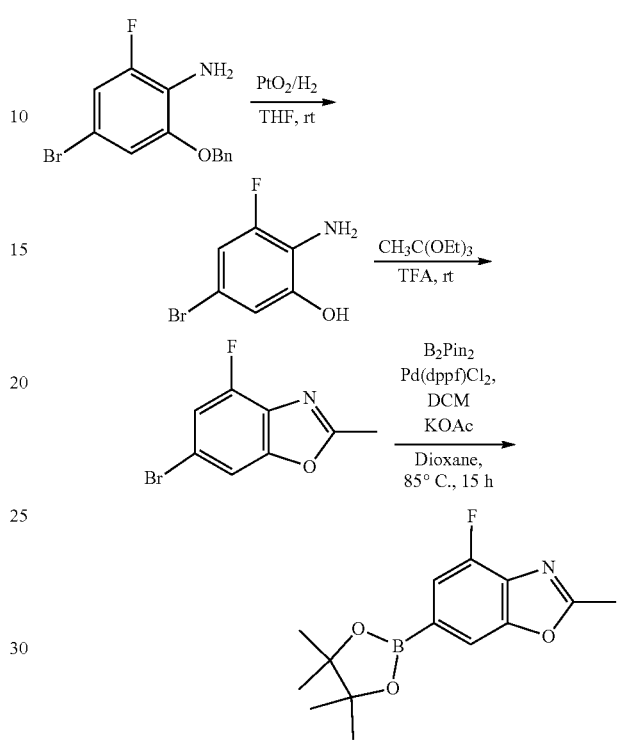

Part 1, Step A: To a solution of 2-(benzyloxy)-4-bromo-6-fluoroaniline (3.74 g, 12.6 mmol) in THF (25 mL), prepared from 1,3-difluoro-2-nitrobenzene in 3 steps according to known procedures (WO2007/067612), was added PtO$_2$ (0.23 g, 1.0 mmol). After stirring under hydrogen (1 atm, balloon) at room temperature for 23 hours, the mixture was filtered through celite. The filtrate was concentrated to give 2-amino-5-bromo-3-fluorophenol as a brown solid, which was used in the next step without further purification. MS m/z 206.1 [M+H]$^+$, 208.0 [M+2+H]$^+$.

Part 1, Step B: To a solution of the crude 2-amino-5-bromo-3-fluorophenol from Step A in 1,1,1-triethoxyethane (10 mL) was added TFA (0.96 mL, 12.6 mmol) at room temperature. After 15 hours, the mixture was neutralized with Na$_2$CO$_3$ and filtered. The filtrated was concentrated and chromatographed with CH$_2$Cl$_2$ to give 6-bromo-4-fluoro-2-methylbenzo[d]oxazole as a tan solid (2.531 g, 88%). MS m/z 230.0 [M+H]$^+$, 232.1 [M+2+H]$^+$.

Part 1, Step C: A mixture of 6-bromo-4-fluoro-2-methylbenzo[d]oxazole (2.531 g, 11.0 mmol), 4,4,4',4',5,5,5',5'-octamethyl-2,2'-bi(1,3,2-dioxaborolane) (3.087 g, 12.2 mmol), KOAc (3.25 g, 33.2 mmol) and Pd(dppf)Cl$_2$·CH$_2$Cl$_2$ (449 mg, 0.55 mmol) in dioxane (25 mL) was degassed and heated under N$_2$ at 85° C. After 15 hours, LC-MS indicated disappearance of the starting material and the products as a mixture of boronic acid and boronic pinacol ester in a ratio of ~2/1:boronic acid product:MS m/z 196.1 [M+H]$^+$; pinacol boronic ester product: MS m/z 278.2 [M+H]$^+$. The reaction mixture was concentrated to dryness and used as is in the next step.

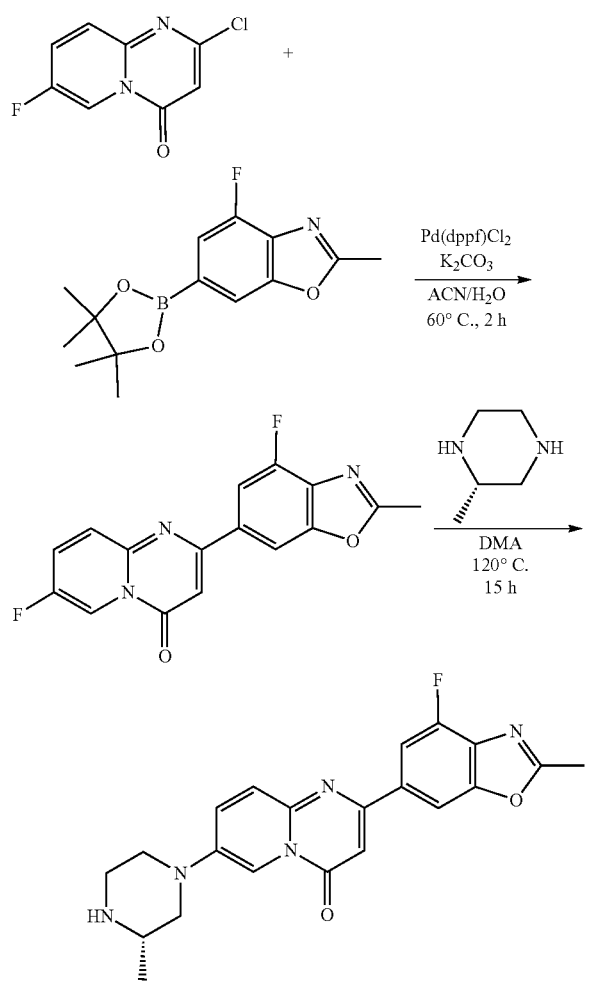

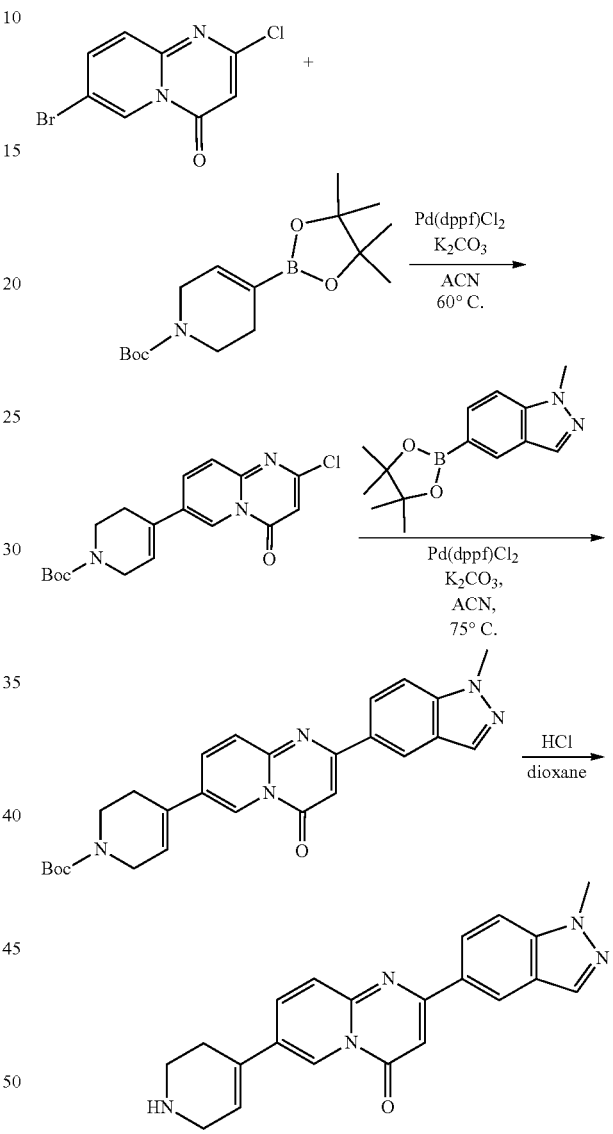

As shown in Table 1 below, additional compounds disclosed herein may be prepared according to Example 36 by substituting the appropriate starting materials, reagents and reaction conditions.

Example 37

Preparation of Cpd 443

Part 2, Step A: A mixture of crude boronic pinacol ester/boronic acid from Part 1 (~4 g, ~4 mmol), 2-chloro-7-fluoro-4H-pyrido[1,2-a]pyrimidin-4-one (0.792 g, 4.0 mmol, prepared in Example 14, Part 1), Pd(dppf)Cl$_2$·CH$_2$Cl$_2$ (146 mg, 0.20 mmol), K$_2$CO$_3$ (2M, 6.0 mL, 12.0 mmol), and CH$_3$CN (12 mL) was degassed and then heated under N$_2$ at 60° C. for 2.5 hours. The volatiles were removed and the residue was washed with water and CH$_3$CN to give 7-fluoro-2-(4-fluoro-2-methylbenzo[d]oxazol-6-yl)-4H-pyrido[1,2-a]pyrimidin-4-one as a grayish solid (1.119 g, 89%). MS m/z 314.2 [M+H]$^+$. $^1$H NMR (500 MHz, DMSO-d$_6$) δ 8.88-9.01 (1H, m), 8.39-8.48 (1H, m), 8.11-8.20 (2H, m), 7.86-7.96 (1H, m), 7.21-7.29 (1H, m), 2.69 (3H, s).

Part 2, Step B: A mixture of 7-fluoro-2-(4-fluoro-2-methylbenzo[d]oxazol-6-yl)-4H-pyrido[1,2-a]pyrimidin-4-one (63 mg, 0.2 mmol) and (S)-2-methylpiperazine (30 mg, 0.3 mmol) in DMA (0.5 mL) was heated at 120° C. for 15 hours. The volatiles were removed and the residue was chromatographed (10-15% MeOH in CH$_2$Cl$_2$) to give the title compound as a yellow solid (26 mg, 33%). M.P. 207-209° C.; MS m/z 394.3 [M+H]$^+$; $^1$H NMR (500 MHz, DMSO-d$_6$) δ 8.39 (1H, d, J=1.3 Hz), 8.20-8.24 (1H, m), 8.05-8.16 (2H, m), 7.71-7.77 (1H, m), 7.11 (1H, s), 3.56-3.68 (2H, m), 2.98-3.06 (1H, m), 2.78-2.88 (2H, m), 2.68 (3H, s), 2.62-2.68 (1H, m), 2.27-2.34 (1H, m), 1.06 (3H, d, J=6.3 Hz).

Step A: A mixture of 7-bromo-2-(3,4-dimethoxyphenyl)-4H-pyrido[1,2-a]pyrimidin-4-one (516 mg, 2.0 mmol), tert-butyl 4-(4,4,5,5-tetramethyl-1,3,2-dioxaborolan-2-yl)-5,6-dihydropyridine-1(2H)-carboxylate (740 mg, 2.4 mmol), potassium carbonate (828 mg, 6.0 mmol) and Pd(dppf)Cl$_2$ (144 mg, 0.2 mmol) in acetonitrile (4 mL) was degassed and then heated under N$_2$ at 60° C. overnight. The volatiles were removed and the residue was chromatographed (30% EtOAc/CH$_2$Cl$_2$) to give tert-butyl 4-(2-(3,4-dimethoxyphenyl)-4-oxo-4H-pyrido[1,2-a]pyrimidin-7-yl)-5,6-dihydropyridine-1(2H)-carboxylate as a yellow solid (579 mg, 80%). MS m/z 362.8 [M+H]$^+$.

Step B: To the product from Step A (400 mg, 1.1 mmol) was added 1-methyl-5-(4,4,5,5-tetramethyl-1,3,2-dioxaborolan-2-yl)-1H-indazole (220 mg, 1.2 mmol), Pd(dppf)Cl₂ (40 mg, 0.05 mmol), potassium carbonate (455 Mg, 3.3 mmol) and CH₃CN (2 mL). The mixture was degassed and then heated at 75° C. overnight. The mixture was washed with water and CHAN. The volatiles were removed and the residue was chromatographed with 0-2% MeOH in CH₂Cl₂ to give tert-butyl 4-(2-(1-methyl-1H-indazol-5-yl)-4-oxo-4H-pyrido[1,2-a]pyrimidin-7-yl)-5,6-dihydropyridine-1(2H)-carboxylate as an off-white solid (327 mg, 65%). MS m/z 458.5 [M+H]⁺.

Step C: Following the procedure in Example 22, Step D, the above product from Step B (327 mg, 0.72 mmol) and HCl in dioxane (4 M, 5 mL) provided the title compound as an off-white solid (194 mg, 76%). M.P. 200-203° C.; MS m/z 358.2 [M+H]⁺; ¹H NMR (DMSO-d₆, 500 MHz) δ 8.80 (d, J=1.6 Hz, 1H), 8.72 (d, J=1.6 Hz, 1H), 8.30-8.26 (m, 2H), 8.22 (d, J=1.6 Hz, 1H), 7.77 (d, J=1.6 Hz, 2H), 7.09 (s, 1H), 6.62 (s, 1H), 4.11 (s, 3H), 3.46-3.44 (m, 2H), 2.98-2.96 (m, 2H), 2.43-2.39 (m, 2H).

As shown in Table 1 below, additional compounds disclosed herein may be prepared according to Example 37 by substituting the appropriate starting materials, reagents and reaction conditions.

Example 38

Preparation of Cpd 342

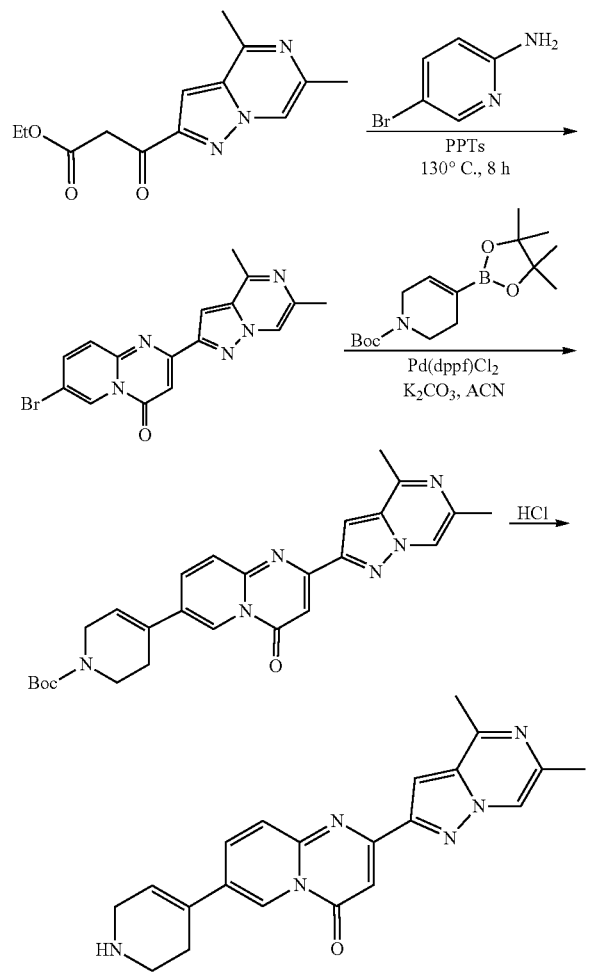

Step A: Following the procedure in Example 9, Step G, 2-amino-5-bromo-pyridine (415 mg, 2.4 mmol), ethyl 3-(4,6-dimethylpyrazolo[1,5-a]pyrazin-2-yl)-3-oxopropanoate (520 mg, 2.0 mmol) and PPTs (25 mg, 0.1 mmol) gave 2-(4,6-dimethylpyrazolo[1,5-a]pyrazin-2-yl)-7-bromo-4H-pyrido[1,2-a]pyrimidin-4-one as a yellow solid (498 mg, 67%). MS m/z 370.2 [M+H]⁺, 372.2 [M+2+H]⁺; ¹H NMR (500 MHz, DMSO-d₆) δ 8.99-9.09 (1H, m), 8.53-8.62 (1H, m), 8.08-8.18 (1H, m), 7.68-7.75 (1H, m), 7.55-7.63 (1H, m), 7.01-7.09 (1H, m), 2.74 (3H, s), 2.44 (3H, s).

Step B: Following the procedure in Example 22, Step C, 7-bromo-2-(4,6-dimethylpyrazolo[1,5-a]pyrazin-2-yl)-4H-pyrido[1,2-a]pyrimidin-4-one (498 mg, 1.3 mmol), tert-butyl 4-(4,4,5,5-tetramethyl-1,3,2-dioxaborolan-2-yl)-5,6-dihydropyridine-1(2H)-carboxylate (482 mg, 1.56 mmol), potassium carbonate (538 mg, 3.9 mmol) and Pd(dppf)Cl₂ (95 mg, 0.13 mmol) in acetonitrile (3 mL) gave tert-butyl 4-(2-(4,6-dimethylpyrazolo[1,5-a]pyrazin-2-yl)-4-oxo-4H-pyrido[1,2-a]pyrimidin-7-yl)-5,6-dihydropyridine-1(2H)-carboxylate as an off-white solid (0.57 g, 84%). MS m/z Δ73.5 [M+H]⁺; ¹H NMR (500 MHz, DMSO-d₆) δ 8.80-8.89 (1H, m), 8.53-8.61 (1H, m), 8.23-8.32 (1H, m), 7.71-7.79 (1H, m), 7.55-7.61 (1H, m), 6.99-7.04 (1H, m), 4.03-4.14 (2H, m), 3.55-3.65 (2H, m), 2.74 (3H, s), 2.53-2.58 (2H, m), 2.43 (3H, s), 1.44 (9H, s).

Step C: Following the procedure in example 22, Step D, tert-butyl 4-(2-(4,6-dimethylpyrazolo[1,5-a]pyrazin-2-yl)-4-oxo-4H-pyrido[1,2-a]pyrimidin-7-yl)-5,6-dihydropyridine-1(2H)-carboxylate, HCl (2 mL, 4N in dioxane) in CH₂Cl₂ (4 mL) gave the title compound as an off-white solid (234 mg, 84%). M.P. 207-210° C.; MS m/z 373.4 [M+H]⁺; ¹H NMR (500 MHz, DMSO-d₆) δ 8.80 (1H, s), 8.55-8.60 (1H, m), 8.27-8.32 (1H, m), 7.73-7.78 (1H, m), 7.58-7.63 (1H, m), 7.00-7.05 (1H, m), 6.57-6.65 (1H, m), 3.42-3.47 (2H, m), 2.93-2.98 (2H, m), 2.72-2.76 (2H, m), 2.44 (3H, s), 2.39 (3H, s).

As shown in Table 1 below, additional compounds disclosed herein may be prepared according to Example 38 by substituting the appropriate starting materials, reagents and reaction conditions.

Example 39

Preparation of Cpd 629

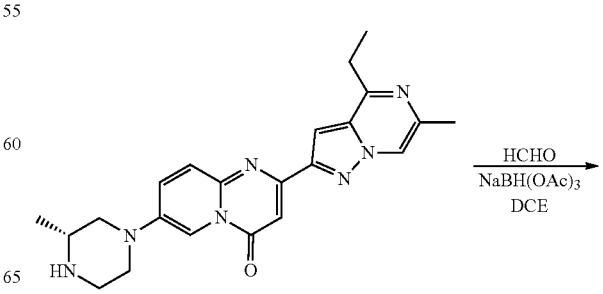

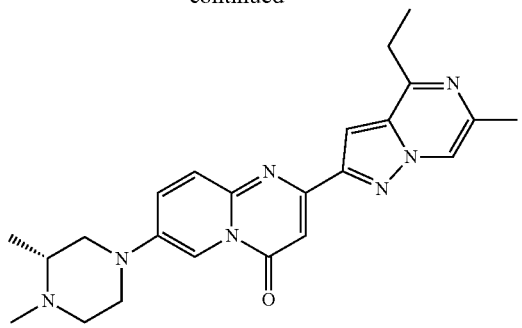

A mixture of (R)-2-(4-ethyl-6-methylpyrazolo[1,5-a]pyrazin-2-yl)-7-(3-methylpiperazin-1-yl)-4H-pyrido[1,2-a]pyrimidin-4-one (48 mg, 0.12 mmol, prepared according to Example 9), formaldehyde (0.039 ml, 0.48 mmol, 37% in water) and sodium triacetoxyborohydride (51 mg, 0.24 mmol) was stirred in dichloromethane (1 mL) for 1 hour. The reaction mixture was diluted with dichloromethane and neutralized with sodium bicarbonate. The organics were dried, concentrated and chromatographed with 0-5% MeOH/CH$_2$Cl$_2$ to provide the title compound as a yellow solid (45 mg, 90%). M.P. 257-259° C.; MS m/z 418.5 [M+H]$^+$; $^1$H NMR (500 MHz, DMSO-d$_6$) δ 8.56 (1H, s), 8.25-8.26 (1H, m), 8.12-8.14 (1H, m), 7.72-7.74 (1H, m), 7.55 (1H, s), 6.95 (1H, s), 3.60-3.65 (2H, m), 3.08 (2H, q, J=7.6 Hz), 2.84-2.89 (2H, m), 2.43-2.52 (2H, m, obscured by DMSO-d$_6$), 2.45 (3H, s), 2.29-2.31 (1H, m), 2.24 (3H, s), 1.33 (3H, t, J=7.6 Hz), 1.91 (3H, d, J=6.2 Hz).

As shown in Table 1 below, additional compounds disclosed herein may be prepared according to Example 39 by substituting the appropriate starting materials, reagents and reaction conditions.

Example 40

Preparation of Cpd 625 and Cpd 626

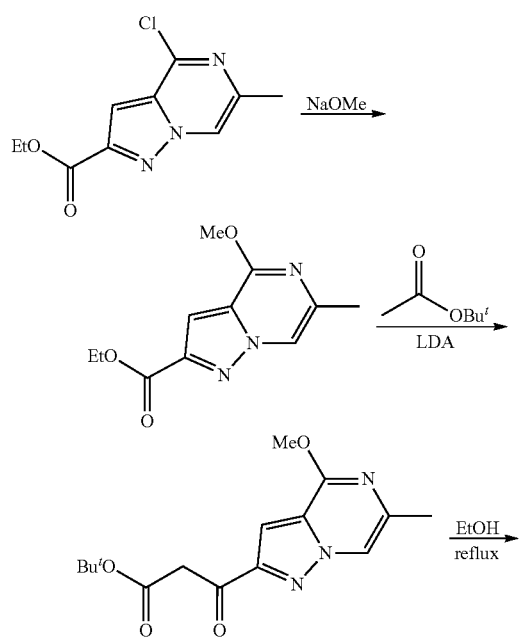

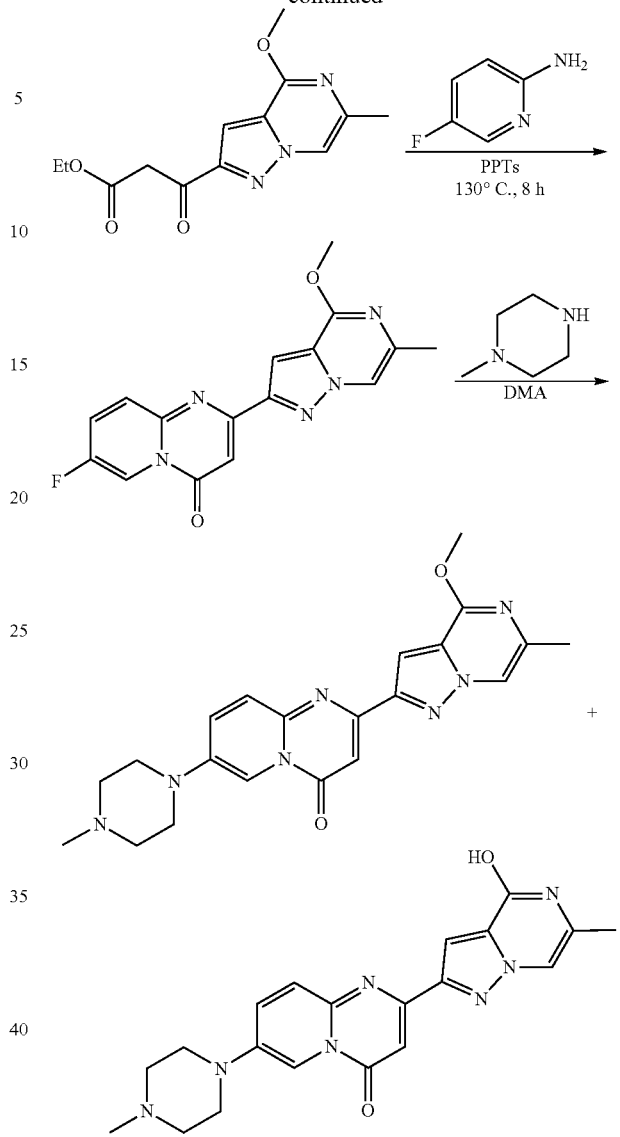

Step A: A mixture of ethyl 4-chloro-6-methylpyrazolo[1,5-a]pyrazine-2-carboxylate (2.39 g, 10 mmol, prepared in Example 9, Step C) and sodium methoxide (60 mL, 30 mmol, 0.5 M in MeOH) was stirred at 30° C. for 1 hour. The mixture was concentrated to remove most of the methanol, diluted with water and neutralized with 6 N HCl. A white solid precipitated out and was filtered, washed with water and CH$_3$CN, and dried to give ethyl 4-methoxy-6-methylpyrazolo[1,5-a]pyrazine-2-carboxylate as a white solid (1.387 g, 62%). MS m/z 222.2 [M–CH$_3$+H]$^+$.

Step B: Following the procedure in Example 9, Step E, tert-butyl acetate (1.6 mL, 12.3 mmol), LDA (10.2 mL, 15.4 mmol, 1.5 M in THF) and ethyl 4-methoxy-6-methylpyrazolo[1,5-a]pyrazine-2-carboxylate (1.387 g, 6.2 mmol) gave tert-butyl 3-(4-methoxy-6-methylpyrazolo[1,5-a]pyrazin-2-yl)-3-oxopropanoate as an oil (1.35 g, 72%). MS m/z 306.3 [M+H]$^+$; $^1$H NMR (500 MHz, DMSO-d$_6$) δ 8.35 (1H, s), 7.27 (1H, s) 4.05 (3H, s), 4.01 (2H, s), 2.36 (3H, s), 1.38 (9H, s).

Step C: Following the procedure in Example 9, Step F, tert-butyl 3-(4-methoxy-6-methylpyrazolo[1,5-a]pyrazin-2- yl)-3-oxopropanoate (1.35 g, 4.43 mmol) and EtOH (10 mL) gave ethyl 3-(4-methoxy-6-methylpyrazolo[1,5-a]pyrazin-2-yl)-3-oxopropanoate as a yellowish solid, which was used directly in the next step without further purification. MS m/z 278.3 [M+H]⁺.

Step D: A mixture of ethyl 3-(4-methoxy-6-methylpyrazolo[1,5-a]pyrazin-2-yl)-3-oxopropanoate (~4.43 mmol), 2-amino-5-fluoro-pyridine (0.596 g, 5.3 mmol), PPTs (100 mg, 0.4 mmol) and tetraethyl orthosilicate (1.0 mL, 4.43 mmol) in m-xylene (2.2 mL) was heated at 130° C. After 15 hours, the mixture was cooled to room temperature and washed with CH₂Cl₂ to give 7-fluoro-2-(4-methoxy-6-methylpyrazolo[1,5-a]pyrazin-2-yl)-4H-pyrido[1,2-a]pyrimidin-4-one as a yellow solid (1.015 g, 70%). MS m/z 326.3 [M+H]⁺.

Step E: A mixture of 7-fluoro-2-(4-methoxy-6-methylpyrazolo[1,5-a]pyrazin-2-yl)-4H-pyrido[1,2-a]pyrimidin-4-one (98 mg, 0.30 mmol) and N-methyl-piperazine (150 mg, 1.5 mmol) in DMA (0.6 mL) was heated at 130° C. After 6 hours, the mixture was cooled to room temperature and chromatographed with 5% MeOH/CH₂Cl₂ and 10% 3.5 N NH₃ in MeOH/CH₂Cl₂ to give Cpd 625 (12 mg, 10%) and Cpd 626 (8.5 mg, 7%), each as yellow solids.

Cpd 625: M.P. 242-244° C.; MS m/z 406.5 [M+H]⁺; ¹H NMR (500 MHz, DMSO-d₆) δ 8.33-8.38 (1H, m), 8.24-8.30 (1H, m), 8.09-8.15 (1H, m), 7.70-7.74 (1H, m), 7.34-7.39 (1H, m), 6.92-6.96 (1H, m), 4.07 (3H, s), 3.21-3.29 (4H, m), 2.5 (4H, m, obscured by DMSO-d₆), 2.37 (3H, s), 2.26 (3H, s).

Cpd 626: M.P. 280-283° C.; MS m/z 392.4 [M+H]⁺; ¹H NMR (500 MHz, DMSO-d₆) δ 11.4 (1H, s), 8.24-8.28 (1H, m), 8.09-8.14 (1H, m), 7.70-7.75 (1H, m), 7.63-7.67 (1H, m), 7.48 (1H, s), 6.88 (1H, s), 3.22-3.29 (4H, m), 2.51-2.56 (4H, m), 2.24-2.30 (3H, s), 2.15 (3H, s).

Example 41

Preparation of Cpd 688

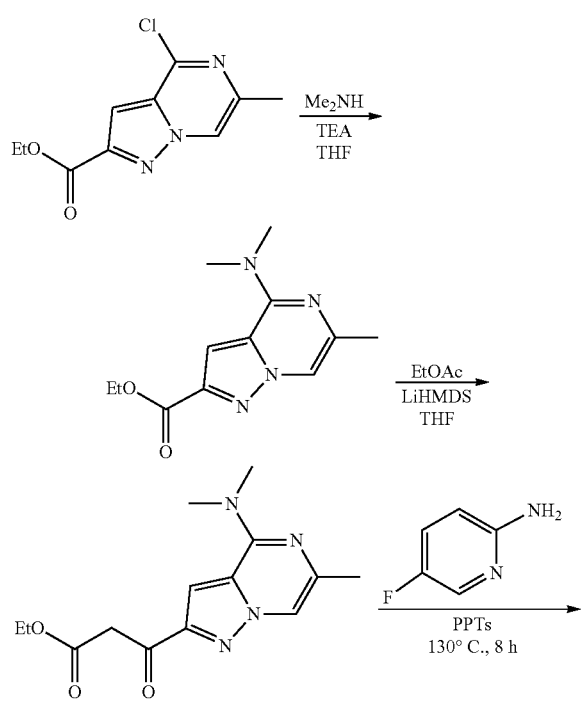

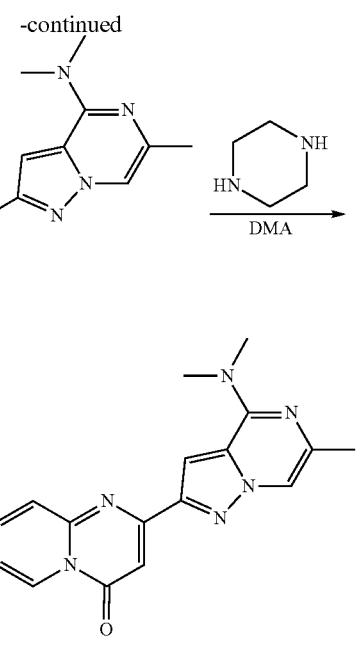

Step A: A mixture of ethyl 4-chloro-6-methylpyrazolo[1,5-a]pyrazine-2-carboxylate (0.956 g, 4 mmol, prepared in Example 9, Step C), dimethylamine (2.1 mL, 4.2 mmol, 2.0 M in THF) and Et₃N (0.84 mL, 6.0 mmol) was heated at 60° C. After 15 hours, the mixture was concentrated, the residue was dissolved in EtOAc, washed with water, dried and concentrated to give ethyl 4-(dimethylamino)-6-methylpyrazolo[1,5-a]pyrazine-2-carboxylate as an off-white solid (0.99 g, 99%). MS m/z 249.3 [M+H]⁺.

Step B: To a solution of ethyl 4-(dimethylamino)-6-methylpyrazolo[1,5-a]pyrazine-2-carboxylate (0.99 g, 4.0 mmol) and EtOAc (1.95 mL, 20 mmol) in THF (30 mL) at −20° C. was added LiHMDS (11.1 mL, 10 mmol, 0.9 M in THF). After 1 hours, the mixture was quenched with saturated NH₄Cl, extracted with EtOAc. The organics were concentrated and chromatographed with 2% MeOH/DCM to give ethyl 3-(4-(dimethylamino)-6-methylpyrazolo[1,5-a]pyrazin-2-yl)-3-oxopropanoate as a pale yellow oil (0.48 g, 40%). MS m/z 291.3 [M+H]⁺; ¹H NMR (500 MHz, DMSO-d₆) δ 7.73 (1H, s), 7.05 (1H, s), 5.43 (2H, s), 3.96 (2H, q, J=7.0 Hz), 3.28 (6H, s), 2.20 (3H, s), 1.16 (3H, t, J=7.0 Hz)

Step C: Following the procedure in Example 40, Step D, ethyl 3-(4-(dimethylamino)-6-methylpyrazolo[1,5-a]pyrazin-2-yl)-3-oxopropanoate (0.48 g, 1.6 mmol), 2-amino-5-fluoro-pyridine (179 mg, 1.6 mmol), PPTs (40 mg, 0.16 mmol) and tetraethyl orthosilicate (0.36 mL, 1.6 mmol) in m-xylene (0.8 mL) gave 2-(4-(dimethylamino)-6-methylpyrazolo[1,5-a]pyrazin-2-yl)-7-fluoro-4H-pyrido[1,2-a]pyrimidin-4-one as a yellow solid (0.39 g, 72%). MS m/z 339.2 [M+H]⁺; ¹H NMR (500 MHz, DMSO-d₆) δ 8.92-9.00 (1H, m), 8.06-8.18 (1H, m), 7.91-7.94 (1H, m), 7.85-7.91 (1H, m), 7.55-7.61 (1H, m), 6.98-7.08 (1H, m), 3.36 (6H, s), 2.25 (3H, s).

Step D: A mixture of 7-fluoro-2-(4-methoxy-6-methylpyrazolo[1,5-a]pyrazin-2-yl)-4H-pyrido[1,2-a]pyrimidin-4-one (50 mg, 0.15 mmol) and piperazine (86 mg, 1.0 mmol) in DMA (0.5 mL) was heated at 150° C. After 2 hours, the mixture was cooled to room temperature and washed with CH₃CN to give the title compound as a yellow solid (60 mg, 98%). M.P. 245-248° C.; MS m/z 405.4 [M+H]⁺; ¹H NMR (500 MHz, DMSO-d₆) δ 8.23-8.28 (1H, m), 8.06-8.11 (1H, m), 7.89-7.92 (1H, m), 7.69-7.75 (1H, m), 7.50-7.55 (1H, m), 6.92 (1H, s), 3.35 (6H, s), 3.12-3.19 (4H, m), 2.87-2.92 (4H, m), 2.80 (1H, s), 2.24 (3H, s).

Example 42

Preparation of Cpd 694

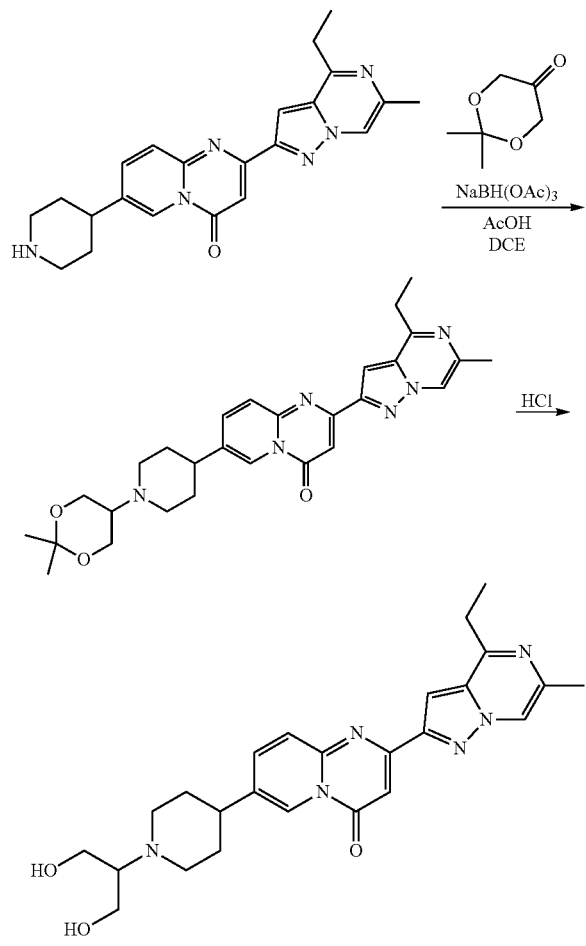

Step A: To a mixture of 2-(4-ethyl-6-methylpyrazolo[1,5-a]pyrazin-2-yl)-7-(piperidin-4-yl)-4H-pyrido[1,2-a]pyrimidin-4-one (78 mg, 0.2 mmol, prepared according to the procedure in Examples 38 and 24) and 2,2-dimethyl-1,3-dioxan-5-one (72 mg, 0.5 mmol, 90% tech grade) in dichloroethane (1 mL) were added $NaBH(OAc)_3$ (106 mg, 0.5 mmol) and 1 drop of AcOH. The mixture was stirred at 60° C. After 1 hour, the mixture was quenched with saturated $NaHCO_3$, extracted with $CH_2Cl_2$, concentrated and chromatographed (2-5% $MeOH/CH_2Cl_2$) to give 7-(1-(2,2-dimethyl-1,3-dioxan-5-yl)piperidin-4-yl)-2-(4-ethyl-6-methylpyrazolo[1,5-a]pyrazin-2-yl)-4H-pyrido[1,2-a]pyrimidin-4-one as a white solid (70 mg, 70%). MS m/z 503.5 [M+H]$^+$; $^1$H NMR (500 MHz, DMSO-$d_6$) δ 8.75-8.82 (1H, m), 8.54-8.61 (1H, m), 8.00-8.10 (1H, m), 7.72-7.79 (1H, m), 7.58-7.63 (1H, m), 6.99-7.03 (1H, m), 3.86-3.95 (2H, m), 3.71-3.81 (2H, m), 3.06-3.15 (2H, m), 3.00-3.06 (2H, m), 2.70-2.80 (1H, m), 2.53-2.59 (1H, m), 2.45 (3H, s), 2.28-2.38 (2H, m), 1.82-1.90 (2H, m), 1.59-1.71 (2H, m), 1.32-1.37 (6H, m), 1.27 (3H, s).

Step B: To a mixture of 7-(1-(2,2-dimethyl-1,3-dioxan-5-yl)piperidin-4-yl)-2-(4-ethyl-6-methylpyrazolo[1,5-a]pyrazin-2-yl)-4H-pyrido[1,2-a]pyrimidin-4-one (50 mg, 0.1 mmol) in THF (10 mL) was added HCl (1.3 mL, 2.6 mmol, 2 N). The mixture was stirred at room temperature. After 15 hours, the mixture was treated with excess of 7N $NH_3$ in MeOH, concentrated and chromatographed (10% 2.5 N $NH_3$ in $MeOH/CH_2Cl_2$) to give the title compound as a yellow solid (45 mg, 97%). M.P. 228-230° C.; MS m/z 463.6 [M+H]$^+$; $^1$H NMR (500 MHz, DMSO-$d_6$) δ 8.77-8.84 (1H, m), 8.54-8.61 (1H, m), 8.02-8.10 (1H, m), 7.90-7.94 (1H, m), 7.74-7.79 (1H, m), 7.57-7.63 (1H, m), 6.99-7.05 (1H, m), 4.21-4.31 (2H, m), 3.42-3.59 (4H, m), 3.10 (2H, q, J=7.5 Hz), 2.89-3.00 (2H, m), 2.70-2.72 (1H, m), 2.57-2.62 (1H, m), 2.45 (3H, s), 1.79-1.89 (2H, m), 1.63-1.75 (2H, m), 1.34 (3H, t, J=7.5 Hz).

Example 43

Preparation of Cpd 662

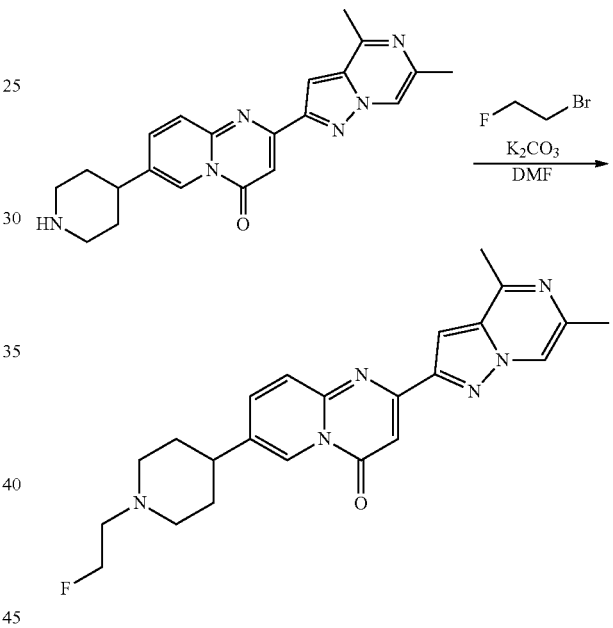

A mixture of 2-(4,6-dimethylpyrazolo[1,5-a]pyrazin-2-yl)-7-(piperazin-1-yl)-4H-pyrido[1,2-a]pyrimidin-4-one (56 mg, 0.15 mmol, prepared according to the procedure in Example 24), 1-bromo-2-fluoroethane (23 mg, 0.18 mmol) and $K_2CO_3$ (23 mg, 0.18 mmol) in DMF (1 mL) was heated at 80° C. After 7 hours, the mixture was cooled to room temperature and chromatographed (5% $MeOH/CH_2Cl_2$) to give the title compound as a yellow solid (29 mg, 44%). M.P. 197-199° C.; MS m/z 421.4 [M+H]$^+$; $^1$H NMR (500 MHz, DMSO-$d_6$) δ 8.79-8.85 (1H, m), 8.55-8.60 (1H, m), 8.05-8.11 (1H, m), 7.73-7.80 (1H, m), 7.57-7.62 (1H, m), 7.02 (1H, s), 4.59-4.65 (1H, m), 4.48-4.55 (1H, m), 3.01-3.07 (2H, m), 2.69-2.75 (1H, m), 2.74 (3H, s), 2.68-2.72 (1H, m), 2.62-2.67 (1H, m), 2.43 (3H, s), 2.12-2.21 (2H, m), 1.85-1.88 (2H, m), 1.70-1.88 (2H, m).

As shown in Table 1 below, additional compounds disclosed herein may be prepared according to Example 43 by substituting the appropriate starting materials, reagents and reaction conditions.

Example 44

Preparation of Cpd 798

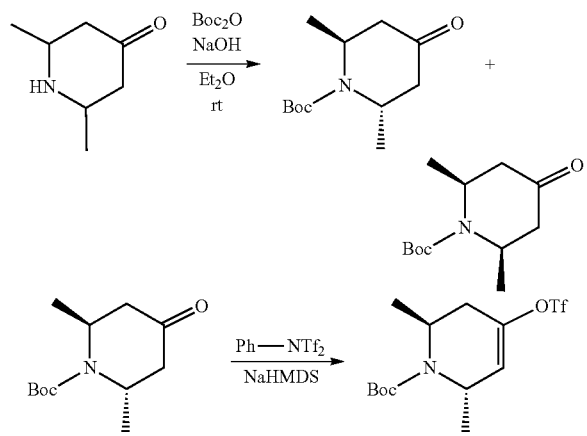

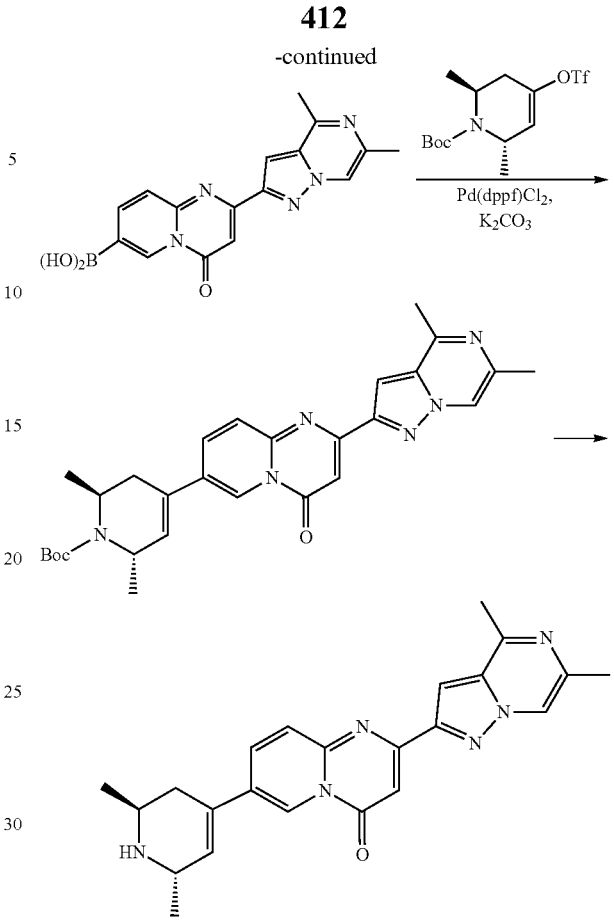

Part 1, Step A: To a solution of 2,6-dimethylpiperidin-4-one (1.27 g, 10 mmol, a mixture of trans/cis isomers in a ratio of ~1.5/1) and di-tert-butyl dicarbonate (2.40 g, 11 mmol) in ether was added NaOH (11 mL, 11 mmol, 1 N in water). The mixture was stirred at room temperature. After 36 hours, the mixture was extracted with ether. The organics were concentrated and chromatographed (5-30% EtOAc/Hexanes) to give a mixture of tert-butyl 2,6-dimethyl-4-oxopiperidine-1-carboxylate as a Tran/cis mixture in a ratio of ~1.2/1 (1.99 g, 87%, clear oil). Upon standing overnight, a solid precipitated from the oil, which was filtered and washed with ether to give the tert-butyl trans-2,6-dimethyl-4-oxopiperidine-1-carboxylate (0.376 g, 16%) (95% trans by $^1$H NMR). $^1$H NMR (500 MHz, CDCl$_3$) δ 4.33-4.45 (2H, m), 2.80-2.90 (2H, m), 2.33-2.44 (2H, m), 1.50 (9H, s), 1.26 (6H, d, J=6.9 Hz). The $^1$H NMR is consistent with that of the trans-isomer in a mixture of cis and trans-isomers (US200839454, JOC, 1993, 58, 1109-1117).

Part 1, Step B: To a solution of the tert-butyl trans-2,6-dimethyl-4-oxopiperidine-1-carboxylate (266 mg, 1.17 mmol) in THF (7 mL) at −78° C. was added NaHMDS. After 1 hour, N-Phenyl-bis(trifluoromethanesulfonimide) (0.50 g, 1.4 mmol) in THF (3 mL) was added. The reaction mixture was stirred at room temperature for 2 hours, quenched with saturated NH$_4$Cl and extracted with ether. The organics were concentrated and chromatographed with 1% EtOAc/Hexanes to give tert-butyl-trans-2,6-dimethyl-4-(trifluoromethylsulfonyloxy)-5,6-dihydropyridine-1(2H)-carboxylate (0.415 g, 98%). $^1$H NMR (500 MHz, CDCl$_3$) δ 5.77-5.85 (1H, m), 4.29-4.44 (2H, m), 2.81-2.90 (1H, m), 2.15-2.23 (1H, m), 1.48 (9H, s), 1.37 (3H, d, J=6.6 Hz), 1.24 (3H, d, J=6.6 Hz).

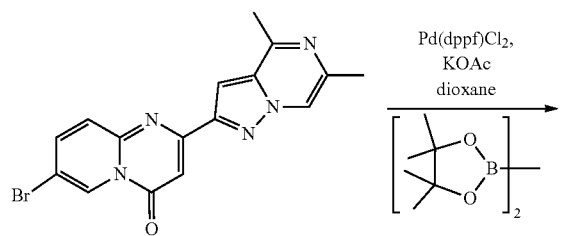

Part 2, Step A: Following the procedure of Example 14, Part 2, 7-bromo-2-(4,6-dimethylpyrazolo[1,5-a]pyrazin-2-yl)-4H-pyrido[1,2-a]pyrimidin-4-one (0.74 g, 2.0 mmol, prepared in Example 38, Step A), KOAc (590 mg, 6.0 mmol), bis(pincolato)diboron (560 mg, 2.2 mmol), and Pd(dppf)Cl$_2$·CH$_2$Cl$_2$ (82 mg, 0.1 mmol) in dioxane (6 mL) provided 2-(4,6-dimethylpyrazolo[1,5-a]pyrazin-2-yl)-4-oxo-4H-pyrido[1,2-a]pyrimidin-7-ylboronic acid. The crude intermediate was used directly in the next step. MS m/z 336.3 [M+H]$^+$.

Part 2, Step B: Following the procedure of Example 14, Part 3, Step A, 2-(4,6-dimethylpyrazolo[1,5-a]pyrazin-2-yl)-4-oxo-4H-pyrido[1,2-a]pyrimidin-7-ylboronic acid (~2 mmol), tert-butyl-trans-2,6-dimethyl-4-(trifluoromethylsulfonyloxy)-5,6-dihydropyridine-1(2H)-carboxylate (0.415 g, 1.15 mmol), potassium carbonate (3.5 mL, 2.0M) and Pd(dppf)Cl$_2$·CH$_2$Cl$_2$ (82 mg, 0.1 mmol) in acetonitrile (10 mL) provided tert-butyl 4-(2-(4,6-dimethylpyrazolo[1,5-a]pyrazin-2-yl)-4-oxo-4H-pyrido[1,2-a]pyrimidin-7-yl)-trans-2,6-dimethyl-5,6-dihydropyridine-1(2H)-carboxylate as a yellow solid (0.5 g, 87%). MS m/z 501.4 [M+H]$^+$.

Part 2, Step C: Following the procedure in Example 38, Step C, tert-butyl 4-(2-(4,6-dimethylpyrazolo[1,5-a]pyrazin-2-yl)-4-oxo-4H-pyrido[1,2-a]pyrimidin-7-yl)-trans-2,6-dimethyl-5,6-dihydropyridine-1(2H)-carboxylate (50 mg, 0.1 mmol) and HCl in dioxane (4 M, 0.5 mL) provided the title compound as a yellow solid (25 mg, 62%). M.P. 228-231° C.; MS m/z 401.3 [M+H]$^+$; $^1$H NMR (500 MHz, DMSO-d$_6$) δ 8.77-8.82 (1H, m), 8.54-8.58 (1H, m), 8.25-8.32 (1H, m), 7.70-7.76 (1H, m), 7.57 (1H, s), 7.02 (1H, s), 6.50-6.58 (1H, m), 3.64-3.75 (1H, m), 3.08-3.18 (1H, m), 2.73 (3H, s), 2.41-2.44 (1H, m), 2.43 (3H, s), 1.99-2.08 (1H, m), 1.21 (3H, d, J=6.6 Hz), 1.16 (3H, d, J=6.3 Hz).

Example 45

Preparation of Cpd 764

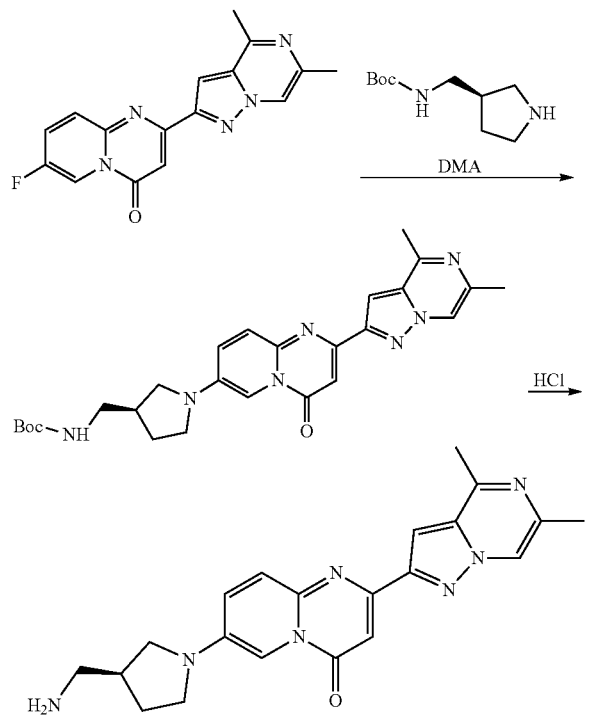

Step A: Following the procedure in Example 9, Step H, 2-(4,6-dimethylpyrazolo[1,5-a]pyrazin-2-yl)-7-fluoro-4H-pyrido[1,2-a]pyrimidin-4-one (618 mg, 2.0 mmol), (R)-tert-butyl pyrrolidin-3-ylmethylcarbamate (481 mg, 2.4 mmol) and DMA (2.0 mL) provided (S)-tert-butyl (1-(2-(4,6-dimethylpyrazolo[1,5-a]pyrazin-2-yl)-4-oxo-4H-pyrido[1,2-a]pyrimidin-7-yl)pyrrolidin-3-yl)methylcarbamate (0.90 g, 92%) as a yellow solid. MS m/z 490.5 [M+H]⁺; ¹H NMR (500 MHz, DMSO-d₆) δ 8.50-8.59 (1H, m), 7.97-8.03 (1H, m), 7.72-7.82 (2H, m), 7.48-7.57 (1H, m), 7.04-7.08 (1H, m), 6.87-6.94 (1H, m), 3.41-3.50 (2H, m), 3.35-3.41 (1H, m), 2.97-3.16 (3H, m), 2.73 (3H, s), 2.47-2.51 (1H, m, obscured by DMSO-d₆), 2.43 (3H, s), 2.04-2.16 (1H, m), 1.71-1.83 (1H, m), 1.39 (9H, s).

Step B: Following the procedure in Example 38, Step C, (S)-tert-butyl (1-(2-(4,6-dimethylpyrazolo[1,5-a]pyrazin-2-yl)-4-oxo-4H-pyrido[1,2-a]pyrimidin-7-yl)pyrrolidin-3-yl)methylcarbamate (0.39 g, 0.8 mmol), HCl (2.0 mL, 4 M in dioxane) and CH₂Cl₂ (10 mL) provided the title compound as a yellow solid (0.19 g, 62%). M.P. 244-246° C.; MS m/z 390.4 [M+H]⁺; ¹H NMR (500 MHz, DMSO-d₆) δ 8.52-8.57 (1H, m), 7.96-8.03 (1H, m), 7.73-7.80 (2H, m), 7.52 (1H, s), 6.90 (1H, s), 3.42-3.50 (2H, m), 3.34-3.41 (1H, m), 3.10-3.18 (1H, m), 2.73 (3H, s), 2.59-2.70 (2H, m), 2.43 (3H, s), 2.34-2.42 (1H, m), 2.09-2.16 (1H, m), 1.73-1.82 (1H, m).

As shown in Table 1 below, additional compounds disclosed herein may be prepared according to Example 45 by substituting the appropriate starting materials, reagents and reaction conditions.

Example 46

Preparation of Cpd 294

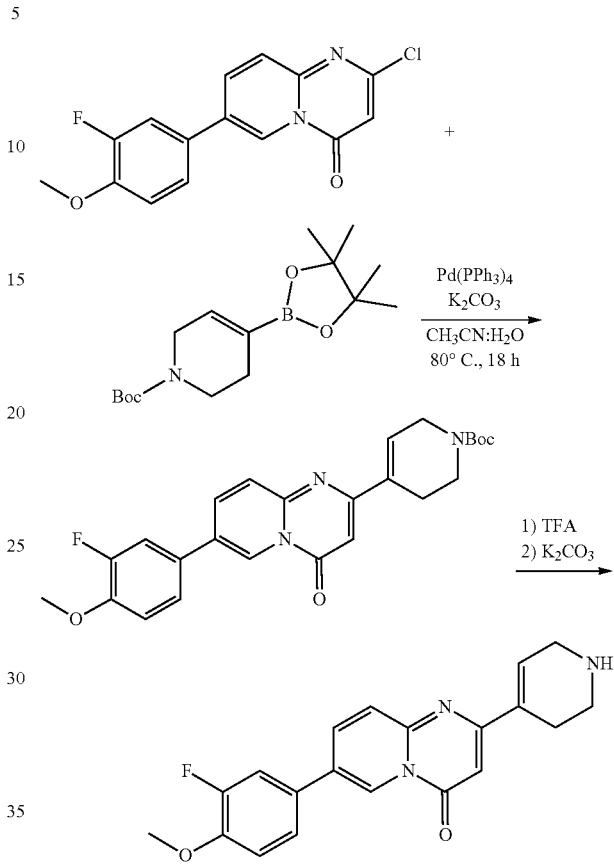

Step A: 2-chloro-7-(3-fluoro-4-methoxyphenyl)-4H-pyrido[1,2-a]pyrimidin-4-one (182 mg, 0.6 mmol), prepared according to Example 30, Step A, was combined with tert-butyl 4-(4,4,5,5-tetramethyl-1,3,2-dioxaborolan-2-yl)-5,6-dihydropyridine-1(2H)-carboxylate (222 mg, 0.72 mmol), tetrakis(triphenylphosphine) palladium(0) (67 mg, 0.06 mmol), CH₃CN (2 mL) and aqueous K₂CO₃ (1 M, 2 mL). The mixture was heated at 80° C. for 18 hours. After cooling to room temperature, the mixture was filtered, providing tert-butyl 4-(7-(3-fluoro-4-methoxyphenyl)-4-oxo-4H-pyrido[1,2-a]pyrimidin-2-yl)-5,6-dihydropyridine-1(2H)-carboxylate as a crude product that was used directly in the next step.

Step B: The tert-butyl 4-(7-(3-fluoro-4-methoxyphenyl)-4-oxo-4H-pyrido[1,2-a]pyrimidin-2-yl)-5,6-dihydropyridine-1(2H)-carboxylate from step A was dissolved in TFA (2 mL). After 10 minutes, volatiles were removed with a nitrogen stream. The residue was partitioned in CH₂Cl₂ and aqueous K₂CO₃ (1 M). The organic layer was loaded onto silica gel, eluting with 0-10% MeOH (3% NH₃) in CH₂Cl₂, affording the title compound as a white powder (150 mg, 72%). M.P. 188-192° C.; MS m/z 352.1 [M+H]⁺; ¹H NMR (DMSO-d₆, 500 MHz): δ 9.05 (1H, d, J=2.3 Hz), 8.28 (1H, dd, J=9.4 Hz, 2.2 Hz), 7.76 (1H, dd, J=12.7 Hz, 2.3 Hz), 7.70 (1H, d, J=9.3 Hz), 7.63 (1H, m), 7.33 (1H, t, J=8.8 Hz), 7.14 (1H, m), 6.44 (1H, s), 3.92 (3H, s), 3.46 (2H, m), 2.91 (2H, m), 2.39 (2H, m).

As shown in Table 1 below, additional compounds disclosed herein may be prepared according to Example 46 by substituting the appropriate starting materials, reagents and reaction conditions.

Example 47

Preparation of Cpd 714

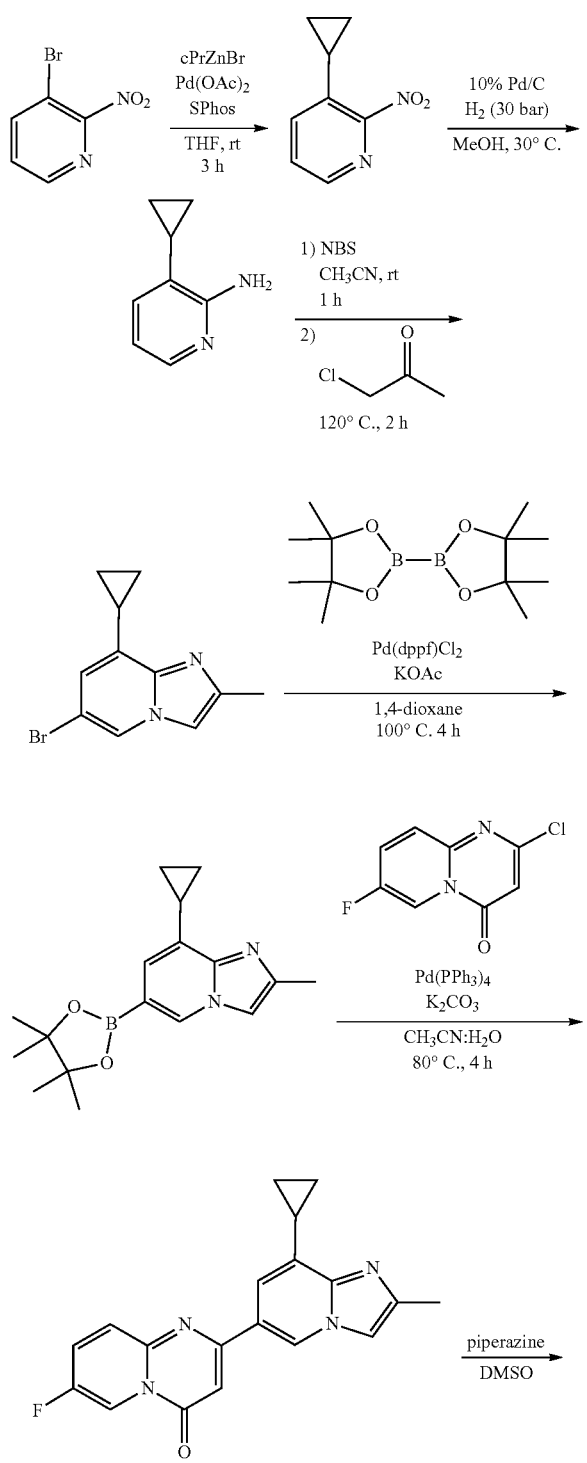

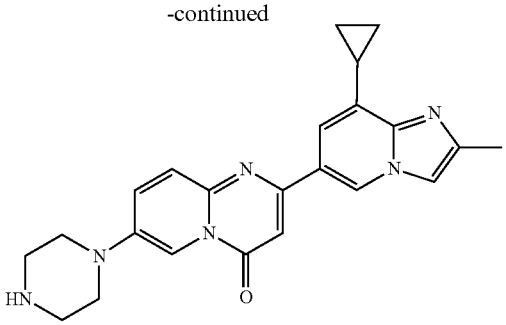

Step A: 3-Bromo-2-nitropyridine (2.0 g, 10 mmol) was dissolved in THF (20 mL). 2-Dicyclohexylphosphino-2',6'-dimethoxybiphenyl (205 mg, 0.5 mmol) and palladium(II) acetate (113 mg, 0.5 mmol) were added to the mixture. To the mixture was added cyclopropylzinc bromide (15 mmol, 0.5 M in THF). The mixture was stirred at room temperature for 3 hours. The mixture was concentrated and chromatographed on silica gel, eluting with 0-5% EtOAc in $CH_2Cl_2$ to provide 3-cyclopropyl-2-nitropyridine (1.1 g, 67%) as a white solid. MS m/z 165.2 $[M+H]^+$.

Step B: 3-Cyclopropyl-2-nitropyridine (1.1 g, 6.7 mmol) was dissolved in MeOH (150 mL). The solution was passed over a cartridge containing 10% Pd/C under $H_2$ (30 bar) at 30° C. The solution was concentrated leaving 3-cyclopropyl-2-aminopyridine (898 mg, quant.) as colorless oil. MS m/z 135.1 $[M+H]^+$.

Step C: Following the procedure in Example 16, Step A, 3-cyclopropyl-2-aminopyridine (898 mg, 6.7 mmol), N-bromosuccinimide (1.3 g, 7.4 mmol), $CH_3CN$ (15 mL) and chloroacetone (0.81 mL, 10 mmol) provided 6-bromo-8-cyclopropyl-2-methylimidazo[1,2-a]pyridine as a tan powder (255 mg, 15%). MS m/z 251.1 $[M+H]^+$, 253.1 $[M+2+H]t$ Step D: Following the procedure in Example 14, Part 2, 6-Bromo-8-fluoro-2-methylimidazo[1,2-a]pyridine (255 mg, 1.0 mmol), 4,4,4',4',5,5,5',5'-octamethyl-2,2'-bi(1,3,2-dioxaborolane) (380 mg, 1.5 mmol), [1,1'-bis(diphenylphosphino)ferrocene]-dichloropalladium(II) (41 mg, 0.05 mmol) and potassium acetate (196 mg, 2 mmol) provided 8-cyclopropyl-2-methyl-6-(4,4,5,5-tetramethyl-1,3,2-dioxaborolan-2-yl)imidazo[1,2-a]pyridine. The crude product was used directly in the next step.

Step E: Following the procedure in Example 14, Part 3, Step A, the crude product of 8-cyclopropyl-2-methyl-6-(4,4,5,5-tetramethyl-1,3,2-dioxaborolan-2-yl)imidazo[1,2-a] pyridine from Step D and 2-chloro-7-fluoro-4H-pyrido[1,2-a]pyrimidin-4-one (1 mmol, prepared in Example 14, Part 1, Step B), tetrakis(triphenylphosphine) palladium(0) (112 mg, 0.1 mmol), $CH_3CN$ (4 mL) and aqueous $K_2CO_3$ (1M, 4 mL) provided 2-(8-cyclopropyl-2-methylimidazo[1,2-a]pyridin-6-yl)-7-fluoro-4H-pyrido[1,2-a]pyrimidin-4-one as a tan powder (330 mg, 99%). MS m/z 335.2 $[M+H]^+$.

Step F: Following the procedure in Example 14, Part 3, Step B, 2-(8-cyclopropyl-2-methylimidazo[1,2-a]pyridin-6-yl)-7-fluoro-4H-pyrido[1,2-a]pyrimidin-4-one (50 mg, 0.15 mmol) and piperazine (65 mg, 0.75 mmol) afforded the title compound as a tan powder (38 mg, 63%). M.P. 274-277° C.; MS m/z 401.4 $[M+H]^+$; $^1H$ NMR (DMSO-$d_6$, 500 MHz): δ 9.14 (1H, d, J=1.7 Hz), 8.21 (1H, d, J=2.9 Hz), 8.07 (1H, dd, J=9.7 Hz, 2.8 Hz), 7.79 (1H, d, J=1.0 Hz), 7.67 (1H, d, J=9.2 Hz), 7.43 (1H, m), 6.99 (1H, s), 3.14 (4H, m), 2.89 (4H, m), 2.48 (1H, m), 2.37 (3H, s), 2.35 (1H, br s), 1.13 (2H, m), 1.04 (2H, m).

As shown in Table 1 below, additional compounds disclosed herein may be prepared according to Example Δ7 by substituting the appropriate starting materials, reagents and reaction conditions.

Example 48

Preparation of Cpd 674

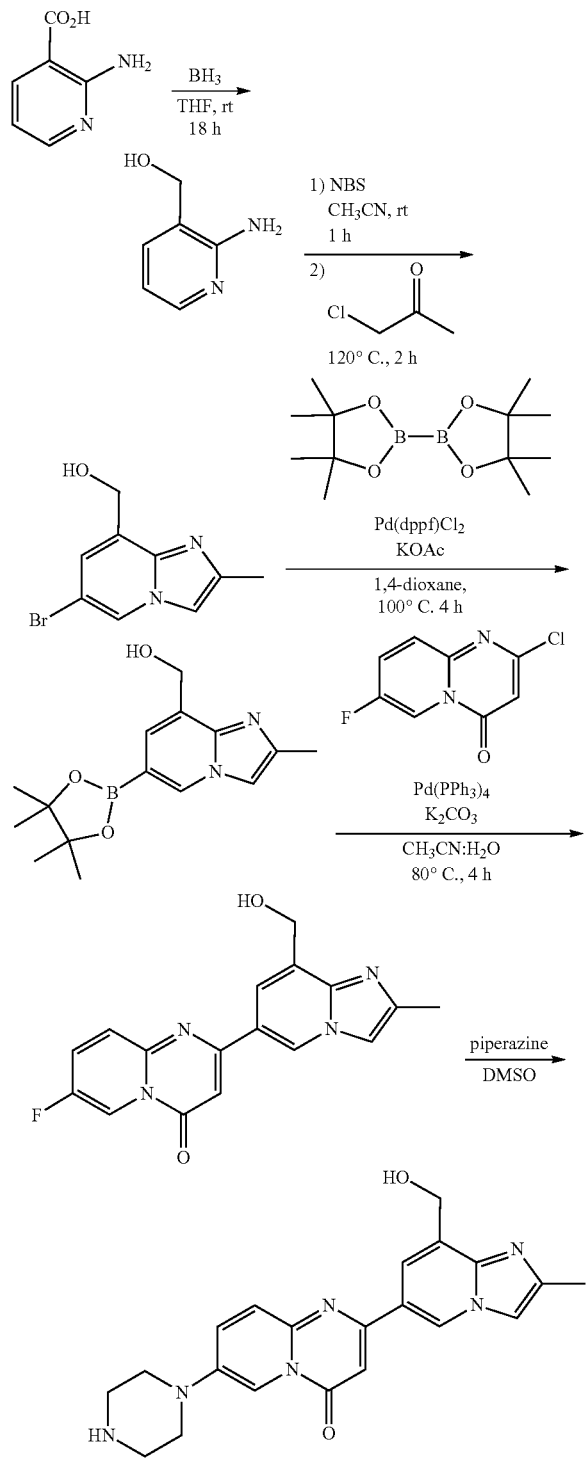

Step A: 2-Aminonicotinic acid (4.8 g, 35 mmol) was suspended in THF (100 mL). To the mixture was added borane THF complex (40 mmol, 1 M in THF). The mixture was stirred at room temperature for 18 hours. The excess reagent was quenched by the addition of aqueous potassium hydroxide (2 M, 15 mL). The mixture was stirred vigorously for 10 minutes. The organic layer was collected and concentrated. The residue was chromatographed on silica gel, eluting with 0-10% MeOH in $CH_2Cl_2$ to provide (2-aminopyridin-3-yl)methanol (1.0 g, 23%) as a white solid. MS m/z 125.1 $[M+H]^+$.

Step B: Following the procedure in Example 16, Step A, (2-aminopyridin-3-yl)methanol (1.0 g, 8 mmol), N-bromosuccinimide (1.57 g, 8.8 mmol), $CH_3CN$ (16 mL) and chloroacetone (0.81 mL, 10 mmol) provided (6-bromo-2-methylimidazo[1,2-a]pyridin-8-yl)methanol as a tan powder (82 mg, 4%). MS m/z 241.1 $[M+H]^+$, 243.1 $[M+2+H]t$ Step C: Following the procedure in Example 14, Part 2, 6-Bromo-8-fluoro-2-methylimidazo[1,2-a]pyridine (85 mg, 0.35 mmol), 4,4,4',4',5,5,5',5'-octamethyl-2,2'-bi(1,3,2-dioxaborolane) (133 mg, 0.53 mmol), [1,1'-bis(diphenylphosphino)ferrocene]-dichloropalladium(II) (30 mg, 0.035 mmol) and potassium acetate (69 mg, 0.7 mmol) provided (2-methyl-6-(4,4,5,5-tetramethyl-1,3,2-dioxaborolan-2-yl) imidazo[1,2-a]pyridin-8-yl)methanol. The crude product was used directly in the next step.

Step D: Following the procedure in Example 14, Part 3, Step A, the crude product of (2-methyl-6-(4,4,5,5-tetramethyl-1,3,2-dioxaborolan-2-yl)imidazo[1,2-a]pyridin-8-yl) methanol from Step C and 2-chloro-7-fluoro-4H-pyrido[1,2-a]pyrimidin-4-one (0.35 mmol, prepared in Example 14, Part 1, Step B, tetrakis(triphenylphosphine) palladium(0) (39 mg, 0.035 mmol), $CH_3CN$ (2 mL) and aqueous $K_2CO_3$ (1 M, 2 mL) provided 7-fluoro-2-(8-(hydroxymethyl)-2-methylimidazo[1,2-a]pyridin-6-yl)-4H-pyrido[1,2-a]pyrimidin-4-one as a tan powder (100 mg, 88%). MS m/z 325.2 $[M+H]^+$.

Step E: Following the procedure in Example 14, Part 3, Step B, 7-fluoro-2-(8-(hydroxymethyl)-2-methylimidazo[1,2-a]pyridin-6-yl)-4H-pyrido[1,2-a]pyrimidin-4-one (120 mg, 0.15 mmol) and piperazine (65 mg, 0.75 mmol) afforded the title compound as a tan powder (120 mg, 99%). M.P.>320° C.; MS m/z 391.3 $[M+H]^+$; $^1$H NMR (DMSO-$d_6$, 500 MHz): δ 9.23 (1H, s), 8.24 (1H, d, J=2.6 Hz), 8.07 (1H, dd, J=9.7 Hz, 2.6 Hz), 7.96 (1H, s), 7.79 (1H, s), 7.73 (1H, d, J=6.7 Hz), 6.87 (1H, s), 4.86 (2H, s), 3.14 (4H, m), 2.89 (4H, m), 2.37 (3H, s).

Example 49

Preparation of Cpd 353

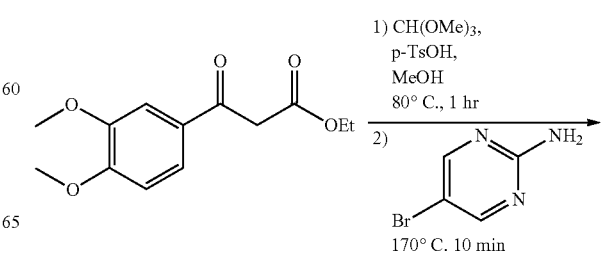

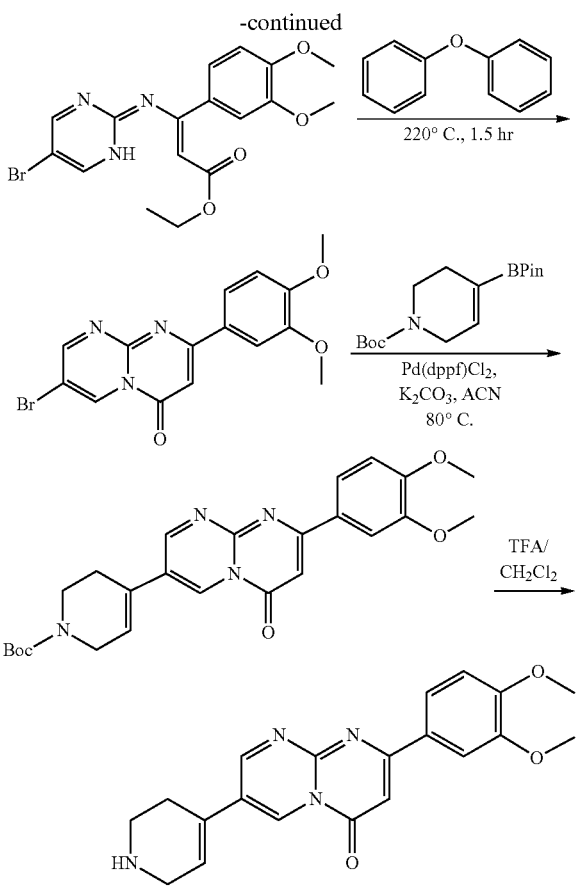

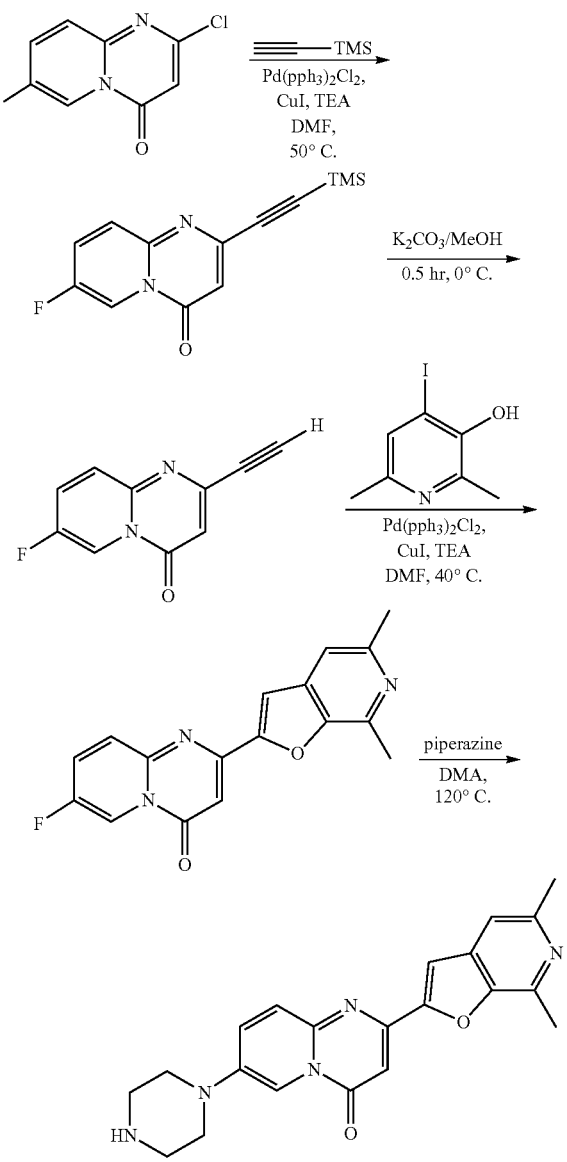

under N₂ at 80° C. overnight. The volatiles were removed and the residue was used in the next step without purification. MS m/z 465.4 [M+H]⁺.

Step D: A solution of tert-butyl 4-(2-(3,4-dimethoxyphenyl)-4-oxo-4H-pyrimido[1,2-a]pyrimidin-7-yl)-5,6-dihydropyridine-1(2H)-carboxylate in CH₂Cl₂/TFA (0.5 mL/0.5 mL) was stirred at 0° C. for 2 hours. After most of the TFA and CH₂Cl₂ were removed by rotary evaporation, ice-cold saturated NaHCO₃ was added to the reaction mixture. The mixture was extracted with CH₂Cl₂. The organic layer was dried over MgSO₄, concentrated, and chromatographed (5% MeOH/CH₂Cl₂) to provide the title compound as a yellow solid. MS m/z 365.1 [M+H⁺].

Example 50

Preparation of Cpd 486

Step A: Ethyl 3-(3,4-dimethoxyphenyl)-3-oxopropanoate (907 mg, 3.6 mmol) was dissolved in methanol (2 mL). p-Toluenesulfonic acid monohydrate (34.2 mg, 0.18 mmol) was added to the solution, followed by trimethylorthoformate (0.59 mL, 5.4 mmol). The solution was stirred at 80° C. for 1 hour. Volatiles were removed with a stream of nitrogen. To the crude material were added 5-bromopyrimidin-2-amine (550 mg, 3.1 mmol) and diphenyl ether (2 mL). The mixture was heated at 170° C. for 10 minutes. The reaction mixture was passed through a through a flash silica column (33% Hexanes/CH₂Cl₂) to give ethyl-3-(-5-bromopyrimidin-2(1H)-ylideneamino)-3-(3,4-dimethoxyphenyl)acrylate as a yellow solid. MS m/z 408.0 [M+H]⁺, 410.0 [M+2+H]⁺.

Step B: To ethyl-3-(-5-bromopyrimidin-2(1H)-ylideneamino)-3-(3,4-dimethoxyphenyl)acrylate was added diphenyl ether (2 mL). The reaction was heated to 220° C. for 1.5 hours. The mixture was purified by chromatography (100% CH₂Cl₂) to provide 7-bromo-2-(3,4-dimethoxyphenyl)-4H-pyrimido[1,2-a]pyrimidin-4-one (314 mg, 28% for 2 steps) as a yellow solid. MS m/z 361.9 [M+H]⁺, 363.9 [M+2+H]⁺; ¹H NMR (500 MHz, DMSO-d₆): δ 9.30 (1H, d, J=2.7 Hz), 9.20 (1H, d, J=2.9 Hz), 7.88 (1H, dd, J=8.5 Hz, 2.6 Hz), 7.79 (1H, d, J=2.2 Hz), 7.15 (1H, s), 7.11 (1H, d, J=8.5 Hz), 3.88 (3H, s), 3.85 (3H, s).

Step C: A mixture of 7-bromo-2-(3,4-dimethoxyphenyl)-4H-pyrimido[1,2-a]pyrimidin-4-one (53.7 mg, 0.15 mmol), tert-butyl 4-(4,4,5,5-tetramethyl-1,3,2-dioxaborolan-2-yl)-5,6-dihydropyridine-1(2H)-carboxylate (50.5 mg, 0.016 mmol), Pd(dppf)Cl₂ (11 mg, 0.015 mmol), K₂CO₃ (62.2 mg, 0.45 mmol), and ACN (1 mL) was degassed and then heated Step A: A mixture of 2-chloro-7-fluoro-4H-pyrido[1,2-a]pyrimidin-4-one (995 mg, 5 mmol, prepared in Example 14, Part 1), CuI (19.0 mg, 0.1 mmol), PdCl₂(PPh₃)₂ (70.2 mg, 0.1 mmol), ethynyltrimethylsilane (2.1 mL, 15 mmol), triethylamine (2.1 mL, 15 mmol) in DMF (10 mL) was degassed and then heated under N₂ at 50° C. overnight. The volatiles were removed and the crude 7-fluoro-2-((trimethylsilyl)ethynyl)-4H-pyrido[1,2-a]pyrimidin-4-one was used directly for the next step. MS m/z 261.1 [M−H⁺].

Step B: Potassium carbonate (1.0 g, 7.5 mmol) was added to the solution of crude 7-fluoro-2-((trimethylsilyl)ethynyl)-4H-pyrido[1,2-a]pyrimidin-4-one in MeOH (33 mL). The mixture was stirred at 0° C. for 0.5 hours. After MeOH was removed by rotary evaporation, water was added. The precipitate was filtered and purified by silica chromatography (8% EtOAc/CH₂Cl₂) to give 2-ethynyl-7-fluoro-4H-pyrido[1,2-a]pyrimidin-4-one (192.1 mg, 20% for 2 steps) as a yellow solid. MS m/z 189.1 [M−H⁺].

Step C: A mixture of 2-ethynyl-7-fluoro-4H-pyrido[1,2-a]pyrimidin-4-one (192.1 mg, 1.0 mmol), 4-iodo-2,6-dimethylpyridin-3-ol (305.3 mg, 1.2 mmol), CuI (9.7 mg, 0.05 mmol), PdCl₂(PPh₃)₂ (35.8 mg, 0.05 mmol), triethylamine (288 µL, 2 mmol) in DMF (1.7 mL) was degassed and then heated under N₂ at 40° C. overnight. After most of the DMF was removed, water was added. The precipitate was filtered and purified by chromatography (14% EtOAC/CH₂Cl₂) to give 2-(5,7-dimethylfuro[2,3-c]pyridin-2-yl)-7-fluoro-4H-pyrido[1,2-a]pyrimidin-4-one (126.3 mg, 41%) as a yellow solid. MS m/z 310.1 [M−H⁺].

Step D: Piperazine (64.6 mg, 0.75 mmol) was added to a solution of 2-(5,7-dimethylfuro[2,3-c]pyridin-2-yl)-7-fluoro-4H-pyrido[1,2-a]pyrimidin-4-one (46.4 mg, 0.15 mmol) in DMA (0.5 mL). The reaction mixture was heated at 120° C. for 2 hours. After most of the DMA was removed, CH₃CN was added to the reaction mixture, and a precipitate was formed. The precipitate was filtered, washed with water and dried to provide the title compound as a yellow solid (30 mg, 53%). M.P. 198-200° C.; MS m/z 376.3 [M+H⁺]; ¹H NMR (500 MHz, DMSO-d₆): δ 8.25 (1H, d, J=2.5 Hz), 8.13 (1H, dd, J=9.9 Hz, 2.5 Hz), 7.73 (1H, d, J=9.8 Hz), 7.64 (1H, s), 7.41 (1H, s), 6.94 (1H, s), 3.17 (4H, m), 2.90 (4H, m), 2.71 (3H, s), 2.51 (3H, s), 2.07 (1H, s).

As shown in Table 1 below, additional compounds disclosed herein may be prepared according to Example 50 by substituting the appropriate starting materials, reagents and reaction conditions.

Example 51

Preparation of Cpd 603

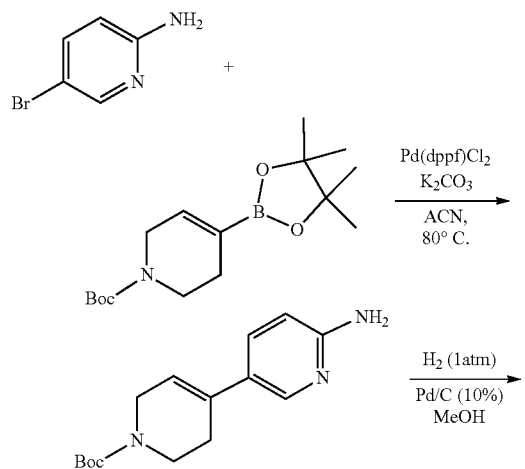

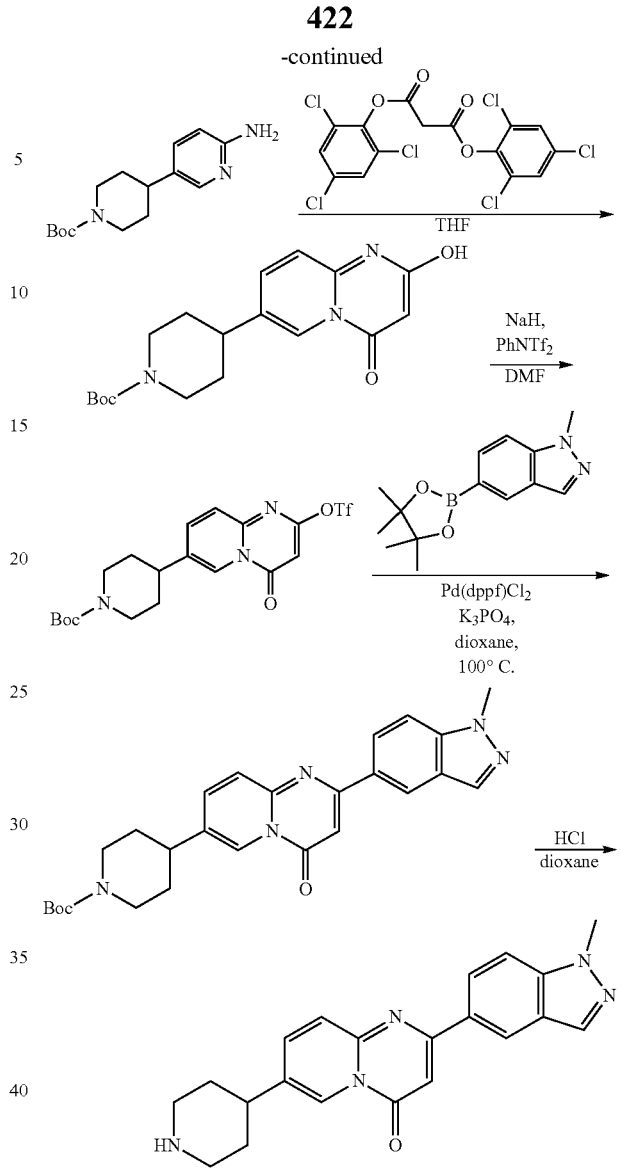

Step A: A mixture of 5-bromopyridin-2-amine (433 mg, 2.5 mmol), tert-butyl 4-(4,4,5,5-tetramethyl-1,3,2-dioxaborolan-2-yl)-5,6-dihydropyridine-1(2H)-carboxylate (928 mg, 3.0 mmol), PdCl₂dppf (204 mg, 0.25 mmol), K₂CO₃ (1.04 g, 7.5 mmol) in acetonitrile (8.0 mL) was degassed and then stirred at 80° C. overnight. The volatiles were removed and the residue was chromatographed with 7% MeOH in CH₂Cl₂ to provide tert-butyl 4-(6-aminopyridin-3-yl)-5,6-dihydropyridine-1(2H)-carboxylate as a light yellow oil (599 mg, 87%). MS m/z 276.3 [M+H]⁺.

Step B: A solution of the product from Step A (599 mg, 2.2 mmol) in methanol (10 mL) was hydrogenated using Pd/C (10%, 60 mg) in a Parr shaker (60 psi) overnight. The mixture was filtered through Celite, evaporated and chromatographed with 7% MeOH in DCM to provide tert-butyl 4-(6-aminopyridin-3-yl)piperidine-1-carboxylate as a brown oil (600 mg, 99%). MS m/z 278.3 [M+H]⁺.

Step C: A mixture of the product from Step B (600 mg, 2.2 mmol) and bis(2,4,6-trichlorophenyl) malonate (1.0 g, 2.2 mmol) in THF (8.0 mL) was stirred at room temperature for 1 hour. The mixture was then filtered and the solid was washed with DCM. The cake was collected and dried to give tert-butyl 4-(2-hydroxy-4-oxo-4H-pyrido[1,2-a]pyrimidin-7-yl)piperidine-1-carboxylate as an off-white solid (455 mg, 63%). MS m/z 346.4 [M+H]$^+$.

Step D: Into a solution of the product from Step C (455 mg, 1.3 mmol) in DMF (6 mL) at room temperature was added NaH (60%, 62 mg, 1.6 mmol). The mixture was stirred for 15 minutes, then N-phenylbis(trifluoromethanesulfonimide) (511 mg, 1.4 mmol) was added in one portion. The mixture was stirred at room temperature overnight. Aqueous workup followed by purification with 3% MeOH in CH$_2$Cl$_2$ provided tert-butyl 4-(4-oxo-2-(trifluoromethylsulfonyloxy)-4H-pyrido[1,2-a]pyrimidin-7-yl)piperidine-1-carboxylate as an off-white solid (521 mg, 84%).

Step E: A mixture of the product from Step D (300 mg, 0.62 mmol), 1-methyl-5-(4,4,5,5-tetramethyl-1,3,2-dioxaborolan-2-yl)-1H-indazole (142 mg, 0.81 mmol), PdCl$_2$dppf (51 mg, 0.062 mmol), K$_3$PO$_4$ (193 mg, 0.93 mmol) in dioxane (2.0 mL) was degassed and then stirred at 100° C. overnight. The volatiles were removed and the residue was chromatographed with 10% MeOH in CH$_2$Cl$_2$ to give tert-butyl 4-(2-(1-methyl-1H-indazol-5-yl)-4-oxo-4H-pyrido[1,2-a]pyrimidin-7-yl)piperidine-1-carboxylate with some impurities (~300 mg), which was used directly in the next step. MS m/z 460.5 [M+H]$^+$.

Step F: Following the procedure in Example 22, Step D, the above product from Step E (~300 mg) and HCl in dioxane (4 M, 5 mL) provided the title compound as a white solid (196 mg, 88%, in two steps). M.P. 268-270° C.; MS m/z 360.4 [M+H]$^+$; $^1$H NMR (DMSO-d$_6$, 500 MHz) δ 8.75 (s, 1H), 8.70 (s, 1H), 8.27 (dd, J=9.0 Hz, 1.6 Hz, 1H), 8.21 (s, 1H), 8.00 (dd, J=9 Hz, 1.6 Hz, 1H), 7.76 (d, J=9 Hz, 2H), 7.06 (s, 1H), 4.10 (s, 3H), 3.06 (d, J=10 Hz, 2H), 2.84-2.79 (m, 1H), 2.64-2.59 (m, 2H), 2.04 (bs, 1H), 1.81 (d, J=10 Hz, 2H), 1.56-1.53 (m, 2H).

As shown in Table 1 below, additional compounds disclosed herein may be prepared according to Example 51 by substituting the appropriate starting materials, reagents and reaction conditions.

Example 52

Preparation of Cpd 769

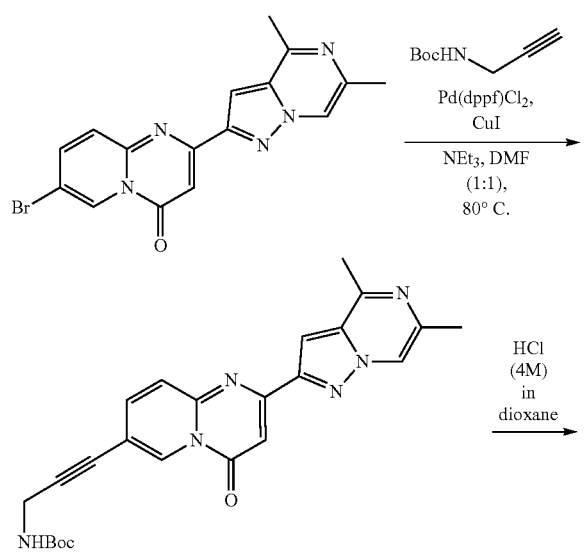

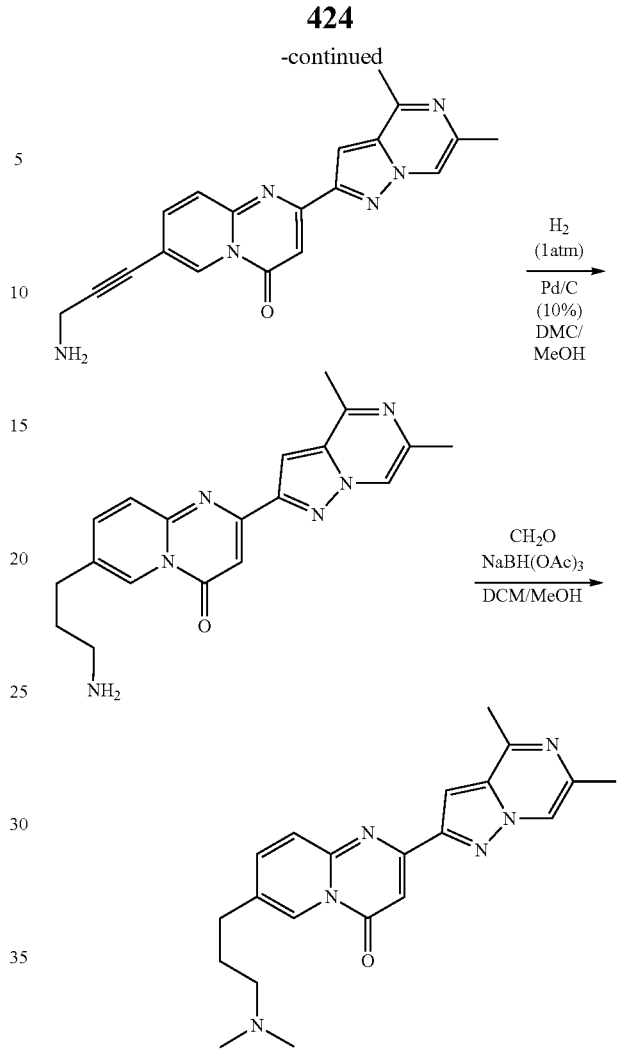

Step A: To an oven dried, argon filled flask was added 7-bromo-2-(4,6-dimethylpyrazolo[1,5-a]pyrazin-2-yl)-4H-pyrido[1,2-a]pyrimidin-4-one (270 mg, 0.73 mmol, prepared in Example 38, Step A), CuI (3.4 mg, 5%), PdCl$_2$(PPh$_3$)$_2$ (30 mg, 5%), triethylamine (1 mL) and DMF (1 mL). The resulting mixture was purged with argon three times and then a solution of tert-butyl prop-2-ynylcarbamate (0.14 g, 0.88 mmol) in DMF (1 mL) was added. The mixture was heated at 80° C. overnight, then cooled to room temperature. After addition of water, the resulting solids were filtered and washed with water and CH$_3$CN sequentially to provide tert-butyl 3-(2-(4,6-dimethylpyrazolo[1,5-a]pyrazin-2-yl)-4-oxo-4H-pyrido[1,2-a]pyrimidin-7-yl)prop-2-ynylcarbamate (260 mg, 80%). MS m/z 445.2 [M+H]$^+$.

Step B: Following the procedure in Example 22, Step D, the above product from Step A (100 mg, 0.23 mmol) and HCl in dioxane (4 M, 3 mL) provided 7-(3-aminoprop-1-ynyl)-2-(4,6-dimethylpyrazolo[1,5-a]pyrazin-2-yl)-4H-pyrido[1,2-a]pyrimidin-4-one as an off-white solid (50 mg, 66%). MS m/z 345.4 [M+H]$^+$.

Step C: The above product from Step C (50 mg, 0.15 mmol) was mixed with Pd/C (10%, 5 mg) in dichloromethane/methanol (1:1, 2 mL) and stirred under 1 atmosphere of hydrogen overnight. The reaction mixture was filtered through celite, concentrated and chromatographed on a silica column, eluting with CH$_2$Cl$_2$/MeOH (85/15) to provide 7-(3-aminopropyl)-2-(4,6-dimethylpyrazolo[1,5-a]

pyrazin-2-yl)-4H-pyrido[1,2-a]pyrimidin-4-one (45 mg, 89%). MS m/z 349.3 [M+H]+.

Step D: Following the procedure in Example 23, the above product from Step B (45 mg, 0.13 mmol), formaldehyde (0.05 mL, 37%, ~0.8 mmol) and sodium triacetoxyborohydride (50 mg, 0.24 mmol) in dichloromethane/methanol (10:1, 1 mL) provided the title compound as a white solid (20 mg, 41%). M.P. 136-138° C.; MS m/z 377.3 [M+H]+; 1H NMR (DMSO-d6, 500 MHz) δ 8.84 (d, J=1.6 Hz, 1H), 8.58 (d, J=1.6 Hz, 1H), 8.00 (d, J=9 Hz, 1H), 7.77 (d, J=9 Hz, 1H), 7.60 (d, J=1.6 Hz, 1H), 7.02 (s, 1H), 2.79-2.75 (m, 5H), 2.45 (s, 3H), 2.25 (t, J=10 Hz, 2H), 2.15 (bs, 6H), 1.83-1.76 (m, 2H).

As shown in Table 1 below, additional compounds disclosed herein may be prepared according to Example 52 by substituting the appropriate starting materials, reagents and reaction conditions.

Example 53

Preparation of Cpd 407

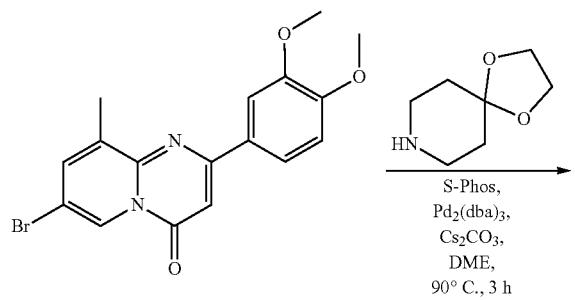

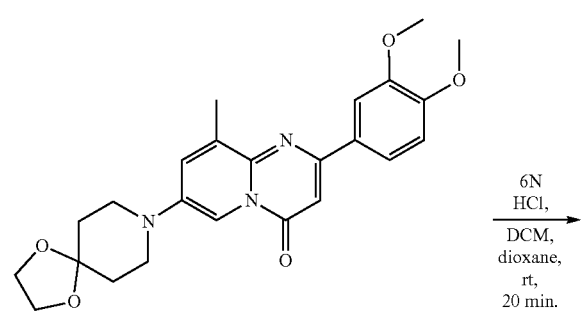

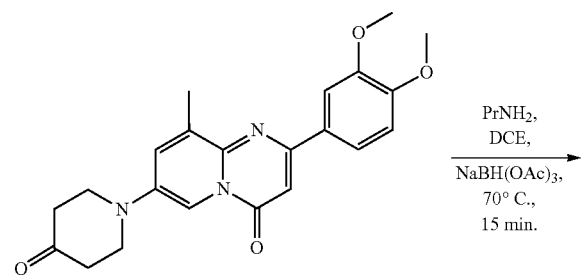

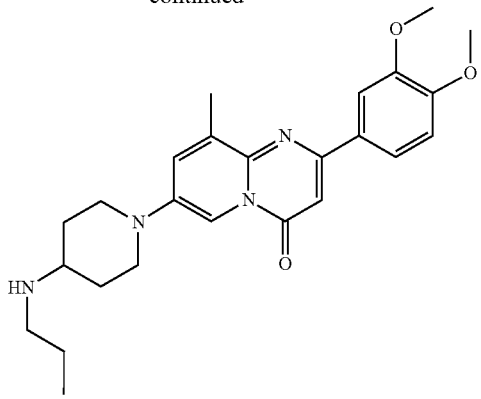

Step A: A mixture of 7-bromo-2-(3,4-dimethoxyphenyl)-9-methyl-4H-pyrido[1,2-a]pyrimidin-4-one (1.5 g, 4.0 mmol, prepared in a manner exemplified in Example 22, Steps A and B), 1,4-dioxa-8-azaspiro[4.5]decane (660 μL, 5.05 mmol), S-Phos (140 mg, 0.34 mmol), Pd2(dba)3 (92 mg, 0.1 mmol), Cs2CO3 (3.0 g, 9.2 mmol), and DME (12 mL) was heated under argon at 90° C. for 3 hours. The reaction mixture was then suspended in a solution of CH2Cl2 and acetone, and was filtered. The filtrate was concentrated under vacuum. Purification by silica gel chromatography (1:1 CH2Cl2/EtOAc, then 20% acetone in CH2Cl2), followed by trituration with 1:1 hexanes/ether, yielded 2-(3,4-dimethoxyphenyl)-9-methyl-7-(1,4-dioxa-8-azaspiro[4.5]decan-8-yl)-4H-pyrido[1,2-a]pyrimidin-4-one (878 mg, 50%) as a yellow solid. MS m/z 438.2 [M+H]+.

Step B: A solution of 2-(3,4-dimethoxyphenyl)-9-methyl-7-(1,4-dioxa-8-azaspiro[4.5]decan-8-yl)-4H-pyrido[1,2-a]pyrimidin-4-one (875 mg, 2.0 mmol) in CH2Cl2/dioxane (1:1 v/v, 28 mL) was treated with 6 N HCl (7 mL). The mixture was stirred at room temperature for 20 minutes, then made basic with aqueous K2CO3. The mixture was extracted into CH2Cl2. The organic layer was dried over MgSO4, filtered, and concentrated under vacuum. Trituration with 1:1 hexanes/acetone yielded 2-(3,4-dimethoxyphenyl)-9-methyl-7-(4-oxopiperidin-1-yl)-4H-pyrido[1,2-a]pyrimidin-4-one (758 mg, 96%) as a yellow solid. MS m/z 394.3 [M+H]+; 1H NMR (500 MHz, DMSO-d6): δ 8.27 (1H, d J=2.5 Hz), 8.08 (1H, s), 7.85 (1H, dd, J=8.5 Hz, 2.5 Hz), 7.81 (1H, m), 7.09 (1H, d, J=8.5 Hz), 6.96 (1H, s), 3.88 (3H, s), 3.84 (3H, s), 3.67 (4H, t, J=6 Hz), 2.64 (3H, s), 2.53 (4H, m, obscured by DMSO-d6).

Step C: A mixture of 2-(3,4-dimethoxyphenyl)-9-methyl-7-(4-oxopiperidin-1-yl)-4H-pyrido[1,2-a]pyrimidin-4-one (50 mg, 0.13 mmol), NaBH(OAc)3 (65 mg, 0.31 mmol), DCE (500 μL), and n-propylamine (40 μL, 0.49 mmol) was heated at 70° C. for 15 minutes. The reaction mixture was partitioned between aqueous K2CO3 and CH2Cl2. The organic layer was concentrated under vacuum. Purification by silica gel chromatography (10% MeOH in CH2Cl2, followed by 9:1:0.1 CH2Cl2:MeOH:NH4OH) yielded the title compound (Δ7 mg, 87%) as a yellow solid. M.P. 178-184° C.; MS m/z 437.5 [M+H]+; 1H NMR (500 MHz, DMSO-d6): δ 8.17 (1H, d, J=3 Hz), 8.00 (1H, m), 7.84 (1H, dd, J=8.5 Hz, 2 Hz), 7.80 (1H, d, J=2 Hz), 7.08 (1H, d, J=8.5 Hz), 6.95 (1H, s), 3.88 (3H, s), 3.84 (3H, s), 3.67 (2H, d, J=12.5 Hz), 2.84 (2H, t, J=12.5 Hz), 2.61 (3H, s), 2.57 (1H, m), 2.54 (2H, m, obscured by DMSO-d6 peak), 1.95 (2H, d, J=12.5 Hz), 1.41 (4H, m), 0.89 (3H, t, J=7.5 Hz).

As shown in Table 1 below, additional compounds disclosed herein may be prepared according to Example 53 by substituting the appropriate starting materials, reagents and reaction conditions.

Example 54

Preparation of Cpd 322

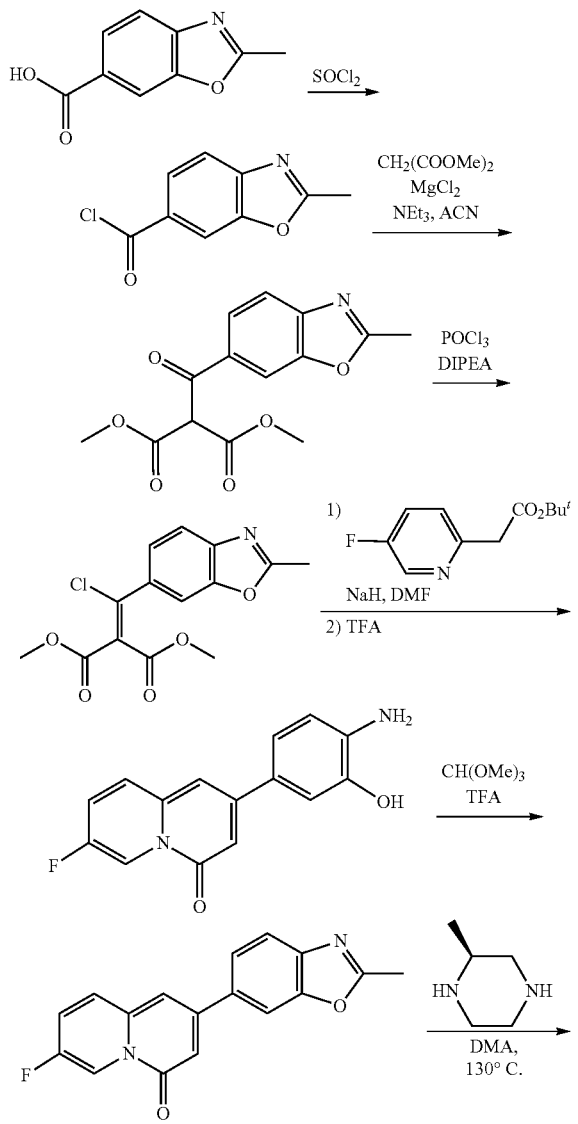

Step A: Into a mixture of 2-methylbenzo[d]oxazole-6-carboxylic acid (2.54 g, 14.4 mmol) and SOCl$_2$ (2.05 g, 17.2 mmol) in toluene (70 mL) was added 6 drops of DMF. The mixture was then stirred at 70° C. for 3 hours, cooled and evaporated to give 2-methylbenzo[d]oxazole-6-carbonyl chloride as an oil, which solidified on standing (2.9 g, 100%). $^1$H NMR (500 MHz, CDCl$_3$) δ 8.27-8.30 (1H, m), 8.13 (1H, dd, J=8.4, 1.7 Hz), 7.74 (1H, dd, J=8.5, 0.6 Hz), 2.73 (3H, s).

Step B: Following the procedure in Example 31, Part 1, Step A, reaction of 2-methylbenzo[d]oxazole-6-carbonyl chloride (2.9 g, 14.4 mmol), dimethylmalonate (1.9 g, 14.4 mmol), MgCl$_2$ (1.37 g, 14.4 mmol), and triethylamine (2.9 mL, 28.8 mmol) in acetonitrile (15 mL) provided dimethyl 2-(2-methylbenzo[d]oxazole-6-carbonyl)malonate (2.75 g, 66%). MS m/z 292.0 [M+H]$^+$.

Step C: Following the procedure in Example 31, Part 1, Step B, reaction of dimethyl 2-(2-methylbenzo[d]oxazole-6-carbonyl)malonate (2.75 g, 9.5 mmol), POCl$_3$ (10 mL) and DIPEA (2.6 mL, 15.8 mmol) provided dimethyl 2-(chloro(2-methylbenzo[d]oxazol-6-yl)methylene)malonate (0.7 g, 24%). MS m/z 310.1 [M+H]$^+$.

Step D: Following the procedure in Example 33, Step B and C, reaction of dimethyl 2-(chloro(2-methylbenzo[d]oxazol-6-yl)methylene)malonate (0.7 g, 2.3 mmol), tert-butyl 2-(5-fluoropyridin-2-yl)acetate (0.57 g, 2.7 mmol), prepared as in Example 33, Step A, NaH (0.18 g, 4.5 mmol) in DMF followed by reaction with TFA and water at 100° C. provided 2-(4-amino-3-hydroxyphenyl)-7-fluoro-4H-quinolizin-4-one (0.3 g, 48%). MS m/z 271.2 [M+H]$^+$.

Step E: Into a mixture of 2-(4-amino-3-hydroxyphenyl)-7-fluoro-4H-quinolizin-4-one (0.3 g, 1.1 mmol) and trimethyl orthoformate (1.4 mL, 11.1 mmol) was added TFA (0.13 mL, 1.8 mmol). The mixture was stirred for 2 hours at room temperature and then evaporated to give 7-fluoro-2-(2-methylbenzo[d]oxazol-6-yl)-4H-quinolizin-4-one (0.3 g, 99%). MS m/z 295.2 [M+H]$^+$.

Step F: A mixture of 7-fluoro-2-(2-methylbenzo[d]oxazol-6-yl)-4H-quinolizin-4-one (0.15 g, 0.51 mmol) and (S)-2-methylpiperazine (0.2 g, 2.0 mmol) in DMA (1.0 mL) was stirred at 130° C. overnight. The solvent was removed by a stream of nitrogen and the residue was purified with methanol in dichloromethane (10%) to give the title compound as a yellow solid (69 mg, 36%). M.P. 115-117° C.; MS m/z 375.3 [M+H]$^+$; $^1$H NMR (500 MHz, CDCl$_3$) δ 8.55 (1H, d, J=2.2 Hz), 7.79 (1H, d, J=1.3 Hz), 7.73 (1H, d, J=7.9 Hz), 7.64 (1H, dd, J=8.2, 1.6 Hz), 7.49 (1H, d, J=9.5 Hz), 7.33 (1H, d, J=2.5 Hz), 6.86-6.91 (2H, m), 3.60 (2H, br. s.), 3.25-3.34 (1H, m), 3.10-3.22 (2H, m), 2.93-3.03 (1H, m), 2.62-2.70 (4H, m), 1.31 (3H, d, J=6.3 Hz).

As shown in Table 1 below, additional compounds disclosed herein may be prepared according to Example 54 by substituting the appropriate starting materials, reagents and reaction conditions.

Example 55

Preparation of Cpd 380

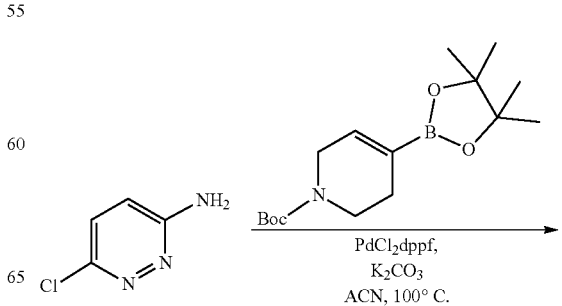

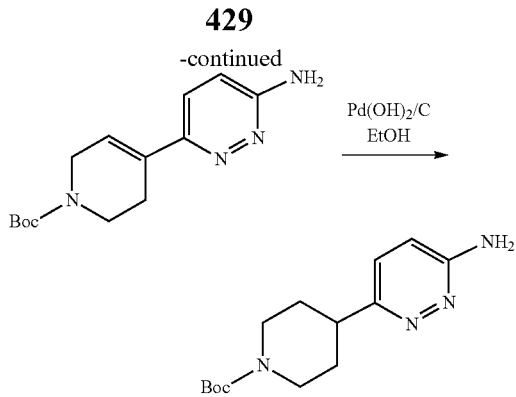

Part 1, Step A: A mixture of 6-chloropyridazin-3-amine (0.26 g, 2.0 mmol), tert-butyl 4-(4,4,5,5-tetramethyl-1,3,2-dioxaborolan-2-yl)-5,6-dihydropyridine-1(2H)-carboxylate (0.62 g, 2.0 mmol), PdCl$_2$dppf (0.16 g, 0.2 mmol), K$_2$CO$_3$ (2.0 M, 3.0 mL, 6.0 mmol) in acetonitrile (6.0 mL) was stirred at 100° C. overnight. Aqueous workup followed by purification with methanol in dichloromethane (0-10%) provided tert-butyl 4-(6-aminopyridazin-3-yl)-5,6-dihydropyridine-1(2H)-carboxylate (0.51 g, 93%). MS m/z 277.2 [M+H]$^+$.

Part 1, Step B: A solution of tert-butyl 4-(6-aminopyridazin-3-yl)-5,6-dihydropyridine-1(2H)-carboxylate (0.4 g, 1.4 mmol) in ethanol (25 mL) was hydrogenated using Pd(OH)$_2$ on carbon (20%, 0.2 g) in a Parr shaker (60 psi) overnight. The mixture was filtered through Celite, evaporated and purified with methanol in dichloromethane (0-10%) to give tert-butyl 4-(6-aminopyridazin-3-yl)piperidine-1-carboxylate (0.25 g, 62%). MS m/z 279.2 [M+H]$^+$.

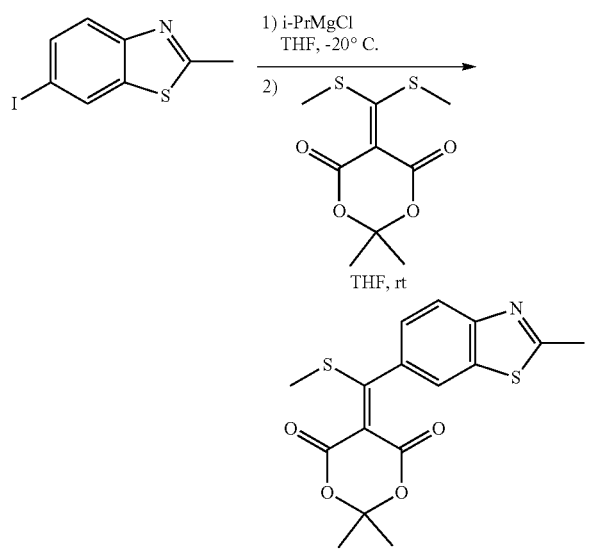

Part 2, Into a solution of 6-iodo-2-methylbenzo[d]thiazole (2.24 g, 7.3 mmol) in THF (15 mL) at −20° C. was added i-PrMgCl in THF (2.0 M, 3.7 mL, 7.4 mmol). The mixture was kept between −10° C. to −20° C. for 1 hour, then transferred via a cannula to a solution of 5-(bis(methylthio)methylene)-2,2-dimethyl-1,3-dioxane-4,6-dione (1.4 g, 5.6 mmol) in THF (15 mL). The reaction was slightly exothermic. The mixture was stirred at room temperature for 90 minutes before quenching with aqueous NH$_4$Cl solution. Aqueous workup followed by purification with ethyl acetate in dichloromethane (0-10%) provided 2,2-dimethyl-5-((2-methylbenzo[d]thiazol-6-yl)(methylthio)methylene)-1,3-dioxane-4,6-dione (1.26 g, 64%). MS m/z 350.1 [M+H]$^+$.

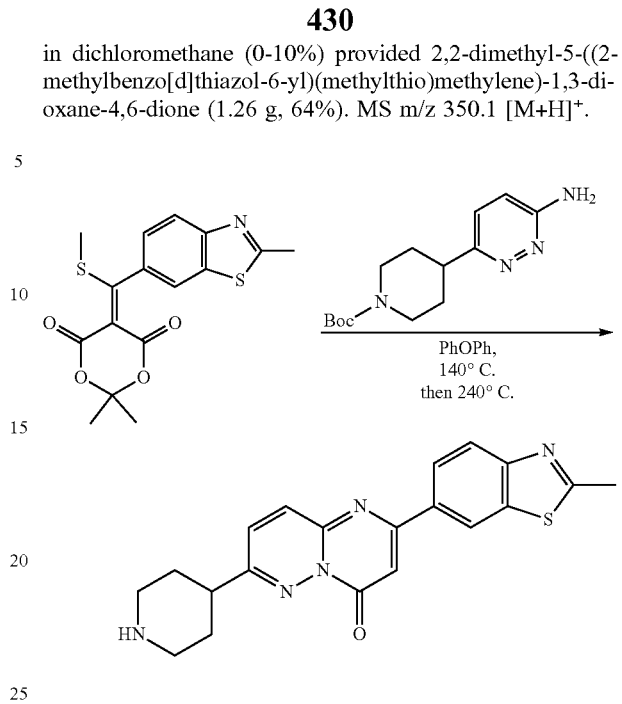

Part 3, A mixture of 2,2-dimethyl-5-((2-methylbenzo[d]thiazol-6-yl)(methylthio)methylene)-1,3-dioxane-4,6-dione (0.13 g, 0.36 mmol) and tert-butyl 4-(6-aminopyridazin-3-yl)piperidine-1-carboxylate (0.1 g, 0.36 mmol) in diphenyl ether (2.0 mL) was stirred at 140° C. for 1 hour. The temperature was then raised to 240° C. and stirred for 30 minutes. The mixture was evaporated and the residue was purified by prep HPLC to give the title compound as a yellow solid (33 mg, 24%) trifluoroacetic acid salt. M.P. 230-235° C.; MS m/z 378.2 [M+H]$^+$; $^1$H NMR (500 MHz, DMSO-d$_6$) δ 8.87-8.92 (1H, m), 8.28-8.33 (1H, m), 8.08 (1H, d, J=9.1 Hz), 7.99-8.04 (1H, m), 7.79 (1H, s), 7.26 (1H, s), 3.41-3.48 (2H, m), 3.22-3.32 (1H, m), 3.03-3.11 (2H, m), 2.84 (3H, s), 2.14-2.22 (2H, m), 2.08 (1H, s), 1.92-2.03 (2H, m).

Example 56

Preparation of Cpd 398

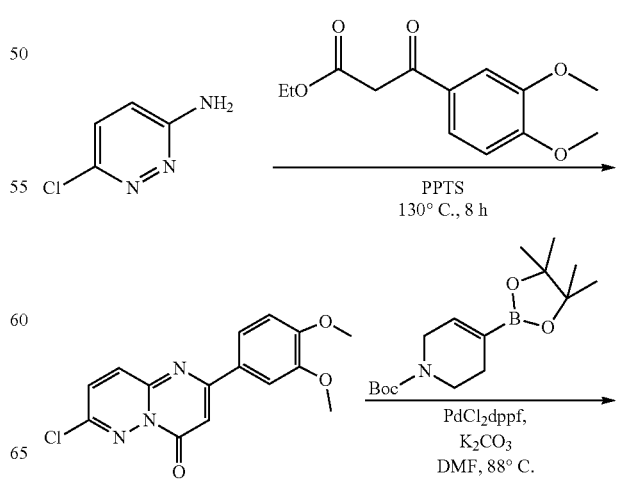

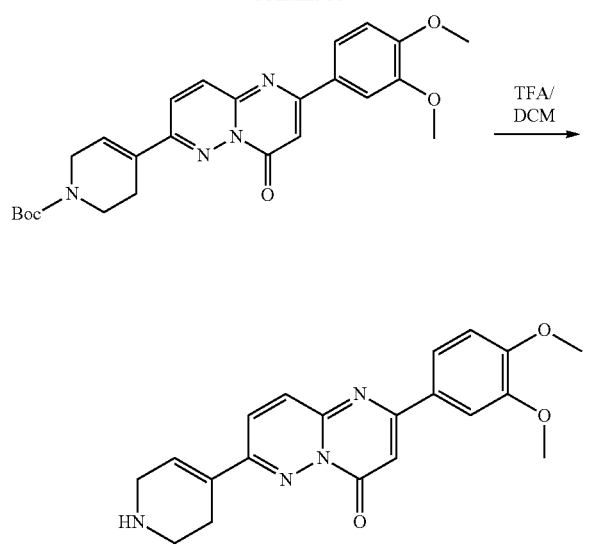

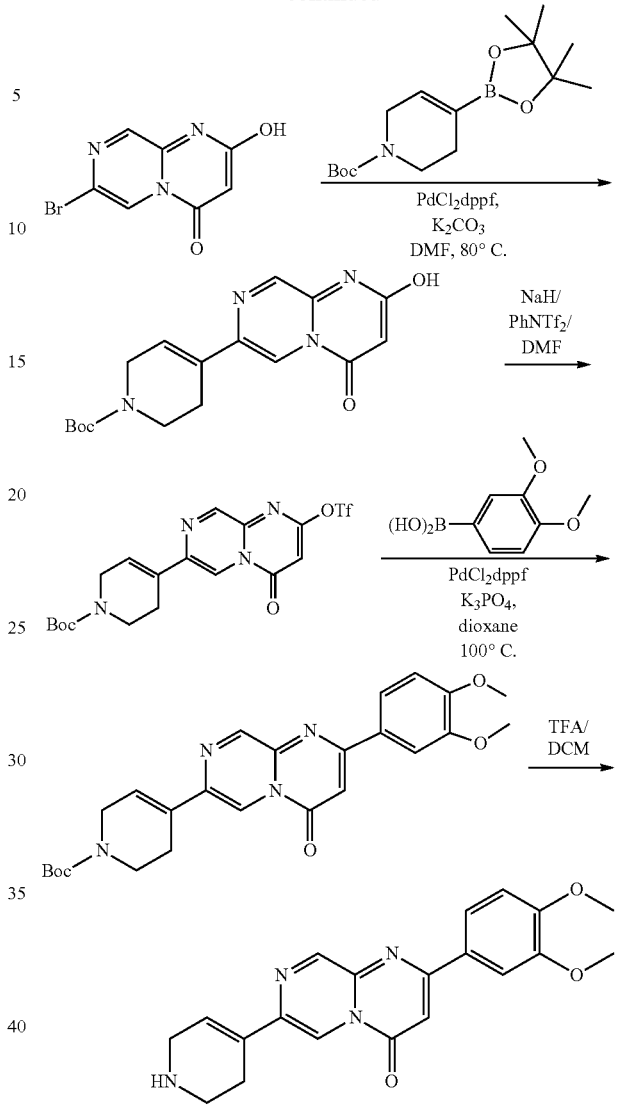

Step A: Following the procedure of Example 9, Step G, reaction of 6-chloropyridazin-3-amine (0.65 g, 5.0 mmol), ethyl 3-(3,4-dimethoxyphenyl)-3-oxopropanoate (1.77 g, 7.0 mmol) and PPTs (63 mg, 0.25 mmol) provided 7-chloro-2-(3,4-dimethoxyphenyl)-4H-pyrimido[1,2-b]pyridazin-4-one (0.23 g, 14%). MS m/z 318.1 [M+H]$^+$.

Step B: Following the procedure of Example 34, Step C, reaction of 7-chloro-2-(3,4-dimethoxyphenyl)-4H-pyrimido[1,2-b]pyridazin-4-one (0.12 g, 0.38 mmol), tert-butyl 4-(4,4,5,5-tetramethyl-1,3,2-dioxaborolan-2-yl)-5,6-dihydropyridine-1(2H)-carboxylate (0.14 g, 0.45 mmol), PdCl$_2$dppf (35 mg, 0.038 mmol), K$_2$CO$_3$ (2.0 M, 0.6 mL, 1.2 mmol) in acetonitrile (1.2 mL) provided tert-butyl 4-(2-(3,4-dimethoxyphenyl)-4-oxo-4H-pyrimido[1,2-b]pyridazin-7-yl)-5,6-dihydropyridine-1(2H)-carboxylate (100 mg, 56%). MS m/z 465.3 [M+H]$^+$.

Step C: Following the procedure of Example 34, Step D, treatment of tert-butyl 4-(2-(3,4-dimethoxyphenyl)-4-oxo-4H-pyrimido[1,2-b]pyridazin-7-yl)-5,6-dihydropyridine-1(2H)-carboxylate (100 mg, 0.21 mmol) with TFA (1.0 mL) and dichloromethane (1.0 mL) provided the title compound as a yellow solid (50 mg, 65%). M.P.195-200° C.; MS m/z 365.3 [M+H]$^+$; $^1$H NMR (500 MHz, DMSO-d$_6$) δ 8.13 (1H, d, J=9.8 Hz), 7.96 (1H, d, J=9.8 Hz), 7.82 (1H, dd, J=8.5, 2.2 Hz), 7.74 (1H, d, J=2.2 Hz), 7.15 (1H, s), 7.08 (1H, d, J=8.8 Hz), 7.01 (1H, br. s.), 3.87 (3H, s), 3.83 (3H, s), 3.57 (2H, br. s.), 3.00 (2H, br. s.), 2.58 (2H, br. s.).

Example 57

Preparation of Cpd 402

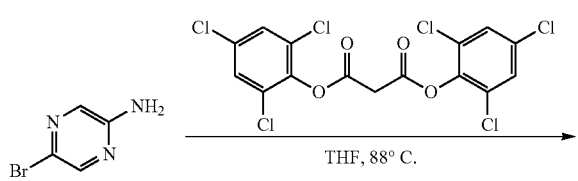

Step A: A mixture of 5-bromopyrazin-2-amine (0.17 g, 1.0 mmol) and bis(2,4,6-trichlorophenyl)malonate (0.56 g, 1.2 mmol) in THF (4.0 mL) was stirred at 88° C. for 1 hour. The mixture was then filtered and the solid was washed with ethyl acetate. The cake was collected and dried to give 7-bromo-2-hydroxy-4H-pyrazino[1,2-a]pyrimidin-4-one (0.18 g, 74%). MS m/z 242.0 [M+H]$^+$, 244.0 [M+2H]$^+$.

Step B: Following the procedure of Example 34, Step C, reaction of 7-bromo-2-hydroxy-4H-pyrazino[1,2-a]pyrimidin-4-one (0.18 g, 0.74 mmol), tert-butyl 4-(4,4,5,5-tetramethyl-1,3,2-dioxaborolan-2-yl)-5,6-dihydropyridine-1(2H)-carboxylate (0.27 g, 0.89 mmol), PdCl$_2$dppf (60 mg, 0.074 mmol), K$_2$CO$_3$ (0.31 g, 2.2 mmol) in DMF (2.5 mL) provided tert-butyl 4-(2-hydroxy-4-oxo-4H-pyrazino[1,2-a]pyrimidin-7-yl)-5,6-dihydropyridine-1(2H)-carboxylate (0.18 g, 70%). MS m/z 345.3 [M+H]$^+$.

Step C: Into a solution of tert-butyl 4-(2-hydroxy-4-oxo-4H-pyrazino[1,2-a]pyrimidin-7-yl)-5,6-dihydropyridine-1(2H)-carboxylate (0.18 g, 0.52 mmol) in DMF (3.0 mL) at room temperature was added NaH (60%, 23 mg, 0.57 mmol). The mixture was stirred for 15 minutes then PhNTf$_2$ (0.22 g, 0.62 mmol) was added in one portion. The mixture was stirred overnight. Aqueous workup followed by purification with ethyl acetate in dichloromethane (0-20%) provided tert-butyl 4-(4-oxo-2-(trifluoromethylsulfonyloxy)-4H-pyrazino[1,2-a]pyrimidin-7-yl)-5,6-dihydropyridine-1(2H)-carboxylate (0.1 g, 40%). MS m/z 377.1 [M−Boc+H]⁺.

Step D: A mixture of tert-butyl 4-(4-oxo-2-(trifluoromethylsulfonyloxy)-4H-pyrazino[1,2-a]pyrimidin-7-yl)-5,6-dihydropyridine-1(2H)-carboxylate (80 mg, 0.17 mmol), 3,4-dimethoxyphenylboronic acid (46 mg, 0.25 mmol), PdCl₂dppf (14 mg, 0.017 mmol), K₃PO₄ (54 mg, 0.25 mmol) in dioxane (2.0 mL) was stirred at 100° C. for 24 hours. The mixture was filtered, evaporated and purified with ethyl acetate in dichloromethane (0-20%) to give tert-butyl 4-(2-(3,4-dimethoxyphenyl)-4-oxo-4H-pyrazino[1,2-a]pyrimidin-7-yl)-5,6-dihydropyridine-1(2H)-carboxylate (43 mg, 55%). ¹H NMR (500 MHz, CDCl₃) δ 9.10 (1H, s), 8.61 (1H, s), 7.72 (1H, s), 7.70 (1H, d, J=1.8 Hz), 7.00 (3H, m), 4.19-4.26 (2H, m), 4.03 (3H, s), 3.98 (3H, s), 3.69-3.76 (2H, m), 2.56-2.67 (2H, m), 1.51 (9H, s).

Step E: Following the procedure of Example 34, Step D, treatment of tert-butyl 4-(2-(3,4-dimethoxyphenyl)-4-oxo-4H-pyrazino[1,2-a]pyrimidin-7-yl)-5,6-dihydropyridine-1(2H)-carboxylate (43 mg, 0.09 mmol) with TFA (1.0 mL) and dichloromethane (1.0 mL) provided the title compound as a yellow solid (34 mg, 100%). M.P. 205-208° C.; MS m/z 365.4 [M+H]⁺; NMR (500 MHz, DMSO-d₆) δ 9.15 (1H, d, J=0.9 Hz), 8.41 (1H, s), 7.85-7.94 (1H, m), 7.78 (1H, d, J=1.9 Hz), 7.27 (1H, s), 7.11 (1H, d, J=8.5 Hz), 6.97-7.05 (1H, m), 3.89 (3H, s), 3.84 (3H, s), 3.58 (2H, br. s.), 3.21-3.42 (3H, m), 3.07 (2H, t, J=5.7 Hz).

As shown in Table 1 below, additional compounds disclosed herein may be prepared according to Example 57 by substituting the appropriate starting materials, reagents and reaction conditions.

Example 58

Preparation of Cpd 499

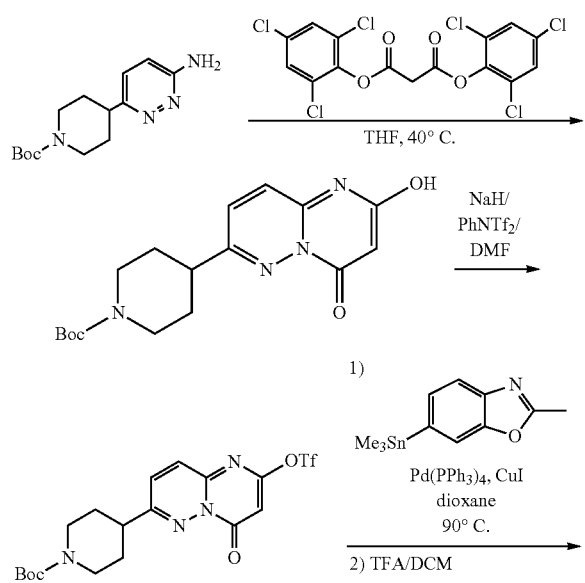

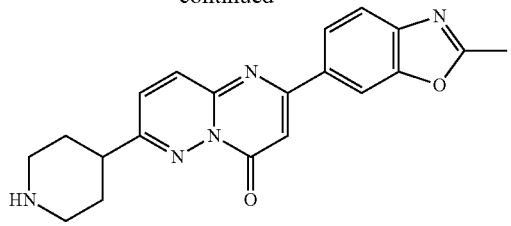

Step A: A mixture of tert-butyl 4-(6-aminopyridazin-3-yl)piperidine-1-carboxylate (0.88 g, 3.2 mmol) and bis(2,4,6-trichlorophenyl) malonate (1.76 g, 3.8 mmol) in THF (12 mL) was stirred at 40° C. for 1 hour. The mixture was then evaporated and purified with methanol in dichloromethane (0-10%) to give tert-butyl 4-(2-hydroxy-4-oxo-4H-pyrimido[1,2-b]pyridazin-7-yl)piperidine-1-carboxylate (0.69 g, 63%). MS m/z 347.2 [M+H]⁺.

Step B: Following the procedure of Example 57, Step C, reaction of tert-butyl 4-(2-hydroxy-4-oxo-4H-pyrimido[1,2-b]pyridazin-7-yl)piperidine-1-carboxylate (0.69 g, 2.0 mmol), NaH (60%, 88 mg, 2.2 mmol), PhNTf₂ (0.79 g, 2.2 mmol) in DMF (12 mL) provided tert-butyl 4-(4-oxo-2-(trifluoromethylsulfonyloxy)-4H-pyrimido[1,2-b]pyridazin-7-yl)piperidine-1-carboxylate (0.87 g, 91%). ¹H NMR (500 MHz, CDCl₃) δ 7.90 (1H, d, J=9.5 Hz), 7.61 (1H, d, J=9.5 Hz), 6.45 (1H, s), 4.28-4.36 (2H, m), 3.20-3.30 (1H, m), 2.82-2.93 (2H, m), 1.94-2.02 (2H, m), 1.75-1.85 (2H, m), 1.49 (9H, s).

Step C: A mixture of tert-butyl 4-(4-oxo-2-(trifluoromethylsulfonyloxy)-4H-pyrimido[1,2-b]pyridazin-7-yl)piperidine-1-carboxylate (0.24 g, 0.5 mmol), 2-methyl-6-(trimethylstannyl)benzo[d]oxazole (0.18 g, 0.6 mmol), Pd(PPh₃)₄ (58 mg, 0.05 mmol), CuI (23 mg, 0.12 mmol) in dioxane (2.0 mL) was stirred at 90° C. overnight. The mixture was concentrated and purified with methanol in dichloromethane (0-10%). The desired fractions were combined and evaporated. The residue was treated with TFA (1.0 mL) and dichloromethane (1.0 mL) and worked up as described in Example 34, Step D to give the title compound as a yellow solid (86 mg, 48%). M.P. 126-128° C.; MS m/z 362.2 [M+H]⁺; ¹H NMR (500 MHz, methanol-d₄) δ 8.20 (1H, s), 7.91-7.99 (2H, m), 7.67 (2H, d, J=8.2 Hz), 7.07 (1H, s), 3.45 (2H, d, J=12.3 Hz), 3.07-3.21 (2H, m), 3.30-3.24 (1H, m), 2.61 (3H, s), 2.14 (4H, br. s.).

As shown in Table 1 below, additional compounds disclosed herein may be prepared according to Example 58 by substituting the appropriate starting materials, reagents and reaction conditions.

Example 59

Preparation of Cpd 502

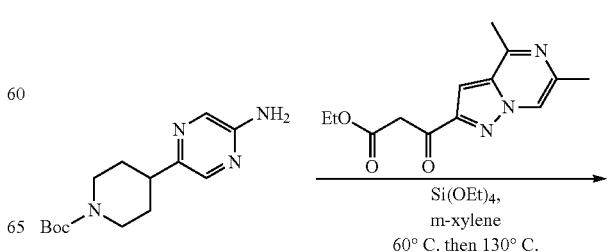

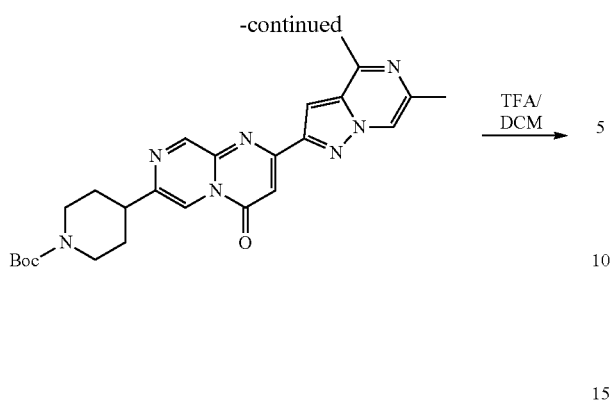

Step A: A mixture of tert-butyl 4-(5-aminopyrazin-2-yl)piperidine-1-carboxylate (0.2 g, 0.72 mmol), ethyl 3-(4,6-dimethylpyrazolo[1,5-a]pyrazin-2-yl)-3-oxopropanoate (0.21 g, 0.79 mmol), Si(OEt)$_4$ (0.16 mL, 0.72 mmol), PPTs (18 mg, 0.072 mmol) in m-xylene (0.36 mL) was stirred at 60° C. for 1 hour then 130° C. overnight. The mixture was cooled and loaded directly onto a silica column and purified with methanol in dichloromethane (0-10%). Further purification with ethyl acetate in dichloromethane (20-100%) provided tert-butyl 4-(2-(4,6-dimethylpyrazolo[1,5-a]pyrazin-2-yl)-4-oxo-4H-pyrazino[1,2-a]pyrimidin-7-yl)piperidine-1-carboxylate (0.117 g, 34%). MS m/z Δ76.4 [M+H]$^+$.

Step B: Following the procedure of Example 34, Step D, treatment of tert-butyl 4-(2-(4,6-dimethylpyrazolo[1,5-a]pyrazin-2-yl)-4-oxo-4H-pyrazino[1,2-a]pyrimidin-7-yl)piperidine-1-carboxylate (117 mg, 0.25 mmol) with TFA (1.0 mL) and dichloromethane (2.0 mL) provided the title compound as a yellow solid (93 mg, 100%). MS m/z 376.4 [M+H]$^+$; $^1$H NMR (500 MHz, methanol-d$_4$) δ 9.13 (1H, d, J=1.3 Hz), 8.53 (1H, s), 8.27 (1H, d, J=0.6 Hz), 7.55 (1H, d, J=1.3 Hz), 7.28 (1H, s), 3.27-3.34 (2H, m), 2.99-3.09 (1H, m), 2.85-2.96 (2H, m), 2.75 (3H, s), 2.47 (3H, d, J=0.9 Hz), 2.05-2.14 (2H, m), 1.84-1.95 (2H, m).

As shown in Table 1 below, additional compounds disclosed herein may be prepared according to Example 59 by substituting the appropriate starting materials, reagents and reaction conditions.

Example 60

Preparation of Cpd 512

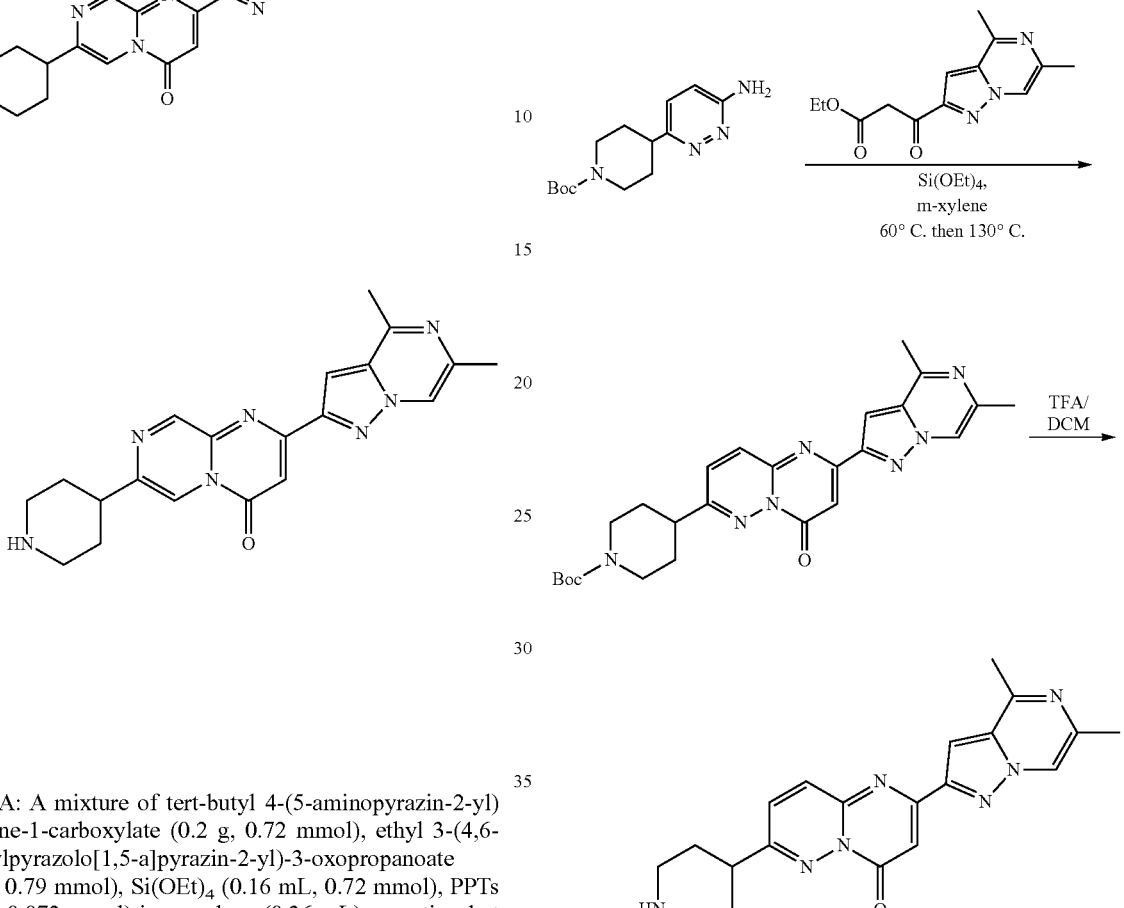

Step A: Following the procedure of Example 59, Step A, the reaction of tert-butyl 4-(6-aminopyridazin-3-yl)piperidine-1-carboxylate (0.28 g, 1.0 mmol), ethyl 3-(4,6-dimethylpyrazolo[1,5-a]pyrazin-2-yl)-3-oxopropanoate (0.28 g, 1.1 mmol), Si(OEt)$_4$ (0.22 mL, 1.0 mL), PPTs (25 mg, 0.1 mmol) in m-xylene (0.5 mL) provided tert-butyl 4-(2-(4,6-dimethylpyrazolo[1,5-a]pyrazin-2-yl)-4-oxo-4H-pyrimido[1,2-b]pyridazin-7-yl)piperidine-1-carboxylate (60 mg, 13%). MS m/z Δ76.4 [M+H]$^+$.

Step B: Following the procedure of Example 34, Step D, treatment of tert-butyl 4-(2-(4,6-dimethylpyrazolo[1,5-a]pyrazin-2-yl)-4-oxo-4H-pyrimido[1,2-b]pyridazin-7-yl)piperidine-1-carboxylate (60 mg, 0.13 mmol) with TFA (1.0 mL) and dichloromethane (1.0 mL) provided the title compound as a yellow solid (Δ7 mg, 100%). MS m/z 376.4 [M+H]$^+$; $^1$H NMR (500 MHz, methanol-d$_4$) δ 8.27-8.31 (1H, m), 8.06 (1H, d, J=9.5 Hz), 7.78 (1H, s), 7.57 (1H, d, J=0.9 Hz), 7.39 (1H, s), 3.25-3.30 (2H, m), 3.15-3.23 (1H, m), 2.82-2.90 (2H, m), 2.79 (3H, s), 2.51 (3H, d, J=0.9 Hz), 2.02-2.09 (2H, m), 1.85-1.96 (2H, m).

Example 61

Preparation of Cpd 586

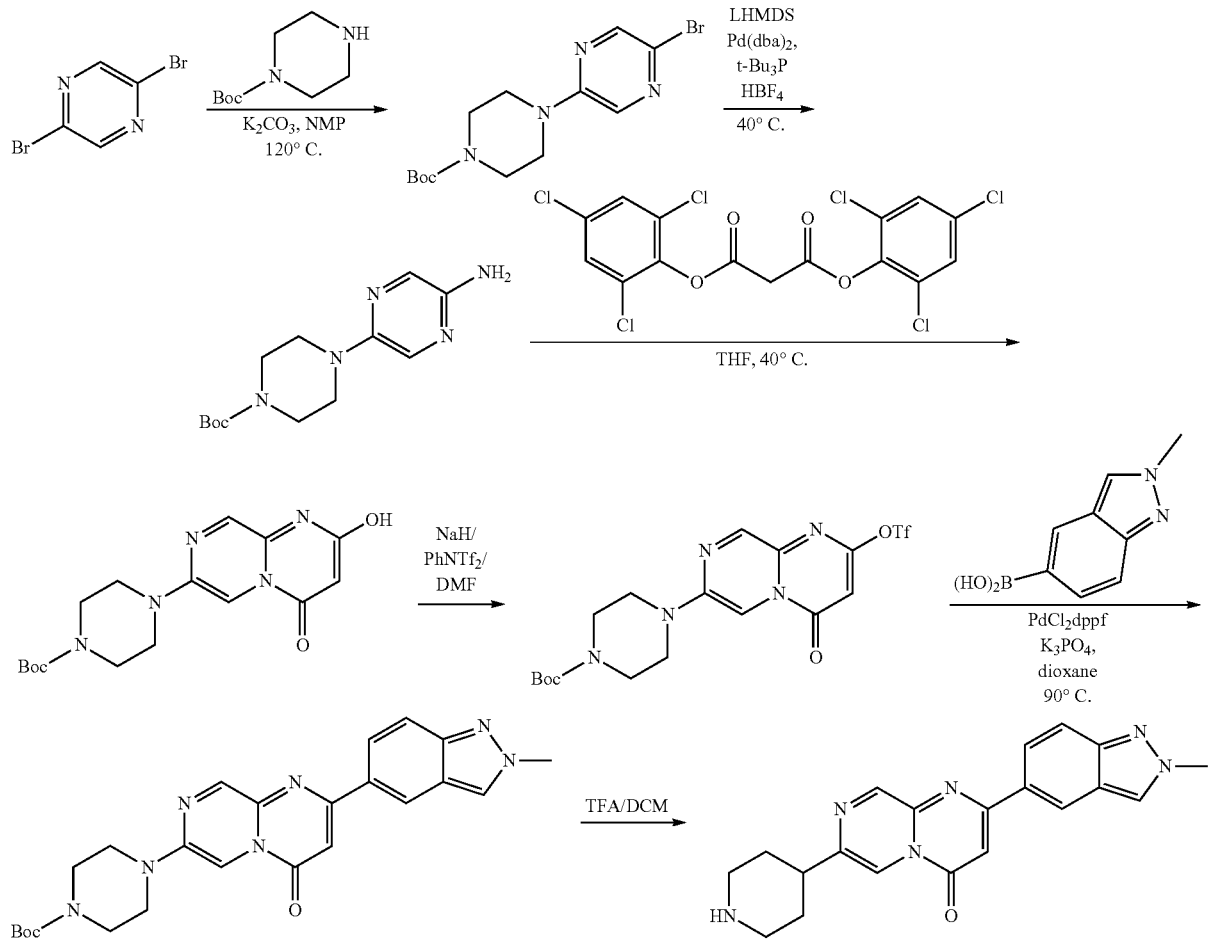

Step A: A mixture of 2,5-dibromopyrazine (1.45 g, 6.1 mmol), tert-butyl piperazine-1-carboxylate (1.13 g, 6.1 mmol) and K$_2$CO$_3$ (1.26 g, 9.2 mmol) in NMP (6.0 mL) was stirred at 120° C. overnight. The mixture was cooled, then aqueous workup followed by purification with ethyl acetate in dichloromethane (0-15%) provided tert-butyl 4-(5-bromopyrazin-2-yl)piperazine-1-carboxylate (1.45 g, 69%). MS m/z 343.3 [M+H]$^+$, 345.3 [M+2+H]t Step B: A mixture of tert-butyl 4-(5-bromopyrazin-2-yl)piperazine-1-carboxylate (1.25 g, 3.6 mmol), LiHMDS (1.0 M, 4.4 mL, 4.4 mmol), Pd(dba)$_2$ (105 mg, 0.18 mmol), P$^t$Bu$_3$ HBF$_4$ (53 mg, 0.18 mmol) in toluene (4.4 mL) was stirred at 40° C. overnight under an Ar atmosphere. The mixture was then cooled, treated with acetonitrile (2.0 mL) and 1N HCl (0.2 mL), stirred for 15 minutes and purified over silica gel with methanol in dichloromethane (0-10%) to give tert-butyl 4-(5-aminopyrazin-2-yl)piperazine-1-carboxylate (0.96 g, 94%). MS m/z 280.2 [M+H]$^+$.

Step C: A mixture of tert-butyl 4-(5-aminopyrazin-2-yl)piperazine-1-carboxylate (0.68 g, 2.4 mmol), bis(2,4,6-trichlorophenyl) malonate (1.36 g, 2.9 mmol) in THF (15 mL) was stirred at room temperature for 64 hours. The mixture was then filtered. The solid was washed with ethyl acetate and dried to give tert-butyl 4-(2-hydroxy-4-oxo-4H-pyrazino[1,2-a]pyrimidin-7-yl)piperazine-1-carboxylate (0.65 g, 77%). MS m/z 348.3 [M+H]$^+$.

Step D: Following the procedure in Example 57, Step C, reaction of tert-butyl 4-(2-hydroxy-4-oxo-4H-pyrazino[1,2-a]pyrimidin-7-yl)piperazine-1-carboxylate (0.65 g, 1.9 mmol), NaH (60%, 82 mg, 2.1 mmol) and PhNTf$_2$ (0.74 g, 2.1 mmol) in DMF (10 mL) provided tert-butyl 4-(4-oxo-2-(trifluoromethylsulfonyloxy)-4H-pyrazino[1,2-a]pyrimidin-7-yl)piperazine-1-carboxylate (0.72 g, 80%). MS m/z 480.2 [M+H]$^+$.

Step E: Following the procedure in Example 57, Step D, reaction of tert-butyl 4-(4-oxo-2-(trifluoromethylsulfonyloxy)-4H-pyrazino[1,2-a]pyrimidin-7-yl)piperazine-1-carboxylate (0.38 g, 0.79 mmol) and 2-methyl-2H-indazol-5-ylboronic acid (0.21 g, 1.2 mmol) in the presence of PdCl$_2$dppf (64 mg, 0.08 mmol) an K$_3$PO$_4$ (0.25 g, 1.2 mmol) in dioxane (6.0 mL) provided tert-butyl 4-(2-(2-methyl-2H-indazol-5-yl)-4-oxo-4H-pyrazino[1,2-a]pyrimidin-7-yl)piperazine-1-carboxylate (0.22 g, 60%). MS m/z 462.3 [M+H]$^+$.

Step F: Following the procedure of Example 34, Step D, treatment of tert-butyl 4-(2-(2-methyl-2H-indazol-5-yl)-4-oxo-4H-pyrazino[1,2-a]pyrimidin-7-yl)piperazine-1-carboxylate (0.22 g, 0.48 mmol) with TFA (1.0 mL) and dichloromethane (1.0 mL) provided the title compound as a yellow solid (0.17 mg, 99%). M.P. 160-162° C.; MS m/z 362.3 [M+H]$^+$; $^1$H NMR (500 MHz, methanol-d$_4$) δ 9.04 (1H, d, J=1.3 Hz), 8.50 (1H, dd, J=1.6, 0.9 Hz), 8.18 (1H, s), 7.97-8.02 (2H, m), 7.71 (1H, d, J=9.1 Hz), 7.01 (1H, s), 4.23 (3H, s), 3.61-3.67 (4H, m), 3.13-3.20 (4H, m).

Example 62

Preparation of Cpd 695

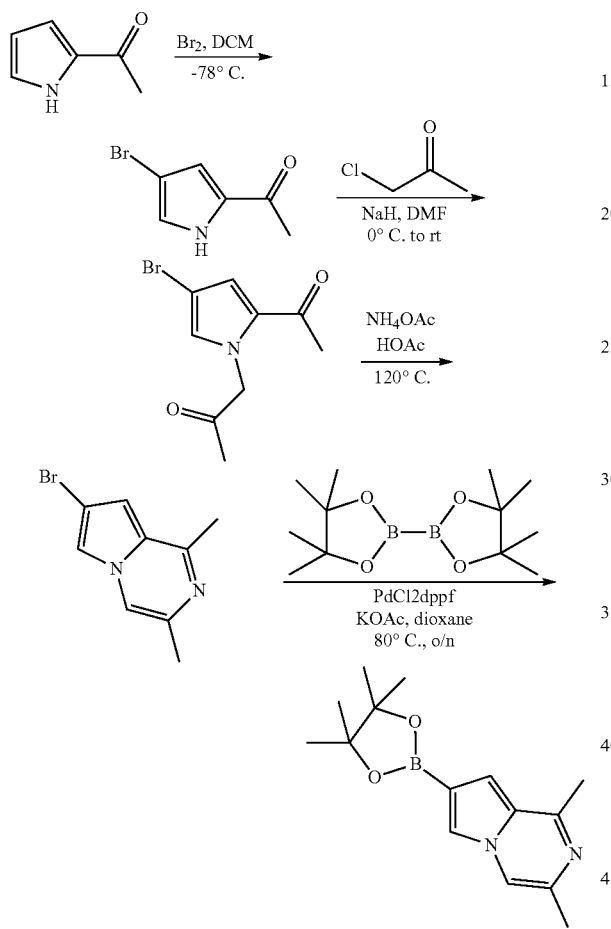

Part 1, Step A: Into a suspension of 1-(1H-pyrrol-2-yl)ethanone (2.18 g, 20 mmol) in dichloromethane (100 mL) at −78° C. was added a solution of bromine (1.23 mL, 24 mmol) in dichloromethane (25 mL) dropwise over 30 minutes. The mixture was stirred for 10 minutes at −78° C. after the addition and then poured into ice-water. The aqueous layer was extracted with dichloromethane. The organic extracts were combined, dried and evaporated. The residue was purified with ethyl acetate in dichloromethane (0-20%) to give 1-(4-bromo-1H-pyrrol-2-yl)ethanone (3.48 g, 92%). MS m/z 188.0 [M+H]$^+$, 190.0 [M+2+H]$^+$.

Part 1, Step B: Into a solution of 1-(4-bromo-1H-pyrrol-2-yl)ethanone (3.48 g, 18.5 mmol) in DMF (40 mL) at 0° C. was added NaH (60%, 0.81 g, 20.4 mmol) portionwise. The temperature was allowed to rise to room temperature and 1-chloropropan-2-one (1.54 mL, 19.4 mmol) was added dropwise. The mixture was stirred at room temperature overnight. Aqueous workup followed by purification with ethyl acetate in hexane (5-30%) provided 1-(2-acetyl-4-bromo-1H-pyrrol-1-yl)propan-2-one (2.9 g, 64%). $^1$H NMR (500 MHz, CDCl$_3$) δ 6.99 (1H, d, J=1.9 Hz), 6.77 (1H, d, J=1.6 Hz), 5.00 (2H, s), 2.39 (3H, s), 2.25 (3H, s).

Part 1, Step C: A mixture of 1-(2-acetyl-4-bromo-1H-pyrrol-1-yl)propan-2-one (2.9 g, 11.9 mmol) and ammonium acetate (18 g, 238 mmol) in acetic acid (100 mL) was stirred at 120° C. overnight. The acetic acid was then removed by rotary evaporation, then ice water was added to the residue and the mixture was made basic with NaOH to pH 9. The mixture was extracted with ethyl acetate. The organic extracts were combined, dried, and evaporated. The residue was purified with ethyl acetate in dichloromethane (0-10%) to provide 7-bromo-1,3-dimethylpyrrolo[1,2-a]pyrazine (2.4 g, 90%). MS m/z 225.1 [M+H]$^+$, 227.1 [M+2+H]t Part 1, Step D: Following the procedure in Example 14, Part 2, reaction of 7-bromo-1,3-dimethylpyrrolo[1,2-a]pyrazine (0.67 g, 3.0 mmol), 4,4,4',4',5,5,5',5'-octamethyl-2,2'-bi(1,3,2-dioxaborolane) (0.99 g, 3.9 mmol), PdCl$_2$dppf (0.24 g, 0.3 mmol), KOAc (0.88 g, 9.0 mmol) in dioxane (10 mL) provided 1,3-dimethyl-7-(4,4,5,5-tetramethyl-1,3,2-dioxaborolan-2-yl)pyrrolo[1,2-a]pyrazine, which was used directly in the next step without further purification. MS m/z 191.2 [M−pinacol+H]$^+$.

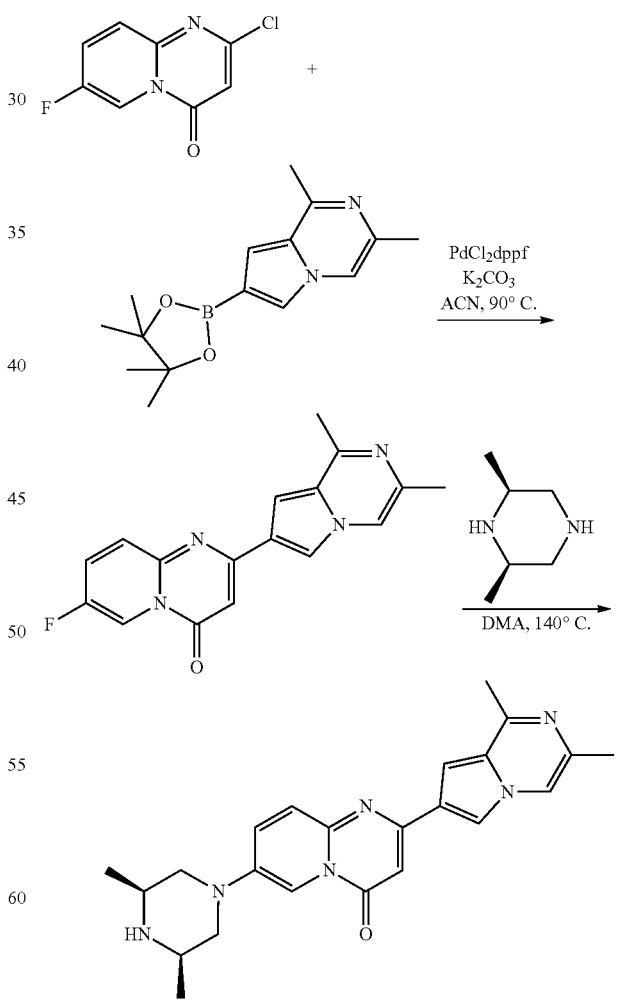

Part 2, Step A: Following the procedure in Example 14, Part 3, Step A, reaction of 2-chloro-7-fluoro-4H-pyrido[1, 2-a]pyrimidin-4-one (0.3 g, 1.5 mmol) with 1,3-dimethyl-7-(4,4,5,5-tetramethyl-1,3,2-dioxaborolan-2-yl)pyrrolo[1,2-a]pyrazine (1.5 mmol) provided 2-(1,3-dimethylpyrrolo[1,2-a]pyrazin-7-yl)-7-fluoro-4H-pyrido[1,2-a]pyrimidin-4-one (0.34 g, 74%). MS m/z 309.2 [M+H]⁺.

Part 2, Step B: Following the procedure in Example 14, Part 3, Step B, reaction of 2-(1,3-dimethylpyrrolo[1,2-a]pyrazin-7-yl)-7-fluoro-4H-pyrido[1,2-a]pyrimidin-4-one (0.14 g, 0.45 mmol) with 2,6-dimethylpiperazine (0.26 g, 2.27 mmol) provided the title compound as a yellow solid (57 mg, 32%). M.P. 254-256° C.; MS m/z 403.4 [M+H]⁺; ¹H NMR (500 MHz, methanol-d₄) δ 8.20 (1H, d, J=2.8 Hz), 7.99 (1H, d, J=1.6 Hz), 7.84-7.90 (1H, m), 7.72 (1H, d, J=0.6 Hz), 7.58 (1H, d, J=9.5 Hz), 7.25 (1H, t, J=1.1 Hz), 6.69 (1H, s), 3.60 (2H, d, J=9.5 Hz), 3.03-3.11 (2H, m), 2.62 (3H, s), 2.37 (2H, t, J=11.3 Hz), 2.31 (3H, d, J=0.9 Hz), 1.21 (6H, d, J=6.3 Hz).

As shown in Table 1 below, additional compounds disclosed herein may be prepared according to Example 62 by substituting the appropriate starting materials, reagents and reaction conditions.

Example 63

Preparation of Cpd 731

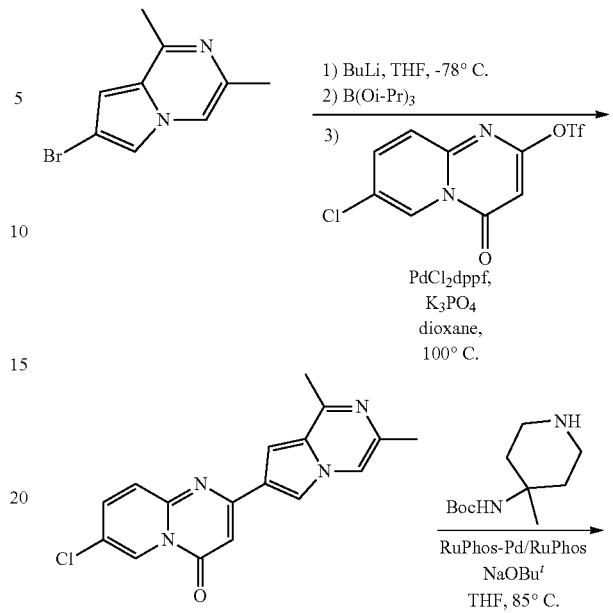

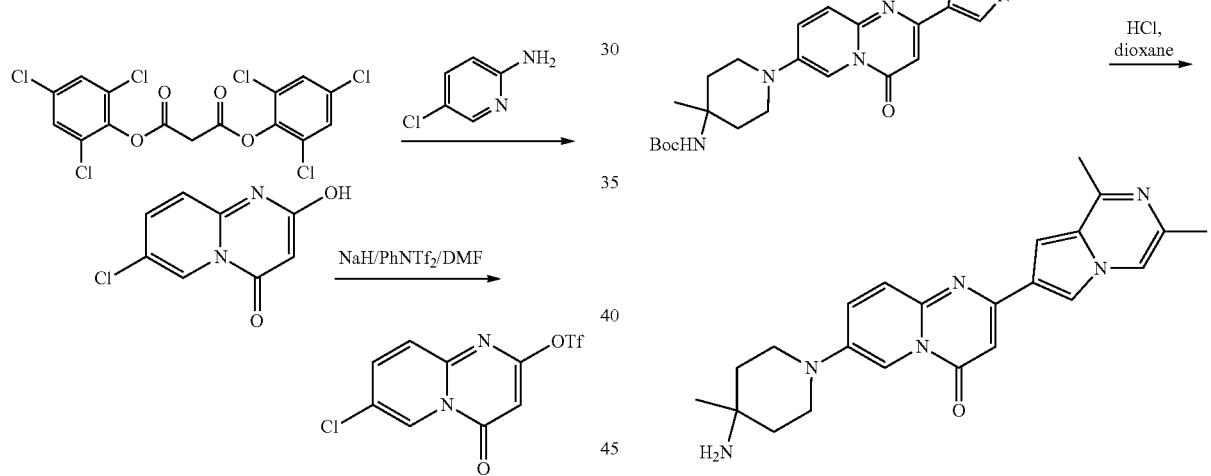

Part 1, Step A: Following the procedure in Example 57, Step A, reaction of 5-chloropyridin-2-amine (2.57 g, 20 mmol) and bis(2,4,6-trichlorophenyl) malonate (10.2 g, 22 mmol) in THF (100 mL) provided 7-chloro-2-hydroxy-4H-pyrido[1,2-a]pyrimidin-4-one (3.89 g, 97%). ¹H NMR (500 MHz, DMSO-d₆) δ 12.01 (1H, br. s.), 8.89 (1H, d, J=2.2 Hz), 8.10 (1H, dd, J=9.3, 2.4 Hz), 7.44 (1H, d, J=9.5 Hz), 5.19 (1H, br. s.).

Part 1, Step B: Following the procedure in Example 57, Step C, reaction of 7-chloro-2-hydroxy-4H-pyrido[1,2-a]pyrimidin-4-one (3.89 g, 19.8 mmol) with NaH (60%, 0.87 g, 21.8 mmol) and PhNTf₂ (7.78 g, 21.8 mmol) in DMF (50 mL) provided 7-chloro-4-oxo-4H-pyrido[1,2-a]pyrimidin-2-yltrifluoromethanesulfonate (5.9 g, 91%). MS m/z 370.0 [M+H]⁺.

Part 2, Step A: Into a solution of 7-bromo-1,3-dimethylpyrrolo[1,2-a]pyrazine (1.1 g, 4.9 mmol) in THF (20 mL) at –78° C. was added BuLi (1.6 M, 4.7 mL, 7.5 mmol) dropwise. The mixture was stirred at –78° C. for 30 minutes, triisopropyl borate (1.7 mL, 7.4 mmol) was added. The temperature was allowed to rise to room temperature slowly. The reaction was quenched with water (1.0 mL) and the mixture was evaporated to dryness under vacuum. Into the residue was added 7-chloro-4-oxo-4H-pyrido[1,2-a]pyrimidin-2-yl trifluoromethanesulfonate (1.6 g, 4.9 mmol), PdCl₂dppf (0.4 g, 0.49 mmol), K₃PO₄ (1.55 g, 7.3 mmol) and dioxane (40 mL). The mixture was stirred at 100° C. overnight under an Ar atmosphere, after which the mixture was cooled, evaporated and purified through silica with methanol in dichloromethane (0-10%) to give 7-chloro-2-(1,3-dimethylpyrrolo[1,2-a]pyrazin-7-yl)-4H-pyrido[1,2-a]pyrimidin-4-one (0.34 g, 22%). MS m/z 325.2 [M+H]⁺.

Part 2, Step B: A mixture of 7-chloro-2-(1,3-dimethylpyrrolo[1,2-a]pyrazin-7-yl)-4H-pyrido[1,2-a]pyrimidin-4-one (0.2 g, 0.62 mmol), tert-butyl 4-methylpiperidin-4-ylcarbamate (0.17 g, 0.8 mmol), RuPhos-Pd (22 mg, 0.031 mmol), RuPhos (14 mg, 0.031 mmol) and sodium t-butoxide (83 mg, 0.87 mmol) in THF (1.5 mL) was stirred at 85° C. overnight under an Ar atmosphere. The mixture was then cooled, into which was added acetic acid (1.4 eq) and then purified over silica with methanol in dichloromethane (0-10%) to give tert-butyl 1-(2-(1,3-dimethylpyrrolo[1,2-a]pyrazin-7-yl)-4-oxo-4H-pyrido[1,2-a]pyrimidin-7-yl)-4-methylpiperidin-4-ylcarbamate (70 mg, 22%). MS m/z 503.4 [M+H]$^+$.

Part 2, Step C: The compound tert-butyl 1-(2-(1,3-dimethylpyrrolo[1,2-a]pyrazin-7-yl)-4-oxo-4H-pyrido[1,2-a]pyrimidin-7-yl)-4-methylpiperidin-4-ylcarbamate (70 mg, 0.14 mmol) was treated with HCl in dioxane (4 N, 1.0 mL) for 30 minutes. The solvent was then removed. The residue was re-treated with ammonia in methanol and evaporated. The residue was purified with methanol in dichloromethane (0-10%) to give the title compound as a yellow solid (36 mg, 64%). M.P. 244-246° C.; MS m/z 403.3 [M+H]$^+$; $^1$H NMR (500 MHz, DMSO-d$_6$) δ 8.22-8.27 (2H, m), 8.04 (1H, dd, J=9.8, 2.8 Hz), 7.96 (1H, s), 7.60 (1H, d, J=9.8 Hz), 7.41 (1H, t, J=1.3 Hz), 6.82 (1H, s), 3.25-3.30 (4H, m), 2.58 (3H, s), 2.27 (3H, d, J=0.9 Hz), 1.47-1.65 (6H, m), 1.10 (3H, s).

Example 64

Preparation of Cpd 743

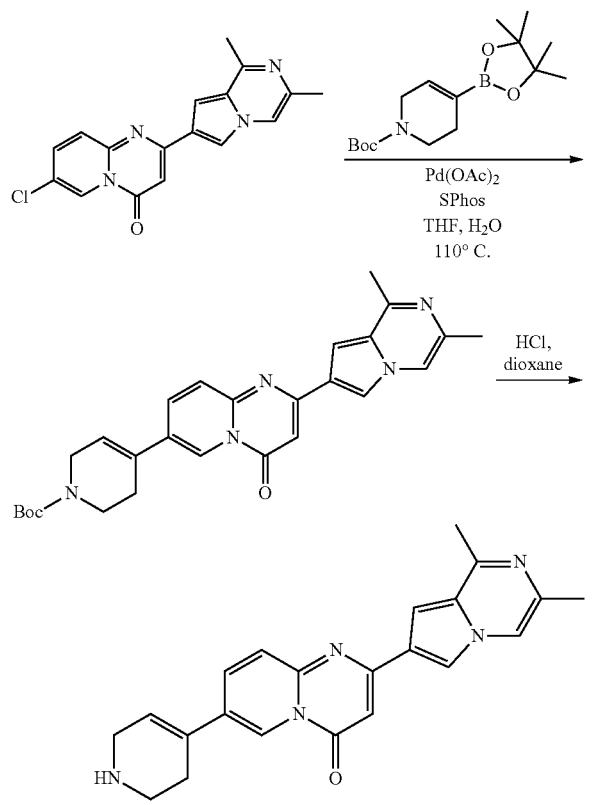

Step A: A mixture of 7-chloro-2-(1,3-dimethylpyrrolo[1,2-a]pyrazin-7-yl)-4H-pyrido[1,2-a]pyrimidin-4-one (0.14 g, 0.43 mmol) and tert-butyl 4-(4,4,5,5-tetramethyl-1,3,2-dioxaborolan-2-yl)-5,6-dihydropyridine-1(2H)-carboxylate (0.2 g, 0.65 mmol), Pd(OAc)$_2$ (1.9 mg, 0.0086 mmol), SPhos (7.0 mg, 0.0172 mmol) and K$_3$PO$_4$ (0.18 g, 0.86 mmol) in THF (1.0 mL) and water (0.5 mL) was stirred at 110° C. overnight. Aqueous workup followed by purification with methanol in dichloromethane (0-10%) provided tert-butyl 4-(2-(1,3-dimethylpyrrolo[1,2-a]pyrazin-7-yl)-4-oxo-4H-pyrido[1,2-a]pyrimidin-7-yl)-5,6-dihydropyridine-1(2H)-carboxylate (0.13 g, 65%). MS m/z Δ72.3 [M+H]$^+$.

Step B: Following the procedure in Example 63, Part 2, Step C, treatment of tert-butyl 4-(2-(1,3-dimethylpyrrolo[1,2-a]pyrazin-7-yl)-4-oxo-4H-pyrido[1,2-a]pyrimidin-7-yl)-5,6-dihydropyridine-1(2H)-carboxylate (0.13 g, 0.28 mmol) with HCl in dioxane (1.0 mL) provided the title compound as a yellow solid (5 mg, 5%). M.P. 189-191° C.; MS m/z 372.3 [M+H]$^+$; $^1$H NMR (500 MHz, methanol-d$_4$) δ 8.81 (1H, d, J=1.9 Hz), 8.03 (2H, d, J=1.6 Hz), 7.71 (1H, s), 7.62 (1H, d, J=9.5 Hz), 7.28 (1H, s), 6.76 (1H, s), 6.41-6.50 (1H, m), 3.58 (2H, d, J=2.5 Hz), 3.15 (2H, t, J=5.8 Hz), 2.63 (3H, s), 2.54 (2H, br. s.), 2.32 (3H, d, J=0.6 Hz).

Example 65

Preparation of Cpd 804

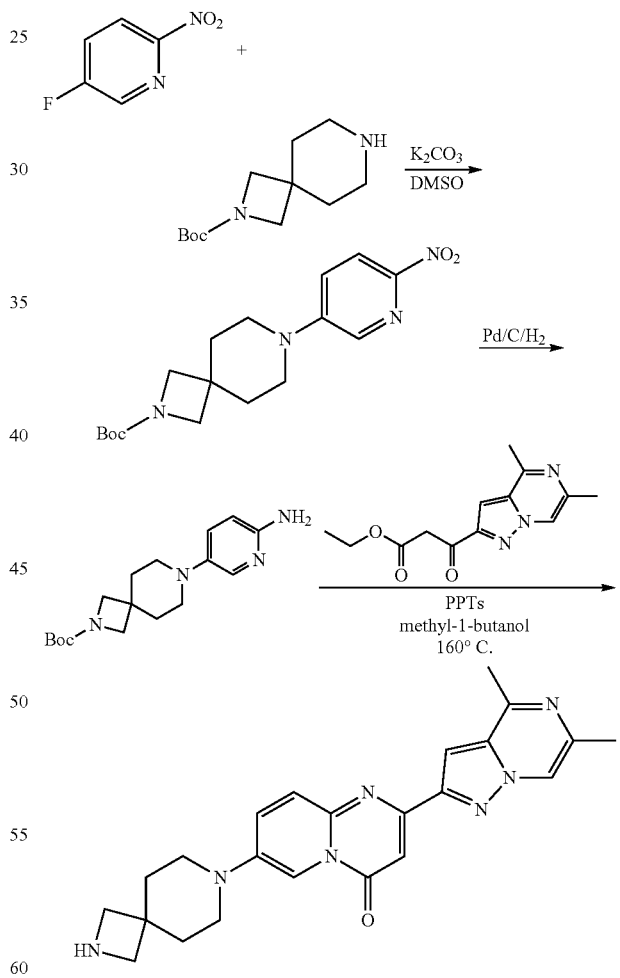

Step A: 5-fluoro-2-nitropyridine (200 mg, 1.41 mmol), tert-butyl 2,7-diazaspiro[3.5]-nonane-2-carboxylate (319 mg, 1.41 mmol) and K$_2$CO$_3$ (195 mg, 1.41 mmol) were combined in DMSO (8 mL). The reaction mixture was heated at 70° C. for 15 hours and cooled to room temperature, before the solvent was evaporated. An extraction (CH₂Cl₂ and H₂O) followed by chromatography with silica gel (CH₂Cl₂/MeOH: 98/2) gave 7-(6-nitro-pyridin-3-yl)-2,7-diaza-spiro[3.5]nonane-2-carboxylic acid tert-butyl ester (320 mg, 65%) as a yellow solid. MS m/z 349.5 [M+H]⁺.

Step B: 7-(6-nitro-pyridin-3-yl)-2,7-diaza-spiro[3.5]nonane-2-carboxylic acid tert-butyl ester (315 mg, 0.90 mmol) and Pd/C (32 mg) were combined in MeOH (40 mL) and placed under a hydrogen atmosphere (H₂ balloon) for 15 hours. The reaction mixture was filtered through celite and chromatographed with silica gel (CH₂Cl₂/MeOH: 98/2) to give 7-(6-amino-pyridin-3-yl)-2,7-diaza-spiro [3.5]nonane-2-carboxylic acid tert-butyl ester (227 mg, 78%) as an off-white solid. MS m/z 319.6 [M+H]

Step C: A mixture of 7-(6-amino-pyridin-3-yl)-2,7-diaza-spiro[3.5]nonane-2-carboxylic acid tert-butyl ester (100 mg, 0.31 mmol), ethyl 3-(4,6-dimethylpyrazolo[1,5-a]pyrazin-2-yl)-3-oxopropanoate (90 mg, 0.31 mmol, preparation described in Example 9, Steps A to F) and PPTs (87 mg, 0.345 mmol) in methyl-1-butanol (2 mL) was heated at 160° C. for 15 hours. The mixture was cooled to room temperature, poured into an aqueous NaOH (1M) solution and extracted with CH₂Cl₂. The combined organic phases were dried over Na₂SO₄ and the residue was chromatographed with silica gel (CH₂Cl₂/MeOH: 9/1; and, 1% aqueous NH3) to give the title product (40 mg, 31%) as a yellow solid. MS m/z 416.2 [M+H]⁺. ¹H NMR (CDCl₃, 600 MHz) δ 8.18 (d, J=1.1 Hz, 1H), 8.15 (s, 1H), 7.45 (dd, 1H) 7.80 (d, 1H), 7.32 (s, 1H), 7.11 (s, 1H), 3.51 (m, 2H), 3.42 (d, 1H), 3.36 (d, 1H), 3.15 (m, 2H), 3.00 (d, 1H), 2.97 (d, 1H), 2.79 (s, 3H), 2.52 (s, 3H), 2.10 (m, 2H), 1.89 (m, 2H).

Example 66

Preparation of Cpd 811

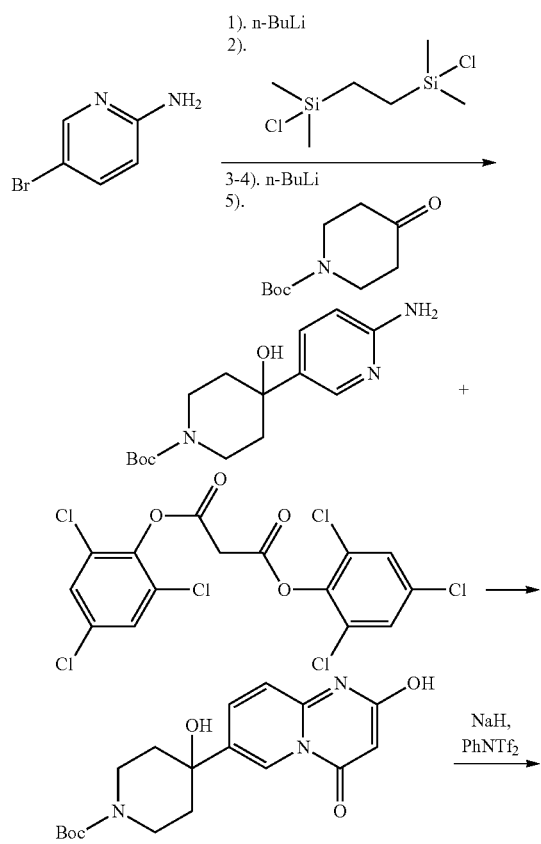

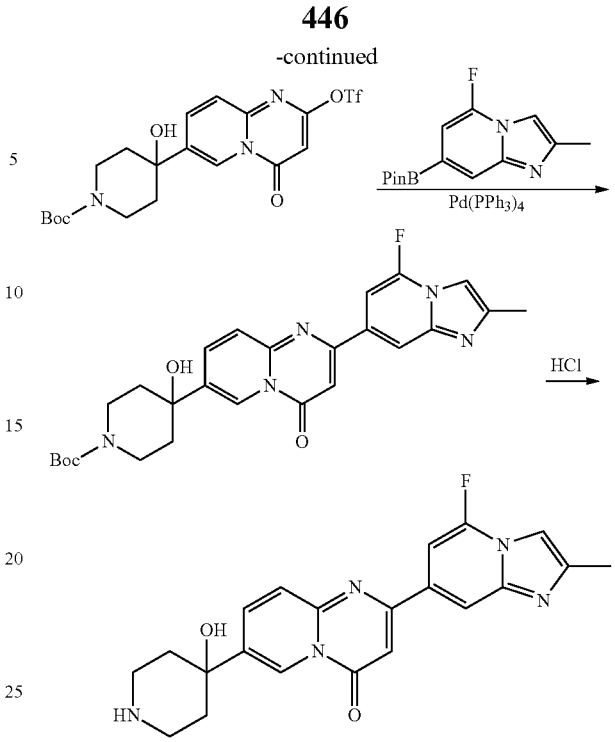

Step A: 5-Bromopyridin-2-amine (1.0 g, 5.8 mmol) in THF (20 mL), cooled to −78° C. under Ar, was combined with n-BuLi (3.6 ml, 5.8 mmol, 1.6 M in hexanes) and stirred for 0.5 hours. 1,2-Bis(chlorodimethylsilyl)ethane (1.2 g, 5.8 mmol) in THF (10 mL) was added and the mixture was allowed to warm to ambient temperature over 1 hour. The mixture was then re-cooled to −78° C. and a second equivalent of n-BuLi (3.6 ml, 5.8 mmol, 1.6 M in hexanes) was added. The mixture was stirred for 0.5 hours at −78° C. and then allowed to warm to ambient temperature over 1 hour. The mixture was then re-cooled to −78° C. and a third equivalent of n-BuLi (3.6 ml, 5.8 mmol, 1.6 M in hexanes) was added. The mixture was stirred for 1 hour at −78° C., then tert-butyl 4-oxopiperidine-1-carboxylate (1.3 g, 6.4 mmol) in THF (10 mL) was added and the reaction was allowed to come to ambient temperature. The mixture was diluted with EtOAc, washed with brine, dried (Na₂SO₄) and concentrated. The residue was eluted from silica with EtOAc (0-100%) in n-heptane to afford tert-butyl 4-(6-aminopyridin-3-yl)-4-hydroxypiperidine-1-carboxylate as a light yellow solid (1.1 g, 64%). MS m/z 294.2 [M+H]⁺.

Step B: A mixture of bis(2,4,6-trichlorophenyl) malonate (0.80 g, 1.7 mmol) and tert-butyl 4-(6-aminopyridin-3-yl)-4-hydroxypiperidine-1-carboxylate (0.50 g, 1.7 mmol) was heated in toluene (10 mL) at 60° C. for 2 hours. The reaction was concentrated to remove the volatiles. The residue was eluted from silica with MeOH (0-20%) in CH₂Cl₂ to afford tert-butyl 4-hydroxy-4-(2-hydroxy-4-oxo-4H-pyrido[1,2-a]pyrimidin-7-yl)piperidine-1-carboxylate as a light yellow solid (0.43 g, 70%). MS m/z 362.3 [M+H]⁺.

Step C: A mixture of tert-butyl 4-hydroxy-4-(2-hydroxy-4-oxo-4H-pyrido[1,2-a]pyrimidin-7-yl)piperidine-1-carboxylate (0.17 g, 0.5 mmol), 1,1,1-trifluoro-N-phenyl-N-(trifluoromethylsulfonyl)methanesulfonamide (0.19 g, 0.5 mmol) and potassium carbonate (0.13 g, 0.9 mmol) in DMF (3 mL) was stirred at ambient temperature. After 1 hour, the mixture was diluted with EtOAc, washed with water, brine, dried (Na₂SO₄) and concentrated. The residue was eluted from silica with EtOAc (10-50%) in n-heptane to afford tert-butyl 4-hydroxy-4-(4-oxo-2-(trifluoromethylsulfonyloxy)-4H-pyrido[1,2-a]pyrimidin-7-yl)piperidine-1-carboxylate as a crystalline yellow solid (0.08 g, 35%). MS m/z 494.3 [M+H]$^+$.

Step D: Following the procedure in Example 15, Step A, tert-butyl 4-hydroxy-4-(4-oxo-2-(trifluoromethylsulfonyloxy)-4H-pyrido[1,2-a]pyrimidin-7-yl)piperidine-1-carboxylate (80 mg, 0.16 mmol), 8-fluoro-2-methyl-6-(4,4,5,5-tetramethyl-1,3,2-dioxaborolan-2-yl)imidazo[1,2-a]pyridine (67 mg, 0.24 mmol, Prepared in Example 16, Step B), tetrakis(triphenylphosphine)palladium(0) (9 mg, 0.01 mmol) and K$_2$CO$_3$ (31 mg, 0.32 mmol) in MeCN/water (2 ml/0.3 mL) provided tert-butyl 4-(2-(8-fluoro-2-methylimidazo[1,2-a]pyridin-6-yl)-4-oxo-4H-pyrido[1,2-a]pyrimidin-7-yl)-4-hydroxypiperidine-1-carboxylate as an off-white crystalline solid (60 mg, 75%). MS m/z 494.5 [M+H]$^+$.

Step E: Following the procedure in Example 24, Step B, the above product from Step D and HCl in dioxane (4M, 2 mL) provided 2-(8-fluoro-2-methylimidazo[1,2-a]pyridin-6-yl)-7-(4-hydroxypiperidin-4-yl)-4H-pyrido[1,2-a]pyrimidin-4-one as a white solid (11 mg, 49%). MS m/z 394.4 [M+H]$^+$. $^1$H NMR (DMSO-d$_6$, 300 MHz) δ 9.31 (d, J=1.2 Hz, 1H), 9.01 (d, J=1.8 Hz, 1H), 8.12 (dd, J=9.3, 1.8 Hz, 1H), 7.96 (d, J=2.4 Hz, 1H), 7.88 (dd, J=12.6, 1.2 Hz, 1H), 7.75 (d, J=9.3 Hz, 1H), 7.06 (s, 1H), 5.34 (br s, 1H), 2.91 (apparent t, J=12.0 Hz, 2H), 2.79 (d, J=12.0 Hz, 2H), 2.39 (s, 3H), 1.89-1.84 (m, 2H), 1.60 (d, J=12.0 Hz, 2H).

Table 1 provides isolated compounds of a free base form of a compound of Formula (I) that may be prepared according to the procedures of the indicated Example by substituting the appropriate starting materials, reagents and reaction conditions. The preparation of any salt, isotopologue, stereoisomer, racemate, enantiomer, diastereomer or tautomer from a free base form of a compound of Formula (I) is also contemplated and further included within the scope of the description herein. Where a free base form of the compound was not isolated from the salt form, a person of ordinary skill in the art could be expected to perform the required reactions to prepare and isolate the free base form of the compound.

The term "Cpd" represents Compound number, the term "Ex" represents "Example Number" (wherein * indicates that the corresponding Example for the Compound is provided above), the term "M.P." represents "Melting Point (° C.)," the term "MS" represents "Mass Spectroscopy Peak(s) m/z [M+H]$^+$, [M+2+H]$^+$, [M–H] or [M+2–H]$^-$," the term "D" represents "Decomposition/Decomposed," the term "DR" represents "Decomposition Range," the term "S" represents "Softens," the term "ND" indicates that the value was "Not Determined" and the term "NI" indicates that the compound was "Not Isolated."

TABLE 1

| Ex | Cpd | Name | M.P. | MS |
|---|---|---|---|---|
| 4* | 1 | 2-(4-methoxyphenyl)-7-(piperazin-1-yl)-4H-pyrido[1,2-a]pyrimidin-4-one | 182-184 | 337.3 |
| 4 | 2 | 2-(4-methoxyphenyl)-7-(4-methylpiperazin-1-yl)-4H-pyrido[1,2-a]pyrimidin-4-one | 178-182 | 351.3 |
| 4 | 3 | 2-(4-methoxyphenyl)-7-[(3R)-3-methylpiperazin-1-yl]-4H-pyrido[1,2-a]pyrimidin-4-one | 152-154 | 351.3 |
| 4 | 4 | 7-[(3R,5S)-3,5-dimethylpiperazin-1-yl]-2-(4-methoxyphenyl)-4H-pyrido[1,2-a]pyrimidin-4-one | 185-187 | 365.3 |
| 4 | 5 | 7-(1,4-diazepan-1-yl)-2-(4-methoxyphenyl)-4H-pyrido[1,2-a]pyrimidin-4-one | 149-152 | 351.3 |
| 3* | 6 | 2-(3,4-dimethoxyphenyl)-7-(piperazin-1-yl)-4H-pyrido[1,2-a]pyrimidin-4-one | 182-184 | 367.5 |
| 3 | 7 | 2-(3,4-dimethoxyphenyl)-7-(3,3-dimethylpiperazin-1-yl)-4H-pyrido[1,2-a]pyrimidin-4-one | 138-140 | 395.3 |
| 3 | 8 | 2-(3,4-dimethoxyphenyl)-7-[(3R)-3-methylpiperazin-1-yl]-4H-pyrido[1,2-a]pyrimidin-4-one | 181-184 | 381.3 |
| 3 | 9 | 2-(3,4-dimethoxyphenyl)-7-(4-ethylpiperazin-1-yl)-4H-pyrido[1,2-a]pyrimidin-4-one | 159-162 | 395.3 |
| 3 | 10 | 7-(1,4-diazepan-1-yl)-2-(3,4-dimethoxyphenyl)-4H-pyrido[1,2-a]pyrimidin-4-one | ND | 381.3 |
| 3 | 11 | 2-(3,4-dimethoxyphenyl)-7-(4-methyl-1,4-diazepan-1-yl)-4H-pyrido[1,2-a]pyrimidin-4-one | 166-168 | 395.3 |
| 3 | 12 | 2-(4-methoxyphenyl)-7-[(3S)-3-methylpiperazin-1-yl]-4H-pyrido[1,2-a]pyrimidin-4-one | 158-160 | 351.3 |
| 3 | 13 | 2-(3,4-dimethoxyphenyl)-7-(4-methylpiperazin-1-yl)-4H-pyrido[1,2-a]pyrimidin-4-one | 183-185 | 381.3 |
| 3 | 14 | 2-(3,4-dimethoxyphenyl)-7-[(3R,5S)-3,5-dimethylpiperazin-1-yl]-4H-pyrido[1,2-a]pyrimidin-4-one | 182-187 | 395.3 |
| 3 | 15 | 2-(3,4-dimethoxyphenyl)-7-(4-propylpiperazin-1-yl)-4H-pyrido[1,2-a]pyrimidin-4-one | 185-189 | 409.3 |
| 4 | 16 | 2-(4-methoxyphenyl)-7-(4-methyl-1,4-diazepan-1-yl)-4H-pyrido[1,2-a]pyrimidin-4-one | 137-141 | 365.3 |
| 4 | 17 | 7-(3,3-dimethylpiperazin-1-yl)-2-(4-methoxyphenyl)-4H-pyrido[1,2-a]pyrimidin-4-one | ND | 365.3 |
| 4 | 18 | 2-(1,3-benzodioxol-5-yl)-7-(piperazin-1-yl)-4H-pyrido[1,2-a]pyrimidin-4-one | 198-201 | 351.3 |
| 4 | 19 | 2-(1,3-benzodioxol-5-yl)-7-(4-methylpiperazin-1-yl)-4H-pyrido[1,2-a]pyrimidin-4-one | 235-237 | 365.2 |
| 4 | 20 | 2-(1,3-benzodioxol-5-yl)-7-[(3R)-3-methylpiperazin-1-yl]-4H-pyrido[1,2-a]pyrimidin-4-one | 195-197 | 365.3 |
| 4 | 21 | 2-(1,3-benzodioxol-5-yl)-7-[(3R,5S)-3,5-dimethylpiperazin-1-yl]-4H-pyrido[1,2-a]pyrimidin-4-one | 198-201 | 379.3 |

TABLE 1-continued

| Ex | Cpd | Name | M.P. | MS |
|---|---|---|---|---|
| 4 | 22 | 2-(3-methoxyphenyl)-7-(piperazin-1-yl)-4H-pyrido[1,2-a]pyrimidin-4-one | 147-149 | 337.2 |
| 4 | 23 | 2-(3-methoxyphenyl)-7-(4-methylpiperazin-1-yl)-4H-pyrido[1,2-a]pyrimidin-4-one | 173-175 | 351.2 |
| 4 | 24 | 2-(3-methoxyphenyl)-7-[(3R)-3-methylpiperazin-1-yl]-4H-pyrido[1,2-a]pyrimidin-4-one | 164-166 | 351.2 |
| 4 | 25 | 7-[(3R,5S)-3,5-dimethylpiperazin-1-yl]-2-(3-methoxyphenyl)-4H-pyrido[1,2-a]pyrimidin-4-one | 189-191 | 365.3 |
| 4 | 26 | 7-(4-ethylpiperazin-1-yl)-2-(3-methoxyphenyl)-4H-pyrido[1,2-a]pyrimidin-4-one | 158-160 | 365.3 |
| 4 | 27 | 7-(1,4-diazepan-1-yl)-2-(3-methoxyphenyl)-4H-pyrido[1,2-a]pyrimidin-4-one | ND | 351.2 |
| 4 | 28 | 2-(3-methoxyphenyl)-7-(4-methyl-1,4-diazepan-1-yl)-4H-pyrido[1,2-a]pyrimidin-4-one | 130-132 | 365.2 |
| 8* | 29 | 2-(6-methylimidazo[1,2-a]pyridin-2-yl)-7-(piperazin-1-yl)-4H-pyrido[1,2-a]pyrimidin-4-one | 193-198 | 361.3 |
| 3 | 30 | 2-(3,4-dimethoxyphenyl)-7-[(3S)-3-methylpiperazin-1-yl]-4H-pyrido[1,2-a]pyrimidin-4-one | 153-158 | 381.3 |
| 4 | 31 | 2-(2,3-dihydro-1,4-benzodioxin-6-yl)-7-(piperazin-1-yl)-4H-pyrido[1,2-a]pyrimidin-4-one | 230-232 | 365.3 |
| 4 | 32 | 2-(2,3-dihydro-1,4-benzodioxin-6-yl)-7-[(3S)-3-methylpiperazin-1-yl]-4H-pyrido[1,2-a]pyrimidin-4-one | 205-207 | 379.3 |
| 3 | 33 | 2-phenyl-7-(piperazin-1-yl)-4H-pyrido[1,2-a]pyrimidin-4-one | 151-153 | 307.2 |
| 3 | 34 | 7-[(3S)-3-methylpiperazin-1-yl]-2-phenyl-4H-pyrido[1,2-a]pyrimidin-4-one | 170-173 | 321.3 |
| 4 | 35 | 2-(2,3-dihydro-1,4-benzodioxin-6-yl)-7-[(3R)-3-methylpiperazin-1-yl]-4H-pyrido[1,2-a]pyrimidin-4-one | 212-214 | 379.2 |
| 4 | 36 | 2-(2,3-dihydro-1,4-benzodioxin-6-yl)-7-(3,3-dimethylpiperazin-1-yl)-4H-pyrido[1,2-a]pyrimidin-4-one | 196-198 | 393.3 |
| 4 | 37 | 2-(2,3-dihydro-1,4-benzodioxin-6-yl)-7-[(3R,5S)-3,5-dimethylpiperazin-1-yl]-4H-pyrido[1,2-a]pyrimidin-4-one | 247-250 | 393.3 |
| 4 | 38 | 7-(1,4-diazepan-1-yl)-2-(2,3-dihydro-1,4-benzodioxin-6-yl)-4H-pyrido[1,2-a]pyrimidin-4-one | 180-182 | 379.3 |
| 4 | 39 | 2-(2,3-dihydro-1,4-benzodioxin-6-yl)-7-(4-methyl-1,4-diazepan-1-yl)-4H-pyrido[1,2-a]pyrimidin-4-one | 150-152 | 393.3 |
| 1 | 40 | 2-(3,4-dimethoxyphenyl)-9-fluoro-7-(4-methylpiperazin-1-yl)-4H-pyrido[1,2-a]pyrimidin-4-one | 183-185 | 399.3 |
| 1 | 41 | 2-(3-chlorophenyl)-7-(piperazin-1-yl)-4H-pyrido[1,2-a]pyrimidin-4-one | 185-189 | 341.2 |
| 1 | 42 | 2-(4-chlorophenyl)-7-(piperazin-1-yl)-4H-pyrido[1,2-a]pyrimidin-4-one | 207-212 | 341.2 |
| 1 | 43 | 7-(piperazin-1-yl)-2-[3-(trifluoromethyl)phenyl]-4H-pyrido[1,2-a]pyrimidin-4-one | 199-207 | 375.2 |
| 1 | 44 | 7-(piperazin-1-yl)-2-[4-(trifluoromethyl)phenyl]-4H-pyrido[1,2-a]pyrimidin-4-one | 285 (D) | 375.2 |
| 1 | 45 | 2-(3-methylphenyl)-7-(piperazin-1-yl)-4H-pyrido[1,2-a]pyrimidin-4-one | 183-187 | 321.2 |
| 1 | 46 | 2-(4-fluorophenyl)-7-(piperazin-1-yl)-4H-pyrido[1,2-a]pyrimidin-4-one | 214-218 | 325.2 |
| 1 | 47 | 2-(4-nitrophenyl)-7-(piperazin-1-yl)-4H-pyrido[1,2-a]pyrimidin-4-one | 237-242 | 352.2 |
| 1 | 48 | 2-(3,4-dimethoxyphenyl)-9-fluoro-7-(piperidin-4-ylamino)-4H-pyrido[1,2-a]pyrimidin-4-one | 224-226 | 399.3 |
| 3 | 49 | 2-[4-(dimethylamino)phenyl]-9-fluoro-7-(piperazin-1-yl)-4H-pyrido[1,2-a]pyrimidin-4-one | 216-218 | 368.3 |
| 3 | 50 | 2-[4-(dimethylamino)phenyl]-9-fluoro-7-[(3R)-3-methylpiperazin-1-yl]-4H-pyrido[1,2-a]pyrimidin-4-one | 205-207 | 382.3 |
| 1 | 51 | 2-(2-fluorophenyl)-7-(piperazin-1-yl)-4H-pyrido[1,2-a]pyrimidin-4-one | 142-146 | 325.2 |
| 28* | 52 | 3-(3,4-dimethoxyphenyl)-8-(piperazin-1-yl)-4H-pyrido[1,2-a]pyrimidin-4-one | 175-179 | 367.2 |
| 3 | 53 | 2-[4-(dimethylamino)phenyl]-7-(piperazin-1-yl)-4H-pyrido[1,2-a]pyrimidin-4-one | 211-215 | 350.3 |
| 3 | 54 | 2-[4-(dimethylamino)phenyl]-7-[(3S)-3-methylpiperazin-1-yl]-4H-pyrido[1,2-a]pyrimidin-4-one | 199-202 | 364.3 |
| 3 | 55 | 2-(3,4-dimethylphenyl)-7-(piperazin-1-yl)-4H-pyrido[1,2-a]pyrimidin-4-one | 186-188 | 335.2 |

TABLE 1-continued

| Ex | Cpd | Name | M.P. | MS |
|---|---|---|---|---|
| 3 | 56 | 2-(3,4-dimethylphenyl)-7-[(3S)-3-methylpiperazin-1-yl]-4H-pyrido[1,2-a]pyrimidin-4-one | 207-209 | 349.3 |
| 3 | 57 | 2-[3-(dimethylamino)phenyl]-7-(piperazin-1-yl)-4H-pyrido[1,2-a]pyrimidin-4-one | 178-180 | 350.2 |
| 3 | 58 | 2-[3-(dimethylamino)phenyl]-7-[(3S)-3-methylpiperazin-1-yl]-4H-pyrido[1,2-a]pyrimidin-4-one | 144-146 | 364.3 |
| 3 | 59 | 2-[4-(difluoromethoxy)phenyl]-7-(piperazin-1-yl)-4H-pyrido[1,2-a]pyrimidin-4-one | 131-133 | 373.5 |
| 3 | 60 | 2-[4-(difluoromethoxy)phenyl]-7-[(3S)-3-methylpiperazin-1-yl]-4H-pyrido[1,2-a]pyrimidin-4-one | 166-168 | 387.2 |
| 1 | 61 | 2-(3-fluorophenyl)-7-(piperazin-1-yl)-4H-pyrido[1,2-a]pyrimidin-4-one | 153-156 | 325.2 |
| 1 | 62 | 2-(3-nitrophenyl)-7-(piperazin-1-yl)-4H-pyrido[1,2-a]pyrimidin-4-one | 175 (D) | 352.2 |
| 1 | 63 | 2-(4-methylphenyl)-7-(piperazin-1-yl)-4H-pyrido[1,2-a]pyrimidin-4-one | 192-195 | 321.2 |
| 3 | 64 | 2-(2-fluoro-4,5-dimethoxyphenyl)-7-(piperazin-1-yl)-4H-pyrido[1,2-a]pyrimidin-4-one | 177-180 | 385.2 |
| 3 | 65 | 2-(2-fluoro-4,5-dimethoxyphenyl)-7-[(3S)-3-methylpiperazin-1-yl]-4H-pyrido[1,2-a]pyrimidin-4-one | 167-170 | 399.2 |
| 3 | 66 | 7-(3,8-diazabicyclo[3.2.1]oct-3-yl)-2-(3,4-dimethoxyphenyl)-4H-pyrido[1,2-a]pyrimidin-4-one | 158-161 | 393.3 |
| 1 | 67 | 2-[4-methoxy-3-(trifluoromethyl)phenyl]-7-(piperazin-1-yl)-4H-pyrido[1,2-a]pyrimidin-4-one | 177-181 | 405.1 |
| 1 | 68 | 2-[4-methoxy-3-(trifluoromethyl)phenyl]-7-[(3R)-3-methylpiperazin-1-yl]-4H-pyrido[1,2-a]pyrimidin-4-one | 205-212 | 419.3 |
| 1 | 69 | 2-[4-methoxy-3-(trifluoromethyl)phenyl]-7-[(3S)-3-methylpiperazin-1-yl]-4H-pyrido[1,2-a]pyrimidin-4-one | 195-200 | 419.3 |
| 6* | 70 | 2-(3,4-dimethoxyphenyl)-9-methoxy-7-(piperazin-1-yl)-4H-pyrido[1,2-a]pyrimidin-4-one | 185-187 | 397.3 |
| 11 | 71a | 2-(3,5-difluoro-4-hydroxyphenyl)-7-(piperazin-1-yl)-4H-pyrido[1,2-a]pyrimidin-4-one | NI | NI |
| 1* | 72 | 2-(3-fluoro-4-methoxyphenyl)-7-(piperazin-1-yl)-4H-pyrido[1,2-a]pyrimidin-4-one | 191-195 | 355.0 |
| 3 | 73 | 4-[4-oxo-7-(piperazin-1-yl)-4H-pyrido[1,2-a]pyrimidin-2-yl]benzonitrile | 146-151 | 332.1 |
| 7* | 74 | 2-(6-methylimidazo[1,2-a]pyrazin-2-yl)-7-(piperazin-1-yl)-4H-pyrido[1,2-a]pyrimidin-4-one | 221-225 | 362.2 |
| 7 | 75 | 2-(6-methylimidazo[1,2-a]pyrazin-2-yl)-7-[(3S)-3-methylpiperazin-1-yl]-4H-pyrido[1,2-a]pyrimidin-4-one | 235-238 | 376.2 |
| 1 | 76 | 2-[3-fluoro-5-(trifluoromethyl)phenyl]-7-(piperazin-1-yl)-4H-pyrido[1,2-a]pyrimidin-4-one | ND | 393 |
| 1 | 77 | 2-[4-fluoro-3-(trifluoromethyl)phenyl]-7-(piperazin-1-yl)-4H-pyrido[1,2-a]pyrimidin-4-one | 214-217 | 393.1 |
| 1 | 78 | 2-[2-methoxy-3-(trifluoromethyl)phenyl]-7-(piperazin-1-yl)-4H-pyrido[1,2-a]pyrimidin-4-one | 194-200 | 405.1 |
| 1 | 79 | 2-(3,5-difluorophenyl)-7-(piperazin-1-yl)-4H-pyrido[1,2-a]pyrimidin-4-one | 195-198 | 343 |
| 1 | 80 | 7-(piperazin-1-yl)-2-[3-(trifluoromethoxy)phenyl]-4H-pyrido[1,2-a]pyrimidin-4-one | 140-143 | 391 |
| 5* | 81 | 2-[4-methoxy-3-(trifluoromethoxy)phenyl]-7-(piperazin-1-yl)-4H-pyrido[1,2-a]pyrimidin-4-one | 158-162 | 421.1 |
| 5* | 82 | 2-[4-hydroxy-3-(trifluoromethoxy)phenyl]-7-(piperazin-1-yl)-4H-pyrido[1,2-a]pyrimidin-4-one | 245-248 | 407.2 |
| 5 | 83 | 2-[4-methoxy-3-(trifluoromethoxy)phenyl]-7-[(3S)-3-methylpiperazin-1-yl]-4H-pyrido[1,2-a]pyrimidin-4-one | 176-178 | 435.9 |
| 5 | 84 | 2-[4-hydroxy-3-(trifluoromethoxy)phenyl]-7-[(3S)-3-methylpiperazin-1-yl]-4H-pyrido[1,2-a]pyrimidin-4-one | 152-155 | 421.2 |
| 31* | 85 | 2-(3,4-dimethoxyphenyl)-4-oxo-7-(piperazin-1-yl)-4H-quinolizine-1-carbonitrile | 199-202 | 391.2 |
| 1 | 86 | 2-(3-fluoro-4-methoxyphenyl)-7-[(3R)-3-methylpiperazin-1-yl]-4H-pyrido[1,2-a]pyrimidin-4-one | 175-178 | 369.1 |
| 1 | 87 | 2-(3-fluoro-4-methoxyphenyl)-7-[(3S)-3-methylpiperazin-1-yl]-4H-pyrido[1,2-a]pyrimidin-4-one | 175-178 | 369.1 |
| 1 | 88 | 2-(6-methoxypyridin-3-yl)-7-(piperazin-1-yl)-4H-pyrido[1,2-a]pyrimidin-4-one | 173-178 | 338.2 |
| 1 | 89 | 2-(2,4-dimethoxyphenyl)-7-(piperazin-1-yl)-4H-pyrido[1,2-a]pyrimidin-4-one | 171-173 | 367.3 |

TABLE 1-continued

| Ex | Cpd | Name | M.P. | MS |
|---|---|---|---|---|
| 1 | 90 | 2-(2,4-dimethoxyphenyl)-7-[(3S)-3-methylpiperazin-1-yl]-4H-pyrido[1,2-a]pyrimidin-4-one | 172-177 | 381.2 |
| 32* | 91 | 2-(3,4-dimethoxyphenyl)-7-[(3S)-3-methylpiperazin-1-yl]-4H-quinolizin-4-one | 243-245 | 380.2 |
| 11* | 92 | 2-(5-fluoropyridin-3-yl)-7-(piperazin-1-yl)-4H-pyrido[1,2-a]pyrimidin-4-one | 201-208 | 326.2 |
| 11 | 93 | 2-(5-fluoropyridin-3-yl)-7-[(3S)-3-methylpiperazin-1-yl]-4H-pyrido[1,2-a]pyrimidin-4-one | 191-199 | 340.1 |
| 11 | 94 | 2-(5-chloropyridin-3-yl)-7-(piperazin-1-yl)-4H-pyrido[1,2-a]pyrimidin-4-one | 208-218 | 342 |
| 11 | 95 | 2-(5-chloropyridin-3-yl)-7-[(3S)-3-methylpiperazin-1-yl]-4H-pyrido[1,2-a]pyrimidin-4-one | 227-232 | 356 |
| 1 | 96 | 2-(5-chloro-6-methoxypyridin-3-yl)-7-(piperazin-1-yl)-4H-pyrido[1,2-a]pyrimidin-4-one | 201-209 | 372.1 |
| 12 | 97 | 2-(1H-indol-6-yl)-7-(piperazin-1-yl)-4H-pyrido[1,2-a]pyrimidin-4-one | 202-206 | 346.2 |
| 12* | 98 | 2-(1H-indol-5-yl)-7-(piperazin-1-yl)-4H-pyrido[1,2-a]pyrimidin-4-one | 266-272 | 346.2 |
| 3 | 99 | 2-[3-(difluoromethoxy)-4-methoxyphenyl]-7-(piperazin-1-yl)-4H-pyrido[1,2-a]pyrimidin-4-one | ND | 403.4 |
| 3 | 100 | 2-[3-(difluoromethoxy)-4-hydroxyphenyl]-7-(piperazin-1-yl)-4H-pyrido[1,2-a]pyrimidin-4-one | 233-237 | 389.2 |
| 3 | 101 | 2-[3-(difluoromethoxy)-4-methoxyphenyl]-7-[(3S)-3-methylpiperazin-1-yl]-4H-pyrido[1,2-a]pyrimidin-4-one | 167-169 | 417 |
| 3 | 102 | 2-[3-(difluoromethoxy)-4-hydroxyphenyl]-7-[(3S)-3-methylpiperazin-1-yl]-4H-pyrido[1,2-a]pyrimidin-4-one | 192-197 | 403.2 |
| 33 | 103 | 2-(3-fluoro-4-methoxyphenyl)-7-(piperazin-1-yl)-4H-quinolizin-4-one | 200-202 | 354.1 |
| 33 | 104 | 2-(3-fluoro-4-methoxyphenyl)-7-[(3S)-3-methylpiperazin-1-yl]-4H-quinolizin-4-one | 188-192 | 368.1 |
| 1 | 105 | 2-(3,5-difluorophenyl)-7-[(3S)-3-methylpiperazin-1-yl]-4H-pyrido[1,2-a]pyrimidin-4-one | 189-194 | 357.2 |
| 33* | 106 | 2-(3,4-dimethoxyphenyl)-7-(piperazin-1-yl)-4H-quinolizin-4-one | 170-172 | 366.1 |
| 13* | 107 | 2-(imidazo[1,2-a]pyridin-7-yl)-7-(piperazin-1-yl)-4H-pyrido[1,2-a]pyrimidin-4-one | 258-270 | 347 |
| 12 | 108 | 2-(imidazo[1,2-a]pyridin-6-yl)-7-(piperazin-1-yl)-4H-pyrido[1,2-a]pyrimidin-4-one | ND | 347 |
| 15* | 109 | 2-(2-methylimidazo[1,2-a]pyridin-6-yl)-7-(piperazin-1-yl)-4H-pyrido[1,2-a]pyrimidin-4-one | 259-267 | 361.1 |
| 3 | 110 | 2-(3-chloro-4-methoxyphenyl)-7-(piperazin-1-yl)-4H-pyrido[1,2-a]pyrimidin-4-one | 201-203 | 371.4, 373.4 |
| 3 | 111 | 2-(3-chloro-4-methoxyphenyl)-7-[(3S)-3-methylpiperazin-1-yl]-4H-pyrido[1,2-a]pyrimidin-4-one | 187-189 | 385.5, 387.5 |
| 1 | 112 | 2-(3-ethoxy-4-methoxyphenyl)-7-(piperazin-1-yl)-4H-pyrido[1,2-a]pyrimidin-4-one | 194-196 | 381.1 |
| 1 | 113 | 2-(3-ethoxy-4-methoxyphenyl)-7-[(3S)-3-methylpiperazin-1-yl]-4H-pyrido[1,2-a]pyrimidin-4-one | 159-162 | 395.1 |
| 15 | 114 | 2-(2-methylimidazo[1,2-a]pyridin-6-yl)-7-(4-methylpiperazin-1-yl)-4H-pyrido[1,2-a]pyrimidin-4-one | ND | 375.1 |
| 15 | 115 | 2-(2-methylimidazo[1,2-a]pyridin-6-yl)-7-[(3S)-3-methylpiperazin-1-yl]-4H-pyrido[1,2-a]pyrimidin-4-one | ND | 375.1 |
| 15 | 116 | 7-(1,4-diazepan-1-yl)-2-(2-methylimidazo[1,2-a]pyridin-6-yl)-4H-pyrido[1,2-a]pyrimidin-4-one | ND | 375.1 |
| 15 | 117 | 7-[(3R,5S)-3,5-dimethylpiperazin-1-yl]-2-(2-methylimidazo[1,2-a]pyridin-6-yl)-4H-pyrido[1,2-a]pyrimidin-4-one | 181-186 | 389.1 |
| 7 | 118 | 2-(6,8-dimethylimidazo[1,2-a]pyrazin-2-yl)-7-(piperazin-1-yl)-4H-pyrido[1,2-a]pyrimidin-4-one | 189-192 | 376.5 |
| 7 | 119 | 2-(6,8-dimethylimidazo[1,2-a]pyrazin-2-yl)-7-[(3S)-3-methylpiperazin-1-yl]-4H-pyrido[1,2-a]pyrimidin-4-one | 202-208 | 390.5 |
| 9 | 120 | 2-(4,6-dimethylpyrazolo[1,5-a]pyrazin-2-yl)-7-(piperazin-1-yl)-4H-pyrido[1,2-a]pyrimidin-4-one | 195-200 | 376.5 |
| 9 | 121 | 2-(4,6-dimethylpyrazolo[1,5-a]pyrazin-2-yl)-7-[(3S)-3-methylpiperazin-1-yl]-4H-pyrido[1,2-a]pyrimidin-4-one | 192-194 | 390.5 |
| 22 | 122 | 2-(3,4-dimethoxyphenyl)-7-(2-methylpyridin-4-yl)-4H-pyrido[1,2-a]pyrimidin-4-one | 197-200 | 374 |

TABLE 1-continued

| Ex | Cpd | Name | M.P. | MS |
|---|---|---|---|---|
| 15 | 123 | 7-(piperazin-1-yl)-2-[2-(trifluoromethyl)imidazo[1,2-a]pyridin-6-yl]-4H-pyrido[1,2-a]pyrimidin-4-one | 250-255 | 415.5 |
| 15 | 124 | 2-(2-ethylimidazo[1,2-a]pyridin-6-yl)-7-(piperazin-1-yl)-4H-pyrido[1,2-a]pyrimidin-4-one | 228-232 | 375.5 |
| 15 | 125 | 2-(2,3-dimethylimidazo[1,2-a]pyridin-6-yl)-7-(piperazin-1-yl)-4H-pyrido[1,2-a]pyrimidin-4-one | 236-240 | 375.5 |
| 2 | 126 | 2-(3,4-dimethoxyphenyl)-7-[(3aR,6aS)-hexahydropyrrolo[3,4-c]pyrrol-2(1H)-yl]-4H-pyrido[1,2-a]pyrimidin-4-one | 286-290 | 393.1 |
| 2 | 127 | 7-(4-aminopiperidin-1-yl)-2-(3,4-dimethoxyphenyl)-4H-pyrido[1,2-a]pyrimidin-4-one | 182-185 | 381.1 |
| 19* | 128 | 7-(piperazin-1-yl)-2-(1H-pyrrolo[2,3-b]pyridin-5-yl)-4H-pyrido[1,2-a]pyrimidin-4-one | 252-255 | 347.1 |
| 19 | 129 | 2-(1-methyl-1H-pyrrolo[2,3-b]pyridin-5-yl)-7-(piperazin-1-yl)-4H-pyrido[1,2-a]pyrimidin-4-one | 230-233 | 361.1 |
| 19 | 130 | 7-[(3R,5S)-3,5-dimethylpiperazin-1-yl]-2-(1-methyl-1H-pyrrolo[2,3-b]pyridin-5-yl)-4H-pyrido[1,2-a]pyrimidin-4-one | 265-268 | 389.1 |
| 9 | 131 | 7-[(3R,5S)-3,5-dimethylpiperazin-1-yl]-2-(4,6-dimethylpyrazolo[1,5-a]pyrazin-2-yl)-4H-pyrido[1,2-a]pyrimidin-4-one | ND | 404.5 |
| 9 | 132 | 7-(1,4-diazepan-1-yl)-2-(4,6-dimethylpyrazolo[1,5-a]pyrazin-2-yl)-4H-pyrido[1,2-a]pyrimidin-4-one | ND | 390.5 |
| 14 | 133 | 2-(2-methyl-1,3-benzoxazol-6-yl)-7-(piperazin-1-yl)-4H-pyrido[1,2-a]pyrimidin-4-one | 219-222 | 362.5 |
| 14 | 134 | 2-(2-methyl-1,3-benzoxazol-6-yl)-7-[(3S)-3-methylpiperazin-1-yl]-4H-pyrido[1,2-a]pyrimidin-4-one | 191-193 | 376.5 |
| 14 | 135 | 2-(2-methyl-1,3-benzothiazol-5-yl)-7-[(3S)-3-methylpiperazin-1-yl]-4H-pyrido[1,2-a]pyrimidin-4-one | 174-180 | 392.2 |
| 14 | 136 | 2-(2-methyl-1,3-benzothiazol-5-yl)-7-(piperazin-1-yl)-4H-pyrido[1,2-a]pyrimidin-4-one | 228-230 | 378.1 |
| 14 | 137 | 2-(2-methyl-2H-indazol-5-yl)-7-(piperazin-1-yl)-4H-pyrido[1,2-a]pyrimidin-4-one | 175-180 | 361.5 |
| 14 | 138 | 2-(2-methyl-2H-indazol-5-yl)-7-[(3S)-3-methylpiperazin-1-yl]-4H-pyrido[1,2-a]pyrimidin-4-one | 166-170 | 375.5 |
| 14 | 139 | 2-(3-fluoro-5-methoxyphenyl)-7-(piperazin-1-yl)-4H-pyrido[1,2-a]pyrimidin-4-one | 168-170 | 355.5 |
| 14 | 140 | 2-(3-fluoro-5-methoxyphenyl)-7-[(3S)-3-methylpiperazin-1-yl]-4H-pyrido[1,2-a]pyrimidin-4-one | 154-156 | 369.5 |
| 16 | 141 | 2-(2,8-dimethylimidazo[1,2-a]pyridin-6-yl)-7-(piperazin-1-yl)-4H-pyrido[1,2-a]pyrimidin-4-one | 270-274 | 375.1 |
| 2 | 142 | 2-(3,4-dimethoxyphenyl)-9-methyl-7-[(3S)-3-methylpiperazin-1-yl]-4H-pyrido[1,2-a]pyrimidin-4-one | 176-182 | 395.5 |
| 22* | 143 | 2-(3,4-dimethoxyphenyl)-7-(1,2,3,6-tetrahydropyridin-4-yl)-4H-pyrido[1,2-a]pyrimidin-4-one | 196-198 | 364.1 |
| 24* | 144 | 2-(3,4-dimethoxyphenyl)-7-(piperidin-4-yl)-4H-pyrido[1,2-a]pyrimidin-4-one | 214-217 | 366.4 |
| 1 | 145 | 2-(3-fluoro-4,5-dimethoxyphenyl)-7-(piperazin-1-yl)-4H-pyrido[1,2-a]pyrimidin-4-one | ND | 385.5 |
| 3 | 146 | 2-(3,4-dimethoxyphenyl)-7-(4-hydroxypiperazin-1-yl)-4H-pyrido[1,2-a]pyrimidin-4-one | 202-204 | 383.5 |
| 2 | 147 | 2-(3,4-dimethoxyphenyl)-7-[(3S)-3-(dimethylamino)pyrrolidin-1-yl]-4H-pyrido[1,2-a]pyrimidin-4-one | 156-158 | 395.4 |
| 2 | 148 | 2-(3,4-dimethoxyphenyl)-7-[4-(dimethylamino)piperidin-1-yl]-4H-pyrido[1,2-a]pyrimidin-4-one | 158-161 | 409.1 |
| 14 | 149 | 2-(4-methoxy-3-methylphenyl)-7-(piperazin-1-yl)-4H-pyrido[1,2-a]pyrimidin-4-one | 198-203 | 351.5 |
| 14 | 150 | 3-[4-oxo-7-(piperazin-1-yl)-4H-pyrido[1,2-a]pyrimidin-2-yl]benzonitrile | 224-231 | 332.1 |
| 14 | 151 | 2-methoxy-5-[4-oxo-7-(piperazin-1-yl)-4H-pyrido[1,2-a]pyrimidin-2-yl]benzonitrile | 191-197 | 362 |
| 14 | 152 | 2-(3-fluoro-4-hydroxyphenyl)-7-(piperazin-1-yl)-4H-pyrido[1,2-a]pyrimidin-4-one | 259-266 | 341.5 |
| 20* | 153 | 2-(4-ethoxy-3-fluorophenyl)-7-(piperazin-1-yl)-4H-pyrido[1,2-a]pyrimidin-4-one | 180-186 | 369.1 |
| 20 | 154 | 2-[3-fluoro-4-(2,2,2-trifluoroethoxy)phenyl]-7-(piperazin-1-yl)-4H-pyrido[1,2-a]pyrimidin-4-one | 198-201 | 423.1 |

TABLE 1-continued

| Ex | Cpd | Name | M.P. | MS |
|---|---|---|---|---|
| 14 | 155 | 2-(2-methyl-1,3-benzoxazol-5-yl)-7-(piperazin-1-yl)-4H-pyrido[1,2-a]pyrimidin-4-one | 178-183 | 362 |
| 14 | 156 | 2-(2-methyl-1,3-benzoxazol-5-yl)-7-[(3S)-3-methylpiperazin-1-yl]-4H-pyrido[1,2-a]pyrimidin-4-one | ND | 376.5 |
| 14 | 157 | 2-(3-fluoro-4-methylphenyl)-7-(piperazin-1-yl)-4H-pyrido[1,2-a]pyrimidin-4-one | 174-176 | 339.5 |
| 14 | 158 | 2-(3-fluoro-4-methylphenyl)-7-[(3S)-3-methylpiperazin-1-yl]-4H-pyrido[1,2-a]pyrimidin-4-one | 175-178 | 353.5 |
| 2 | 159 | 7-[(3S)-3-aminopyrrolidin-1-yl]-2-(3,4-dimethoxyphenyl)-4H-pyrido[1,2-a]pyrimidin-4-one | 148-151 | 367.1 |
| 2 | 160 | 2-(3,4-dimethoxyphenyl)-9-methyl-7-(piperazin-1-yl)-4H-pyrido[1,2-a]pyrimidin-4-one | 175 (S), 216-222 | 381.1 |
| 14 | 161 | 7-(1,4-diazepan-1-yl)-2-(2-methyl-1,3-benzothiazol-5-yl)-4H-pyrido[1,2-a]pyrimidin-4-one | 208-212 | 392.2 |
| 10 | 162 | 7-[(3S)-3-methylpiperazin-1-yl]-2-(4-methyl-1,3-thiazol-2-yl)-4H-pyrido[1,2-a]pyrimidin-4-one | 225-230 | 342.1 |
| 10* | 163 | 2-(4-methyl-1,3-thiazol-2-yl)-7-(piperazin-1-yl)-4H-pyrido[1,2-a]pyrimidin-4-one | 142-147 | 328.2 |
| 25* | 164 | 2-(3,4-dimethoxyphenyl)-7-(1-methylpiperidin-4-yl)-4H-pyrido[1,2-a]pyrimidin-4-one | 181-183 | 380.1 |
| 2 | 165 | 2-(3,4-dimethoxyphenyl)-7-[(3S)-3-(propan-2-ylamino)pyrrolidin-1-yl]-4H-pyrido[1,2-a]pyrimidin-4-one | 169-172 | 409.1 |
| 1 | 166 | 2-(3-fluoro-4-methoxyphenyl)-7-(4-methyl-1,4-diazepan-1-yl)-4H-pyrido[1,2-a]pyrimidin-4-one | 176-178 | 383.1 |
| 14 | 167 | 2-(4-methoxy-3-nitrophenyl)-7-(piperazin-1-yl)-4H-pyrido[1,2-a]pyrimidin-4-one | 183-187 | 382.5 |
| 14 | 168 | 2-[3-fluoro-4-(methylsulfanyl)phenyl]-7-(piperazin-1-yl)-4H-pyrido[1,2-a]pyrimidin-4-one | 174-176 | 371.1 |
| 15 | 169 | 7-(4-methyl-1,4-diazepan-1-yl)-2-(2-methylimidazo[1,2-a]pyridin-6-yl)-4H-pyrido[1,2-a]pyrimidin-4-one | 208-213 | 389.1 |
| 9* | 170 | 2-(4,6-dimethylpyrazolo[1,5-a]pyrazin-2-yl)-7-(4-methylpiperazin-1-yl)-4H-pyrido[1,2-a]pyrimidin-4-one | 254-256 | 390.4 |
| 14* | 171 | 2-(2-methyl-1,3-benzoxazol-6-yl)-7-(4-methylpiperazin-1-yl)-4H-pyrido[1,2-a]pyrimidin-4-one | 178-183 | 376.5 |
| 14 | 172 | 7-[(3R,5S)-3,5-dimethylpiperazin-1-yl]-2-(2-methyl-1,3-benzoxazol-6-yl)-4H-pyrido[1,2-a]pyrimidin-4-one | 233-235 | 390.3 |
| 17 | 173 | 2-(5-fluoro-6-methoxypyridin-3-yl)-7-[(3S)-3-methylpiperazin-1-yl]-4H-pyrido[1,2-a]pyrimidin-4-one | 175-180 | 370.5 |
| 17 | 174 | 7-[(3R,5S)-3,5-dimethylpiperazin-1-yl]-2-(5-fluoro-6-methoxypyridin-3-yl)-4H-pyrido[1,2-a]pyrimidin-4-one | 160-165 | 384.5 |
| 14 | 175 | 7-[(3R,5S)-3,5-dimethylpiperazin-1-yl]-2-(2-methyl-1,3-benzothiazol-5-yl)-4H-pyrido[1,2-a]pyrimidin-4-one | 208-212 | 406.1 |
| 14 | 176 | 2-(2-methyl-1,3-benzothiazol-5-yl)-7-(4-methylpiperazin-1-yl)-4H-pyrido[1,2-a]pyrimidin-4-one | 214-218 | 392.1 |
| 14 | 177 | 2-(2-methyl-1,3-benzothiazol-5-yl)-7-(4-methyl-1,4-diazepan-1-yl)-4H-pyrido[1,2-a]pyrimidin-4-one | 165-170 | 406.1 |
| 14 | 178 | 7-[(8aS)-hexahydropyrrolo[1,2-a]pyrazin-2(1H)-yl]-2-(2-methyl-1,3-benzothiazol-5-yl)-4H-pyrido[1,2-a]pyrimidin-4-one | 254-256 | 418.1 |
| 21* | 179 | 2-(4-methyl-1H-imidazol-1-yl)-7-(piperazin-1-yl)-4H-pyrido[1,2-a]pyrimidin-4-one | 204-206 | 311.1 |
| 21 | 180 | 2-(4-methyl-1H-imidazol-1-yl)-7-[(3S)-3-methylpiperazin-1-yl]-4H-pyrido[1,2-a]pyrimidin-4-one | 204-206 | 325.5 |
| 2 | 181 | 2-(3,4-dimethoxyphenyl)-7-{[2-(methylamino)ethyl]amino}-4H-pyrido[1,2-a]pyrimidin-4-one | 135-138 | 355 |
| 17* | 182 | 2-(5-fluoro-6-methoxypyridin-3-yl)-7-(piperazin-1-yl)-4H-pyrido[1,2-a]pyrimidin-4-one | 166-170 | 356.4 |
| 17 | 183 | 2-(3,5-difluoro-4-methoxyphenyl)-7-(piperazin-1-yl)-4H-pyrido[1,2-a]pyrimidin-4-one | 167-169 | 373.4 |
| 17 | 184 | 2-(3,5-difluoro-4-methoxyphenyl)-7-[(3S)-3-methylpiperazin-1-yl]-4H-pyrido[1,2-a]pyrimidin-4-one | 182-184 | 387.5 |

TABLE 1-continued

| Ex | Cpd | Name | M.P. | MS |
|---|---|---|---|---|
| 2 | 185 | 7-[4-(dimethylamino)piperidin-1-yl]-2-(3-fluoro-4-methoxyphenyl)-4H-pyrido[1,2-a]pyrimidin-4-one | 196-201 | 397.1 |
| 2 | 186 | 2-(3-fluoro-4-methoxyphenyl)-7-(1,2,3,6-tetrahydropyridin-4-yl)-4H-pyrido[1,2-a]pyrimidin-4-one | 182-184 | 352 |
| 2 | 187 | 2-(3,4-dimethoxyphenyl)-7-(piperidin-4-ylamino)-4H-pyrido[1,2-a]pyrimidin-4-one | ND | 381.1 |
| 23* | 188 | 2-(3,4-dimethoxyphenyl)-7-(1-methyl-1,2,3,6-tetrahydropyridin-4-yl)-4H-pyrido[1,2-a]pyrimidin-4-one | 165-168 | 378.3 |
| 14 | 189 | 2-(3-chloro-5-fluorophenyl)-7-[(3S)-3-methylpiperazin-1-yl]-4H-pyrido[1,2-a]pyrimidin-4-one | 188-190 | 373 |
| 14 | 190 | 2-(3-chloro-5-fluorophenyl)-7-(piperazin-1-yl)-4H-pyrido[1,2-a]pyrimidin-4-one | 180-184 | 359.1 |
| 18* | 191 | 7-[(3S)-3-methylpiperazin-1-yl]-2-(1-methyl-1H-pyrazol-4-yl)-4H-pyrido[1,2-a]pyrimidin-4-one | 168-170 | 325.2 |
| 18 | 192 | 2-(1-methyl-1H-pyrazol-4-yl)-7-(piperazin-1-yl)-4H-pyrido[1,2-a]pyrimidin-4-one | ND | 311.1 |
| 14 | 193 | 2-(2-methyl-1,3-benzoxazol-6-yl)-7-[(3R)-3-methylpiperazin-1-yl]-4H-pyrido[1,2-a]pyrimidin-4-one | 175-177 | 376.5 |
| 14 | 194 | 7-(3,3-dimethylpiperazin-1-yl)-2-(2-methyl-1,3-benzoxazol-6-yl)-4H-pyrido[1,2-a]pyrimidin-4-one | 160-162 | 390.5 |
| 14 | 195 | 7-(1,4-diazepan-1-yl)-2-(2-methyl-1,3-benzoxazol-6-yl)-4H-pyrido[1,2-a]pyrimidin-4-one | 134-137 | 376.5 |
| 14 | 196 | 2-(2-methyl-1,3-benzoxazol-6-yl)-7-(4-methyl-1,4-diazepan-1-yl)-4H-pyrido[1,2-a]pyrimidin-4-one | 146-150 | 390.5 |
| 14 | 197 | 7-[(8aS)-hexahydropyrrolo[1,2-a]pyrazin-2(1H)-yl]-2-(2-methyl-1,3-benzoxazol-6-yl)-4H-pyrido[1,2-a]pyrimidin-4-one | 214-217 | 402.5 |
| 14 | 198 | 7-[(8aR)-hexahydropyrrolo[1,2-a]pyrazin-2(1H)-yl]-2-(2-methyl-1,3-benzoxazol-6-yl)-4H-pyrido[1,2-a]pyrimidin-4-one | 194-199 | 402.5 |
| 14 | 199 | 2-(4,5-dimethoxypyridin-2-yl)-7-(piperazin-1-yl)-4H-pyrido[1,2-a]pyrimidin-4-one | 207-209 | 368.4 |
| 33 | 200 | 7-[3-(dimethylamino)pyrrolidin-1-yl]-2-(3-fluoro-4-methoxyphenyl)-4H-quinolizin-4-one | 259-261 | 382.1 |
| 33 | 201 | 7-(4-aminopiperidin-1-yl)-2-(3-fluoro-4-methoxyphenyl)-4H-quinolizin-4-one | ND | 368.2 |
| 14 | 202 | 7-(4-ethylpiperazin-1-yl)-2-(2-methyl-1,3-benzoxazol-6-yl)-4H-pyrido[1,2-a]pyrimidin-4-one | 212-216 | 390.5 |
| 33 | 203a | 7-[4-(dimethylamino)piperidin-1-yl]-2-(3-fluoro-4-methoxyphenyl)-4H-quinolizin-4-one | NI | NI |
| 23 | 204 | 2-(3-fluoro-4-methoxyphenyl)-7-(1-methyl-1,2,3,6-tetrahydropyridin-4-yl)-4H-pyrido[1,2-a]pyrimidin-4-one | 129-132 | 366 |
| 2 | 205 | 7-[(3S)-3-(dimethylamino)pyrrolidin-1-yl]-2-(3-fluoro-4-methoxyphenyl)-4H-pyrido[1,2-a]pyrimidin-4-one | 187-192 | 383.1 |
| 2 | 206 | 7-[(3R,4R)-3-(dimethylamino)-4-hydroxypyrrolidin-1-yl]-2-(3-fluoro-4-methoxyphenyl)-4H-pyrido[1,2-a]pyrimidin-4-one | 223-228 | 399 |
| 2 | 207 | 7-(4-aminopiperidin-1-yl)-2-(3-fluoro-4-methoxyphenyl)-4H-pyrido[1,2-a]pyrimidin-4-one | 173-179 | 369.1 |
| 2 | 208 | 2-(3-fluoro-4-methoxyphenyl)-7-[4-(methylamino)piperidin-1-yl]-4H-pyrido[1,2-a]pyrimidin-4-one | 167-171 | 383.1 |
| 16* | 209 | 2-(8-fluoro-2-methylimidazo[1,2-a]pyridin-6-yl)-7-(piperazin-1-yl)-4H-pyrido[1,2-a]pyrimidin-4-one | 282-288 | 379.4 |
| 16 | 210 | 7-[(3R,5S)-3,5-dimethylpiperazin-1-yl]-2-(8-fluoro-2-methylimidazo[1,2-a]pyridin-6-yl)-4H-pyrido[1,2-a]pyrimidin-4-one | 255-259 | 407.1 |
| 16 | 211 | 2-(8-fluoro-2-methylimidazo[1,2-a]pyridin-6-yl)-7-(4-methyl-1,4-diazepan-1-yl)-4H-pyrido[1,2-a]pyrimidin-4-one | 262-266 | 407.6 |
| 2 | 212 | 2-(3-fluoro-4-methoxyphenyl)-7-[(3aR,6aS)-hexahydropyrrolo[3,4-c]pyrrol-2(1H)-yl]-4H-pyrido[1,2-a]pyrimidin-4-one | 195-200 | 381.1 |
| 2 | 213 | 2-(3-fluoro-4-methoxyphenyl)-7-[(3aR,6aS)-5-methylhexahydropyrrolo[3,4-c]pyrrol-2(1H)-yl]-4H-pyrido[1,2-a]pyrimidin-4-one | 204-210 | 395.1 |
| 25 | 214 | 2-(3,4-dimethoxyphenyl)-7-[1-(2-hydroxyethyl)piperidin-4-yl]-4H-pyrido[1,2-a]pyrimidin-4-one | 145-148 | 410 |
| 14 | 215 | 2-(4-fluoro-3-methoxyphenyl)-7-[(3S)-3-methylpiperazin-1-yl]-4H-pyrido[1,2-a]pyrimidin-4-one | 130-135 | 369.2 |

TABLE 1-continued

| Ex | Cpd | Name | M.P. | MS |
|---|---|---|---|---|
| 14 | 216 | 2-(4-fluoro-3-methoxyphenyl)-7-(piperazin-1-yl)-4H-pyrido[1,2-a]pyrimidin-4-one | 170-172 | 355.2 |
| 14 | 217 | 2-(3,4-difluoro-5-methoxyphenyl)-7-[(3S)-3-methylpiperazin-1-yl]-4H-pyrido[1,2-a]pyrimidin-4-one | 160-164 | 387.1 |
| 14 | 218 | 2-(3,4-difluoro-5-methoxyphenyl)-7-(piperazin-1-yl)-4H-pyrido[1,2-a]pyrimidin-4-one | 155-160 | 373.1 |
| 14 | 219 | 2-(2-methyl-1,3-benzothiazol-6-yl)-7-(piperazin-1-yl)-4H-pyrido[1,2-a]pyrimidin-4-one | 218-220 | 378.1 |
| 29* | 220 | 7-(3-fluoro-4-methoxyphenyl)-2-(piperazin-1-yl)-4H-pyrido[1,2-a]pyrimidin-4-one | 202-206 | 355 |
| 14 | 221 | 2-(2-methyl-1,3-benzothiazol-6-yl)-7-[(3S)-3-methylpiperazin-1-yl]-4H-pyrido[1,2-a]pyrimidin-4-one | 214-216 | 392.1 |
| 2 | 222 | 2-(3-fluoro-4-methoxyphenyl)-7-[(3S)-3-(methylamino)pyrrolidin-1-yl]-4H-pyrido[1,2-a]pyrimidin-4-one | 208-216 | 369.1 |
| 2 | 223 | 2-(3-fluoro-4-methoxyphenyl)-7-{4-[(methylamino)methyl]piperidin-1-yl}-4H-pyrido[1,2-a]pyrimidin-4-one | 163-170 | 397.1 |
| 2 | 224 | 7-[(3S)-3-aminopyrrolidin-1-yl]-2-(3-fluoro-4-methoxyphenyl)-4H-pyrido[1,2-a]pyrimidin-4-one | 193-198 | 355 |
| 2 | 225 | 2-(3-fluoro-4-methoxyphenyl)-7-{[(3R)-1-methylpyrrolidin-3-yl]amino}-4H-pyrido[1,2-a]pyrimidin-4-one | 197-202 | 369.1 |
| 2 | 226 | 7-{4-[(dimethylamino)methyl]piperidin-1-yl}-2-(3-fluoro-4-methoxyphenyl)-4H-pyrido[1,2-a]pyrimidin-4-one | 178-185 | 411.1 |
| 14 | 227 | 2-(6-methoxypyridin-2-yl)-7-(piperazin-1-yl)-4H-pyrido[1,2-a]pyrimidin-4-one | 214-218 | 338.1 |
| 14 | 228 | 7-(piperazin-1-yl)-2-(pyridin-3-yl)-4H-pyrido[1,2-a]pyrimidin-4-one | 175-178 | 308 |
| 14 | 229 | 2-(5-methoxypyridin-3-yl)-7-(piperazin-1-yl)-4H-pyrido[1,2-a]pyrimidin-4-one | 192-195 | 338 |
| 14 | 230 | 3-fluoro-5-{7-[(3S)-3-methylpiperazin-1-yl]-4-oxo-4H-pyrido[1,2-a]pyrimidin-2-yl}benzonitrile | 185-188 | 364.2 |
| 14 | 231 | 3-fluoro-5-[4-oxo-7-(piperazin-1-yl)-4H-pyrido[1,2-a]pyrimidin-2-yl]benzonitrile | 238-244 | 350.1 |
| 2 | 232 | 2-(3-fluoro-4-methoxyphenyl)-7-[(3'S,4'S)-4'-hydroxy-1,3'-bipyrrolidin-1'-yl]-4H-pyrido[1,2-a]pyrimidin-4-one | 226-232 | 425.1 |
| 2 | 233 | 2-(3-fluoro-4-methoxyphenyl)-7-{methyl[(3R)-pyrrolidin-3-yl]amino}-4H-pyrido[1,2-a]pyrimidin-4-one | 143-147 | 369.1 |
| 14 | 234 | 7-[(3S)-3,4-dimethylpiperazin-1-yl]-2-(2-methyl-1,3-benzoxazol-6-yl)-4H-pyrido[1,2-a]pyrimidin-4-one | 205-209 | 390.6 |
| 27 | 235 | 2-(3,4-dimethoxyphenyl)-7-[(1-methylpiperidin-4-yl)oxy]-4H-pyrido[1,2-a]pyrimidin-4-one | ND | 396.2 |
| 27 | 236 | 2-(3,4-dimethoxyphenyl)-7-[(3S)-pyrrolidin-3-yloxy]-4H-pyrido[1,2-a]pyrimidin-4-one | 164-166 | 368.1 |
| 27* | 237 | 2-(3,4-dimethoxyphenyl)-7-(piperidin-4-yloxy)-4H-pyrido[1,2-a]pyrimidin-4-one | 221-224 | 382.2 |
| 2 | 238 | 7-(1,4-diazepan-1-yl)-2-(3,4-dimethoxyphenyl)-9-methyl-4H-pyrido[1,2-a]pyrimidin-4-one | 160-177 | 395.5 |
| 2* | 239 | 2-(3-fluoro-4-methoxyphenyl)-7-{methyl[(3R)-1-methylpyrrolidin-3-yl]amino}-4H-pyrido[1,2-a]pyrimidin-4-one | 143-149 | 383.5 |
| 14 | 240 | 7-[4-(dimethylamino)piperidin-1-yl]-2-(2-methyl-1,3-benzoxazol-6-yl)-4H-pyrido[1,2-a]pyrimidin-4-one | 206-210 | 404.5 |
| 14 | 241 | 7-[(3S)-3-(dimethylamino)pyrrolidin-1-yl]-2-(2-methyl-1,3-benzoxazol-6-yl)-4H-pyrido[1,2-a]pyrimidin-4-one | 189-193 | 390.5 |
| 14 | 242 | 7-(4-aminopiperidin-1-yl)-2-(2-methyl-1,3-benzoxazol-6-yl)-4H-pyrido[1,2-a]pyrimidin-4-one | ND | 376.2 |
| 14 | 243 | 7-[(3aR,6aS)-hexahydropyrrolo[3,4-c]pyrrol-2(1H)-yl]-2-(2-methyl-1,3-benzoxazol-6-yl)-4H-pyrido[1,2-a]pyrimidin-4-one | ND | 388.3 |
| 14 | 244 | 7-[(3R)-3,4-dimethylpiperazin-1-yl]-2-(2-methyl-1,3-benzoxazol-6-yl)-4H-pyrido[1,2-a]pyrimidin-4-one | 181-187 | 390.5 |
| 34* | 245 | 2-(3,4-dimethoxyphenyl)-7-(1,2,3,6-tetrahydropyridin-4-yl)-4H-quinolizin-4-one | 174-176 | 363.2 |
| 2 | 246 | 2-(3-fluoro-4-methoxyphenyl)-7-[(3aR,6aR)-1-methylhexahydropyrrolo[3,4-b]pyrrol-5(1H)-yl]-4H-pyrido[1,2-a]pyrimidin-4-one | 205-209 | 395.2 |

TABLE 1-continued

| Ex | Cpd | Name | M.P. | MS |
|---|---|---|---|---|
| 2 | 247 | 2-(3,4-dimethoxyphenyl)-9-methyl-7-(1,2,3,6-tetrahydropyridin-4-yl)-4H-pyrido[1,2-a]pyrimidin-4-one | 186-191 | 378.2 |
| 23 | 248 | 2-(3,4-dimethoxyphenyl)-7-[1-(2-hydroxyethyl)-1,2,3,6-tetrahydropyridin-4-yl]-4H-pyrido[1,2-a]pyrimidin-4-one | 134-137 | 408.2 |
| 35* | 249 | 2-(3,4-dimethoxyphenyl)-7-(1-methyl-1,2,3,6-tetrahydropyridin-4-yl)-4H-quinolizin-4-one | 194-196 | 377.2 |
| 24 | 250 | 2-(3,4-dimethoxyphenyl)-9-methyl-7-(piperidin-4-yl)-4H-pyrido[1,2-a]pyrimidin-4-one | 176-181 | 380.3 |
| 23 | 251 | 2-(3,4-dimethoxyphenyl)-9-methyl-7-(1-methyl-1,2,3,6-tetrahydropyridin-4-yl)-4H-pyrido[1,2-a]pyrimidin-4-one | 187-196 | 392.2 |
| 25 | 252 | 2-(3,4-dimethoxyphenyl)-9-methyl-7-(1-methylpiperidin-4-yl)-4H-pyrido[1,2-a]pyrimidin-4-one | 170-174 | 394.2 |
| 14 | 253 | 7-(1,4-diazepan-1-yl)-2-(2-methyl-1,3-benzothiazol-6-yl)-4H-pyrido[1,2-a]pyrimidin-4-one | 205-207 | 392.2 |
| 14 | 254 | 2-(2-methyl-1,3-benzothiazol-6-yl)-7-(4-methyl-1,4-diazepan-1-yl)-4H-pyrido[1,2-a]pyrimidin-4-one | 158-160 | 406.1 |
| 14 | 255 | 7-[(8aS)-hexahydropyrrolo[1,2-a]pyrazin-2(1H)-yl]-2-(2-methyl-1,3-benzothiazol-6-yl)-4H-pyrido[1,2-a]pyrimidin-4-one | 250-260 (DR) | 418.1 |
| 14 | 256 | 2-(2-methyl-1,3-benzothiazol-6-yl)-7-(4-methylpiperazin-1-yl)-4H-pyrido[1,2-a]pyrimidin-4-one | 230-234 | 392.1 |
| 2 | 257 | 2-(3,4-dimethoxyphenyl)-7-[(3aR,6aS)-hexahydropyrrolo[3,4-c]pyrrol-2(1H)-yl]-9-methyl-4H-pyrido[1,2-a]pyrimidin-4-one | 215 (S), 246-251 | 407.3 |
| 9 | 258 | 7-[(3S)-3,4-dimethylpiperazin-1-yl]-2-(4,6-dimethylpyrazolo[1,5-a]pyrazin-2-yl)-4H-pyrido[1,2-a]pyrimidin-4-one | 220-223 | 404.3 |
| 9 | 259 | 2-(4,6-dimethylpyrazolo[1,5-a]pyrazin-2-yl)-7-[(3R,5S)-3,4,5-trimethylpiperazin-1-yl]-4H-pyrido[1,2-a]pyrimidin-4-one | 254-260 | 418.3 |
| 2 | 260 | 2-(3,4-dimethoxyphenyl)-9-methyl-7-[(3aR,6aS)-5-methylhexahydropyrrolo[3,4-c]pyrrol-2(1H)-yl]-4H-pyrido[1,2-a]pyrimidin-4-one | 212-218 | 421.2 |
| 2 | 261 | 2-(3,4-dimethoxyphenyl)-7-[4-(dimethylamino)piperidin-1-yl]-9-methyl-4H-pyrido[1,2-a]pyrimidin-4-one | 167-171 | 423.3 |
| 22 | 262 | 7-[(1R,5S)-8-azabicyclo[3.2.1]oct-2-en-3-yl]-2-(3,4-dimethoxyphenyl)-4H-pyrido[1,2-a]pyrimidin-4-one | 191-194 | 390.2 |
| 26* | 263 | 2-(3,4-dimethoxyphenyl)-7-(1,2,5,6-tetrahydropyridin-3-yl)-4H-pyrido[1,2-a]pyrimidin-4-one | 146-150 | 364.2 |
| 14 | 264 | 7-[(3R)-3-(dimethylamino)pyrrolidin-1-yl]-2-(2-methyl-1,3-benzoxazol-6-yl)-4H-pyrido[1,2-a]pyrimidin-4-one | 203-207 | 390.2 |
| 14 | 265 | 2-(2-ethyl-1,3-benzoxazol-6-yl)-7-(piperazin-1-yl)-4H-pyrido[1,2-a]pyrimidin-4-one | 170-175 | 376.2 |
| 14 | 266 | 2-(2-ethyl-1,3-benzoxazol-6-yl)-7-[(3S)-3-methylpiperazin-1-yl]-4H-pyrido[1,2-a]pyrimidin-4-one | 168-170 | 390.2 |
| 14 | 267 | 2-(2-methyl-1,3-benzoxazol-6-yl)-7-[(3aR,6aS)-5-methylhexahydropyrrolo[3,4-c]pyrrol-2(1H)-yl]-4H-pyrido[1,2-a]pyrimidin-4-one | 200-204 | 402.2 |
| 29 | 268 | 7-(8-fluoro-2-methylimidazo[1,2-a]pyridin-6-yl)-2-(piperazin-1-yl)-4H-pyrido[1,2-a]pyrimidin-4-one | 308 (D) | 379.2 |
| 16 | 269 | 2-(8-fluoro-2-methylimidazo[1,2-a]pyridin-6-yl)-7-(4-methylpiperazin-1-yl)-4H-pyrido[1,2-a]pyrimidin-4-one | 283-286 | 393.3 |
| 16 | 270 | 2-(8-fluoro-2-methylimidazo[1,2-a]pyridin-6-yl)-7-[(3R)-3-methylpiperazin-1-yl]-4H-pyrido[1,2-a]pyrimidin-4-one | ND | 393.3 |
| 16 | 271 | 2-(8-fluoro-2-methylimidazo[1,2-a]pyridin-6-yl)-7-[(8aS)-hexahydropyrrolo[1,2-a]pyrazin-2(1H)-yl]-4H-pyrido[1,2-a]pyrimidin-4-one | 270-274 | 419.3 |
| 16 | 272 | 2-(8-fluoro-2-methylimidazo[1,2-a]pyridin-6-yl)-7-[(8aR)-hexahydropyrrolo[1,2-a]pyrazin-2(1H)-yl]-4H-pyrido[1,2-a]pyrimidin-4-one | 277-280 | 419.2 |
| 16 | 273 | 7-(4-aminopiperidin-1-yl)-2-(8-fluoro-2-methylimidazo[1,2-a]pyridin-6-yl)-4H-pyrido[1,2-a]pyrimidin-4-one | ND | 393.3 |

TABLE 1-continued

| Ex | Cpd | Name | M.P. | MS |
|---|---|---|---|---|
| 16 | 274 | 7-[(3R)-3-(dimethylamino)pyrrolidin-1-yl]-2-(8-fluoro-2-methylimidazo[1,2-a]pyridin-6-yl)-4H-pyrido[1,2-a]pyrimidin-4-one | 300 (D) | 407.3 |
| 16 | 275 | 7-[(3S)-3-(dimethylamino)pyrrolidin-1-yl]-2-(8-fluoro-2-methylimidazo[1,2-a]pyridin-6-yl)-4H-pyrido[1,2-a]pyrimidin-4-one | 294-297 | 407.3 |
| 30* | 276 | 2-(4-aminopiperidin-1-yl)-7-(3-fluoro-4-methoxyphenyl)-4H-pyrido[1,2-a]pyrimidin-4-one | 268-283 | 369.3 |
| 30 | 277 | 2-[(3R)-3-(dimethylamino)pyrrolidin-1-yl]-7-(3-fluoro-4-methoxyphenyl)-4H-pyrido[1,2-a]pyrimidin-4-one | 167-170 | 383.2 |
| 30 | 278 | 2-[(3S)-3-(dimethylamino)pyrrolidin-1-yl]-7-(3-fluoro-4-methoxyphenyl)-4H-pyrido[1,2-a]pyrimidin-4-one | 167-169 | 383.2 |
| 2 | 279 | 2-(3-fluoro-4-methoxyphenyl)-7-[(3aR,6aS)-5-(2-hydroxyethyl)hexahydropyrrolo[3,4-c]pyrrol-2(1H)-yl]-4H-pyrido[1,2-a]pyrimidin-4-one | 180-186 | 425.3 |
| 2 | 280 | 2-(3-fluoro-4-methoxyphenyl)-7-[(3aS,6aS)-1-methylhexahydropyrrolo[3,4-b]pyrrol-5(1H)-yl]-4H-pyrido[1,2-a]pyrimidin-4-one | 207-211 | 395.3 |
| 2 | 281 | 2-(3-fluoro-4-methoxyphenyl)-7-[(3aR,6aS)-5-(propan-2-yl)hexahydropyrrolo[3,4-c]pyrrol-2(1H)-yl]-4H-pyrido[1,2-a]pyrimidin-4-one | 189-192 | 423.3 |
| 2 | 282 | 7-[(3R)-3-(dimethylamino)pyrrolidin-1-yl]-2-(3-fluoro-4-methoxyphenyl)-4H-pyrido[1,2-a]pyrimidin-4-one | 188-191 | 383.3 |
| 14 | 283 | 7-(3,3-dimethylpiperazin-1-yl)-2-(2-methyl-1,3-benzothiazol-6-yl)-4H-pyrido[1,2-a]pyrimidin-4-one | 200-202 | 406.3 |
| 14 | 284 | 7-[(8aR)-hexahydropyrrolo[1,2-a]pyrazin-2(1H)-yl]-2-(2-methyl-1,3-benzothiazol-6-yl)-4H-pyrido[1,2-a]pyrimidin-4-one | 254-256 | 418.2 |
| 14 | 285 | 7-[4-(dimethylamino)piperidin-1-yl]-2-(2-methyl-1,3-benzothiazol-6-yl)-4H-pyrido[1,2-a]pyrimidin-4-one | ND | 420.2 |
| 27 | 286 | 2-(2-methyl-1,3-benzothiazol-6-yl)-7-(piperidin-4-yloxy)-4H-pyrido[1,2-a]pyrimidin-4-one | 218-220 | 393.1 |
| 16 | 287 | 2-(8-chloro-2-methylimidazo[1,2-a]pyridin-6-yl)-7-(piperazin-1-yl)-4H-pyrido[1,2-a]pyrimidin-4-one | 245-251 | 395.2 |
| 16 | 288 | 2-(8-chloro-2-methylimidazo[1,2-a]pyridin-6-yl)-7-[(3R,5S)-3,5-dimethylpiperazin-1-yl]-4H-pyrido[1,2-a]pyrimidin-4-one | 289-295 | 423.1 |
| 16 | 289 | 2-(8-chloro-2-methylimidazo[1,2-a]pyridin-6-yl)-7-(4-methyl-1,4-diazepan-1-yl)-4H-pyrido[1,2-a]pyrimidin-4-one | 239-244 | 423.2 |
| 16 | 290 | 2-(8-chloro-2-methylimidazo[1,2-a]pyridin-6-yl)-7-[(3R)-3-methylpiperazin-1-yl]-4H-pyrido[1,2-a]pyrimidin-4-one | 236-239 | 409.1 |
| 16 | 291 | 2-(8-chloro-2-methylimidazo[1,2-a]pyridin-6-yl)-7-[(3S)-3-methylpiperazin-1-yl]-4H-pyrido[1,2-a]pyrimidin-4-one | 236-239 | 409.1 |
| 16 | 292 | 2-(8-chloro-2-methylimidazo[1,2-a]pyridin-6-yl)-7-[(8aR)-hexahydropyrrolo[1,2-a]pyrazin-2(1H)-yl]-4H-pyrido[1,2-a]pyrimidin-4-one | 274-280 | 435.2 |
| 16 | 293 | 2-(8-chloro-2-methylimidazo[1,2-a]pyridin-6-yl)-7-[(8aS)-hexahydropyrrolo[1,2-a]pyrazin-2(1H)-yl]-4H-pyrido[1,2-a]pyrimidin-4-one | 269-275 | 435.2 |
| 46* | 294 | 7-(3-fluoro-4-methoxyphenyl)-2-(1,2,3,6-tetrahydropyridin-4-yl)-4H-pyrido[1,2-a]pyrimidin-4-one | 188-192 | 352.1 |
| 39 | 295 | 7-[(3S)-3,4-dimethylpiperazin-1-yl]-2-(8-fluoro-2-methylimidazo[1,2-a]pyridin-6-yl)-4H-pyrido[1,2-a]pyrimidin-4-one | 269-275 | 407.3 |
| 39 | 296 | 7-[(3R)-3,4-dimethylpiperazin-1-yl]-2-(8-fluoro-2-methylimidazo[1,2-a]pyridin-6-yl)-4H-pyrido[1,2-a]pyrimidin-4-one | 279-282 | 407.3 |
| 39 | 297 | 7-[4-(dimethylamino)piperidin-1-yl]-2-(8-fluoro-2-methylimidazo[1,2-a]pyridin-6-yl)-4H-pyrido[1,2-a]pyrimidin-4-one | 250-257 | 421.3 |
| 39 | 298 | 2-[4-(dimethylamino)piperidin-1-yl]-7-(3-fluoro-4-methoxyphenyl)-4H-pyrido[1,2-a]pyrimidin-4-one | 157-160 | 397.2 |
| 37 | 299 | 2-(4-fluoro-2-methyl-1,3-benzoxazol-6-yl)-7-(1,2,3,6-tetrahydropyridin-4-yl)-4H-pyrido[1,2-a]pyrimidin-4-one | 177-180 | 377.2 |
| 23 | 300 | 2-(4-fluoro-2-methyl-1,3-benzoxazol-6-yl)-7-(1-methyl-1,2,3,6-tetrahydropyridin-4-yl)-4H-pyrido[1,2-a]pyrimidin-4-one | 178-181 | 391.3 |

TABLE 1-continued

| Ex | Cpd | Name | M.P. | MS |
|---|---|---|---|---|
| 2 | 301 | 2-(3-fluoro-4-methoxyphenyl)-7-[(4aR,7aR)-octahydro-6H-pyrrolo[3,4-b]pyridin-6-yl]-4H-pyrido[1,2-a]pyrimidin-4-one | 194-201 | 395.2 |
| 37 | 302 | 2-(2-methyl-1,3-benzoxazol-6-yl)-7-(1,2,3,6-tetrahydropyridin-4-yl)-4H-pyrido[1,2-a]pyrimidin-4-one | ND | 359.2 |
| 23 | 303 | 2-(2-methyl-1,3-benzoxazol-6-yl)-7-(1-methyl-1,2,3,6-tetrahydropyridin-4-yl)-4H-pyrido[1,2-a]pyrimidin-4-one | 132-135 | 373.3 |
| 23 | 304 | 7-(1-ethyl-1,2,3,6-tetrahydropyridin-4-yl)-2-(2-methyl-1,3-benzoxazol-6-yl)-4H-pyrido[1,2-a]pyrimidin-4-one | 128-131 | 387.3 |
| 36 | 305 | 2-(4-fluoro-2-methyl-1,3-benzoxazol-6-yl)-7-(piperazin-1-yl)-4H-pyrido[1,2-a]pyrimidin-4-one | 184-186 | 380.3 |
| 36* | 306 | 2-(4-fluoro-2-methyl-1,3-benzoxazol-6-yl)-7-[(3S)-3-methylpiperazin-1-yl]-4H-pyrido[1,2-a]pyrimidin-4-one | 207-209 | 394.3 |
| 39 | 307 | 7-[(3S)-3,4-dimethylpiperazin-1-yl]-2-(4-fluoro-2-methyl-1,3-benzoxazol-6-yl)-4H-pyrido[1,2-a]pyrimidin-4-one | 194-196 | 408.3 |
| 36 | 308 | 2-(4-fluoro-2-methyl-1,3-benzoxazol-6-yl)-7-(4-methylpiperazin-1-yl)-4H-pyrido[1,2-a]pyrimidin-4-one | 219-221 | 394.1 |
| 36 | 309 | 7-(4-ethylpiperazin-1-yl)-2-(4-fluoro-2-methyl-1,3-benzoxazol-6-yl)-4H-pyrido[1,2-a]pyrimidin-4-one | 212-214 | 408.2 |
| 36 | 310 | 2-(4-fluoro-2-methyl-1,3-benzoxazol-6-yl)-7-(4-propylpiperazin-1-yl)-4H-pyrido[1,2-a]pyrimidin-4-one | 175-178 | 422.1 |
| 2 | 311 | 7-[(3aR,6aS)-5-ethylhexahydropyrrolo[3,4-c]pyrrol-2(1H)-yl]-2-(3-fluoro-4-methoxyphenyl)-4H-pyrido[1,2-a]pyrimidin-4-one | 157-167 | 409.1 |
| 22 | 312 | 2-(3-fluoro-4-methoxyphenyl)-9-methyl-7-(1,2,3,6-tetrahydropyridin-4-yl)-4H-pyrido[1,2-a]pyrimidin-4-one | 211-215 | 366.1 |
| 2 | 313 | 2-(3-fluoro-4-methoxyphenyl)-7-[(4aR,7aR)-1-methyloctahydro-6H-pyrrolo[3,4-b]pyridin-6-yl]-4H-pyrido[1,2-a]pyrimidin-4-one | 223-227 | 409.1 |
| 2 | 314 | 2-(3,4-dimethoxyphenyl)-9-methyl-7-[(3R)-3-methylpiperazin-1-yl]-4H-pyrido[1,2-a]pyrimidin-4-one | 177-184 | 395.2 |
| 23 | 315 | 2-(3-fluoro-4-methoxyphenyl)-9-methyl-7-(1-methyl-1,2,3,6-tetrahydropyridin-4-yl)-4H-pyrido[1,2-a]pyrimidin-4-one | 184-190 | 380.1 |
| 24 | 316 | 7-(3-fluoro-4-methoxyphenyl)-2-(piperidin-4-yl)-4H-pyrido[1,2-a]pyrimidin-4-one | 278-281 | 354.1 |
| 25 | 317 | 7-(3-fluoro-4-methoxyphenyl)-2-(1-methylpiperidin-4-yl)-4H-pyrido[1,2-a]pyrimidin-4-one | 202-205 | 368.1 |
| 23 | 318 | 7-(1-ethyl-1,2,3,6-tetrahydropyridin-4-yl)-2-(4-fluoro-2-methyl-1,3-benzoxazol-6-yl)-4H-pyrido[1,2-a]pyrimidin-4-one | 151-154 | 405.2 |
| 23 | 319 | 2-(4-fluoro-2-methyl-1,3-benzoxazol-6-yl)-7-(1-propyl-1,2,3,6-tetrahydropyridin-4-yl)-4H-pyrido[1,2-a]pyrimidin-4-one | 159-162 | 419.3 |
| 25 | 320 | 2-(3,4-dimethoxyphenyl)-7-[(1R,5S)-8-methyl-8-azabicyclo[3.2.1]oct-3-yl]-4H-pyrido[1,2-a]pyrimidin-4-one | ND | 406.2 |
| 2 | 321 | 2-(3,4-dimethoxyphenyl)-7-[(2R)-2-methylpiperazin-1-yl]-4H-pyrido[1,2-a]pyrimidin-4-one | ND | 381.1 |
| 54* | 322 | 2-(2-methyl-1,3-benzoxazol-6-yl)-7-[(3S)-3-methylpiperazin-1-yl]-4H-quinolizin-4-one | 115-117 | 375.3 |
| 54 | 323 | 2-(2-methyl-1,3-benzoxazol-6-yl)-7-(4-methylpiperazin-1-yl)-4H-quinolizin-4-one | ND | 375.1 |
| 39 | 324 | 7-[(3S)-4-ethyl-3-methylpiperazin-1-yl]-2-(2-methyl-1,3-benzoxazol-6-yl)-4H-quinolizin-4-one | 288-290 | 403.2 |
| 39 | 325 | 7-[(3S)-3,4-dimethylpiperazin-1-yl]-2-(2-methyl-1,3-benzoxazol-6-yl)-4H-quinolizin-4-one | >300 | 389.2 |
| 45 | 326 | 7-(4-aminopiperidin-1-yl)-2-(2-methyl-1,3-benzoxazol-6-yl)-4H-quinolizin-4-one | 288-290 | 375.2 |
| 2 | 327 | 2-(3-fluoro-4-methoxyphenyl)-9-methyl-7-[(3S)-3-methylpiperazin-1-yl]-4H-pyrido[1,2-a]pyrimidin-4-one | 198-202 | 383.1 |
| 2 | 328 | 7-[4-(dimethylamino)piperidin-1-yl]-2-(3-fluoro-4-methoxyphenyl)-9-methyl-4H-pyrido[1,2-a]pyrimidin-4-one | 141-145 | 411.2 |
| 25 | 329 | 2-(3-fluoro-4-methoxyphenyl)-9-methyl-7-(1-methylpiperidin-4-yl)-4H-pyrido[1,2-a]pyrimidin-4-one | 198-203 | 382.2 |

TABLE 1-continued

| Ex | Cpd | Name | M.P. | MS |
|---|---|---|---|---|
| 53 | 330 | 7-[4-(cyclopropylamino)piperidin-1-yl]-2-(3,4-dimethoxyphenyl)-9-methyl-4H-pyrido[1,2-a]pyrimidin-4-one | 141 (S), 158-161 | 435.3 |
| 39 | 331 | 2-(8-chloro-2-methylimidazo[1,2-a]pyridin-6-yl)-7-[(3S)-3,4-dimethylpiperazin-1-yl]-4H-pyrido[1,2-a]pyrimidin-4-one | 258-262 | 423.2 |
| 2 | 332 | 2-(3,4-dimethoxyphenyl)-7-[(3R,5S)-3,5-dimethylpiperazin-1-yl]-9-methyl-4H-pyrido[1,2-a]pyrimidin-4-one | 225-233 | 409.3 |
| 2 | 333 | 2-(3,4-dimethoxyphenyl)-7-[(3R)-3,4-dimethylpiperazin-1-yl]-9-methyl-4H-pyrido[1,2-a]pyrimidin-4-one | 148 (S), 168-177 | 409.3 |
| 9 | 334 | 2-(4,6-dimethylpyrazolo[1,5-a]pyrazin-2-yl)-7-(4-methyl-1,4-diazepan-1-yl)-4H-pyrido[1,2-a]pyrimidin-4-one | 169-171 | 404.4 |
| 9 | 335 | 2-(4,6-dimethylpyrazolo[1,5-a]pyrazin-2-yl)-7-[(3R)-3-methylpiperazin-1-yl]-4H-pyrido[1,2-a]pyrimidin-4-one | ND | 390.4 |
| 9 | 336 | 2-(4,6-dimethylpyrazolo[1,5-a]pyrazin-2-yl)-7-[(8aS)-hexahydropyrrolo[1,2-a]pyrazin-2(1H)-yl]-4H-pyrido[1,2-a]pyrimidin-4-one | 215-218 | 416.3 |
| 9 | 337 | 2-(4,6-dimethylpyrazolo[1,5-a]pyrazin-2-yl)-7-[(8aR)-hexahydropyrrolo[1,2-a]pyrazin-2(1H)-yl]-4H-pyrido[1,2-a]pyrimidin-4-one | 228-230 | 416.4 |
| 9 | 338 | 2-(4,6-dimethylpyrazolo[1,5-a]pyrazin-2-yl)-7-(4-ethylpiperazin-1-yl)-4H-pyrido[1,2-a]pyrimidin-4-one | 251-253 | 404.4 |
| 9 | 339 | 7-[4-(dimethylamino)piperidin-1-yl]-2-(4,6-dimethylpyrazolo[1,5-a]pyrazin-2-yl)-4H-pyrido[1,2-a]pyrimidin-4-one | 208-210 | 418.4 |
| 9 | 340 | 7-(3,3-dimethylpiperazin-1-yl)-2-(4,6-dimethylpyrazolo[1,5-a]pyrazin-2-yl)-4H-pyrido[1,2-a]pyrimidin-4-one | 195-197 | 404.4 |
| 9 | 341 | 7-(4-cyclopropylpiperazin-1-yl)-2-(4,6-dimethylpyrazolo[1,5-a]pyrazin-2-yl)-4H-pyrido[1,2-a]pyrimidin-4-one | 189-192 | 416.4 |
| 38* | 342 | 2-(4,6-dimethylpyrazolo[1,5-a]pyrazin-2-yl)-7-(1,2,3,6-tetrahydropyridin-4-yl)-4H-pyrido[1,2-a]pyrimidin-4-one | 207-210 | 373.3 |
| 39 | 343 | 2-(4,6-dimethylpyrazolo[1,5-a]pyrazin-2-yl)-7-[(3R)-4-ethyl-3-methylpiperazin-1-yl]-4H-pyrido[1,2-a]pyrimidin-4-one | ND | 418.4 |
| 2 | 344 | 2-(3,4-dimethoxyphenyl)-9-methyl-7-(4-methylpiperazin-1-yl)-4H-pyrido[1,2-a]pyrimidin-4-one | 191-198 | 395.3 |
| 2 | 345 | 2-(3,4-dimethoxyphenyl)-7-[4-(dimethylamino)piperidin-1-yl]-9-ethyl-4H-pyrido[1,2-a]pyrimidin-4-one | 146-150 | 437.3 |
| 23 | 346 | 2-(3,4-dimethoxyphenyl)-7-[1-(2-hydroxyethyl)-1,2,3,6-tetrahydropyridin-4-yl]-9-methyl-4H-pyrido[1,2-a]pyrimidin-4-one | 169-179 | 422.3 |
| 14 | 347 | 7-[4-(dimethylamino)piperidin-1-yl]-2-(2-methyl-1,3-benzothiazol-5-yl)-4H-pyrido[1,2-a]pyrimidin-4-one | 218-220 | 420.2 |
| 45 | 348 | 7-(4-aminopiperidin-1-yl)-2-(2-methyl-1,3-benzothiazol-5-yl)-4H-pyrido[1,2-a]pyrimidin-4-one | 190-192 | 392.1 |
| 45 | 349 | 7-[(3aR,6aS)-hexahydropyrrolo[3,4-c]pyrrol-2(1H)-yl]-2-(2-methyl-1,3-benzothiazol-5-yl)-4H-pyrido[1,2-a]pyrimidin-4-one | ND | 404.1 |
| 23 | 350 | 2-(4,6-dimethylpyrazolo[1,5-a]pyrazin-2-yl)-7-(1-methyl-1,2,3,6-tetrahydropyridin-4-yl)-4H-pyrido[1,2-a]pyrimidin-4-one | 193-197 | 387.4 |
| 23 | 351 | 2-(4,6-dimethylpyrazolo[1,5-a]pyrazin-2-yl)-7-(1-ethyl-1,2,3,6-tetrahydropyridin-4-yl)-4H-pyrido[1,2-a]pyrimidin-4-one | 202-204 | 401.4 |
| 23 | 352 | 2-(4,6-dimethylpyrazolo[1,5-a]pyrazin-2-yl)-7-(1-propyl-1,2,3,6-tetrahydropyridin-4-yl)-4H-pyrido[1,2-a]pyrimidin-4-one | 191-193 | 415.5 |
| 49* | 353 | 2-(3,4-dimethoxyphenyl)-7-(1,2,3,6-tetrahydropyridin-4-yl)-4H-pyrimido[1,2-a]pyrimidin-4-one | ND | 365.1 |
| 23 | 354 | 7-(1-cyclopropyl-1,2,3,6-tetrahydropyridin-4-yl)-2-(4,6-dimethylpyrazolo[1,5-a]pyrazin-2-yl)-4H-pyrido[1,2-a]pyrimidin-4-one | ND | 413.4 |

TABLE 1-continued

| Ex | Cpd | Name | M.P. | MS |
|---|---|---|---|---|
| 23 | 355 | 2-(4,6-dimethylpyrazolo[1,5-a]pyrazin-2-yl)-7-[1-(propan-2-yl)-1,2,3,6-tetrahydropyridin-4-yl]-4H-pyrido[1,2-a]pyrimidin-4-one | 186-189 | 415.4 |
| 23 | 356 | 7-(1-cyclobutyl-1,2,3,6-tetrahydropyridin-4-yl)-2-(4,6-dimethylpyrazolo[1,5-a]pyrazin-2-yl)-4H-pyrido[1,2-a]pyrimidin-4-one | 191-193 | 427.4 |
| 23 | 357 | 2-(4,6-dimethylpyrazolo[1,5-a]pyrazin-2-yl)-7-[1-(oxetan-3-yl)-1,2,3,6-tetrahydropyridin-4-yl]-4H-pyrido[1,2-a]pyrimidin-4-one | ND | 429.3 |
| 53 | 358 | 2-(3,4-dimethoxyphenyl)-9-methyl-7-[4-(methylamino)piperidin-1-yl]-4H-pyrido[1,2-a]pyrimidin-4-one | ND | 409.3 |
| 53 | 359 | 2-(3,4-dimethoxyphenyl)-7-[4-(ethylamino)piperidin-1-yl]-9-methyl-4H-pyrido[1,2-a]pyrimidin-4-one | ND | 423.4 |
| 2 | 360 | 2-(3,4-dimethoxyphenyl)-8-methyl-7-(piperazin-1-yl)-4H-pyrido[1,2-a]pyrimidin-4-one | 161-169 | 381.3 |
| 39 | 361 | 2-(3,4-dimethoxyphenyl)-7-[4-(propan-2-ylamino)piperidin-1-yl]-4H-pyrido[1,2-a]pyrimidin-4-one | ND | 423.3 |
| 23 | 362 | 7-(1-cyclobutyl-1,2,3,6-tetrahydropyridin-4-yl)-2-(3,4-dimethoxyphenyl)-4H-pyrido[1,2-a]pyrimidin-4-one | 152-154 | 418.3 |
| 23 | 363 | 2-(3,4-dimethoxyphenyl)-7-[1-(propan-2-yl)-1,2,3,6-tetrahydropyridin-4-yl]-4H-pyrido[1,2-a]pyrimidin-4-one | 116-118 | 406.3 |
| 23 | 364 | 2-(3,4-dimethoxyphenyl)-7-[1-(oxetan-3-yl)-1,2,3,6-tetrahydropyridin-4-yl]-4H-pyrido[1,2-a]pyrimidin-4-one | 178-180 | 420.3 |
| 23 | 365 | 2-(3,4-dimethoxyphenyl)-7-(1-propyl-1,2,3,6-tetrahydropyridin-4-yl)-4H-pyrido[1,2-a]pyrimidin-4-one | 158-160 | 406.2 |
| 22 | 366 | 2-(3,4-dimethoxyphenyl)-7-[4-(methylamino)cyclohex-1-en-1-yl]-4H-pyrido[1,2-a]pyrimidin-4-one | 232-235 | 392.3 |
| 23 | 367 | 2-(3,4-dimethoxyphenyl)-7-[4-(dimethylamino)cyclohex-1-en-1-yl]-4H-pyrido[1,2-a]pyrimidin-4-one | 162-164 | 406.2 |
| 23 | 368 | 2-(3,4-dimethoxyphenyl)-7-{4-[ethyl(methyl)amino]cyclohex-1-en-1-yl}-4H-pyrido[1,2-a]pyrimidin-4-one | 132-134 | 420.4 |
| 23 | 369 | 2-(3,4-dimethoxyphenyl)-7-{4-[methyl(propyl)amino]cyclohex-1-en-1-yl}-4H-pyrido[1,2-a]pyrimidin-4-one | 116-118 | 434.4 |
| 23 | 370 | 2-(3,4-dimethoxyphenyl)-7-(1-ethyl-1,2,3,6-tetrahydropyridin-4-yl)-4H-pyrido[1,2-a]pyrimidin-4-one | 170-172 | 392.3 |
| 46 | 371 | 7-(3,4-dimethoxyphenyl)-2-(1,2,3,6-tetrahydropyridin-4-yl)-4H-pyrido[1,2-a]pyrimidin-4-one | 172-178 | 364.3 |
| 46 | 372 | 7-(8-fluoro-2-methylimidazo[1,2-a]pyridin-6-yl)-2-(1,2,3,6-tetrahydropyridin-4-yl)-4H-pyrido[1,2-a]pyrimidin-4-one | ND | 376.2 |
| 16 | 373 | 2-(8-fluoro-2-methylimidazo[1,2-a]pyridin-6-yl)-7-[4-(propan-2-yl)piperazin-1-yl]-4H-pyrido[1,2-a]pyrimidin-4-one | 260-264 | 421.3 |
| 16 | 374 | 2-(8-chloro-2-methylimidazo[1,2-a]pyridin-6-yl)-7-[4-(propan-2-yl)piperazin-1-yl]-4H-pyrido[1,2-a]pyrimidin-4-one | 287-292 | 437.4 |
| 46 | 375 | 7-(2-methylimidazo[1,2-a]pyridin-6-yl)-2-(1,2,3,6-tetrahydropyridin-4-yl)-4H-pyrido[1,2-a]pyrimidin-4-one | 197-201 | 358.2 |
| 23 | 376 | 7-(2-methylimidazo[1,2-a]pyridin-6-yl)-2-(1-methyl-1,2,3,6-tetrahydropyridin-4-yl)-4H-pyrido[1,2-a]pyrimidin-4-one | 203-207 | 372.2 |
| 23 | 377 | 7-(3,4-dimethoxyphenyl)-2-(1-methyl-1,2,3,6-tetrahydropyridin-4-yl)-4H-pyrido[1,2-a]pyrimidin-4-one | 149-152 | 378.3 |
| 23 | 378 | 2-(3,4-dimethoxyphenyl)-9-methyl-7-(1-propyl-1,2,3,6-tetrahydropyridin-4-yl)-4H-pyrido[1,2-a]pyrimidin-4-one | 171-177 | 420.3 |
| 23 | 379 | 7-(1-cyclobutyl-1,2,3,6-tetrahydropyridin-4-yl)-2-(3,4-dimethoxyphenyl)-9-methyl-4H-pyrido[1,2-a]pyrimidin-4-one | 167-178 | 432.3 |
| 55 | 380a | 2-(2-methyl-1,3-benzothiazol-6-yl)-7-(piperidin-4-yl)-4H-pyrimido[1,2-b]pyridazin-4-one | NI | NI |
| 45 | 381 | 7-(4-aminopiperidin-1-yl)-2-(2-methyl-1,3-benzothiazol-6-yl)-4H-pyrido[1,2-a]pyrimidin-4-one | 190-194 | 392.2 |

TABLE 1-continued

| Ex | Cpd | Name | M.P. | MS |
|---|---|---|---|---|
| 45 | 382 | 7-(3-aminopyrrolidin-1-yl)-2-(2-methyl-1,3-benzothiazol-6-yl)-4H-pyrido[1,2-a]pyrimidin-4-one | 196-200 | 378.2 |
| 14 | 383 | 7-[(3R)-3-(dimethylamino)pyrrolidin-1-yl]-2-(2-methyl-1,3-benzothiazol-6-yl)-4H-pyrido[1,2-a]pyrimidin-4-one | 235-240 | 406.3 |
| 37 | 384 | 2-(2-methyl-1,3-benzothiazol-6-yl)-7-(1,2,3,6-tetrahydropyridin-4-yl)-4H-pyrido[1,2-a]pyrimidin-4-one | 124-126 | 375.2 |
| 16 | 385 | 2-(8-fluoro-2-methylimidazo[1,2-a]pyridin-6-yl)-7-[4-(2-methoxyethyl)piperazin-1-yl]-4H-pyrido[1,2-a]pyrimidin-4-one | 258-262 | 437.5 |
| 23 | 386 | 2-(3,4-dimethoxyphenyl)-9-methyl-7-[1-(oxetan-3-yl)-1,2,3,6-tetrahydropyridin-4-yl]-4H-pyrido[1,2-a]pyrimidin-4-one | 180-195 (DR) | 434.3 |
| 23 | 387 | 2-(3,4-dimethoxyphenyl)-9-methyl-7-[1-(propan-2-yl)-1,2,3,6-tetrahydropyridin-4-yl]-4H-pyrido[1,2-a]pyrimidin-4-one | 153-163 | 420.4 |
| 23 | 388 | 2-(3,4-dimethoxyphenyl)-7-(1-ethyl-1,2,3,6-tetrahydropyridin-4-yl)-9-methyl-4H-pyrido[1,2-a]pyrimidin-4-one | ND | 406.4 |
| 22 | 389 | 2-(3,4-dimethoxyphenyl)-8-methyl-7-(1,2,3,6-tetrahydropyridin-4-yl)-4H-pyrido[1,2-a]pyrimidin-4-one | 175 (D) | 378.3 |
| 23 | 390 | 7-(1-cyclopropyl-1,2,3,6-tetrahydropyridin-4-yl)-2-(3,4-dimethoxyphenyl)-9-methyl-4H-pyrido[1,2-a]pyrimidin-4-one | 180-189 | 418.4 |
| 23 | 391 | 2-(3,4-dimethoxyphenyl)-8-methyl-7-(1-methyl-1,2,3,6-tetrahydropyridin-4-yl)-4H-pyrido[1,2-a]pyrimidin-4-one | 174-178 | 392.4 |
| 23 | 392 | 2-(2-methyl-1,3-benzothiazol-6-yl)-7-(1-methyl-1,2,3,6-tetrahydropyridin-4-yl)-4H-pyrido[1,2-a]pyrimidin-4-one | 170-172 | 389.2 |
| 23 | 393 | 7-[1-(2-hydroxyethyl)-1,2,3,6-tetrahydropyridin-4-yl]-2-(2-methyl-1,3-benzothiazol-6-yl)-4H-pyrido[1,2-a]pyrimidin-4-one | 178-180 | 419.2 |
| 23 | 394 | 2-(2-methyl-1,3-benzothiazol-6-yl)-7-[1-(propan-2-yl)-1,2,3,6-tetrahydropyridin-4-yl]-4H-pyrido[1,2-a]pyrimidin-4-one | 168-170 | 417.2 |
| 23 | 395 | 7-(1-cyclopropyl-1,2,3,6-tetrahydropyridin-4-yl)-2-(2-methyl-1,3-benzothiazol-6-yl)-4H-pyrido[1,2-a]pyrimidin-4-one | 158-160 | 415.3 |
| 23 | 396 | 7-(1-ethyl-1,2,3,6-tetrahydropyridin-4-yl)-2-(2-methyl-1,3-benzothiazol-6-yl)-4H-pyrido[1,2-a]pyrimidin-4-one | 128-130 (DR) | 403.2 |
| 39 | 397 | 7-[(3R)-3,4-dimethylpiperazin-1-yl]-2-(4,6-dimethylpyrazolo[1,5-a]pyrazin-2-yl)-4H-pyrido[1,2-a]pyrimidin-4-one | 247-249 | 404.5 |
| 56* | 398 | 2-(3,4-dimethoxyphenyl)-7-(1,2,3,6-tetrahydropyridin-4-yl)-4H-pyrimido[1,2-b]pyridazin-4-one | 195-200 | 365.3 |
| 9 | 399 | 7-[(1S,4S)-2,5-diazabicyclo[2.2.1]hept-2-yl]-2-(4,6-dimethylpyrazolo[1,5-a]pyrazin-2-yl)-4H-pyrido[1,2-a]pyrimidin-4-one | 218-221 | 388.3 |
| 39 | 400 | 2-(4,6-dimethylpyrazolo[1,5-a]pyrazin-2-yl)-7-[(1S,4S)-5-methyl-2,5-diazabicyclo[2.2.1]hept-2-yl]-4H-pyrido[1,2-a]pyrimidin-4-one | 188-191 | 402.3 |
| 39 | 401 | 2-(4,6-dimethylpyrazolo[1,5-a]pyrazin-2-yl)-7-[(1S,4S)-5-ethyl-2,5-diazabicyclo[2.2.1]hept-2-yl]-4H-pyrido[1,2-a]pyrimidin-4-one | 175-177 | 416.4 |
| 57* | 402 | 2-(3,4-dimethoxyphenyl)-7-(1,2,3,6-tetrahydropyridin-4-yl)-4H-pyrazino[1,2-a]pyrimidin-4-one | 205-208 | 365.4 |
| 24 | 403 | 2-(3-fluoro-4-methoxyphenyl)-7-(piperidin-4-yl)-4H-pyrido[1,2-a]pyrimidin-4-one | 122-125 | 354.3 |
| 25 | 404 | 2-(3,4-dimethoxyphenyl)-7-(1-ethylpiperidin-4-yl)-4H-pyrido[1,2-a]pyrimidin-4-one | 155-157 | 394.4 |
| 24 | 405 | 2-(3,4-dimethoxyphenyl)-7-[cis-4-(methylamino)cyclohexyl]-4H-pyrido[1,2-a]pyrimidin-4-one | 156-158 | 394.4 |
| 24 | 406 | 2-(3,4-dimethoxyphenyl)-7-(piperidin-3-yl)-4H-pyrido[1,2-a]pyrimidin-4-one | 126-129 | 366.3 |
| 53* | 407 | 2-(3,4-dimethoxyphenyl)-9-methyl-7-[4-(propylamino)piperidin-1-yl]-4H-pyrido[1,2-a]pyrimidin-4-one | 178-184 | 437.5 |

TABLE 1-continued

| Ex | Cpd | Name | M.P. | MS |
|---|---|---|---|---|
| 22 | 408 | 2-(3,4-dimethoxyphenyl)-9-ethyl-7-(1,2,3,6-tetrahydropyridin-4-yl)-4H-pyrido[1,2-a]pyrimidin-4-one | 171-177 | 392.4 |
| 24 | 409 | 7-(2-methylimidazo[1,2-a]pyridin-6-yl)-2-(piperidin-4-yl)-4H-pyrido[1,2-a]pyrimidin-4-one | 255-258 | 360.4 |
| 24 | 410 | 7-(8-fluoro-2-methylimidazo[1,2-a]pyridin-6-yl)-2-(piperidin-4-yl)-4H-pyrido[1,2-a]pyrimidin-4-one | 295-298 | 378.4 |
| 23 | 411 | 7-(8-fluoro-2-methylimidazo[1,2-a]pyridin-6-yl)-2-(1-methyl-1,2,3,6-tetrahydropyridin-4-yl)-4H-pyrido[1,2-a]pyrimidin-4-one | 218-222 | 390.4 |
| 16 | 412 | 7-(4-cyclopropylpiperazin-1-yl)-2-(8-fluoro-2-methylimidazo[1,2-a]pyridin-6-yl)-4H-pyrido[1,2-a]pyrimidin-4-one | 254-258 | 419.4 |
| 57 | 413a | 2-(1,3-dimethylpyrrolo[1,2-a]pyrazin-7-yl)-7-(1,2,3,6-tetrahydropyridin-4-yl)-4H-pyrazino[1,2-a]pyrimidin-4-one | NI | NI |
| 2 | 414 | 2-(3,4-dimethoxyphenyl)-7-[(8aR)-hexahydropyrrolo[1,2-a]pyrazin-2(1H)-yl]-9-methyl-4H-pyrido[1,2-a]pyrimidin-4-one | ND | 421.4 |
| 23 | 415 | 2-(3,4-dimethoxyphenyl)-9-ethyl-7-(1-methyl-1,2,3,6-tetrahydropyridin-4-yl)-4H-pyrido[1,2-a]pyrimidin-4-one | 177-182 | 406.4 |
| 53 | 416 | 2-(3,4-dimethoxyphenyl)-9-methyl-7-[4-(propan-2-ylamino)piperidin-1-yl]-4H-pyrido[1,2-a]pyrimidin-4-one | 178-183 | 437.5 |
| 2 | 417 | 2-(3,4-dimethoxyphenyl)-7-[(8aS)-hexahydropyrrolo[1,2-a]pyrazin-2(1H)-yl]-9-methyl-4H-pyrido[1,2-a]pyrimidin-4-one | 183-189 | 421.4 |
| 23 | 418 | 2-(3,4-dimethoxyphenyl)-9-ethyl-7-(1-ethyl-1,2,3,6-tetrahydropyridin-4-yl)-4H-pyrido[1,2-a]pyrimidin-4-one | 148-153 | 420.5 |
| 53 | 419 | 2-(3,4-dimethoxyphenyl)-9-methyl-7-[4-(morpholin-4-yl)piperidin-1-yl]-4H-pyrido[1,2-a]pyrimidin-4-one | 219-224 | 465.5 |
| 9 | 420 | 2-(6-methylpyrazolo[1,5-a]pyrazin-2-yl)-7-(piperazin-1-yl)-4H-pyrido[1,2-a]pyrimidin-4-one | 202-204 | 362.2 |
| 57 | 421 | 2-(2-methyl-1,3-benzoxazol-6-yl)-7-(1,2,3,6-tetrahydropyridin-4-yl)-4H-pyrazino[1,2-a]pyrimidin-4-one hydrochloride (1:1) | ND | 360.1 |
| 23 | 422 | 2-(2-methyl-1,3-benzoxazol-6-yl)-7-(1-methyl-1,2,3,6-tetrahydropyridin-4-yl)-4H-pyrazino[1,2-a]pyrimidin-4-one | 240-242 | 374.3 |
| 23 | 423 | 7-(1-ethyl-1,2,3,6-tetrahydropyridin-4-yl)-2-(2-methyl-1,3-benzoxazol-6-yl)-4H-pyrazino[1,2-a]pyrimidin-4-one | 225-227 | 388.4 |
| 24 | 424 | 2-(2-methyl-1,3-benzothiazol-6-yl)-7-(piperidin-4-yl)-4H-pyrido[1,2-a]pyrimidin-4-one | 222-224 | 377.1 |
| 9 | 425 | 2-(4,6-dimethylpyrazolo[1,5-a]pyrazin-2-yl)-7-[4-(pyrrolidin-1-yl)piperidin-1-yl]-4H-pyrido[1,2-a]pyrimidin-4-one | 215-218 | 444.4 |
| 9 | 426 | 7-(1,4'-bipiperidin-1'-yl)-2-(4,6-dimethylpyrazolo[1,5-a]pyrazin-2-yl)-4H-pyrido[1,2-a]pyrimidin-4-one | 236-238 | 458.4 |
| 9 | 427 | 2-(4,6-dimethylpyrazolo[1,5-a]pyrazin-2-yl)-7-[4-(4-methylpiperazin-1-yl)piperidin-1-yl]-4H-pyrido[1,2-a]pyrimidin-4-one | 198-200 | 473.5 |
| 9 | 428 | 2-(4,6-dimethylpyrazolo[1,5-a]pyrazin-2-yl)-7-[4-(morpholin-4-yl)piperidin-1-yl]-4H-pyrido[1,2-a]pyrimidin-4-one | 192-195 | 460.4 |
| 37 | 429 | 2-(2-methylimidazo[1,2-a]pyridin-6-yl)-7-(1,2,3,6-tetrahydropyridin-4-yl)-4H-pyrido[1,2-a]pyrimidin-4-one | 206-208 | 358.4 |
| 23 | 430 | 2-(2-methylimidazo[1,2-a]pyridin-6-yl)-7-(1-methyl-1,2,3,6-tetrahydropyridin-4-yl)-4H-pyrido[1,2-a]pyrimidin-4-one | 137-140 | 372.2 |
| 23 | 431 | 7-(1-ethyl-1,2,3,6-tetrahydropyridin-4-yl)-2-(2-methylimidazo[1,2-a]pyridin-6-yl)-4H-pyrido[1,2-a]pyrimidin-4-one | 220-223 | 386.4 |
| 14 | 432 | 7-[4-(dimethylamino)piperidin-1-yl]-2-(2-methylimidazo[1,2-a]pyridin-6-yl)-4H-pyrido[1,2-a]pyrimidin-4-one | 204-206 | 403.4 |
| 53 | 433 | 2-(3,4-dimethoxyphenyl)-7-{4-[(2-hydroxyethyl)amino]piperidin-1-yl}-9-methyl-4H-pyrido[1,2-a]pyrimidin-4-one | 185-193 | 439.4 |

TABLE 1-continued

| Ex | Cpd | Name | M.P. | MS |
|---|---|---|---|---|
| 25 | 434 | 2-(3,4-dimethoxyphenyl)-9-ethyl-7-(1-methylpiperidin-4-yl)-4H-pyrido[1,2-a]pyrimidin-4-one | 146 (S), 166-169 | 408.4 |
| 53 | 435 | 7-[4-(diethylamino)piperidin-1-yl]-2-(3,4-dimethoxyphenyl)-9-methyl-4H-pyrido[1,2-a]pyrimidin-4-one | 149-155 | 451.5 |
| 25 | 436 | 2-(3,4-dimethoxyphenyl)-9-ethyl-7-(1-ethylpiperidin-4-yl)-4H-pyrido[1,2-a]pyrimidin-4-one | 157-162 | 422.4 |
| 14 | 437 | 2-(2-methylimidazo[1,2-a]pyridin-6-yl)-7-[4-(pyrrolidin-1-yl)piperidin-1-yl]-4H-pyrido[1,2-a]pyrimidin-4-one | 230-232 | 429.4 |
| 51 | 438 | 2-(2-methylimidazo[1,2-a]pyridin-6-yl)-7-(piperidin-4-yl)-4H-pyrido[1,2-a]pyrimidin-4-one | 298-300 | 360.1 |
| 25 | 439 | 2-(2-methyl-1,3-benzothiazol-6-yl)-7-(1-methylpiperidin-4-yl)-4H-pyrido[1,2-a]pyrimidin-4-one | 240-242 | 391.4 |
| 9 | 440 | 7-(4-methylpiperazin-1-yl)-2-(6-methylpyrazolo[1,5-a]pyrazin-2-yl)-4H-pyrido[1,2-a]pyrimidin-4-one | 230-240 (DR) | 376.2 |
| 9 | 441 | 7-[(3S)-3-methylpiperazin-1-yl]-2-(6-methylpyrazolo[1,5-a]pyrazin-2-yl)-4H-pyrido[1,2-a]pyrimidin-4-one | 235-240 (DR) | 376.2 |
| 9 | 442 | 7-[(3R,5S)-3,5-dimethylpiperazin-1-yl]-2-(6-methylpyrazolo[1,5-a]pyrazin-2-yl)-4H-pyrido[1,2-a]pyrimidin-4-one | 258-260 | 390.3 |
| 37* | 443 | 2-(1-methyl-1H-indazol-5-yl)-7-(1,2,3,6-tetrahydropyridin-4-yl)-4H-pyrido[1,2-a]pyrimidin-4-one | 200-203 | 358.2 |
| 37 | 444 | 2-[6-(dimethylamino)pyridin-3-yl]-7-(1,2,3,6-tetrahydropyridin-4-yl)-4H-pyrido[1,2-a]pyrimidin-4-one | 255-257 | 348.4 |
| 37 | 445 | 7-[4-(diethylamino)piperidin-1-yl]-2-(2-methylimidazo[1,2-a]pyridin-6-yl)-4H-pyrido[1,2-a]pyrimidin-4-one | 208-210 | 431.4 |
| 53 | 446 | 2-(3,4-dimethoxyphenyl)-7-{4-[(2-hydroxyethyl)(methyl)amino]piperidin-1-yl}-9-methyl-4H-pyrido[1,2-a]pyrimidin-4-one | 164-171 | 453.5 |
| 2 | 447 | 2-(3,4-dimethoxyphenyl)-9-ethyl-7-[(3R)-3-methylpiperazin-1-yl]-4H-pyrido[1,2-a]pyrimidin-4-one | 140-147 | 409.2 |
| 25 | 448 | 2-(2-methylimidazo[1,2-a]pyridin-6-yl)-7-(1-methylpiperidin-4-yl)-4H-pyrido[1,2-a]pyrimidin-4-one | 218-220 | 374.3 |
| 23 | 449 | 2-(1-methyl-1H-indazol-5-yl)-7-(1-methyl-1,2,3,6-tetrahydropyridin-4-yl)-4H-pyrido[1,2-a]pyrimidin-4-one | 148-150 | 372.3 |
| 23 | 450 | 2-[6-(dimethylamino)pyridin-3-yl]-7-(1-methyl-1,2,3,6-tetrahydropyridin-4-yl)-4H-pyrido[1,2-a]pyrimidin-4-one | 214-216 | 362.4 |
| 9 | 451 | 7-[4-(diethylamino)piperidin-1-yl]-2-(4,6-dimethylpyrazolo[1,5-a]pyrazin-2-yl)-4H-pyrido[1,2-a]pyrimidin-4-one | 232-235 | 446.5 |
| 24 | 452 | 2-(4,6-dimethylpyrazolo[1,5-a]pyrazin-2-yl)-7-(piperidin-4-yl)-4H-pyrido[1,2-a]pyrimidin-4-one | ND | 375.4 |
| 25 | 453 | 2-(4,6-dimethylpyrazolo[1,5-a]pyrazin-2-yl)-7-(1-methylpiperidin-4-yl)-4H-pyrido[1,2-a]pyrimidin-4-one | 220-222 | 389.3 |
| 25 | 454 | 2-(4,6-dimethylpyrazolo[1,5-a]pyrazin-2-yl)-7-(1-ethylpiperidin-4-yl)-4H-pyrido[1,2-a]pyrimidin-4-one | 170-172 | 403.3 |
| 2 | 455 | 2-(3,4-dimethoxyphenyl)-9-ethyl-7-[(8aR)-hexahydropyrrolo[1,2-a]pyrazin-2(1H)-yl]-4H-pyrido[1,2-a]pyrimidin-4-one | 180-184 | 435.3 |
| 53 | 456 | 2-(3,4-dimethoxyphenyl)-7-{4-[(2-methoxyethyl)amino]piperidin-1-yl}-9-methyl-4H-pyrido[1,2-a]pyrimidin-4-one | 178-182 | 453.3 |
| 9 | 457 | 2-(4,6-dimethylpyrazolo[1,5-a]pyrazin-2-yl)-9-methyl-7-(4-methylpiperazin-1-yl)-4H-pyrido[1,2-a]pyrimidin-4-one | 262-271 | 404.2 |
| 2 | 458 | 2-(4,6-dimethylpyrazolo[1,5-a]pyrazin-2-yl)-7-[(8aR)-hexahydropyrrolo[1,2-a]pyrazin-2(1H)-yl]-9-methyl-4H-pyrido[1,2-a]pyrimidin-4-one | 244-256 | 430.3 |
| 2 | 459 | 7-[4-(dimethylamino)piperidin-1-yl]-2-(4,6-dimethylpyrazolo[1,5-a]pyrazin-2-yl)-9-methyl-4H-pyrido[1,2-a]pyrimidin-4-one | 231-241 | 432.4 |
| 25 | 460 | 7-(2-methylimidazo[1,2-a]pyridin-6-yl)-2-(1-methylpiperidin-4-yl)-4H-pyrido[1,2-a]pyrimidin-4-one | 227-230 | 374.3 |

TABLE 1-continued

| Ex | Cpd | Name | M.P. | MS |
|---|---|---|---|---|
| 25 | 461 | 7-(2-methylimidazo[1,2-a]pyridin-6-yl)-2-[1-(propan-2-yl)piperidin-4-yl]-4H-pyrido[1,2-a]pyrimidin-4-one | 215-218 | 402.3 |
| 25 | 462 | 7-(8-fluoro-2-methylimidazo[1,2-a]pyridin-6-yl)-2-(1-methylpiperidin-4-yl)-4H-pyrido[1,2-a]pyrimidin-4-one | 235-238 | 392.3 |
| 23 | 463 | 7-(1-ethyl-1,2,3,6-tetrahydropyridin-4-yl)-2-(1-methyl-1H-indazol-5-yl)-4H-pyrido[1,2-a]pyrimidin-4-one | 172-174 | 386.3 |
| 23 | 464 | 2-(1-methyl-1H-indazol-5-yl)-7-(1-propyl-1,2,3,6-tetrahydropyridin-4-yl)-4H-pyrido[1,2-a]pyrimidin-4-one | 152-154 | 400.4 |
| 24 | 465 | 2-[6-(dimethylamino)pyridin-3-yl]-7-(piperidin-4-yl)-4H-pyrido[1,2-a]pyrimidin-4-one | 208-210 | 350.3 |
| 9 | 466 | 7-(4-ethylpiperazin-1-yl)-2-(6-methylpyrazolo[1,5-a]pyrazin-2-yl)-4H-pyrido[1,2-a]pyrimidin-4-one | 220-230 (DR) | 390.3 |
| 9 | 467 | 7-[(8aR)-hexahydropyrrolo[1,2-a]pyrazin-2(1H)-yl]-2-(6-methylpyrazolo[1,5-a]pyrazin-2-yl)-4H-pyrido[1,2-a]pyrimidin-4-one | 240-250 (DR) | 402.3 |
| 9 | 468 | 7-[4-(dimethylamino)piperidin-1-yl]-2-(6-methylpyrazolo[1,5-a]pyrazin-2-yl)-4H-pyrido[1,2-a]pyrimidin-4-one | 240-242 | 404.3 |
| 9 | 469 | 7-[4-(2-hydroxyethyl)piperazin-1-yl]-2-(6-methylpyrazolo[1,5-a]pyrazin-2-yl)-4H-pyrido[1,2-a]pyrimidin-4-one | 254-256 | 406.3 |
| 25 | 470 | 2-(2-methylimidazo[1,2-a]pyridin-6-yl)-7-(1-propylpiperidin-4-yl)-4H-pyrido[1,2-a]pyrimidin-4-one | 159-161 | 402.4 |
| 23 | 471 | 7-[1-(2-hydroxyethyl)-1,2,3,6-tetrahydropyridin-4-yl]-2-(1-methyl-1H-indazol-5-yl)-4H-pyrido[1,2-a]pyrimidin-4-one | ND | 402.3 |
| 9 | 472 | 7-[(3R)-3-methylpiperazin-1-yl]-2-(6-methylpyrazolo[1,5-a]pyrazin-2-yl)-4H-pyrido[1,2-a]pyrimidin-4-one | 240-244 | 376.2 |
| 38 | 473 | 2-(6-methylpyrazolo[1,5-a]pyrazin-2-yl)-7-(1,2,3,6-tetrahydropyridin-4-yl)-4H-pyrido[1,2-a]pyrimidin-4-one | 260-265 (DR) | 359.2 |
| 37 | 474 | 2-(2-methyl-2H-indazol-5-yl)-7-(1,2,3,6-tetrahydropyridin-4-yl)-4H-pyrido[1,2-a]pyrimidin-4-one | 239-241 | 358.4 |
| 37 | 475 | 2-(1-methyl-1H-indazol-5-yl)-7-(1-methylpiperidin-4-yl)-4H-pyrido[1,2-a]pyrimidin-4-one | 216-218 | 374.4 |
| 25 | 476 | 2-(2-methyl-2H-indazol-5-yl)-7-(1-methyl-1,2,3,6-tetrahydropyridin-4-yl)-4H-pyrido[1,2-a]pyrimidin-4-one | 226-228 | 372.3 |
| 23 | 477 | 7-(1-ethyl-1,2,3,6-tetrahydropyridin-4-yl)-2-(2-methyl-2H-indazol-5-yl)-4H-pyrido[1,2-a]pyrimidin-4-one | 198-200 | 386.4 |
| 23 | 478 | 7-(1-ethylpiperidin-4-yl)-2-(2-methylimidazo[1,2-a]pyridin-6-yl)-4H-pyrido[1,2-a]pyrimidin-4-one | 190-192 | 388.4 |
| 23 | 479 | 2-(1,3-dimethylpyrrolo[1,2-a]pyrazin-7-yl)-7-[1-(propan-2-yl)-1,2,3,6-tetrahydropyridin-4-yl]-4H-pyrazino[1,2-a]pyrimidin-4-one | 220-222 | 415.3 |
| 22 | 480 | 2-(4,6-dimethylpyrazolo[1,5-a]pyrazin-2-yl)-9-methyl-7-(1,2,3,6-tetrahydropyridin-4-yl)-4H-pyrido[1,2-a]pyrimidin-4-one | >300 | 387.4 |
| 23 | 481 | 2-(4,6-dimethylpyrazolo[1,5-a]pyrazin-2-yl)-9-methyl-7-(1-methyl-1,2,3,6-tetrahydropyridin-4-yl)-4H-pyrido[1,2-a]pyrimidin-4-one | ND | 401.4 |
| 23 | 482 | 2-(4,6-dimethylpyrazolo[1,5-a]pyrazin-2-yl)-7-(1-ethyl-1,2,3,6-tetrahydropyridin-4-yl)-9-methyl-4H-pyrido[1,2-a]pyrimidin-4-one | ND | 415.5 |
| 23 | 483 | 7-(1-cyclopropyl-1,2,3,6-tetrahydropyridin-4-yl)-2-(4,6-dimethylpyrazolo[1,5-a]pyrazin-2-yl)-9-methyl-4H-pyrido[1,2-a]pyrimidin-4-one | ND | 427.4 |
| 23 | 484 | 2-(6-methylpyrazolo[1,5-a]pyrazin-2-yl)-7-(1-methyl-1,2,3,6-tetrahydropyridin-4-yl)-4H-pyrido[1,2-a]pyrimidin-4-one | 126-128 (DR) | 373.2 |
| 23 | 485 | 7-(1-ethyl-1,2,3,6-tetrahydropyridin-4-yl)-2-(6-methylpyrazolo[1,5-a]pyrazin-2-yl)-4H-pyrido[1,2-a]pyrimidin-4-one | ND | 387.3 |
| 50* | 486 | 2-(5,7-dimethylfuro[2,3-c]pyridin-2-yl)-7-(piperazin-1-yl)-4H-pyrido[1,2-a]pyrimidin-4-one | 198-200 | 376.3 |
| 50 | 487 | 2-(5,7-dimethylfuro[2,3-c]pyridin-2-yl)-7-(4-methylpiperazin-1-yl)-4H-pyrido[1,2-a]pyrimidin-4-one | 256-258 | 390.2 |

TABLE 1-continued

| Ex | Cpd | Name | M.P. | MS |
|---|---|---|---|---|
| 50 | 488 | 2-(5,7-dimethylfuro[2,3-c]pyridin-2-yl)-7-[(3S)-3-methylpiperazin-1-yl]-4H-pyrido[1,2-a]pyrimidin-4-one | 202-204 | 390.3 |
| 14 | 489 | 2-(1-methyl-1H-indazol-5-yl)-7-(4-methylpiperazin-1-yl)-4H-pyrido[1,2-a]pyrimidin-4-one | 194-196 | 375.3 |
| 14 | 490 | 2-(1-methyl-1H-indazol-5-yl)-7-(piperazin-1-yl)-4H-pyrido[1,2-a]pyrimidin-4-one | 206-208 | 361.3 |
| 14 | 491 | 7-[4-(dimethylamino)piperidin-1-yl]-2-(1-methyl-1H-indazol-5-yl)-4H-pyrido[1,2-a]pyrimidin-4-one | 209-212 | 403.5 |
| 14 | 492 | 7-(4-methyl-1,4-diazepan-1-yl)-2-(1-methyl-1H-indazol-5-yl)-4H-pyrido[1,2-a]pyrimidin-4-one | ND | 389.4 |
| 23 | 493 | 7-(1-ethyl-1,2,3,6-tetrahydropyridin-4-yl)-2-(2-methyl-1,3-benzoxazol-6-yl)-4H-pyrimido[1,2-b]pyridazin-4-one | 205-207 | 388.4 |
| 16 | 494 | 2-(8-chloro-2-methylimidazo[1,2-a]pyridin-6-yl)-7-(4-ethylpiperazin-1-yl)-4H-pyrido[1,2-a]pyrimidin-4-one | 264-268 | 423.4 |
| 39 | 495 | 2-(8-chloro-2-methylimidazo[1,2-a]pyridin-6-yl)-7-[(3R)-4-ethyl-3-methylpiperazin-1-yl]-4H-pyrido[1,2-a]pyrimidin-4-one | 239-245 | 437.5 |
| 39 | 496 | 2-(8-chloro-2-methylimidazo[1,2-a]pyridin-6-yl)-7-[(3S)-4-ethyl-3-methylpiperazin-1-yl]-4H-pyrido[1,2-a]pyrimidin-4-one | 234-245 | 437.5 |
| 39 | 497 | 2-(8-chloro-2-methylimidazo[1,2-a]pyridin-6-yl)-7-[(3R)-3-methyl-4-(propan-2-yl)piperazin-1-yl]-4H-pyrido[1,2-a]pyrimidin-4-one | 278-281 | 451.3 |
| 39 | 498 | 2-(8-chloro-2-methylimidazo[1,2-a]pyridin-6-yl)-7-[(3S)-3-methyl-4-(propan-2-yl)piperazin-1-yl]-4H-pyrido[1,2-a]pyrimidin-4-one | 264-270 | 451.3 |
| 58* | 499 | 2-(2-methyl-1,3-benzoxazol-6-yl)-7-(piperidin-4-yl)-4H-pyrimido[1,2-b]pyridazin-4-one | 126-128 | 362.2 |
| 25 | 500 | 2-(2-methyl-1,3-benzoxazol-6-yl)-7-(1-methylpiperidin-4-yl)-4H-pyrimido[1,2-b]pyridazin-4-one | 272-275 | 376.3 |
| 25 | 501 | 7-(1-ethylpiperidin-4-yl)-2-(2-methyl-1,3-benzoxazol-6-yl)-4H-pyrimido[1,2-b]pyridazin-4-one | 284-286 | 390.4 |
| 59* | 502 | 2-(4,6-dimethylpyrazolo[1,5-a]pyrazin-2-yl)-7-(piperidin-4-yl)-4H-pyrazino[1,2-a]pyrimidin-4-one | ND | 376.4 |
| 25 | 503 | 2-(4,6-dimethylpyrazolo[1,5-a]pyrazin-2-yl)-7-(1-methylpiperidin-4-yl)-4H-pyrazino[1,2-a]pyrimidin-4-one | 257-259 | 390.3 |
| 25 | 504 | 2-(4,6-dimethylpyrazolo[1,5-a]pyrazin-2-yl)-7-(1-ethylpiperidin-4-yl)-4H-pyrazino[1,2-a]pyrimidin-4-one | ND | 404.3 |
| 57 | 505 | 2-(1-methyl-1H-indazol-5-yl)-7-(1,2,3,6-tetrahydropyridin-4-yl)-4H-pyrazino[1,2-a]pyrimidin-4-one | 228-230 | 359.2 |
| 23 | 506 | 2-(1-methyl-1H-indazol-5-yl)-7-(1-methyl-1,2,3,6-tetrahydropyridin-4-yl)-4H-pyrazino[1,2-a]pyrimidin-4-one | 234-236 | 373.3 |
| 23 | 507 | 7-(1-ethyl-1,2,3,6-tetrahydropyridin-4-yl)-2-(1-methyl-1H-indazol-5-yl)-4H-pyrazino[1,2-a]pyrimidin-4-one | ND | 387.4 |
| 2 | 508 | 2-(4,6-dimethylpyrazolo[1,5-a]pyrazin-2-yl)-7-(4-ethylpiperazin-1-yl)-9-methyl-4H-pyrido[1,2-a]pyrimidin-4-one | 241-252 | 418.5 |
| 2 | 509 | 2-(4,6-dimethylpyrazolo[1,5-a]pyrazin-2-yl)-9-methyl-7-[(3R)-3-methylpiperazin-1-yl]-4H-pyrido[1,2-a]pyrimidin-4-one | 213-222 | 404.5 |
| 2 | 510 | 7-[(3R)-3,4-dimethylpiperazin-1-yl]-2-(4,6-dimethylpyrazolo[1,5-a]pyrazin-2-yl)-9-methyl-4H-pyrido[1,2-a]pyrimidin-4-one | 244-253 | 418.4 |
| 2 | 511 | 2-(4,6-dimethylpyrazolo[1,5-a]pyrazin-2-yl)-7-[(3R)-4-ethyl-3-methylpiperazin-1-yl]-9-methyl-4H-pyrido[1,2-a]pyrimidin-4-one | 240-245 | 432.5 |
| 60* | 512 | 2-(4,6-dimethylpyrazolo[1,5-a]pyrazin-2-yl)-7-(piperidin-4-yl)-4H-pyrimido[1,2-b]pyridazin-4-one | ND | 376.4 |
| 25 | 513 | 2-(4,6-dimethylpyrazolo[1,5-a]pyrazin-2-yl)-7-(1-methylpiperidin-4-yl)-4H-pyrimido[1,2-b]pyridazin-4-one | 265-267 | 390.3 |
| 25 | 514 | 2-(4,6-dimethylpyrazolo[1,5-a]pyrazin-2-yl)-7-(1-ethylpiperidin-4-yl)-4H-pyrimido[1,2-b]pyridazin-4-one | 283-285 | 404.4 |

TABLE 1-continued

| Ex | Cpd | Name | M.P. | MS |
|---|---|---|---|---|
| 2 | 515 | 2-(4,6-dimethylpyrazolo[1,5-a]pyrazin-2-yl)-7-(octahydro-5H-pyrrolo[3,2-c]pyridin-5-yl)-4H-pyrido[1,2-a]pyrimidin-4-one | 198-200 | 416.3 |
| 24 | 516 | 2-(8-chloro-2-methylimidazo[1,2-a]pyridin-6-yl)-7-(piperidin-4-yl)-4H-pyrido[1,2-a]pyrimidin-4-one | 287-293 | 394.2 |
| 25 | 517 | 2-(8-chloro-2-methylimidazo[1,2-a]pyridin-6-yl)-7-(1-methylpiperidin-4-yl)-4H-pyrido[1,2-a]pyrimidin-4-one | 292-296 | 408.3 |
| 25 | 518 | 2-(8-chloro-2-methylimidazo[1,2-a]pyridin-6-yl)-7-(1-ethylpiperidin-4-yl)-4H-pyrido[1,2-a]pyrimidin-4-one | 240-246 | 422.3 |
| 25 | 519 | 2-(8-chloro-2-methylimidazo[1,2-a]pyridin-6-yl)-7-[1-(propan-2-yl)piperidin-4-yl]-4H-pyrido[1,2-a]pyrimidin-4-one | 279-285 | 436.5 |
| 2 | 520 | 2-(4,6-dimethylpyrazolo[1,5-a]pyrazin-2-yl)-9-methyl-7-(4-methyl-1,4-diazepan-1-yl)-4H-pyrido[1,2-a]pyrimidin-4-one | ND | 418.3 |
| 58 | 521 | 2-(2-methyl-2H-indazol-5-yl)-7-(piperidin-4-yl)-4H-pyrimido[1,2-b]pyridazin-4-one | ND | 361.4 |
| 25 | 522 | 2-(2-methyl-2H-indazol-5-yl)-7-(1-methylpiperidin-4-yl)-4H-pyrimido[1,2-b]pyridazin-4-one | 260-262 | 375.2 |
| 25 | 523 | 7-(1-ethylpiperidin-4-yl)-2-(2-methyl-2H-indazol-5-yl)-4H-pyrimido[1,2-b]pyridazin-4-one | 253-255 | 389.3 |
| 25 | 524 | 2-(8-chloro-2-methylimidazo[1,2-a]pyridin-6-yl)-7-(1-methylpiperidin-4-yl)-4H-pyrimido[1,2-b]pyridazin-4-one | 289-291 | 409.3 |
| 25 | 525 | 2-(8-chloro-2-methylimidazo[1,2-a]pyridin-6-yl)-7-(1-ethylpiperidin-4-yl)-4H-pyrimido[1,2-b]pyridazin-4-one | 284-286 | 423.2 |
| 25 | 526 | 2-(8-chloro-2-methylimidazo[1,2-a]pyridin-6-yl)-7-[1-(2-hydroxyethyl)piperidin-4-yl]-4H-pyrimido[1,2-b]pyridazin-4-one | 255-257 | 439.3 |
| 50 | 527 | 2-(5,7-dimethylfuro[2,3-c]pyridin-2-yl)-7-[(3R,5S)-3,5-dimethylpiperazin-1-yl]-4H-pyrido[1,2-a]pyrimidin-4-one | 260-262 | 404.3 |
| 50 | 528 | 7-[4-(dimethylamino)piperidin-1-yl]-2-(5,7-dimethylfuro[2,3-c]pyridin-2-yl)-4H-pyrido[1,2-a]pyrimidin-4-one | 200-202 | 418.3 |
| 50 | 529 | 2-(5,7-dimethylfuro[2,3-c]pyridin-2-yl)-7-[4-(2-hydroxyethyl)piperazin-1-yl]-4H-pyrido[1,2-a]pyrimidin-4-one | 256-258 | 420.3 |
| 25 | 530 | 2-(4,6-dimethylpyrazolo[1,5-a]pyrazin-2-yl)-7-[1-(2-hydroxyethyl)piperidin-4-yl]-4H-pyrido[1,2-a]pyrimidin-4-one | 228-230 | 419.3 |
| 9 | 531 | 2-(4,6-dimethylpyrazolo[1,5-a]pyrazin-2-yl)-7-[4-(2-hydroxyethyl)piperazin-1-yl]-4H-pyrido[1,2-a]pyrimidin-4-one | 246-248 | 420.4 |
| 39 | 532 | 2-(4,6-dimethylpyrazolo[1,5-a]pyrazin-2-yl)-7-[(3R)-4-(2-hydroxyethyl)-3-methylpiperazin-1-yl]-4H-pyrido[1,2-a]pyrimidin-4-one | 238-240 | 434.3 |
| 43 | 533 | 2-(8-chloro-2-methylimidazo[1,2-a]pyridin-6-yl)-7-[(3S)-4-(2-methoxyethyl)-3-methylpiperazin-1-yl]-4H-pyrido[1,2-a]pyrimidin-4-one | 179-183 | 467.3 |
| 43 | 534 | 2-(8-chloro-2-methylimidazo[1,2-a]pyridin-6-yl)-7-{(3S)-4-[2-(2-hydroxyethoxy)ethyl]-3-methylpiperazin-1-yl}-4H-pyrido[1,2-a]pyrimidin-4-one | 201-205 | 497.3 |
| 39 | 535 | 2-(8-chloro-2-methylimidazo[1,2-a]pyridin-6-yl)-7-[(3S)-4-cyclopropyl-3-methylpiperazin-1-yl]-4H-pyrido[1,2-a]pyrimidin-4-one | 253-257 | 449.3 |
| 39 | 536 | 2-(8-chloro-2-methylimidazo[1,2-a]pyridin-6-yl)-7-[(3S)-4-cyclobutyl-3-methylpiperazin-1-yl]-4H-pyrido[1,2-a]pyrimidin-4-one | 228-232 | 463.3 |
| 43 | 537 | 2-(8-chloro-2-methylimidazo[1,2-a]pyridin-6-yl)-7-[(3S)-4-(2-hydroxyethyl)-3-methylpiperazin-1-yl]-4H-pyrido[1,2-a]pyrimidin-4-one | 228-234 | 453.3 |
| 43 | 538 | 2-(8-fluoro-2-methylimidazo[1,2-a]pyridin-6-yl)-7-[(3S)-4-(2-methoxyethyl)-3-methylpiperazin-1-yl]-4H-pyrido[1,2-a]pyrimidin-4-one | 215-219 | 451.3 |
| 43 | 539 | 2-(8-fluoro-2-methylimidazo[1,2-a]pyridin-6-yl)-7-[(3S)-4-(2-hydroxyethyl)-3-methylpiperazin-1-yl]-4H-pyrido[1,2-a]pyrimidin-4-one | 270-274 | 437.3 |
| 43 | 540 | 2-(8-fluoro-2-methylimidazo[1,2-a]pyridin-6-yl)-7-{(3S)-4-[2-(2-hydroxyethoxy)ethyl]-3-methylpiperazin-1-yl}-4H-pyrido[1,2-a]pyrimidin-4-one | 175-181 | 481.3 |

TABLE 1-continued

| Ex | Cpd | Name | M.P. | MS |
|---|---|---|---|---|
| 39 | 541 | 2-(8-fluoro-2-methylimidazo[1,2-a]pyridin-6-yl)-7-[(3S)-3-methyl-4-(propan-2-yl)piperazin-1-yl]-4H-pyrido[1,2-a]pyrimidin-4-one | 191-194 | 435.3 |
| 39 | 542 | 7-[(3S)-4-cyclopropyl-3-methylpiperazin-1-yl]-2-(8-fluoro-2-methylimidazo[1,2-a]pyridin-6-yl)-4H-pyrido[1,2-a]pyrimidin-4-one | 242-246 | 433.4 |
| 39 | 543 | 7-[(3S)-4-cyclobutyl-3-methylpiperazin-1-yl]-2-(8-fluoro-2-methylimidazo[1,2-a]pyridin-6-yl)-4H-pyrido[1,2-a]pyrimidin-4-one | 264-267 | 447.3 |
| 2 | 544 | 7-(3,3-dimethylpiperazin-1-yl)-2-(4,6-dimethylpyrazolo[1,5-a]pyrazin-2-yl)-9-methyl-4H-pyrido[1,2-a]pyrimidin-4-one | ND | 418.3 |
| 14 | 545 | 2-(1-methyl-1H-indazol-5-yl)-7-[(3R)-3-methylpiperazin-1-yl]-4H-pyrido[1,2-a]pyrimidin-4-one | 190-192 | 375.3 |
| 9 | 546 | 2-(4-ethyl-6-methylpyrazolo[1,5-a]pyrazin-2-yl)-7-(piperazin-1-yl)-4H-pyrido[1,2-a]pyrimidin-4-one | 230-233 | 390.5 |
| 9 | 547 | 2-(4-ethyl-6-methylpyrazolo[1,5-a]pyrazin-2-yl)-7-(4-methylpiperazin-1-yl)-4H-pyrido[1,2-a]pyrimidin-4-one | 250-252 | 404.5 |
| 9 | 548 | 2-(4-ethyl-6-methylpyrazolo[1,5-a]pyrazin-2-yl)-7-(4-ethylpiperazin-1-yl)-4H-pyrido[1,2-a]pyrimidin-4-one | 250-252 | 418.5 |
| 9 | 549 | 2-(4-ethyl-6-methylpyrazolo[1,5-a]pyrazin-2-yl)-7-[4-(2-hydroxyethyl)piperazin-1-yl]-4H-pyrido[1,2-a]pyrimidin-4-one | 240-242 | 434.5 |
| 9 | 550 | 7-[4-(dimethylamino)piperidin-1-yl]-2-(4-ethyl-6-methylpyrazolo[1,5-a]pyrazin-2-yl)-4H-pyrido[1,2-a]pyrimidin-4-one | 258-260 | 432.5 |
| 9 | 551 | 7-[4-(diethylamino)piperidin-1-yl]-2-(4-ethyl-6-methylpyrazolo[1,5-a]pyrazin-2-yl)-4H-pyrido[1,2-a]pyrimidin-4-one | 232-235 | 460.6 |
| 14 | 552 | 7-[(3R,5S)-3,5-dimethylpiperazin-1-yl]-2-(1-methyl-1H-indazol-5-yl)-4H-pyrido[1,2-a]pyrimidin-4-one | 240-242 | 389.5 |
| 14 | 553 | 2-(1-methyl-1H-indazol-5-yl)-7-[(3S)-3-methylpiperazin-1-yl]-4H-pyrido[1,2-a]pyrimidin-4-one | 206-208 | 375.4 |
| 25 | 554 | 2-(2-methylimidazo[1,2-a]pyridin-6-yl)-7-[1-(propan-2-yl)piperidin-4-yl]-4H-pyrido[1,2-a]pyrimidin-4-one | 218-220 | 402.4 |
| 16 | 555 | 2-(2-methylimidazo[1,2-a]pyridin-7-yl)-7-(piperazin-1-yl)-4H-pyrido[1,2-a]pyrimidin-4-one | 272-277 | 361.3 |
| 24 | 556 | 2-(2-methylimidazo[1,2-a]pyridin-7-yl)-7-(piperidin-4-yl)-4H-pyrido[1,2-a]pyrimidin-4-one | 257-260 | 360.3 |
| 39 | 557 | 2-(2-methylimidazo[1,2-a]pyridin-7-yl)-7-(4-methylpiperazin-1-yl)-4H-pyrido[1,2-a]pyrimidin-4-one | 285-288 | 375.3 |
| 39 | 558 | 7-(4-ethylpiperazin-1-yl)-2-(2-methylimidazo[1,2-a]pyridin-7-yl)-4H-pyrido[1,2-a]pyrimidin-4-one | 219-222 | 389.3 |
| 25 | 559 | 2-(2-methylimidazo[1,2-a]pyridin-7-yl)-7-(1-methylpiperidin-4-yl)-4H-pyrido[1,2-a]pyrimidin-4-one | 255-260 | 374.3 |
| 25 | 560 | 7-(1-ethylpiperidin-4-yl)-2-(2-methylimidazo[1,2-a]pyridin-7-yl)-4H-pyrido[1,2-a]pyrimidin-4-one | 229-233 | 388.4 |
| 2 | 561 | 2-(4,6-dimethylpyrazolo[1,5-a]pyrazin-2-yl)-9-methyl-7-[(3S)-3-methylpiperazin-1-yl]-4H-pyrido[1,2-a]pyrimidin-4-one | 210-219 | 404.4 |
| 2 | 562 | 7-[(3R,5S)-3,5-dimethylpiperazin-1-yl]-2-(4,6-dimethylpyrazolo[1,5-a]pyrazin-2-yl)-9-methyl-4H-pyrido[1,2-a]pyrimidin-4-one | 273-283 | 418.4 |
| 2 | 563 | 7-[(3S)-3,4-dimethylpiperazin-1-yl]-2-(4,6-dimethylpyrazolo[1,5-a]pyrazin-2-yl)-9-methyl-4H-pyrido[1,2-a]pyrimidin-4-one | 244-253 | 418.4 |
| 2 | 564 | 2-(4,6-dimethylpyrazolo[1,5-a]pyrazin-2-yl)-9-methyl-7-[(3R,5S)-3,4,5-trimethylpiperazin-1-yl]-4H-pyrido[1,2-a]pyrimidin-4-one | 297-310 | 432.4 |
| 23 | 565 | 2-(2-methylimidazo[1,2-a]pyridin-6-yl)-7-[1-(propan-2-yl)-1,2,3,6-tetrahydropyridin-4-yl]-4H-pyrido[1,2-a]pyrimidin-4-one | 230-232 | 400.5 |
| 58 | 566 | 2-(2-methyl-2H-indazol-5-yl)-7-(piperidin-4-yl)-4H-pyrazino[1,2-a]pyrimidin-4-one | 235-237 | 361.3 |
| 25 | 567 | 2-(2-methyl-2H-indazol-5-yl)-7-(1-methylpiperidin-4-yl)-4H-pyrazino[1,2-a]pyrimidin-4-one | 275-277 | 375.3 |
| 25 | 568 | 7-(1-ethylpiperidin-4-yl)-2-(2-methyl-2H-indazol-5-yl)-4H-pyrazino[1,2-a]pyrimidin-4-one | 198-200 | 389.3 |

TABLE 1-continued

| Ex | Cpd | Name | M.P. | MS |
|---|---|---|---|---|
| 25 | 569 | 7-[1-(2-hydroxyethyl)piperidin-4-yl]-2-(2-methyl-2H-indazol-5-yl)-4H-pyrazino[1,2-a]pyrimidin-4-one | 230-232 | 405.3 |
| 9 | 570 | 7-{4-[(dimethylamino)methyl]piperidin-1-yl}-2-(4,6-dimethylpyrazolo[1,5-a]pyrazin-2-yl)-4H-pyrido[1,2-a]pyrimidin-4-one | 206-208 | 432.3 |
| 9 | 571 | 2-(4,6-dimethylpyrazolo[1,5-a]pyrazin-2-yl)-7-[4-(pyrrolidin-1-ylmethyl)piperidin-1-yl]-4H-pyrido[1,2-a]pyrimidin-4-one | 177-180 | 458.5 |
| 9 | 572 | 2-(4,6-dimethylpyrazolo[1,5-a]pyrazin-2-yl)-7-[4-(piperidin-1-ylmethyl)piperidin-1-yl]-4H-pyrido[1,2-a]pyrimidin-4-one | 192-195 | 472.6 |
| 9 | 573 | 2-(3,4-dimethoxyphenyl)-7-{4-[(dimethylamino)methyl]piperidin-1-yl}-4H-pyrido[1,2-a]pyrimidin-4-one | 182-184 | 423.3 |
| 9 | 574 | 2-(3,4-dimethoxyphenyl)-7-[4-(pyrrolidin-1-ylmethyl)piperidin-1-yl]-4H-pyrido[1,2-a]pyrimidin-4-one | 194-196 | 449.5 |
| 9 | 575 | 2-(3,4-dimethoxyphenyl)-7-[4-(piperidin-1-ylmethyl)piperidin-1-yl]-4H-pyrido[1,2-a]pyrimidin-4-one | 184-186 | 463.5 |
| 25 | 576 | 7-[1-(2-hydroxyethyl)piperidin-4-yl]-2-(2-methylimidazo[1,2-a]pyridin-6-yl)-4H-pyrido[1,2-a]pyrimidin-4-one | 200-202 | 404.4 |
| 23 | 577 | 7-[1-(2-hydroxyethyl)-1,2,3,6-tetrahydropyridin-4-yl]-2-(2-methylimidazo[1,2-a]pyridin-6-yl)-4H-pyrido[1,2-a]pyrimidin-4-one | 248-250 | 402.2 |
| 25 | 578 | 2-(2-methyl-2H-indazol-5-yl)-7-(1-methylpiperidin-4-yl)-4H-pyrido[1,2-a]pyrimidin-4-one | 256-258 | 374.3 |
| 25 | 579 | 2-(2-methylimidazo[1,2-a]pyridin-6-yl)-7-(1-methylpiperidin-4-yl)-4H-pyrazino[1,2-a]pyrimidin-4-one | 277-280 | 375.3 |
| 25 | 580 | 7-(1-ethylpiperidin-4-yl)-2-(2-methylimidazo[1,2-a]pyridin-6-yl)-4H-pyrazino[1,2-a]pyrimidin-4-one | 255-258 | 389.3 |
| 25 | 581 | 7-[1-(2-hydroxyethyl)piperidin-4-yl]-2-(2-methylimidazo[1,2-a]pyridin-6-yl)-4H-pyrazino[1,2-a]pyrimidin-4-one | 250-252 | 405.3 |
| 53 | 582 | 2-(4,6-dimethylpyrazolo[1,5-a]pyrazin-2-yl)-7-{4-[(2-hydroxyethyl)(methyl)amino]piperidin-1-yl}-9-methyl-4H-pyrido[1,2-a]pyrimidin-4-one | 250-259 | 462.4 |
| 53 | 583 | 2-(4,6-dimethylpyrazolo[1,5-a]pyrazin-2-yl)-9-methyl-7-[4-(propylamino)piperidin-1-yl]-4H-pyrido[1,2-a]pyrimidin-4-one | 231-241 | 446.4 |
| 2 | 584 | 7-(4-amino-4-methylpiperidin-1-yl)-2-(4,6-dimethylpyrazolo[1,5-a]pyrazin-2-yl)-4H-pyrido[1,2-a]pyrimidin-4-one | 200-203 | 404.5 |
| 58 | 585 | 2-(2-methylimidazo[1,2-a]pyridin-6-yl)-7-(piperidin-4-yl)-4H-pyrazino[1,2-a]pyrimidin-4-one | ND | 361.3 |
| 61* | 586 | 2-(2-methyl-2H-indazol-5-yl)-7-(piperazin-1-yl)-4H-pyrazino[1,2-a]pyrimidin-4-one | 160-162 | 362.3 |
| 58 | 587 | 2-(8-chloro-2-methylimidazo[1,2-a]pyridin-6-yl)-7-(piperidin-4-yl)-4H-pyrazino[1,2-a]pyrimidin-4-one | ND | 395.3 |
| 58 | 588 | 2-(2,8-dimethylimidazo[1,2-a]pyridin-6-yl)-7-(piperidin-4-yl)-4H-pyrazino[1,2-a]pyrimidin-4-one | ND | 375.4 |
| 39 | 589 | 2-(2-methyl-2H-indazol-5-yl)-7-(4-methylpiperazin-1-yl)-4H-pyrazino[1,2-a]pyrimidin-4-one | ND | 376.4 |
| 39 | 590 | 7-(4-ethylpiperazin-1-yl)-2-(2-methyl-2H-indazol-5-yl)-4H-pyrazino[1,2-a]pyrimidin-4-one | 214-216 | 390.4 |
| 39 | 591 | 7-[4-(2-hydroxyethyl)piperazin-1-yl]-2-(2-methyl-2H-indazol-5-yl)-4H-pyrazino[1,2-a]pyrimidin-4-one | 200-202 | 406.4 |
| 25 | 592 | 2-(2,8-dimethylimidazo[1,2-a]pyridin-6-yl)-7-(1-methylpiperidin-4-yl)-4H-pyrazino[1,2-a]pyrimidin-4-one | 249-251 | 389.3 |
| 25 | 593 | 2-(2,8-dimethylimidazo[1,2-a]pyridin-6-yl)-7-(1-ethylpiperidin-4-yl)-4H-pyrazino[1,2-a]pyrimidin-4-one | 242-244 | 403.4 |
| 25 | 594 | 2-(2,8-dimethylimidazo[1,2-a]pyridin-6-yl)-7-[1-(2-hydroxyethyl)piperidin-4-yl]-4H-pyrazino[1,2-a]pyrimidin-4-one | 242-244 | 419.4 |
| 25 | 595 | 2-(8-chloro-2-methylimidazo[1,2-a]pyridin-6-yl)-7-[1-(propan-2-yl)piperidin-4-yl]-4H-pyrazino[1,2-a]pyrimidin-4-one | 243-245 | 437.3 |
| 53 | 596 | 2-(4,6-dimethylpyrazolo[1,5-a]pyrazin-2-yl)-7-[4-(ethylamino)piperidin-1-yl]-9-methyl-4H-pyrido[1,2-a]pyrimidin-4-one | 228-236 | 432.4 |

TABLE 1-continued

| Ex | Cpd | Name | M.P. | MS |
|---|---|---|---|---|
| 53 | 597 | 7-{4-[bis(2-hydroxyethyl)amino]piperidin-1-yl}-2-(4,6-dimethylpyrazolo[1,5-a]pyrazin-2-yl)-9-methyl-4H-pyrido[1,2-a]pyrimidin-4-one | 218-227 | 492.4 |
| 25 | 598 | 7-[1-(2-hydroxyethyl)piperidin-4-yl]-2-(2-methyl-1,3-benzoxazol-6-yl)-4H-pyrimido[1,2-b]pyridazin-4-one | 205-207 | 406.3 |
| 25 | 599 | 2-(8-chloro-2-methylimidazo[1,2-a]pyridin-6-yl)-7-[1-(2-hydroxyethyl)piperidin-4-yl]-4H-pyrazino[1,2-a]pyrimidin-4-one | 266-268 | 439.3 |
| 25 | 600 | 2-(4,6-dimethylpyrazolo[1,5-a]pyrazin-2-yl)-7-[1-(oxetan-3-yl)piperidin-4-yl]-4H-pyrido[1,2-a]pyrimidin-4-one | 150-152 | 431.3 |
| 50 | 601 | 2-(5,7-dimethylfuro[2,3-c]pyridin-2-yl)-7-(4-ethylpiperazin-1-yl)-4H-pyrido[1,2-a]pyrimidin-4-one | 202-204 | 404.3 |
| 39 | 602 | 2-(4,6-dimethylpyrazolo[1,5-a]pyrazin-2-yl)-7-(1-methyloctahydro-5H-pyrrolo[3,2-c]pyridin-5-yl)-4H-pyrido[1,2-a]pyrimidin-4-one | 210-212 | 430.3 |
| 51* | 603 | 2-(1-methyl-1H-indazol-5-yl)-7-(piperidin-4-yl)-4H-pyrido[1,2-a]pyrimidin-4-one | 268-270 | 360.4 |
| 25 | 604 | 7-(1-ethylpiperidin-4-yl)-2-(1-methyl-1H-indazol-5-yl)-4H-pyrido[1,2-a]pyrimidin-4-one | 184-186 | 388.5 |
| 25 | 605 | 7-[1-(2-hydroxyethyl)piperidin-4-yl]-2-(1-methyl-1H-indazol-5-yl)-4H-pyrido[1,2-a]pyrimidin-4-one | 204-206 | 404.5 |
| 24 | 606 | 2-(2-methyl-2H-indazol-5-yl)-7-(piperidin-4-yl)-4H-pyrido[1,2-a]pyrimidin-4-one | 194-196 | 360.4 |
| 24 | 607 | 2-(2,8-dimethylimidazo[1,2-a]pyridin-6-yl)-7-(piperidin-4-yl)-4H-pyrido[1,2-a]pyrimidin-4-one | 282-284 | 374.3 |
| 25 | 608 | 2-(2-methyl-2H-indazol-5-yl)-7-[1-(propan-2-yl)piperidin-4-yl]-4H-pyrido[1,2-a]pyrimidin-4-one | ND | 402.5 |
| 53 | 609 | 2-(4,6-dimethylpyrazolo[1,5-a]pyrazin-2-yl)-7-{4-[(2-hydroxyethyl)amino]piperidin-1-yl}-9-methyl-4H-pyrido[1,2-a]pyrimidin-4-one | 221-232 | 448.4 |
| 53 | 610 | 2-(4,6-dimethylpyrazolo[1,5-a]pyrazin-2-yl)-9-methyl-7-[4-(methylamino)piperidin-1-yl]-4H-pyrido[1,2-a]pyrimidin-4-one | 218-227 | 418.4 |
| 53 | 611 | 2-(4,6-dimethylpyrazolo[1,5-a]pyrazin-2-yl)-9-methyl-7-[4-(propan-2-ylamino)piperidin-1-yl]-4H-pyrido[1,2-a]pyrimidin-4-one | 215-225 | 446.4 |
| 25 | 612 | 7-(1-ethylpiperidin-4-yl)-2-(2-methyl-2H-indazol-5-yl)-4H-pyrido[1,2-a]pyrimidin-4-one | 202-204 | 388.5 |
| 25 | 613 | 7-[1-(2-hydroxyethyl)piperidin-4-yl]-2-(2-methyl-2H-indazol-5-yl)-4H-pyrido[1,2-a]pyrimidin-4-one | 170-172 | 404.5 |
| 25 | 614 | 2-(2,8-dimethylimidazo[1,2-a]pyridin-6-yl)-7-(1-methylpiperidin-4-yl)-4H-pyrido[1,2-a]pyrimidin-4-one | 200-202 | 388.5 |
| 25 | 615 | 2-(2,8-dimethylimidazo[1,2-a]pyridin-6-yl)-7-(1-ethylpiperidin-4-yl)-4H-pyrido[1,2-a]pyrimidin-4-one | 202-204 | 402.5 |
| 25 | 616 | 2-(2,8-dimethylimidazo[1,2-a]pyridin-6-yl)-7-[1-(propan-2-yl)piperidin-4-yl]-4H-pyrido[1,2-a]pyrimidin-4-one | 242-244 | 416.5 |
| 25 | 617 | 2-(2,8-dimethylimidazo[1,2-a]pyridin-6-yl)-7-[1-(2-hydroxyethyl)piperidin-4-yl]-4H-pyrido[1,2-a]pyrimidin-4-one | ND | 418.5 |
| 9 | 618 | 2-(4-ethyl-6-methylpyrazolo[1,5-a]pyrazin-2-yl)-7-(4-propylpiperazin-1-yl)-4H-pyrido[1,2-a]pyrimidin-4-one | 243-245 | 432.5 |
| 9 | 619 | 2-(4-ethyl-6-methylpyrazolo[1,5-a]pyrazin-2-yl)-7-[4-(propan-2-yl)piperazin-1-yl]-4H-pyrido[1,2-a]pyrimidin-4-one | 255-258 | 432.5 |
| 9 | 620 | 7-(4-cyclopropylpiperazin-1-yl)-2-(4-ethyl-6-methylpyrazolo[1,5-a]pyrazin-2-yl)-4H-pyrido[1,2-a]pyrimidin-4-one | 258-260 | 430.5 |
| 39 | 621 | 7-(4-cyclobutylpiperazin-1-yl)-2-(4-ethyl-6-methylpyrazolo[1,5-a]pyrazin-2-yl)-4H-pyrido[1,2-a]pyrimidin-4-one | 275-278 | 444.5 |
| 39 | 622 | 2-(4-ethyl-6-methylpyrazolo[1,5-a]pyrazin-2-yl)-7-[4-(oxetan-3-yl)piperazin-1-yl]-4H-pyrido[1,2-a]pyrimidin-4-one | 205-208 | 446.5 |
| 39 | 623 | 2-(4,6-dimethylpyrazolo[1,5-a]pyrazin-2-yl)-7-(1-ethyloctahydro-5H-pyrrolo[3,2-c]pyridin-5-yl)-4H-pyrido[1,2-a]pyrimidin-4-one | 176-178 | 444.5 |

TABLE 1-continued

| Ex | Cpd | Name | M.P. | MS |
|---|---|---|---|---|
| 39 | 624 | 2-(4,6-dimethylpyrazolo[1,5-a]pyrazin-2-yl)-7-[1-(2-hydroxyethyl)octahydro-5H-pyrrolo[3,2-c]pyridin-5-yl]-4H-pyrido[1,2-a]pyrimidin-4-one | 184-187 | 460.5 |
| 40* | 625 | 2-(4-methoxy-6-methylpyrazolo[1,5-a]pyrazin-2-yl)-7-(4-methylpiperazin-1-yl)-4H-pyrido[1,2-a]pyrimidin-4-one | 242-244 | 406.5 |
| 40* | 626 | 2-(4-hydroxy-6-methylpyrazolo[1,5-a]pyrazin-2-yl)-7-(4-methylpiperazin-1-yl)-4H-pyrido[1,2-a]pyrimidin-4-one | 280-283 | 392.4 |
| 25 | 627 | 2-(2-methylimidazo[1,2-a]pyridin-6-yl)-7-[1-(propan-2-yl)piperidin-4-yl]-4H-pyrazino[1,2-a]pyrimidin-4-one | 229-231 | 403.3 |
| 25 | 628 | 7-(1-cyclobutylpiperidin-4-yl)-2-(2-methylimidazo[1,2-a]pyridin-6-yl)-4H-pyrazino[1,2-a]pyrimidin-4-one | 249-251 | 415.2 |
| 39* | 629 | 7-[(3R)-3,4-dimethylpiperazin-1-yl]-2-(4-ethyl-6-methylpyrazolo[1,5-a]pyrazin-2-yl)-4H-pyrido[1,2-a]pyrimidin-4-one | 257-259 | 418.5 |
| 39 | 630 | 7-[(3R)-4-ethyl-3-methylpiperazin-1-yl]-2-(4-ethyl-6-methylpyrazolo[1,5-a]pyrazin-2-yl)-4H-pyrido[1,2-a]pyrimidin-4-one | 256-258 | 432.5 |
| 39 | 631 | 2-(4-ethyl-6-methylpyrazolo[1,5-a]pyrazin-2-yl)-7-[(3R)-3-methyl-4-propylpiperazin-1-yl]-4H-pyrido[1,2-a]pyrimidin-4-one | 243-245 | 446.5 |
| 39 | 632 | 2-(4-ethyl-6-methylpyrazolo[1,5-a]pyrazin-2-yl)-7-[(3R)-4-(2-hydroxyethyl)-3-methylpiperazin-1-yl]-4H-pyrido[1,2-a]pyrimidin-4-one | 238-241 | 448.5 |
| 9 | 633 | 7-[(3R,5S)-3,5-dimethylpiperazin-1-yl]-2-(4-ethyl-6-methylpyrazolo[1,5-a]pyrazin-2-yl)-4H-pyrido[1,2-a]pyrimidin-4-one | 258-260 | 418.4 |
| 9 | 634 | 2-(4-ethyl-6-methylpyrazolo[1,5-a]pyrazin-2-yl)-7-[4-(pyrrolidin-1-yl)piperidin-1-yl]-4H-pyrido[1,2-a]pyrimidin-4-one | 229-232 | 458.6 |
| 9 | 635 | 2-(4-ethyl-6-methylpyrazolo[1,5-a]pyrazin-2-yl)-7-[(3S)-3-methylpiperazin-1-yl]-4H-pyrido[1,2-a]pyrimidin-4-one | 202-204 | 404.4 |
| 9 | 636 | 2-(4-ethyl-6-methylpyrazolo[1,5-a]pyrazin-2-yl)-7-(4-methyl-1,4-diazepan-1-yl)-4H-pyrido[1,2-a]pyrimidin-4-one | 175-180 | 418.4 |
| 16 | 637 | 2-(8-ethyl-2-methylimidazo[1,2-a]pyridin-6-yl)-7-(piperazin-1-yl)-4H-pyrido[1,2-a]pyrimidin-4-one | 264-271 | 389.4 |
| 16 | 638 | 2-(8-ethyl-2-methylimidazo[1,2-a]pyridin-6-yl)-7-[(3R)-3-methylpiperazin-1-yl]-4H-pyrido[1,2-a]pyrimidin-4-one | 230-234 | 403.4 |
| 16 | 639 | 2-(8-ethyl-2-methylimidazo[1,2-a]pyridin-6-yl)-7-[(3S)-3-methylpiperazin-1-yl]-4H-pyrido[1,2-a]pyrimidin-4-one | 232-236 | 403.4 |
| 25 | 640 | 2-(4,6-dimethylpyrazolo[1,5-a]pyrazin-2-yl)-7-[1-(propan-2-yl)piperidin-4-yl]-4H-pyrido[1,2-a]pyrimidin-4-one | 196-198 | 417.5 |
| 25 | 641 | 7-(1-cyclopropylpiperidin-4-yl)-2-(4,6-dimethylpyrazolo[1,5-a]pyrazin-2-yl)-4H-pyrido[1,2-a]pyrimidin-4-one | 180-183 | 415.5 |
| 25 | 642 | 7-(1-cyclobutylpiperidin-4-yl)-2-(4,6-dimethylpyrazolo[1,5-a]pyrazin-2-yl)-4H-pyrido[1,2-a]pyrimidin-4-one | 189-191 | 429.5 |
| 39 | 643 | 2-(4-ethyl-6-methylpyrazolo[1,5-a]pyrazin-2-yl)-7-[(3R)-3-methyl-4-(propan-2-yl)piperazin-1-yl]-4H-pyrido[1,2-a]pyrimidin-4-one | 242-244 | 446.5 |
| 39 | 644 | 7-[(3R)-4-cyclopropyl-3-methylpiperazin-1-yl]-2-(4-ethyl-6-methylpyrazolo[1,5-a]pyrazin-2-yl)-4H-pyrido[1,2-a]pyrimidin-4-one | 244-247 | 444.5 |
| 39 | 645 | 7-[(3R)-4-cyclobutyl-3-methylpiperazin-1-yl]-2-(4-ethyl-6-methylpyrazolo[1,5-a]pyrazin-2-yl)-4H-pyrido[1,2-a]pyrimidin-4-one | 261-264 | 458.6 |
| 39 | 646 | 2-(4-ethyl-6-methylpyrazolo[1,5-a]pyrazin-2-yl)-7-[(3R)-3-methyl-4-(oxetan-3-yl)piperazin-1-yl]-4H-pyrido[1,2-a]pyrimidin-4-one | 216-219 | 460.5 |
| 39 | 647 | 2-(8-ethyl-2-methylimidazo[1,2-a]pyridin-6-yl)-7-[4-(2-hydroxyethyl)piperazin-1-yl]-4H-pyrido[1,2-a]pyrimidin-4-one | 248-253 | 433.3 |
| 39 | 648 | 7-(4-cyclobutylpiperazin-1-yl)-2-(8-ethyl-2-methylimidazo[1,2-a]pyridin-6-yl)-4H-pyrido[1,2-a]pyrimidin-4-one | 274-279 | 443.5 |

TABLE 1-continued

| Ex | Cpd | Name | M.P. | MS |
|---|---|---|---|---|
| 39 | 649 | 2-(8-ethyl-2-methylimidazo[1,2-a]pyridin-6-yl)-7-[(3R)-4-(2-hydroxyethyl)-3-methylpiperazin-1-yl]-4H-pyrido[1,2-a]pyrimidin-4-one | 217-220 | 447.4 |
| 39 | 650 | 7-[(3R)-4-cyclobutyl-3-methylpiperazin-1-yl]-2-(8-ethyl-2-methylimidazo[1,2-a]pyridin-6-yl)-4H-pyrido[1,2-a]pyrimidin-4-one | 209-212 | 457.4 |
| 39 | 651 | 2-(8-ethyl-2-methylimidazo[1,2-a]pyridin-6-yl)-7-[(3S)-4-(2-hydroxyethyl)-3-methylpiperazin-1-yl]-4H-pyrido[1,2-a]pyrimidin-4-one | 220-223 | 447.4 |
| 39 | 652 | 7-[(3S)-4-cyclobutyl-3-methylpiperazin-1-yl]-2-(8-ethyl-2-methylimidazo[1,2-a]pyridin-6-yl)-4H-pyrido[1,2-a]pyrimidin-4-one | ND | 457.5 |
| 59 | 653 | 2-(4-ethyl-6-methylpyrazolo[1,5-a]pyrazin-2-yl)-7-(piperidin-4-yl)-4H-pyrazino[1,2-a]pyrimidin-4-one | ND | 390.4 |
| 25 | 654 | 2-(4-ethyl-6-methylpyrazolo[1,5-a]pyrazin-2-yl)-7-(1-methylpiperidin-4-yl)-4H-pyrazino[1,2-a]pyrimidin-4-one | 261-263 | 404.5 |
| 25 | 655 | 2-(4-ethyl-6-methylpyrazolo[1,5-a]pyrazin-2-yl)-7-(1-ethylpiperidin-4-yl)-4H-pyrazino[1,2-a]pyrimidin-4-one | 273-275 | 418.3 |
| 24 | 656 | 2-(4-ethyl-6-methylpyrazolo[1,5-a]pyrazin-2-yl)-7-(piperidin-4-yl)-4H-pyrido[1,2-a]pyrimidin-4-one | 236-238 | 389.4 |
| 25 | 657 | 2-(4-ethyl-6-methylpyrazolo[1,5-a]pyrazin-2-yl)-7-(1-methylpiperidin-4-yl)-4H-pyrido[1,2-a]pyrimidin-4-one | 190-192 | 403.5 |
| 25 | 658 | 2-(4-ethyl-6-methylpyrazolo[1,5-a]pyrazin-2-yl)-7-(1-ethylpiperidin-4-yl)-4H-pyrido[1,2-a]pyrimidin-4-one | 194-196 | 417.5 |
| 25 | 659 | 2-(4-ethyl-6-methylpyrazolo[1,5-a]pyrazin-2-yl)-7-[1-(2-hydroxyethyl)piperidin-4-yl]-4H-pyrido[1,2-a]pyrimidin-4-one | 207-209 | 433.5 |
| 25 | 660 | 2-(4-ethyl-6-methylpyrazolo[1,5-a]pyrazin-2-yl)-7-(1-propylpiperidin-4-yl)-4H-pyrido[1,2-a]pyrimidin-4-one | 203-204 | 431.5 |
| 9 | 661 | 2-(4-ethyl-6-methylpyrazolo[1,5-a]pyrazin-2-yl)-7-[(3R)-3-methylpiperazin-1-yl]-4H-pyrido[1,2-a]pyrimidin-4-one | 185-188 | 404.5 |
| 43* | 662 | 2-(4,6-dimethylpyrazolo[1,5-a]pyrazin-2-yl)-7-[1-(2-fluoroethyl)piperidin-4-yl]-4H-pyrido[1,2-a]pyrimidin-4-one | 197-199 | 421.5 |
| 43 | 663 | 2-(4,6-dimethylpyrazolo[1,5-a]pyrazin-2-yl)-7-[1-(3-fluoropropyl)piperidin-4-yl]-4H-pyrido[1,2-a]pyrimidin-4-one | 186-188 | 435.5 |
| 43 | 664 | 2-(4-ethyl-6-methylpyrazolo[1,5-a]pyrazin-2-yl)-7-[4-(2-fluoroethyl)piperazin-1-yl]-4H-pyrido[1,2-a]pyrimidin-4-one | 245-247 | 436.5 |
| 43 | 665 | 2-(4-ethyl-6-methylpyrazolo[1,5-a]pyrazin-2-yl)-7-[4-(3-fluoropropyl)piperazin-1-yl]-4H-pyrido[1,2-a]pyrimidin-4-one | 240-242 | 450.6 |
| 43 | 666 | 2-(4-ethyl-6-methylpyrazolo[1,5-a]pyrazin-2-yl)-7-[(3R)-4-(2-fluoroethyl)-3-methylpiperazin-1-yl]-4H-pyrido[1,2-a]pyrimidin-4-one | 255-257 | 450.6 |
| 43 | 667 | 2-(4-ethyl-6-methylpyrazolo[1,5-a]pyrazin-2-yl)-7-[(3R)-4-(3-fluoropropyl)-3-methylpiperazin-1-yl]-4H-pyrido[1,2-a]pyrimidin-4-one | 244-246 | 464.6 |
| 43 | 668 | 2-(4-ethyl-6-methylpyrazolo[1,5-a]pyrazin-2-yl)-7-[1-(2-fluoroethyl)piperidin-4-yl]-4H-pyrido[1,2-a]pyrimidin-4-one | 206-208 | 435.6 |
| 43 | 669 | 2-(4-ethyl-6-methylpyrazolo[1,5-a]pyrazin-2-yl)-7-[1-(3-fluoropropyl)piperidin-4-yl]-4H-pyrido[1,2-a]pyrimidin-4-one | 216-218 | 449.6 |
| 43 | 670 | 2-(4,6-dimethylpyrazolo[1,5-a]pyrazin-2-yl)-7-{(3R)-4-[2-(2-hydroxyethoxy)ethyl]-3-methylpiperazin-1-yl}-9-methyl-4H-pyrido[1,2-a]pyrimidin-4-one | ND | 492.4 |
| 24 | 671 | 2-(4,6-dimethylpyrazolo[1,5-a]pyrazin-2-yl)-9-methyl-7-(piperidin-4-yl)-4H-pyrido[1,2-a]pyrimidin-4-one | 247-255 | 389.3 |
| 25 | 672 | 2-(4,6-dimethylpyrazolo[1,5-a]pyrazin-2-yl)-9-methyl-7-(1-methylpiperidin-4-yl)-4H-pyrido[1,2-a]pyrimidin-4-one | 237-248 | 403.4 |
| 39 | 673 | 2-(4,6-dimethylpyrazolo[1,5-a]pyrazin-2-yl)-7-[(3R)-4-(2-hydroxyethyl)-3-methylpiperazin-1-yl]-9-methyl-4H-pyrido[1,2-a]pyrimidin-4-one | 273-281 | 448.4 |

TABLE 1-continued

| Ex | Cpd | Name | M.P. | MS |
|---|---|---|---|---|
| 48* | 674 | 2-[8-(hydroxymethyl)-2-methylimidazo[1,2-a]pyridin-6-yl]-7-(piperazin-1-yl)-4H-pyrido[1,2-a]pyrimidin-4-one | >320 | 391.3 |
| 16 | 675 | 7-[(3R,5S)-3,5-dimethylpiperazin-1-yl]-2-(8-ethyl-2-methylimidazo[1,2-a]pyridin-6-yl)-4H-pyrido[1,2-a]pyrimidin-4-one | ND | 417.4 |
| 16 | 676 | 2-(8-ethyl-2-methylimidazo[1,2-a]pyridin-6-yl)-7-(4-methyl-1,4-diazepan-1-yl)-4H-pyrido[1,2-a]pyrimidin-4-one | ND | 417.3 |
| 39 | 677 | 2-[8-(hydroxymethyl)-2-methylimidazo[1,2-a]pyridin-6-yl]-7-(4-methylpiperazin-1-yl)-4H-pyrido[1,2-a]pyrimidin-4-one | 262-266 | 405.3 |
| 39 | 678 | 7-(4-ethylpiperazin-1-yl)-2-[8-(hydroxymethyl)-2-methylimidazo[1,2-a]pyridin-6-yl]-4H-pyrido[1,2-a]pyrimidin-4-one | 258-262 | 419.3 |
| 25 | 679 | 2-(4-ethyl-6-methylpyrazolo[1,5-a]pyrazin-2-yl)-7-[1-(propan-2-yl)piperidin-4-yl]-4H-pyrido[1,2-a]pyrimidin-4-one | 228-230 | 431.5 |
| 25 | 680 | 7-(1-cyclopropylpiperidin-4-yl)-2-(4-ethyl-6-methylpyrazolo[1,5-a]pyrazin-2-yl)-4H-pyrido[1,2-a]pyrimidin-4-one | 196-199 | 429.5 |
| 25 | 681 | 7-(1-cyclobutylpiperidin-4-yl)-2-(4-ethyl-6-methylpyrazolo[1,5-a]pyrazin-2-yl)-4H-pyrido[1,2-a]pyrimidin-4-one | 227-229 | 443.5 |
| 25 | 682 | 2-(4-ethyl-6-methylpyrazolo[1,5-a]pyrazin-2-yl)-7-[1-(oxetan-3-yl)piperidin-4-yl]-4H-pyrido[1,2-a]pyrimidin-4-one | 190-192 | 445.5 |
| 9 | 683 | 2-(4-cyclopropyl-6-methylpyrazolo[1,5-a]pyrazin-2-yl)-7-(piperazin-1-yl)-4H-pyrido[1,2-a]pyrimidin-4-one | 226-229 | 402.4 |
| 9 | 684 | 2-(4-cyclopropyl-6-methylpyrazolo[1,5-a]pyrazin-2-yl)-7-(4-methylpiperazin-1-yl)-4H-pyrido[1,2-a]pyrimidin-4-one | 238-240 | 416.5 |
| 9 | 685 | 2-(4-cyclopropyl-6-methylpyrazolo[1,5-a]pyrazin-2-yl)-7-(4-ethylpiperazin-1-yl)-4H-pyrido[1,2-a]pyrimidin-4-one | 236-238 | 430.5 |
| 9 | 686 | 2-(4-cyclopropyl-6-methylpyrazolo[1,5-a]pyrazin-2-yl)-7-[4-(2-hydroxyethyl)piperazin-1-yl]-4H-pyrido[1,2-a]pyrimidin-4-one | 239-241 | 446.5 |
| 25 | 687 | 2-(4,6-dimethylpyrazolo[1,5-a]pyrazin-2-yl)-7-(1-propylpiperidin-4-yl)-4H-pyrido[1,2-a]pyrimidin-4-one | 185-187 | 417.4 |
| 41* | 688 | 2-[4-(dimethylamino)-6-methylpyrazolo[1,5-a]pyrazin-2-yl]-7-(piperazin-1-yl)-4H-pyrido[1,2-a]pyrimidin-4-one | 245-248 | 405.4 |
| 14 | 689 | 2-(2-methyl-1H-benzimidazol-6-yl)-7-(4-methylpiperazin-1-yl)-4H-pyrido[1,2-a]pyrimidin-4-one | 292-294 | 375.3 |
| 39 | 690 | 7-(4-ethylpiperazin-1-yl)-2-(2-methyl-1H-benzimidazol-6-yl)-4H-pyrido[1,2-a]pyrimidin-4-one | 283-285 | 389.3 |
| 58 | 691 | 2-(2,8-dimethylimidazo[1,2-a]pyridin-6-yl)-7-(piperidin-4-yl)-4H-pyrimido[1,2-b]pyridazin-4-one | 215-217 | 375.4 |
| 58 | 692 | 2-(2-methylimidazo[1,2-a]pyridin-6-yl)-7-(piperidin-4-yl)-4H-pyrimido[1,2-b]pyridazin-4-one | 249-251 | 361.3 |
| 25 | 693 | 7-[1-(2,2-dimethyl-1,3-dioxan-5-yl)piperidin-4-yl]-2-(4-ethyl-6-methylpyrazolo[1,5-a]pyrazin-2-yl)-4H-pyrido[1,2-a]pyrimidin-4-one | 236-238 | 503.5 |
| 42* | 694 | 7-[1-(1,3-dihydroxypropan-2-yl)piperidin-4-yl]-2-(4-ethyl-6-methylpyrazolo[1,5-a]pyrazin-2-yl)-4H-pyrido[1,2-a]pyrimidin-4-one | 228-230 | 463.6 |
| 62* | 695 | 7-[(3R,5S)-3,5-dimethylpiperazin-1-yl]-2-(1,3-dimethylpyrrolo[1,2-a]pyrazin-7-yl)-4H-pyrido[1,2-a]pyrimidin-4-one | 254-256 | 403.4 |
| 24 | 696 | 2-(8-ethyl-2-methylimidazo[1,2-a]pyridin-6-yl)-7-(piperidin-4-yl)-4H-pyrido[1,2-a]pyrimidin-4-one | 221-224 | 388.3 |
| 25 | 697 | 2-(8-ethyl-2-methylimidazo[1,2-a]pyridin-6-yl)-7-(1-methylpiperidin-4-yl)-4H-pyrido[1,2-a]pyrimidin-4-one | 214-218 | 402.4 |
| 25 | 698 | 2-(8-ethyl-2-methylimidazo[1,2-a]pyridin-6-yl)-7-(1-ethylpiperidin-4-yl)-4H-pyrido[1,2-a]pyrimidin-4-one | 196-200 | 416.5 |
| 25 | 699 | 2-(8-ethyl-2-methylimidazo[1,2-a]pyridin-6-yl)-7-[1-(2-hydroxyethyl)piperidin-4-yl]-4H-pyrido[1,2-a]pyrimidin-4-one | 244-247 | 432.4 |

TABLE 1-continued

| Ex | Cpd | Name | M.P. | MS |
|---|---|---|---|---|
| 39 | 700 | 7-[(3R)-3,4-dimethylpiperazin-1-yl]-2-(8-ethyl-2-methylimidazo[1,2-a]pyridin-6-yl)-4H-pyrido[1,2-a]pyrimidin-4-one | 217-220 | 417.4 |
| 39 | 701 | 2-(8-ethyl-2-methylimidazo[1,2-a]pyridin-6-yl)-7-[(3R)-4-ethyl-3-methylpiperazin-1-yl]-4H-pyrido[1,2-a]pyrimidin-4-one | 179-182 | 431.4 |
| 25 | 702 | 2-(4,6-dimethylpyrazolo[1,5-a]pyrazin-2-yl)-7-(1-ethylpiperidin-4-yl)-9-methyl-4H-pyrido[1,2-a]pyrimidin-4-one | 231-240 | 417.4 |
| 25 | 703 | 2-(4,6-dimethylpyrazolo[1,5-a]pyrazin-2-yl)-7-[1-(2-hydroxyethyl)piperidin-4-yl]-9-methyl-4H-pyrido[1,2-a]pyrimidin-4-one | 224-233 | 433.3 |
| 25 | 704 | 7-(1-cyclobutylpiperidin-4-yl)-2-(4,6-dimethylpyrazolo[1,5-a]pyrazin-2-yl)-9-methyl-4H-pyrido[1,2-a]pyrimidin-4-one | 228-237 | 443.5 |
| 25 | 705 | 9-methyl-2-(2-methyl-2H-indazol-5-yl)-7-(1-methylpiperidin-4-yl)-4H-pyrido[1,2-a]pyrimidin-4-one | 222-227 | 388.3 |
| 2 | 706 | 7-[4-(dimethylamino)-4-methylpiperidin-1-yl]-2-(4,6-dimethylpyrazolo[1,5-a]pyrazin-2-yl)-4H-pyrido[1,2-a]pyrimidin-4-one | 237-239 | 432.4 |
| 2 | 707 | 2-(4,6-dimethylpyrazolo[1,5-a]pyrazin-2-yl)-7-[4-(ethylamino)-4-methylpiperidin-1-yl]-4H-pyrido[1,2-a]pyrimidin-4-one | 187-189 | 432.4 |
| 2 | 708 | 2-(4,6-dimethylpyrazolo[1,5-a]pyrazin-2-yl)-7-[4-methyl-4-(propylamino)piperidin-1-yl]-4H-pyrido[1,2-a]pyrimidin-4-one | 181-183 | 446.4 |
| 2 | 709 | 2-(4,6-dimethylpyrazolo[1,5-a]pyrazin-2-yl)-7-{4-[(2-hydroxyethyl)amino]-4-methylpiperidin-1-yl}-4H-pyrido[1,2-a]pyrimidin-4-one | 196-198 | 448.4 |
| 25 | 710 | 7-(1-cyclobutylpiperidin-4-yl)-9-methyl-2-(2-methyl-2H-indazol-5-yl)-4H-pyrido[1,2-a]pyrimidin-4-one | 232-235 | 428.4 |
| 25 | 711 | 7-[1-(2-hydroxyethyl)piperidin-4-yl]-9-methyl-2-(2-methyl-2H-indazol-5-yl)-4H-pyrido[1,2-a]pyrimidin-4-one | 216-222 | 418.4 |
| 25 | 712 | 2-(4,6-dimethylpyrazolo[1,5-a]pyrazin-2-yl)-9-methyl-7-(1-propylpiperidin-4-yl)-4H-pyrido[1,2-a]pyrimidin-4-one | 216-223 | 431.4 |
| 62 | 713 | 2-(1,3-dimethylpyrrolo[1,2-a]pyrazin-7-yl)-7-[(3R)-3-methylpiperazin-1-yl]-4H-pyrido[1,2-a]pyrimidin-4-one | ND | 389.3 |
| 47* | 714 | 2-(8-cyclopropyl-2-methylimidazo[1,2-a]pyridin-6-yl)-7-(piperazin-1-yl)-4H-pyrido[1,2-a]pyrimidin-4-one | 274-277 | 401.4 |
| 47 | 715 | 2-(8-cyclopropyl-2-methylimidazo[1,2-a]pyridin-6-yl)-7-[(3R)-3-methylpiperazin-1-yl]-4H-pyrido[1,2-a]pyrimidin-4-one | 246-250 | 415.4 |
| 47 | 716 | 2-(8-cyclopropyl-2-methylimidazo[1,2-a]pyridin-6-yl)-7-[(3S)-3-methylpiperazin-1-yl]-4H-pyrido[1,2-a]pyrimidin-4-one | 246-250 | 415.4 |
| 47 | 717 | 2-(8-cyclopropyl-2-methylimidazo[1,2-a]pyridin-6-yl)-7-[(3R,5S)-3,5-dimethylpiperazin-1-yl]-4H-pyrido[1,2-a]pyrimidin-4-one | 205-209 | 429.5 |
| 25 | 718 | 7-(1-cyclopropylpiperidin-4-yl)-9-methyl-2-(2-methyl-2H-indazol-5-yl)-4H-pyrido[1,2-a]pyrimidin-4-one | 226-231 | 414.4 |
| 25 | 719 | 7-(1-ethylpiperidin-4-yl)-9-methyl-2-(2-methyl-2H-indazol-5-yl)-4H-pyrido[1,2-a]pyrimidin-4-one | 237-241 | 402.5 |
| 2 | 720 | 2-(4,6-dimethylpyrazolo[1,5-a]pyrazin-2-yl)-9-methyl-7-(piperazin-1-yl)-4H-pyrido[1,2-a]pyrimidin-4-one | 254-264 | 390.4 |
| 24 | 721 | 9-methyl-2-(2-methyl-2H-indazol-5-yl)-7-(piperidin-4-yl)-4H-pyrido[1,2-a]pyrimidin-4-one | 211 (S), 223-227 | 374.3 |
| 27 | 722 | 2-(4,6-dimethylpyrazolo[1,5-a]pyrazin-2-yl)-7-[(1-methylpiperidin-4-yl)oxy]-4H-pyrido[1,2-a]pyrimidin-4-one | 249-252 | 405.4 |
| 9 | 723 | 2-(6-methyl-4-propylpyrazolo[1,5-a]pyrazin-2-yl)-7-(piperazin-1-yl)-4H-pyrido[1,2-a]pyrimidin-4-one | 250-252 | 404.4 |
| 9 | 724 | 7-(4-methylpiperazin-1-yl)-2-(6-methyl-4-propylpyrazolo[1,5-a]pyrazin-2-yl)-4H-pyrido[1,2-a]pyrimidin-4-one | 246-248 | 418.4 |
| 9 | 725 | 7-(4-ethylpiperazin-1-yl)-2-(6-methyl-4-propylpyrazolo[1,5-a]pyrazin-2-yl)-4H-pyrido[1,2-a]pyrimidin-4-one | 231-233 | 432.5 |
| 9 | 726 | 7-[4-(2-hydroxyethyl)piperazin-1-yl]-2-(6-methyl-4-propylpyrazolo[1,5-a]pyrazin-2-yl)-4H-pyrido[1,2-a]pyrimidin-4-one | 225-227 | 448.4 |

TABLE 1-continued

| Ex | Cpd | Name | M.P. | MS |
|---|---|---|---|---|
| 9 | 727 | 7-[(3R)-3-methylpiperazin-1-yl]-2-(6-methyl-4-propylpyrazolo[1,5-a]pyrazin-2-yl)-4H-pyrido[1,2-a]pyrimidin-4-one | 195-197 | 418.4 |
| 9 | 728 | 7-[(3S)-3-methylpiperazin-1-yl]-2-(6-methyl-4-propylpyrazolo[1,5-a]pyrazin-2-yl)-4H-pyrido[1,2-a]pyrimidin-4-one | 195-197 | 418.4 |
| 9 | 729 | 7-[(3R,5S)-3,5-dimethylpiperazin-1-yl]-2-(6-methyl-4-propylpyrazolo[1,5-a]pyrazin-2-yl)-4H-pyrido[1,2-a]pyrimidin-4-one | 249-251 | 432.5 |
| 39 | 730 | 2-(1,3-dimethylpyrrolo[1,2-a]pyrazin-7-yl)-7-[(3R)-3-methyl-4-(propan-2-yl)piperazin-1-yl]-4H-pyrido[1,2-a]pyrimidin-4-one | 249-251 | 431.3 |
| 63* | 731 | 7-(4-amino-4-methylpiperidin-1-yl)-2-(1,3-dimethylpyrrolo[1,2-a]pyrazin-7-yl)-4H-pyrido[1,2-a]pyrimidin-4-one | 244-246 | 403.3 |
| 2 | 732 | 2-(4,6-dimethylpyrazolo[1,5-a]pyrazin-2-yl)-7-[(3S)-3-ethylpiperazin-1-yl]-9-methyl-4H-pyrido[1,2-a]pyrimidin-4-one | 243-251 | 418.5 |
| 16 | 733 | 2-[2-methyl-8-(trifluoromethyl)imidazo[1,2-a]pyridin-6-yl]-7-(piperazin-1-yl)-4H-pyrido[1,2-a]pyrimidin-4-one | 325-328 | 429.3 |
| 16 | 734 | 7-[(3R)-3-methylpiperazin-1-yl]-2-[2-methyl-8-(trifluoromethyl)imidazo[1,2-a]pyridin-6-yl]-4H-pyrido[1,2-a]pyrimidin-4-one | 303-306 | 443.2 |
| 16 | 735 | 7-[(3S)-3-methylpiperazin-1-yl]-2-[2-methyl-8-(trifluoromethyl)imidazo[1,2-a]pyridin-6-yl]-4H-pyrido[1,2-a]pyrimidin-4-one | >320 | 443.2 |
| 16 | 736 | 7-[(3R,5S)-3,5-dimethylpiperazin-1-yl]-2-[2-methyl-8-(trifluoromethyl)imidazo[1,2-a]pyridin-6-yl]-4H-pyrido[1,2-a]pyrimidin-4-one | 293-296 | 457.3 |
| 2 | 737 | 7-(4-amino-4-methylpiperidin-1-yl)-2-(4-ethyl-6-methylpyrazolo[1,5-a]pyrazin-2-yl)-4H-pyrido[1,2-a]pyrimidin-4-one | 216-218 | 418.5 |
| 14 | 738 | 2-(2,7-dimethyl-2H-indazol-5-yl)-7-(piperazin-1-yl)-4H-pyrido[1,2-a]pyrimidin-4-one | 194-196 | 375.4 |
| 24 | 739 | 2-(2,7-dimethyl-2H-indazol-5-yl)-7-(piperidin-4-yl)-4H-pyrido[1,2-a]pyrimidin-4-one | 228-230 | 374.4 |
| 52 | 740 | 7-(3-aminoprop-1-yn-1-yl)-2-(4,6-dimethylpyrazolo[1,5-a]pyrazin-2-yl)-4H-pyrido[1,2-a]pyrimidin-4-one | 242-244 | 345.4 |
| 14 | 741 | 2-(2,7-dimethyl-2H-indazol-5-yl)-7-[(3R)-3-methylpiperazin-1-yl]-4H-pyrido[1,2-a]pyrimidin-4-one | 170-172 | 389.4 |
| 52 | 742 | 7-(3-aminopropyl)-2-(4,6-dimethylpyrazolo[1,5-a]pyrazin-2-yl)-4H-pyrido[1,2-a]pyrimidin-4-one | ND | 349.3 |
| 64* | 743 | 2-(1,3-dimethylpyrrolo[1,2-a]pyrazin-7-yl)-7-(1,2,3,6-tetrahydropyridin-4-yl)-4H-pyrido[1,2-a]pyrimidin-4-one | 189-191 | 372.3 |
| 38 | 744 | 2-(4,6-dimethylpyrazolo[1,5-a]pyrazin-2-yl)-7-(2,2,6,6-tetramethyl-1,2,3,6-tetrahydropyridin-4-yl)-4H-pyrido[1,2-a]pyrimidin-4-one | 218-221 | 429.5 |
| 38 | 745 | 2-(4-ethyl-6-methylpyrazolo[1,5-a]pyrazin-2-yl)-7-(2,2,6,6-tetramethyl-1,2,3,6-tetrahydropyridin-4-yl)-4H-pyrido[1,2-a]pyrimidin-4-one | 255-258 | 443.5 |
| 45 | 746 | 2-(4,6-dimethylpyrazolo[1,5-a]pyrazin-2-yl)-7-[(3aR,6aS)-hexahydropyrrolo[3,4-c]pyrrol-2(1H)-yl]-4H-pyrido[1,2-a]pyrimidin-4-one | 239-242 | 402.4 |
| 2 | 747 | 2-(4-ethyl-6-methylpyrazolo[1,5-a]pyrazin-2-yl)-7-[(3aR,6aS)-hexahydropyrrolo[3,4-c]pyrrol-2(1H)-yl]-4H-pyrido[1,2-a]pyrimidin-4-one | 246-249 | 416.4 |
| 62 | 748 | 7-[(3R,5S)-3,5-dimethylpiperazin-1-yl]-2-(1-ethyl-3-methylpyrrolo[1,2-a]pyrazin-7-yl)-4H-pyrido[1,2-a]pyrimidin-4-one | 238-241 | 417.4 |
| 62 | 749 | 7-(1,4-diazepan-1-yl)-2-(1-ethyl-3-methylpyrrolo[1,2-a]pyrazin-7-yl)-4H-pyrido[1,2-a]pyrimidin-4-one | 200-202 | 403.4 |
| 14 | 750 | 2-(2,7-dimethyl-2H-indazol-5-yl)-7-[(3S)-3-methylpiperazin-1-yl]-4H-pyrido[1,2-a]pyrimidin-4-one | 308-310 | 389.4 |
| 39 | 751 | 2-(2,7-dimethyl-2H-indazol-5-yl)-7-[(3S)-3,4-dimethylpiperazin-1-yl]-4H-pyrido[1,2-a]pyrimidin-4-one | 202-204 | 403.4 |
| 25 | 752 | 2-(2,7-dimethyl-2H-indazol-5-yl)-7-(1-methylpiperidin-4-yl)-4H-pyrido[1,2-a]pyrimidin-4-one | 208-210 | 388.3 |
| 25 | 753 | 2-(2,7-dimethyl-2H-indazol-5-yl)-7-(1-ethylpiperidin-4-yl)-4H-pyrido[1,2-a]pyrimidin-4-one | 162-164 | 402.4 |

TABLE 1-continued

| Ex | Cpd | Name | M.P. | MS |
|---|---|---|---|---|
| 2 | 754 | 9-methyl-2-(2-methyl-2H-indazol-5-yl)-7-(piperazin-1-yl)-4H-pyrido[1,2-a]pyrimidin-4-one | 233-243 | 375.3 |
| 2 | 755 | 9-methyl-2-(2-methyl-2H-indazol-5-yl)-7-[(3R)-3-methylpiperazin-1-yl]-4H-pyrido[1,2-a]pyrimidin-4-one | ND | 389.4 |
| 2 | 756 | 9-methyl-2-(2-methyl-2H-indazol-5-yl)-7-[(3S)-3-methylpiperazin-1-yl]-4H-pyrido[1,2-a]pyrimidin-4-one | ND | 389.3 |
| 2 | 757 | 7-[3-(dimethylamino)azetidin-1-yl]-2-(4,6-dimethylpyrazolo[1,5-a]pyrazin-2-yl)-4H-pyrido[1,2-a]pyrimidin-4-one | 226-228 | 390.4 |
| 2 | 758 | 7-[3-(diethylamino)azetidin-1-yl]-2-(4,6-dimethylpyrazolo[1,5-a]pyrazin-2-yl)-4H-pyrido[1,2-a]pyrimidin-4-one | 231-233 | 418.5 |
| 2 | 759 | 2-(4,6-dimethylpyrazolo[1,5-a]pyrazin-2-yl)-7-[3-(pyrrolidin-1-yl)azetidin-1-yl]-4H-pyrido[1,2-a]pyrimidin-4-one | 235-237 | 416.4 |
| 9 | 760 | 7-(1,4-diazepan-1-yl)-2-(4-ethyl-6-methylpyrazolo[1,5-a]pyrazin-2-yl)-4H-pyrido[1,2-a]pyrimidin-4-one | 212-214 | 404.4 |
| 45 | 761 | 7-[(3aR,6aS)-hexahydropyrrolo[3,4-c]pyrrol-2(1H)-yl]-2-(6-methyl-4-propylpyrazolo[1,5-a]pyrazin-2-yl)-4H-pyrido[1,2-a]pyrimidin-4-one | 212-214 | 430.4 |
| 38 | 762 | 2-(6-methyl-4-propylpyrazolo[1,5-a]pyrazin-2-yl)-7-(1,2,3,6-tetrahydropyridin-4-yl)-4H-pyrido[1,2-a]pyrimidin-4-one | 257-260 | 401.4 |
| 38 | 763 | 2-(4-ethyl-6-methylpyrazolo[1,5-a]pyrazin-2-yl)-7-(1,2,3,6-tetrahydropyridin-4-yl)-4H-pyrido[1,2-a]pyrimidin-4-one | 287-289 | 387.4 |
| 45* | 764 | 7-[(3S)-3-(aminomethyl)pyrrolidin-1-yl]-2-(4,6-dimethylpyrazolo[1,5-a]pyrazin-2-yl)-4H-pyrido[1,2-a]pyrimidin-4-one | 244-246 | 390.4 |
| 2 | 765 | 2-(4,6-dimethylpyrazolo[1,5-a]pyrazin-2-yl)-7-[3-(piperidin-1-yl)azetidin-1-yl]-4H-pyrido[1,2-a]pyrimidin-4-one | 220-223 | 430.5 |
| 24 | 766 | 2-(6-methyl-4-propylpyrazolo[1,5-a]pyrazin-2-yl)-7-(piperidin-4-yl)-4H-pyrido[1,2-a]pyrimidin-4-one | 228-230 | 403.4 |
| 2 | 767 | 7-(2,7-diazaspiro[4.4]non-2-yl)-2-(4,6-dimethylpyrazolo[1,5-a]pyrazin-2-yl)-4H-pyrido[1,2-a]pyrimidin-4-one | 208-210 | 416.4 |
| 14 | 768 | 2-(2,7-dimethyl-2H-indazol-5-yl)-7-(4-methylpiperazin-1-yl)-4H-pyrido[1,2-a]pyrimidin-4-one | 216-218 | 389.5 |
| 52* | 769 | 7-[3-(dimethylamino)propyl]-2-(4,6-dimethylpyrazolo[1,5-a]pyrazin-2-yl)-4H-pyrido[1,2-a]pyrimidin-4-one | 136-138 | 377.3 |
| 39 | 770 | 7-{(3S)-3-[(dimethylamino)methyl]pyrrolidin-1-yl}-2-(4,6-dimethylpyrazolo[1,5-a]pyrazin-2-yl)-4H-pyrido[1,2-a]pyrimidin-4-one | 239-241 | 418.4 |
| 24 | 771 | 2-(4-ethyl-6-methylpyrazolo[1,5-a]pyrazin-2-yl)-9-methyl-7-(piperidin-4-yl)-4H-pyrido[1,2-a]pyrimidin-4-one | 241-249 | 403.4 |
| 24 | 772 | 9-methyl-2-(1-methyl-1H-indazol-5-yl)-7-(piperidin-4-yl)-4H-pyrido[1,2-a]pyrimidin-4-one | 212-217 | 374.3 |
| 22 | 773 | 2-(4-ethyl-6-methylpyrazolo[1,5-a]pyrazin-2-yl)-9-methyl-7-(1,2,3,6-tetrahydropyridin-4-yl)-4H-pyrido[1,2-a]pyrimidin-4-one | 265 (D) | 401.3 |
| 25 | 774 | 2-(4-ethyl-6-methylpyrazolo[1,5-a]pyrazin-2-yl)-9-methyl-7-(1-methylpiperidin-4-yl)-4H-pyrido[1,2-a]pyrimidin-4-one | 220-227 | 417.3 |
| 51 | 775 | 2-(1,7-dimethyl-1H-indazol-5-yl)-7-(piperidin-4-yl)-4H-pyrido[1,2-a]pyrimidin-4-one | 220-222 | 374.2 |
| 14 | 776 | 2-(1,7-dimethyl-1H-indazol-5-yl)-7-(piperazin-1-yl)-4H-pyrido[1,2-a]pyrimidin-4-one | 160-163 | 375.3 |
| 14 | 777 | 2-(1,7-dimethyl-1H-indazol-5-yl)-7-[(3S)-3-methylpiperazin-1-yl]-4H-pyrido[1,2-a]pyrimidin-4-one | 248-250 | 389.3 |
| 39 | 778 | 7-{(3S)-3-[(diethylamino)methyl]pyrrolidin-1-yl}-2-(4,6-dimethylpyrazolo[1,5-a]pyrazin-2-yl)-4H-pyrido[1,2-a]pyrimidin-4-one | 194-196 | 446.4 |
| 39 | 779 | 2-(4,6-dimethylpyrazolo[1,5-a]pyrazin-2-yl)-7-{(3S)-3-[(ethylamino)methyl]pyrrolidin-1-yl}-4H-pyrido[1,2-a]pyrimidin-4-one | ND | 418.4 |
| 2 | 780 | 7-{3-[(dimethylamino)methyl]azetidin-1-yl}-2-(4,6-dimethylpyrazolo[1,5-a]pyrazin-2-yl)-4H-pyrido[1,2-a]pyrimidin-4-one | 228-230 | 404.4 |

TABLE 1-continued

| Ex | Cpd | Name | M.P. | MS |
|---|---|---|---|---|
| 2 | 781 | 7-{3-[(diethylamino)methyl]azetidin-1-yl}-2-(4,6-dimethylpyrazolo[1,5-a]pyrazin-2-yl)-4H-pyrido[1,2-a]pyrimidin-4-one | 205-207 | 432.4 |
| 62 | 782 | 2-(1-ethyl-3-methylpyrrolo[1,2-a]pyrazin-7-yl)-7-[(8aS)-hexahydropyrrolo[1,2-a]pyrazin-2(1H)-yl]-4H-pyrido[1,2-a]pyrimidin-4-one | 220-222 | 429.3 |
| 2 | 783 | 2-(4-ethyl-6-methylpyrazolo[1,5-a]pyrazin-2-yl)-9-methyl-7-[(3R)-3-methylpiperazin-1-yl]-4H-pyrido[1,2-a]pyrimidin-4-one | 223-233 | 418.4 |
| 25 | 784 | 9-methyl-2-(1-methyl-1H-indazol-5-yl)-7-(1-methylpiperidin-4-yl)-4H-pyrido[1,2-a]pyrimidin-4-one | 255-263 | 388.3 |
| 39 | 785 | 7-[(3R)-3,4-dimethylpiperazin-1-yl]-2-(4-ethyl-6-methylpyrazolo[1,5-a]pyrazin-2-yl)-9-methyl-4H-pyrido[1,2-a]pyrimidin-4-one | 234-240 | 432.4 |
| 25 | 786 | 7-(1-ethylpiperidin-4-yl)-9-methyl-2-(1-methyl-1H-indazol-5-yl)-4H-pyrido[1,2-a]pyrimidin-4-one | 236-240 | 402.4 |
| 2 | 787 | 2-(4-ethyl-6-methylpyrazolo[1,5-a]pyrazin-2-yl)-9-methyl-7-[(3S)-3-methylpiperazin-1-yl]-4H-pyrido[1,2-a]pyrimidin-4-one | 227-236 | 418.4 |
| 2 | 788 | 7-[1-(2-hydroxyethyl)piperidin-4-yl]-9-methyl-2-(1-methyl-1H-indazol-5-yl)-4H-pyrido[1,2-a]pyrimidin-4-one | 225-228 | 418.4 |
| 2 | 789 | 7-[(3S)-3,4-dimethylpiperazin-1-yl]-2-(4-ethyl-6-methylpyrazolo[1,5-a]pyrazin-2-yl)-9-methyl-4H-pyrido[1,2-a]pyrimidin-4-one | 235-241 | 432.4 |
| 25 | 790 | 2-(4-ethyl-6-methylpyrazolo[1,5-a]pyrazin-2-yl)-7-(1-ethylpiperidin-4-yl)-9-methyl-4H-pyrido[1,2-a]pyrimidin-4-one | 201-208 | 431.4 |
| 22 | 791 | 9-methyl-2-(2-methyl-2H-indazol-5-yl)-7-(1,2,3,6-tetrahydropyridin-4-yl)-4H-pyrazino[1,2-a]pyrimidin-4-one | >240 (D) | 373.3 |
| 25 | 792 | 7-(1-cyclobutylpiperidin-4-yl)-2-(4-ethyl-6-methylpyrazolo[1,5-a]pyrazin-2-yl)-9-methyl-4H-pyrido[1,2-a]pyrimidin-4-one | 231-237 | 457.3 |
| 25 | 793 | 2-(4-ethyl-6-methylpyrazolo[1,5-a]pyrazin-2-yl)-7-[1-(2-hydroxyethyl)piperidin-4-yl]-9-methyl-4H-pyrido[1,2-a]pyrimidin-4-one | 210-216 | 447.4 |
| 16 | 794 | 2-(8-ethyl-2-methylimidazo[1,2-a]pyridin-6-yl)-7-[(8aR)-hexahydropyrrolo[1,2-a]pyrazin-2(1H)-yl]-4H-pyrido[1,2-a]pyrimidin-4-one | 231-235 | 429.3 |
| 16 | 795 | 2-(8-ethyl-2-methylimidazo[1,2-a]pyridin-6-yl)-7-[(8aS)-hexahydropyrrolo[1,2-a]pyrazin-2(1H)-yl]-4H-pyrido[1,2-a]pyrimidin-4-one | 229-233 | 429.3 |
| 51 | 796 | 9-methyl-2-(2-methyl-2H-indazol-5-yl)-7-(piperidin-4-yl)-4H-pyrazino[1,2-a]pyrimidin-4-one | 229-235 | 375.3 |
| 2 | 797 | 7-[(3R)-3-(aminomethyl)pyrrolidin-1-yl]-2-(4,6-dimethylpyrazolo[1,5-a]pyrazin-2-yl)-4H-pyrido[1,2-a]pyrimidin-4-one | 214-217 | 390.4 |
| 44* | 798 | 2-(4,6-dimethylpyrazolo[1,5-a]pyrazin-2-yl)-7-[(2S,6S)-2,6-dimethyl-1,2,3,6-tetrahydropyridin-4-yl]-4H-pyrido[1,2-a]pyrimidin-4-one | 228-231 | 401.3 |
| 2 | 799 | 7-{(3R)-3-[(dimethylamino)methyl]pyrrolidin-1-yl}-2-(4,6-dimethylpyrazolo[1,5-a]pyrazin-2-yl)-4H-pyrido[1,2-a]pyrimidin-4-one | 229-231 | 418.4 |
| 24 | 800 | 7-[(2S,6S)-2,6-dimethylpiperidin-4-yl]-2-(4,6-dimethylpyrazolo[1,5-a]pyrazin-2-yl)-4H-pyrido[1,2-a]pyrimidin-4-one | 248-250 | 403.3 |
| 16 | 801 | 2-(8-fluoro-2-methylimidazo[1,2-a]pyridin-6-yl)-7-[4-(2-hydroxyethyl)piperazin-1-yl]-4H-pyrido[1,2-a]pyrimidin-4-one | ND | 423.5 |
| 16 | 802 | 2-(imidazo[1,2-a]pyridin-6-yl)-7-(4-methylpiperazin-1-yl)-4H-pyrido[1,2-a]pyrimidin-4-one | ND | 361.5 |
| 36 | 803 | 2-(4-fluoro-2-methyl-1,3-benzoxazol-6-yl)-7-[(8aS)-hexahydropyrrolo[1,2-a]pyrazin-2(1H)-yl]-4H-pyrido[1,2-a]pyrimidin-4-one | ND | 420.6 |
| 65* | 804 | 7-(2,7-diazaspiro[3.5]non-7-yl)-2-(4,6-dimethylpyrazolo[1,5-a]pyrazin-2-yl)-4H-pyrido[1,2-a]pyrimidin-4-one | ND | 416.2 |
| 14 | 805 | 7-(4-methylpiperazin-1-yl)-2-(2-methyl[1,2,4]triazolo[1,5-a]pyridin-6-yl)-4H-pyrido[1,2-a]pyrimidin-4-one | ND | 376.1 |
| 16 | 806 | 7-(4-methylpiperazin-1-yl)-2-[2-methyl-8-(trifluoromethyl)imidazo[1,2-a]pyridin-6-yl]-4H-pyrido[1,2-a]pyrimidin-4-one | ND | 443.6 |
| 16 | 807 | 2-methyl-6-[7-(4-methylpiperazin-1-yl)-4-oxo-4H-pyrido[1,2-a]pyrimidin-2-yl]imidazo[1,2-a]pyridine-8-carbonitrile | ND | 400.6 |

TABLE 1-continued

| Ex | Cpd | Name | M.P. | MS |
|---|---|---|---|---|
| 16 | 808 | 2-(2,8-dimethylimidazo[1,2-a]pyridin-6-yl)-7-(4-methylpiperazin-1-yl)-4H-pyrido[1,2-a]pyrimidin-4-one | ND | 389.5 |
| 16 | 809 | 7-(4,7-diazaspiro[2.5]oct-7-yl)-2-(2,8-dimethylimidazo[1,2-a]pyridin-6-yl)-4H-pyrido[1,2-a]pyrimidin-4-one | ND | 401.4 |
| 25 | 810 | 2-(8-fluoro-2-methylimidazo[1,2-a]pyridin-6-yl)-7-(1-methylpiperidin-4-yl)-4H-pyrido[1,2-a]pyrimidin-4-one | ND | 392.4 |
| 66* | 811 | 2-(8-fluoro-2-methylimidazo[1,2-a]pyridin-6-yl)-7-(4-hydroxypiperidin-4-yl)-4H-pyrido[1,2-a]pyrimidin-4-one | ND | 394.4 |
| 9 | 812 | 2-(4-ethyl-6-methylpyrazolo[1,5-a]pyrazin-2-yl)-7-[(8aS)-hexahydropyrrolo[1,2-a]pyrazin-2(1H)-yl]-4H-pyrido[1,2-a]pyrimidin-4-one | ND | 430.7 |
| 9 | 813 | 2-(4-ethyl-6-methylpyrazolo[1,5-a]pyrazin-2-yl)-7-[(8aR)-hexahydropyrrolo[1,2-a]pyrazin-2(1H)-yl]-4H-pyrido[1,2-a]pyrimidin-4-one | ND | 430.6 |
| 9 | 814 | 7-[(3R)-3-(dimethylamino)pyrrolidin-1-yl]-2-(4-ethyl-6-methylpyrazolo[1,5-a]pyrazin-2-yl)-4H-pyrido[1,2-a]pyrimidin-4-one | ND | 418.7 |
| 9 | 815 | 7-[(3S)-3-(dimethylamino)pyrrolidin-1-yl]-2-(4-ethyl-6-methylpyrazolo[1,5-a]pyrazin-2-yl)-4H-pyrido[1,2-a]pyrimidin-4-one | ND | 418.7 |
| 16 | 816 | 2-(8-fluoro-2-methylimidazo[1,2-a]pyridin-6-yl)-7-[(8aS)-8a-methylhexahydropyrrolo[1,2-a]pyrazin-2(1H)-yl]-4H-pyrido[1,2-a]pyrimidin-4-one | ND | 433.6 |
| 9 | 817 | 2-(4-ethyl-6-methylpyrazolo[1,5-a]pyrazin-2-yl)-7-(4-ethylpiperazin-1-yl)-9-methyl-4H-pyrido[1,2-a]pyrimidin-4-one | ND | 432.6 |
| 9 | 818 | 2-(4-ethyl-6-methylpyrazolo[1,5-a]pyrazin-2-yl)-7-[(8aS)-hexahydropyrrolo[1,2-a]pyrazin-2(1H)-yl]-9-methyl-4H-pyrido[1,2-a]pyrimidin-4-one | ND | 444.6 |
| 16 | 819 | 2-(2,8-dimethylimidazo[1,2-a]pyridin-6-yl)-7-(4-ethylpiperazin-1-yl)-4H-pyrido[1,2-a]pyrimidin-4-one | ND | 403.7 |
| 16 | 820 | 2-(2,8-dimethylimidazo[1,2-a]pyridin-6-yl)-7-[(8aS)-hexahydropyrrolo[1,2-a]pyrazin-2(1H)-yl]-4H-pyrido[1,2-a]pyrimidin-4-one | ND | 415.7 |
| 16 | 821 | 2-(2,8-dimethylimidazo[1,2-a]pyridin-6-yl)-7-(8a-methylhexahydropyrrolo[1,2-a]pyrazin-2(1H)-yl)-4H-pyrido[1,2-a]pyrimidin-4-one | ND | 429.7 |
| 9 | 822 | 7-[(3R)-3-(dimethylamino)pyrrolidin-1-yl]-2-(4-ethyl-6-methylpyrazolo[1,5-a]pyrazin-2-yl)-9-methyl-4H-pyrido[1,2-a]pyrimidin-4-one | ND | 432.6 |
| 9 | 823 | 2-(4-ethyl-6-methylpyrazolo[1,5-a]pyrazin-2-yl)-7-{[2-(morpholin-4-yl)ethyl]amino}-4H-pyrido[1,2-a]pyrimidin-4-one | ND | 434.6 |
| 9 | 824 | 7-{[2-(dimethylamino)ethyl]amino}-2-(4-ethyl-6-methylpyrazolo[1,5-a]pyrazin-2-yl)-4H-pyrido[1,2-a]pyrimidin-4-one | ND | 392.6 |
| 9 | 825 | 7-{[2-(dimethylamino)ethyl](methyl)amino}-2-(4-ethyl-6-methylpyrazolo[1,5-a]pyrazin-2-yl)-4H-pyrido[1,2-a]pyrimidin-4-one | ND | 406.6 |
| 9 | 826 | 2-(4-ethyl-6-methylpyrazolo[1,5-a]pyrazin-2-yl)-7-{methyl[2-(methylamino)ethyl]amino}-4H-pyrido[1,2-a]pyrimidin-4-one | ND | 392.6 |
| 16 | 827 | 7-[(3R)-3-(dimethylamino)pyrrolidin-1-yl]-2-(2,8-dimethylimidazo[1,2-a]pyridin-6-yl)-4H-pyrido[1,2-a]pyrimidin-4-one | ND | 403.7 |
| 16 | 828 | 7-[(3S)-3-(dimethylamino)pyrrolidin-1-yl]-2-(2,8-dimethylimidazo[1,2-a]pyridin-6-yl)-4H-pyrido[1,2-a]pyrimidin-4-one | ND | 403.7 |
| 27 | 829 | 7-[2-(dimethylamino)ethoxy]-2-(4-ethyl-6-methylpyrazolo[1,5-a]pyrazin-2-yl)-9-methyl-4H-pyrido[1,2-a]pyrimidin-4-one | ND | 407.6 |
| 27 | 830 | 7-[2-(dimethylamino)ethoxy]-2-(4-ethyl-6-methylpyrazolo[1,5-a]pyrazin-2-yl)-4H-pyrido[1,2-a]pyrimidin-4-one | ND | 393.6 |
| 27 | 831 | 2-(4-ethyl-6-methylpyrazolo[1,5-a]pyrazin-2-yl)-7-(piperidin-4-ylmethoxy)-4H-pyrido[1,2-a]pyrimidin-4-one | ND | 419.5 |
| 27 | 832 | 2-(4-ethyl-6-methylpyrazolo[1,5-a]pyrazin-2-yl)-7-[2-(piperidin-1-yl)ethoxy]-4H-pyrido[1,2-a]pyrimidin-4-one | ND | 433.6 |
| 27 | 833 | 2-(4-ethyl-6-methylpyrazolo[1,5-a]pyrazin-2-yl)-7-[3-(morpholin-4-yl)propoxy]-4H-pyrido[1,2-a]pyrimidin-4-one | ND | 449.6 |

TABLE 1-continued

| Ex | Cpd | Name | M.P. | MS |
|---|---|---|---|---|
| 27 | 834 | 7-[3-(dimethylamino)propoxy]-2-(4-ethyl-6-methylpyrazolo[1,5-a]pyrazin-2-yl)-4H-pyrido[1,2-a]pyrimidin-4-one | ND | 407.6 |
| 9 | 835 | 2-(4,6-dimethylpyrazolo[1,5-a]pyrazin-2-yl)-7-[(3aR,6aS)-5-methylhexahydropyrrolo[3,4-c]pyrrol-2(1H)-yl]-4H-pyrido[1,2-a]pyrimidin-4-one | ND | 416.5 | or a salt, isotopologue, stereoisomer, racemate, enantiomer, diastereomer or tautomer thereof.

Table 2 further provides certain isolated compounds of a salt form of a compound of Formula (I) that may be prepared according to the procedures of the indicated Example by using the appropriate reactants, reagents and reaction conditions. The preparation of any free base, isotopologue, stereoisomer, racemate, enantiomer, diastereomer or tautomer from a salt form of a compound of Formula (I) is also contemplated and further included within the scope of the description herein. Where a free base form of the compound was not isolated from the salt form, a person of ordinary skill in the art could be expected to perform the required reactions to prepare and isolate the free base form of the compound.

The term "Cpd" represents Compound number, the term "Ex" represents "Example Number" (wherein * indicates that the corresponding Example for the Compound is provided above), the term "M.P." represents "Melting Point (° C.)," the term "MS" represents "Mass Spectroscopy Peak(s) m/z $[M+H]^+$, $[M+2+H]^+$, $[M-H]^-$ or $[M+2-H]^-$," the term "D" represents "Decomposition/Decomposed," the term "DR" represents "Decomposition Range," the term "S" represents "Softens" and the term "ND" indicates that the value was "Not Determined."

TABLE 2

| Ex | Cpd | Name | M.P. | MS |
|---|---|---|---|---|
| 1 | 71 | 2-(3,5-difluoro-4-hydroxyphenyl)-7-(piperazin-1-yl)-4H-pyrido[1,2-a]pyrimidin-4-one hydrochloride | 290 (D) | 359.2 |
| 33 | 203 | 7-[4-(dimethylamino)piperidin-1-yl]-2-(3-fluoro-4-methoxyphenyl)-4H-quinolizin-4-one acetate | 188-192 | 396.2 |
| 55* | 380 | 2-(2-methyl-1,3-benzothiazol-6-yl)-7-(piperidin-4-yl)-4H-pyrimido[1,2-b]pyridazin-4-one trifluoroacetate (1:1) | 230-235 | 378.2 |
| 57 | 413 | 2-(1,3-dimethylpyrrolo[1,2-a]pyrazin-7-yl)-7-(1,2,3,6-tetrahydropyridin-4-yl)-4H-pyrazino[1,2-a]pyrimidin-4-one hydrochloride (1:2) | >300 | 373.3 | or a free base, isotopologue, stereoisomer, racemate, enantiomer, diastereomer or tautomer thereof.

BIOLOGICAL EXAMPLES

To describe in more detail and assist in understanding the present description, the following non-limiting biological examples are offered to more fully illustrate the scope of the description and are not to be construed as specifically limiting the scope thereof. Such variations of the present description that may be now known or later developed, which would be within the purview of one skilled in the art to ascertain, are considered to fall within the scope of the present description and as hereinafter claimed. These examples illustrate the testing of certain compounds described herein in vitro and/or in vivo and demonstrate the usefulness of the compounds for treating of SMA by enhancing the inclusion of exon 7 of SMN2 into mRNA transcribed from the SMN2 gene. Compounds of Formula (I) enhance inclusion of exon 7 of SMN2 into mRNA transcribed from the SMN2 gene and increase levels of Smn protein produced from the SMN2 gene, and thus can be used to treat SMA in a human subject in need thereof.

Example 1

SMN2 Minigene Construct
Preparation of the Minigene Constructs
DNA corresponding to a region of the SMN2 gene starting from the 5' end of exon 6 (ATAATTCCCCC) (SEQ ID NO. 14) and ending at nucleic acid residue 23 of exon 8 (CAGCAC) (SEQ ID NO. 15) was amplified by PCR using the following primers:

```
Forward primer:
                                     (SEQ ID NO. 16)
5'-CGCGGATCCATAATTCCCCCACCACCTC-3'

Reverse primer:
                                     (SEQ ID NO. 17)
5'-CGCGGATCCGTGCTGCTCTATGCCAGCA-3'
```

The 5' end of each primer was designed to add a BamHI restriction endonuclease recognition site at both the 5' end of exon 6 (GGATCC) (SEQ ID NO. 18) and the 3' end after the $23^{rd}$ nucleotide of exon 8. Using the BamHI restriction endonuclease recognition sites, the PCR fragment was cloned into a derivative of the original pcDNA 3.1/Hygro vector which was modified as disclosed in United States Patent Publication US2005/0048549.

New UTRs were added to the modified vector using the HindIII site and the BamHI restriction sites comprising a 5'DEG UTR: 5'-TAGCTTCTTACCCGTACTC-CACCGTTGGCAGCACGATCGCACGTCCCACGT-GAAC CATTGGTAAACCCTG-3' (SEQ ID NO. 19) cloned into the modified pcDNA3.1/Hygro vector together with a start codon upstream of the BamHI restriction site, and; a 3'DEG UTR: 5'-ATCGAAAGTA-CAGGACTAGCCTTCCTAGCAACCGCGGGCTGG-GAGTCTGAGACAT CACTCAAGATATATGC-TCGGTAACGTATGCTCTAGCCATCTAACTATTCCC-TATGTCT TATAGGG-3' (SEQ ID NO. 20) cloned into the modified pcDNA3.1/Hygro vector using the NotI restriction endonuclease recognition site and the XhoI restriction endonuclease recognition site with a stop codon immediately downstream of the NotI restriction site. In addition, a firefly luciferase gene lacking the start codon was cloned into the vector using the BamHI and NotI restriction sites.

The resulting minigene comprises, in 5' to 3' order: the 5'-DEG UTR, the start codon, six additional nucleotides forming a BamHI restriction site, the nucleic acid residues of exon 6, the nucleic acid residues of intron 6 of SMN2, the nucleic acid residues of exon 7 of SMN2, the nucleic acid residues of intron 7 of SMN2, and the first 23 nucleic acid residues of exon 8 of SMN2, an additional six nucleotides forming a BamHI restriction site and the firefly luciferase gene lacking the start codon.

A single adenine residue was inserted after nucleotide 48 of exon 7 of SMN2 by site-directed mutagenesis. This minigene construct is referred to as SMN2-A.

SMN2 transcripts derived from minigenes containing exon 6 through 8 and the intervening introns recapitulate the splicing of their endogenous pre-mRNA (Lorson et al, Proc. Natl. Acad. Sci. U.S.A., 1999, 96 (11), 6307). An SMN2-alternative splicing reporter construct which contains exons 6 through 8 and the intervening introns followed by a luciferase reporter gene was generated. Salient features of this construct are the lack of the start codon in the luciferase gene, inactivation of the termination codon (in the open reading frame that encodes the SMN protein) of exon 7 by insertion of a nucleotide after nucleic acid 48 of exon 7 and addition of a start codon (ATG) immediately upstream of exon 6. A single adenine (SMN2-A) was inserted after nucleic residue 48 of exon 7.

Figure 1:
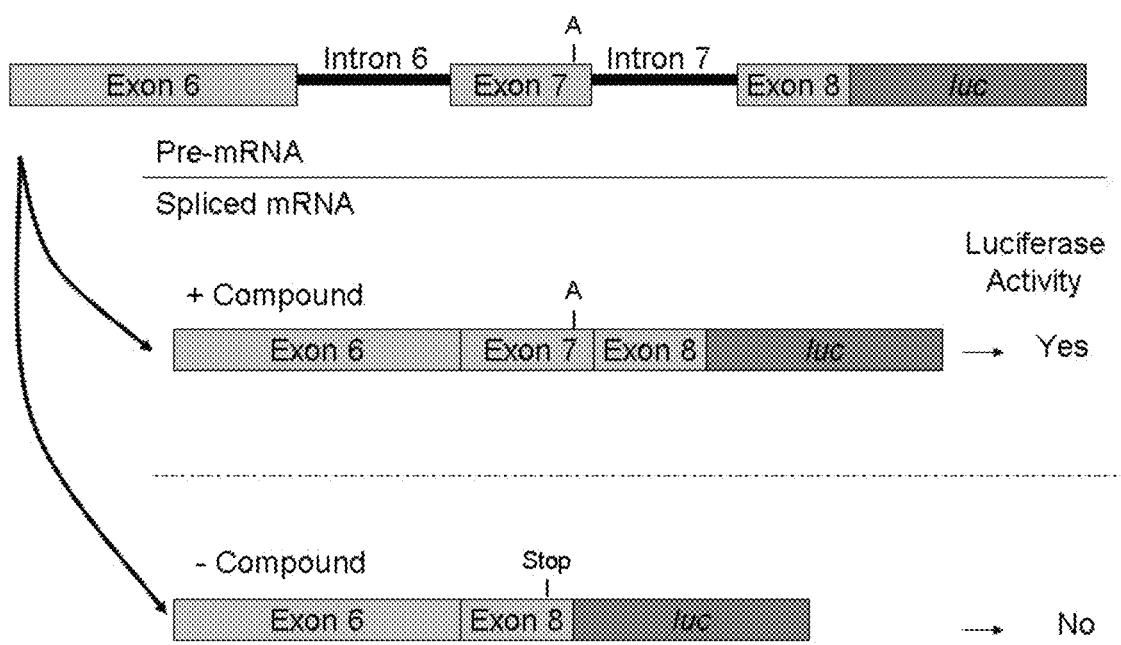
FIG. 1, referenced in Biological Example 1, is a schematic drawing of the SMN2-A minigene construct, which produces two alternatively spliced mRNA transcripts: a full length mRNA that contains exon 7 and a Δ7 mRNA that lacks exon 7. The adenine nucleotide inserted in exon 7 of SMN2-A after nucleic residue 48 is represented by the letter "A." Alternatively, the nucleotide may also be selected from cytosine or thymine. Due to the insertion of one nucleotide (A, C, or T) after nucleic residue 48, the full length mRNA does not contain a stop codon in the SMN open reading frame, whereas the Δ7 mRNA has a stop codon in Exon 8 that is indicated by the word "Stop."

The SMN2 minigene was designed such that the luciferase reporter is in frame with the ATG start codon immediately upstream of exon 6 when exon 7 is present in the mRNA and the luciferase reporter is out of frame with the ATG start codon immediately upstream of exon 6 if exon 7 of SMN2 is removed during splicing of the pre-mRNA. In addition, in the absence of exon 7, the open reading frame that starts from the ATG start codon immediately upstream of exon 6 contains a stop codon in the fragment of exon 8 of SMN. Thus, in the presence of compounds that increase the inclusion of exon 7 of SMN2 into mRNA transcribed from the SMN2 gene, more transcripts containing exon 7 and more functional reporter are produced. A schematic illustration of this description can be found in FIG. 1.

Figure 2B:
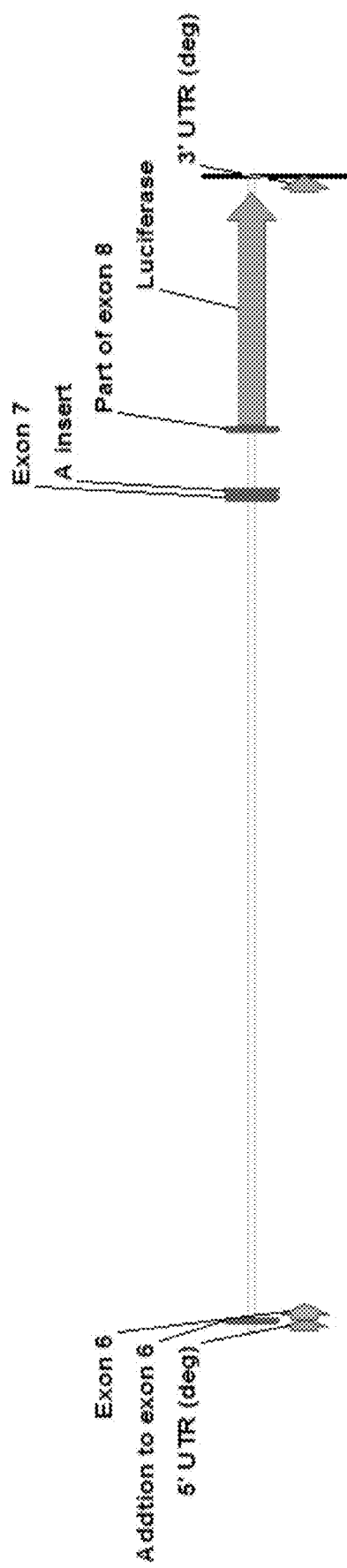

The DNA sequence of the minigene from the SMN2-A construct SEQ ID NO. 21 is provided in FIG. 2a. A picture of the minigene SMN2-A subsequences is shown in FIG. 2b.

Example 2

SMN2 Minigene mRNA Splicing RT-qPCR Assay in Cultured Cells

The reverse transcription-quantitative PCR-based (RT-qPCR) assay is used to quantify the level of the full length SMN2 minigene mRNA containing SMN2 exon 7 in a HEK293H cell line stably transfected with said minigene and treated with a test compound.

Materials

| Material | Source |
| --- | --- |
| HEK293H cells | ATCC Catalog No. CRL-1573 |
| Cells-To-Ct lysis buffer | Life Technologies, Inc. (formerly Applied Biosystems) Catalog No.: 4399002 |
| DMEM | Life Technologies, Inc. (formerly Invitrogen) Catalog No.: 11960-044 |
| 96-well flat-bottom plates | Becton Dickinson Catalog No.: 353072 |
| RT-PCR Enzyme Mix | Life Technologies, Inc. (formerly Applied Biosystems) Part No.: 4388520 (also included in AgPath-ID Kit Catalog No.: 4387391) |
| RT-PCR buffer | Life Technologies, Inc. (formerly Applied Biosystems) Part No.: 4388519 (also included in AgPath-ID Kit Catalog No.: 4387391) |
| AgPath-ID One-Step RT-PCR Kit | Life Technologies, Inc. (formerly Applied Biosystems) Catalog No.: 4387391 |
| Thermocycler | Life Technologies, Inc. (formerly Applied Biosystems) 7900HT |

Protocol. HEK293H cells stably transfected with the SMN2-A minigene construct described above (10,000 cells/well) are seeded in 200 µL of cell culture medium (DMEM plus 10% FBS, with 200 µg/mL hygromycin) in 96-well flat-bottom plates and the plate is immediately swirled to ensure proper dispersal of cells, forming an even monolayer of cells. Cells are allowed to attach for at least 4-6 hours. Test compounds are serially diluted 3.16-fold in 100% DMSO to generate a 7-point concentration curve. A solution of test compound (1 µL, 200× in DMSO) is added to each cell-containing well and the plate is incubated for 24 hours in a cell culture incubator (37° C., 5% $CO_2$, 100% relative humidity). 2 replicates are prepared for each test compound concentration. The cells are then lysed in Cells-To-Ct lysis buffer and the lysate is stored at −80° C.

Full length SMN2-A minigene and GAPDH mRNA are quantified using the following primers and probes provided in Table 3. Primer SMN Forward A (SEQ ID NO. 1) hybridizes to a nucleotide sequence in exon 7 (nucleotide 22 to nucleotide 40), primer SMN Reverse A (SEQ ID NO. 2) hybridizes to a nucleotide sequence in the coding sequence of Firefly luciferase, SMN Probe A (SEQ ID NO. 3) hybridizes to a nucleotide sequence in exon 7 (nucleotide 50 to nucleotide 54) and exon 8 (nucleotide 1 to nucleotide 21). The combination of these three oligonucleotides detects only SMN1 or SMN2 minigenes (RT-qPCR) and will not detect endogenous SMN1 or SMN2 genes.

TABLE 3

| Primers/Probes | Sequence | Source |
| --- | --- | --- |
| SMN Forward Primer A | SEQ ID NO. 1: GAAGGAAGGTGCTCACATT | PTC[1] |
| SMN Reverse Primer A | SEQ ID NO. 2: TCTTTATGTTTTTGGCGTCTTC | PTC[1] |

TABLE 3-continued

| Primers/Probes | Sequence | Source |
|---|---|---|
| SMN Forward Probe A | SEQ ID NO. 3: 6FAM-AAGGAGAAATGCTGGCATAGAGCAGC-TAMRA | PTC[1] |
| hGAPDH Forward Probe | SEQ ID NO. 4: VIC-CGCCTGGTCACCAGGGCTGCT-TAMRA | LTI[2] |
| hGAPDH Forward Primer | SEQ ID NO. 5: CAACGGATTTGGTCGTATTGG | LTI[2] |
| hGAPDH Reverse Primer | SEQ ID NO. 6: TGATGGCAACAATATCCACTTTACC | LTI[2] |

[1]Primers and probe designed by PTC Therapeutics, Inc.;
[2]Commercially available from Life Technologies, Inc. (formerly Invitrogen).

The SMN forward and reverse primers are used at final concentrations of 0.4 µM. The SMN probe is used at a final concentration of 0.15 µM. The GAPDH primers are used at final concentrations of 0.2 µM and the probe at 0.15 µM.

The SMN2-minigene GAPDH mix (15 µL total volume) is prepared by combining 7.5 µL of 2× RT-PCR buffer, 0.4 µL of 25× RT-PCR enzyme mix, 0.75 µL of 20× GAPDH primer-probe mix, 4.0075 µL of water, 2 µL of 10-fold diluted cell lysate, 0.06 µL of 100 µM SMN forward primer, 0.06 µL of 100 µM SMN reverse primer, and 0.225 µL of 100 µM SMN probe.

PCR is carried out at the following temperatures for the indicated time: Step 1: 48° C. (15 min); Step 2: 95° C. (10 min); Step 3: 95° C. (15 sec); Step 4: 60° C. (1 min); then repeat Steps 3 and 4 for a total of 40 cycles.

Each reaction mixture contains both SMN2-A minigene and GAPDH primers/probe sets (multiplex design), allowing simultaneous measurement of the levels of two transcripts.

Two SMN spliced products are generated from the SMN2 minigene. The first spliced product containing exon 7, corresponding to full length SMN2 mRNA, is referred to herein using the term "SMN2 minigene FL." The second spliced product lacking exon 7 is referred to herein using the term "SMN2 minigene Δ7."

The increase of SMN2 minigene FL mRNA relative to that in cells treated with vehicle control is determined from real-time PCR data using a modified ΔΔCt method (as described in Livak and Schmittgen, Methods, 2001, 25:402-8). The amplification efficiency (E) is calculated from the slope of the amplification curve for SMN2 minigene FL and GAPDH individually. The abundances of SMN2 minigene FL and GAPDH are then calculated as $(1+E)^{-Ct}$, where Ct is the threshold value for each amplicon. The abundance of SMN2 minigene FL is normalized to GAPDH abundance. The normalized SMN2 minigene FL abundance from test compound-treated samples is then divided by normalized SMN2 minigene FL abundance from vehicle-treated cells to determine the level of SMN2 FL mRNA relative to vehicle control.

Results. As seen in FIG. 3, cells treated with Compound 6 (FIG. 3a) and Compound 170 (FIG. 3b) increased SMN2 minigene FL mRNA at low concentrations. The two test compounds fully restored exon 7 inclusion relative to untreated cells.

For compounds of Formula (I) or a form thereof disclosed herein, Table 4 provides the $IC_{1.5x}$ for production of full length SMN2 mRNA that was obtained from the 7-point concentration data generated for each test compound according to the procedure of Biological Example 2. The term "$EC_{1.5x}$ for production of full length SMN2 mRNA" is defined as that concentration of test compound that is effective in increasing the amount of full length SMN2 mRNA to a level 1.5-fold greater relative to that in vehicle-treated cells. An $EC_{1.5x}$ for production of full length SMN2 mRNA between >3 µM and <30 µM is indicated by one star (*), an $EC_{1.5x}$ between >1 µM and <3 µM is indicated by two stars (), an $EC_{1.5x}$ between >0.3 µM and ≤1 µM is indicated by three stars (*), an $EC_{1.5x}$ between >0.1 µM and ≤0.3 µM is indicated by four stars (**) and an $EC_{1.5x}$<0.1 µM is indicated by five stars (***).

TABLE 4

| Cpd | $EC_{1.5x}$ |
|---|---|
| 1 | *** |
| 2 | ** |
| 3 | *** |
| 4 | ** |
| 5 | * |
| 6 | ***** |
| 7 | *** |
| 8 | **** |
| 9 | ** |
| 10 | ** |
| 11 | *** |
| 12 | *** |
| 13 | ** |
| 14 | ** |
| 15 | ** |
| 16 | ** |
| 17 | ** |
| 18 | *** |
| 19 | ** |
| 20 | ** |
| 21 | * |
| 22 | *** |
| 23 | * |
| 24 | ** |
| 25 | ** |
| 26 | * |
| 27 | * |
| 28 | * |
| 29 | * |
| 30 | ***** |
| 31 | ** |
| 32 | ** |
| 33 | ** |
| 34 | ** |
| 35 | * |
| 36 | * |
| 37 | ** |
| 38 | * |
| 39 | * |
| 40 | * |
| 41 | *** |
| 42 | ** |
| 43 | **** |
| 44 | ** |
| 45 | * |
| 46 | ** |
| 47 | ** |
| 48 | * |
| 49 | * |
| 50 | * |
| 51 | * |
| 52 | * |
| 53 | ** |
| 54 | ** |
| 55 | ** |
| 56 | ** |
| 57 | * |
| 58 | * |
| 59 | ** |

TABLE 4-continued

| Cpd | EC$_{1.5x}$ |
|---|---|
| 60 | ** |
| 61 | *** |
| 62 | **** |
| 63 | ** |
| 64 | * |
| 65 | * |
| 66 | *** |
| 67 | **** |
| 68 | **** |
| 69 | *** |
| 70 | ** |
| 71 | ** |
| 72 | ***** |
| 73 | * |
| 74 | ***** |
| 75 | ***** |
| 76 | *** |
| 77 | *** |
| 78 | ** |
| 79 | **** |
| 80 | ** |
| 81 | *** |
| 82 | ** |
| 83 | *** |
| 84 | ** |
| 85 | ** |
| 86 | **** |
| 87 | **** |
| 88 | ** |
| 89 | ** |
| 90 | ** |
| 91 | ** |
| 92 | ** |
| 93 | ** |
| 94 | ** |
| 95 | ** |
| 96 | *** |
| 97 | ** |
| 98 | ** |
| 99 | *** |
| 100 | *** |
| 101 | *** |
| 102 | *** |
| 103 | *** |
| 104 | *** |
| 105 | **** |
| 106 | *** |
| 107 | *** |
| 108 | **** |
| 109 | ***** |
| 110 | **** |
| 111 | **** |
| 112 | *** |
| 113 | ** |
| 114 | ** |
| 115 | ***** |
| 116 | **** |
| 117 | ***** |
| 118 | **** |
| 119 | **** |
| 120 | ***** |
| 121 | ***** |
| 122 | ** |
| 123 | ** |
| 124 | *** |
| 125 | *** |
| 126 | **** |
| 127 | *** |
| 128 | *** |
| 129 | *** |
| 130 | ** |
| 131 | ***** |
| 132 | ***** |
| 133 | ***** |
| 134 | ***** |
| 135 | ***** |
| 136 | ***** |
| 137 | **** |
| 138 | **** |
| 139 | ** |
| 140 | ** |
| 141 | ***** |
| 142 | *** |
| 143 | ***** |
| 144 | ***** |
| 145 | ** |
| 146 | ** |
| 147 | ** |
| 148 | **** |
| 149 | *** |
| 150 | *** |
| 151 | **** |
| 152 | **** |
| 153 | *** |
| 154 | ** |
| 155 | **** |
| 156 | *** |
| 157 | ** |
| 158 | ** |
| 159 | ** |
| 160 | ***** |
| 161 | *** |
| 162 | *** |
| 163 | ** |
| 164 | *** |
| 165 | ** |
| 166 | *** |
| 167 | ***** |
| 168 | *** |
| 169 | ***** |
| 170 | ***** |
| 171 | ***** |
| 172 | *** |
| 173 | *** |
| 174 | ** |
| 175 | ***** |
| 176 | *** |
| 177 | **** |
| 178 | *** |
| 179 | *** |
| 180 | ** |
| 181 | ** |
| 182 | *** |
| 183 | ** |
| 184 | ** |
| 185 | ***** |
| 186 | ***** |
| 187 | ** |
| 188 | **** |
| 189 | *** |
| 190 | *** |
| 191 | ** |
| 192 | ** |
| 193 | ***** |
| 194 | ***** |
| 195 | ***** |
| 196 | ***** |
| 197 | **** |
| 198 | ***** |
| 199 | *** |
| 200 | ** |
| 201 | ***** |
| 202 | *** |
| 203 | ** |
| 204 | ***** |
| 205 | *** |
| 206 | ** |
| 207 | ***** |
| 208 | ***** |
| 209 | ***** |
| 210 | ***** |
| 211 | ***** |
| 212 | **** |
| 213 | **** |
| 214 | *** |
| 215 | *** |

TABLE 4-continued

| Cpd | EC$_{1.5x}$ |
|---|---|
| 216 | *** |
| 217 | *** |
| 218 | **** |
| 219 | ***** |
| 220 | *** |
| 221 | ***** |
| 222 | *** |
| 223 | *** |
| 224 | *** |
| 225 | ** |
| 226 | *** |
| 227 | ** |
| 228 | ** |
| 229 | *** |
| 230 | *** |
| 231 | *** |
| 232 | ** |
| 233 | *** |
| 234 | ***** |
| 235 | *** |
| 236 | ** |
| 237 | ** |
| 238 | *** |
| 239 | ** |
| 240 | ***** |
| 241 | **** |
| 242 | ***** |
| 243 | ***** |
| 244 | ***** |
| 245 | *** |
| 246 | ** |
| 247 | ***** |
| 248 | *** |
| 249 | *** |
| 250 | ***** |
| 251 | ***** |
| 252 | **** |
| 253 | ** |
| 254 | **** |
| 255 | *** |
| 256 | *** |
| 257 | ***** |
| 258 | ***** |
| 259 | ***** |
| 260 | **** |
| 261 | ***** |
| 262 | **** |
| 263 | *** |
| 264 | ***** |
| 265 | ** |
| 266 | ** |
| 267 | ***** |
| 268 | ***** |
| 269 | ***** |
| 270 | ***** |
| 271 | ***** |
| 272 | ***** |
| 273 | ***** |
| 274 | ***** |
| 275 | ***** |
| 276 | *** |
| 277 | ** |
| 278 | ** |
| 279 | **** |
| 280 | ** |
| 281 | **** |
| 282 | *** |
| 283 | ***** |
| 284 | *** |
| 285 | ***** |
| 286 | *** |
| 287 | ***** |
| 288 | ***** |
| 289 | ***** |
| 290 | ***** |
| 291 | ***** |
| 292 | ***** |
| 293 | ***** |

TABLE 4-continued

| Cpd | EC$_{1.5x}$ |
|---|---|
| 294 | ***** |
| 295 | ***** |
| 296 | ***** |
| 297 | ***** |
| 298 | *** |
| 299 | ***** |
| 300 | ***** |
| 301 | ** |
| 302 | ***** |
| 303 | ***** |
| 304 | ***** |
| 305 | ***** |
| 306 | ***** |
| 307 | ***** |
| 308 | ***** |
| 309 | ***** |
| 310 | ***** |
| 311 | **** |
| 312 | ***** |
| 313 | ** |
| 314 | ***** |
| 315 | ***** |
| 316 | **** |
| 317 | *** |
| 318 | ***** |
| 319 | ***** |
| 320 | *** |
| 321 | ** |
| 322 | ***** |
| 323 | **** |
| 324 | *** |
| 325 | *** |
| 326 | ** |
| 327 | ***** |
| 328 | ***** |
| 329 | ***** |
| 330 | **** |
| 331 | ***** |
| 332 | *** |
| 333 | **** |
| 334 | ***** |
| 335 | ***** |
| 336 | **** |
| 337 | ***** |
| 338 | ***** |
| 339 | ***** |
| 340 | ***** |
| 341 | *** |
| 342 | ***** |
| 343 | ***** |
| 344 | **** |
| 345 | ***** |
| 346 | ***** |
| 347 | ***** |
| 348 | **** |
| 349 | ***** |
| 350 | ***** |
| 351 | ***** |
| 352 | ***** |
| 353 | **** |
| 354 | ***** |
| 355 | ***** |
| 356 | ***** |
| 357 | **** |
| 358 | ***** |
| 359 | ***** |
| 360 | ** |
| 361 | **** |
| 362 | *** |
| 363 | *** |
| 364 | ** |
| 365 | **** |
| 366 | ***** |
| 367 | ***** |
| 368 | ***** |
| 369 | ***** |
| 370 | **** |
| 371 | **** |

TABLE 4-continued

| Cpd | EC$_{1.5x}$ |
|---|---|
| 372 | ***** |
| 373 | ***** |
| 374 | ***** |
| 375 | ***** |
| 376 | ***** |
| 377 | *** |
| 378 | ***** |
| 379 | **** |
| 380 | **** |
| 381 | **** |
| 382 | ***** |
| 383 | *** |
| 384 | ***** |
| 385 | ***** |
| 386 | *** |
| 387 | *** |
| 388 | ***** |
| 389 | ** |
| 390 | *** |
| 391 | ** |
| 392 | **** |
| 393 | ***** |
| 394 | **** |
| 395 | *** |
| 396 | **** |
| 397 | ***** |
| 398 | *** |
| 399 | *** |
| 400 | **** |
| 401 | **** |
| 402 | ***** |
| 403 | ***** |
| 404 | *** |
| 405 | **** |
| 406 | *** |
| 407 | ***** |
| 408 | ***** |
| 409 | ***** |
| 410 | ***** |
| 411 | ***** |
| 412 | ***** |
| 413 | ***** |
| 414 | ***** |
| 415 | ***** |
| 416 | ***** |
| 417 | **** |
| 418 | ***** |
| 419 | **** |
| 420 | ***** |
| 421 | ***** |
| 422 | ***** |
| 423 | ***** |
| 424 | ***** |
| 425 | ***** |
| 426 | *** |
| 427 | ** |
| 428 | *** |
| 429 | ***** |
| 430 | ***** |
| 431 | ***** |
| 432 | ***** |
| 433 | ***** |
| 434 | *** |
| 435 | **** |
| 436 | *** |
| 437 | **** |
| 438 | ***** |
| 439 | **** |
| 440 | ***** |
| 441 | ***** |
| 442 | ***** |
| 443 | ***** |
| 444 | *** |
| 445 | ***** |
| 446 | ***** |
| 447 | **** |
| 448 | ***** |
| 449 | ***** |

TABLE 4-continued

| Cpd | EC$_{1.5x}$ |
|---|---|
| 450 | *** |
| 451 | ***** |
| 452 | ***** |
| 453 | ***** |
| 454 | ***** |
| 455 | **** |
| 456 | **** |
| 457 | ***** |
| 458 | ***** |
| 459 | ***** |
| 460 | **** |
| 461 | *** |
| 462 | ***** |
| 463 | ***** |
| 464 | **** |
| 465 | *** |
| 466 | ***** |
| 467 | ***** |
| 468 | ***** |
| 469 | **** |
| 470 | ***** |
| 471 | ***** |
| 472 | ***** |
| 473 | ***** |
| 474 | ***** |
| 475 | *** |
| 476 | ***** |
| 477 | ***** |
| 478 | ***** |
| 479 | ***** |
| 480 | ***** |
| 481 | ***** |
| 482 | ***** |
| 483 | ***** |
| 484 | ***** |
| 485 | ***** |
| 486 | ***** |
| 487 | **** |
| 488 | ***** |
| 489 | **** |
| 490 | ***** |
| 491 | *** |
| 492 | *** |
| 493 | ***** |
| 494 | ***** |
| 495 | ***** |
| 496 | ***** |
| 497 | ***** |
| 498 | ***** |
| 499 | ***** |
| 500 | **** |
| 501 | **** |
| 502 | ***** |
| 503 | ***** |
| 504 | ***** |
| 505 | ***** |
| 506 | ***** |
| 507 | **** |
| 508 | ***** |
| 509 | ***** |
| 510 | ***** |
| 511 | ***** |
| 512 | ***** |
| 513 | **** |
| 514 | **** |
| 515 | ***** |
| 516 | ***** |
| 517 | ***** |
| 518 | ***** |
| 519 | ***** |
| 520 | **** |
| 521 | **** |
| 522 | ***** |
| 523 | ***** |
| 524 | **** |
| 525 | **** |
| 526 | *** |
| 527 | ***** |

TABLE 4-continued

| Cpd | EC$_{1.5x}$ |
|---|---|
| 528 | ***** |
| 529 | ***** |
| 530 | ***** |
| 531 | **** |
| 532 | ***** |
| 533 | ***** |
| 534 | ***** |
| 535 | ***** |
| 536 | ***** |
| 537 | ***** |
| 538 | ***** |
| 539 | ***** |
| 540 | ***** |
| 541 | **** |
| 542 | ***** |
| 543 | ***** |
| 544 | ***** |
| 545 | **** |
| 546 | ***** |
| 547 | ***** |
| 548 | ***** |
| 549 | ***** |
| 550 | ***** |
| 551 | **** |
| 552 | *** |
| 553 | **** |
| 554 | **** |
| 555 | ** |
| 556 | *** |
| 557 | ** |
| 558 | ** |
| 559 | ** |
| 560 | ** |
| 561 | ***** |
| 562 | *** |
| 563 | **** |
| 564 | ** |
| 565 | ***** |
| 566 | ***** |
| 567 | **** |
| 568 | ***** |
| 569 | ***** |
| 570 | *** |
| 571 | *** |
| 572 | *** |
| 573 | *** |
| 574 | *** |
| 575 | *** |
| 576 | ***** |
| 577 | ***** |
| 578 | ***** |
| 579 | **** |
| 580 | ***** |
| 581 | **** |
| 582 | ***** |
| 583 | ***** |
| 584 | ***** |
| 585 | ***** |
| 586 | **** |
| 587 | ***** |
| 588 | ***** |
| 589 | **** |
| 590 | *** |
| 591 | *** |
| 592 | **** |
| 593 | ***** |
| 594 | **** |
| 595 | ***** |
| 596 | ***** |
| 597 | **** |
| 598 | **** |
| 599 | ***** |
| 600 | **** |
| 601 | ***** |
| 602 | ***** |
| 603 | **** |
| 604 | *** |
| 605 | *** |

TABLE 4-continued

| Cpd | EC$_{1.5x}$ |
|---|---|
| 606 | ***** |
| 607 | ***** |
| 608 | **** |
| 609 | ***** |
| 610 | ***** |
| 611 | *** |
| 612 | ***** |
| 613 | ***** |
| 614 | ***** |
| 615 | ***** |
| 616 | ***** |
| 617 | ***** |
| 618 | ***** |
| 619 | **** |
| 620 | *** |
| 621 | *** |
| 622 | ** |
| 623 | ***** |
| 624 | ***** |
| 625 | ** |
| 626 | *** |
| 627 | **** |
| 628 | *** |
| 629 | ***** |
| 630 | ***** |
| 631 | **** |
| 632 | ***** |
| 633 | ***** |
| 634 | ***** |
| 635 | ***** |
| 636 | ***** |
| 637 | ***** |
| 638 | ***** |
| 639 | ***** |
| 640 | ***** |
| 641 | ***** |
| 642 | ***** |
| 643 | **** |
| 644 | **** |
| 645 | ***** |
| 646 | *** |
| 647 | ***** |
| 648 | ***** |
| 649 | ***** |
| 650 | ***** |
| 651 | ***** |
| 652 | ***** |
| 653 | ***** |
| 654 | ***** |
| 655 | ***** |
| 656 | ***** |
| 657 | ***** |
| 658 | ***** |
| 659 | ***** |
| 660 | ***** |
| 661 | ***** |
| 662 | ***** |
| 663 | ***** |
| 664 | *** |
| 665 | **** |
| 666 | **** |
| 667 | ***** |
| 668 | ***** |
| 669 | ***** |
| 670 | ***** |
| 671 | ***** |
| 672 | ***** |
| 673 | ***** |
| 674 | ***** |
| 675 | ***** |
| 676 | ***** |
| 677 | ***** |
| 678 | ***** |
| 679 | ***** |
| 680 | ***** |
| 681 | ***** |
| 682 | *** |
| 683 | ***** |

TABLE 4-continued

| Cpd | EC$_{1.5x}$ |
|---|---|
| 684 | **** |
| 685 | **** |
| 686 | *** |
| 687 | ***** |
| 688 | ** |
| 689 | **** |
| 690 | ***** |
| 691 | ***** |
| 692 | **** |
| 693 | ** |
| 694 | ***** |
| 695 | ***** |
| 696 | ***** |
| 697 | ***** |
| 698 | ***** |
| 699 | ***** |
| 700 | ***** |
| 701 | ***** |
| 702 | ***** |
| 703 | ***** |
| 704 | **** |
| 705 | ***** |
| 706 | ***** |
| 707 | ***** |
| 708 | ***** |
| 709 | ***** |
| 710 | ***** |
| 711 | ***** |
| 712 | ***** |
| 713 | ***** |
| 714 | ***** |
| 715 | ***** |
| 716 | ***** |
| 717 | **** |
| 718 | ***** |
| 719 | ***** |
| 720 | ***** |
| 721 | ***** |
| 722 | ***** |
| 723 | ***** |
| 724 | *** |
| 725 | **** |
| 726 | *** |
| 727 | ***** |
| 728 | **** |
| 729 | **** |
| 730 | ***** |
| 731 | ***** |
| 732 | *** |
| 733 | ***** |
| 734 | ***** |
| 735 | ***** |
| 736 | ***** |
| 737 | ***** |
| 738 | ***** |
| 739 | ***** |
| 740 | *** |
| 741 | ***** |
| 742 | **** |
| 743 | ***** |
| 744 | ***** |
| 745 | ***** |
| 746 | ***** |
| 747 | ***** |
| 748 | ***** |
| 749 | ***** |
| 750 | ***** |
| 751 | ***** |
| 752 | ***** |
| 753 | ***** |
| 754 | ***** |
| 755 | ***** |
| 756 | ***** |
| 757 | *** |
| 758 | *** |
| 759 | **** |
| 760 | ***** |
| 761 | ***** |

TABLE 4-continued

| Cpd | EC$_{1.5x}$ |
|---|---|
| 762 | ***** |
| 763 | ***** |
| 764 | ** |
| 765 | ** |
| 766 | ***** |
| 767 | ***** |
| 768 | ***** |
| 769 | **** |
| 770 | ***** |
| 771 | ***** |
| 772 | ***** |
| 773 | ***** |
| 774 | ***** |
| 775 | *** |
| 776 | ** |
| 777 | ** |
| 778 | ***** |
| 779 | ***** |
| 780 | ***** |
| 781 | ***** |
| 782 | ***** |
| 783 | ***** |
| 784 | **** |
| 785 | ***** |
| 786 | **** |
| 787 | ***** |
| 788 | ***** |
| 789 | ***** |
| 790 | ***** |
| 791 | ***** |
| 792 | ***** |
| 793 | ***** |
| 794 | ***** |
| 795 | ***** |
| 796 | ***** |
| 797 | ** |
| 798 | ***** |
| 799 | ***** |
| 800 | ***** |
| 801 | **** |
| 802 | ** |
| 803 | ***** |
| 804 | ***** |
| 805 | **** |
| 806 | ***** |
| 807 | ***** |
| 808 | ***** |
| 809 | ***** |
| 810 | ***** |
| 811 | *** |
| 812 | ***** |
| 813 | ***** |
| 814 | ***** |
| 815 | ***** |
| 816 | ***** |
| 817 | ***** |
| 818 | **** |
| 819 | ***** |
| 820 | ***** |
| 821 | ***** |
| 822 | **** |
| 823 | * |
| 824 | *** |
| 825 | *** |
| 826 | **** |
| 827 | ***** |
| 828 | ***** |
| 829 | **** |
| 830 | ***** |
| 831 | **** |
| 832 | **** |
| 833 | ***** |
| 834 | ***** |
| 835 | ***** |

Example 3

Endogenous SMN2 mRNA RT-qPCR Splicing Assay in Cultured Cells

The reverse transcription-quantitative PCR-based (RT-qPCR) assay is used to quantify the levels of the full length and Δ7 SMN2 mRNA in primary cells and cell lines containing the SMN2 gene treated with a test compound.

Materials

| Material | Source |
| --- | --- |
| SMA Type 1 human cells | GM03813 (Coriell Institute) |
| Cells-To-Ct lysis buffer | Life Technologies, Inc. (formerly Applied Biosystems) Catalog No.: 4399002 |
| DMEM | Life Technologies, Inc. (formerly Invitrogen) Catalog No.: 11960-044 |
| 96-well flat-bottom plates | Becton Dickinson Catalog # 353072 |
| RT-PCR Enzyme Mix | Life Technologies, Inc. (formerly Applied Biosystems) Part No.: 4388520 (also included in AgPath-ID Kit Catalog No.: 4387391) |
| RT-PCR buffer | Life Technologies, Inc. (formerly Applied Biosystems) Part No.: 4388519 (also included in AgPath-ID Kit Catalog No.: 4387391) |
| AgPath-ID One-Step RT-PCR Kit | Life Technologies, Inc. (formerly Applied Biosystems) Catalog No.: 4387391 |
| Thermocycler | Life Technologies, Inc. (formerly Applied Biosystems) 7900HT |

Protocol. GM03813 SMA patient cells (5,000 cells/well) are seeded in 200 μL of cell culture medium (DMEM plus 10% FBS) in 96-well flat-bottom plates and the plate is immediately swirled to ensure proper dispersal of cells, forming an even monolayer of cells. Cells are allowed to attach for at least 4-6 hrs. Test compounds are serially diluted 3.16-fold in 100% DMSO to generate a 7-point concentration curve. A solution of test compound (1 μL, 200× in DMSO) is added to each test well and 1 μL DMSO is added to each control well. The plate is incubated for 24 hrs in a cell culture incubator (37° C., 5% $CO_2$, 100% relative humidity). The cells are then lysed in Cells-To-Ct lysis buffer and the lysate is stored at −80° C.

SMN2-specific spliced products and GAPDH mRNA are identified using the following primers and probes in Table 5. Primer SMN FL Forward B (SEQ ID NO. 7) hybridizes to a nucleotide sequence in exon 7 (nucleotide 32 to nucleotide 54) and exon 8 (nucleotide 1 to nucleotide 4), primer SMN Δ7 Forward B (SEQ ID NO. 8) hybridizes to a nucleotide sequence in exon 6 (nucleotide 87 to nucleotide 111) and exon 8 (nucleotide 1 to nucleotide 3), primer SMN Reverse B (SEQ ID NO. 9) hybridizes to a nucleotide sequence in exon 8 (nucleotide 39 to nucleotide 62), probe SMN Probe B (SEQ ID NO. 10) hybridizes to a nucleotide sequence in exon 8 (nucleotide 7 to nucleotide 36). These primers and probes hybridize to nucleotide sequences common to human SMN1 and SMN2 mRNA. Since the SMA patient cells used in Example 3 contain only the SMN2 gene, RT-qPCR can quantify only SMN2 full-length and Δ7 mRNA.

TABLE 5

| Primer/Probe | Sequence | Source |
| --- | --- | --- |
| SMN FL Forward Primer B | SEQ ID NO. 7: GCTCACATTCCTTAAATTAAGGAGAAA | PTC[1] |
| SMN Δ7 Forward Primer B | SEQ ID NO. 8: TGGCTATCATACTGGCTATTATATGGAA | PTC[1] |
| SMN Reverse Primer B | SEQ ID NO. 9: TCCAGATCTGTCTGATCGTTTCTT | PTC[1] |
| SMN Forward Probe B | SEQ ID NO. 10: 6FAM-CTGGCATAGAGCAGCACTAAATGACACCAC-TAMRA | PTC[1] |
| hGAPDH Forward Probe | SEQ ID NO. 4: VIC-CGCCTGGTCACCAGGGCTGCT-TAMRA | LTI[2] |
| hGAPDH Forward Primer | SEQ ID NO. 5: CAACGGATTTGGTCGTATTGG | LTI[2] |
| hGAPDH Reverse Primer | SEQ ID NO. 6: TGATGGCAACAATATCCACTTTACC | LTI[2] |

[1]Primers and probe designed by PTC Therapeutics, Inc.;
[2]Commercially available from Life Technologies, Inc. (formerly Invitrogen).

The SMN forward and reverse primers are used at final concentrations of 0.4 μM. The SMN probe is used at a final concentration of 0.15 μM. GAPDH primers are used at final concentrations of 0.1 μM and the probe at 0.075 μM.

The SMN-GAPDH mix (10 μL total volume) is prepared by combining 5 μL of 2× RT-PCR buffer, 0.4 μL of 25× RT-PCR enzyme mix, 0.25 μL of 20× GAPDH primer-probe mix, 1.755 μL water, 2.5 μL of cell lysate, 0.04 μL of 100 μM SMN FL or SMN Δ7 forward primer, 0.04 μL of 100 μM SMN reverse primer, and 0.015 μL of 100 μM probe.

PCR is carried out at the following temperatures for the indicated time: Step 1: 48° C. (15 min); Step 2: 95° C. (10 min); Step 3: 95° C. (15 sec); Step 4: 60° C. (1 min); then, repeat Steps 3 and 4 for a total of 40 cycles.

Each reaction mixture contains either SMN2 FL and GAPDH or SMN2 Δ7 and GAPDH primers/probe sets (multiplex design), allowing simultaneous measurement of the levels of two transcripts.

The endogenous SMN2 gene gives rise to two alternatively spliced mRNA. The full length SMN2 mRNA that contains exon 7 is referred to herein using the term "SMN2 FL." The truncated mRNA that lacks exon 7 is referred to herein using the term "SMN2 Δ7."

The increase of SMN2 FL and decrease in SMN2 Δ7 mRNA relative to those in cells treated with vehicle control are determined from real-time PCR data using a modified ΔΔCt method (as described in Livak and Schmittgen, Methods, 2001, 25:402-8). The amplification efficiency (E) is calculated from the slope of the amplification curve for SMN2 FL, SMN2 Δ7, and GAPDH individually. The abundances of SMN2 FL, SMN2 Δ7, and GAPDH are then calculated as $(1+E)^{-Ct}$, where Ct is the threshold value for each amplicon. The abundances of SMN2 FL and SMN2 Δ7 are normalized to GAPDH abundance. The normalized SMN2 FL and SMN2 Δ7 abundances from test compound-treated samples are then divided by normalized SMN2 FL and SMN2 Δ7 abundances, respectively, from vehicle-treated cells to determine the levels of SMN2 FL and SMN2 Δ7 mRNA relative to vehicle control.

Results. As seen in FIG. 4, cells treated with increasing concentrations of Compound 6 (FIG. 4a) and Compound 170 (FIG. 4b) contain progressively more SMN2 FL mRNA and less SMN2 Δ7 mRNA than those treated with vehicle, indicating a correction of SMN2 alternative splicing.

Example 4

Endogenous SMN2 mRNA End-Point Semi-Quantitative RT-PCR Splicing Assay in Cultured Cells The endpoint reverse transcription-PCR splicing assay is used to visualize and quantify the levels of the full length and Δ7 SMN2 mRNA in primary cells and cell lines containing the SMN2 gene treated with a test compound.

Materials

C, SEQ ID NO. 12) (nucleotide 51 to nucleotide 73) common to human SMN1 and SMN2 mRNA. Since the SMA patient cells used in Example 4 contain only the SMN2 gene, RT-PCR can visualize and quantify only SMN2 full-length and SMN2 Δ7 mRNA.

TABLE 6

| Primer | Sequence | Source |
| --- | --- | --- |
| SMN Forward C | SEQ ID NO. 11: GATGCTGATGCTTTGGGAAGT | PTC[1] |
| SMN Reverse C | SEQ ID NO. 12: CGCTTCACATTCCAGATCTGTC | PTC[1] |

[1]Primers designed by PTC Therapeutics, Inc.

To synthesize cDNA, 5 μL of lysate, 4 μL of 5× iScript reaction mix, 1 μL of reverse transcriptase, and 10 μL of water are combined and incubated 5 min at 25° C. followed by 30 min at 42° C., followed by 5 min at 85° C. The cDNA solution is stored at −20° C.

To perform endpoint PCR, 5 μL of cDNA, 0.2 μL of 100 μM forward primer, 0.2 μL of 100 μM reverse primer, and 22.5 μL of polymerase super mix are combined in a 96 well semiskirted PCR plate. PCR is carried out at the following temperatures for the indicated time: Step 1: 94° C. (2 min), Step 2: 94° C. (30 sec), Step 3: 55° C. (30 sec), Step 4: 68° C. (1 min), then repeat Steps 2 to 4 for a total of 33 cycles, then hold at 4° C.

10 μL of each PCR sample is electrophoretically separated on a 2% agarose E-gel for 14 minutes stained with double-

| Material | Source |
| --- | --- |
| SMA Type 1 human cells | GM03813 (Coriell Institute) |
| Cells-To-Ct lysis buffer | Life Technologies, Inc. (formerly Applied Biosystems) Catalog No.: 4399002 |
| DMEM | Life Technologies, Inc. (formerly Invitrogen) Catalog No.: 11960-044 |
| 96-well flat-bottom plates | Becton Dickinson Catalog No.: 353072 |
| Platinum Taq HiFi DNA Polymerase Super Mix | Life Technologies, Inc. (formerly Invitrogen) Catalog No.: 11304-016 |
| iScript RT enzyme Kit | BioRad: Catalog No.: 170-8890 |
| Ethidium bromide 2% agarose E gels 48-Well Double Comb | Life Technologies, Inc. (formerly Invitrogen) Catalog No.: G8008-02 |
| Gel Documentation System | UVP Gel Doc It 310 Imaging system |

Protocol. GM03813 SMA patient cells (5,000 cells/well) are seeded in 200 μL of cell culture medium (DMEM plus 10% FBS) in 96-well flat-bottom plates and the plate is immediately swirled to ensure proper dispersal of cells, forming an even monolayer of cells. Cells are allowed to attach for at least 4-6 hrs. Test compounds are serially diluted 3.16-fold in 100% DMSO to generate a 7-point concentration curve. A solution of test compound (1 μL, 200× in DMSO) is added to each test well and 1 μL DMSO is added to each control well. The plate is incubated for 24 hrs in a cell culture incubator (37° C., 5% $CO_2$, 100% relative humidity). The cells are then lysed in Cells-To-Ct lysis buffer and the lysate is stored at −80° C.

SMN FL and Δ7 mRNA are identified using the following primers in Table 6. These primers hybridize to a nucleotide sequence in exon 6 (SMN Forward C, SEQ ID NO. 11) (nucleotide 43 to nucleotide 63) and exon 8 (SMN Reverse stranded DNA (dsDNA) staining reagents (e.g., ethidium bromide) and visualized using a gel imager.

Results. As seen in FIG. 5, cells treated with increasing concentrations of Compound 6 (FIG. 5a) or Compound 170 (FIG. 5b) contain progressively more SMN2 FL mRNA and less SMN2 Δ7 mRNA, indicating a correction of SMN2 alternative splicing.

Example 5

SMN2 mRNA RT-qPCR Splicing Assay in Animal Tissues

The reverse transcription-quantitative PCR-based (RT-qPCR) assay is used to quantify the levels of the full length and Δ7 SMN2 mRNA in tissues from mice treated with test compound.

Materials

| Material | Source |
| --- | --- |
| Tissues from C/C-allele SMA mice | The Jackson Laboratory, strain No.: 008714 (B6.129-Smn1$^{tm5(Smn1/SMN2)Mrph}$/J) |
| Tissues from Δ7 SMA mice | The Jackson Laboratory, strain No.: 005025 (FVB.Cg-Tg(SMN2*delta7)4299Ahmb Tg(SMN2)89Ahmb Smn1$^{tm1Msd}$/J) |
| RT-PCR Enzyme Mix | Life Technologies, Inc. (formerly Applied Biosystems) Part No.: 4388520 (also included in AgPath-ID Kit Catalog No.: 4387391) |
| RT-PCR buffer | Life Technologies, Inc. (formerly Applied Biosystems) Part No.: 4388519 (also included in AgPath-ID Kit Catalog No.: 4387391) |
| AgPath-ID One-Step RT-PCR Kit | Life Technologies, Inc. (formerly Applied Biosystems) Catalog No.: 4387391 |
| Mouse GAPDH primers and probes | Life Technologies, Inc. (formerly Applied Biosystems) Catalog No.: 4352339E |
| QIAzol Lysis Reagent | Qiagen Catalog No.: 79306 |
| RNeasy Lipid Tissue Mini Kit | Qiagen Catalog No.: 74804 |
| 5 mm Stainless Steel Bead | Qiagen Catalog No.: 69989 |
| TissueLyzer II | Qiagen Catalog No.: 85300 |
| Thermocycler | Life Technologies, Inc. (formerly Applied Biosystems) 7900HT |

Protocol. C/C-allele SMA mice are treated by oral gavage two times per day (BID) for 10 days with test compounds re-suspended in 0.5% HPMC and 0.1% Tween-80. Tissue samples were collected and snap frozen for RNA purification.

Tissue samples (20-40 mg) are homogenized in QIAzol Lysis Reagent for 2 minutes at 20 Hz in the TissueLyser II using one stainless steel bead. After addition of chloroform, the homogenate is separated into aqueous and organic phases by centrifugation. RNA partitioned to the upper, aqueous phase is extracted and ethanol is added to provide appropriate binding conditions. The sample is then applied to the RNeasy spin column from the RNeasy Mini Kit, where total RNA binds to the membrane. The RNA is eluted in RNase-free water then stored at −20° C. and subsequently analyzed using the TaqMan RT-qPCR on the 7900HT Thermocycler. Total RNA is diluted ten fold and 2.5 μL of the diluted sample is added to the TaqMan RT-qPCR mixture.

SMN2 spliced products are identified using the following primers and probe in Table 7. Primer SMN FL Forward B (SEQ ID NO. 7) hybridizes to a nucleotide sequence in exons 7 and 8, primer SMN Δ7 Forward B (SEQ ID NO. 8) hybridizes to a nucleotide sequence in exons 6 and 8, primer SMN Reverse B (SEQ ID NO. 9) hybridizes to a nucleotide sequence in exon 8, probe SMN Probe B (SEQ ID NO. 10) hybridizes to a nucleotide sequence in exon 8. These primers and probe hybridize to nucleotide sequences common to human SMN1 and SMN2 mRNA. Since the SMA patient cells used in Example 5 contain only the SMN2 gene, RT-qPCR can quantify only SMN2 full-length and Δ7 mRNA.

TABLE 7

| Primer/Probe | Sequence | Source |
| --- | --- | --- |
| SMN FL Forward Primer B | SEQ ID NO. 7: GCTCACATTCCTTAAATTAAGGAGAAA | PTC[1] |
| SMN Δ7 Forward Primer B | SEQ ID NO. 8: TGGCTATCATACTGGCTATTATATGGAA | PTC[1] |

TABLE 7-continued

| Primer/Probe | Sequence | Source |
| --- | --- | --- |
| SMN Reverse Primer B | SEQ ID NO. 9: TCCAGATCTGTCTGATCGTTTCTT | PTC[1] |
| SMN Forward Probe B | SEQ ID NO. 10: 6FAM-CTGGCATAGAGCAGCACTAAATGACACCAC-TAMRA | PTC[1] |

[1]Primers and probe designed by PTC Therapeutics, Inc.

The SMN forward and reverse primers are used at final concentrations of 0.4 μM. The SMN probe is used at a final concentration of 0.15 μM. The SMN-GAPDH Mix (10 μL total volume) is prepared by combining 5 μL of 2× RT-PCR buffer, 0.4 μL of 25× RT-PCR enzyme mix, 0.5 μL of 20× GAPDH primer-probe mix, 1.505 μL of water, 2.5 μL of RNA solution, 0.04 μL of 100 μM forward primer, 0.04 μL of 100 μM reverse primer, and 0.015 μL of 100 μM SMN probe.

Each PCR cycle was carried out at the following temperatures for the indicated time: Step 1: 48° C. (15 min); Step 2: 95° C. (10 min); Step 3: 95° C. (15 sec); Step 4: 60° C. (1 min); then, repeat Steps 3 and 4 for a total of 40 cycles.

Each reaction mixture contains either SMN2 FL and mGAPDH or SMN2 Δ7 and mGAPDH primers/probe sets (multiplex design), allowing simultaneous measurement of the levels of two transcripts.

The increase of SMN2 FL and decrease in SMN2 Δ7 mRNA relative to those in tissues from animals treated with vehicle control are determined from real-time PCR data using a modified ΔΔCt method (as described in Livak and Schmittgen, Methods, 2001, 25:402-8). The amplification efficiency (E) is calculated from the slope of the amplification curve for SMN2 FL, SMN2 Δ7, and GAPDH individually. The abundances of SMN2 FL, SMN2 Δ7, and GAPDH are then calculated as $(1+E)^{-Ct}$, where Ct is the threshold value for each amplicon. The abundances of SMN2 FL and SMN2 Δ7 are normalized to GAPDH abundance. The normalized SMN2 FL and SMN2 Δ7 abundances from test compound-treated samples are then divided by normalized SMN2 FL and SMN2 Δ7 abundances, respectively, from vehicle-treated cells to determine the levels of SMN2 FL and SMN2 Δ7 mRNA relative to vehicle control.

Results. As seen in FIG. 6, tissues of animals treated with Compound 6 (FIG. 6a) and Compound 170 (FIG. 6b) contain substantially more SMN2 FL mRNA and less SMN2 Δ7 mRNA than those treated with vehicle, indicating a correction of SMN2 alternative splicing.

Example 6

Endogenous SMN2 mRNA End-Point Semi-Quantitative RT-PCR Splicing Assay in Animal Tissues The endpoint reverse transcription-PCR (RT-PCR) splicing assay is used to quantify the levels of the full length and Δ7 SMN2 mRNA in tissues from mice treated with test compound.

Materials

| Material | Source |
| --- | --- |
| Tissues from C/C-allele SMA mice | The Jackson Laboratory, strain No.: 008714 (B6.129-Smn1$^{tm5(Smn1/SMN2)Mrph}$/J) |
| Tissues from ΔExon7 SMA mice | The Jackson Laboratory, strain No.: 005025 (FVB.Cg-Tg(SMN2*delta7)4299Ahmb Tg(SMN2)89Ahmb Smn1$^{tm1Msd}$/J) |
| Qiagen RNeasy lipid Kit | Qiagen Catalog No.: 74804 |
| Platinum Taq HiFi DNA Polymerase Super Mix | Life Technologies, Inc. (formerly Invitrogen) Catalog No.: 11304-016 |
| iScript RT enzyme Kit | BioRad Catalog No.: 170-8890 |
| Twin.tec 96-Well Semiskirted PCR Plate | Eppendorf Catalog No.: 951020389 |
| Ethidium bromide 2% agarose E gels 48-Well Double Comb | Life Technologies, Inc. (formerly Invitrogen) Catalog No.: G8008-02 |
| Gel Documentation System | UVP Gel Doc It 310 Imaging system |

Protocol. C/C-allele SMA mice are treated by oral gavage BID for 10 days with test compounds in 0.5% HPMC and 0.1% Tween-80. Tissue samples are collected and snap frozen for RNA purification.

Tissue samples (20-40 mg) are homogenized in QIAzol Lysis Reagent for 2 minutes at 20 Hz in the TissueLyser II using one stainless steel bead. After addition of chloroform, the homogenate is separated into aqueous and organic phases by centrifugation. RNA partitioned to the upper, aqueous phase is extracted and ethanol is added to provide appropriate binding conditions. The sample is then applied to the RNeasy spin column from the RNeasy Mini Kit, where total RNA binds to the membrane. The RNA is eluted in RNase-free water then stored at −20° C.

SMN2 spliced products are identified using the following amplification primers in Table 8. These primers hybridize to a nucleotide sequence in exon 6 (SMN Forward D, SEQ ID NO. 13) (nucleotide 22 to nucleotide 46) and exon 8 (SMN Reverse C, SEQ ID NO. 12), common to human SMN1 and SMN2 mRNA.

TABLE 8

| Primer | Sequence | Source |
| --- | --- | --- |
| SMN Forward D | SEQ ID NO. 13: ATATGTCCAGATTCTCTTGATGATG | PTC[1] |
| SMN Reverse C | SEQ ID NO. 12: CGCTTCACATTCCAGATCTGTC | PTC[1] |

[1]Primers designed by PTC Therapeutics, Inc.

To synthesize cDNA, combine 1 μL of RNA solution (25-50 ng), 4 μL of 5× iScript reaction mix, 1 μL of reverse transcriptase, and 10 μL of water are combined and incubates 25° C. for 5 min followed by 42° C. for 30 min followed by 85° C. for 5 min. The cDNA solution is stored at −20° C.

To perform endpoint PCR, 5 μL of cDNA, 0.2 μL of 100 μM forward primer, 0.2 μL of 100 μM reverse primer, and 22.5 μL of polymerase super mix are combined in a 96 well semiskirted PCR plate. PCR is carried out at the following temperatures for the indicated time: Step 1: 94° C. (2 min), Step 2: 94° C. (30 sec), Step 3: 55° C. (30 sec), Step 4: 68° C. (1 min), then repeat Steps 2 to 4 for a total of 33 cycles, then hold at 4° C.

10 μL of each PCR sample is electrophoretically separated on a 2% agarose E-gel for 14 minutes stained with dsDNA staining reagents (e.g., ethidium bromide) and visualized using a gel imager.

Results. As seen in FIG. 7, tissues from mice treated with increasing concentrations of Compound 6 (FIG. 7a) and Compound 170 (FIG. 7b) contain progressively more SMN2 FL mRNA and less SMN2 Δ7 mRNA, indicating a correction of SMN2 alternative splicing.

Example 7

Smn Protein Assay in Cultured Cells

The SMN HTRF (homogeneous time resolved fluorescence) assay is used to quantify the level of Smn protein in SMA patient fibroblast cells treated with test compounds. The results of the assay are shown in Table 9.

Materials

| Material | Source |
| --- | --- |
| SMA Type 1 human cells | GM03813 (Coriell Institute) |
| Protease inhibitor cocktail | Roche Applied Science Catalog No.: 11836145001 |
| Anti-SMN d2 | Blue cap Cisbio Catalog No.: 63IDC002-SMN |
| Anti-SMN kryptate | Red cap Cisbio Catalog No.: 63IDC002-SMN |
| SMN reconstitution buffer | Cisbio Catalog No.: 63IDC002-SMN-Buffer |
| DMEM | Life Technologies, Inc. (formerly Invitrogen) Catalog No.: 11960-044 |
| RIPA Lysis Buffer | 20 mM Tris-HCl pH 7.5, 150 mM NaCl, 1 mM EDTA, 1% NP-40, 1% Sodium deoxycholate |
| Diluent Buffer | 20 mM Tris-HCl pH 7.5, 150 mM NaCl |
| Envision Plate Reader | Perkin Elmer Model No.: 2103 |

Protocol. Cells are thawed and cultured in DMEM-10% FBS for 72 hours. Cells are trypsinized, counted and re-suspended to a concentration of 25,000 cells/mL in DMEM-10% FBS. The cell suspension is plated at 5,000 cells per well in a 96 well microtiter plate and incubated for 3 to 5 hours. To provide a control signal, three (3) wells in the 96 well plate do not receive cells and, thus, serve as Blank control wells. Test compounds are serially diluted 3.16-fold in 100% DMSO to generate a 7-point concentration curve. 1 µL of test compound solution is transferred to cell-containing wells and cells are incubated for 48 hours in a cell culture incubator (37° C., 5% CO$_2$, 100% relative humidity). Triplicate samples are set up for each test compound concentration. After 48 hours, the supernatant is removed from the wells and 25 µL of the RIPA lysis buffer, containing protease inhibitors, is added to the wells and incubated with shaking at room temperature for 1 hour. 25 µL of the diluent is added and then 35 µL of the resulting lysate is transferred to a 384-well plate, where each well contains 5 µL of the antibody solution (1:100 dilution of anti-SMN d2 and anti-SMN kryptate in SMN reconstitution buffer). The plate is centrifuged for 1 minute to bring the solution to the bottom of the wells, then incubated overnight at room temperature. Fluorescence for each well of the plate at 665 nm and 620 nm is measured on an EnVision multilabel plate reader (Perkin-Elmer).

The normalized fluorescence signal is calculated for each sample, Blank and vehicle control well by dividing the signal at 665 nm by the signal at 620 nm. Normalizing the signal accounts for possible fluorescence quenching due to the matrix effect of the lysate. The ΔF value (a measurement of Smn protein abundance as a percent value) for each sample well is calculated by subtracting the normalized average fluorescence for the Blank control wells from the normalized fluorescence for each sample well, then dividing this difference by the normalized average fluorescence for the Blank control wells and multiplying the resulting value by 100. The ΔF value for each sample well represents the Smn protein abundance from test compound-treated samples. The ΔF value for each sample well is divided by the ΔF value for the vehicle control wells to calculate the fold increase in Smn protein abundance relative to the vehicle control.

Results. As seen in FIG. 8, SMA Type 1 patient fibroblast cells treated with Compound 6 (FIG. 8a) and Compound 170 (FIG. 8b) show a dose dependent increase in Smn protein expression as measured by the SMN HTRF assay.

For compounds of Formula (I) or a form thereof disclosed herein, Table 9 provides the $EC_{1.5x}$ for Smn protein expression that was obtained from the 7-point concentration data generated for each test compound according to the procedure of Biological Example 7. The term "$EC_{1.5x}$ for Smn protein expression" is defined as that concentration of test compound that is effective in producing 1.5 times the amount of Smn protein in an SMA patient fibroblast cell compared to the amount produced from the DMSO vehicle control. An $EC_{1.5x}$ for Smn protein expression between >3 µM and ≤10 µM is indicated by one star (*), an $EC_{1.5x}$ between >1 µM and ≤3 µM is indicated by two stars (), an $EC_{1.5x}$ between >0.3 µM and ≤1 µM is indicated by three stars (*) and an $EC_{1.5x}$≤0.3 µM is indicated by four stars (****).

TABLE 9

| Cpd | $EC_{1.5x}$ |
| --- | --- |
| 3 | ** |
| 6 | *** |
| 8 | ** |
| 18 | ** |
| 20 | ** |
| 22 | ** |
| 24 | * |
| 30 | ** |
| 43 | ** |
| 61 | *** |
| 62 | *** |
| 66 | * |
| 67 | *** |
| 69 | *** |
| 71 | * |
| 72 | *** |
| 74 | *** |
| 75 | **** |
| 79 | *** |
| 82 | ** |
| 84 | ** |
| 85 | * |
| 86 | **** |
| 87 | *** |
| 90 | * |
| 95 | ** |
| 96 | *** |
| 99 | *** |
| 100 | *** |
| 102 | *** |
| 105 | *** |
| 106 | ** |
| 109 | **** |
| 115 | **** |
| 116 | * |
| 117 | **** |
| 118 | *** |
| 119 | *** |
| 120 | **** |
| 121 | **** |
| 127 | * |
| 129 | * |
| 130 | * |
| 131 | ** |
| 132 | **** |

TABLE 9-continued

| Cpd | EC$_{1.5x}$ |
|---|---|
| 133 | **** |
| 134 | **** |
| 135 | **** |
| 136 | **** |
| 137 | *** |
| 138 | *** |
| 141 | **** |
| 143 | **** |
| 144 | **** |
| 148 | ** |
| 150 | ** |
| 152 | **** |
| 160 | *** |
| 161 | ** |
| 162 | ** |
| 164 | ** |
| 167 | ** |
| 169 | **** |
| 170 | **** |
| 171 | **** |
| 172 | **** |
| 175 | *** |
| 176 | * |
| 179 | *** |
| 180 | ** |
| 182 | *** |
| 186 | *** |
| 188 | *** |
| 189 | *** |
| 190 | ** |
| 191 | ** |
| 192 | ** |
| 193 | **** |
| 194 | **** |
| 195 | *** |
| 196 | **** |
| 197 | **** |
| 198 | **** |
| 199 | ** |
| 201 | *** |
| 204 | **** |
| 208 | *** |
| 209 | **** |
| 210 | **** |
| 211 | **** |
| 212 | **** |
| 213 | **** |
| 214 | ** |
| 218 | ** |
| 219 | **** |
| 221 | **** |
| 224 | *** |
| 229 | * |
| 230 | ** |
| 231 | ** |
| 234 | **** |
| 235 | ** |
| 236 | * |
| 240 | **** |
| 241 | **** |
| 242 | **** |
| 243 | **** |
| 244 | **** |
| 247 | **** |
| 248 | *** |
| 250 | **** |
| 251 | **** |
| 252 | *** |
| 254 | ** |
| 256 | ** |
| 257 | ** |
| 258 | *** |
| 259 | *** |
| 260 | ** |
| 261 | **** |
| 262 | *** |
| 263 | *** |
| 264 | **** |

TABLE 9-continued

| Cpd | EC$_{1.5x}$ |
|---|---|
| 267 | **** |
| 268 | **** |
| 269 | **** |
| 270 | **** |
| 271 | **** |
| 272 | **** |
| 273 | **** |
| 274 | **** |
| 275 | **** |
| 283 | **** |
| 284 | *** |
| 285 | **** |
| 286 | *** |
| 287 | **** |
| 288 | **** |
| 289 | **** |
| 290 | **** |
| 291 | **** |
| 292 | **** |
| 293 | **** |
| 294 | * |
| 295 | **** |
| 296 | **** |
| 297 | **** |
| 299 | **** |
| 300 | **** |
| 302 | **** |
| 303 | **** |
| 304 | **** |
| 305 | **** |
| 306 | **** |
| 307 | **** |
| 308 | **** |
| 309 | **** |
| 310 | *** |
| 312 | **** |
| 314 | *** |
| 316 | ** |
| 317 | ** |
| 318 | **** |
| 319 | **** |
| 320 | ** |
| 322 | *** |
| 323 | ** |
| 326 | ** |
| 327 | **** |
| 329 | ** |
| 331 | **** |
| 333 | ** |
| 334 | **** |
| 335 | **** |
| 336 | **** |
| 337 | **** |
| 338 | **** |
| 339 | **** |
| 340 | **** |
| 341 | *** |
| 342 | **** |
| 343 | **** |
| 344 | *** |
| 346 | **** |
| 349 | ** |
| 350 | **** |
| 351 | **** |
| 352 | **** |
| 354 | *** |
| 355 | *** |
| 356 | *** |
| 357 | *** |
| 358 | ** |
| 359 | ** |
| 366 | **** |
| 367 | * |
| 368 | *** |
| 369 | ** |
| 370 | *** |
| 371 | *** |
| 372 | **** |

TABLE 9-continued

| Cpd | EC$_{1.5x}$ |
|---|---|
| 373 | **** |
| 374 | **** |
| 375 | **** |
| 376 | *** |
| 377 | ** |
| 378 | ** |
| 380 | *** |
| 381 | * |
| 382 | *** |
| 384 | **** |
| 385 | *** |
| 393 | *** |
| 396 | *** |
| 397 | **** |
| 398 | ** |
| 399 | *** |
| 400 | *** |
| 401 | *** |
| 402 | ** |
| 403 | ** |
| 404 | ** |
| 405 | *** |
| 406 | * |
| 409 | **** |
| 410 | **** |
| 412 | **** |
| 413 | **** |
| 414 | *** |
| 416 | ** |
| 417 | ** |
| 420 | **** |
| 422 | ** |
| 423 | *** |
| 424 | **** |
| 425 | **** |
| 426 | *** |
| 427 | * |
| 428 | ** |
| 429 | **** |
| 430 | **** |
| 431 | **** |
| 432 | **** |
| 437 | *** |
| 438 | **** |
| 439 | ** |
| 440 | **** |
| 441 | **** |
| 442 | **** |
| 443 | **** |
| 444 | ** |
| 445 | *** |
| 446 | ** |
| 448 | **** |
| 449 | **** |
| 451 | *** |
| 452 | **** |
| 453 | **** |
| 454 | **** |
| 457 | **** |
| 458 | *** |
| 460 | *** |
| 461 | ** |
| 462 | **** |
| 463 | *** |
| 464 | ** |
| 466 | *** |
| 467 | **** |
| 468 | *** |
| 469 | *** |
| 470 | **** |
| 471 | **** |
| 472 | **** |
| 473 | **** |
| 474 | **** |
| 475 | ** |
| 476 | **** |
| 477 | **** |
| 478 | **** |
| 480 | **** |
| 481 | **** |
| 482 | * |
| 484 | **** |
| 485 | **** |
| 486 | **** |
| 487 | **** |
| 488 | **** |
| 489 | ** |
| 490 | *** |
| 491 | ** |
| 492 | ** |
| 493 | *** |
| 494 | **** |
| 495 | **** |
| 496 | **** |
| 497 | *** |
| 498 | **** |
| 499 | **** |
| 500 | *** |
| 501 | *** |
| 502 | **** |
| 503 | **** |
| 504 | **** |
| 505 | **** |
| 506 | **** |
| 507 | *** |
| 508 | *** |
| 509 | *** |
| 510 | **** |
| 511 | ** |
| 512 | **** |
| 513 | **** |
| 514 | ** |
| 515 | **** |
| 516 | **** |
| 517 | **** |
| 518 | **** |
| 519 | **** |
| 520 | **** |
| 521 | **** |
| 522 | *** |
| 523 | **** |
| 524 | *** |
| 525 | *** |
| 526 | ** |
| 527 | **** |
| 528 | **** |
| 529 | *** |
| 530 | **** |
| 531 | *** |
| 532 | **** |
| 533 | *** |
| 534 | **** |
| 535 | *** |
| 536 | **** |
| 537 | **** |
| 538 | *** |
| 539 | **** |
| 541 | *** |
| 542 | *** |
| 543 | **** |
| 544 | *** |
| 545 | **** |
| 546 | **** |
| 547 | **** |
| 548 | **** |
| 549 | **** |
| 550 | **** |
| 551 | **** |
| 552 | *** |
| 553 | **** |
| 554 | **** |
| 555 | ** |
| 556 | ** |
| 561 | **** |
| 563 | **** |
| 565 | *** |

TABLE 9-continued

| Cpd | $EC_{1.5x}$ |
|---|---|
| 566 | **** |
| 567 | *** |
| 568 | **** |
| 569 | **** |
| 570 | ** |
| 571 | ** |
| 572 | ** |
| 573 | ** |
| 576 | **** |
| 577 | **** |
| 578 | **** |
| 579 | *** |
| 580 | *** |
| 581 | *** |
| 582 | **** |
| 583 | **** |
| 584 | **** |
| 585 | **** |
| 586 | **** |
| 587 | **** |
| 588 | **** |
| 589 | *** |
| 590 | ** |
| 591 | ** |
| 592 | *** |
| 593 | **** |
| 594 | *** |
| 595 | **** |
| 596 | **** |
| 597 | *** |
| 598 | *** |
| 599 | **** |
| 600 | ** |
| 601 | *** |
| 602 | **** |
| 603 | *** |
| 604 | **** |
| 605 | *** |
| 606 | ** |
| 607 | **** |
| 608 | ** |
| 609 | **** |
| 610 | **** |
| 612 | **** |
| 613 | **** |
| 614 | **** |
| 615 | **** |
| 616 | **** |
| 617 | **** |
| 618 | **** |
| 619 | *** |
| 620 | ** |
| 621 | **** |
| 622 | ** |
| 623 | **** |
| 624 | **** |
| 626 | ** |
| 627 | ** |
| 628 | * |
| 629 | **** |
| 630 | **** |
| 631 | *** |
| 632 | **** |
| 633 | **** |
| 634 | **** |
| 635 | **** |
| 636 | **** |
| 637 | **** |
| 638 | **** |
| 639 | **** |
| 640 | **** |
| 641 | **** |
| 642 | **** |
| 643 | *** |
| 644 | *** |
| 645 | **** |
| 646 | ** |
| 647 | **** |

TABLE 9-continued

| Cpd | $EC_{1.5x}$ |
|---|---|
| 648 | **** |
| 649 | **** |
| 650 | **** |
| 651 | **** |
| 652 | **** |
| 653 | **** |
| 654 | **** |
| 655 | **** |
| 656 | **** |
| 657 | **** |
| 658 | **** |
| 659 | **** |
| 660 | **** |
| 661 | **** |
| 662 | **** |
| 663 | **** |
| 664 | *** |
| 665 | **** |
| 666 | *** |
| 667 | **** |
| 668 | **** |
| 669 | **** |
| 670 | **** |
| 671 | **** |
| 672 | **** |
| 673 | **** |
| 674 | **** |
| 675 | **** |
| 676 | *** |
| 677 | *** |
| 678 | **** |
| 679 | **** |
| 680 | **** |
| 681 | **** |
| 682 | ** |
| 683 | *** |
| 684 | *** |
| 685 | ** |
| 686 | ** |
| 687 | **** |
| 688 | ** |
| 689 | *** |
| 690 | *** |
| 691 | **** |
| 692 | *** |
| 693 | ** |
| 694 | **** |
| 695 | **** |
| 696 | **** |
| 697 | **** |
| 698 | **** |
| 699 | **** |
| 700 | **** |
| 701 | **** |
| 702 | **** |
| 703 | **** |
| 704 | **** |
| 705 | **** |
| 706 | **** |
| 707 | **** |
| 708 | **** |
| 709 | **** |
| 710 | **** |
| 711 | **** |
| 712 | **** |
| 713 | **** |
| 714 | **** |
| 715 | **** |
| 716 | *** |
| 717 | *** |
| 718 | *** |
| 719 | **** |
| 720 | **** |
| 721 | **** |
| 722 | **** |
| 723 | **** |
| 724 | *** |
| 725 | *** |

TABLE 9-continued

| Cpd | $EC_{1.5x}$ |
|---|---|
| 726 | ** |
| 727 | **** |
| 728 | **** |
| 729 | *** |
| 730 | **** |
| 731 | **** |
| 732 | *** |
| 733 | **** |
| 734 | **** |
| 735 | **** |
| 736 | **** |
| 737 | **** |
| 738 | **** |
| 739 | **** |
| 740 | *** |
| 741 | **** |
| 742 | *** |
| 743 | **** |
| 744 | *** |
| 745 | **** |
| 746 | **** |
| 747 | **** |
| 748 | **** |
| 749 | **** |
| 750 | **** |
| 751 | **** |
| 752 | **** |
| 753 | **** |
| 754 | **** |
| 755 | **** |
| 756 | **** |
| 757 | *** |
| 759 | *** |
| 760 | **** |
| 761 | **** |
| 762 | **** |
| 763 | **** |
| 764 | * |
| 765 | ** |
| 766 | **** |
| 767 | **** |
| 768 | **** |
| 769 | *** |
| 770 | *** |
| 771 | **** |
| 772 | **** |
| 773 | **** |
| 774 | **** |
| 777 | ** |
| 778 | *** |
| 779 | **** |
| 780 | **** |
| 781 | **** |
| 782 | **** |
| 783 | **** |
| 784 | *** |
| 785 | **** |
| 786 | *** |
| 787 | **** |
| 788 | **** |
| 789 | **** |
| 790 | **** |
| 791 | **** |
| 792 | *** |
| 793 | **** |
| 794 | **** |
| 795 | **** |
| 796 | **** |
| 797 | * |
| 798 | **** |
| 799 | **** |
| 800 | **** |
| 801 | *** |
| 802 | * |
| 803 | **** |
| 804 | **** |
| 805 | *** |
| 806 | **** |
| 807 | **** |
| 808 | **** |
| 809 | **** |
| 810 | **** |
| 811 | *** |
| 812 | **** |
| 813 | **** |
| 814 | **** |
| 815 | **** |
| 816 | **** |
| 817 | **** |
| 818 | *** |
| 819 | **** |
| 820 | **** |
| 821 | **** |
| 822 | *** |
| 824 | * |
| 825 | ** |
| 826 | ** |
| 827 | *** |
| 828 | **** |
| 829 | ** |
| 830 | *** |
| 831 | ** |
| 832 | *** |
| 833 | ** |
| 834 | **** |
| 835 | **** |

For compounds of Formula (I) or a form thereof disclosed herein, Table 10 provides the maximum fold (Fold) increase of Smn protein that was obtained from the 7-point concentration data generated for each test compound according to the procedure of Biological Example 7. A maximum fold increase of ≤1.2 is indicated by one star (*), a fold increase between >1.2 and ≤1.35 is indicated by two stars (), a fold increase between >1.35 and ≤1.5 is indicated by three stars (*), a fold increase between >1.5 and ≤1.65 is indicated by four stars (**) and a fold increase >1.65 is indicated by five stars (***).

TABLE 10

| Cpd | Fold |
|---|---|
| 1 | ** |
| 2 | ** |
| 3 | *** |
| 4 | * |
| 5 | * |
| 6 | **** |
| 7 | *** |
| 8 | **** |
| 9 | *** |
| 10 | ** |
| 11 | *** |
| 12 | *** |
| 13 | ** |
| 14 | *** |
| 15 | *** |
| 16 | * |
| 17 | * |
| 18 | **** |
| 19 | ** |
| 20 | **** |
| 21 | * |
| 22 | *** |
| 23 | *** |
| 24 | *** |
| 25 | * |
| 26 | ** |
| 27 | * |
| 28 | ** |
| 29 | *** |

TABLE 10-continued

| Cpd | Fold |
|---|---|
| 30 | **** |
| 31 | * |
| 32 | * |
| 33 | * |
| 34 | ** |
| 35 | * |
| 36 | * |
| 37 | * |
| 38 | * |
| 39 | * |
| 40 | * |
| 41 | *** |
| 42 | * |
| 43 | *** |
| 44 | * |
| 45 | ** |
| 46 | *** |
| 47 | *** |
| 48 | * |
| 49 | * |
| 50 | ** |
| 51 | ** |
| 52 | * |
| 53 | * |
| 54 | * |
| 55 | * |
| 56 | * |
| 57 | * |
| 58 | * |
| 59 | * |
| 60 | * |
| 61 | **** |
| 62 | ***** |
| 63 | ** |
| 64 | ** |
| 65 | ** |
| 66 | *** |
| 67 | *** |
| 68 | ** |
| 69 | **** |
| 70 | * |
| 71 | **** |
| 72 | *** |
| 73 | ** |
| 74 | ***** |
| 75 | ***** |
| 76 | ** |
| 77 | ** |
| 78 | * |
| 79 | **** |
| 80 | * |
| 81 | ** |
| 82 | ***** |
| 83 | * |
| 84 | ***** |
| 85 | *** |
| 86 | **** |
| 87 | **** |
| 88 | ** |
| 89 | *** |
| 90 | *** |
| 91 | ** |
| 92 | ** |
| 93 | ** |
| 94 | *** |
| 95 | **** |
| 96 | **** |
| 97 | ** |
| 98 | *** |
| 99 | **** |
| 100 | ***** |
| 101 | *** |
| 102 | ***** |
| 103 | *** |
| 104 | *** |
| 105 | **** |
| 106 | **** |
| 107 | ** |

TABLE 10-continued

| Cpd | Fold |
|---|---|
| 108 | *** |
| 109 | **** |
| 110 | *** |
| 111 | *** |
| 112 | *** |
| 113 | *** |
| 114 | *** |
| 115 | **** |
| 116 | *** |
| 117 | **** |
| 118 | ***** |
| 119 | ***** |
| 120 | ***** |
| 121 | ***** |
| 122 | *** |
| 123 | * |
| 124 | ** |
| 125 | *** |
| 126 | ** |
| 127 | *** |
| 128 | *** |
| 129 | *** |
| 130 | *** |
| 131 | *** |
| 132 | ***** |
| 133 | **** |
| 134 | ***** |
| 135 | **** |
| 136 | ***** |
| 137 | ***** |
| 138 | ***** |
| 139 | *** |
| 140 | *** |
| 141 | ***** |
| 142 | *** |
| 143 | ***** |
| 144 | **** |
| 145 | * |
| 146 | * |
| 147 | * |
| 148 | *** |
| 149 | ** |
| 150 | **** |
| 151 | *** |
| 152 | ***** |
| 153 | ** |
| 154 | * |
| 155 | ** |
| 156 | *** |
| 157 | ** |
| 158 | * |
| 159 | *** |
| 160 | *** |
| 161 | *** |
| 162 | **** |
| 163 | *** |
| 164 | **** |
| 165 | ** |
| 166 | ** |
| 167 | *** |
| 168 | * |
| 169 | **** |
| 170 | ***** |
| 171 | ***** |
| 172 | ***** |
| 173 | ** |
| 174 | ** |
| 175 | **** |
| 176 | *** |
| 177 | *** |
| 178 | ** |
| 179 | ***** |
| 180 | **** |
| 181 | * |
| 182 | **** |
| 183 | ** |
| 184 | ** |
| 185 | *** |

TABLE 10-continued

| Cpd | Fold |
|---|---|
| 186 | **** |
| 187 | ** |
| 188 | ***** |
| 189 | **** |
| 190 | **** |
| 191 | **** |
| 192 | ***** |
| 193 | ***** |
| 194 | ***** |
| 195 | **** |
| 196 | **** |
| 197 | ***** |
| 198 | **** |
| 199 | **** |
| 200 | * |
| 201 | *** |
| 202 | ** |
| 203 | * |
| 204 | **** |
| 205 | ** |
| 206 | ** |
| 207 | *** |
| 208 | *** |
| 209 | **** |
| 210 | **** |
| 211 | **** |
| 212 | **** |
| 213 | *** |
| 214 | **** |
| 215 | *** |
| 216 | *** |
| 217 | *** |
| 218 | *** |
| 219 | **** |
| 220 | ** |
| 221 | ***** |
| 222 | *** |
| 223 | *** |
| 224 | **** |
| 225 | * |
| 226 | * |
| 227 | *** |
| 228 | ** |
| 229 | *** |
| 230 | **** |
| 231 | **** |
| 232 | * |
| 233 | * |
| 234 | ***** |
| 235 | **** |
| 236 | *** |
| 237 | *** |
| 238 | ** |
| 239 | * |
| 240 | **** |
| 241 | ***** |
| 242 | **** |
| 243 | **** |
| 244 | **** |
| 245 | ** |
| 246 | * |
| 247 | ***** |
| 248 | **** |
| 249 | * |
| 250 | ***** |
| 251 | ***** |
| 252 | **** |
| 253 | * |
| 254 | *** |
| 255 | ** |
| 256 | **** |
| 257 | **** |
| 258 | **** |
| 259 | **** |
| 260 | *** |
| 261 | **** |
| 262 | ***** |
| 263 | **** |
| 264 | ***** |
| 265 | *** |
| 266 | ** |
| 267 | ***** |
| 268 | ***** |
| 269 | ***** |
| 270 | **** |
| 271 | ***** |
| 272 | ***** |
| 273 | ***** |
| 274 | ***** |
| 275 | ***** |
| 276 | * |
| 277 | *** |
| 278 | ** |
| 279 | ** |
| 280 | * |
| 281 | ** |
| 282 | ** |
| 283 | **** |
| 284 | **** |
| 285 | ***** |
| 286 | **** |
| 287 | ***** |
| 288 | ***** |
| 289 | **** |
| 290 | ***** |
| 291 | ***** |
| 292 | **** |
| 293 | ***** |
| 294 | *** |
| 295 | **** |
| 296 | ***** |
| 297 | ***** |
| 298 | *** |
| 299 | ***** |
| 300 | ***** |
| 301 | * |
| 302 | ***** |
| 303 | **** |
| 304 | ***** |
| 305 | ***** |
| 306 | ***** |
| 307 | **** |
| 308 | ***** |
| 309 | **** |
| 310 | *** |
| 311 | ** |
| 312 | **** |
| 313 | * |
| 314 | **** |
| 315 | *** |
| 316 | ***** |
| 317 | **** |
| 318 | ***** |
| 319 | **** |
| 320 | **** |
| 321 | *** |
| 322 | **** |
| 323 | *** |
| 324 | *** |
| 325 | *** |
| 326 | *** |
| 327 | **** |
| 328 | *** |
| 329 | **** |
| 330 | ** |
| 331 | ***** |
| 332 | * |
| 333 | **** |
| 334 | ***** |
| 335 | ***** |
| 336 | ***** |
| 337 | ***** |
| 338 | ***** |
| 339 | ***** |
| 340 | ***** |
| 341 | ***** |

TABLE 10-continued

| Cpd | Fold |
|---|---|
| 342 | ***** |
| 343 | ***** |
| 344 | ***** |
| 345 | *** |
| 346 | **** |
| 347 | *** |
| 348 | ** |
| 349 | *** |
| 350 | ***** |
| 351 | ***** |
| 352 | **** |
| 353 | ** |
| 354 | **** |
| 355 | **** |
| 356 | **** |
| 357 | **** |
| 358 | *** |
| 359 | *** |
| 360 | * |
| 361 | *** |
| 362 | *** |
| 363 | ** |
| 364 | * |
| 365 | *** |
| 366 | **** |
| 367 | *** |
| 368 | **** |
| 369 | *** |
| 370 | ***** |
| 371 | **** |
| 372 | ***** |
| 373 | **** |
| 374 | ***** |
| 375 | **** |
| 376 | *** |
| 377 | **** |
| 378 | **** |
| 379 | *** |
| 380 | **** |
| 381 | *** |
| 382 | **** |
| 383 | ** |
| 384 | ***** |
| 385 | ***** |
| 386 | * |
| 387 | ** |
| 388 | *** |
| 389 | ** |
| 390 | * |
| 391 | * |
| 392 | *** |
| 393 | *** |
| 394 | ** |
| 395 | ** |
| 396 | **** |
| 397 | ***** |
| 398 | ***** |
| 399 | **** |
| 400 | **** |
| 401 | ***** |
| 402 | **** |
| 403 | **** |
| 404 | **** |
| 405 | **** |
| 406 | *** |
| 407 | *** |
| 408 | ** |
| 409 | **** |
| 410 | ***** |
| 411 | *** |
| 412 | ***** |
| 413 | **** |
| 414 | ***** |
| 415 | *** |
| 416 | *** |
| 417 | **** |
| 418 | *** |
| 419 | ** |

TABLE 10-continued

| Cpd | Fold |
|---|---|
| 420 | **** |
| 421 | *** |
| 422 | *** |
| 423 | **** |
| 424 | ***** |
| 425 | ***** |
| 426 | ***** |
| 427 | *** |
| 428 | *** |
| 429 | **** |
| 430 | **** |
| 431 | ***** |
| 432 | ***** |
| 433 | *** |
| 434 | ** |
| 435 | *** |
| 436 | ** |
| 437 | **** |
| 438 | ***** |
| 439 | *** |
| 440 | **** |
| 441 | ***** |
| 442 | ***** |
| 443 | ***** |
| 444 | *** |
| 445 | *** |
| 446 | *** |
| 447 | * |
| 448 | ***** |
| 449 | **** |
| 450 | ** |
| 451 | ***** |
| 452 | ***** |
| 453 | ***** |
| 454 | ***** |
| 455 | ** |
| 456 | *** |
| 457 | ***** |
| 458 | **** |
| 459 | *** |
| 460 | **** |
| 461 | **** |
| 462 | ***** |
| 463 | ***** |
| 464 | **** |
| 465 | *** |
| 466 | ***** |
| 467 | ***** |
| 468 | **** |
| 469 | ***** |
| 470 | **** |
| 471 | ***** |
| 472 | ***** |
| 473 | ***** |
| 474 | **** |
| 475 | *** |
| 476 | ***** |
| 477 | **** |
| 478 | ***** |
| 479 | ** |
| 480 | ***** |
| 481 | **** |
| 482 | *** |
| 483 | ** |
| 484 | ***** |
| 485 | ***** |
| 486 | **** |
| 487 | **** |
| 488 | **** |
| 489 | **** |
| 490 | ***** |
| 491 | **** |
| 492 | **** |
| 493 | **** |
| 494 | **** |
| 495 | ***** |
| 496 | ***** |
| 497 | **** |

TABLE 10-continued

| Cpd | Fold |
|-----|------|
| 498 | ***** |
| 499 | ***** |
| 500 | ***** |
| 501 | ***** |
| 502 | ***** |
| 503 | ***** |
| 504 | ***** |
| 505 | **** |
| 506 | **** |
| 507 | **** |
| 508 | **** |
| 509 | **** |
| 510 | ***** |
| 511 | **** |
| 512 | ***** |
| 513 | ***** |
| 514 | ***** |
| 515 | ***** |
| 516 | **** |
| 517 | ***** |
| 518 | **** |
| 519 | ***** |
| 520 | **** |
| 521 | ***** |
| 522 | ***** |
| 523 | ***** |
| 524 | ***** |
| 525 | ***** |
| 526 | ***** |
| 527 | ***** |
| 528 | **** |
| 529 | ***** |
| 530 | ***** |
| 531 | ***** |
| 532 | ***** |
| 533 | ***** |
| 534 | ***** |
| 535 | ***** |
| 536 | **** |
| 537 | **** |
| 538 | **** |
| 539 | **** |
| 540 | *** |
| 541 | ***** |
| 542 | ***** |
| 543 | ***** |
| 544 | **** |
| 545 | ***** |
| 546 | ***** |
| 547 | ***** |
| 548 | ***** |
| 549 | ***** |
| 550 | ***** |
| 551 | ***** |
| 552 | **** |
| 553 | ***** |
| 554 | ***** |
| 555 | *** |
| 556 | *** |
| 557 | * |
| 558 | ** |
| 559 | * |
| 560 | * |
| 561 | **** |
| 562 | ** |
| 563 | ***** |
| 564 | * |
| 565 | **** |
| 566 | ***** |
| 567 | **** |
| 568 | ***** |
| 569 | ***** |
| 570 | **** |
| 571 | **** |
| 572 | **** |
| 573 | **** |
| 574 | ** |
| 575 | *** |
| 576 | ***** |
| 577 | ***** |
| 578 | ***** |
| 579 | ***** |
| 580 | ***** |
| 581 | ***** |
| 582 | ***** |
| 583 | ***** |
| 584 | ***** |
| 585 | ***** |
| 586 | ***** |
| 587 | **** |
| 588 | ***** |
| 589 | **** |
| 590 | **** |
| 591 | **** |
| 592 | ***** |
| 593 | ***** |
| 594 | **** |
| 595 | **** |
| 596 | **** |
| 597 | **** |
| 598 | ***** |
| 599 | ***** |
| 600 | **** |
| 601 | **** |
| 602 | **** |
| 603 | ***** |
| 604 | ***** |
| 605 | ***** |
| 606 | **** |
| 607 | ***** |
| 608 | **** |
| 609 | ***** |
| 610 | ***** |
| 611 | *** |
| 612 | ***** |
| 613 | ***** |
| 614 | ***** |
| 615 | **** |
| 616 | ***** |
| 617 | ***** |
| 618 | ***** |
| 619 | ***** |
| 620 | *** |
| 621 | ***** |
| 622 | **** |
| 623 | ***** |
| 624 | ***** |
| 625 | ** |
| 626 | ***** |
| 627 | **** |
| 628 | **** |
| 629 | ***** |
| 630 | ***** |
| 631 | ***** |
| 632 | ***** |
| 633 | ***** |
| 634 | ***** |
| 635 | ***** |
| 636 | ***** |
| 637 | ***** |
| 638 | ***** |
| 639 | ***** |
| 640 | **** |
| 641 | ***** |
| 642 | ***** |
| 643 | ***** |
| 644 | ***** |
| 645 | ***** |
| 646 | ***** |
| 647 | ***** |
| 648 | ***** |
| 649 | ***** |
| 650 | ***** |
| 651 | ***** |
| 652 | ***** |
| 653 | ***** |

TABLE 10-continued

| Cpd | Fold |
|---|---|
| 654 | ***** |
| 655 | **** |
| 656 | **** |
| 657 | ***** |
| 658 | ***** |
| 659 | ***** |
| 660 | **** |
| 661 | ***** |
| 662 | ***** |
| 663 | ***** |
| 664 | ***** |
| 665 | ***** |
| 666 | ***** |
| 667 | ***** |
| 668 | ***** |
| 669 | ***** |
| 670 | ***** |
| 671 | ***** |
| 672 | ***** |
| 673 | **** |
| 674 | ***** |
| 675 | ***** |
| 676 | ***** |
| 677 | ***** |
| 678 | ***** |
| 679 | ***** |
| 680 | ***** |
| 681 | ***** |
| 682 | ***** |
| 683 | ***** |
| 684 | ***** |
| 685 | **** |
| 686 | ***** |
| 687 | **** |
| 688 | *** |
| 689 | **** |
| 690 | **** |
| 691 | ***** |
| 692 | ***** |
| 693 | **** |
| 694 | ***** |
| 695 | ***** |
| 696 | ***** |
| 697 | ***** |
| 698 | ***** |
| 699 | ***** |
| 700 | ***** |
| 701 | ***** |
| 702 | ***** |
| 703 | ***** |
| 704 | **** |
| 705 | ***** |
| 706 | ***** |
| 707 | ***** |
| 708 | ***** |
| 709 | ***** |
| 710 | ***** |
| 711 | ***** |
| 712 | ***** |
| 713 | ***** |
| 714 | ***** |
| 715 | ***** |
| 716 | ***** |
| 717 | ***** |
| 718 | **** |
| 719 | **** |
| 720 | ***** |
| 721 | ***** |
| 722 | ***** |
| 723 | ***** |
| 724 | ***** |
| 725 | ***** |
| 726 | **** |
| 727 | ***** |
| 728 | ***** |
| 729 | ***** |
| 730 | ***** |
| 731 | ***** |
| 732 | **** |
| 733 | ***** |
| 734 | ***** |
| 735 | **** |
| 736 | ***** |
| 737 | ***** |
| 738 | ***** |
| 739 | ***** |
| 740 | ***** |
| 741 | ***** |
| 742 | ***** |
| 743 | ***** |
| 744 | *** |
| 745 | ***** |
| 746 | ***** |
| 747 | ***** |
| 748 | ***** |
| 749 | ***** |
| 750 | ***** |
| 751 | ***** |
| 752 | ***** |
| 753 | ***** |
| 754 | ***** |
| 755 | ***** |
| 756 | ***** |
| 757 | **** |
| 758 | *** |
| 759 | ***** |
| 760 | ***** |
| 761 | ***** |
| 762 | ***** |
| 763 | ***** |
| 764 | *** |
| 765 | **** |
| 766 | ***** |
| 767 | ***** |
| 768 | ***** |
| 769 | ***** |
| 770 | **** |
| 771 | ***** |
| 772 | ***** |
| 773 | ***** |
| 774 | ***** |
| 775 | *** |
| 776 | ** |
| 777 | *** |
| 778 | ***** |
| 779 | ***** |
| 780 | ***** |
| 781 | ***** |
| 782 | ***** |
| 783 | ***** |
| 784 | **** |
| 785 | ***** |
| 786 | **** |
| 787 | ***** |
| 788 | ***** |
| 789 | ***** |
| 790 | ***** |
| 791 | ***** |
| 792 | ***** |
| 793 | ***** |
| 794 | ***** |
| 795 | ***** |
| 796 | ***** |
| 797 | *** |
| 798 | ***** |
| 799 | ***** |
| 800 | ***** |
| 801 | ***** |
| 802 | ***** |
| 803 | ***** |
| 804 | ***** |
| 805 | ***** |
| 806 | ***** |
| 807 | ***** |
| 808 | ***** |
| 809 | ***** |

TABLE 10-continued

| Cpd | Fold |
|---|---|
| 810 | ***** |
| 811 | ***** |
| 812 | ***** |
| 813 | ***** |
| 814 | ***** |
| 815 | ***** |
| 816 | **** |
| 817 | ***** |
| 818 | ***** |
| 819 | ***** |
| 820 | ***** |
| 821 | ***** |
| 822 | **** |
| 823 | ** |
| 824 | **** |
| 825 | ***** |
| 826 | ***** |
| 827 | ***** |
| 828 | ***** |
| 829 | ***** |
| 830 | ***** |
| 831 | **** |
| 832 | ***** |
| 833 | ***** |
| 834 | ***** |
| 835 | ***** |

Example 8

Gems Count (Smn-Dependent Nuclear Speckle Count) Assay

The level of Smn protein directly correlates with the amount of nuclear foci, also known as gems, produced upon staining the cell with a fluorescently labeled anti-Smn antibody (Liu and Dreyfuss, EMBO J., 1996, 15:3555). Gems are multi-protein complexes whose formation is nucleated by the Smn protein and the gems count assay is used to evaluate the level of Smn protein in the cell. As described herein, the gems count assay is used to quantify the level of Smn protein in SMA patient fibroblast cells treated with a test compound.

Materials

| Material | Source |
|---|---|
| SMA Type 1 human cells | GM03813 (Coriell Institute) |
| Primary Antibody-mouse anti-SMN clone 2B1 | Sigma Catalog No.: S2944 |
| Secondary Antibody-anti-mouse Alexa Fluor 555 | Life Technologies, Inc. (formerly Invitrogen) Catalog No.: A21422 |
| Bovine Serum Albumin (BSA) | Sigma Catalog No.: A3294 |
| 4% Paraformaldehyde | Electron Microscopy Sciences Catalog No.: 15710 |
| Bortezomib | LC Labs, Catalog No.: B-1408 |
| 0.05% Triton X-100 | Sigma Catalog No.: 93443-100 mL |
| Mounting medium-ProLong Gold Antifade Reagent with DAPI | Life Technologies, Inc. (formerly Invitrogen) Catalog Nos.: P7481 and P36935 |
| 22 x 22 #1 sterile Cover slips | Fisher Catalog No.: 12-548-B |
| DMEM | Life Technologies, Inc. (formerly Invitrogen) Catalog No.: 11960-044 |
| PBS | Life Technologies, Inc. (formerly Invitrogen) Catalog No.: 10010-031 |
| Clear-coat nail polish | Revlon brand Catalog No.: 1271-76 |
| Zeiss Axovert 135 Fluorescence microscope | Zeiss |

Protocol: Cells are thawed and incubated in DMEM-10% FBS for 72 hours, then trypsinized, counted and resuspended to 100,000 cells/mL in DMEM-10% FBS. The cell suspension (2 mL) is plated in a 6-well cell culture plate with a sterile cover slip and incubated for 3 to 5 hours. Test compounds are serially diluted 3.16-fold in 100% DMSO to generate a 7-point dilution curve. 10 µL of test compound solution is added to each cell-containing well and incubated for 48 hours in a cell culture incubator (37° C., 5% $CO_2$, 100% relative humidity). Duplicates are set up for each test compound concentration. Cells containing DMSO at a final concentration of 0.5% are used as controls.

Cell culture medium is aspirated from the wells containing cover slips and gently washed three times with cold PBS. The cells are fixed by incubation for 20 minutes at room temperature while in paraformaldehyde. The cells are then washed two times with cold PBS followed by incubation for 5 minutes at room temperature with 0.05% Triton X-100 in PBS to permeabilize the cells. After the fixed cells are washed three times with cold PBS, they are blocked with 10% FBS for 1 hour. 60 µL of primary antibody diluted 1:1000 in blocking buffer is added and the mixture is incubated for one hour at room temperature. The cells are washed three times with PBS and 60 µL of secondary antibody diluted 1:5000 in blocking buffer is added, then the mixture is incubated for one hour at room temperature. The cover slips are mounted onto the slides with the aid of mounting medium and allowed to dry overnight. Nail polish is applied to the sides of the cover slip and the slides are stored, protected from light. A Zeiss Axovert 135 with a 63× Plan-Apochromat, NA=1.4 objective is used for immunofluorescence detection and counting. The number of gems is counted per >150 nuclei and % activation is calculated using DMSO and 10 nM bortezomib as controls. For each test compound, the cells are examined at all wavelengths to identify test compounds with inherent fluorescence.

Results. As seen in FIG. 9, SMA Type 1 patient cells treated with Compound 6 (FIG. 9a) and Compound 170 (FIG. 9b) contain progressively more gems relative to cells treated with DMSO.

Example 9

Smn Protein Assay in Human Motor Neurons

Smn immunofluorescent confocal microscopy is used to quantify the level of Smn protein in human motor neurons treated with test compounds.

Protocol. Human motor neurons derived from SMA iPS cells (Ebert et al., Nature, 2009, 457:2770; and, Rubin et al., BMC Biology, 2011, 9:42) are treated with test compound at various concentrations for 72 hours. The level of Smn protein in the cell nucleus is quantified using Smn immunostaining and confocal fluorescence microscopy essentially as described in Makhortova et al., Nature Chemical Biology, 2011, 7:544. The level of Smn protein in compound-treated samples is normalized to that in vehicle-treated samples and plotted as a function of the compound concentration.

Results. As seen in FIG. 10, human motor neurons treated for 72 hours with increasing concentrations of Compound 6 contain progressively more Smn protein in the nucleus.

Example 10

Smn Protein Assay in Animal Tissues

This Smn protein assay compares tissues from test compound treated mice with those from DMSO vehicle treated mice to determine the increase in levels of Smn protein produced from the human SMN2 gene.

Materials

| Material | Source |
|---|---|
| Tissues from C/C-allele SMA mice | The Jackson Laboratory, strain No.: 008714 (B6.129-Smn1$^{tm5(Smn1/SMN2)Mrph}$/J) |
| Tissues from Δ7 SMA mice | The Jackson Laboratory, strain No.: 005025 (FVB.Cg-Tg(SMN2*delta7)4299Ahmb Tg(SMN2)89Ahmb Smn1$^{tm1Msd}$/J) |
| Protease inhibitor cocktail | Roche Applied Science Catalog No.: 11836145001 |
| Anti-SMN d2 | Blue cap Cisbio Catalog No.: 63IDC002-SMN |
| Anti-SMN kryptate | Red cap Cisbio Catalog No.: 63IDC002-SMN |
| SMN reconstitution buffer | Cisbio Catalog No.: 63IDC002-SMN-Buffer |
| RIPA Lysis Buffer | 20 mM Tris-HCl pH 7.5, 150 mM NaCl, 1 mM EDTA, 1% NP-40, 1% Sodium deoxycholate |
| Diluent Buffer | 20 mM Tris-HCl pH 7.5, 150 mM NaCl |
| BCA protein assay Kit | Pierce Catalog No.: 23225 |
| White 384 well plate | Nunc Catalog No.: 351190 |
| Polypropylene V-bottom plate | Falcon Catalog No.: 165195 |
| Clear 96 well polystyrene plate | Nunc Catalog No.: 442404 |
| 5 mm Stainless Steel Beads | Qiagen Catalog No.: 69989 |
| Safe-Lock Tubes 2.0 mL | Eppendorf Catalog No.: 022363352 |
| Twin.tec 96-Well Semiskirted PCR Plate | Eppendorf Catalog No.: 951020389 |
| TissueLyzer II | Qiagen Catalog No.: 85300 |
| Envision Plate Reader | Perkin Elmer Model No.: 2103 |

Protocol. The tissue samples in Safe-Lock tubes are weighed and the volume of RIPA buffer containing the protease inhibitor cocktail is added based on the weight to volume ratios for each type of tissue: Brain (50 mg/mL), Muscle (50 mg/mL) and Spinal Cord (25 mg/mL).

Tissues are homogenized using the TissueLyzer by bead milling. 5 mm stainless steel beads are added to the sample and shaken vigorously for 5 minutes at 30 Hz in the TissueLyzer. The samples are then centrifuged for 20 minutes at 14,000×g in a microcentrifuge and the homogenates transferred to the PCR plate. The homogenates are diluted in RIPA buffer to approximately 1 mg/mL for HTRF and approximately 0.5 mg/mL for total protein measurement using the BCA protein assay. For the SMN HTRF assay, 35 µL of the tissue homogenate is transferred to a 384-well plate containing 5 µL of the antibody solution (1:100 dilution of each of the anti-SMNd2 and anti-SMN Kryptate in reconstitution buffer). To provide a control signal, three (3) wells in the plate contain only RIPA Lysis Buffer and, thus, serve as Blank control wells. The plate is centrifuged for 1 minute to bring the solution to the bottom of the wells and then incubated overnight at room temperature. Fluorescence for each well of the plate at 665 nm and 620 nm is measured on an EnVision multilabel plate reader (Perkin-Elmer). The total protein in the tissue homogenate is measured using the BCA assay according to the manufacturer's protocol.

The normalized fluorescence signal is calculated for each sample, Blank and vehicle control well by dividing the signal at 665 nm by the signal at 620 nm. Normalizing the signal accounts for possible fluorescence quenching due to the matrix effect of the tissue homogenate. The ΔF value (a measurement of Smn protein abundance as a percent value) for each tissue sample well is calculated by subtracting the normalized average fluorescence for the Blank control wells from the normalized fluorescence for each tissue sample well, then dividing this difference by the normalized average fluorescence for the Blank control wells and multiplying the resulting value by 100. The ΔF value for each tissue sample well is divided by the total protein quantity (determined using the BCA assay) for that tissue sample. The change in Smn protein abundance for each tissue sample relative to the vehicle control is calculated as the percent difference in the ΔF value of the tissue sample in the presence of the test compound and the averaged ΔF value of the vehicle control signal divided by the averaged ΔF value of the vehicle control signal.

Example 11

Smn Protein Assay in Tissues of Adult C/C-Allele SMA Mice

The tissues for use in the assay for Smn protein in adult C/C-allele SMA mice are prepared as described in Example 10. The assay assesses whether treatment of C/C-allele SMA mice with a test compound for 10 days increases levels of Smn protein produced from the SMN2 gene.

Materials

| Material | Source |
|---|---|
| Tissues from C/C-allele SMA mice | The Jackson Laboratory, strain No.: 008714 (B6.129-Smn1$^{tm5(Smn1/SMN2)Mrph}$/J) |

Protocol. C/C-allele SMA mice are dosed BID orally (in 0.5% hydroxypropylmethyl cellulose (HPMC) with 0.1% Tween-80) with a test compound or vehicle at 10 mg/kg for 10 days. Age-matched heterozygous mice are dosed with vehicle for use as a control. Tissues are collected for analysis of protein levels according to Example 10.

Results. As seen in FIG. 11, total protein-normalized Smn level was increased in brain, spinal cord, and muscle tissues of adult C/C-allele SMA mice treated at 100 mg/kg BID for 10 days with Compound 6 (FIG. 11a) or treated at 10 mg/kg BID for 10 days with Compound 170 (FIG. 11b) relative to the vehicle group.

Example 12

Smn Protein in Tissues of Neonatal Δ7 SMA Mice

The assay for Smn protein in neonatal SMA mice tissues is used to determine whether treatment with a test compound increases Smn protein levels produced from the SMN2 gene.

Materials

| Material | Source |
|---|---|
| Tissues from Δ7 SMA mice | The Jackson Laboratory, strain No.: 005025 (FVB.Cg-Tg(SMN2*delta7)4299Ahmb Tg(SMN2)89Ahmb Smn1$^{tm1Msd}$/J) |

Protocol. SMA Δ7 homozygous knockout mice are dosed once a day (QD) intraperitoneally (IP) with a test compound or vehicle (100% DMSO) from postnatal day (PND) 3 to PND 9. Tissues are collected for analysis of protein levels according to Example 10.

Results. As seen in FIG. 12, total protein normalized Smn level was dose dependently increased in brain, spinal cord, muscle, and skin tissues of neonatal SMA Δ7 homozygous knockout mice treated with Compound 6 (FIGS. 12a, 12b, 12c and 12d, respectively) and in brain, spinal cord, and muscle of neonatal SMA Δ7 homozygous knockout mice treated with Compound 170 (FIGS. 12e, 12f and 12g respectively).

Example 13

Body Weight of Neonatal Δ7 SMA Mice

The change in body weight of neonatal SMA mice is used to determine whether treatment with a test compound improves body weight.

Materials

| Material | Source |
| --- | --- |
| Tissues from ΔExon7 SMA mice | The Jackson Laboratory, strain No.: 005025 (FVB.Cg-Tg(SMN2*delta7)4299Ahmb Tg(SMN2)89Ahmb Smn1$^{tm1Msd}$/J) |

Protocol. SMA Δ7 homozygous knockout mice are dosed intraperitoneally (IP) with test compound or vehicle (100% DMSO) QD from PND 3 until the dose regimen is switched to an oral dose BID in 0.5% hydroxypropylmethyl cellulose (HPMC) with 0.1% Tween-80 at a dose 3.16-fold higher than the dose used for IP. Body weights of SMA Δ7 mice treated with test compound or vehicle and age matched heterozygous mice are recorded every day.

Results. As seen in FIG. 13, body weight of neonatal SMA Δ7 homozygous knockout mice treated with Compound 6, dosed IP QD from PND 3 to PND 30, then orally BID from PND 31 until study end (FIG. 13a) and Compound 170, dosed IP QD from PND 3 to PND 23, then orally BID from PND 24 until study end (FIG. 13b), improved compared to vehicle treated mice.

Example 14

Righting Reflex in Neonatal Δ7 SMA Mice

The functional change in righting reflex of neonatal SMA mice is used to determine whether treatment with a test compound improves righting reflex.

Materials

| Material | Source |
| --- | --- |
| Tissues from ΔExon7 SMA mice | The Jackson Laboratory, strain No.: 005025 (FVB.Cg-Tg(SMN2*delta7)4299Ahmb Tg(SMN2)89Ahmb Smn1$^{tm1Msd}$/J) |

Protocol. SMA Δ7 homozygous knockout mice are dosed intraperitoneally (IP) with test compound or vehicle (100% DMSO) QD from PND 3 until the dose regimen is switched to an oral dose BID in 0.5% hydroxypropylmethyl cellulose (HPMC) with 0.1% Tween-80 at a dose 3.16-fold higher than the dose used for IP. The righting reflex time is measured as the time taken by a mouse to flip over onto its feet after being laid on its back. Righting reflex is measured five times for each mouse (allowing a maximal time of 30 sec for each try) with 5 minutes between each measurement. The righting reflex time for SMA Δ7 homozygous knockout mice treated with test compound or vehicle and age-matched heterozygous mice is measured on PND 10, 14 and 18 and plotted.

Results. As seen in FIG. 14, the righting reflex of neonatal SMA Δ7 homozygous knockout mice treated with Compound 6 (FIG. 14a) and Compound 170 (FIG. 14b) dosed IP QD from PND 3 improved compared to vehicle treated mice. The righting time of the compound treated neonatal SMA Δ7 homozygous knockout mice was similar to that of the age matched heterozygous mice on PND 18.

Example 15

Survival of Neonatal Δ7 SMA Mice

The change in the number of surviving mice over time is used to determine whether treatment with a test compound improves survival.

Materials

| Material | Source |
| --- | --- |
| Tissues from Δ7 SMA mice | The Jackson Laboratory, strain No.: 005025 (FVB.Cg-Tg(SMN2*delta7)4299Ahmb Tg(SMN2)89Ahmb Smn1$^{tm1Msd}$/J) |

Protocol. SMA Δ7 homozygous knockout mice are dosed intraperitoneally (IP) with test compound or vehicle (100% DMSO) QD from PND 3 until the dose regimen is switched to an oral dose BID in 0.5% hydroxypropylmethyl cellulose (HPMC) with 0.1% Tween-80 at a dose 3.16-fold higher than the dose used for IP and later switched to an oral dose QD in 0.5% hydroxypropylmethyl cellulose (HPMC) with 0.1% Tween-80 at a dose 6.32-fold higher than the dose used for IP. The number of surviving mice in each group is recorded every day and plotted as a percent of total number of mice. Tissues of SMA Δ7 and age-matched heterozygous mice are collected for the measurement of Smn protein levels and processed as detailed in Example 10. The total protein normalized Smn protein levels measured in the tissues are plotted as a percent of those in the age-matched heterozygous mice tissues, with the Smn level in heterozygous mice set to 100 percent. The level of Smn protein in the test compound treated mice tissue relative to that in heterozygous mice tissue is indicated as a percent value above each bar in the graph.

Results. As seen in FIG. 15, survival of neonatal SMA Δ7 homozygous knockout mice treated with Compound 6 (FIG. 15a), dosed IP QD from PND 3 to PND 30, then orally BID from PND 31 until study end, and Compound 170 (FIG. 15b), dosed IP QD from PND 3 to PND 23, then orally BID from PND 24 until study end, improved compared to vehicle treated mice. As seen in FIG. 16, Smn protein levels in brain, spinal cord, and muscle tissues of SMA Δ7 homozygous knockout mice after treatment with Compound 6 dosed IP 10 mg/kg QD from PND 3 to PND 30, then orally 30 mg/kg BID from PND 31 to PND 156 (FIG. 16a) and Compound 170 dosed IP 3 mg/kg QD from PND 3 to PND 23, then orally 10 mg/kg BID from PND 24 to PND 88, orally 20 mg/kg QD from PND 89 to PND185 (FIG. 16b) was measured and plotted relative to vehicle treated and age-matched heterozygous mice.

Example 16

Human SMN1 Minigene mRNA End-Point Semi-Quantitative RT-PCR Splicing Assay in Cultured Cells The RT-PCR assay is used to visualize and quantify the levels of the human SMN1 minigene full length and Δ7 mRNA in primary cells and cell lines expressing the human SMN1 minigene construct treated with a test compound.

Materials

| Material | Source |
|---|---|
| HEK293H cells | ATCC Catalog No.: CRL-1573 |
| Cells-To-Ct lysis buffer | Life Technologies, Inc. (formerly Applied Biosystems) Catalog No.: 4399002 |
| FuGENE-6 lipid transfection reagent | Roche Applied Science, Catalog No.: 11 814 443 001 |
| DMEM | Life Technologies, Inc. (formerly Invitrogen) Catalog No.: 11960-044 |
| 96-well flat-bottom plates | Becton Dickinson Catalog No.: 353072 |
| Platinum Taq HiFi DNA Polymerase Super Mix | Life Technologies, Inc. (formerly Invitrogen) Catalog No.: 11304-016 |
| iScript RT enzyme Kit | BioRad Catalog No.: 170-8890 |
| Ethidium bromide | Life Technologies, Inc. |
| 2% agarose E gels 48-Well Double Comb | (formerly Invitrogen) Catalog No.: G8008-02 |
| Material | Source |
| Gel Documentation System | UVP Gel Doc It 310 Imaging system |

SMN1 Minigene Construct
Preparation of the Minigene Constructs

Using the procedure for the preparation of the SMN2 minigene construct described in Biological Example 1, the SMN1 version of the minigene is generated by replacing the sixth nucleotide of exon 7 (a thymine residue) of the SMN2-A minigene construct to cytosine using site-directed mutagenesis. Thus, similar to the SMN2-A minigene construct, the SMN1 minigene construct has a single adenine residue inserted after nucleic residue 48 of exon 7. The SMN1 minigene construct is referred to as SMN1-A.

Protocol. HEK293H cells (10,000 cells/well/199 µL) were transfected, using FuGENE-6 reagent, in a 96-well plate with 15 ng of the SMN1-A minigene reporter plasmid per well. Cells were incubated for 24 hours following transfection. Test compounds were serially diluted 3.16-fold in 100% DMSO to generate a 7-point concentration curve. A solution of test compound (1 µL, 200× in DMSO) was added to each test well. 1 µL DMSO was added to each control well. The plate was incubated for 7 hours in a cell culture incubator (37° C., 5% $CO_2$, 100% relative humidity). The cells were then lysed in Cells-To-Ct lysis buffer and the lysates were stored at −80° C.

Two SMN spliced mRNA are generated from the SMN1 minigene. The term "SMN1 minigene FL" refers to the first spliced product containing exon 7, corresponding to full length SMN1 mRNA. The term "SMN1 minigene Δ7" refers to the second product lacking exon 7.

SMN minigene FL and Δ7 mRNA are amplified using the primers in Table 11. Primer SMN Forward C (SEQ ID NO. 11) hybridizes to a nucleotide sequence in exon 6 (nucleotide 43 to nucleotide 63), primer SMN Reverse A (SEQ ID NO. 2) hybridizes to a nucleotide sequence in the coding sequence of Firefly luciferase. The combination of these two oligonucleotides detects only SMN1 or SMN2 minigenes (RT-PCR) and will not detect endogenous SMN1 or SMN2 genes. Since the HEK293H cells used in Example 16 were transfected with only the human SMN1 minigene, RT-PCR can visualize and quantify only SMN1 minigene full-length and SMN1 minigene Δ7 mRNA.

TABLE 11

| Primer | Sequence | Source |
|---|---|---|
| SMN Forward C | SEQ ID NO. 11: GATGCTGATGCTTTGGGAAGT | PTC[1] |
| SMN Reverse A | SEQ ID NO. 2: CGCTTCACATTCCAGATCTGTC | PTC[1] |

[1]Primers designed by PTC Therapeutics, Inc.

To synthesize cDNA, 5 µL of lysate, 4 µL of 5× iScript reaction mix, 1 µL of reverse transcriptase, and 10 µL of water are combined and incubated 5 min at 25° C. followed by 30 min at 42° C., followed by 5 min at 85° C. The cDNA solution is stored at −20° C.

To perform endpoint PCR, 5 µL of cDNA, 0.2 µL of 100 µM forward primer, 0.2 µL of 100 µM reverse primer, and 22.5 µL of polymerase super mix are combined in a 96 well semiskirted PCR plate. PCR is carried out at the following temperatures for the indicated time: Step 1: 94° C. (2 min), Step 2: 94° C. (30 sec), Step 3: 55° C. (30 sec), Step 4: 68° C. (1 min), then repeat Steps 2 to 4 for a total of 33 cycles, then hold at 4° C.

10 µL of each PCR sample is electrophoretically separated on a 2% agarose E-gel for 14 minutes stained with dsDNA staining reagents (e.g., ethidium bromide) and visualized using a gel imager.

Results. As seen in FIG. 17, cells treated with increasing concentrations of Compound 6 (FIG. 17a) and Compound 170 (FIG. 17b) contain progressively more SMN1 minigene FL mRNA and less SMN1 minigene Δ7 mRNA, indicating a correction of SMN1 alternative splicing.

Without regard to whether a document cited herein was specifically and individually indicated as being incorporated by reference, all documents referred to herein are incorporated by reference into the present application for any and all purposes to the same extent as if each individual reference was fully set forth herein.

Although certain embodiments have been described in detail above, those having ordinary skill in the art will clearly understand that many modifications are possible in the embodiments without departing from the teachings thereof. All such modifications are intended to be encompassed within the claims as described herein.

The invention claimed is:

1. A compound of Formula (XIa):

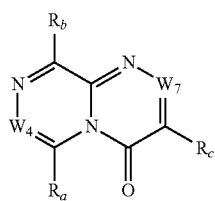

or a free acid, free base, salt, isotopologue, stereoisomer, racemate, enantiomer, diastereomer or tautomer thereof, wherein:

$w_4$ is C—$R_1$ or C—$R_2$;
$w_7$ is C—$R_1$ or C—$R_2$;
wherein one of $w_4$ and $w_7$ is C—$R_1$ and one other of $w_4$ and $w_7$ is C—$R_2$, provided that, $R_1$ is $C_{1-8}$alkyl, amino, $C_{1-8}$alkyl-amino, $(C_{1-8}$alkyl$)_2$-amino, $C_{1-8}$alkoxy-$C_{1-8}$alkyl-amino, $(C_{1-8}$alkoxy-$C_{1-8}$alkyl$)_2$-amino, $(C_{1-8}$alkoxy-$C_{1-8}$alkyl$)(C_{1-8}$alkyl$)$amino, amino-$C_{1-8}$alkyl, $C_{1-8}$alkyl-amino-$C_{1-8}$alkyl, $(C_{1-8}$alkyl$)_2$-amino-$C_{1-8}$alkyl, $C_{1-8}$alkoxy-$C_{1-8}$alkyl-amino-$C_{1-8}$alkyl, $(C_{1-8}$alkoxy-$C_{1-8}$alkyl$)_2$-amino-$C_{1-8}$alkyl, $(C_{1-8}$alkoxy-$C_{1-8}$alkyl$)(C_{1-8}$alkyl$)$amino-$C_{1-8}$alkyl, amino-$C_{1-8}$alkyl-amino, (amino-$C_{1-8}$alkyl$)_2$-amino, (amino-$C_{1-8}$alkyl$)(C_{1-8}$alkyl$)$amino, $C_{1-8}$alkyl-amino-$C_{1-8}$alkyl-amino, $(C_{1-8}$alkyl-amino-$C_{1-8}$alkyl$)_2$-amino, $(C_{1-8}$alkyl-amino-$C_{1-8}$alkyl$)(C_{1-8}$alkyl$)$amino, $(C_{1-8}$alkyl$)_2$-amino-$C_{1-8}$alkyl-amino, $[(C_{1-8}$alkyl$)_2$-amino-$C_{1-8}$alkyl$](C_{1-8}$alkyl$)$amino, amino-$C_{1-8}$alkoxy, $C_{1-8}$alkyl-amino-$C_{1-8}$alkoxy, $(C_{1-8}$alkyl$)_2$-amino-$C_{1-8}$alkoxy, $C_{1-8}$alkoxy-$C_{1-8}$alkyl-amino-$C_{1-8}$alkoxy, $C_{1-8}$alkoxy-$C_{1-8}$alkyl-amino-$C_{1-8}$alkoxy, $(C_{1-8}$alkoxy-$C_{1-8}$alkyl$)(C_{1-8}$alkyl$)$amino-$C_{1-8}$alkoxy, amino-$C_{2-8}$alkenyl, $C_{1-8}$alkyl-amino-$C_{2-8}$alkenyl, $(C_{1-8}$alkyl$)_2$-amino-$C_{2-8}$alkenyl, amino-$C_{2-8}$alkynyl, $C_{1-8}$alkyl-amino-$C_{2-8}$alkynyl, $(C_{1-8}$alkyl$)_2$-amino-$C_{2-8}$alkynyl, halo-$C_{1-8}$alkyl-amino, (halo-$C_{1-8}$alkyl$)_2$-amino, (halo-$C_{1-8}$alkyl$)(C_{1-8}$alkyl$)$amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl$)_2$-amino, (hydroxy-$C_{1-8}$alkyl$)(C_{1-8}$alkyl$)$amino, hydroxy-$C_{1-8}$alkyl-amino-$C_{1-8}$alkyl, (hydroxy-$C_{1-8}$alkyl$)_2$-amino-$C_{1-8}$alkyl, (hydroxy-$C_{1-8}$alkyl)($C_{1-8}$alkyl)amino-$C_{1-8}$alkyl, hydroxy-$C_{1-8}$alkyl-amino-$C_{1-8}$alkoxy, (hydroxy-$C_{1-8}$alkyl)$_2$-amino-$C_{1-8}$alkoxy, (hydroxy-$C_{1-8}$alkyl)($C_{1-8}$alkyl)amino-$C_{1-8}$alkoxy, hydroxy-$C_{1-8}$alkyl-amino-$C_{1-8}$alkyl-amino, (hydroxy-$C_{1-8}$alkyl-amino-$C_{1-8}$alkyl)$_2$-amino, (hydroxy-$C_{1-8}$alkyl)$_2$-amino-$C_{1-8}$alkyl-amino, (hydroxy-$C_{1-8}$alkyl-amino-$C_{1-8}$alkyl)($C_{1-8}$alkyl)amino, (hydroxy-$C_{1-8}$alkyl)($C_{1-8}$alkyl)amino-$C_{1-8}$alkyl-amino, [(hydroxy-$C_{1-8}$alkyl)$_2$-amino-$C_{1-8}$alkyl]($C_{1-8}$alkyl)amino, [(hydroxy-$C_{1-8}$alkyl)($C_{1-8}$alkyl)amino-$C_{1-8}$alkyl]($C_{1-8}$alkyl)amino, heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl;

wherein, each instance of heterocyclyl, $C_{3-14}$cycloalkyl, aryl and heteroaryl is optionally substituted with one, two or three $R_3$ substituents and optionally, with one additional $R_4$ substituent; or, wherein, each instance of heterocyclyl, $C_{3-14}$cycloalkyl, aryl and heteroaryl is optionally substituted with one, two, three or four $R_3$ substituents;

$R_2$ is aryl, aryl-amino, aryl-amino-carbonyl, heterocyclyl, heteroaryl or heteroaryl-amino;

wherein, each instance of aryl, heterocyclyl and heteroaryl is optionally substituted with one, two or three $R_6$ substituents and optionally, with one additional $R_7$ substituent;

$R_a$ is, in each instance, independently hydrogen, halogen or $C_{1-8}$alkyl;

$R_b$ is hydrogen, halogen, $C_{1-8}$alkyl or $C_{1-8}$alkoxy;

$R_c$ is hydrogen, halogen or $C_{1-8}$alkyl;

$R_3$ is, in each instance, independently cyano, halogen, hydroxy, oxo, $C_{1-8}$alkyl, halo-$C_{1-8}$alkyl, $C_{1-8}$alkyl-carbonyl, $C_{1-8}$alkoxy, halo-$C_{1-8}$alkoxy, $C_{1-8}$alkoxy-$C_{1-8}$alkyl, $C_{1-8}$alkoxy-carbonyl, amino, $C_{1-8}$alkyl-amino, ($C_{1-8}$alkyl)$_2$-amino, amino-$C_{1-8}$alkyl, $C_{1-8}$alkyl-amino-$C_{1-8}$alkyl, ($C_{1-8}$alkyl)$_2$-amino-$C_{1-8}$alkyl, amino-$C_{1-8}$alkyl-amino, $C_{1-8}$alkyl-amino-$C_{1-8}$alkyl-amino, ($C_{1-8}$alkyl-amino-$C_{1-8}$alkyl)$_2$-amino, ($C_{1-8}$alkyl)$_2$-amino-$C_{1-8}$alkyl-amino, [($C_{1-8}$alkyl)$_2$-amino-$C_{1-8}$alkyl]$_2$-amino, ($C_{1-8}$alkyl-amino-$C_{1-8}$alkyl)($C_{1-8}$alkyl)amino, [($C_{1-8}$alkyl)$_2$-amino-$C_{1-8}$alkyl]($C_{1-8}$alkyl)amino, $C_{1-8}$alkoxy-$C_{1-8}$alkyl-amino, ($C_{1-8}$alkoxy-$C_{1-8}$alkyl)$_2$-amino, ($C_{1-8}$alkoxy-$C_{1-8}$alkyl)($C_{1-8}$alkyl)amino, $C_{1-8}$alkyl-carbonyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino or (hydroxy-$C_{1-8}$alkyl)($C_{1-8}$alkyl)amino;

$R_4$ is $C_{3-14}$cycloalkyl, $C_{3-14}$cycloalkyl-$C_{1-8}$alkyl, $C_{3-14}$cycloalkyl-amino, aryl-$C_{1-8}$alkyl, aryl-$C_{1-8}$alkoxy-carbonyl, aryl-sulfonyloxy-$C_{1-8}$alkyl, heterocyclyl or heterocyclyl-$C_{1-8}$alkyl; wherein, each instance of $C_{3-14}$cycloalkyl, aryl and heterocyclyl is optionally substituted with one, two or three $R_5$ substituents;

$R_5$ is, in each instance, independently halogen, hydroxy, cyano, nitro, $C_{1-8}$alkyl, halo-$C_{1-8}$alkyl, $C_{1-8}$alkoxy, halo-$C_{1-8}$alkoxy, amino, $C_{1-8}$alkyl-amino, ($C_{1-8}$alkyl)$_2$-amino or $C_{1-8}$alkyl-thio;

$R_6$ is, in each instance, independently halogen, hydroxy, cyano, nitro, $C_{1-8}$alkyl, $C_{2-8}$alkenyl, halo-$C_{1-8}$alkyl, hydroxy-$C_{1-8}$alkyl, $C_{1-8}$alkoxy, halo-$C_{1-8}$alkoxy, $C_{1-8}$alkoxy-$C_{1-8}$alkyl, amino, $C_{1-8}$alkyl-amino, ($C_{1-8}$alkyl)$_2$-amino or $C_{1-8}$alkyl-thio; and, $R_7$ is $C_{3-14}$cycloalkyl, $C_{3-14}$cycloalkyl-oxy, aryl, heterocyclyl or heteroaryl.

2. The compound of claim 1, wherein the compound is Formula (XIa1) or Formula (XIa2):

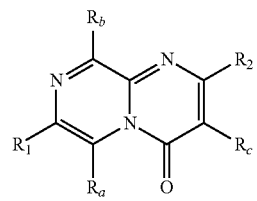

(XIa1)

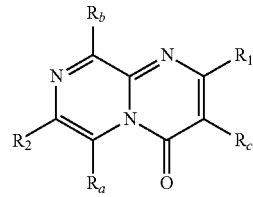

(XIa2)

or a free acid, free base, salt, isotopologue, stereoisomer, racemate, enantiomer, diastereomer or tautomer thereof.

3. The compound of claim 2, wherein the compound is Formula (XIa1):

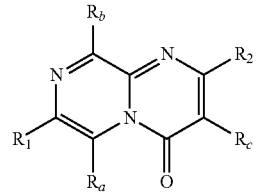

(XIa1)

or a free acid, free base, salt, isotopologue, stereoisomer, racemate, enantiomer, diastereomer or tautomer thereof.

4. The compound of claim 3, wherein $R_1$ is heterocyclyl;

wherein, heterocyclyl is optionally substituted with one, two or three $R_3$ substituents and optionally, with one additional $R_4$ substituent; or, wherein, heterocyclyl is optionally substituted with one, two, three or four $R_3$ substituents; and $R_2$ is aryl or heteroaryl;

wherein, aryl or heteroaryl is optionally substituted with one, two or three $R_6$ substituents and optionally, with one additional $R_7$ substituent.

5. The compound of claim 1, wherein the salt form is a chloride, hydrobromide, hydrochloride, dihydrochloride, acetate, trifluoroacetate or trifluoroacetic acid salt.

6. The compound of claim 1, wherein the compound is selected from the group consisting of:
- 2-(3,4-dimethoxyphenyl)-7-(1,2,3,6-tetrahydropyridin-4-yl)-4H-pyrazino[1,2-a]pyrimidin-4-one;
- 2-(1,3-dimethylpyrrolo[1,2-a]pyrazin-7-yl)-7-(1,2,3,6-tetrahydropyridin-4-yl)-4H-pyrazino[1,2-a]pyrimidin-4-one;
- 2-(2-methyl-1,3-benzoxazol-6-yl)-7-(1,2,3,6-tetrahydropyridin-4-yl)-4H-pyrazino[1,2-a]pyrimidin-4-one; hydrochloride (1:1)
- 2-(2-methyl-1,3-benzoxazol-6-yl)-7-(1-methyl-1,2,3,6-tetrahydropyridin-4-yl)-4H-pyrazino[1,2-a]pyrimidin-4-one;
- 7-(1-ethyl-1,2,3,6-tetrahydropyridin-4-yl)-2-(2-methyl-1,3-benzoxazol-6-yl)-4H-pyrazino[1,2-a]pyrimidin-4-one;
- 2-(1,3-dimethylpyrrolo[1,2-a]pyrazin-7-yl)-7-[1-(propan-2-yl)-1,2,3,6-tetrahydropyridin-4-yl]-4H-pyrazino[1,2-a]pyrimidin-4-one;
- 2-(4,6-dimethylpyrazolo[1,5-a]pyrazin-2-yl)-7-(piperidin-4-yl)-4H-pyrazino[1,2-a]pyrimidin-4-one;
- 2-(4,6-dimethylpyrazolo[1,5-a]pyrazin-2-yl)-7-(1-methylpiperidin-4-yl)-4H-pyrazino[1,2-a]pyrimidin-4-one;
- 2-(4,6-dimethylpyrazolo[1,5-a]pyrazin-2-yl)-7-(1-ethylpiperidin-4-yl)-4H-pyrazino[1,2-a]pyrimidin-4-one;
- 2-(1-methyl-1H-indazol-5-yl)-7-(1,2,3,6-tetrahydropyridin-4-yl)-4H-pyrazino[1,2-a]pyrimidin-4-one;
- 2-(1-methyl-1H-indazol-5-yl)-7-(1-methyl-1,2,3,6-tetrahydropyridin-4-yl)-4H-pyrazino[1,2-a]pyrimidin-4-one;
- 7-(1-ethyl-1,2,3,6-tetrahydropyridin-4-yl)-2-(1-methyl-1H-indazol-5-yl)-4H-pyrazino[1,2-a]pyrimidin-4-one;
- 2-(2-methyl-2H-indazol-5-yl)-7-(piperidin-4-yl)-4H-pyrazino[1,2-a]pyrimidin-4-one;
- 2-(2-methyl-2H-indazol-5-yl)-7-(1-methylpiperidin-4-yl)-4H-pyrazino[1,2-a]pyrimidin-4-one;
- 7-(1-ethylpiperidin-4-yl)-2-(2-methyl-2H-indazol-5-yl)-4H-pyrazino[1,2-a]pyrimidin-4-one;
- 7-[1-(2-hydroxyethyl)piperidin-4-yl]-2-(2-methyl-2H-indazol-5-yl)-4H-pyrazino[1,2-a]pyrimidin-4-one;
- 2-(2-methylimidazo[1,2-a]pyridin-6-yl)-7-(1-methylpiperidin-4-yl)-4H-pyrazino[1,2-a]pyrimidin-4-one;
- 7-(1-ethylpiperidin-4-yl)-2-(2-methylimidazo[1,2-a]pyridin-6-yl)-4H-pyrazino[1,2-a]pyrimidin-4-one;
- 7-[1-(2-hydroxyethyl)piperidin-4-yl]-2-(2-methylimidazo[1,2-a]pyridin-6-yl)-4H-pyrazino[1,2-a]pyrimidin-4-one;
- 2-(2-methylimidazo[1,2-a]pyridin-6-yl)-7-(piperidin-4-yl)-4H-pyrazino[1,2-a]pyrimidin-4-one;
- 2-(2-methyl-2H-indazol-5-yl)-7-(piperazin-1-yl)-4H-pyrazino[1,2-a]pyrimidin-4-one;
- 2-(8-chloro-2-methylimidazo[1,2-a]pyridin-6-yl)-7-(piperidin-4-yl)-4H-pyrazino[1,2-a]pyrimidin-4-one;
- 2-(2,8-dimethylimidazo[1,2-a]pyridin-6-yl)-7-(piperidin-4-yl)-4H-pyrazino[1,2-a]pyrimidin-4-one;
- 2-(2-methyl-2H-indazol-5-yl)-7-(4-methylpiperazin-1-yl)-4H-pyrazino[1,2-a]pyrimidin-4-one;
- 7-(4-ethylpiperazin-1-yl)-2-(2-methyl-2H-indazol-5-yl)-4H-pyrazino[1,2-a]pyrimidin-4-one;
- 7-[4-(2-hydroxyethyl)piperazin-1-yl]-2-(2-methyl-2H-indazol-5-yl)-4H-pyrazino[1,2-a]pyrimidin-4-one;
- 2-(2,8-dimethylimidazo[1,2-a]pyridin-6-yl)-7-(1-methylpiperidin-4-yl)-4H-pyrazino[1,2-a]pyrimidin-4-one;
- 2-(2,8-dimethylimidazo[1,2-a]pyridin-6-yl)-7-(1-ethylpiperidin-4-yl)-4H-pyrazino[1,2-a]pyrimidin-4-one;
- 2-(2,8-dimethylimidazo[1,2-a]pyridin-6-yl)-7-[1-(2-hydroxyethyl)piperidin-4-yl]-4H-pyrazino[1,2-a]pyrimidin-4-one;
- 2-(8-chloro-2-methylimidazo[1,2-a]pyridin-6-yl)-7-[1-(propan-2-yl)piperidin-4-yl]-4H-pyrazino[1,2-a]pyrimidin-4-one;
- 2-(8-chloro-2-methylimidazo[1,2-a]pyridin-6-yl)-7-[1-(2-hydroxyethyl)piperidin-4-yl]-4H-pyrazino[1,2-a]pyrimidin-4-one;
- 2-(2-methylimidazo[1,2-a]pyridin-6-yl)-7-[1-(propan-2-yl)piperidin-4-yl]-4H-pyrazino[1,2-a]pyrimidin-4-one;
- 7-(1-cyclobutylpiperidin-4-yl)-2-(2-methylimidazo[1,2-a]pyridin-6-yl)-4H-pyrazino[1,2-a]pyrimidin-4-one;
- 2-(4-ethyl-6-methylpyrazolo[1,5-a]pyrazin-2-yl)-7-(piperidin-4-yl)-4H-pyrazino[1,2-a]pyrimidin-4-one;
- 2-(4-ethyl-6-methylpyrazolo[1,5-a]pyrazin-2-yl)-7-(1-methylpiperidin-4-yl)-4H-pyrazino[1,2-a]pyrimidin-4-one;
- 2-(4-ethyl-6-methylpyrazolo[1,5-a]pyrazin-2-yl)-7-(1-ethylpiperidin-4-yl)-4H-pyrazino[1,2-a]pyrimidin-4-one;
- 9-methyl-2-(2-methyl-2H-indazol-5-yl)-7-(1,2,3,6-tetrahydropyridin-4-yl)-4H-pyrazino[1,2-a]pyrimidin-4-one; and
- 9-methyl-2-(2-methyl-2H-indazol-5-yl)-7-(piperidin-4-yl)-4H-pyrazino[1,2-a]pyrimidin-4-one;

or a salt, enantiomer, diastereomer or tautomer thereof.

7. A pharmaceutical composition comprising an effective amount of the compound of claim 1 and a pharmaceutically acceptable carrier, excipient or diluent.

8. A method for enhancing the inclusion of exon 6 of SMN2 into mRNA that is transcribed from the SMN2 gene, comprising contacting a human cell with the compound of claim 1.

9. A method for increasing the amount of Smn protein, comprising contacting a human cell with the compound of claim 1.

10. The method of claim 8, wherein the human cell is a human cell from a human spinal muscular atrophy patient.

11. The method of claim 9, wherein the human cell is a human cell from a human spinal muscular atrophy patient.

12. A method for treating spinal muscular atrophy in a human subject in need thereof, comprising administering to the subject an effective amount of the compound of claim 1.

13. A method for treating spinal muscular atrophy in a human subject in need thereof, comprising administering to the subject the pharmaceutical composition of claim 7.

* * * * *